(12) United States Patent
Singh et al.

(10) Patent No.: US 11,883,526 B2
(45) Date of Patent: Jan. 30, 2024

(54) ESKETAMINE FOR THE TREATMENT OF DEPRESSION

(71) Applicant: Janssen Pharmaceutica NV, Beerse (BE)

(72) Inventors: Jaskaran Singh, San Diego, CA (US); Ella Daly, Titusville, NJ (US); Margaret Fedgchin, Collegeville, PA (US); David Hough, Yardley, PA (US); Vanina Popova, Nijlen (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/711,277

(22) Filed: Apr. 1, 2022

(65) Prior Publication Data

US 2022/0362144 A1 Nov. 17, 2022

Related U.S. Application Data

(63) Continuation of application No. 17/436,188, filed as application No. PCT/IB2020/051344 on Feb. 18, 2020.

(60) Provisional application No. 62/813,767, filed on Mar. 5, 2019, provisional application No. 62/814,274, filed on Mar. 5, 2019.

(51) Int. Cl.
*A61K 31/135* (2006.01)
*A61K 9/00* (2006.01)
*A61P 25/24* (2006.01)

(52) U.S. Cl.
CPC .......... *A61K 9/0043* (2013.01); *A61K 9/0053* (2013.01); *A61K 31/135* (2013.01); *A61P 25/24* (2018.01)

(58) Field of Classification Search
CPC .................................................. A61K 31/135
See application file for complete search history.

(56) References Cited

U.S. PATENT DOCUMENTS

| | | | |
|---|---|---|---|
| 4,994,467 A | 2/1991 | Zimmerman | |
| 5,024,998 A | 6/1991 | Bodor | |
| 5,543,434 A | 8/1996 | Weg | |
| 6,017,961 A | 1/2000 | Flores et al. | |
| 6,040,479 A | 3/2000 | Steiner et al. | |
| 6,176,242 B1 | 1/2001 | Rise | |
| 6,321,942 B1 | 11/2001 | Krampen et al. | |
| 6,427,680 B1 | 8/2002 | Oechsel | |
| 6,572,849 B2 | 6/2003 | Shahinian, Jr. | |
| 6,599,883 B1 | 7/2003 | Romeo et al. | |
| 7,273,889 B2 | 9/2007 | Mermelstein et al. | |
| 7,638,651 B2 | 12/2009 | Gant et al. | |
| 7,687,080 B2 | 3/2010 | Wolicki | |
| 7,745,665 B2 | 6/2010 | Gant et al. | |
| 7,896,850 B2 | 3/2011 | Kronestedt et al. | |
| 7,973,043 B2 | 7/2011 | Migaly | |
| 8,710,070 B2 | 4/2014 | Holtman et al. | |
| 8,785,500 B2 | 7/2014 | Charney et al. | |
| 9,073,819 B2 | 7/2015 | Amin et al. | |
| 9,592,207 B2 | 3/2017 | Charney et al. | |
| 9,650,352 B2 | 5/2017 | Wainer et al. | |
| 10,098,854 B2 | 10/2018 | Drevets et al. | |
| 10,307,385 B2 | 6/2019 | Boudy et al. | |
| 10,335,379 B2 | 7/2019 | Manthei et al. | |
| 10,406,121 B2 | 9/2019 | Hashimoto | |
| 10,653,629 B2 | 5/2020 | Nivorozhkin et al. | |
| 10,869,844 B2 * | 12/2020 | Caers ................... | A61K 9/0043 |
| 11,173,134 B2 * | 11/2021 | Caers ................... | A61K 31/135 |
| 11,191,734 B2 | 12/2021 | Tang et al. | |
| 11,446,260 B2 | 9/2022 | Basstanie et al. | |
| 2004/0138298 A1 | 7/2004 | Mermelstein et al. | |
| 2004/0214215 A1 | 10/2004 | Yu et al. | |
| 2004/0248964 A1 | 12/2004 | Crooks et al. | |
| 2004/0265364 A1 | 12/2004 | Ozturk et al. | |
| 2005/0095277 A1 | 5/2005 | Ozturk et al. | |
| 2005/0209218 A1 | 9/2005 | Meyerson et al. | |
| 2006/0223788 A1 | 10/2006 | Cathcart | |
| 2006/0276550 A1 | 12/2006 | Bhagwat | |
| 2007/0256688 A1 | 11/2007 | Schuster et al. | |
| 2007/0287753 A1 | 12/2007 | Charney et al. | |
| 2008/0171075 A1 | 7/2008 | Ozturk et al. | |
| 2009/0306137 A1 | 12/2009 | Wolfgang et al. | |
| 2011/0038807 A1 | 2/2011 | Papolos | |
| 2011/0112131 A1 | 5/2011 | Holtman et al. | |
| 2011/0240012 A1 | 10/2011 | Pilon | |
| 2011/0306674 A1 | 12/2011 | Schiene et al. | |
| 2012/0059666 A1 | 3/2012 | Kost et al. | |
| 2012/0225949 A1 | 9/2012 | Papolos | |
| 2013/0172361 A1 | 7/2013 | Fava et al. | |
| 2013/0209585 A1 | 8/2013 | Kim | |
| 2013/0236573 A1 | 9/2013 | Singh et al. | |
| 2014/0079740 A1 | 3/2014 | Salama | |
| 2014/0093592 A1 | 4/2014 | Singh et al. | |
| 2014/0221473 A1 | 8/2014 | Amin et al. | |
| 2014/0256821 A1 | 9/2014 | Charney et al. | |

(Continued)

FOREIGN PATENT DOCUMENTS

AU  2016203771 A1  6/2016
CN  101466364 A  6/2009

(Continued)

OTHER PUBLICATIONS

Auer et al., "The nature and time course of neuronal vacuolation induced by the N-methyl-D-aspartate antagonist MK-801", Acta Neuropathol., 1994, 87, 1-7.

(Continued)

*Primary Examiner* — Rei Tsang Shiao
(74) *Attorney, Agent, or Firm* — BakerHostetler

(57) ABSTRACT

The present invention provides methods for treating depression in a patient, comprising administering to the patient in need of the treatment a therapeutically effective amount of esketamine. In some embodiments, the depression is major depressive disorder or treatment resistant depression. In other embodiments, the therapeutically effective amount is clinically proven safe and/or effective. Also provided are methods to mitigate the risk or misuse or abuse of esketamine, instructions for use of the esketamine product, and methods for selling a drug product containing esketamine.

33 Claims, 77 Drawing Sheets

(56) References Cited

U.S. PATENT DOCUMENTS

| | | |
|---|---|---|
| 2015/0057306 A1 | 2/2015 | Fava et al. |
| 2015/0196501 A1 | 7/2015 | Erickson et al. |
| 2016/0074340 A1 | 3/2016 | Caers et al. |
| 2016/0175266 A1 | 6/2016 | Mermelstein et al. |
| 2016/0332962 A1 | 11/2016 | Chen et al. |
| 2016/0338977 A1* | 11/2016 | Singh .................. A61K 31/135 |
| 2017/0049780 A1 | 2/2017 | Wainer et al. |
| 2017/0071242 A1 | 3/2017 | Crespo et al. |
| 2017/0095429 A1 | 4/2017 | Erickson et al. |
| 2017/0136477 A1 | 5/2017 | Heldt et al. |
| 2017/0151191 A1 | 6/2017 | Charney et al. |
| 2018/0015054 A1 | 1/2018 | Charney et al. |
| 2018/0042936 A1 | 2/2018 | Lombard |
| 2018/0296478 A1 | 10/2018 | Salce et al. |
| 2021/0106545 A1 | 4/2021 | Singh et al. |

FOREIGN PATENT DOCUMENTS

| | | | |
|---|---|---|---|
| CN | 103705909 A | | 4/2014 |
| CN | 104519878 A | | 4/2015 |
| CN | 104798728 A | | 7/2015 |
| DE | 2062620 | | 7/1971 |
| DE | 4312016 A1 | | 10/1994 |
| DE | 19619665 A1 | | 11/1997 |
| DE | 102007009888 A1 | | 9/2008 |
| EP | 1103256 A1 | | 5/2001 |
| ES | 2484068 A1 | | 8/2014 |
| FR | 2739294 A1 | | 4/1997 |
| GB | 1330878 A | | 9/1973 |
| JP | 63-002932 A | | 1/1988 |
| JP | 2009-530385 A | | 8/2009 |
| JP | 2015-512418 A | | 4/2015 |
| JP | 2017-514503 A | | 6/2017 |
| NZ | 619257 A | | 7/2015 |
| WO | 94/23711 A1 | | 10/1994 |
| WO | 95/22965 | | 8/1995 |
| WO | 96/25925 | | 8/1996 |
| WO | 97/07750 | | 3/1997 |
| WO | 00/04875 | | 2/2000 |
| WO | 02/34293 A2 | | 5/2002 |
| WO | 2004/045601 A1 | | 6/2004 |
| WO | 2006/058022 A1 | | 6/2006 |
| WO | 2007/111880 A2 | | 10/2007 |
| WO | 2009/131794 A1 | | 10/2009 |
| WO | 2011/020061 A2 | | 2/2011 |
| WO | 2013/003669 A2 | | 1/2013 |
| WO | 2013/056229 A1 | | 4/2013 |
| WO | 2013/149102 A1 | | 10/2013 |
| WO | 2014/020155 A1 | | 2/2014 |
| WO | 2014/031975 A1 | | 2/2014 |
| WO | 2014/033680 A1 | | 3/2014 |
| WO | 2014/169272 A1 | | 10/2014 |
| WO | 2015/031410 A1 | | 3/2015 |
| WO | 2015/037248 A1 | | 3/2015 |
| WO | 2015/101693 A1 | | 7/2015 |
| WO | 2015/158854 A1 | | 10/2015 |
| WO | 2016/001599 A1 | | 1/2016 |
| WO | 2016/044150 A1 | | 3/2016 |
| WO | 2016/109427 A1 | | 7/2016 |
| WO | 2016/172672 A1 | | 10/2016 |
| WO | 2016/187491 A1 | | 11/2016 |
| WO | 2017/003935 A1 | | 1/2017 |
| WO | 2019/126108 A1 | | 6/2019 |

OTHER PUBLICATIONS

Auer, "Effect of age and sex on N-methyl-D-aspartate antagonist-induced neuronal necrosis in rats", Stroke, 1996, 27, 743-746.
Bender, "Comparative analyses of the neurodegeneration induced by the non-competitive NMDA-receptor-antagonist drug MK801 in mice and rats", Neurotoxicology and Teratology, 2010, 32, 542-550.
Bender, "Involvement of AMPA/Kainate-Excitotoxicity in MK801-Induced Neuronal Death in the Retrosplenial Cortex", Neuroscience, 2010, 169, 720-732.
Bentley, "Ketamine: an update for its use in complex regional pain syndrome and major depressive disorder", Clinical & Experimental Pharmacology, 2015, 5(2), 1000169/1-1000169/3.
Berge, "Pharmaceutical Salts", J. Pharm. Sci., 1977, 66, 1-19.
Bloch, "Effects of Ketamine in Treatment-Refractory Obsessive-Compulsive Disorder", Biological Psychiatry, 2012, 72(11), 964-970.
Bolon, Toxicol. Pathol., 2013, 41(7), 1028-1048.
Bremner et al., "Measurement of Dissociative States with the Clinician-Administered Dissociative states scale (CADSS)", Journal of Traumatic Stress, 1998, vol. 11, Issue 1, 125-136.
Bretz, "Combining multiple comparisons and modeling techniques in dose-response studies", Biometrics, 2005, 61, 738-748.
Bueno, Experimental and Toxicologic Pathology, 2003, 54, 319-334.
Canuso, "Efficacy and Safety of intranasal Esketamine for the Rapid Reduction of Symptoms of Depression and Suicidality in Patients at Imminent Risk for Suicide: Results of a Double-Blind, Randomized Placebo-Controlled Study", Am. J. Psych., 2018, 1-11.
Chen, "A sequential enriched design for target patient population in psychiatric clinical trails", Stat. Med., 2014, 33(17), 2953-2967.
Chen, "Evaluation of performance of some enrichment designs dealing with high placebo response in psychiatric clinical trials", Contemp, Clin. Trials, 2011, 32(4), 592-604.
Chi, "On clinical trials with a high placebo rate. Contemporary Clinical Trials Communications", 2016, 2, 34-53.
ClinicalTrials.gov NCT02497287, A Long-term, Safety and Efficacy Study of Intranasal Esketamine in Treatment-resistant Depression (Sustain-2), 2015.
Cohen, Anesthesiol., 1973, 39, 370-376.
Colbourne et al., "The effects of temperature and scopolamine on N-methyl-D-aspartate antagonist-induced neuronal necrosis in the rat", Neurosc., 1999, 90(1), 87-94.
Compton et al., International Journal of Life Science and Medical Research, 2013, vol. 3, issue 5, 179-192.
Corya et al., Journal of Clinical Psychiatry, 2003, 64(11), 1349-1356.
Daly et al., Society of Biological Psychiatry's (SOBP) 71st Annual Meeting, May 12-14, 2016, Atlanta, Georgia, USA, Poster 594.
DeOlmos, Neuroscience, 2009, 164(3), 1347-1359.
Farber et al., "Age-specific neurotoxicity in the rat associated with NMDA receptor blockade: potential relevance to schizophrenia?", Biol. Psychiatry, 1995, 38, 788-796.
Feder et al., "Efficacy of intravenous ketamine for treatment of chronic posttraumatic stress disorder a randomized clinical trial", JAMA Psychiatry, 2014, 71(6), 681-688.
Fix et al., "Integrated evaluation of central nervous system lesions: stains for neurons, astrocytes, and microglia reveal the spatial and temporal features of MK-801-induced neuronal necrosis in the rat cerebral cortex", Toxicol. Pathol., 1996, 24(3), 291-304.
Fix et al., "MK-801 neurotoxicity in cupric silver-stained sections: lesion reconstruction by 3-dimensional computer image analysis", Toxicol. Pathol., 2000, 28(1), 84-90.
Fix et al., "Pathomorphologic effects of N-methyl-D-aspartate antagonists in the rat posterior cingulate/retrosplenial cerebral cortex: a review", Drug Development Res., 1994, 32, 147-152.
Gingerich HOP Live, https://www.mdmag.com/medical-news, Sep. 4, 2018.
Green, Lab. Anim, 1981, 15, 163-170.
Guy, Clinical Global Impression of Severity (CGI-S) scale (Guy, "ECDEU Assessment Manual for Psychopharmacology—Revised (DHEW Publ No. Adm 76-338)" Rockville, MD: U.S. Department of Health, Education and Welfare, Public Health Service, Alcohol, Drug Abuse and Mental Health Administration, NIMH Psychopharmacology Research Branch, Division of Extramural Research Programs, 1976, 218-222.
Hoffman, Pharmacology, Biochemistry and Behavior, 2003, 74, 933-941.
Horvath, Brain Res., 1997, 753(2), 181-195.
Howland, Journal of Psychosocial Nursing and Mental Health Services, 2008, 46(10), 21-24.
Huang, "Comparison of test statistics for the sequential parallel design", Statistics in Biopharmaceutical Research, 2010, 2(1), 42-50.

(56) References Cited

OTHER PUBLICATIONS

Hur, Environmental Toxicology and Pharmacology, 1999, 7, 143-146.
Jevtovic-Todorovic et al., "A comparative evaluation of the neurotoxic properties of ketamine and nitrous oxide", Brain Res., 2001, 895, 264-267.
Jevtovic-Todorovic et al., "Ketamine potentiates cerebrocortical damage induced by the common anesthetic agent nitrous oxide in adults rats", Br. J. Pharmacol., 2000, 130, 1692-1698.
Jevtovic-Todorovic et al., "Isoflurane and Propofol Block Neurotoxicity Caused by MK-801 in the Rat Posterior Cingulate/Retrosplenial Cortex", Journal of Cerebral Blood Flow and Metabolism, 1997, 17,168-174.
Juven-Wetzler, "Alzbeta: Immediate ketamine treatment does not prevent posttraumatic stress responses in an animal model for PTSD", European Neuropsychopharmacology, 2014, 24(3), 469-479.
Kennedy et al., "Canadian Network for Mood and Anxiety Treatments (CAN MAT) 2016 Clinical Guidelines for the Management of Adults with Major Depressive Disorder: Section 3. Pharmacological Treatments", The Canadian Journal of Psychiatry, 2016, 61(9), 540-560.
Khan, "Has the rising placebo response impacted antidepressant clinical trail outcome? Data from the US Food and Drug Administration 1987-2013", World Psychiatry, 2017, 16(2), 181-192.
Lin et al., "Research progress of depression and the application of esketamine", Journal of Southern Medical University, Apr. 2016, vol. 37, No. 4, 567-569.
Loss, Brain Research, 2012, 1474, 110-117.
McIntyre et al., "Florida Best Practice Psychotherapeutic Medication Guidelines for Adults With Major Depressive Disorder", J. Clin. Psychiatry, Jun. 2017, 78:6, 703-713.
Montgomery, "A new depression scale designed to be sensitive to change", Br. J. Psychiatry, 1979, 134, 382-389.
Olney et al., "Pathological changes induced in cerebrocortical neurons by phencyclidine and related drugs", Science, 1989, 240, 1360-1362.
Papakostas, "L-methylfolate as adjunctive therapy for SSRI-resistant major depression: results of two randomized, double-blind, parallel-sequential trials", Am J. Psychiatry, 2012, 169(12), 1267-1274.
Paulekuhn, "Trends in Active Pharmaceutical Ingredient Salt Selection based on Analysis of the Orange Book Database", J Med. Chem., 2007, 50, 6665-6672.
Proescholdt, Brain Res., 2001, 904, 245-251.
Rodriquez et al., "Randomized Controlled Crossover Trial of Ketamine in Obsessive-Compulsive Disorder: Proof-of-Concept Rodriguez", Neuropsychopharmacology, 2013, 38(12), 2475-2483.
Rush et al., "The 16-item quick inventory of depressive symptomatology (QIDS), Clinician Rating (QIDS-C) and Self-Report (QIDS-SR): A psychometric evaluation in patients with chronic major depression", Biol. Psychiatry, 2003, 54(5), 573-583.
Rush, CNS Drugs, 2009, 23(8), 627-647.
Rush, et al., Massachusetts General Hospital Antidepressant Treatment Response Questionnaire; Rush, "The Inventory of Depressive Symptomatology (IDS): Psychometric Properties", Psychol. Med., 1996, 26(3), 477-486.
Rybin, "Placebo non-response measure in sequential parallel comparison design studies", Stat. Med., 2015, 34(15), 2281-2293.
Schoenenberg, Michael: Effects of peritraumatic ketamine medication on early and sustained posttraumatic stress symptoms in moderately injured accident victims; Germany Psychopharmacology (Berlin, Germany) (2005), 182 (3), 420-425.
Spitzer, JAMA, 1999, 282(18), 1737-1744.
Tamura, "An examination of the efficiency of the sequential parallel design in psychiatric clinical trials", Clin. Trials, 2007, 4(4), 309-317.
Tamura, "Estimation of treatment effect for the sequential parallel design", Stat. Med., 2011, 30(30), 3496-3506.

Trivedi et al., "The Inventory of Depressive Symptomatology, Clinical Rating (IDS-C) and Self-Report (IDS-SR) in public sector patients with mood disorders: a psychometric evaluation", Psychol. Med., 2004, 34(1), 73-82.
Willis, C.L., Ray, D.E., 2007. Antioxidants attenuate MK-801-induced cortical neurotoxicity in the rat. NeuroToxicology 28, 161-167.
Wilson, Pharmacology, Biochemistry and Behavior 81, 2005, 530-534.
Wozniak, Neurobiology of Disease, 1998, 5(5), 305-322.
Wozniak, Psychopharmacology, 1990, 101(1), 47-56.
Yazdi, Bijan; Comparison of additive oral Clonidine with Ketamine, on post-operative pain and hemodynamic in cataract extraction under topical anesthesia and sedation; Pharmaceutical and Biomedical Sciences (2015), 4(5), 37-42.
Zajackowski, Neurotox. Res., 2000,1(4), 299-310.
University of Alberta., Effects or Low-dose Ketamlne as an Adjunct to Propofol-based Anesthesia for Electroconvulsive Therapy, ClinicalTrials.gov, Oct. 19, 2015, Ketamine, NCT02579542.
University of Arizona., Intranasal Ketamine for Pediatric Procedural Sedation: a Feasibility Study, ClinicalTrials.gov, Mar. 1, 2017, Ketamine, NCT03067974.
University of British Columbia., Prehospital Analgaia With Intra-Nasal Ketamine (PAIN-K), ClinicalTrials.gov, Apr. 27, 2016, Ketamine, NCT02753114.
University of Calgary., Pre-hospital Care With Intra-Nasal Ketamine for Transport (PRECINKT): A Pilot Study (PRECINKT), ClinicalTrials.gov, Jan. 10, 2014, Ketamine, NCT02033434.
University of California, Davis, ED Treatment of Suicidal Patients With Ketamine Infusion, ClinicalTrials.gov, Apr. 18, 2018, Ketamine, NCT03502551.
University of California, Los Angeles., Biomarkers of Fast Acting Therapies in Major Depression, ClinicalTrials.gov, Jun. 17, 2014, Ketamine, NCT02165449.
University of Cincinnati., Emergency Ketamine Treatment of Suicidal Ideation, ClinicalTrials.gov, Jul. 8, 2014, Ketamine, NCT02183272.
University of Glasgow., Ketamine Hydrochloride and Best Pain Management in Treating Cancer Patients With Neuropathic Pain, ClinicalTrials.gov, Mar. 16, 2011, Ketamine, NCT01316744.
University of Iowa., Intranasal Ketamine Versus Intramuscular Ketamine for Procedural Sedation in Pediatlic Patients, ClinicalTrials.gov, Jul. 27, 2010, Ketamine, NCT01170247.
University of Manitoba, Hyperventilation Combined With Etomidate or Ketamine Anesthesia in ECT Treatment of Major Deprassion, ClinicalTrials.gov, Oct. 5, 2016, Ketamine, NCT02924090.
University of Massachusetts, Worcester., Memantine Augmentation of Antidepressants, ClinicalTrials.gov, Jun. 27, 2006, memantine, NCT00344682.
University of Michigan, Anesthesia and Functional Connectivity: An Analysis of fMRI Changes, ClinicalTrials.gov, Jul. 22, 2014, Anesthetics, NCT02196259.
University of Michigan, Relationship Between Postpartum Mood Disorders and Delivery Experience, ClinicalTrials.gov, Dec. 29, 2016, Postpartum Period, NCT03004872.
University of Minnesota . . . , Ketamine in Adolescents With Treatment-Resistant Depression, ClinicalTrials.gov, Mar. 5, 2014, Ketamine, NCT02078817.
University of Mississippi Medical Center., Ketamine: Its Effects on Suicidal Ideations and Inpatient Hospital Length of Stay, ClinicalTrials.gov, Dec. 20, 2016, Ketamine, NCT02997722.
University of Monastir., Ketamine Intra Nasal Traumatology (Ket), ClinicalTrials.gov, Jul. 28, 2017, Ketamine, NCT03233035.
University of New Mexico., Spreading Depolarization and Ketamine Suppression (SAKS), ClinicalTrials.gov, Jul. 17, 2015, Ketamine, NCT02501941.
University of Ottawa., Action of Ketamine in Treatment-Resistant Depression, ClinicalTrials.gov, Sep. 18, 2013, Ketamine, NCT01945047.
University of Padova., Ketamine in Bariatric Surgery, ClinicalTrials.gov, Nov. 12, 2012, Ketamine, NCT01724983.
University of Pennsylvania., Alternative Sedation During Bronchosoopy (DEX), ClinicalTrials.gov, Jul. 8, 2010, ketamine, NCT01158820.

(56) References Cited

OTHER PUBLICATIONS

University of Saskatchewan, Comparing Ketamine and Propofol Anesthesia for Electroconvulsive Therapy, ClinicalTrials.gov, Sep. 4, 2013, Ketamine, NCT01935115.
University of Saskatchewan., ECT With Ketamine Anesthesia vs High Intensity Ketamine With ECT Rescue for Treatment-Resistant Depression, ClinicalTrials.gov, Sep. 5, 2017, Ketamine, NCT03272698.
University of Saskatchewan., Efficacy of Opioid-free Anesthesia in Reducing Postoperative Respiratory Depression in Children Undergoing Tonsillectomy, ClinicalTrials.gov, Dec. 9, 2016, Ketamine, NCT02987985.
University of Tennessee Health Science Center., IN Ketamine Vs IN Midazolam and Fentanyl for Abscess I&D, ClinicalTrials.gov, Dec. 18, 2015, Ketamine, NCT02635282.
University of Turku, The Neural Mechanisms of Anesthesia and Human Consciousness (Part 6), ClinicalTrials.gov, Dec. 8, 2015, S-ketamine, NCT02624401.
University of Utah, Endogenous Opioid Modulation by Ketamine, ClinicalTrials.gov, Feb. 14, 2017, Ketamine, NCT03051945.
U.S. Appl. No. 16/956,403, filed Jun. 19, 2020.
U.S. Appl. No. 17/129,508, filed Dec. 21, 2020.
U.S. Appl. No. 16/727,594, Entitled "Methods for the Treatment of Depression", filed Dec. 26, 2019.
VA Connecticut Healthcare System., Open Label Ketamine Treatment for Major Depressive Disorder in Veterans (Ket-MOD), ClinicalTrials.gov, Feb. 15, 2017, Ketamine, NCT03053830.
VA Office of Research and Development, Efficacy of Repeated Ketamine Infusions for Treatment-resistant Depression, ClinicalTrials.gov, Feb. 10, 2015, Ketamine, NCT02360280.
VA Office of Research and Development, Ketamine for the Rapid Treatment of Major Depressive Disorder and Alcohol Use Disorder, ClinicalTrials.gov, Jun. 3, 2015, Ketamine, NCT02461927.
VA Office of Research and Development., ketamine for Treatment Resistant Lale-Life Depression, ClinicalTrials.gov, Sep. 22, 2015, ketamine, NCT02556606.
VA Puget Sound Health Care System., Ketamine Anesthesia for Improvement of Depression in ECT (KAID), ClinicalTrials.gov, Apr. 27, 2016, Ketamine, NCT02752724.
Valois., Unit-Dose Nasal Sprays:, Valois., 2004, pp. 1-2, Page Number.
Vann et al. Everyday Health Dec. 2, 2011 (8 pgs.).
Venancio, et al., Impaired Spatial Memory after Ketamine Administration in Chronic Low Doses, Current Neuropharmacology, 2011, pp. 251-255, vol. 9 Issue 1.
Vitiello, et al., Depressive Symptoms and Clinical Status during the Treatment of Adolescent Suicide Attempters Study (TASA), Am Acad Child Adolesc Psychiatry, 2009, pp. 997-1004, vol. 48 Issue 10.
Vollenweider et al., Differential psychopathology and patterns of cerebral glucose utilisation produced by (S)-and (R)-ketamine in healthy volunteers using positron emission tomography (PET), European Neuropsychopharmacology (1997) pp. 25-38, vol. 7.
Voort, et al., Continuation phase intravenous ketamine in adults with treatment-resistant depression, Journal of Affective Disorders, Sep. 12, 2016, pp. 300-304, vol. 206.
Vos, et al., Years lived with disability (YLDs)10r 1160 sequelae of 289 diseases and injuries 1990-2010: a systematic analysis for the Global Burden of Disease Study 2010, Lancet, Dec. 29, 2012, pp. 2163-2196, vol. 380.
Vranken et al, "iontophoretic administration of S(+)-ketamine in patients with intractable central pain: a placebo-controlled trial". Pain, 2005, 118(1-2), pp. 224-231.
Vranken, et al, Iontophoretic administration of S(C)-ketamine in patients with intractable central pain: A placebo-controlled trial, Pain, Aug. 15, 2005, pp. 224-231, vol. 118.
Vranken, et al., Neuropathological findings after continuous intrathecal administration of S(C)-ketamine for the management of neuropathic cancer pain, Pain, Jun. 13, 2005, pp. 231-235, vol. 117.

Wan, et al., Ketamine Safety and Tolerability in Clinical Trials for Treatment-Resistant Depression, J Clin Psychiatry, 2015, pp. 1-11, vol. 76 Issue 3.
Wang et al, "Effects of penetration enhancers on the permeability of ketarnine hydrochloride through an isolated rabbit's nasal mucosa", Journal of Shenyang Pharmaceutical University, 2004, Issue 5, pp. 321-323 & 340.
Wang, et al., Independent Telephone-based Assessment of Depressive Symptoms in China, Csp, 2018, pp. 1-1.
Wang, et al., NMDA/NR2B Selective Antagonists in the Treatment of Ischemic Brain Injury, Current Drug Targets—CNS & Neurological Disorders, 2005, pp. 143-151, vol. 4 Issue 2.
Washington et al., Determination of baseline human nasal pH and the effect of intranasally administered buffers, International Journal of Pharmaceutics 198:139-146, 2000.
Washington University School of Medicine, Cognitive Recovery After Electroconvulsive Therapy and General Anesthesia (RCC2), ClinicalTrials.gov, May 4, 2016, Ketamine, NCT02761330.
Marangell, et al., Effects of Intrathecal Thyrotropin-Releasing Hormone (protirelin) in Refractory Depressed Patients, Arch Gen Psychiatry, 1997, pp. 214-222, vol. 54.
Marhofer, P., et al, "S(+)-ketamine for caudal block in pediatric anesthesia". British Journal of Anaesthesia, 2000, vol. 84, No. 3, pp. 341-345.
Marije et al., "Safety and Efficacy of Repeated-Dose Intravenous Ketamine for Treatment-Resistant Depression", Biol Psychiatry, Aug. 2009, vol. 67, pp. 139-145, vol. 67.
Markus Kosel, Study of Depression-Ketamine-Brain Function, ClinicalTrials.gov, Jun. 3, 2010, Ketamine, NCT01135758.
Marlow, et al., Hernodynamic response to induction of anesthesia with ketamine/midazolam, Canadian Journal of Anaesthesia, May 28, 1991, pp. 844-848, vol. 38 Issue 7.
Massachusetis General Hospital, A Study of Brexpiprazole Plus Ketamine in Treatment-Resistant Depression (TRD), ClinicalTrials.gov, May 11, 2017, Ketamine, NCT03149991.
Massachusetis General Hospital, Double-Blind, Placebo-Controlled Trial of Ketamine Therapy in Treatment-Resistant Depression (TRD), ClinicalTrials.gov, Aug, 12, 2013, Ketamine, NCT01920555.
Massachusetis General Hospital, Intranasal Ketamine for Late-Life Depression and Suicidal Ideation, ClinicalTrials.gov, Nov. 20, 2014, Ketamine, NCT02295787.
Massachusetis General Hospital, Ketamine and Scopolamine Infusions for Treatment-resistant Major Depressive Disorder, ClinicalTrials.gov, Jun. 7, 2012, Ketamine, NCT01613820.
Massachusetis General Hospital, Ketamine Infusion for Treatment-resistant Major Depressive Disorder, ClinicalTrials.gov, Apr. 23, 2012, Ketamine, NCT01582945.
Massachusetis General Hospital, N-methyl-D-aspartate Antagonist (Ketamine) Augmentation of Electroconvulsive Treatment for Severe Major Depression, ClinicalTrials.gov, Dec. 15, 2010, Ketamine, NCT01260649.
Massachusetis General Hospital, The Impact of Ketamine on the Reward Circuitry of Suicidal Patients, ClinicalTrials.gov, Aug. 25, 2015, Ketamine, NCT02532153.
Massachusetis General Hospital., Ketamine Versus Placebo for Treatment Resistant Major Depressive Disorder, ClinicalTrials.gov, Aug. 17, 2012, Ketamine, NCT01667926.
Massachusetis General Hospital., Neurocognitive Features of Patients With Treatment-Resistant Depression, ClinicalTrials.gov, Apr. 28, 2017, Depression, NCT03134066.
Massachusetis General Hospital., Physiological and Cognitive Biomarkers for Ketamine's Antidepressant Effects, ClinicalTrials.gov, Jan. 29, 2016, Ketamine's, NCT02669043.
Massachusetts General Hospital., Ketamine for Depression: An MRI Study, ClinicalTrials.gov, Sep. 9, 2015, Ketamine, NCT02544607.
Mathew Sanjay J et al: "Ketamine for treatment-resistant unipolar depression: current evidence.", CNS Drugs Mar. 1, 2012, vol. 26, No. 3, Mar. 1, 2012, pp. 189-204.
Mathew, et al., Glutamate modulators as novel interventions for mood disorders Moduladores de glutamato como novas interven9oes em transtomos do humor, Rev Bras Psiquiatr, Jul. 15, 2005, pp. 243-248, vol. 27 Issue 3.

(56) References Cited

OTHER PUBLICATIONS

Mathew, et al., Riluzole for relapse prevention following intravenous ketamine in treatment-resistant depression: a pilot randomized, placebo controlled continuation trial, Int J Neuropsychopharmacol, 2010, pp. 1-19, vol. 13 Issue 1.
Mathew_et_al, Ketamine for Treatment-Resistant Unipolar Depression, CNS Drugs, 2012, pp. 189-204, vol. 26 Issue 3, Adis Data Information BV.
May, et al., Predicting future suicide attempts among depressed suicide ideators: A 10-year longitudinal study, Journal of Psychiatric Research, Apr. 5, 2012, pp. 946-952.
Mayo Clinic, The Bio-K Study: A Single-Arm, Open-Label, Biomarker Development Clinical Trial of Ketamine for Non-Psychotic Unipolar Major Depression and Bipolar I or II Depression. (Bio-K), ClinicalTrials.gov, May 17, 2017, Ketamine, NCT03156504.
Mayo Clinic., Glutamate MRS During Ketamine Infusion, ClinicalTrials. gov, Jun. 29, 2018, Ketamine, NCT03573349.
Mayo Clinic., Ketamine Anesthesia in Electroconvulsive Therapy, ClinicalTrials.gov, Jun. 6, 2011, Ketamine, NCT01367119.
Mayo Clinic., Ketamine for Depression and Suicide Risk (Ketamine), ClinicalTrials.gov, Mar. 24, 2014, Ketamine, NCT02094898.
Mayo Clinic., Oral Ketamine in the Treatment of Depression and Anxiety in Patients With Cancer, ClinicalTrials.gov, Sep. 7, 2012, Ketamine, NCT01680172.
McClean, et al., Ketamine concentrations during cardio-pulmonary bypass, Canadian Journal of Anaesthesia, Jan. 31, 1996, pp. 580-584, vol. 43 Issue 6.
McGhee, et al., The Correlation Between Ketamine and Post-traumatic Stress Disorder in Burned Service Members, The Journal of Trauma, Oct. 31, 2007, pp. S195-8199, vol. 64 Issue 2.
McGirr, et al., A systematic review and meta-analysis of randomized, double-blind, placebo-controlled trails of ketamine in the rapid treatment of major depressive episodes, Psychological Medicine, 2015, pp. 693-704, vol. 42.
McLean Hospital., A Trial of Intranasal Ketamine for the Treatment of Obsessive-Compulsive Disorder, ClinicalTrials.gov, Sep. 9, 2014, Ketamine, NCT02234011.
Medical University of Graz., The Preemptive Analgetic Potency of Low Dose S-Ketamine (Miniket), ClinicalTrials.gov, Dec. 1, 2009, S-Ketamine, NCT01022840.
Medical University of Vienna., Investigation of Antidepressant Efficacy of Oral Ketamine Treatment, ClinicalTrials.gov, Dec. 14, 2016, Ketamine, NCT02992496.
Medical University of Vienna., Network Dysfunction, Schizophrenia and Pharmacological Magnetic Resonance Imaging (phMRI), ClinicalTrials.gov, Jul. 14, 2011, Esketamine, NCT01394757.
Medical University of Vienna., Positron Emission Tomography Assessment of Ketamine Binding of the Serotonin Transporter, ClinicalTrials.gov, Mar. 23, 2016, Ketamine, NCT02717052.
Mellon, et al., Blockade of NMDA Receptors and Apoptotic Neurodegeneration in the Developing Brain, Science, Mar. 10, 2011, pp. 70-74, vol. 283.
Mellon, et al., Use of Anesthetic Agents in Neonates and Young Children, Anesth Analg, 2007, pp. 509-520, vol. 104.
Mental Health Serv Admin., Results From the 2013 National Survey on Drug Use and Health: Mental Health Detailed Tables, Mental Health Sery Admin, Nov. 14, 2014, pp. 1-577.
Messer, et al., The Use of a Series of Ketamine Infusions in Two Patients With Treatment-Resistant Depression, J Neuropsychiatry Clin Neurosci, 2010, pp. 442-444, vol. 22 Issue 4.
Meuronen, MD., "Intranasal Esketamine and Fentanyl for Pain in Minor Trauma", ClinicalTrials.gov, Feb. 5, 2018, Esketamine, NCT03421275.
Meyer, et al., Suicidality and Risk of Suicide-Definition, Drug Safety Concerns, and a Necessary Target for Drug Development: A brief Report, J Clin Psychiatry, Jul. 13, 2010, pp. e1-e7.
Millennium Pharmaceuticals, Inc.., Efficacy and Safety of TAK-653 in Treatment-Resistant Depression, ClinicalTrials.gov, Oct. 18, 2017, TAK-653, NCT03312894.

Minneapolis Veterans Affairs Medical Center., Ketamine Infusions for PTSD and Treatment-Resistant Depression, ClinicalTrials.gov, Oct. 16, 2015, Ketamine, NCT02577250.
Moaddel, et al., D-serine plasma concentration is a potential biomarker of (R,S)-ketamine antidepressant response in subjects with treatment-resistant depression, Psychopharmacology, Jul. 24, 2014, pp. 399-409, vol. 232.
Moharil, et al., Nasal Dosage Forms and Devices for Intranasal Drug Delivery, World Journal of Pharmacy and Pharmaceutical Sciences, Apr. 5, 2014, pp. 554-571, vol. 3 Issue 4.
Molero, et al., Antidepressant Efficacy and Tolerability of Ketamine and Esketamine: A Critical Review, CNS Drugs, May 7, 2018, pp. 411-420, vol. 32.
Moore, et al., A comparison between propofol and thiopentone as induction agents in obstetric anesthesia, Anaesthesia, Feb. 27, 1989, pp. 753-757, vol. 44.
Moran, et al., The natural history of self-harm from adolescence to young adulthood: a population-based cohort study, Lancet, Nov. 17, 2011, pp. 236-243, vol. 379.
Morrison, Effect of intranasal esketamine on cognitive functioning in healthy participants: a randomized, double-blind, placebo-controlled study, Psychopharmacology, Feb. 1, 2018, pp. 1107-1119, vol. 235.
Moryl, et al., Potential Antidepressive Properties of Amantadine, Memantine and Bifemelane, Pharmacology & Toxicology, Feb. 3, 1993, pp. 394-397, vol. 72.
Mundt, et al., Risk of Prospective Suicidal Behavior Reports among Psychiatric and non-Psychiatric Patients using Lifetime Reports at Baseline, Healthcare Technology Systems, Feb. 19, 2013, pp. 1-1, Poster.
Barbe, et al., Suicidality and Its Relationship to Treatment Outcome in Depressed Adolescents, Suicide and Life-Threatening Behavior, Aug. 15, 2003, pp. 44-55, vol. 34 Issue 1.
Bartova, et al., Combination of intravenous S-ketamine and oral tranylcypromine in treatment-resistant depression: A report of two cases, European Neuropsychopharmacology, Jul. 28, 2015, pp. 2183-2184, vol. 25.
Bartova, et al., Intravenous Administration of S-ketamine in a Severely Depressed Treatment-resistant Patient Receiving Tranylcypromine: a Case Report, Eur. Psychiat, 2015, Issue S1, Abstracts of the 23rd European Congress of Psychiatry, pp. 1-1.
Baylor College of Medicine., Optimization of IV Ketamine for Treatment Resistant Depression, ClinicalTrials.gov, Oct. 8, 2008, Ketamine, NCT00768430.
Baylor College of Medicine., Research Study for Major Depressive Disorder: Investigation of Glutamate Medications, ClinicalTrials. gov, Jan. 5, 2007, ketamine, NCT00419003.
Beardslee, et al., A Family-Based Approach to the Prevention of Depressive Symptoms in Children at Risk: Evidence of Parental and Child Change, Pediatrics, 2003, pp. e119-e131, vol. 112 Issue 2.
Beck, et al., Assessment of Depression : The Depression Inventory, Psychological Measurements in Psychopharmacology. Mod. Probl. Pharmacopsychait., 1974, pp. 151-169, vol. 7.
Beck, et al., Assessment of Suicidal Intention: The Scale for Suicide Ideation, Journal of Consulting and Clinical Psychology, 1979, pp. 343-352, vol. 47 Issue 2.
Beck, et al., Scale for Suicide Ideation: Psychometric Properties of a Self-Report Version, Journal of Clinical Psychology, 1988, pp. 499-505, vol. 44 Issue 4.
Begec et al: Rev Bras Anestesiol, The antimicrobial effects of ketamine combined with propofol: An in vitro study, 2013, 63(6): 461-465.
Beijing Tiantan Hospital, Ketamine and Postoperative Depressive Symptom, ClinicalTrials.gov, Mar. 22, 2017, Ketamine, NCT03086148.
Bently et al. Med. Clin N Am. 98, 981-1005 (2014).
Berlim, et al., Definition, Assessment, and staging of Treatment-Resistant Refractory Major Depression: A Review of Current Concepts and Methods, Can J Psychiatry, 2007, pp. 46-54, vol. 52 Issue 1.
Berman, et al., "Antidepressant Effects of Ketamine in Depressed Patients", Biol Psychiatry, Aug. 12, 2000, 351-354, vol. 47.
Berman, et al., The Efficacy and Safety of Aripiprazole as Adjunctive Therapy in Major Depressive Disorder: A Multicenter, Ran-

(56) References Cited

OTHER PUBLICATIONS domized, Double-Blind, Placebo-Controlled Study, J Clin Psychiatry, 2007, pp. 843-853, vol. 68 Issue 6.

Bertolote, et al., Aglobal perspective on the mangnitude of suicide mortality, British Library, 2009, pp. 91-98, Chapter 14.

Bertolote, et al., Suicide attempts, plans, and ideation in culturally diverse sites: the WHO Supre-Miss community survey, Psychological Medicine, 2005, pp. 1457-1465, vol. 35.

Best., Combined ketamine and transcranial magnetic stimulation for treatment resistant depression in the context of chronic OCD: a case report, Devore Best Neuropsychiatric Electrophysiology, 2015, pp. 1-4, vol. 1 Issue 2.

Bickley, et al., Suicide Within Two Weeks of Discharge From Psychiatric Inpatient Care: A Case-Control Study, Psychiatric Services in Advance, Apr. 1, 2013, pp. 653-659.

Birmaher, et al., Childhood and Adolescent Depression: A Review of the Past 10 Years. Part I, J. Am. Acad. Child Adolesc. Psychiatry, Jan. 4, 1996, pp. 1427-1439, vol. 35 Issue 11.

Birmaher, et al., Clinical Presentation and Course of Depression in Youth: Does Onset in Childhood Differ From Onset in Adolescence? ,. Am. Acad. Child Adolesc. Psychiatry, Aug. 23, 2003, pp. 63-70, vol. 43 Issue 1.

Birmaher, et al., Course and outcome of child and adolescent major depressive disorder, Child Adolesc Psychiatric Clin N Am, 2002, pp. 619-637, vol. 11.

Birmaher, et al., Practice Parameter for the Assessment and Treatment of Children and Adolescents With Depressive Disorders, J. Am. Acad. Child Adolesc. Psychiatry, 2007, pp. 1503-1526, vol. 46 Issue 11.

Birmaher, et al., Randomized, Controlled Trail of Amitriptyline Versus Placebo for Adolescents With "Treatment-Resistant" Major Depression, J.Am. Acad. Child Adolesc. Psychiatry, Nov. 26, 1998, pp. 527-535, vol. 37 Issue 5.

Birmaher, et al., Summary of the Practice Parameters for the Assessment and Treatment of Children and Adolescents With Depressive Disorders, J. Am. Acad. Child Adolesc. Psychiatry, 1998, pp. 1234-1238, vol. 37 Issue 11.

Bitter, Christoph: Transmucosal Nasal Drug Delivery: Pharmacokinetics and Pharmacodynamics of Nasally Applied Esketamine, Inaugural dissertation, zurErlangung der Würde eines Doktors der Philosophie vorgelegt der Philosophisch-Naturwissenschaftlichen Fakultät der Universität Basel 2011, 1-208.

Bjorkhem, et al., Clearance of Fentanyl, Alfentanil, Methohexitone, Thiopentone and Ketamine in Relation to Estimated Hepatic Blood Flow in Several Animal Species: Application to Prediction of Clearance in Man, J. Pharm. Pharmacol., Apr. 20, 2000, pp. 1065-1074, vol. 52.

Bjorkhem-Bergman, et al., Comparison of Endogenous 4b-Hydroxycholesterol with Midazolam as Markers for CYP3A4 Induction by Rifampicin, Drug Metabolism and Disposition, May 14, 2013, pp. 1488-1493, vol. 41.

Blakemore., The social brain in adolescence, Nature Reviews! Neuroscience, 2008, pp. 267-277, vol. 9.

Blier Pierre, Aripiprazole in the Treatment of Delusional Parasitosis With Ocular and Dermatologic Presentations, Journal of Clinical Psychopharmacology, 2013, pp. 271-272, vol. 33 Issue 2.

Blier, et al., On the Safety and Benefits of Repeated Intravenous Injections of Ketamine for Depression, Biol Psychiatry, 2012, pp. e11-e12, vol. 72.

Bodin, et al., Antiepileptic Drugs Increase Plasma Levels of 4-Hydroxycholesterol in Humans, J. Biol. Chem., Oct. 19, 2001, pp. 38685-38689, vol. 276 Issue 42.

Bolshakov, et al., Determinants of trapping block of N-methyl-D-aspartate receptor channels, Journal of Neurochemistry, Jun. 6, 2003, pp. 56-65, vol. 87.

Bolze, et al., HPLC determination of ketamine, norketamine, and dehydronorketamine in plasma with a high-purity reversed-phase sorbent, Clinical Chemistry, Nov. 13, 19997, pp. 560-564, vol. 44 Issue 3.

Bonanno, et al., Ketamine in war/tropical surgery (a final tribute to the racemic mixture), Injury International Journal of the Care of the Injured, 2002, pp. 323-327, vol. 33.

Bongiovi-Garcia, et al., Comparison of clinical and research assessments of diagnosis. Suicide attempt history and suicidal ideation in major depression, Journal of Affective Disorders, Sep. 23, 2008, pp. 183-188, vol. 115.

Bonnet, M.D., Long-Term Ketamine Self-Injections in Major Depressive Disorder: Focus on Tolerance in Ketamine's Antidepressant Response and the Development of Ketamine Addiction, Journal of Psychoactive Drugs, 2015, pp. 276-285, vol. 47 Issue 4.

Borges, et al., Risk factors for twelve-month suicide attempts in the National Comorbidity Survey Replication (NCS-R), Psychol Med, 2006, pp. 1747-1757, vol. 36 Issue 12.

Borges, et al., Twelve-Month Prevalence of and Risk Factors for Suicide Attempts in the World Health Organization World Mental Health Surveys, J Clin Psychiatry, Jul. 10, 2009, pp. 1617-1628, vol. 71 Issue 12.

Botieron, et al, Refractory Depression in Children and Adolescents, Depression and Anxiety, Jul. 28, 1997, pp. 212-223, vol. 5.

Bovill, et al., Alterations in Response to Somatic Pain Associated With Anaesthesia, British Journal of Anaesthesia, 1971, pp. 496-499, vol. 43.

Bowdle, et al., Psychedelic Effects of Ketamine in Healthy Volunteers Relationship to Steady-State Plasma Concentrations, Anesthesiology, 1998, pp. 82-88, vol. 88 Issue 1.

Boyer, et al., Chronic Administration of Imipramine and citalopram Alters the Expression of NMDA Receptor Subunit mRNAs in Mouse Brain, Journal of Molecular Neuroscience, Apr. 9, 1988, pp. 219-233, vol. 10.

Braincells Inc., A Multiple Ascending Dose Study of BCI-838 in Healthy Volunteers, ClinicalTrials.gov, Mar. 2, 2012, BCI-838, NCT01548703.

Braincells Inc.., A Study of BCI-838 and Several BCI-632 Prodrugs in Healthy Volunteers, ClinicalTrials.gov, Mar. 7, 2012, BCI-838, NCT01546051.

Braun, et al, Ketamine induces apoptosis via the mitochondrial pathway in human lymphocytes and neuronal cells, British Journal of Anaesthesia, Apr. 26, 2010, pp. 347-354, vol. 3.

Breakthrough Therapy Design, One Hundred Twelfth Congress of the United States of America at the Second Session, Breakthrough Therapy Design, 2012, pp. S.3187-2-S.3187-140.

Brent, et al., Association of FKBP5 Polymorphisms With Suicidal Events in the Treatment of Resistant Depression in Adolescents (TORDIA) Study, Am J Psychiatry, 2010, pp. 190-197, vol. 167 Issue 2.

Brent, et al., Switching to Another SSRI or to Venlafaxine With or Without Cognitive Behavioral Therapy for Adolescents With SSRI-Resistant Depression The TORDIA Randomized Controlled Trial, JAMA, Feb. 27, 2008, pp. 901-913, vol. 299 Issue 8.

Brent, et al., The Treatment of Adolescent Suicide Attempters Study (TASA): Predictors of Suicidal Events in an Open Treatment Trial, J. Am. Acad. Child Adolesc. Psychiatry, 2009, pp. 987-996, vol. 48 Issue 10.

Straiko, et al., Lithium Protects Against Anesthesia-Induced Developmental Neuroapoptosis, Anesthesiology, 2009, pp. 862-868, vol. 110 Issue 4.

Stucki et al, "Development of ready-to-use ketamine hydrochloride syringes for safe use in post-operative pain", European Journal of Hospital Pharmacy, 2008, vol. 14, Issue 1, pp. 14-18.

Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (Synapse); Submitted Dale: Feb. 14, 2014 (v2).

Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (Synapse); Submitted Dale: Mar. 18, 2014 (v3).

Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (Synapse); Submitted Dale: Nov. 25, 2013 (v1).

(56) References Cited

OTHER PUBLICATIONS

Su, et al., Dose-Related Effects of Adjunctive Ketamine in Taiwanese Patients with Treatment-Resistant Depression, Neuropsychopharmacology, May 11, 2017, pp. 2482-2492, vol. 42.
Sunnybrook Health Sciences Centre, Effect of Ketamine vs. Active Placebo on Suicidal Ideation in Depressed Inpatients With Major Depressive Disorder or Bipolar Depression., ClinicalTrials.gov, Nov. 2, 2015, Ketamine, NCT02593643.
Szymkowicz, et al., A 12-month naturalistic observation of three patients receiving repeat intravenous ketamine infusions for their treatment resistant depression, J Affect Disord, 2013, pp. 1416-1420, vol. 147.
Tagum, "Redefining affective disorders: relevance for drug Development", CNS Neurosci. ther., 2008, 14(1), 2-9.
Tampere University Hospital., Inhaled Nebulised S(+)-Ketamine for Postoperative Analgesia, ClinicalTrials. gov, Mar. 24, 2015, Ketamine, NCT02397356.
Tamura, "Estimation of treatment effect for the sequential parallel design", Stal. Med., 2011, 30(30), 3496-3506.
Tansey et al., Contribution of Common Genetic Variants to Antidepressant Response, Biol Psychiatry, 2013, pp. 679-682, 73.
TC Erciyes University, Intranasal Dexmedetomidine vs Midazolam-ketamine Combination for Premedication of Pediatric Patients, ClinicalTrials.gov, Feb. 26, 2014, ketamine, NCT02072083.
Technische Universitat Monchen, Anesthetics and Auditory, Visceral, and Heat Evoked Potentials, ClinicalTrials.gov, Sep. 26, 2007, S-Ketamine, NCT00534586.
Tel Aviv Medical Center., Intranasal Ketamine for Acute Traumatic Pain, ClinicalTrials.gov, Jun. 29, 2016, Ketamine, NCT02817477.
Tel-Aviv Sourasky Medical Center., Oral Ketamine for Suicidal Ideation, ClinicalTrials.gov, Jan. 16, 2014, Ketamine, NCT02037503.
Thase, et al., Remission Rates Following Antidepressant Therapy With Bupropion or Selective Serotonin Reuptake Inhibitors: A Meta-Analysis of Original Data From 7 Randomized Controlled Trials, J Clin Psychiatry, 2005, pp. 974-981, vol. 66 Issue 8.
Thase, et al., When at First You Dont Succeed: Sequential Strategies for Antidepressant Nonresponders, J Clin Psychiatry, 1997, pp. 23-29, vol. 58 Supplement 13.
The Cleveland Clinic, Elekt-D: Electroconvulsive Therapy (ECT) vs. Ketamine in Patients With Treatment Resistant Depression (TRD) (Elekt-D), ClinicalTrials.gov, Apr. 14, 2017, Ketamine, NCT03113968.
The Cleveland Clinic., Administration of Subanesthetic Dose of Ketamine and Electroconvulsive Treatment for Treatment Resistant Depression, ClinicalTrials.gov, Aug. 13, 2015, Ketamine, NCT02522377.
The Neuroscience Center, LLC., Neuromodulation to Facilitate the Effect of Ketamine (TMS/ketamine), ClinicalTrials.gov, Mar. 22, 2013, Ketamine, NCT01816958.
The University of New South Wales, A Study of Ketamine as an Antidepressant, ClinicalTrials.gov, Sep. 27, 2011, Ketamine, NCT01441505.
The University of New South Wales., Ketamine Trial for the Treatment of Depression, ClinicalTrials.gov, Mar. 27, 2015, Ketamine, NCT02401139.
The University of Texas Health Science Center at San Antonio., Effects of Low Dose Ketamine Given at Induction of Anesthesia on Postoperative Mood in Patients With Depressive Symptoms, ClinicalTrials.gov, Apr. 21, 2015, Ketamine, NCT02422303.
The University of Texas Health Science Center, Houston, Trial of the Rapid Antisuicidal Effects of Intranasal Ketamine in Comorbid Depression and Alcohol Abuse, ClinicalTrials.gov, May 28, 2018, Ketamine, NCT03539887.
The University of Texas Health Science Center, Houston., Low Dose Intravenous ketamine in Treatment Resistant Depression Patients (ketamine), ClinicalTrials.gov, Oct. 17, 2016, ketamine, NCT02935595.
The University of Texas Health Science Center, Houston., The UTHealth Ketamine Project, ClinicalTrials.gov, Aug. 30, 2016, Ketamine, NCT02882711.
Torjesen, "Ketamine helps a third of patients with treatment resistant depression, finds small UK study", BMJ, Apr. 3, 2014, pp. 92576-92576, vol. 348.
Trevithick, et al., Study protocol for the randomised controlled trial: Ketamine augmentation of ECT to improve outcomes in depression (Ketamine-ECT study), BMC Psychiatry, 2015, pp. 1-11, vol. 15 Issue 257.
Trivedi, et al., Evaluation of Outcomes With Citalopram for Depression Using Measurement-Based Care in Star*D Implications for Clinical Practice, Am J Psychiatry, 2006, pp. 28-40, vol. 163 Issue 1.
Trottier., Pain Free Laceration Repairs Using Intra-nasal Ketamine, ClinicalTrials.gov, Feb. 15, 2017, Ketamine, NCT03053947.
Trullas, et al., Functional antagonists at the NMDA receptor complex exhibit antidepressant actions, European Journal of Pharmacology, May 29, 1990, pp. 1-10, vol. 185.
Turku University Hospital, Dose-response of Ketamine in Patient Controlled Analgesia in Orthopedic Surgery Patients (DoseRespKeta). ClinicalTrials.gov, Dec. 15, 2016, S-Ketamine, NCT02994173.
Udo Bonnet, M.D., Long-Term Ketamine Self-Injections in Major Depressive Disorder: Focus on Tolerance in Ketamine's Antidepressant Response and the Development of Ketamine Addiction, Journal of Psychoactive Drugs, 2015, pp. 276-285, vol. 47 Issue 4.
UN Convention_Psychotropic Substances, Convention on Psychotropic Substance, UN Convention_Psychotropic Substances, 1971, pp. 1-28.
UN Economic Social Council., Changes in the scope of control of substances Note by the Secretariat, UN Economic Social Council, Dec. 16, 2014, pp. 1-15.
United States Naval Medical Center, San Diego., A Study to Decrease Suicidal Thinking Using Ketamine, ClinicalTrials.gov, Apr. 16, 2015, Ketamine, NCT02418702.
Universidade Federal De Goias., Intranasal Sedation With Dexmedetomidine and Ketamine in Pediatric Dentistry (NASO II), ClinicalTrials.gov, Sep. 25, 2017, Ketamine, NCT03290625.
University Health Network, Toronto., Study of Ketamine for Depression in Cancer Patients Receiving Palliative Care, ClinicalTrials. gov, Jan. 25, 2018, Ketamine, NCT03410446.
University Hospital, Basel, Switzerland., Comparison of Oral Morphine Versus Nasal Ketamine Spray With Chitosan in Cancer Pain Outpatients (Onkemi), ClinicatTrials.gov, Oct. 29, 2015, ketamine, NCT02591017.
University Hospital, Basel, Switzerland., Pharmacokinetics and Pharmacodynamics of Nasally Applied Esketamine, ClinicalTrials. gov, Feb. 19, 2009, Esketamine, NCT00847418.
University Hospital, Basel, Switzerland., The Analgesic Effect of Combined Treatment With Intranasal S-ketamine and Intranasal Midazolam (Naskemi), ClinicalTrials.gov, Jan. 12, 2011, S-ketamine, NCT01275547.
University Hospital, Clermont-Ferrand., Ketamine and Neuropathic Pain (Ketapain), ClinicalTrials.gov, Jun. 10, 2015, Ketamine, NCT02467517.
University Hospital, Grenoble, Estimate the Efficiency of the Association of an Injection of Ketamine and the Venlafaxine in the Severe Major Depressive Disorder for Six Weeks (KETADEP), ClinicalTrials.gov, Mar. 19, 2012, Ketamine, NCT01557712.
University Hospital, Lille., Evaluation of the Initial Prescription of Ketamine and Milnacipran for Depression in Palliative Care (Ketapal), ClinicalTrials.gov, May 26, 2016, Ketamine, NCT02783430.
University Hospital, Montpellier., Intranasal Midazolam Versus Intranasal Ketamine to Sedate Newborns for Intubation in Delivery Room, ClinicalTrials.gov, Jan. 25, 2012, Ketamine, NCT01517828.
University of Aarhus, Sensory Examination and Pharmacological Modulation of Oral Hyperexcitability in Patients With Atypical Odontalgia and Matched Healthy Controls, ClinicalTrials.gov, Jun. 21, 2005, S-ketamine, NCT00115102.
University of Aberdeen, The Use of Ketamine as an Anaesthetic During Electroconvulsive Therapy (Kanect), ClinicalTrials.gov, Mar. 2, 2011, Ketamine, NCT01306760.
University of Alabama at Birmingham, Treatment of Suicidal Ideation With Intravenous Ketamine Infusion, ClinicalTrials.gov, Jun. 27, 2013, Ketamine, NCT01887990.

(56) References Cited

OTHER PUBLICATIONS

University of Alabama at Birmingham., miRNAs, Suicide, and Ketamine—Plasma Exosomal microRNAs as Novel Biomarkers for Suicidality and Treatment Outcome, ClinicalTrials.gov, Apr. 16, 2015, Ketamine, NCT02418195.
European Medicines Agency Inspections (EMEA); Guideline on Excipients in the Dossier for Application for Marketing Authorisation of a Medicinal Product; London, Jun. 19, 2007, Doc. Ref. EMEA/CHMP/QWP/396951/2006; 12 pages.
European Pharmacopoeia—7th Edition; Published Jul. 15, 2010; 11 pages.
Fan, et al., "Ketamine rapidly relieves acute suicidal ideation in cancer patients: a randomized controlled clinical trial", Oncotarget, Dec. 1, 2017, pp. 2356-2360, vol. 8 Issue 2.
Fan, et al., Profiling the psychotic, depressive and anxiety symptoms in chronic ketamine users, Psychiatry Research, Jan. 14, 2016, pp. 311-315, vol. 237.
Fastner, et al., Intravenous S-Ketamine Does Not Inhibit Alveolar Fluid Clearance in a Septic Rat Model, PLOS ONE, Nov. 11, 2014, 2112622, vol. 9 Issue 11.
Fava, "The problem of the placebo response in clinical trials for psychiatric disorders: culprits, possible remedies, and a novel study design approach", Psycholher. Psychosom, 2003, 72(3), 115-127.
Fava., Diagnosis and Definition of Treatment-Resistant Depression, Biol Psychiatry, Feb. 21, 2003, pp. 649-659, vol. 53.
FDA Anesthetic and Life Support Drugs Advisory Committee (ALSDAC), Center for Drug Evaluation and Research, Silver Springs, MD, Mar. 10, 2011. "Ketamine and the Neonatal Brain: Rat Pups vs. Babies." On FDA website in archives Guest Presentation Mar. 10, 2011 pp. 1-76.
FDA., "Drugs@FDA Glossary of Terms." fda.gov, Retrived at https://www.fda.gov/drugs/drug-approvals-and-databases/drugsfda-glossary-terms#:~:text=A%20Reference%20Listed%20Drug%20(RLD,New%20Drug%20Application%20(ANDA), Nov. 14, 2017, pp. 8.
FDA., "What's in a REMS?." fda.gov, Retrived at https://www.fda.gov/drugs/risk-evaluation-and-mitigation-strategies-rems/whats-rems, Jan. 26, 2018, pp. 4.
Feifel, et al., Low-dose ketamine for treatment resistant depression in an academic clinical practice setting, Journal of Affective Disorders, Jun. 20, 2017, pp. 283-288, vol. 221.
First Affiliated Hospital of Chongqing Medical University., Effect of Subanesthetic Dose of Ketamine Combined With Propofol on Cognitive Function in Depressive Patients Undergoing Electroconvulsive Therapy, ClinicalTrials.gov, Dec. 2, 2014, ketamine, NCT02305394.
Fix, A.S., Hom, J.W., Wightman, K.A., Johnson, C.A., Long, G.G., Storts, R.W., Farber, N., Wozniak, D.F., Olney, J.W., 1993. Neuronal Vacuolization and Necrosis Induced by the Noncompetitive N-methyl-d-aspartate (NMDA) Antagonist MK(+)801 (Dizocilpine Maleate): A Light and Electron Microscopic Evaluation of the Rat Retrosplenial Cortex. Exp. Neurol. 123, 204-215.
Fondation Lenval., Intranasal Ketamine and Fracture Reduction in Pediatric Emergencies (Ketaped) (Ketaped), ClinicalTrials.gov, May 16, 2018, Ketamine, NCT03525821.
Ford, et al., Benzodiazepines may reduce the effectiveness of ketamine in the treatment of depression, Australian & New Zealand Journal of Psychiatry, 2015, 49(12):1227.
Frank, et al., Conceptualization and Rationale for Consensus Definitions of Terms in Major Depressive Disorder, Arch Gen Psychiatry, 1991, pp. 851-855, vol. 48.
Friedberg, et al., Hypnosis First, Then Dissociation, Anesth Analg, 2003, pp. 913-914, vol. 96.
Galvez, et al., "Long-Lasting Effects of a Single Subcutaneous Dose of Ketamine for Treating Melancholic Depression: A Case Report", Biol Psychiatry, 2014, pp. e1-e2, vol. 76.
Galvez, et al., Repeated intranasal Ketamine for treatment-resistant depression—the way to go? Results from a pilot randomised controlled trail, Journal of Psychopharmacology, 2018, pp. 1-11.
Galveza, et al., Long-Lasting Effects of a Single Subcutaneous Dose of Ketamine for Treating Melancholic Depression: A Case Report, Biol Psychiatry, 2014, pp. e1-e2, vol. 76.
Garcia, et al., Olfactory deposition of inhaled nanoparticles in humans, Inhalation Toxicology, Jul. 21, 2015, pp. 394-403, vol. 27 Issue 8.
Genbank_AC099753, *Homo sapiens* chromosome 3 clone RP11-466A13, complete sequence. Mar. 20, 2002, [online]. [Retrieved on Oct. 1, 2015]. Retrieved from the Internet: <URL: http://www.ncbi.nlm.nih.gov/nuccore/19551144/> PDF file: p. 1-40.
Gennaro, Alfonso: Remington: The Science and Practice of Pharmacy, 20th ed., 2000, pp. 1042-1047.
George, et al., Pilot Randomized Controlled Trial of Titrated Subcutaneous Ketamine in Older Patients with Treatment-Resistant Depression, Am J Gerialr Psychiatry, 2017, pp. 1-11.
George, Is There Really Nothing New Under the Sun? Is Low-Dose Ketamine a Fast-Acting Antidepressant Simply Because It Is an Opioid?, ajp.psychiatryonline.org, Jul. 10, 2018, pp. 1-2.
Ghasemi, et al., "Rapid antidepressant effects of repeated doses of ketamine compared with electroconvulsive therapy in hospitalized patients with major depressive disorder", Psychiatry Research, Dec. 13, 2014, vol. 215, 355-361.
Gizurarson, Acta Pharm. Nord., 1990, 2(2), 105-122.
Gliatio, et al., Evaluation and Treatment of Patients with Suicidal Ideation, American Family Physician, Mar. 15, 1999, pp. 1500-1506, vol. 59 Issue 6.
Glue, et al: Dose- and Exposure-Response to Ketamine in Depression, Biol Psychiatry 2011; 70: e9-e10.
Gocmen et al., In Vitro Investigation of the Antibacterial Effect of Ketamine; Upsala J Med Sci 113 (1) 2008: pp. 39-46.
Gomes et al., Neurotoxicity of Subarachnoid Preservative-Free S (+)-Ketamine in Dogs, Pain Physician, 14:83-90, 2011.
Gonzalo, Brain-Derived Neurotrophic FAct5or Val66Met Polymorphism and Antidepressant Efficacy of Ketamine in Depressed Patents, Biol Psychiatry, Dec. 1, 2012,vol. 72, NR:11, pp. 1-4 (E27-E28)/.
Gosek, et al., Effectiveness of ketamine in depressed patients resistant to ECT or rTMS therapy, Psychiatr. Pol, 2014, pp. 49-58, vol. 48 Issue 1.
Gregory K. Brown, Ph.D., "A review of suicide assessment measures for intervention research with adults and older adults", National Institute of Mental Health, 2000, pp. 1-57.
Guangzhou Women and Children's Medical Center., Intranasal Ketamine With Dexmedetomidine for the Treatment of Children With Autism Spectrum Disorder, ClinicalTrials.gov, Feb. 15, 2018, Ketamine, NCT03434366.
Gurnan, et al., Role of Ketamine in Severe Depression with suicidal ideation—Insights from a Case Study, Asian Journal of Psychiatry, Apr. 12, 2017, pp. 112-113, vol. 29.
Gutzke, et al., Cardiac Transplantation: A Prospective Comparison of Ketamine and sufentanil for Anesthetic Induction, Journal of Cardiothoracic Anesthesia, 1989, pp. 389-395, vol. 3 Issue 4.
Hamilton, Hamilton Depression Rating Scale (Ham-D), M. Journal of Neurology, Neurosurgery, and Psychiatry, 1960, pp. 56-62, vol. 23.
Hamilton, Ketamine, a Promising Depression Treatment, Seems to Act Like an Opioid www.npr.org, Aug. 29, 2018, pp. 1-8.
Harihar, et al., Intramuscular ketamine in acute depression: A report on two cases, Indian Journal of Psychiatry, 2013, pp. 186-188, vol. 55 Issue 2.
Hassamal, et al., Augmentation Therapy With Serial Intravenous Ketamine Over 18 Months in a Patient With Treatment Resistant Depression, Clin Neuropharm, 2015, pp. 212-216, vol. 38 Issue 5.
Healthcare Quality Report., Highlights From the 2012 National Healthcare Quality and Disparities Reports, Healthcare Quality Report, 2013, pp. 1-212, AHRQ Publication No. 13-0002.
Hedlund, et al., The Hamilton Rating Scale for Depression A Comprehensive Review, Journal of Operational Psychiatry, 1979, pp. 150-165, vol. 10 Issue 2.
Helsinki University., Psilocybin and Depression (Psilo101), ClinicalTrials.gov, Dec. 21, 2017, ketamine, NCT03380442.

(56) References Cited

OTHER PUBLICATIONS

Hijazi et al., Stability of Ketamine and Its Metabolites Norketamine and Dehydronorketamine in Human Biological Samples, Clinical Chemistry 47(9):1713-1715, 2001.
Ho, et al., In vitro effects of preservatives in nasal sprays on human nasal epithelial cells, American Journal of Rhinology, 2008, pp. 125-129, vol. 22.
Holma, et al., Incidence and Predictors of Suicide Attempts in DSM-IV Major Depressive Disorder: A Five-Year Prospective Study, Am J Psychiatry, Jan. 19, 2010, pp. 801-808, vol. 167 Issue 7.
Hong. et al., Allergy to ophthalmic preservatives, Current Opinion in Allergy and Clinical Immunology, 2009, pp. 447-453, vol. 9.
Horr, et al., Ketamine: A Potential Option for Treatment-Refractory Depression in Elder Adults, Conference Poster, 2014, pp. 179-179, Poster C39.
Hospira, Nowa Wholly Owned Subsidiary of Pfizer, Safety and Efficacy of Repeated Doses of PMI-150 (Intranasal Ketamine) in Acute Postoperative Pain Following Orthopedic Surgery, ClinicalTrials. gov, Jul. 3, 2008, Ketamine, NCT00709436.
Sackeim, et al., Vagus Nerve Stimulation (VNS™) for Treatment-Resistant Depression: Efficacy, Side Effects, and Predictors of Outcome, N Europsychopharmacology, 2001, pp. 713-728, vol. 25 Issue 5.
Sackeim, Ph.D., The Definition and Meaning of Treatment-Resistant Depression, J Clin Psychiatry, 2001, pp. 10-17, vol. 62 Issue 16.
Sadove, et al, Analgesic Effects of Ketamine Administered in Subdissociative Doses, Anaesthesia and Analgesia. Current Researches, 1971, pp. 452-457, vol. 50 Issue 3.
Salvadore et al., Anterior cingulate desynchronization and functional connectivity with the amygdala during a working memory task predict rapid antidepressant response to ketamine. Neuropsychopharmacology: official publication of the American College of Neuropsychopharmacology 35, 2010, pp. 1415-1422.
Salvadore G Ed—Sanacora Gerard et al: "Impact of the Val66Met Polymorphism of Brain-Derived Neurotrophic Factor on Esketamine and Ketamine Antidepressant Effects in Patients with Treatment-Resistant Depression", Biological Psychiatry vol. 77, No. 9 supplement, May 1, 2015 (May 1, 2015), p. 360S.
Sanacora, et al., Subtype-Specific Alterations of y-Aminobutyric Acid and Glutamate in Patients With Major Depression, Arch Gen Psychiatry, 2004, pp. 705-713, vol. 61.
Sapolsky, et al., Commentary Is Impaired Neurogenesis Relevant to the Affective Symptoms of Depression?, Biol Psychiatry, 2004, pp. 137-139, vol. 56.
Sarchiapone, et al., Association of Polymorphism (Val66met) of Brain-Derived Neurotrophic Factor with Suicide Attempts in Depressed Patients, Neuropsychobiology, Jul. 7, 2008, pp. 139-145, vol. 57.
Sarchipone et al., Neuropsychobiology, 2008, 58, 139-145.
Saveanu, et al., The International Study to Predict Optimized Treatment in Depression (iSPOT-D): Outcomes from the acute phase of antidepressant treatment, Journal of Psychiatric Research, Dec. 23, 2014, pp. 1-12, vol. 61.
Scheidegger et al., Ketamine administration reduces amygdalo-hippocampal reactivity to emotional stimulation. Human brain mapping 37, 2016, pp. 1941-1952.
Schonenberg, et al., Ketamine aggravates symptoms of acute stress disorder in a naturalistic sample of accident victims, Journal of Psychopharmacology, 2008, pp. 493-497, vol. 22 Issue 5.
Schule, et al., Repeated S-Ketamine Infusions in Treatment-Resistant Depression, Topic: E02-e—Poster Oral Session 02: Depression and Suicide, 2014, pp. 1-1, Article EPA-1659.
Scott A. Irwin, MD, PHO., Study of Oral Ketamine Versus Placebo for Treating Depression in Patients Undergoing Treatment for Cancer, ClinicalTrials.gov, Jul. 19, 2016, Ketamine, NCT02836288.
Shalvata Mental Health Center, Intra-nasal vs. Intravenous Ketamine Administration, ClinicalTrials.gov, Jan. 1, 2016, Ketamine, NCT02644629.

Shaw et al., Ketamine amplifies induced gamma frequency oscillations in the human cerebral cortex. European neuropsychopharmacology : the journal of the European College of Neuropsychopharmacology 25, 2015, pp. 1136-1146.
Sheba Medical Center., D-cycloserine for Relapse Prevention Following Intravenous Ketamine in Treatmentresistant Depression, ClinicalTrials.gov, May 13, 2016, Ketamine, NCT02772211.
Sheba Medical Center., Ketamine Infusions for Major Depression Disorder (Ketamine), ClinicalTrials.gov, Aug. 19, 2014, Ketamine, NCT02219867.
Shi Jinyun, Study of Ketamine as an Antidepressant in Major Depressive Disorder, ClinicalTrials.gov, Apr. 9, 2012, Ketamine, NCT01573741.
Shiroma et al., Neurocognitive performance and serial intravenous subanesthetic ketamine in treatment-resistant depression. The international journal of neuropsychopharmacology / official scientific journal of the Collegium International Neuropsychopharmacologicum 17, 2014, pp. 1805-1813.
Shiroma, et al., Augmentation of response and remission to serial intravenous subanesthetic ketamine in treatment resistant depression, Journal of Affective Disorders, Oct. 29, 2013, pp. 123-129, vol. 155.
Shiroma, et al., Neurocognitive performance and serial intravenous subanesthetic ketamine in treatment-resistant depression, International Journal of Neuropsychopharmacology, 2014, pp. 1805-1813, vol. 17.
Short, al., Side-effects associated with ketamine use in depression: a systematic review, Lancet Psychiatry, 2018, pp. 65-78, vol. 5.
Simon, "What If Ketamine Actually Works Like an Opioid?", Wired, Aug. 29, 2018, 1-10.
Singh et al., A Double-Blind, Randomized, Placebo-Controlled, Dose-Frequency Study of Intravenous Ketamine in Patients With Treatment-Resistant Depression. The American journal of psychiatry, 173(8):816-26, 2016.
Singh Jaskaran: Intranasal sketamine in, Treatment Resistant Depression—A Double-blind, Randomized, Efficacy and Dose Response Study, International Journal of Neuropsychopharmacology, Cambridge Univ. Press, Cambridge, vol. 19, No. Suppl. 1, May 31, 2016 (May 31, 2016), XP009511636, p. 24, ISSN: 1461-1457, DOI: 10.7490/F1000RESEARCH.1111967.1.
Singh, Intranasal sketamine in, Treatment Resistant Depression—A Double-blind, Randomized, Efficacy and Dose Response Study, International Journal of Neuropsychopharmacology, Cambridge Univ. Press, Cambridge, vol. 19, No. Suppl. 1, May 31, 2016 (May 31, 2016), XP009511636, p. 24, ISSN: 1461-1457, DOI: 10.7490/F1000RESEARCH.1111967.1.
Skolnick et al, Glutamate-based antidepressants: 20 years on, Trends in Pharmacological Sciences, 2006, pp. 563-569, vol. 30 Issue 11.
Skolnick, et al., Adaptation of N-Methyl-D-Aspartate (NMDA) Receptors following Antidepressant Treatment: Implications for the Pharmacotherapy of Depression, Pharamacopsychiat, 1996, pp. 23-26, vol. 29.
Skolnick, et al., Antidepressants for the new millennium, European Journal of Pharmacology, Apr. 30, 1999, pp. 31-40, vol. 375.
Skolnick, et al., Modulation of glutamate receptors: Strategies for the development of novel antidepressants, Amino Acids, Jun. 17, 2002, pp. 153-159, vol. 23.
Smith, et al., Properties of the Optical Isomers and Metabolites of Ketamine on the High Affinity Transport and Catabolism of Monoamines, Neuropharmacology, 1981, pp. 391-396, vol. 20.
Sofia, et al., Evaluation of Ketamine HCl for Anti-Depressant Activity, Arch. int. Pharmacodyn., 1975, pp. 68-74, vol. 214.
Soni, et al., Safety assessment of esters of p-hydroxybenzoic acid (parabens, Food and Chemical Toxicology, Jan. 31, 2005, pp. 985-1015, vol. 43, Elsevier Ltd.
Soni, et al., Safety assessment of propyl paraben: a review of the published literature, Food and Chemical Toxicology, Sep. 25, 2000, pp. 513-532, vol. 39, Elsevier Science Ltd.
Soni, M.G. et al., Food Chem Toxicol., 2001, pp. 513-532, 39(6).
Soni, M.G. et al., Food Chem Toxicol., 2005, pp. 985-1015, 43(7).
Sos, et al., Relationship of ketamine's antidepressant and psychotomimetic effects in unipolar depression, Activitas Nervosa Superior Rediviva, Aug. 30, 2013, pp. 57-63, vol. 55 Issue 1-2.

(56) References Cited

OTHER PUBLICATIONS

Spitzer, "A brief measure for assessing generalized anxiety disorder—the GAD-7". Arch. Intern. Med., 2006, 166(10), 1092-1097.
Srivastava, et al., Safety and efficacy of ketamine infusion in late onset depression, and conversion to treatment response, Indian J Psychiatry, 2015, pp. 328-329, vol. 57 Issue 3.
St Patrick's Hospital, Ireland., Ketamine as an Adjunctive Therapy for Major Depression (Karma-dep), ClinicalTrials.gov, Aug. 21, 2017, Ketamine, NCT03256162.
St Patrick's Hospital, Ireland., Ketamine for Depression Relapse Prevention Following ECT (Keep-Well), ClinicalTrials.gov, Apr. 13, 2015, Ketamine, NCT02414932.
St Patrick's Hospital, Ireland., Ketamine for Relapse Prevention in Recurrent Depressive Disorder (Kindred), ClinicalTrials.gov, Jan. 22, 2016, Ketamine, NCT02661061.
Stanford University, Double-Blind Trial of Ketamine Therapy Plus or Minus Naltrexone in Treatment Resistant Depression (TRD) (Ket_Nal), ClinicalTrials.gov, Sep. 22, 2016, Naltrexone, NCT02911597.
Stanford University., Assessing the Effectiveness of Psychiatric Interventions on the Inpatient Unit, ClinicalTrials.gov, Aug. 10, 2018, Ketamine, NCT03626142.
Stannard, et al., Ketamine hydrochloride in the treatment of phantom limb pain, Pain, Apr. 12, 1993, pp. 227-230, vol. 54.
Steven R. Devore Best., Rapid Relief of Treatment Resistant Depression by Facilitated Ketamine Infusion: A Preliminary Report, Activities Nervosa Superior, Jun. 28, 2014, pp. 28-36, vol. 56 Issue 1-2.
Steven Richard Devore Best., Combined ketamine and transcranial magnetic stimulation for treatment resistant depression in the context of chronic OCD: a case report, Devore Best Neuropsychiatric Electrophysiology, 2015, pp. 1-4, vol. 1 Issue 2.
Stevenson, Ketamine: A Review, Update in Anaesthesia, 20:25-29, 2005.
Opposition filed during prosecution of corresponding CL Appl No. 2014-2406.
Oshima, et al., Continuous subcutaneous injection of ketamine for cancer pain, Canadian Journal of Anaesthesia, 1990, pp. 385-392, vol. 37 Issue 3.
Ostroff, et al., Antidepressant Effect of Ketamine During ECT, American Journal of Psychiatry, 2005, pp. 1385-1386, vol. 162 Issue 7.
Overall, et al., Overall et al brief psychiatric rating scale, overall et al brief psychiatric rating scale, 2018, pp. 1-6, page number.
Overall, et al., The Brief Psychiatric Rating Scale1, Psychological Reports, Apr. 17, 1962, pp. 799-812, vol. 10.
Pacella, Single-dose Ketamine for the Reduction of Pain and Depression in the Emergency Department, ClinicalTrials.gov, Feb. 16, 2018, Ketamine, NCT03436121.
Papp, et al., Antidepressant activity of non-competitive and competitive NMDA receptor antagonists in a chronic mild stress model of depression, European Journal of Pharmacology, Jun. 21, 1994, pp. 1-7, vol. 263.
Paslakis G et al: "Oral administration of the NMDA receptor antagonist S-ketamine as add-on therapy of depression: a case series.", Pharmacopsychiatry, vol. 43, No. 1, Jan. 2010, pp. 33-35.
Paul, et al, Comparison of racemic ketamine and S-ketamine in treatment-resistant major depression: Report of two cases, The World Journal of Biological Psychiatry, Sep. 28, 2007, pp. 241-244, vol. 10 Issue 3, Informa UK Ltd.
Paule, et al., Behavioral Effects in Primates Ketamine Anesthesia during the first week of life can cause long-lasting cognitive deficits in rhesus monkey, Neurotoxicology and Teratology, 2011, pp. 1-33.
Paule, et al., Ketamine Anesthesia during the first week of life can cause long-lasting cognitive deficits in rhesus monkeys, Neurotoxicology and Teratology, 2011, pp. 220-230.
Pearson, et al., Intervention Research With Persons at high Risk for Suicidality: Safety and Ethical Considerations, J Clin Psychiatry, 2001, pp. 17-26, vol. 62 Supplement 25.

Pecina M. et al., "Valence-specific effects of BDNF Val66Met polymorphism on dopaminergic stress and reward processing in humans", J. Neurosci., Apr. 23, 2014, vol. 34(17), pp. 5874-5881.
Peking University First Fiospital., Low-dose Ketamine and Postpartum Depression in Patients With Prenatal Depression, ClinicalTrials.gov, Nov. 8, 2017, Ketamine, NCT03336541.
Pennybaker, et al., Symptomatology and Predictors of Antidepressant Efficacy in Extended Responders to a Single Ketamine Infusion, J Affect Disord., Jan. 15, 2015, pp. 560-566, vol. 208.
Per Gisle Djupesland., Nasal drug delivery devices: characteristics and performance in a clinical perspective—a review, Drug Deliv. and Transl. Res, Oct. 18, 2012, pp. 42-62.
Pfeiffer, et al., Treatment-Resistant Depression and Risk of Suicide, Suicide and Life-Threatening Behavior, Dec. 26, 2012, pp. 1-10.
Pfenninger, et al., Cognitive Impairment after Small-dose Ketamine Isomers in Comparison to Equianalgesic Racemic Ketamine in Human Volunteers, Anesthesiology, 2002, pp. 357-366, vol. 96 Issue 2.
Pfizer, (S)-(+)-Ketamine Hydrochloride Solution, Material Safety Data Sheet, Nov. 5, 008, pp. 1-8, Version 1.0.
Phelps et al., Family history of alcohol dependence and initial antidepressant response to an N-methyl-D-aspartate antagonist. Biological psychiatry 65, 2009, pp. 181-184.
PI Mylan Ketamine HCl Injection, Ketamine Hydrochloride—ketamine hydrochloride injection, selution Mylan Institutional LLC, PI Mylan Ketamine HCl Injection, 2012, 1-16.
Pierre Blier., Exploiting N-Methyl-D-Aspartate Channel Blockade for a Rapid Antidepressant Response in Major Depressive Disorder, Biol Psychiatry, May 30, 2013, pp. 238-239, vol. 74.
Poreh, et al., The BPQ: A Scale for the Assessment of Borderline Personality Based on DSM-IV Criteria, Journal of Personality Disorders, 2006, pp. 247-260, vol. 20 Issue 3.
Posner, et al., Columbia Classification Algorithm of Suicide Assessment (C-CASA): Classification of Suicidal Events in the FDA's Pediatric Suicidal Risk Analysis of Antidepressants, Am J Psychiatry, 2007, pp. 1035-1043, vol. 164.
Posner, et al., The Columbia—Suicide Severity Rating Scale: Initial Validity and internal Consistency Findings From Three Multisite studies with adolescents and Adults, Am J Psychiatry, 2011, pp. 1266-1277, vol. 168 Issue 12.
Pouya Movahed Rad., Ketamine as an Alternative Treatment to ECT in Major Depressive Disorder, ClinicalTrials.gov, Jan. 20, 2016, Ketamine, NCT02659085.
PRD3253CLPCT _Opposition BriefTranslation, 2014.
Price et al, Effects of Intravenous Ketamine on Explicit and Impicit Measures of Suicidality in Treatment-Resistant Depression, Biol. Psychiatry, 2009, pp. 522-526, vol. 66, Society of Biological Psychiatry.
Price, et al., Effects of Ketamine on Explicit and Implicit Suicidal Cognition: A Randomized Controlled Trial in Treatment-Resistant Depression, Depress Anxiety., 2014, pp. 1-18, vol. 31, Issue 4.
Price, Intravenous Ketamine Plus Neurocognitive Training for Depression, ClinicalTrials.gov, Aug. 2, 2017, Intravenous ketamine, NCT03237286.
Price_et_al, Effects of Intravenous Ketamine on Explicit and Implicit Measures of Suicidality in Treatment-Resistant Depression, Biol Psychiatry, 2009, pp. 522-526, vol. 66, Society of Biological Psychiatry.
Pringle, et al., A Strategic Approach for Prioritizing Research and Action to Prevent Suicide, Psychiatric Services, 2013, pp. 71-75, vol. 64 Issue 1.
Przegalinski, et al., Antidepressant-like Effects of a Partial Agonist at Strychnine-insensitive Glycine Receptors and a competitive NMDA Receptor Antagonist, Neurophoramacology, 1997, pp. 31-37, vol. 36 Issue 1.
Psychiatric University Hospital, Zurich., A Multimodal Neuroimaging Study of Brain Activation Patterns Under Ketamine, ClinicalTrials.gov, Aug. 1, 2018, Ketamine, NCT03609190.
Quintana, et al., Dose-dependent social-cognitive effects of intranasal oxytocin delivered with novel Breath Powered device in adults with autism spectrum disorder: a randomized placebo-controlled double-blind crossover trial, Translational Psychiatry, May 23, 2017, pp. e1136, vol. 7.

(56) References Cited

OTHER PUBLICATIONS

Rad., Ketamine as an Alternative Treatment to ECT in Major Depressive Disorder, ClinicalTrials.gov, Jan. 20, 2016, Ketamine, NCT02659085.
Randall, et al., Assessment of Self-Harm Risk Using Implicit Thoughts, Psychological Assessment, May 6, 2013, pp. 1-8.
Rasmussen, et al., Serial infusions of low-dose ketamine for major depression, Journal of Psychopharmacology, 2013, pp. 444-450, vol. 27 Issue 5.
Rebecca Price, Intravenous Ketamine Plus Neurocognitive Training for Depression, ClinicalTrials.gov, Aug. 2, 2017, Intravenous ketamine, NCT03237286.
Reeves, et al., Efficacy of Risperidone Augmentation to Antidepressants in the Management of Suicidality in Major Depressive Disorder: A Randomized, Double-Blind, Placebo-Controlled Pilot Study, J Clin Psychiatry, 2008, pp. 1228-1236, vol. 69 Issue 8.
Remigius U Agu., Challenges in nasal drug absorption: how far have we come?, Future Science, Jul. 12, 2016, pp. 1-2, vol. 7 Issue 7.
Remington: The Science and Practice of Pharmacy; 20th Edition; Chapter 78, p. 1398, 2000, (3pp).
Rhode Island Hospital, Intranasal Ketamine for Procedural Sedation in Pediatric Laceration Repair, ClinicalTrials.gov, Mar. 23, 2007, Ketamine, NCT00451724.
Ribeiro, et al., The Use of Ketamine for the Treatment of Depression in the Context of Psychotic Symptoms, Biological Psychiatry, May 1, 2016, pp. e65-e66, vol. 79.
Rot, et al., Ketamine for Depression: Where Do We Go from Here?, Biol Psychiatry, May 9, 2012, pp. 537-547.
Rowe et al: Handbook of Pharmaceutical Excipients, Sixth Edition, 2009, pp. 181-183; 247-250.
Rush, et al, Research Issues in the Study of Difficult-to-Treat Depression, Biol Psychiatry, Jan. 13, 2003, pp. 743-753, vol. 53.
Rush, et al., Acute and Longer-Term Outcomes in Depresses Outpatients Requiring one or Several Treatment Steps; A Star*D Report, Am. J. Psychiatry, 2006, pp. 1905-1917, vol. 163.
Rybakowski et al., Single ketamine infusion in bipolar depression resistant to antidepressants: are neurolrophins involved? Human psychopharmacology 28, 2013, pp. 87-90.
Washington University School of Medicine, Treatment Resistant Depression (Pilot), ClinicalTrials.gov, Aug. 10, 2010, ketamine, NCT01179009.
Washington University School of Medicine., Nitrous Oxide as Treatment for Major Depression—a Pilot Study, ClinicalTrials.gov, May 15, 2014, Nitrous Oxide, NCT02139540.
Washington, et al., Determination of baseline human nasal pH and the effect of intranasally administered buffers, International Journal of Pharmaceutics, Nov. 24, 1999, pp. 139-146, vol. 198, Elsevier Science B.V.
Wasserman, et al., Saving and Empowering Young Lives in Europe (SEYLE): a randomized controlled trial, BMC Public Health, 2010, pp. 1-14, vol. 10 Issue 192.
Weksler, et al., Nasal ketamine for paediatric premedication, Canadian Journal of Anaesthesia, 1993, pp. 119-121, vol. 40 Issue 2.
Weksler, et al., Nasal ketamine for pediatric premedication, Canadian Journal of Anaesthesia, 1993, pp. 119-121, vol. 40 Issue 2.
White et al., Comparative Pharmacology of Ketamine Isomers, Br. J. Anaesth., 57(2):197-203, 1985.
White_et_al, Pharmacology of Ketamine Isomers in surgical Patients, Anesthesiology, 1980, pp. 231-239, vol. 52, The American Society of Anesthesiologists.
WHO Critical Review Ketamine., Introduction, WHO critical review ketamine, 2006, pp. 1-30, 34th ECDD 2006/4.3.
WHO_Depression Fact Sheet., Media centre Depression, WHO_Depression fact sheet, 2012, pp. 1-3, Fact sheet N°369.
WHO_Essential Medicines and Health Products., Essential medicines, WHO_ Essential medicines and health products, 2015, pp. 1-3.
WHO_Expert Peer Review Report, Expert Committee on Drug Dependence Thirty-sixth Meeting, WHO_Expert peer review report, 2014, pp. 1-4, Agenda item 6.2.
Wikipedia, Esketamine, Wikipedia, Sep. 1, 2015, pp. 1-4, Wikipedia.
Wilcock, et al: Therapeutic Reviews, Journal of Pain and Symptom Management, vol. 41, No. 3, Mar. 3, 2011, 640-649.
Wilkinson, et al., Cognitive Behavior Therapy May Sustain Antidepressant Effects of Intravenous Ketamine in Treatment-Resistant Depression, Psychother Psychosom, May 11, 2017, pp. 162-167, vol. 86.
William Beaumont Hospitals., IN Ketamine vs IN Midazolam and Fentanyl for Laceration Repair, ClinicalTrials.gov, May 18, 2018, Ketamine, NCT03528512.
William V. Bobo, M.D., Effect of Lithium Versus Placebo in Adults With Treatment-Resistant Depression Who Are Receiving Ketamine, ClinicalTrials.gov, Sep. 25, 2017, Ketamine, NCT03290963.
Williams, "Development and reliability of a structured interview guide for the Montgomery asberg depression rating Scale (SIGMA)", Br. J. Psychiatry, 2008, 192(1), 52-58 on days 1 (pre-dose and 2 hour post-dose), 2, 8 (pre-dose), 9, and 15, using the structured interview guide (SIGMA). See, Williams 2008.
Williams, et al., Attenuation of Antidepressant Effects of Ketamine by Opioid Receptor Antagonism, ajp.psychiatryonline.org, 2018, pp. 1-11.
Wirz-Justice, et al., Sleep Deprivation in Depression: What Do We Know, Where Do We Go?, Biol Psychiatry, May 18, 1999, pp. 445-453, vol. 46.
Womble, et al., Effects of Ketamine on Major Depressive Disorder in a Patient With Posttraumatic Stress Disorder, AANA Journal, 2013, pp. 118-119, vol. 81 Issue 2.
Wonkwang University Hospital., Dexamethasone and Ketamine on Change of Postoperative Mood, ClinicalTrials.gov, Jun. 21, 2017, Ketamine, NCT03194594.
Wu, et al., Transgenerational impairment of hippocampal Akl-mTOR signaling and behavioral deficits in the offspring of mice that experience postpartum depression-like illness. Progress in Neuro-Psychopharmacology & biological Psychiatry (2017), 73, 11-18.
Xia, et al., Chronic stress prior to pregnancy potentiated regulated by Akt-mTOR signaling in the hippocampus. Scientific Reports (2016), 6, 35042.
Xu, et al., Single bolus low-dose of ketamine does not prevent postpartum depression: a randomized, double-blind, placebo-controlled, prospective clinical trial. Archives of Gynecology and Obstetrics (2017), 295, 1167-1174.
Yale University, Ketamine for Depression and Alcohol Dependence (KetamineDep), ClinicalTrials.gov, Mar. 12, 2012, Ketalar (ketamine), NCT01551329.
Yale University, Trial of Ketamine and Lithium Therapy in Bipolar Depression, ClinicalTrials.gov, Jan. 15, 2013, Ketamine, NCT01768767.
Yale University., Alpha-Amino-3-Hydroxy-5-Methyl-4-Isoxazole Propionic Acid Receptor Components of the Anti-Depressant Ketamine Response, ClinicalTrials.gov, Dec. 8, 2017, Ketamine, NCT03367533.
Yale University., Cognitive Behavioral Therapy in Prolonging the Antidepressant Effects of Intravenous Ketamine, ClinicalTrials.gov, Nov. 13, 2014, Ketamine, NCT02289248.
Yale University., Cognitive Therapy to Sustain the Antidepressant Effects of Intravenous Ketamine in Treatment-resistant Depression, ClinicalTrials.gov, Jan. 23, 2017, ketamine, NCT03027362.
Yale University., Examining the Effect of Ketamine on Glutamate/Glutamine Cycling, ClinicalTrials.gov, Jan. 15, 2014, Ketamine, NCT02037035.
Yale University., Imaging SV2A in Mood Disorders, ClinicalTrials.gov, Apr. 12, 2016, ketamine, NCT02734602.
Yale University., Ketamine for Low Mood States in the ER, ClinicalTrials.gov, Sep. 27, 2010, Ketamine, NCT01209845.
Yale University., Ketamine in Borderline Personality Disorder, ClinicalTrials.gov, Jan. 10, 2018, Ketamine, NCT03395314.
Yale University., Ketamine Infusion for Adolescent Depression and Anxiety, ClinicalTrials.gov, Oct. 20, 2015, Ketamine, NCT02579928.
Yale University., PET Imaging of mGLuRS With Drug Challenge, ClinicalTrials.gov, Sep. 24, 2012, ketamine, NCT01691092.

(56) References Cited

OTHER PUBLICATIONS

Yang et al., "R-Ketamine: A rapid onset and sustained antidepressant without psychotomimetic side effects", Transl. Psychiatry, 2015, 5, 1-11.
Yang et al., Serum interleukin-6 is a predictive biomarker for ketamine's antidepressant effect in treatment-resistant patients with major depression. Biological psychiatry 77, 2015b, pp. e19-e20.
Yang, et al., R-ketamine: a rapid-onset and sustained antidepressant without psychotomimetic side effects, Transl Psychiatry, Sep. 1, 2015, pp. 1-19, vol. 5 Issue 9.
Yilmaz, et al., Prolonged effect of an anesthetic dose of ketamine on behavioral despair, Pharmacology, Biochemistry and Behavior, 2002, pp. 341-344, vol. 71.
Young, et al., Young Mania Rating Scale (YMRS), Br J Psychiatry, 1978, pp. 429-435, vol. 133.
Zanos, et al., Effects of a ketamine metabolite on synaptic NMDAR function, Nature, Jun. 22, 2017, pp. E1-E2.
Zanos, et al., Intracellular Signaling Pathways Involved in (S)-and (R)-Ketamine Antidepressant Actions, Biological Psychiatry, Jan. 1, 2008, pp. 2-4, vol. 83.
Zarate et al., A randomized trial of an N-methyl-D-aspartate antagonist in treatment-resistant major depression. Archives of general psychiatry 63, 2006, pp. 856-864.
Zarate, et al., A Double-Blind, Placebo-Controlled Study of Memantine in the Treatment of Major Depression, Am J Psychiatry, 2006, pp. 153-155, vol. 163 Issue 1.
Zarate, et al., A Randomized Trail of an N-methyl_D-aspartate Antagonist in Treatment-Resistant Major Depression, Arch Gen Psychiatry, 2006, pp. 856-864, vol. 63.
Zarate, et al., An open-Label Trial of Riluzole in Patients With Treatment-Resistant major Depression, Am J Psychiatry, Jan. 1, 2004, pp. 171-174, vol. 161.
Zarate, et al., Brief Reports An Open-Label Trial of the Glutamate-Modulating Agent Riluzole in Combination with Lithium for the Treatment of Bipolar Depression, Biol. Psychiatry, 2005, pp. 430-432, vol. 57.
Zarate, et al., Regulation of Cellular Plasticity Cascades in the Pathophysiology and Treatment of Mood Disorders, Annals New York Academy of Sciences, 2003, pp. 273-291, vol. 1003.
Zarate, et al., Replication of Ketamine's Antidepressant Efficacy in Bipolar Depression: A Randomized Controlled Add-on Trial, Biol Psychiatry, Jun. 1, 2012, pp. 939-46, vol. 71 Issue 11.
Brent, et al., Treatment-Resistant Depression in Adolescents: Recognition and Management, Child Adolesc Psychiatric Clin N Am, 2006, pp. 1015-1034, vol. 15.
Bridge, et al., Clinical Response and Risk for Reported Suicidal Ideation and Suicide Attempts in Pediatric Antidepressant Treatment A Meta-analysis of Randomized Controlled Trials, JAMA, Apr. 18, 2007, pp. 1683-1696, vol. 297 Issue 15.
Bridge, et al., Placebo Response in Randomized Controlled Trials of Antidepressants for Pediatric Major Depressive Disorder, Am J Psychiatry, 2009, pp. 42-49, vol. 166.
Bromet, et al., Cross-national epidemiology of DSM-IV major depressive episode, BMC Medicine, 2011, pp. 1-16, vol. 9 Issue 90.
Brooke Army Medical Center, "THINK Trial: Treatment of Headache With IntraNasal Ketamine: A Randomized Controlled Trial Evaluating the Efficacy of Intranasal Ketamine Versus Standard Therapy in the Management of Primary Headache Syndromes in the Emergency Department" (THINK), ClinicalTrials.gov, Mar. 16, 2017, Ketamine, NCT03081416.
Brooke Army Medical Center, Intranasal Ketamine for Anxiolysis in Pediatric Emergency Department Patients, ClinicalTrials.gov, Feb. 6, 2017, Ketamine, NCT03043430.
Brooke Army Medical Center., Ketamine for Acute Suicidal Ideation in the Emergency Department: Randomized Controlled Trial (LOK-SI), ClinicalTrials.gov, Jul. 8, 2013, Ketamine, NCT01892995.
Brown, et al., Cognitive Therapy for the Prevention of Suicide Attempts, JAMA, Aug. 3, 2005, pp. 563-570, vol. 294 Issue 5.
Brown, et al., the role of randomized trials in testing interventions for the prevention of youth suicide, International Review of Psychiatry, 2007, pp. 1-15, vol. 19 Issue 6.
Brown, Ph.D., A Review of Suicide Assessment Measures for Intervention Research with Adults and Older Adults, Suicide Assessment, NA, pp. 1-57.
Busch, et al., Clinical Correlates of Inpatient Suicide, J Clin Psychiatry, 2003, pp. 14-19, vol. 64.
Byrd, et al., Behavioral effects of phencyclidine and ketamine alone and in combination with other drugs, European Journal of Pharamacology, Sep. 29, 1987, pp. 331-341, vol. 144.
Calabrese, et al., A Double-Blind Placebo-Controlled Study of Lamotrigine Monotherapy in Outpatients With Bipolar 1 Depression, J Clin Psychiatry, 1999, pp. 79-88, vol. 60 Issue 2.
Callahan, et al., EvidenceMap of Prevention and Treatment Interventions for Depression in Young People, Hindawi Publishing Corporation Depression Research and Treatment Volume, Dec. 30, 2011, pp. 1-12, Article ID 820735.
Cameroon Baptist Convention Health., Sub-dissociative Intranasal Ketamine for Pediatric Sickle Cell Pain Crises, ClinicalTrials.gov, Oct. 12, 2015, Ketamine, NCT02573714.
Canuso, et al., Design of Phase 3 Randomized Studies of Intranasal Esketamine to Treat Major Depressive Disorder Symptoms, European Symposium on Suicide & Suicidal Behavior (ESSSB), 2018, pp. 1-1.
Carlson, et al., Neural Correlates of Rapid Antidepressant Response to Ketamine in Treatment-Resistant Unipolar Depression: A Preliminary Positron Emission Tomography Study, Biol Psychiatry, Feb. 1, 2013, pp. 1213-1221, vol. 73.
Carolinas Healthcare System, IN Sub-Dissociative Ketamine vs IN Fentanyl, ClinicalTrials.gov, Aug. 13, 2015, Ketamine. NCT02521415.
Carr et al., "Intranasal Ketamine The Essence of Analgesia and Analgesics", Publisher: Cambridge University Press, 2010, pp. 440-443.
Carr, et al., Safety and efficacy of intranasal ketamine for the treatment of breakthrough pain in patients with chronic pain: a randomized, double-blind, placebo-controlled, crossover study, Pain, 2004, pp. 17-27, vol. 108.
Caspi, et al., "Influence of Life Stress on Depression: Moderation by a Polymorphism in the 5-HTT Gene", Science, Jul. 18, 2003, vol. 301, 986-689.
Cavanagh, et al., Psychological autopsy studies of suicide: a systematic review, Psychological Medicine, 2003, pp. 395-405, vol. 33.
Cedars-Sinai Medical Center., Ketamine for Preventing Depression in Patients Undergoing Treatment for Pancreatic or Head and Neck Cancers, ClinicalTrials.gov, May 13, 2015, Ketamine, NCT02442739.
Celon Pharma SA., Safety and Pharmacokinetic Study of Inhaled Esketamine in Healthy Volunteers, Clinical Trials. gov, Jan. 23, 2018, Esketamine, NCT03407872.
Centre Hospitalier Universitaire De Ntmes., Effects of Ketamine in the Acute Phase of Suicidal Ideation (Ketis), ClinicalTrials.gov, Nov. 24, 2014, Ketamine, NCT02299440.
Chambers, et al., Developmental Neurocircuitry of Motivation in Adolescence: A Critical Period of Addiction Vulnerability, Am J Psychiatry, 2003, pp. 1041-1052, vol. 160 Issue 6.
Chang et al., "Biotransformation and Disposition of Ketamine, Biotransformation and Disposition of Ketamine", N.A., pp. 157-177.
Chang, et al, Metabolic Disposition on Tritium-Labeled Ketamine (Ketalar); c1-581 in Normal Human Subjects, Clinical Pharmacology, 1970, pp. 597-597.
Chang, et al., Major Depressive Disorder Induced by Chronic Ketamine Abuse: A Case Report, Primary Care Companion CNS Disorders, Jun. 23, 2016, pp. 1-3, vol. 18 Issue 3.
Chang, et al., Metabolic Disposition on Tritium-Labelled Ketamine (Ketalar); c1-581 in Normal Human Subjects, Clinical Pharmacology, 1970, pp. 597-597, page number.
Chang, et al., The Depressed Patient and Suicidal Patient in the Emergency Department Evidence-Based Management and Treatment Strategies, EB Medicine, Sep. 1, 2011, pp. 1-24, vol. 13 Issue 9.

(56) References Cited

OTHER PUBLICATIONS

Chen, et al., Determination of ketamine and metabolites in urine by liquid chromatography-mass spectrometry, Talanta, Jan. 16, 2007, pp. 1217-1222, vol. 72.

Chen, et al., Effect of Low Dose of Ketamine on Learning Memory Function in Patients Undergoing Electroconvulsive Therapy—A Randomized, Double-Blind, Controlled Clinical Study, Journal of ECT, 2016, pp. 85-95.

Chen, et al., High prevalence of major depression among treatment-seeking ketamine-dependent patients, Abstracts/ Drug and Alcohol Dependence, 2017, pp. e39-e40, vol. 171.

Cheung, et al., Review of the efficacy and safety of antidepressants in youth depression, Journal of Child Psychology and Psychiatry, 2005, pp. 735-754, vol. 46 Issue 7.

Cheung, et al., The use of antidepressants to treat depression in children and adolescents, CMAJ, Jan. 17, 2006, pp. 193-200, vol. 174 Issue 2.

Children's Hospital Medical Center, Cincinnati., Pain Reduction With Intranasal Medications for Extremity Injuries (Prime), ClinicalTrials.gov, May 20, 2016, ketamine, NCT02778880.

Chong, et al., Development of a Sublingual/Oral Formulation of Ketamine for Use in Neuropathic Pain Preliminary Findings from a Three-Way Randomized, Crossover Study, Clin Drug Invest, 2009, pp. 317-324, vol. 5.

Chu, et al., A Tool for the Culturally Competent Assessment of Suicide: The Cultural Assessment of Risk for Suicide (CARS) Measure, Psychological Assessment, Jan. 28, 2013, pp. 1-12.

Cipriani, et al., Lithium in the Prevention of Suicidal Behavior and All-Cause Mortality in Patients With Mood Disorders: A Systematic Review of Randomized Trials, Am J Psychiatry, 2005, pp. 1805-1819, vol. 162 Issue 10.

Cipriani, et al., Lithium in the prevention of suicide in mood disorders: updated systematic review and meta-analysis, BMJ, Jun. 27, 2013, pp. 1-13, vol. 346.

Clancy, et al., Translating Developmental Time Across Mammalian Species, Neuroscience, Apr. 11, 2011, pp. 7-17, vol. 105 Issue 1.

Clements, et al., Bioavailability, Pharmacokinetics, and Analgesic Activity of Ketamine in Humans, Journal of Pharmaceutical Sciences, 1982, pp. 539-542, vol. 71 Issue 5.

clinical trials.gov _NCT01998958, A Study to Evaluate the Safety and Efficacy of Intranasal Esketamine in Treatment-resistant Depression. ClinicalTrials.gov Identifier: NCT01998958. Jul. 14, 2014 [online], p. 1-40.

Clinical Trials.gov Identifier: NCT02133001, May 7, 2014, URL:https://clinicaltrials.gov/ct2/show/NCT02133001.

Columbia University., Ketamine in the Treatment of Depression, ClinicalTrials.gov, Mar. 20, 2012, Ketamine, NCT01558063.

Compton, et al., Cognitive-Behavioral Psychotherapy for Anxiety and Depressive Disorders in Children and Adolescents: An Evidence-Based Medicine Review, J. Am. Acad. Child Adolesc. Psychiatry, Nov. 17, 2003, pp. 930-959, vol. 43 Issue 8.

Controlled Trial in Treatment-Resistant Depression, Depress Anxiety., 2014, pp. 1-18, vol. 31 D.

Cornwell, et al., Synaptic Potentiation Is Critical for Rapid Antidepressant Response to Ketamine in Treatment-Resistant Major Depression, Biol Psychiatry, Mar. 29, 2012, pp. 555-561, vol. 72.

Correia-Melo, et al., Rapid infusion of esketamine for unipolar and bipolar depression: a retrospective chart review, Neuropsychiatric Disease and Treatment, Jun. 21, 2017, pp. 1627-1632, vol. 13.

Janssen Research & Development, LLC, A Study to Assess the Effects of Hepatic Impairment on the Pharmacokinetics, Safety, and Tolerability of Intranasally Administered Esketamine, ClinicalTrials.gov, Nov. 20, 2015, Esketamine, NCT02611505.

Janssen Research & Development, LLC, A Study to Evaluate the Absolute Bioavailability of Intranasal and Oral Esketamine and the Effects of Clarithromycin on the Pharmacokinetics of Intranasal Esketamine in Healthy Participants, ClinicalTrials.gov, Jan. 21, 2015, Esketamine, NCT02343289.

Janssen Research & Development, LLC, A Study to Evaluate the Effects of a Single-Dose and Repeat-Administration of Intranasal Esketamine on On-Road Driving in Participants With Major Depressive Disorder (DriveSaFe2), ClinicalTrials.gov, Sep. 29, 2016, Esketamine, NCT02919579.

Janssen Research & Development, LLC, A Study to Evaluate the Efficacy, Safety, and Tolerability of Flexible Doses of Intranasal Esketamine Plus an Oral Antidepressant in Adult Participants With Treatment-resistant Depression (Transform-2), ClinicalTrials.gov, Apr. 16, 2015, Esketamine, NCT02418585.

Janssen Research & Development, LLC, Pharmacokinetic, Safety, and Tolerability Study of intranasally Administered Esketamine in Elderly and Healthy Younger Adult Participants, ClinicalTrials.gov, Jan. 26, 2015, Esketamine, NCT02345148.

Janssen Research & Development, LLC, Study to Evaluate the Efficacy and Safety of 3 Fixed Doses of Intranasal Esketamine in Addition to Comprehensive Standard of Care for the Rapid Reduction of the Symptoms of Major Depressive Disorder, Including Suicidal Ideation., ClinicalTrials.gov, Jun. 14, 2017, Esketamine, NCT03185819Esketamine, NCT03185819.

Janssen Research & Development, LLC., A Long-term Safety Study of Intranasal Esketamine in Treatment-resistant Depression (Sustain-3), ClinicalTrials.gov, May 25, 2016, Esketamine, NCT02782104.

Janssen Research & Development, LLC., A Pharmacokinetic, Safety and Tolerability Study of Esketamine in Healthy Elderly and Adult Participants, ClinicalTrials.gov, May 2, 2014, Esketamine, NCT02129088.

Janssen Research & Development, LLC., A Study of Ketamine in Patients With Treatment-resistant Depression, ClinicalTrials.gov, Jun. 26, 2012, ketamine, NCT01627782.

Janssen Research & Development, LLC., A Study to Assess the Effect of Ticlopidine on the Pharmacokinetics, Safety, and Tolerability of Intranasally Administered Esketamine in Healthy Participants, ClinicalTrials.gov, Oct. 2, 2017, Esketamine, NCT03298906.

Janssen Research & Development, LLC., A Study to Assess the Effects of Renal Impairment on the Pharmacokinetics, Safety, and Tolerability of Intranasally Administered Esketamine, ClinicalTrials.gov, Nov. 17, 2015, Esketamine, NCT02606084.

Janssen Research & Development, LLC., A Study to Assess the Pharmacokinetics of Intranasally Administered Esketamine in Healthy Japanese and Caucasian Volunteers, ClinicalTrials.gov, Nov. 8, 2013, Esketamine, NCT01980303.

Janssen Research & Development, LLC., A Study to Assess the Pharmacokinetics, Safety, and Tolerability of intranasally Administered Esketamine in Healthy Participants, ClinicalTrials.gov, Jan. 31, 2013, Esketamine, NCT01780259.

Janssen Research & Development, LLC., A Study to Evaluate the Effect of Intranasal Esketamine on Cognitive Functioning in Healthy Subjects, ClinicalTrials.gov, Mar. 21, 2014, Esketamine, NCT02094378.

Janssen Research & Development, LLC., A Study to Evaluate the Effects of Esketamine on Cardiac Repolarization in Healthy Participants, ClinicalTrials.gov, Apr. 14, 2016, Esketamine, NCT02737605.

Janssen Research & Development, LLC., A Study to Evaluate the Efficacy and Safety of Intranasal Esketamine in Addition to Comprehensive Standard of Care for the Rapid . . . , ClinicalTrials.gov, Mar. 31, 2017, Esketamine, NCT03097133.

Janssen Research & Development, LLC., A Study to Evaluate the Efficacy, Pharmacokinetics, Safety and Tolerability of Flexible Doses of Intranasal Esketamine Plus an Oral Antidepressant in Adult Participants With Treatment-resistant Depression, ClinicalTrials.gov, Feb. 15, 2018, Esketamine, NCT03434041.

Janssen Research & Development, LLC., A Study to Evaluate the Efficacy, Safely, and Tolerability of Fixed Doses of Intranasal Esketamine Plus an Oral Antidepressant in Adult Participants With Treatment-resistant Depression (Transform-1), ClinicalTrials.gov, Apr. 15, 2015, Esketamine, NCT02417064.

Janssen Research & Development, LLC., A Study to Evaluate the Efficacy, Safely, and Tolerability of Intranasal Esketamine Plus an Oral Antidepressant in Elderly Participants With Treatment-resistant Depression (Transform-3), ClinicalTrials.gov, Apr. 21, 2015, Esketamine, NCT02422186.

Janssen Research & Development, LLC., A Study to Evaluate the Pharmacokinetics of Intranasal Esketamine Administered With and Without a Nasal Guide on the Intranasal Device, ClinicalTrials.gov, Feb. 12, 2014, Esketamine, NCT02060929.

(56) References Cited

OTHER PUBLICATIONS

Janssen Research & Development, LLC., A Study to Evaluate the Safety and Efficacy of Intranasal Esketamine in Treatment resistant Depression (Synapse), ClinicalTrials.gov, Dec. 3, 2013, Esketamine, NCT01998958.
Janssen Research & Development, LLC., A Study to Investigate Evoked Potentials as Markers of Ketamine-induced Cortical Plasticity in Patients With Major Depressive Disorder, ClinicalTrials. gov, Oct. 8, 2013, Ketamine, NCT01957410.
Janssen Research & Development, LLC., Crossover Study to Evaluate the Abuse Potential of Intranasal Eskelamine Compared to Racemic Intravenous Ketamine in Nondependent, Recreational Drug Users, ClinicalTrials.gov, Feb. 15, 2016, Esketamine, NCT02682225.
Janssen Research & Development, LLC., Pharmacokinetic Study of Intranasal Esketamine and Its Effects on the Pharmacokinetics of Orally-Administered Midazolam and Bupropion in Healthy Participants, ClinicalTrials.gov, Oct. 5, 2015, Esketamine, NCT02568176.
Janssen Research & Development, LLC., Study to Assess the Effects of Allergic Rhinitis and Co-administration of Mometasone or Oxymetazoline on the Pharmacokinetics, Safety, and Tolerability of Intranasal Esketamine, ClinicalTrials.gov, Jun. 3, 2014, Esketamine, NCT02154334.
Janssen Research & Development, LLC., Study to Assess the Effects of Esketamine on Safety of On-road Driving in Healthy Participants (Drive Safe), ClinicalTrials.gov, Aug. 28, 2014, Esketamine, NCT02228239.
Janssen Research & Development, LLC., The Effect of Minocycline on Relapse After Successful Intravenous Ketamine/Minocycline induced Symptoms Response in Subjects With Depression, ClinicalTrials.gov, Mar. 12, 2013, Ketamine, NCT01809340.
Jason McMullan., Intranasal Ketamine as an Adjunct to Fentanyl for the Prehospital Treatment of Acute Traumatic Pain, ClinicalTrials. gov, Aug. 15, 2016, Ketamine, NCT02866071.
Javelin Pharmaceuticals, Safety and Efficacy of Intranasal Ketamine for the Treatment of Postoperative Dental Pain, ClinicalTrials.gov, Jun. 20, 2001, Ketamine, NCT00488787.
Javelin Pharmaceuticals., Absolute Bioavailability arid Nasopharyngeal Absorption of Intranasal Ketamine, ClinicalTrials.gov, Aug. 23, 2007, ketamine, NCT00520169.
Javelin Pharmaceuticals., Assessing the Effects of a Nasal Corticosteroid on PMI-150 (Intranasal Ketamine), ClinicalTrials.gov, Apr. 21, 2008, Ketamine, NCT00662883.
Javelin Pharmaceuticals., Determination of Drug Interactions of Certain Nasal Medications With Intranasal Ketamine, ClinicalTrials. gov, Aug. 23, 2007, Ketamine, NCT00520104.
Javelin Pharmaceuticals., Multiple Dose Pharmacokinetics of Intranasal Ketamine, ClinicalTrials.gov, Aug. 23, 2007, Ketamine, NCT00519987.
Jevtovic-Todorovic, V., Carter, L.B., 2005. The anesthetics nitrous oxide and ketamine are more neurotoxic to old thar to young rat brain. Neurobiology of Aging. 26, 947-956.
Jick, et al., Antidepressants and the Risk of Suicidal Behaviors, JAMA, Jul. 21, 2004, pp. 338-343, vol. 292 Issue 3.
Johansson J. et al., "Prehospital analgesia using nasal administration of S-ketamine—a case series", Scandinavian Journal of Trauma, Resuscitation and Emergency Medicine, Biomed Central LTD, London UK, vol. 21, No. 38, May 14, 2013 (May 14, 2013), pp. 1-4.
Johnson & Johnson Pharmaceutical Research & Development, L.L.C., The Effect of Ketamine on Attentiveness, ClinicalTrials.gov, Jul. 19, 2010, Ketamine, NCT01165294.
Jokinen, et al., Karolinska Interpersonal Violence Scale Predicts Suicide in Suicide Attempters, J Clin Psychiatry, Mar. 16, 2010, pp. 1025-1032, vol. 71 Issue 8.
Jonkman, et al., Pharmacokinetics and Bioavailability of Inhaled Esketamine in Healthy Volunteers., Anesthesiology, 2017, pp. 675-683, vol. 127 Issue 4.
Journal of Clinical and Experimental Medicine (Igaku No Ayumi), 2006, vol. 219, No. 13, p. 949-953.
JP63002932 A English Translation, Jan. 1988, Translated Jan. 30, 2015.
Juvenile Bipolar Research Foundation., Intranasal Ketamine in the Treatment of Pediatric Bipolar Disorder (IKBP), ClinicalTrials.gov, Jan. 5, 2012, Ketamine, NCT01504659.
Kallmunzer, et al., Treatment escalation in patients not responding to pharmacotherapy, psychotherapy, and electro-convulsive therapy: experiences from a novel regimen using intravenous S-ketamine as add—0n therapy in treatment-resistant depression, J Neural Transm, Dec. 31, 2015, pp. 549-552, vol. 123.
Kane, et al., Clozapine and Haloperidol in Moderately Refractory Schizophrenia, Arch Gen Psychiatry, Mar. 22, 2001, pp. 965-972, vol. 58.
Kapur, et al., Ketamine Has Equal Affinity for NMDA Receptors and the High-Affinity State of the Dopamine 02 Receptor, Biol Psychiatry, 2001, pp. 954-957, vol. 49.
Kapur, et al., Psychiatric inpatient care and suicide in England, 1997 to 2008: a longitudinal study, Psychological Medicine, Jun. 24, 2013, pp. 61-71, vol. 43 Issue 1.
Kaul, et al., *Homo sapiens* chromosome 3 clone RP11-466A13, Complete Sequence, GenBank, 2002, pp. 1-40, AC099753.
Keller, Issues in Treatment-Resistant Depression, J Clin Psychiatry, 2005, pp. 5-12, vol. 66 Supplement 8.
Kellner, et al., Relief of Expressed Suicidal Intent by ECT: A Consortium for Research in ECT Study, Am J Psychiatry, 2005, pp. 972-982, vol. 162 Issue 5.
Kessler, et al., Lifetime Prevalence and Age-of-Onset Distributions of DSM-IV Disorders in the National Comorbidity Survey Replication, Arch Gen Psychiatry, 2005, pp. 593-602, vol. 62.
Ketalar 10mg/ml Injection; Summary of Product Characteristics (SmPC), Mar. 17, 2020, 8 pages.
Ketamine Hydrochloride Injection, Ketamine Hydrochloride—ketamine hydrochloride injection JHP Pharmaceuticals, LLC, Ketamine Hydrochloride Injection, 2013, pp. 1-17.
Ketanest S, Pfizer, Fachinformation, Jan. 2019, 5 pages.
KK Women's and Children's Hospital, S Ketamine Use in Total Abdominal Hysterectomy (SKET), ClinicalTrials.gov, Sep. 7, 2015, S Ketamine, NCT02543385.
KK Women'S and Children'S Hospital, Use of S+Ketamine During Target-Controlled Intravenous Anaesthesia After Abdominal Hysterectomy, ClinicalTrials.gov, Jul. 27, 2017, Esketamine, NCT03231683.
Kollmar, et al., Ketamine followed by memantine for the treatment of major depression, Correspondence, 2008, pp. 1-1.
Kosel, Study of Depression-Ketamine-Brain Function, ClinicalTrials. gov, Jun. 3, 2010, Ketamine, NCT01135758.
Kron, Miriam: Brain activity mapping in Mecp2 mutant mice reveals functional deficits in forebrain circuits, including key nodes in the default mode network, that are reversed with ketamine treatment; Journal of Neuroscience (2012), 32; (40), 13860-13872.
Krystal, et al., Comparative and Interactive Human Psychopharmacologic Effects of Ketamine and Amphetamine, Arch Gen Psychiatry, Mar. 18, 2005, pp. 985-995, vol. 62.
Krystal, et al., Glutamate and GABA systems as targets for novel antidepressant and mood-stabilizing treatments, Molecular Psychiatry, 2002, pp. S71-S80, vol. 7.
Krystal, et al., Interactive effects of subanesthetic ketamine and haloperidol in healthy humans, Psychopharmacology, Feb. 23, 1999, pp. 193-204, vol. 145.
Krystal, et al., Interactive effects of subanesthetic ketamine and subhypnotic lorazepam in humans, Psychopharmacology, 1998, pp. 213-229, vol. 135.
Krystal, et al., Preliminary evidence of attenuation of the disruptive effects of the NMDA glutamate receptor antagonist, ketamine, on working memory by pretreatment with the group II metabotropic glutamate receptor agonist, LY354740, in healthy human subjects, Psychopharmacology, 2005, pp. 303-309, vol. 179.
Krystal, et al., Subanesthetic Effects of the Noncompetitive NMDA Antagonist, Ketamine, in Humans, Arch Gen Psychiatry, 1994, pp. 199-214, vol. 51.
Kudoh, et al., Small-Dose Ketamine Improves the Postoperative State of Depressed Patients, Anesth Analg, Mar. 12, 2002, pp. 114-118, vol. 95.
Lai, et al., Pilot dose—response trial of i.v. ketamine in treatment-resistant depression, The World Journal of Biological Psychiatry, Jun. 9, 2014, pp. 579-584, vol. 15.

(56) References Cited

OTHER PUBLICATIONS

Lally, et al., Neural correlates of change in major depressive disorder anhedonia following open-label ketamine, J Psychopharmacol, 2015, pp. 596-607, vol. 29 Issue 5.

Lamothe., Ketamine for Treatment-resistant Depression: A Multicentric Clinical Trial in Mexican Population, ClinicalTrials.gov, Jun. 5, 2013, Ketamine, NCT01868802.

Lapidus, et al., A Randomized Controlled Trial of Intranasal Ketamine in Major Depressive Disorder, Biol Psychiatry, Dec. 15, 2014, pp. 970-976, vol. 76 Issue 12.

Lapidus, et al., In Vivo Proton Magnetic Resonance Spectroscopy Study of the Relationships Between Lactate, Depression Severity, and Ketamine Treatment in Major Depressive Disorder, Neuropsychopharmacology, 2015, pp. 1-169, Poaste W113.

Lara, et al., Antidepressant, mood stabilizing and procognitive effects of very low dose sublingual ketamine in refractory unipolar and bipolar depression, International Journal of Neuropsychopharmacology, 2013, pp. 2111-2117, vol. 16.

Larkin, et al., A preliminary naturalistic study of low-dose ketamine for depression and suicide ideation in the emergency department, International Journal of Neuropsychopharmacology, May 5, 2011, pp. 1127-1131, vol. 14.

Laughren, Comorbid Mood Disorders and Medical Illness: A Food and Drug Administration Perspective, Biol Psychiatry, 2003, pp. 195-199, vol. 53.

Lavito, "Ketamine is emerging as a popular treatment for depression. New research suggests the drug acts like an opioid", Biotech and Pharmaceuticals, Aug. 29, 2018, pp. 1-5.

Lawson Health Research Institute, Intranasal Ketamine for Procedural Sedation (INK), ClinicalTrials.gov, Jul. 11, 2016, Ketamine, NCT02828566.

Layer, et al., "Antidepressant-like Actions of the Polyamine Site NMDA Antagonist, Eliprodil (SL-82.0715)", Pharmacology Biochemistry and Behavior, 1995, vol. 52, issue 3, 621-627.

Lee, et al., NMDA Receptors Offer More Than One Functionality, Anesth Analg, 2003, pp. 1533-1534, vol. 96.

Lenze, et al., Ninety-six hour ketamine infusion with co-administered clonidine for treatment-resistant depression: a pilot randomized controlled trial, World J Biol Psychiatry, 2016, pp. 230-238, vol. 17 Issue 3.

Levine, et al., Assessment of suicide risk by computer-delivered self-rating questionnaire: preliminary findings, Acta Psychiatr Scand, Feb. 25, 1981, pp. 216-220, vol. 80.

Li, et al., The Effects of Low-Dose Ketamine on the Prefrontal Cortex and Amygdala in Treatment-Resistant Depression: A Randomized Controlled Study, Human Brain Mapping, Jan. 29, 2016, pp. 1080-1090, vol. 37.

Liebrenz, et al., Intravenous ketamine therapy in a patient with a treatment-resistant major depression, Swiss Med Wkly, 2007, pp. 234-236, vol. 137.

Liebrenz, et al., Repeated intravenous ketamine therapy in a patient with treatment-resistant major depression, The World Journal of Biological Psychiatry, Dec. 8, 2009, pp. 640-643, vol. 10 Issue 4.

Lim, Y.Y. et al., (Australian Imaging, Biomarkers and Lifestyle (AIBL) Research Group), "BDNF Val66Met, AB Amyloid and cognitive decline in preclinical Alzheimer's disease", Neurobiol. Aging, Nov. 2013, vol. 34(11), pp. 2457-2464.

Lindefors, et al., Differential effects of single and repeated ketamine administration on dopamine, serotonin and GABA transmission in rat medial prefrontal cortex, Brain Research, Feb. 11, 1997, pp. 205-212, vol. 759.

Lions Gate Hospital, Intra-nasal Ketamine for Analgesia in the Emergency Department (INKA), ClinicalTrials.gov, Sep. 17, 2012, Ketamine, NCT01686009.

Liu, R.Y., Biol. Psychiatry, BDNF Val66Met allele impairs basal and ketamine-stimulated synaptogenesis in prefrontal cortex, 2012, vol. 71 (11), pp. 996-1005.

Liu, Xing-qing; Hu, Xu-dong; Zhang, Wen-li; Ling, Chen; Lin, Jin-bing; Du, Shun-yan, Influence of preinjection of small dose ketamine on Edinburgh postnatal depression scale of cesarean section women, Guangdong Yixue (2013), 34(12), 1917-1919 (Abstract).

Lodge, et al., Ketamine and phencyclidine: the good, the bad and the unexpected, British Journal of Pharmacology, Jun. 3, 2015, pp. 4254-4276, vol. 172.

Logan, et al., Immobilizing Wild Mountain Lions (Felis Concolor) with Ketamine hydrochloride and Xylazine Hydrochloride, Journal of Wildlife Diseases, 1986, pp. 97-103, vol. 22 Issue 1.

Loo, et al., Placebo-controlled pilot trial testing dose titration and intravenous, intramuscular and subcutaneous routes for ketamine in depression, Acta Psychiatr Scand, Feb. 22, 2016, pp. 48-56, vol. 134.

Lopez, et al., Use of repeated intravenous ketamine therapy in treatment-resistant bipolar depression with suicidal behavior: a case report from Spain, Therapeutic Advances in Psychopharmacology, 2017, pp. 137-140, vol. 7 Issue 4.

Louon, et al., Sedation with nasal Ketamine and midazolam for cryotherapy in retinopathy of prematurity, British Journal of Ophthalmology, Mar. 17, 1993, pp. 529-530, vol. 77.

Lu, et al., Intravenous ketamine for treatment-refractory depression in medically complex geriatric patients, Am J Geriatr Psychiatry, 2013, pp. S130-S130, Poster No. NR 06.

Lu, Li-ling, Effect of maternal pre-injection of low dose amphetamine on postpartum depression score in cesarean section, Yixue Zongshu (2015), 21 (24), 4570-4572 (Abstract).

Luckenbaugh, et al., Do the dissociative side effects of ketamine mediate its antidepressant effects?, Journal of Affective Disorders, Feb. 18, 2014, pp. 56-61, vol. 159.

Lund University., Racemic Ketamine Versus S-ketamine With Arterial Spin Labeling (ASL)-MRI in Healthy Volunteers, ClinicalTrials. gov, Jan. 10, 2012, S-ketamine, NCT01506921.

Ma, Jingyi: Deep brain stimulation of the medial septum or nucleus accumbens alleviates psychosis-relevant behavior in ketamine-treated rats; Behavioural Brain Research (2014), 266, 174-182.

Malcolm, et al, Efficacy and Safety of Intravenous Low-Dose Ketamine for Treatment of Refractory Depression in a Naturalistic Cohort, Abstract of Malcolm., 2016, pp. 1-2, Poster.

Maler, et al., Memantine inhibits ethanol-induced NMDA receptor up-regulation in rat hippocampal neurons, Brain Research, Jul. 11, 2005, pp. 156-162, vol. 1052.

Manji, et al., Enhancing Neuronal Plasticity and Cellular Resilience to Develop Novel, Improved Therapeutics for Difficult-to-Treat Depression, Biol Psychiatry, Jan. 23, 2003, pp. 707-742, vol. 53.

Murray, et al., Global mortality, disability, and the contribution of risk factors: Global Burden of Disease Study, The Lancet, May 17, 1997, pp. 1436-1442, vol. 349.

Murrough et al: "Dose- and Exposure-Response to Ketamine in Depression", Biological Psychiatry, vol. 70, No. 4, Aug. 1, 2011, pp. e11-e12, XP055610008, New York, NY; US.

Murrough, et al., Antidepressant Efficacy of Ketamine in Treatment-Resistant Major Depression: A Two-Site Randomized Controlled Trial, Am J Psychiatry, Oct. 1, 2013, pp. 1134-1142, vol. 170 Issue 10.

Murrough, et al., Ketamine for rapid reduction of suicidal ideation: a randomized controlled trial, Psychological Medicine, Jul. 14, 2015, pp. 1-10.

Murrough, et al., Ketamine for rapid reduction of suicidal ideation: a randomized controlled trial, Psychological Medicine, Jul. 14, 2015, pp. 1-10, Page Number.

Murrough, et al., Neurocognitive Effects of Ketamine and Association with Antidepressant Response in Individuals with Treatment-Resistant Depression: A Randomized Controlled Trial, Neuropsychopharmacology, 2015, pp. 1084-1090, vol. 40.

Murrough, et al., Rapid and Longer-Term Antidepressant Effects of Repeated. Ketamine Infusions in Treatment-Resistant Major Depression, Biol Psychiatry, Aug. 15, 2015, pp. 250-256, vol. 74 Issue 4.

Murrough, Ketamine for Suicidal Ideation, ClinicalTrials.gov, Jan. 10, 2012, Ketamine, NCT01507181.

Murrough., Continuation Ketamine in Major Depression, ClinicalTrials. gov, Oct. 25, 2007, Ketamine, NCT00548964.

Murrough., Intranasal Ketamine in Treatment-Resistant Depression, ClinicalTrials.gov, Feb. 25, 2011, Ketamine, NCT01304147.

(56) References Cited

OTHER PUBLICATIONS

Murrough., Use of Ketamine to Enhance Electroconvulsive Therapy (ECT) in Depression, ClinicalTrials. gov, Mar. 7, 2011, Ketamine, NCT01309581.

Nakako, Tomokazu: Effects of lurasidone on ketamine-induced joint visual attention dysfunction as a possible disease model of autism spectrum disorders in common marmosets; Behavioural Brain Research (2014), 274, 349-354.

Narita, et al., Role of the NMDA receptor subunit in the expression of the discriminative stimulus effect induced by ketamine, European Journal of Pharmacology, May 29, 2001, pp. 41-46, vol. 423.

Nasal Powder, Package leaflet: Information for the User, Nasal Powder, 2017, pp. 1-6.

National Institute of Mental Health (NIMH), Antidepressant Effects of the Glycine Receptor Antagonist AV-101 (4-chlorokynurenine) in Major Depressive Disorder, ClinicalTrials.gov, Jun. 29, 2015, AV 101 (4-Chlorokynurenine), NCT02484456.

National Institute of Mental Health (NIMH), Neurobiology of Suicide, ClinicalTrials.gov, Sep. 9, 2015, ketamine, NCT02543983.

National Institute of Mental Health (NIMH), The Neurophysiological Effects of Intravenous Alcohol as Potential Biomarkers of Ketamine's Rapid Antidepressant Effects in Major Depressive Disorder, ClinicalTrials.gov, Apr. 24, 2014, Ketamine, NCT02122562.

National Institute of Mental Health (NIMH)., Neuropharmacologic Imaging and Biomarker Assessments of Response to Acute and Repeated-Dosed Ketamine Infusions in Major Depressive Disorder, ClinicalTrials.gov, Feb. 27, 2017, Ketamine, NCT03065335.

National Institute of Mental Health (NIMH)., Rapid Antidepressant Effects of Ketamine in Major Depression, ClinicalTrials.gov, Aug. 2, 2004, Ketamine, NCT00088699.

National Institute of Neurology and Neurosurgery, Mexico., Clinical Trial of the Use of Ketamine it Treatment Resistant Depression, ClinicalTrials.gov, Nov. 20, 2015, Ketamine, NCT02610712.

National Strategy for Suicide Prevention, Goals and Objectives for Action, National Strategy for Suicide Prevention, 2012, pp. 1-184.

Nationwide Children's Hospital., An Open Prospective Trial of IV Ketamine in Suicidal Adolescents, ClinicalTrials.gov, Jan. 29, 2014, Ketamine, NCT02048423.

Neurorx, Inc., NRX-101 for Maintenance of Remission From Severe Bipolar Depression in Patients With Suicidal Ideation (SBD-ASIB), ClinicalTrials.gov, Jan. 10, 2018, NRX-101, NCT03396068.

Neurorx, Inc., NRX100 vs. Placebo for Rapid Stabilization of Acute Suicidal Ideation and Behavior in Bipolar Depression (SevereBD), ClinicalTrials.gov, Jan. 11, 2018, ketamine, NCT03396601.

Neurorx, Inc., NRX101 Glx Biomarker Validation Study (NRX-GLX), ClinicalTrials.gov, Jan. 18, 2018, NRX-101, NCT03402152.

Neurorx, Inc., Sequential Therapy for the Treatment of Severe Bipolar Depression. (Stabil-B), ClinicalTrials.gov, Nov. 28, 2016, Ketamine, NCT02974010.

New York State Psychiatric Institute, NMDA Antagonists in Bipolar Depression, ClinicalTrials.gov, Apr. 17, 2013, ketamine, NCT01833897.

New York State Psychiatric Institute., Investigation of the NMDA Antagonist Ketamine as a Treatment for Tinnitus, ClinicalTrials. gov, Nov. 8, 2017, Ketamine Hydrochloride in saline, NCT03336398.

New York State Psychiatric Institute., Ketamine for Suicidality in Bipolar Depression, ClinicalThals.gov, Sep. 17, 2013, Ketamine, NCT01944293.

New York State Psychiatric Institute., Ketamine in the Treatment of Suicidal Depression, ClinicalTrials.gov, Oct. 4, 2012, Ketamine, NCT01700829.

New York University School of Medicine, Ketamine as a Rapidly-Acting Antidepressant in Depressed Emergency Department Patients, ClinicalTrials.gov, Apr. 8, 2014, Ketamine, NCT02106325.

New York University School of Medicine, Study on the Use of Low Dose Ketamine After Gastric Bypass and Gastrectomy, ClinicalTrials. gov, May 22, 2015, Ketamine, NCT02452060.

Newcomer, et al., Ketamine-induced NMDA Receptor Hypofunction as a Model of Memory Impairment and Psychosis, Neuropsychopharmacology, 1999, pp. 106-118, vol. 20 Issue 2.

Niciu, et al., Ketamine's Antidepressant Efficacy is Extended for at Least Four Weeks in Subjects with a Family History of an Alcohol Use Disorder, International Journal of Neuropsychopharmacology, Jul. 2, 2014, pp. 1-7.

Niciua, et al., Subanesthetic Dose Ketamine Does Not Induce an Affective Switch in Three Independent Samples of Treatment-Resistant Major Depression, Biol Psychiatry, Nov. 15, 2013, pp. 1-3, vol. 74 Issue 10.

Nierenberg, et al., A Comparison of Lithium and T3 Augmentation Following Two Failed Medication Treatments for Depression: A Star*D Report, Am J Psychiatry, Jun. 23, 2006, pp. 1519-1530, vol. 163 Issue 9.

Nierenberg, et al., Suicide risk management for the sequenced treatment alternatives to relieve depression study: applied NIMH guidelines, Journal of Psychiatric Research, Mar. 12, 2004, pp. 583-589, vol. 38.

Nock, et al., Cross-National Analysis of the Associations among Mental Disorders and Suicidal Behavior: Findings from the WHO World Mental Health Surveys, PLoS Medicine, 2009, pp. 1-17, vol. 6 Issue 8.

Nock, et al., Cross-national prevalence and risk factors for suicidal ideation, plans and attempts, The British Journal of Psychiatry, 2008, pp. 98-105, vol. 192.

Nock, et al., Prevalence, Correlates, and Treatment of Lifetime Suicidal Behavior Among Adolescents, JAMA Psychiatry, Nov. 7, 2013, pp. 300-310, vol. 70 Issue 3.

Noppers, I. et al., "Absence of long-term analgesic effect from a short-term S-ketamine infusion on fibromyalgia pain: A randomized, prospective, double blind, active placebo-controlled trial". European J. of Pain. 2011, 942-49, vol. 15.

Northside Clinic, Australia., Ketamine as an Anaesthetic Agent in Electroconvulsive Therapy (ECT), ClinicalTrials.gov, May 20, 2008, Ketamine, NCT00680433.

Northwell Health., Ketamine as an Augmentation Strategy for Electroconvulsive Therapy (ECT) in Depression, ClinicalTrials. gov, Jun. 20, 2013, Ketamine, NCT01881763.

Northwestern University., Postpartum Perineal Pain After Obstetric Anal Sphincter Injuries, ClinicalTrials.gov, Mar. 20, 2018, ketamine, NCT03470675.

O'Connor, et al., Screening for Suicide Risk in Primary Care: A Systematic Evidence Review for the U.S. Preventive Services Task Force, Evidence Synthesis, 2013, pp. 1-126, AHRQ Publication No. 13-05188-EF-1.

Oishi, et al., Effects of propyl paraben on the male reproductive system, Food and Chemical Toxicology, Jul. 7, 2002, pp. 1807-1813, vol. 40, Elsevier Science Ltd.

Oishi, S., Food Chem Toxicol., 2002, pp. 1807-1813, 40(12).

Okamoto et al, Rapid Antidepressant Effect of Ketamine Anesthesia During Electroconvulsive Therapy of Treatment-Resistant Depression, Journal of ECT, 2010, pp. 223-227, vol. 26 Issue 3.

Okayama Igakkai Zasshi (Journal of Okayama Medical Association), 2008, vol. 119, p. 315-317.

Opler, et al., Ameliorating treatment-refractory depression with intranasal ketamine: potential NMDA receptoractions in the pain circuitry representing mental anguish, CNS Spectrums, Jan. 26, 2016, pp. 12-22.

Hospira, Safety and Efficacy of PMI-150 (Intranasal Ketamine) for the Treatment of Breakthrough Pain in Cancer Patients, ClinicalTrials. gov, Jun. 27, 2007, Ketamine, NCT00492388.

Hospital De Clinicas De Porto Alegre., Intranasal Ketamine as a Sedative for Venipuncture, ClinicalTrials.gov, Oct. 11, 2016, Ketamine, NCT02929524.

http://www.pfizer.com/files/products/material safety data/PZ00892. pdf; 2008.

https://en.wikipedia.org/wiki/Esketamine; 2015.

Hu, et al., Single i.v. ketamine augmentation of newly initialed escitalopram for major depression: results from a randomized, placebo-controlled 4-week study, Psychological Medicine, Oct. 19, 2015, pp. 623-635, vol. 46.

Huang, et al., Mechanism of nasal Absorption of Drugs 1: Physicochemical Parameters Influencing the rate of In Situ Nasal Absorption of Drugs in Rats, Journal of Pharmaceutical Science, Feb. 27, 1985, pp. 608-611, vol. 74 Issue 6.

(56) References Cited

OTHER PUBLICATIONS

Huge, et al., Effects of low—dose intranasal (S)-ketamine in patients with neuropathic pai, European Journal of Pain, Sep. 3, 2009, pp. 387-394, vol. 14, Elsevier Ltd.

Hunt, et al., Suicide amongst psychiatric in-patients who abscond from the ward: a national clinical survey, BMC Psychiatry, Feb. 3, 2010, pp. 1-6, vol. 10 Issue 14.

Husain, et al., Speed of Response and Remission in Major Depressive Disorder With Acute Electroconvulsive Therapy (ECT); A Consortium for Research in ECT (CORE) Report, J Clin Psychiatry, 2004, pp. 485-491, vol. 65 Issue 4.

Hustveit, et al., Interaction of the Chiral Forms of Ketamine with Opioid Phencyclidine, and Muscarinic Receptors, Pharmacology & Toxicology, Apr. 25, 1995, pp. 355-359, vol. 77.

Hvidovre University Hospital., Optimal Multimodal Analgesia in Abdominal Hysterectomy, ClinicalTrials.gov, Sep. 21, 2005, S-ketamine, NCT00209872.

Hvidovre University Hospital., Optimal Multimodal Analgesia in Laparoscopic Cholecystectomy, ClinicalTrials. gov, Sep. 21, 2005, S-ketamine, NCT00209885.

Hyman, et al., Initiation and Adaptation : A Paradigm for Understanding Psychotropic Drug Action, Am J Psychiatry, 1996, pp. 151-162, vol. 153.

Ibrahim, et al., Rapid decrease in depressive symptoms with an N-methyl-d-aspartate antagonist in ECT-resistant major depression, Progress in Neuro-Psychopharmacology & Biological Psychiatry, Apr. 3, 2011, pp. 1155-1159, vol. 35.

Icahn School of Medicine at Mount Sinai, Ketamine and Nitroprusside for Depression, ClinicalTrials.gov, Apr. 6, 2017, Ketamine, NCT03102736.

Icahn School of Medicine at Mount Sinai, Ketamine Plus Lithium in Treatment-Resistant Depression, ClinicalTrials.gov, Jun. 19, 2013, Ketamine, NCT01880593.

Icahn School of Medicine at Mount Sinai, Treatment Study of Bipolar Depression, ClinicalTrials.gov, Jul. 28, 2009, ketamine, NCT00947791.

Icahn School of Medicine at Mount Sinai., MRI Studies of Emotion in Depression, ClinicalThals.gov, Apr. 29, 2015, ketamine, NCT02429011.

Iglewicz, et al., Ketamine for the Treatment of Depression in Patients Receiving Hospice Care: A Retrospective Chart Review of Thirty-One Cases, Psychosomatics., 2015, pp. 329-337, vol. 56 Issue 4.

Ingrid Torjesen., Ketamine helps a third of patients with treatment resistant depression, finds small UK study, BMJ, Apr. 3, 2014, pp. g2576-g2576, vol. 348.

Inonu University., Effect of the Addition of Ketamine to Sevoflurane Anesthesia in Electroconvulsive Therapy, ClinicalTrials.gov, Oct. 20, 2014, Ketamine, NCT02267980.

Inonu University., Effects of Sevoflurane and Ketamine on QT in Electroconvulsive Therapy, ClinicalTrials.gov, Jun. 6, 2013, Ketamine, NCT01870219.

Instituto Mexicano Del Seguro Social., Effect of Ketamine in Depressive Symptoms of Elderly Patients With Visual Impairment, ClinicalTrials.gov, Mar. 22, 2018, Ketamine, NCT03473431.

International Preliminary Report on Patentability received for PCT Patent Application No. PCT/US13/30476, dated Sep. 25, 2014, 11 pages.

International Preliminary Report on Patentability received for PCT Patent Application No. PCT/US14/27074, dated Sep. 24, 2015, 7 pages.

International Preliminary Report on Patentability received for PCT Patent Application No. PCT/US2016/033404, dated Nov. 30, 2017, 8 pages.

International Search Report and Written Opinion received for PCT Patent Application No. PCT/US13/30476, dated Apr. 24, 2013, 11 pages.

International Search Report and Written Opinion received for PCT Patent Application No. PCT/US14/27074, dated May 27, 2014, 9 pages.

International Search Report and Written Opinion received for PCT Patent Application No. PCT/US2016/033404, dated Aug. 16, 2016, 9 pages.

International Search Report re: PCT/EP2016/060922 dated Jul. 28, 2016.

International Search Report re: PCT/US2014/027059 dated Jul. 16, 2014.

International Search Report re: PCT/US2015/049961 dated Jan. 12, 2016.

International Search Report re: PCT/US2015/44830 dated Nov. 23, 2015.

Ionescu, et al., Effect of Baseline Anxious Depression on Initial and Sustained Antidepressant Response to Ketamine, J Clin Psychiatry, 2014, pp. e932-e938, vol. 75 Issue 9.

Ionescu, et al., Rapid and Sustained Reductions in Current Suicidal Ideation Following Repeated Doces of Intravenous Ketamine:, J Clin Psychiatry, 2016, pp. e1-e7.

Irwin, et al., Daily Oral Ketamine for the Treatment of Depression and Anxiety in Patients Receiving Hospice Care: A 28-Day Open-Label Proof-of-Concept Trial, Journal of Palliative Medicine, 2013, pp. 958-965, vol. 16 Issue 8.

Irwin, et al., Oral Ketamine for the Rapid Treatment of Depression and Anxiety in Patients Receiving Hospice Care, Journal of Palliative Medicine, Jan. 13, 2010, pp. 903-908, vol. 13 Issue 7.

Irwin, MD, PHO., Study of Oral Ketamine Versus Placebo for Treating Depression in Patients Undergoing Treatment for Cancer, ClinicalTrials.gov, Jul. 19, 2016, Ketamine, NCT02836288.

Isometsa, et al., Suicide in Major Depression, Aml Psychiatry, 1994, pp. 530-536, vol. 151 Issue 4.

Ivanova, "Optimality, sample size, and power calculations for the sequential parallel comparison design", Stal. Med., 2011, 30(23), 2793-2803.

Jafarinia, et al., Efficacy and safety of oral ketamine versus diclofenac to alleviate mild to moderate depression in chronic pain patients: A double-blind, randomized. Controlled trial, Journal of Affective Disorders, Jun. 1, 2016, pp. 1-8, vol. 204.

Janicak, et al., Ketamine Treatment for Major Depression, Psychopharm Review, 2011, pp. 89-96, vol. 46 Issue 12.

Janssen Pharmaceutical K.K., A Study to Evaluate the Efficacy, Safety and Tolerability of Fixed Doses of Intranasal Esketamine in Japanese Participants With Treatment Resistant Depression, ClinicalTrials.gov, Sep. 28, 2016, Esketamine, NCT02918318.

Janssen Research & Development, LLC, A double-blind study to assess the efficacy and safety of intranasal Esketamine for the rapid reduction of the symptoms of major for the rapid reduction of the symptoms, ClinicalTrials.gov, Jun. 23, 2014, NCT02133001.

Janssen Research & Development, LLC, A Double-blind Study to Assess the Efficacy and Safety of Intranasal Esketamine for the Rapid Reduction of the Symptoms of Major Depressive Disorder, Including Suicidal Ideation, in Participants Who Are Assessed to be at Imminent Risk for Suicide, ClinicalTrials.gov, May. 7, 2014, Esketamine, NCT02133001.

Janssen Research & Development, LLC, A Long-term, Safety and Efficacy Study of Intranasal Esketamine in Treatment-resistant Depression (Sustain-2), ClinicalTrials.gov, Jul. 14, 2015, Esketamine, NCT02497287.

Janssen Research & Development, LLC, A Mass Balance Study With a Microtracer Dose of 14C-esketamine in Healthy Male Participants, ClinicalTrials.gov, Feb. 4, 2016, Esketamine, NCT02674295.

Janssen Research & Development, LLC, A Study of Intranasal Esketamine Plus an Oral Antidepressant for Relapse Prevention in Adult Participants With Treatment-resistant Depression (Sustain-1), ClinicalTrials.gov, Jul. 10, 2015, Esketamine, NCT02493868.

Janssen Research & Development, LLC, A Study of the Efficacy and Safety of Intranasal Esketamine in the Rapid Reduction of Symptoms of Major Depressive Disorder, in Adult at Imminent Risk for Suicide (Aspire I), ClinicalTrials.gov, Feb. 1, 2017, Esketamine, NCT03039192.

Janssen Research & Development, LLC, A Study of the Efficacy of Intravenous Esketamine in Adult Patients With Treatment-Resistant Depression, ClinicalTrials.gov, Jul. 13, 2012, Esketamine, NCT01640080.

(56) References Cited

OTHER PUBLICATIONS

Zarate, National Institute of Mental Health, Brain & Behavior Research Foundation Webinar, Ketamine & Next Generation Therapies With Rapid Antidepressant Effects, Aug. 13, 2013, 47 pages.
Zhang, Li-Ming: Anxiolytic effects of ketamine in animal models of posttraumatic stress disorder; Psychopharmacology (Heidelberg, Germany) (2015), 232 (4), 663-672 Sep. 18, 2014.
Zhang, X., Boulton, A.A., Zuo, D.M., Yu, P.H., 1996. MK-801 induces apoptotic neuronal death in the rat retrosplenial cortex: prevention by cycloheximide and R(-)-2-hexyl-methylpropargylamine. J._ Neurosc. Res. 46, 82-89.
Zhong, et al, Mood and neuropsychological effects of different doses of ketamine in electroconvulsive therapy for treatment-resistant depression, Journal of Affective Disorders, May 12, 2016, pp. 124-130, vol. 201.
Zou, et al, Potential Neurotoxicity of Ketamine in the Developing Rat Brain, Toxicological Sciences, Dec. 6, 2009, pp. 149-158, vol. 108 Issue 1.
Correll, et al., Two Case Studies of Patients with Major Depressive Disorder Given Low-Dose (Subanesthetic) Ketamine Infusions, Pain Medicine, 2006, pp. 92-95, vol. 7 Issue 1.
Corso, et al., Medical Costs and Productivity Losses Due to Interpersonal and Self-Directed Violence in the United States, Am J Prev Med, 2007, pp. 474-482, vol. 32 Issue 6.
Corssen, et al., Computerized Evaluation of Psychic Effects of Ketamine, Anesthesia & Analgesia, 1971, pp. 397-401, vol. 50 Issue 3.
Corwin Boake., Historical Note Edouard Claparede and the Auditory Verbal Learning Test, Journal of Clinical and Experimental Neuropsychology, Oct. 18, 2000, pp. 286-292, vol. 22 Issue 2.
Crosby, et al., Suicidal Thoughts and Behaviors Among Adults Aged greater than & equal 18 Years—United States, 2008-2009, Centers for Disease Control and Prevention, Oct. 21, 2011, pp. 1-28, vol. 60 Issue 13.
Cusin, et al., Ketamine augmentation for outpatients with treatment-resistant depression: Preliminary evidence for two-step intravenous dose escalation, Australian & New Zealand Journal of Psychiatry, 2016, pp. 1-10.
Cusin, et al., Long-Term Maintenance With Intramuscular Ketamine for Treatment-Resistant Bipolar II Depression, Am J Psychiatry, 2012, pp. 868-867, vol. 169 Issue 8.
D'Sa, et al., Antidepressants and neuroplasticity, Bipolar Disorders, Feb. 1, 2002, pp. 183-194, vol. 4.
Daly Ella et al: "Intranasal Esketamine, 'in Treatment-resistant Depression, a Dose Response Study—Double Blind and Open Label Extension Data", Neuropsychopharmacology, vol. 40, No. Suppl. 1, Dec. 1, 2015, S340-5341, *abstract*.
Daly et al, "Intranasa 1 Esketamine, 'in Treatment-resistant Depression, a Dose Response Study—Double Blind and Open Label Extension Data", Neuropsychopharmacology, Elsevier Science Publishing, New York, NY, US, vol. 40, No. Suppl. 1, Dec. 1, 2015 (Dec. 1, 2015), S340-S341, XP009509885, pp. ISSN: 0893-133X abstract*.
Daly et al., "Intranasal, Esketamine in Treatment Resistant Depression—A Double-blind, Randomized, Efficacy and Dose Response Study", Biological Psychiatry, vol. 79, No. 9, Suppl. s, May 1, 2016, pp. 206S-207S, 71st Annual Scientific Convention and Meeting of the Society-of-Biological-Psychiatry (SOBP); Atlanta, GA, USA; May 12-14, 2016.
Daly, et al., Efficacy and Safety of Intranasal Esketamine Adjunctive to Oral Antidepressant Therapy in Treatment-Resistant Depression A Randomized Clinical Trial, JAMA Psychiatry, 2018, pp. 139-148, vol. 75 Issue 2.
Daly, et al., ESKETINTRD3003 ASCP Pipeline Presentation, Janssen Research & Therapeutic Area, May 29, 2018, pp. 1-21.
Danish University of Pharmaceutical Sciences., Nasal Administration of Sufentanil+Ketamine for Procedure-related Pain in Children, ClinicalTrials.gov, Jan. 12, 2010, Ketamine, NCT01047241.
Daros, "A repeated measures model for analysis of continuous outcomes in sequential parallel comparison design studies", Stat. Med., 2013, 32(16), 2767-2789.
Database Medline [Online] US National Library of Medicine (NLM), Bethesda, MD, US; Sep. 2010 (Sep. 2010), Okamoto Nagahisa et al: "Rapid antidepressant effect of ketamine anesthesia during electroconvulsive therapy of treatment-resistant depression: comparing ketamine and propofol anesthesia.", Database accession No. NLM19935085 abstract & The Journal of ECT Sep. 2010, vol. 26, No. 3, Sep. 2010 (Sep. 2010), pp. 223-227.
Davidson, et al., Anesthesia and neurotoxicity to the developing brain: the clinical relevance, Pediatric Anesthesia, 2011, pp. 716-721, vol. 21.
Dawn., Drug Abuse Warning Network, 2011: National Estimates of Drug-Related Emergency Department Visits, National ED Estimates, 2011, pp. 1-100, page number.
De Olmos, S., Bueno, A., Bender, C., Lorenzo, A., de Olmos, J., 2008. Sex differences and influence of gonadal hormones on MK 801-induced neuronal degeneration in the granular retrosplenial cortex of the rat. Brain Struct. Funct. 213, 229-238.
DE102007009888 A1 English Translation, Sep. 2008; Translated Jan. 26, 2015.
Deakin, et al., PharmacoMRI and cognitive effects of the potential antidepressant AZD6765 compared with ketamine in untreated major depressive disorder, Affective disorders and antidepressants— Antidepressants (clinical), 2012, pp. S264-S264, Abstract.
Debattista, et al., Acute Antidepressant Effects of Intravenous Hydrocortisone and CRH in Depressed Patients: A Double-Blind, Placebo-Controlled Study, Am J Psychiatry, Mar. 2, 2000, pp. 1334-1337, vol. 157 Issue 8.
Deisenhammer, et al., How Much Time Is Left for Intervention Between Consideration and Accomplishment of a Suicide Attempt?, J Clin Psychiatry, Mar. 25, 2008, pp. 19-24, vol. 70 Issue 1.
Denk, et al., Figure 1. Western Blot Analysis of Peripheral Blood Cells in a Study of (S)-Ketamine infusion for the Treatment of Depressive Symptoms, Letters to the Editor, 2011, pp. 1-2.
Dennis Charney, Ketamine as a Rapid Treatment for Post-traumatic Stress Disorder (PTSD) (KetPTSD), ClinicalTrials.gov, Sep. 9, 2008, Ketamine, NCT00749203.
Dewilde, et al., The promise of ketamine for treatment-resistant depression: current evidence and future directions, Ann. N.Y. Acad. Sci, 2015, pp. 1-11.
Dhakar et al., "A review on factors affecting the design of nasal drug delivery system," International Journal of Drug Delivery, vol. 3, 2011, pp. 194-208.
Diamond, et al., Ketamine infusions for treatment resistant depression: a series of 28 patients treated weekly or twice weekly in an ECT clinic, Journal of Psychopharmacology, 2014, pp. 536-544, vol. 28 Issue 6.
Diaz, et al., Ineffectiveness of Repeated Intravenous Ketamine Infusions in Treatment-Resistant Depression After a Post-Ketamine Relapse: Time for a Rethink?, Journal of Clinical Psychopharmacology, 2018, pp. 1-2.
Diazgranados et al, Rapid Resolution of Suicidal ideation After a Single Infusion of an N-Methyl-D Aspartate Antagonist in Patient With Treatment-Resistant Major Depressive Disorder, J Clin Psychiatry, 2010, pp. 1605-1611, vol. 71, Issue 12.
Diazgranados et al., A randomized add-on trial of an N-methyl-D-aspartate antagonist in treatment-resistant bipolar depression. Archives of general psychiatry 67, 2010, pp. 793-802.
Diazgranados, N. et al., J. Clin Psychiatry, 2010; 71(12), pp. 1605-1611.
Djupesland, et al., Breath Powered Nasal Delivery: A New Route to Rapid Headache Relief, Headache, Jun. 4, 2013, pp. 72-84, vol. 53 Supplementary 2.
Djupesland., Nasal drug delivery devices: characteristics and performance in a clinical perspective—a review, Drug Deliv. and Transl. Res, Oct. 18, 2012, pp. 1-21.
Domino, et al., Pharmacologic effects of CI-581, a new dissociative anesthetic, in man, Clinical Pharmacology and Therapeutics, Jan. 1, 1965, pp. 279-291, vol. 6 Issue 3.
Donn W Ketcham MD., Where there is no anaesthesiologist; the many usus of ketamine, Tropical Doctor, 1990, pp. 163-166, vol. 20.

(56) References Cited

OTHER PUBLICATIONS

Dougals, et al., Practice Guideline for the Assessment and Treatment of Patients With Suicidal Behaviors, American Psychiatric Association Practice Guidelines, Jul. 28, 2003, pp. 1-120.
Draft Guidance., Guidance for Industry Suicidal Ideation and Behavior: Prospective Assessment of Occurrence in Clinical Trials, Clinical/Medical, 2012, pp. 1-16, Revision 1.
Drevets, et al., Amphetamine-Induced Dopamine Release in Human Ventral Striatum Correlates with Euphoria, Biol Psychiatry, 2001, pp. 81-96, vol. 49.
Duffy, S., "Esketamine Nasal Spray NDA Submitted to FDA for Treatment-Resistant Depression," Psychiatry Advisor, Retrived at https://www.psychiatryadvisor.com/home/topics/mood-disorders/depressive-disorder/esketamine-nasal-spray-nda-submitted-to-fda-for-treatment-resistant-depression, Sep. 5, 2018, pp. 5.
Duman, et al., Synaptic Dysfunction in Depression: Potential Therapeutic Targets, Science, Oct. 5, 2012, pp. 68-72, vol. 338.
Duman, et al., Synaptic plasticity and mood disorders, Molecular Psychiatry, 2002, pp. 1-11, vol. 7 Issue 1.
Duncan, et al., Baseline delta sleep ratio predicts acute ketamine mood response in major depressive disorder, Journal of Affective Disorders, Aug. 5, 2012, pp. 115-119, vol. 145.
Elie Dolgin., The Ultimate Endpoint, Nature Medicine, 2012, pp. 190-194, vol. 18 Issue 2.
Ellioti, et al., N-Methyl-D-Aspartate (NMDA) Receptors, Mu and Kappa Opioid Tolerance, and Perspectives on New Analgesic Drug Development, Neuropsychopharmacology., May 3, 1995, pp. 347-356, vol. 13 Issue 4.
Emory University., Heart Rate Variability in Depression, ClinicalTrials.gov, Aug. 18, 2015, Depressive Disorder, NCT02525978.
Emory University., Intranasal (NAS) Ketamine for Cancer Pain, ClinicalTrials.gov, May 10, 2017, Ketamine, NCT03146806.
Entsuah, et al., Response and Remission Rates in Different Subpopulations With Major Depressive Disorder Administered Venlafaxine, Selective Serotonin Reuptake Inhibitors, or Placebo, J Clin Psychiatry, 2001, pp. 869-877, vol. 62 Issue 11.
Erasme University Hospital, Respiratory Depression During an Analog sedation Combining Remifentanil and Ketamine in TCI for Oocyte Retrieval, ClinicalTrials.gov, Mar. 8, 2018, ketamine, NCT03458143.
Essentia Health., Ketamine Frequency Treatment for Major Depressive Disorder, ClinicalTrials.gov, Mar. 28, 2008, Ketamine, NCT00646087.
A Double-blind Study to Assess the Efficacy and Safety of Intranasal Esketamine for the Rapid Reduction of the Symptoms of Major Depressive Disorder, Including Suicidal Ideation, in Participants Who Are Assessed to be at Imminent Risk for Suicide, submitted May 6, 2014 (v1), NCT02133001.
A Study to Evaluate the Safety and Efficacy of Intranasal Esketamine in Treatment-resistant Depression (Synapse), submitted Nov. 25, 2013 (v1); Feb. 14, 2014 (v2); Mar. 18, 2014 (v3), National Clinical Identifier (NCT)01998958.
AACAP Official Action., Practice Parameter for the Assessment and Treatment of Children and Adolescents With Suicidal Behavior, J. Am. Acad. Child Adolesc. Psychiatry, 2001, pp. 24S-51S, vol. 40 Supplementary 7.
Abdallah et al.," ECT Attenuates the Rapid Antidepressant Effect of Ketamine", Biol Psychiatry, 2012, vol. 71, pp. 294S.
Abdallah, et al., Hippocampal volume and the rapid antidepressant effect of ketamine, Journal of Psychopharmacology, 2015, pp. 591-595, vol. 29 Issue 5.
Abdallah, et al., Ketamine Treatment and Global Brain Connectivity in Major Depression, Neuropsychopharmacology, 2017, pp. 1210-1219, vol. 42.
Abdallah, et al., The Nucleus Accumbens and Ketamine Treatment in Major Depressive Disorder, Neuropsychopharmacology, Mar. 29, 2017, pp. 1739-1746, vol. 42.
Abdallah, et al., The Rapid Antidepressant Effect of Ketamine in the Electroconvulsive Therapy Setting, J ECT, 2012, pp. 157-161, vol. 28 Issue 3.
Adhvaryu, et al., Short Communication Genotoxic efforts of Ketamine on CHO cells, Arch Toxicol, Apr. 3, 1986, pp. 124-125, vol. 59.
Ahlander, Neuropsychopharmacol, 1999, 21, 414-426.
Ahn, et al., Proliposomes as an intranasal dosage form for the sustained delivery of propranolol, Journal of Controlled Release, Oct. 13, 1994, pp. 203-210, vol. 34.
Aiphs, et al., Comparative Validation of the ISST-Plus, the S-STS, and the C-SSRS for Assessing Suicidal Thinking and Behavior When Mapped to C-CASA (2010), Janssen Scientific Affairs, LLC, 2012, pp. 1-1, Poster.
Aitken, et al., Section of Measurement in Medicine., Proc. Roy. Soc. Med., 1969, pp. 989-993, vol. 62.
Al Shirawi, et al., Oral Ketamine in Treatment-Resistant Depression A Clinical Effectiveness Case Series, J Clin Psychopharmacol, 2017, pp. 464-467, vol. 37 Issue 4.
Albott, et al., Neurocognitive Effects of Repeated Ketamine Infusions in Co-Occurring Posttraumatic Stress Disorder and Treatment-Resistant Depression, Biological Psychiatry, May 15, 2017, pp. S405-S405, vol. 81.
Alessandri, et al., Effects of Ketamine on Tunnel Maze and Water Maze Performance in the Rat, Behavioral and Neural Biology, 1989, pp. 194-212, vol. 52.
Aligeti, et al., Rapid Resolution of Suicidal Behavior and Depression With Single Low-Dose Ketamine Intravenous Push Even After 6 Months of Follow-Up, Journal of Clinical Psychopharmacology, 2014, pp. 533-535, vol. 34 Issue 4.
Alison Goate, Changing the Equation for Alzheimer's, Mount Sinai Science & Medicine, 2018, pp. 1-11.
Alizadeh, et al., Antidepressant Effect of Combined Ketamine and Electroconvulsive Therapy on Patients With Major Depressive Disorder: A Randomized Trial, Iran J Psychiatry Behav Sci, Sep. 23, 2015, pp. e1573-e1578, vol. 9 Issue 3.
Allen, et al., Screening for Suicidal Ideation and Attempts among Emergency Department Medical Patients: Instrument and Results from the Psychiatric Emergency Research Collaboration, Suicide and Life-Threatening Behavior, 2013, 43(3):313-23.
Allen, et al., Serum BDNF as a peripheral biomarker of treatment-resistant depression and the rapid antidepressant response: A comparison of ketamine and ECT, Journal of Affective Disorders, Jul. 29, 2015, pp. 306-311, vol. 186.
Alosh, et al., A consistency-adjusted alpha-adaptive strategy for sequential testing, Statistics in Medicine, Apr. 8, 2010, pp. 1559-1571, vol. 29.
Alphs L, et al., Validation of Suicidal Ideation and Behavior Assessment Tool (SIBAT): Intra-and Inter-rater Reliability, European Symposium on Suicide & Suicidal Behavior (ESSSB), 2018, pp. 1-1 Poster 222.
Amercian Association of Suicidology., Facts About Suicide and Depression, American Association of Suicidology, 2010, pp. 1-4.
American Pharmaceutical Review., Controlled Release Roundtable, Lonza, Jun. 30, 2017, pp. 1-10.
Anand, et al., Attenuation of the Neuropsychiatric Effects of Ketamine With Lamotrigine., Arch Gen Psychiatry., 2000, pp. 270-276, vol. 57.
Anderson, et al., Evidence-based guidelines for treating depressive disorders with antidepressants: A revision of the 2000 British Association for Psychopharmacology guidelines, Journal of Psychopharmacology, 2008, pp. 343-396, vol. 22 Issue 4.
Anderson, et al., Ketamine augmentation of electroconvulsive therapy to improve neuropsychological and clinical outcomes in depression (Ketamine-ECT): a multicentre, double-blind, randomised, parallel-group, superiority trial, Lancet Psychiatry, Mar. 27, 2017, pp. 365-377, vol. 4.
Andine, J. Pharmacol. Exp. Ther., 1999,290(3), 1393-1408.
Andrade, et al., Intranasal Drug Delivery in Neuropsychiatry: Focus on Intranasal Ketamine for Refractory Depression, J Clin Psychiatry, 2015, pp. e628-e631, vol. 76 Issue 5.
Angelica Lavito., Ketamine is emerging as a popular treatment for depression. New research suggests the drug acts like an opioid. Biotech and Pharmaceuticals, Aug. 29, 2018, pp. 1-5, N/a.
Angold, et al., Comorbidity, J.Child Psychol. Psychiat, 1999, pp. 57-87, vol. 40 Issue 1.

(56) References Cited

OTHER PUBLICATIONS

Angold, et al., Puberty and depression: the roles of age, pubertal status and pubertal timing, Psychological Medicine, 1998, pp. 51-61, vol. 28.
Angst, et al., Mortality of patients with mood disorders: follow-up over 34-38 years, Journal of Affective Disorders, Apr. 3, 2001, pp. 167-181, vol. 68.
Anna Meuronen, MD., Intranasal Esketamine and Fentanyl for Pain in Minor Trauma, ClinicalTrials.gov, Feb. 5, 2018, Esketamine, NCT03421275.
Anonymous: "NCT02133001 on Jun. 23, 2014; Clinical Trials.gov Archive", pp. 1-6, XP055230128, retrieved on the internet: URL:https://clinicaltrails.gov/archie/NCT02133001/2014-06-23, retrieved on Nov. 20, 2015.
Asarnow, et al., Depression and role impairment among adolescents in primary care clinics, Journal of Adolescent Health, Nov. 4, 2004, pp. 477-483, vol. 37.
Asarnow, et al., Depression in Youth: Psychosocial Interventions, Journal of Clinical Child Psychology, Mar. 14, 2000, pp. 33-47, vol. 30 Issue 1.
Asarnow, et al., Effectiveness of a Quality Improvement Intervention for Adolescent Depression in Primary Care Clinics, JAMA, Jan. 19, 2005, pp. 311-319, vol. 293 Issue 3.
Asarnow, et al., Treatment of Selective Serotonin Reuptake Inhibitor-Resistant Depression in Adolescents: Predictors and Moderators of Treatment Response, J Am Acad Child Adolesc Psychiatry, Sep. 29, 2009, pp. 330-339, vol. 48 Issue 3.
Astrazeneca., Study Where Pharmaco Magnetic Resonance Imaging (MRI) Effects of AZD6765 Will be Comparer to Placebo in Depressive Male and Female Subjects, ClinicalTrials.gov, Jan. 12, 2010, Ketamine, NCT01046630.
Aulton M E: Pharmaceutics, The Science of Dosage Form Design, pp. 254-258; 262-268; 485-490, 1988.
Aulton, Michael: Aulton's Pharmaceutics; Dosage Form Design and Manufacture, 3rd Edition; 2008, pp. 368-369.
Aurora, "Development of Nasal Delivery Systems: A Review", Drug Development and Delivery, vol. 2, No. 7, Oct. 2002.
Ayuso-Mateos, et al., Depressive disorders in Europe: prevalence figures from the ODIN study, British Journal of Psychiatry, Apr. 6, 2001, pp. 308-3016, vol. 179.
Azevedo, et al., Transdermal Ketamine as an Adjuvant for Postoperative Analgesia After Abdominal Gynecological Surgery Using lidocaine Epidural Blockade, Anesth Analg, Aug. 11, 2000, pp. 1479-1482, vol. 91.
Baji, et al., Age and Sex Analyses of Somatic Complaints and Symptom Presentation of Childhood Depression in a Hungarian Clinical Sample, J Clin Psychiatry, 2009, pp. 1467-1472, vol. 70 Issue 10.
Baldessarini, et al., Decreased risk of suicides and attempts during long-term lithium treatment a meta-analytic review, Bipolar Disorders, Mar. 13, 2006, pp. 625-639, vol. 8.
Ballard, et al., Improvement in suicidal ideation after ketamine infusion: Relationship to reductions in depression and anxiety*, Journal of Psychiatric Research, Jul. 31, 2014, pp. 161-166, vol. 58.
Ballard, et al., Neural Correlates of Suicidal Ideation and Its Reduction in Depression, International Journal of Neuropsychopharmacology, 2015, pp. 1-6.
"Label: Afrin Original—oxymetazoline hydrochlorine spray," Oxymetazoline hydrochlorine 0.05%, retrieved from https://dailymed.nlm.nih.gov/dailymed/drugglnfo.cfm?setid=89c165ba-3ad5-49b5-a5bb-423dc8e15bad, Updated Feb. 27, 2023, pp. 6.
"Label: Imipramine Pamote," retrieved from https://dailymed.nlm.nih.gov/dailymed/lookup.cfm?setid=d1ddde497-4424-da7ca6459cf3, Updated May 16, 2023, pp. 24.
"Sprvato™ (esketamine) nasal spray, CII Initial U.S. Approval: 1970 (ketamine)," Highlights of Prescribing Information, 2019, pp. 41.
"ZOLOFT label Zertaline Hydrochlorine tablet label," Highlights of Prescribing Information, 2016, pp. 30.
Allison, "Case study of a client diagnosed with major depressive disorder," Thesis, Rowan University, 2005, pp. 103.
Bahewar et al., "A Comparative Evaluation of Intranasal Midazolam, Ketamine, and their Combination for Sedation of Young Uncooperative Pediatric Dental Patients: A Triple Blind Randomized Crossover Trial," The Journal of clinical pediatric dentistry, vol. 35, Issue 4, 2011, pp. 415-420.
Cetin et al., "Unmet needs in psychiatry and emerging novel pharmacological agents," Klinik Psikofarmakoloji Bulteni-bulletin of Clinical Psychopharmacology, vol. 23, 2013, pp. 199-204.
Declaration of Alan F. Schatzberg, M.D., Under 37 C.F.R. 1.132, Nov. 14, 2013.
Laje et al: "Correspondence Brain-Derived Neutrotrophic Factor Va166Met Polymorphism and Antidepressant Efficacy of Ketamine in Depressed Patients", Biol Psychiatry, vol. 72, No. 11, Dec. 1, 2012 (Dec. 1, 2012), pp. e27-e28.
Letter from Alkem Labroratories Ltd. to Janssen Pharmaceutica NV et al., Apr. 18, 2023, pp. 1-116.
Letter from Hikma Pharmaceuticals USA to Janssen Pharmaceuticals Inc. et al., Apr. 18, 2023, pp. 1-85.
Letter from Sandoz Inc. to Janssen Pharmaceuticals Inc. et al., Apr. 17, 2023, pp. 1-95.
Matthew et al., "Johnson & Johnson Is Reinventing The Party Drug Ketamine To Treat Depression", Healthcare, retrived from https://www.forbes.com/sites/matthewerper/2013/05/2023/johnson-johnson-is-reinventing-the-party-drug-ketamine-to-treat-depression/?sh=1248879f15e2, May 23, 2013, pp. 3.
Meloni et al., "Dizocilpine Antagonizines the Effect of Chronic on Learned Helplessness in Rays," Pharmacol Biochem Behav, vol. 46, 1993, pp. 423-426.
Messer et al., "Maintenance ketamine treatment produces long-term recovery from depression," Primary Psychiatry, vol. 17, Issue 4, 2010, pp. 48-50.
Papp et al., "Andipressant-like effects of 1-aminocrclopropanecarboxylic acid and D-cycloserine in an animal model of depression," Eur J Pharmacol, vol. 316, 1996, pp. 145-151.
Pettypiece et al., "J&S Sees 10 Products Submitted for Approval by 2017"May 23, 2013, Retrieved from https://www.blomberg.com/news.articles/2013-05-23/j-sees-10-products-submitted-for-approval-by-2017#xj4y7vzkg, pp. 2.
Salvadore et al., "Ketamine as a fast acting antidepressant: current knowledge and open questions," CNS neutroscience and therapeutics, vol. 19, Issue 6, 2013, pp. 428-436.
Segmiller et al., "Repeated S-ketamine Infusions in Therappy Resistant Depression: A Case Seriies," Journal of Clinical Pharmacology, vol. 53, Issue 9, 2013, pp. 996-998.
Stafford et al., "National Patterns of Medication Treatment for Depression, 1987 to 2011," Primary care companion to the Journal of clinical psychiatry, vol. 3, Issue 6, 2001, pp. 232-235.
White et al., "Comparative Pharmacology of the Ketamine Isomers", Brit. Journal Anaesth., 1985, 57, 197-203.
Ajub E. "Efficacy of Esketamine in the Treatment of Depression With Psychotic Features: A Case Series", Biological Psychiatry, vol. 83, No. 1, Jan. 1, 2018, e15-e16.
Bjerre J. et al., "Ketamine in melancholic depression", Ugeskr Laeger, Feb. 8, 2010, vol. 172, No. 6, pp. 460-461.
FDA Briefing Information for the Feb. 12, 2019 Joint Meeting of the Psychopharmacologic Drugs Advisory Committe and the Drug Safety and Risk Management Advisory Committee, posted by Feb. 10, 2019.
FDA Presentations for the Feb. 12, 2019 Joint Meeting of the Psychopharmacologic Drugs Advisory Committe and the Drug Safety and Risk Management Advisory Committee, posted by Feb. 10, 2019.
Information Page for the Feb. 12, 2019 Joint Meeting of the Psychopharmacologic Drugs Advisory Committe (PDAC) andthe Drug Safety and Risk Management (DSaRM) Advisory Committee, posted by Feb. 10, 2019.
Janssen Briefing Information for the Feb. 12, 2019 Joint Meeting of the Psychopharmacologic Drugs Advisory Committe and the Drug Safety and Risk Management Advisory Committee, posted by Feb. 10, 2019.

(56) References Cited

OTHER PUBLICATIONS

Janssen Presenations Information for the Feb. 12, 2019 Joint Meeting of the Psychopharmacologic Drugs Advisory Committe and the Drug Safety and Risk Management Advisory Committee, posted by Feb. 10, 2019.

Minutes for the Feb. 12, 2019 Joint Meeting of the Psychopharmacologic Drugs Advisory Committe (PDAC) and the Drug Safety and Risk Management Advisory Committee (DSaRM), Feb. 10, 2019.

Transcript for the Feb. 12, 2019 Joint Meeting of the Psychopharmacologic Drugs Advisory Committe (PDAC) and the Drug Safety and Risk Management Advisory Committee (DSaRM), Feb. 10, 2019.

* cited by examiner

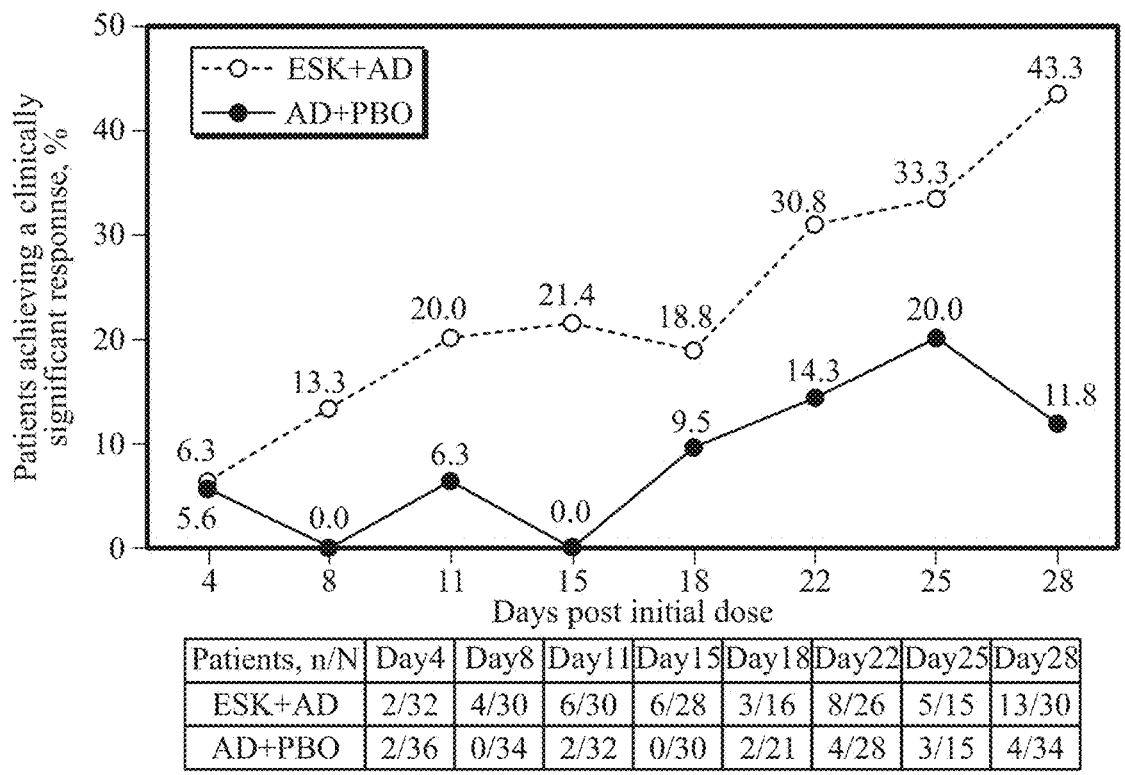

FIG. 35

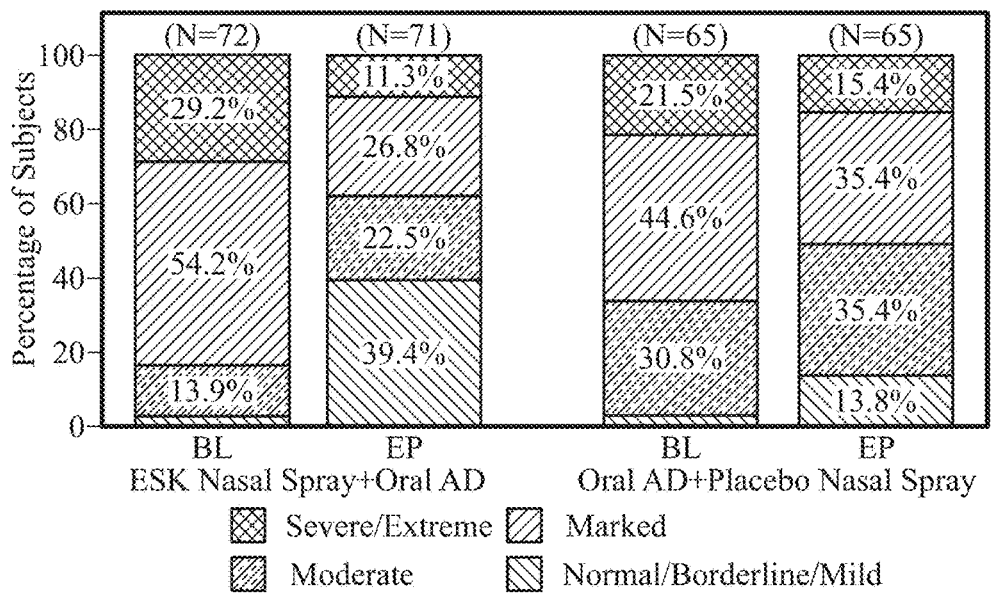

AD=antidepressant, BL=baseline, EP=endpoint, ESK=esketamine

- Median CGI-S scores improved from baseline to the endpoint in the ESK+AD group. The median (range) change from baseline was -1.0(-4, 1). The median (range) change from baseline to the endpoint in the AD+PBO group was 0 (-4, 3)
- The odds ratio for an improved CGI-S score was 5.3, suggesting that patients treated with ESK+AD were 5.3 times more likely than those treated with AD+PBO to have an improved CGI-S score at the end of the double-blind induction phase

FIG. 36

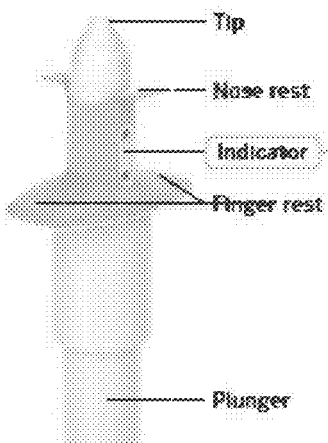
FIG. 83A
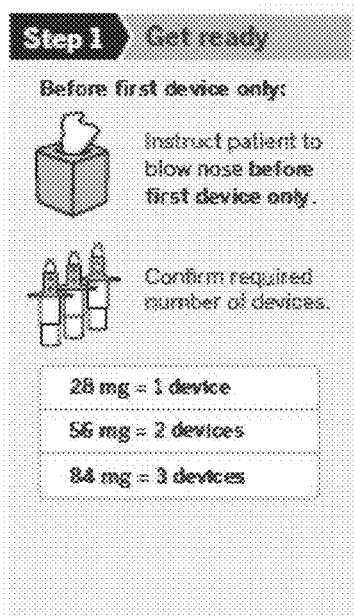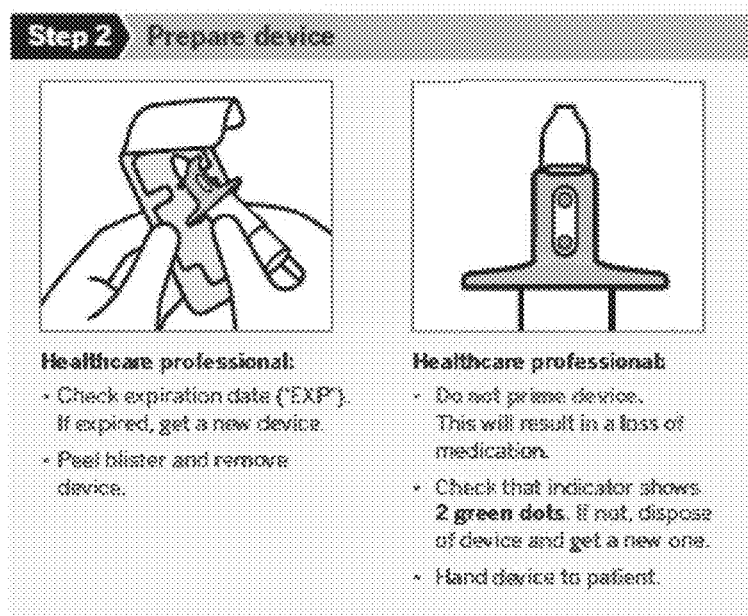
FIG. 83B

Step 3: Prepare patient

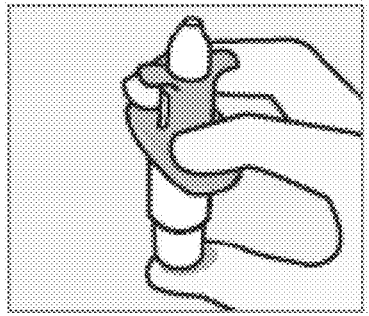
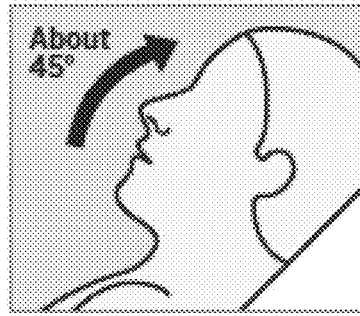

Patient should:
- Hold device as shown with the thumb gently supporting the plunger.
- Do not press the plunger.

Patient should:
- Recline head at about 45 degrees during administration to keep medication inside the nose.

FIG. 83C

Step 4: Patient sprays once into each nostril

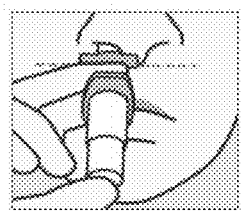
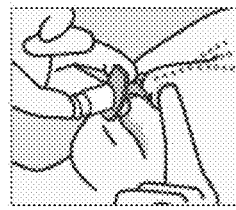
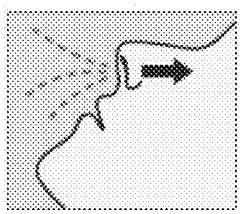
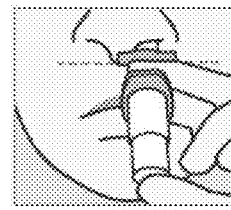

Patient should:
- Insert tip straight into the first nostril.
- Nose rest should touch the skin between the nostrils.

Patient should:
- Close opposite nostril.
- Breathe in through nose while pushing plunger all the way up until it stops.

Patient should:
- Sniff gently after spraying to keep medication inside nose.

Patient should:
- Switch hands to insert tip into the second nostril.
- Repeat Step 4 to deliver second spray.

FIG. 83D

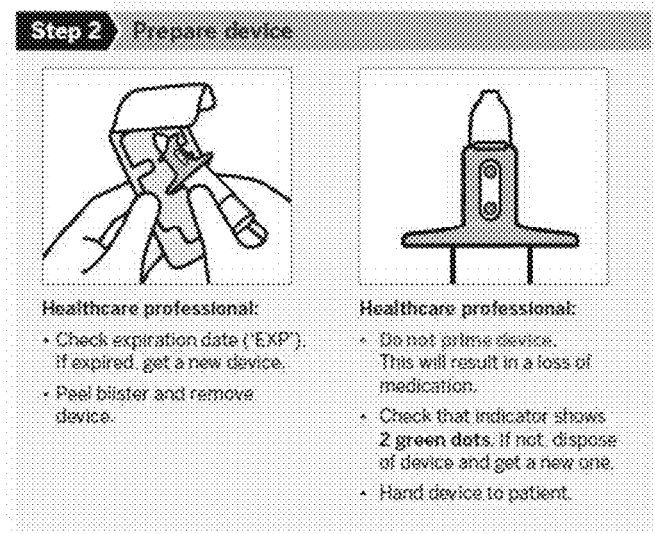
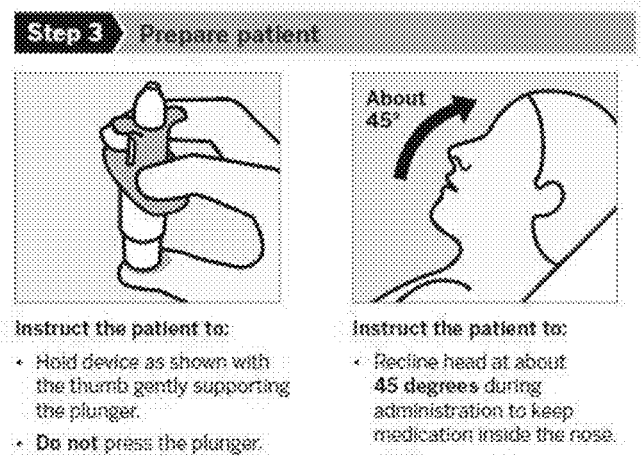
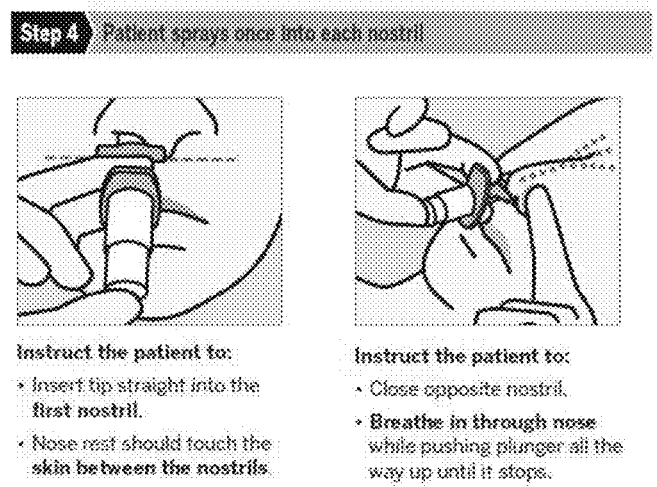
FIG. 85 (cont.)

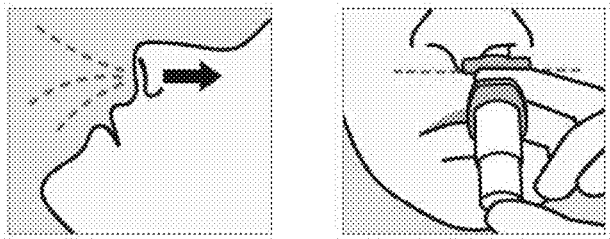
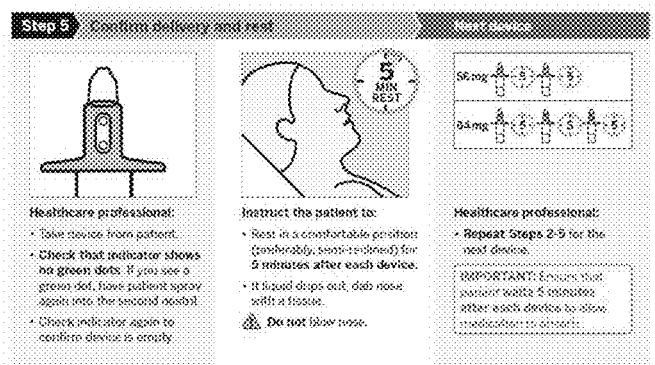
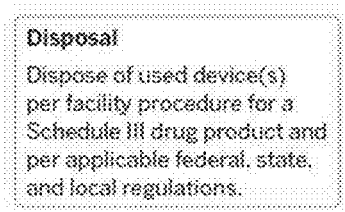
FIG. 85 (cont.)

*Administered 1 hour before intranasal esketamine

* The potential for cytochrome P450 induction by esketamine was assessed. Intranasal esketamine (84 mg) was administered twice weekly for 2 weeks. Bupropion or midazolam was administered at baseline and 24 hours after the last dose of esketamine.

ESKETAMINE FOR THE TREATMENT OF DEPRESSION

CROSS-REFERENCE TO RELATED APPLICATIONS

This application is a continuation of U.S. patent application Ser. No. 17/436,188, filed Sep. 3, 2021, which is a US national stage of International Patent Application No. PCT/IB2020/051344, filed Feb. 18, 2020, which claims the benefit of U.S. Provisional Patent Application 62/813,767, filed Mar. 5, 2019, and U.S. Provisional Patent Application No. 62/814,274, filed Mar. 5, 2019, the disclosures of which are incorporated by reference herein.

FIELD OF THE INVENTION

The present invention is directed to pharmaceutical products, and to methods for the treatment of depression (e.g., major depressive disorder). In some embodiments, the methods are useful for the treatment of treatment-refractory or treatment-resistant depression. In other embodiments, the methods are useful for the treatment of suicidal ideation. The invention comprises administering to a patient in need thereof a clinically proven safe and therapeutically effective amount of esketamine as mono-therapy or as combination therapy with at least one antidepressant.

BACKGROUND OF THE INVENTION

Major depressive disorder (MDD) affects about 7-15% of the general population. MDD is associated with significant morbidity and mortality and the leading cause of disability worldwide. About one third of patients fail to achieve remission despite treatment with multiple antidepressant medications, and are considered to have treatment resistant depression (TRD). Such patients who do benefit with oral ADs have high rates of relapse even with continuation of treatment.

The impact of TRD on patient's lives is difficult to adequately describe. Many patients have depressive episodes lasting years. Severely depressed patients lose the will to carry on with their lives, there is a 7-fold increase in suicide attempts. Life expectancy is lowered by 10 years. In extreme cases they cannot even engage in basic self-care activities such as bathing or eating, or taking care of themselves, leave alone those in their care as a parent, spouse etc. This impacts not only the patient themselves, but also the family and those dependant on them. They also lose the ability to experience pleasure in doing the things that used to enjoy, which robs people of the essence of life and what drives it. In effect their lives are taken away from them by TRD. These effects are theorized to be related to dysregulation of the glutamate pathway.

Glutamate is the major excitatory neurotransmitter in the mammalian brain and has a prominent role in synaptic plasticity, learning and memory. At elevated levels, glutamate is a potent neuronal excitotoxin that may provoke rapid or delayed neurotoxicity. Over the years, there has been a growing interest in the role of glutamate in the pathophysiology of depression since abnormal activity of the glutamatergic system probably contributes to the impairment of synaptic plasticity observed in depressed patients. Ketamine, a classic anesthetic drug, showed activity not only in animal models of depression but also in small scale clinical studies in patients with major depressive disorder including subjects with treatment-resistant depression. At low, sub-anesthetic doses administered by intravenous infusion, ketamine showed a robust antidepressant effect in patients that lasted for a few days after a single dose and could be maintained for several weeks via repeated infusions.

Ketamine (a racemic mixture of the corresponding S- and R-enantiomers) is a nonselective antagonist at the phencyclidine binding site of the glutamate N-methyl-D-aspartate (NMDA) receptor, although this may not primarily mediate the antidepressant effect. The enantiomer S-ketamine (esketamine) displays approximately 3 to 4 fold greater affinity for the glutamate NMDA receptor in vitro than R-ketamine. A major concern associated with ketamine and esketamine is the potential for neurotoxicity associated with long-term use and whether repeated doses of ketamine/esketamine in the longer term can maintain a significant antidepressant effect (Molero, et al., "Antidepressant Efficacy and Tolerability of Ketamine and Esketamine: A Critical Review," CNS Drugs (2018) 32:411-420). In particular, previous studies indicated that esketamine, in contrast to R-ketamine, could not elicit a sustained antidepressant effect in a rodent model (C. Yang et al., "R-Ketamine: a rapid onset and sustained antidepressant without psychotomimetic side effects," Transl. Psychiatry (2015) 5:1-11). Moreover, esketamine showed greater undesirable psychotomimetic side effects compared with R-ketamine, including a significant reduction in PV-positive cells in the brain that is associated with psychosis and cognitive impairment (id.). The literature does not provide guidance concerning the cumulative effect or tolerability of long term dosing of esketamine.

There remains a need to provide an effective, long-term and safe treatment for depression, particularly in patients diagnosed as having treatment-refractory or treatment-resistant depression.

SUMMARY OF THE INVENTION

The present invention is directed to methods for the treatment of depression (e.g., major depressive disorder), comprising administering to a patient in need thereof, a clinically proven safe and therapeutically effective amount of esketamine.

The present invention is further directed to a method for the treatment of depression (e.g., major depressive disorder), comprising administering to a patient in need thereof, combination therapy with a clinically proven safe and therapeutically effective amount of esketamine and at least one antidepressant, as herein defined.

The present invention also is directed to methods of maintaining stable remission or stable response achieved by a patient with depression following administration of a therapeutically effective amount of esketamine during an initial administration phase, comprising continuing administration of a therapeutically effective amount of esketamine for at least five months during a subsequent administration phase. In some embodiments, the depression is major depressive disorder or treatment resistant depression.

The present invention further is directed to methods for the long term treatment of depression in a patient, comprising administering to the patient in need of treatment a clinically proven safe and/or clinically proven effective therapeutically effective amount of esketamine for at least six months. In some embodiments, the depression is major depressive disorder or treatment resistant depression.

The method of treatment includes long term treatment, including durations of at least about six months. In some embodiments, the treatment may be a duration of at least about one year, at least about 18 months, or at least about two years. For example, long term treatment may include a duration range of about six months to about two years. The treatment may extend for much longer periods of time to the extent that the patient is benefiting from the therapy.

In some embodiments, the at least one antidepressant is independently selected from the group consisting of mono-amine oxidase inhibitors, tricyclics, serotonin reuptake inhibitors, serotonin noradrenergic reuptake inhibitors, noradrenergic and specific serotonergic agents, noradrenaline reuptake inhibitors, natural products, dietary supplements, neuropeptides, compounds targeting neuropeptide receptors and hormones.

In other embodiments, methods for the treatment of depression (e.g., major depressive disorder) are provided and comprise administering to a patient in need thereof a clinically proven safe and therapeutically effective amount of esketamine in combination with one or more compounds selected from the group consisting of mono-amine oxidase inhibitors (MAOI) such as irreversible MAOI (phenelzine, tranylcypromine), reversible (MOAI) moclobemide, and the like; tricyclics such as imipramine, amitriptyline, desipramine, nortriptyline, doxepin, protriptyline, trimipramine, domipramine, amoxapine, and the like; tetracyclics such as maprotiline, and the like; non-cydics such as nomifensine, and the like; triazolopyridines such as trazodone, and the like; anticholinergics e.g. scopolamine; serotonin reuptake inhibitors such as fluoxetine, sertraline, paroxetine, citalopram, fluvoxamine, and the like; serotonin receptor antagonists such as nefazadone, tianeptine and the like; serotonin noradrenergic reuptake inhibitors such as venlafaxine, desvenlafaxine, milnacipran, levo-milnacipran, and the like; noradrenergic and specific serotonergic agents such as mirtazapine, and the like; noradrenaline reuptake inhibitors such as reboxetine, and the like; atypical antipsychotics such as bupropion and the like, and the like; lithium, triple reuptake inhibitors, natural products such as Kava-Kava, St. John's Wort, and the like; dietary supplements such as s-adenosylmethionine, and the like; and neuropeptides such as thyrotropin-releasing hormone and the like, and the like; compounds targeting neuropeptide receptors such as neurokinin receptor antagonists and the like; and hormones such as triiodothyronine, and the like.

In other embodiments, methods for the treatment of depression (e.g., major depressive disorder) are provided and comprise administering to a patient in need thereof a clinically proven safe and therapeutically effective amount of esketamine in combination with one or more compounds selected from the group consisting of mono-amine oxidase inhibitors; tricyclics; tetracyclics; non-cyclics; triazolopyridines; serotonin reuptake inhibitors; serotonin receptor antagonists; serotonin noradrenergic reuptake inhibitors; serotonin noradrenergic reuptake inhibitors; noradrenergic and specific serotonergic agents; noradrenaline reuptake inhibitors; atypical antipsychotics; natural products; dietary supplements; neuropeptides; compounds targeting neuropeptide receptors; and hormones. Preferably, esketamine is administered in combination with one or more compounds selected from the group consisting of mono-amine oxidase inhibitors, tricyclics, serotonin reuptake inhibitors, serotonin noradrenergic reuptake inhibitors, noradrenergic and specific serotonergic agents, atypical antipsychotics, and/or adjunctive therapy with antipsychotic medication (e.g. risperidone, olanzapine, quetiapine, aripiprazole and ziprasidone). More preferably, esketamine is administered in combination with one or more compounds selected from the group consisting of mono-amino oxidase inhibitors, tricyclics, serotonin reuptake inhibitors, and serotonin norepinephrine reuptake inhibitors. More preferably, esketamine is administered in combination with one or more compounds selected from the group consisting of serotonin reuptake inhibitors and serotonin norepinephrine reuptake inhibitors.

In yet further embodiments, methods for the treatment of depression (e.g., major depressive disorder) are provided and comprise administering to a patient in need thereof a clinically proven safe and therapeutically effective amount of esketamine in combination with one or more compounds selected from the group consisting of phenelzine, tranylcypromine, moclobemide, imipramine, amitriptyline, desipramine, nortriptyline, doxepin, protriptyline, trimipramine, domipramine, amoxapine, fluoxetine, sertraline, paroxetine, citalopram, fluvoxamine, venlafaxine, milnacipran, mirtazapine, bupropion, thyrotropin-releasing hormone and triiodothyronine.

Preferably, esketamine is administered in combination with one or more compounds selected from the group consisting of lithium, riluzole, phenelzine, tranylcypromine, moclobemide, imipramine, amitriptyline, desipramine, nortriptyline, doxepin, protriptyline, trimipramine, domipramine, amoxapine, fluoxetine, sertraline, paroxetine, citalopram, fluvoxamine, venlafaxine, milnacipran, levomilnacipran, mirtazapine and bupropion. More preferably, esketamine is administered in combination with one or more compounds selected from the group consisting of phenelzine, tranylcypromine, moclobemide, imipramine, amitriptyline, desipramine, nortriptyline, doxepin, protriptyline, trimipramine, clomipramine, amoxapine, fluoxetine, sertraline, paroxetine, citalopram and fluvoxamine. More preferably, esketamine is administered in combination with one or more compounds selected from the group consisting of fluoxetine, sertraline, paroxetine, citalopram, escitalopram and fluvoxamine.

In still further embodiments, methods for the treatment of depression (e.g., major depressive disorder) are provided and comprise administering to a patient in need thereof a clinically proven safe and therapeutically effective amount of esketamine in combination with one or more compounds selected from the group consisting of neuropeptides such as thyrotropin-releasing hormone and the like; compounds targeting neuropeptide receptors such as neurokinin receptors antagonists and the like; and hormones such as triiodothyronine and the like.

In other embodiments, methods for the treatment of depression (e.g., major depressive disorder) are provided and comprise administering to a patient in need thereof, combination therapy with a clinically proven safe and therapeutically effective amount of esketamine, at least one antidepressant, and at least one atypical antipsychotic, as herein defined.

In further embodiments, methods for the treatment of depression (e.g., major depressive disorder) are provided and comprise administering to a patient in need thereof, combination therapy with a clinically proven safe and therapeutically effective amount of esketamine, at least one antidepressant, and at least one atypical antipsychotic selected from the group consisting of quetiapine, aripiprazole, brexpiprazole, olanzapine, lurasidone, risperidone and paliperidone.

In other embodiments, the methods for treatment of depression may be combined with adjunctive therapies such as anti-psychotic therapy, electroconvulsive therapy (ECT), transcranial magnetic stimulation (TMS), or combinations thereof.

The present invention is further directed to uses of esketamine in the preparation of a medicament for treating depression (e.g., major depressive disorder) in a patient in need thereof. In some embodiments, the medicament is for treating treatment-refractory or treatment-resistant depression. In other embodiments, the medicament is for treating suicidal ideation.

The present invention is further directed to esketamine for use in a method for the treatment of depression (e.g., major depressive disorder), preferably treatment-refractory or treatment-resistant depression, in a subject in need thereof.

In another embodiment, compositions comprising esketamine for the treatment of depression (e.g., major depressive disorder) are provided. In some embodiments, the compositions are for the treatment of treatment-refractory or treatment-resistant depression. In other embodiments, the medicament is for treating suicidal behavior and/or suicidal ideation.

The present invention is also directed to methods of treating depression, comprising administering an approved drug product containing esketamine to a subject with depression in an amount that is described in a drug product label for the approved drug product.

The present invention is further directed to methods of selling an approved drug product comprising esketamine, said method comprising selling such drug product, wherein a drug product label for a reference listed drug for such drug product includes instructions for treating depression.

The present invention also is directed to methods of offering for sale a drug product comprising esketamine, said method comprising offering for sale such drug product, wherein a drug product label for a reference listed drug for such drug product includes instructions for treating depression.

The present invention is further directed to approved drug products with at least one approved indication, wherein said approved drug product comprises esketamine.

The present invention also is directed to methods of using the approved product described herein, wherein the approved product comprises one or more intranasal spray devices, the one or more devices comprise the esketamine, and the one or more devices is configured to administer from about 28 to about 84 mg of esketamine.

The present invention is further directed to methods to mitigate the risk of misuse or abuse of esketamine, comprising restricting distribution of an approved esketamine drug product to selected distributors, wherein the distributors are Drug Enforcement Administration registered and deliver the approved esketamine drug product only to a pre-approved site of care.

MMRM by Subgroup during the double-blind induction phase using the full analysis set. Subgroups with fewer than 5 subjects not presented. Results are not adjusted for sample size re-estimation.

Figure 25:
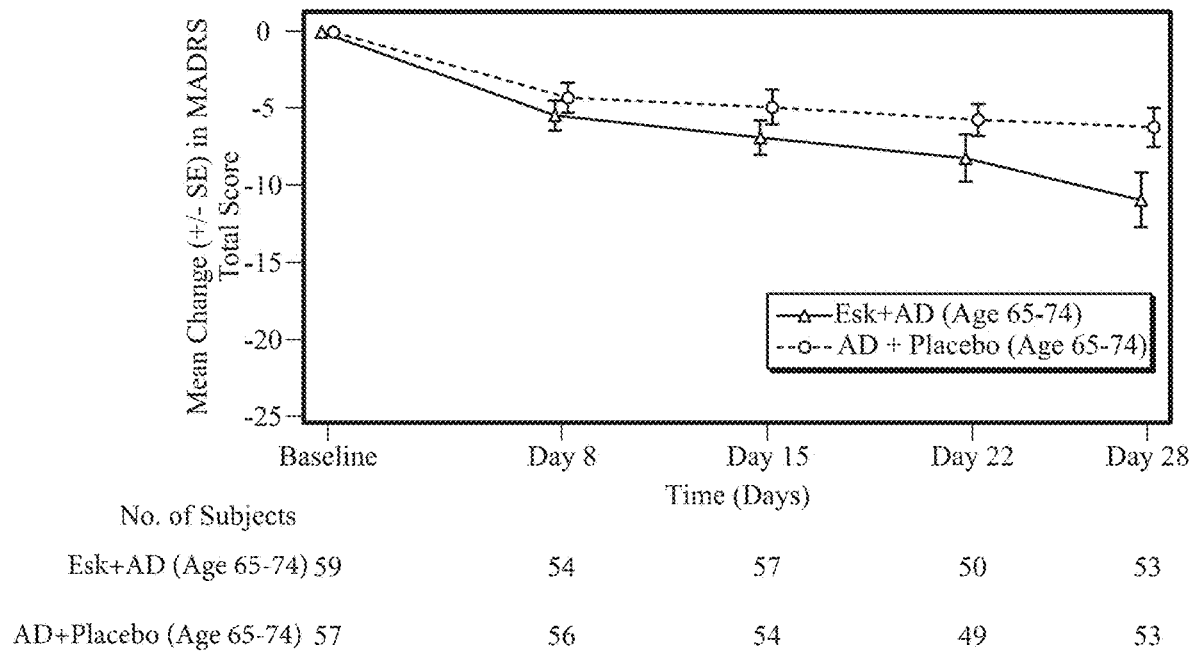

FIG. 25 illustrates the arithmetic mean changes (±SE) in MADRS total score over time observed case for the age 65-74 group during the double-blind induction phase using the full analysis set.

Figure 26:
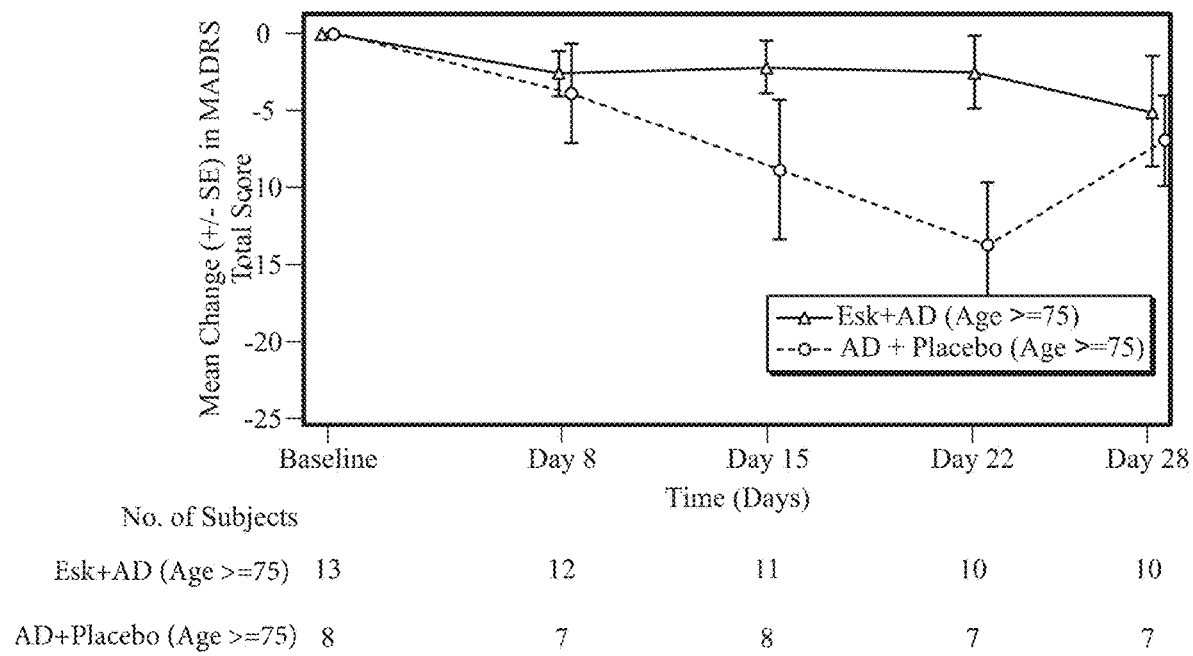

FIG. 26 illustrates the arithmetic mean changes (±SE) in MADRS total score over time observed case for the age ≤75 group during the double-blind induction phase using the full analysis set.

Figure 27:
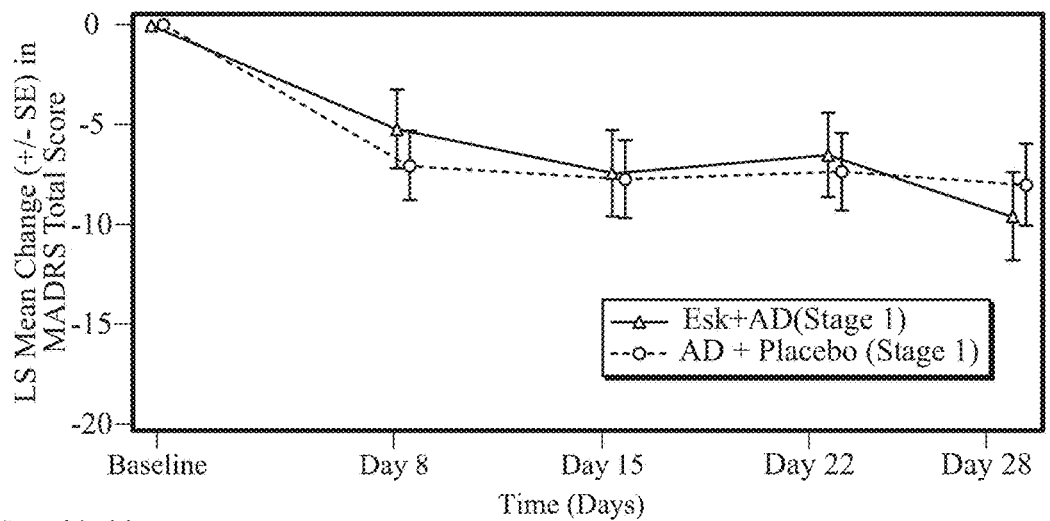

FIG. 27 illustrates the least squares mean changes (±SE) in MADRS total score over time (observed cases) MMRM for Stage 1 during the double-blind induction phase using the full analysis set. LS Mean and SE were based on mixed model for repeated measures (MMRM) with change from baseline as the response variable and the fixed effect model terms for treatment (intranasal esk+oral AD, oral AD+intranasal placebo), day, region, class of oral antidepressant (SNRI or SSRI), and treatment-by-day, and baseline value as a covariate. Results are not adjusted for sample size re-estimation. Negative change in score indicates improvement.

Figure 28:
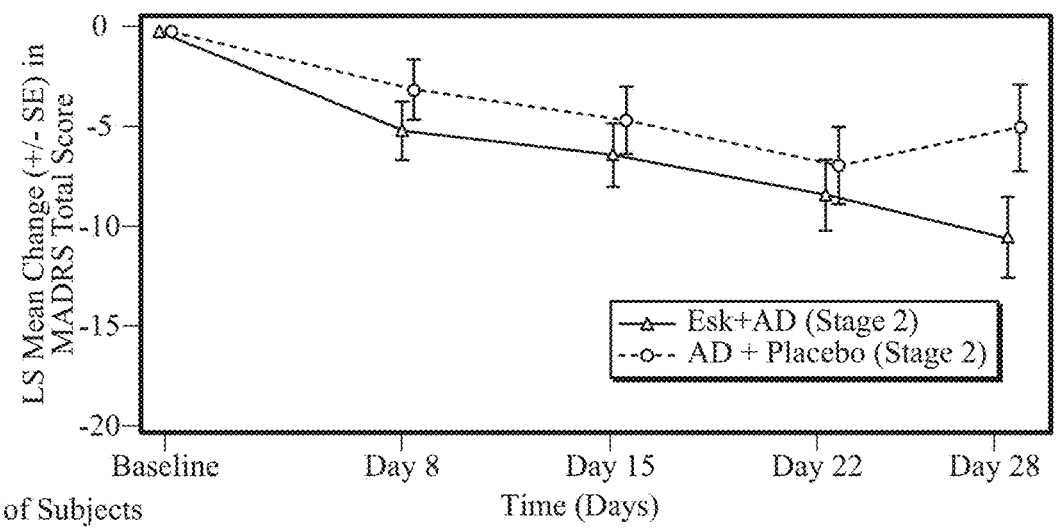

FIG. 28 illustrates the least squares mean changes (±SE) in MADRS total score over time (observed cases) MMRM for stage 2 during the double-blind induction phase using the full analysis set. S Mean and SE were based on mixed model for repeated measures (MMRM) with change from baseline as the response variable and the fixed effect model terms for treatment (intranasal esk+oral AD, oral AD+intranasal placebo), day, region, class of oral antidepressant (SNRI or SSRI), and treatment-by-day, and baseline value as a covariate. Results are not adjusted for sample size re-estimation. Negative change in score indicates improvement.

Figure 29:
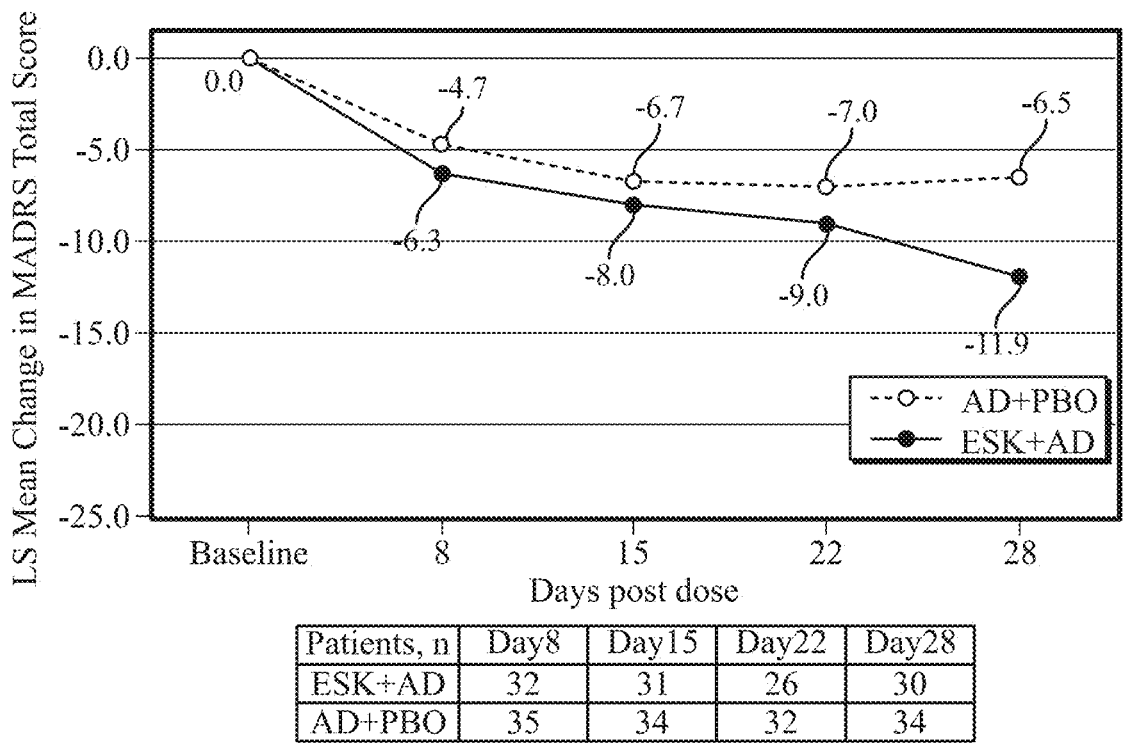

FIG. 29 illustrates that least squares mean change in MADRS total score over time (observed cases) in US patients aged 2:65 years with TRD. MADRS total score ranges from 0 to 60; a higher score indicates a more severe condition.

Figure 30:
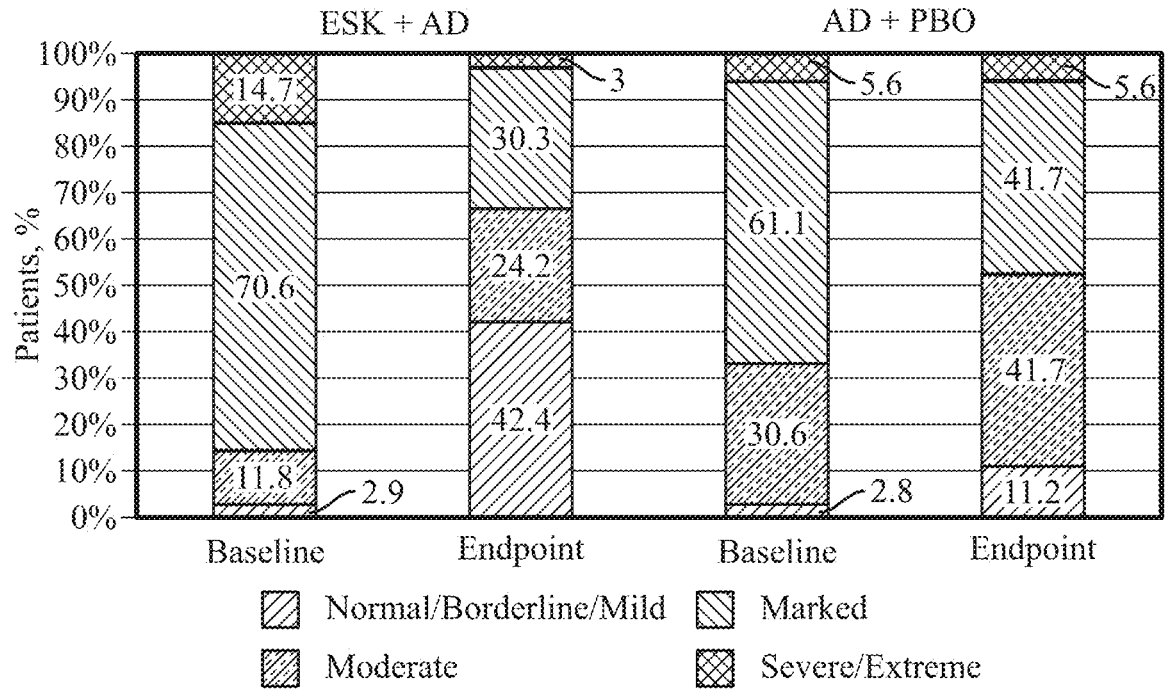

FIG. 30 illustrates that frequency distribution of illness severity based on CGI-S scores at baseline and double-blind phase endpoint (LOCF). CGI-S score ranges from 1 (normal, not at all ill) to 7 (among the most extremely ill patients). CGI-S score ranged from 1 (normal, not at all ill) to 7 (among the most extremely ill patients).

Figure 31:
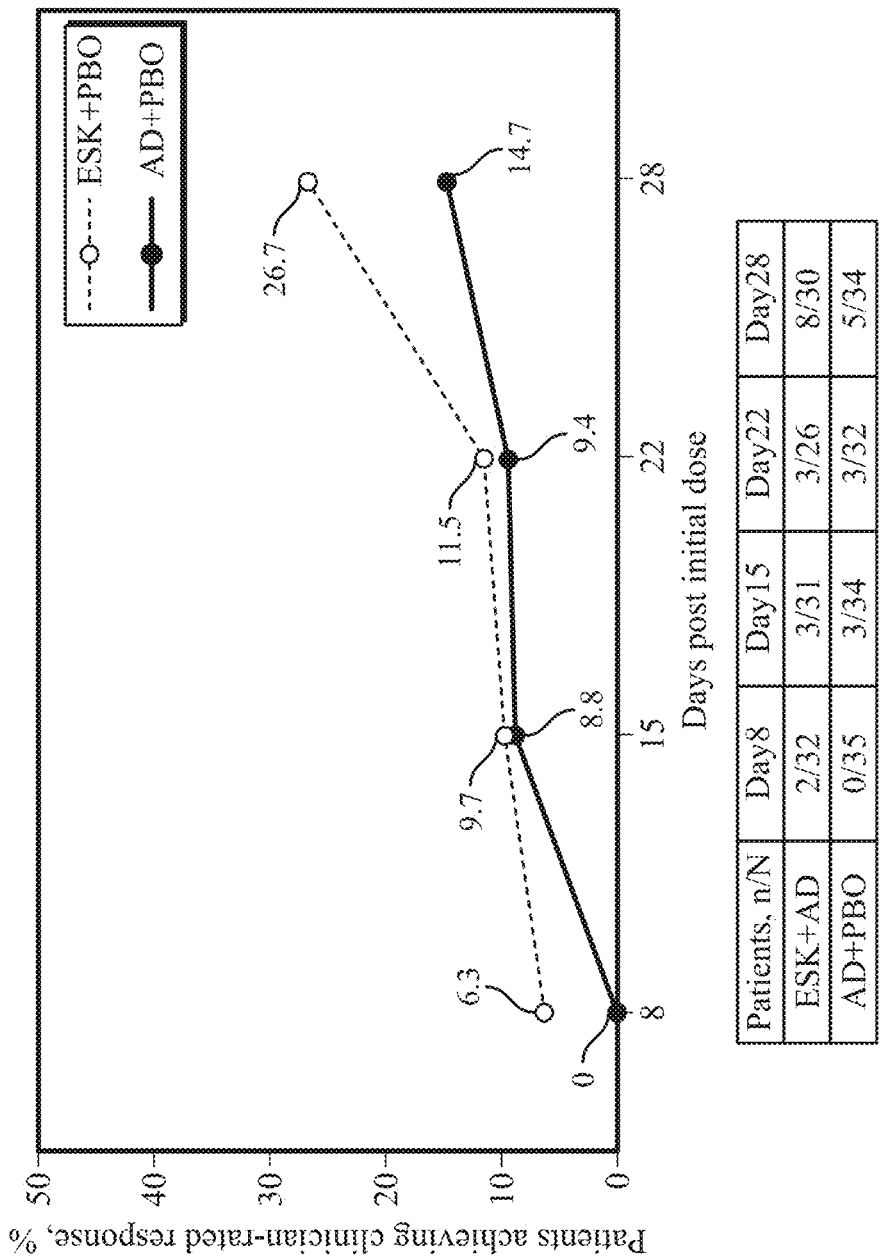

FIG. 31 illustrates the percentage of US patients aged ≤65 years with TRD achieving response (observed case), as assessed by MADRS. Clinician-rated response a was defined as a 250% decrease from baseline in MADRS total score.

Figure 32:
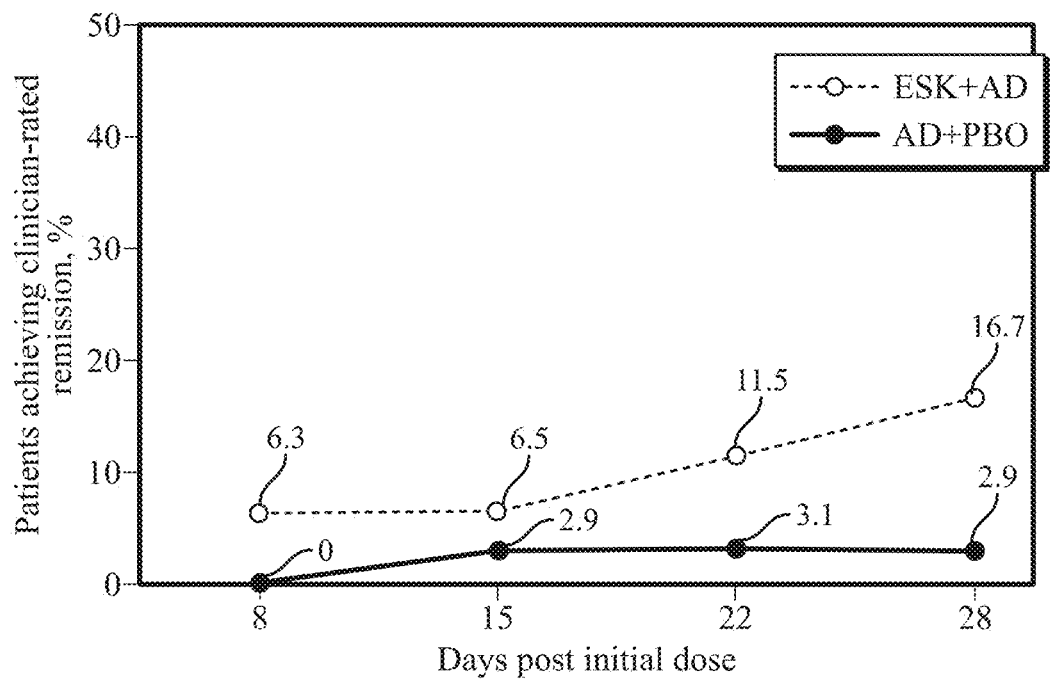

FIG. 32 illustrates the percentage of US patients aged ≤65 years with TRD achieving remission (observed case), as assessed by MADRS. Clinician-rated remission was defined as a MADRS total score of ≤12.

Figure 33:
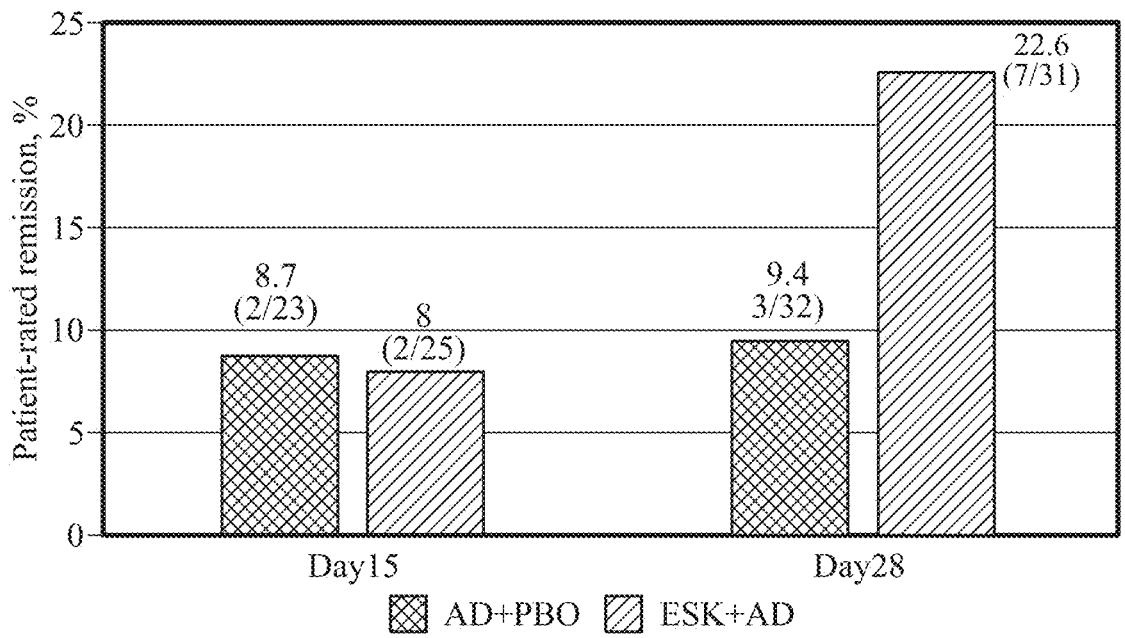

FIG. 33 illustrates the percentage of US patients aged ≥65 years with TRD achieving patient-rated remission (observed case), as assessed by PHQ-9.

Figure 34:
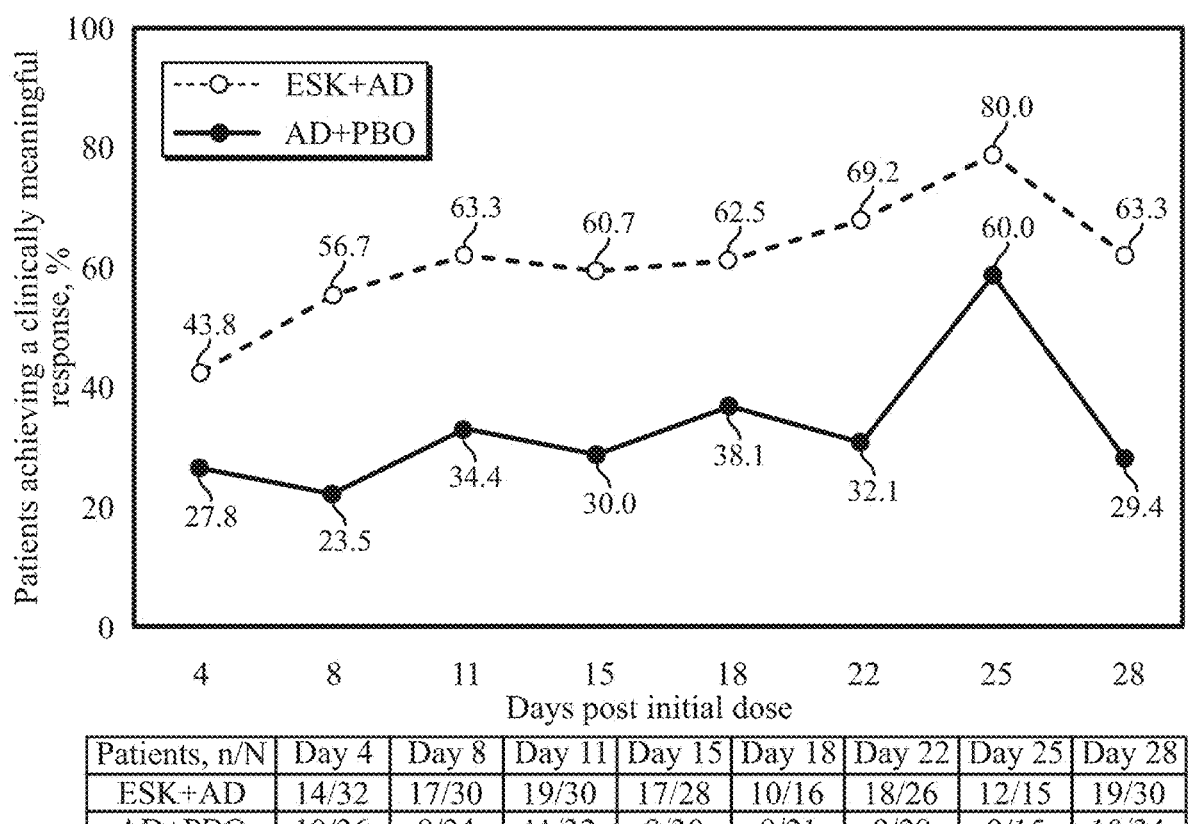

FIG. 34 illustrates the percentage of US patients aged ≥65 years with TRD who had a clinically meaningful response, as assessed by CGI-S.

FIG. 35 illustrates the percentage of US patients aged 65 years with TRD who had a clinically significant response, as assessed by CGI-S. Clinically meaningful and clinically significant responses were defined as a ≥1-point or a ≥2-point decrease in CGI-S from baseline, respectively.

FIG. 36 illustrates the frequency distribution of illness severity based on clinical global impression-severity (CGI-S) scores at baseline and double-blind phase endpoint.

Figure 37:
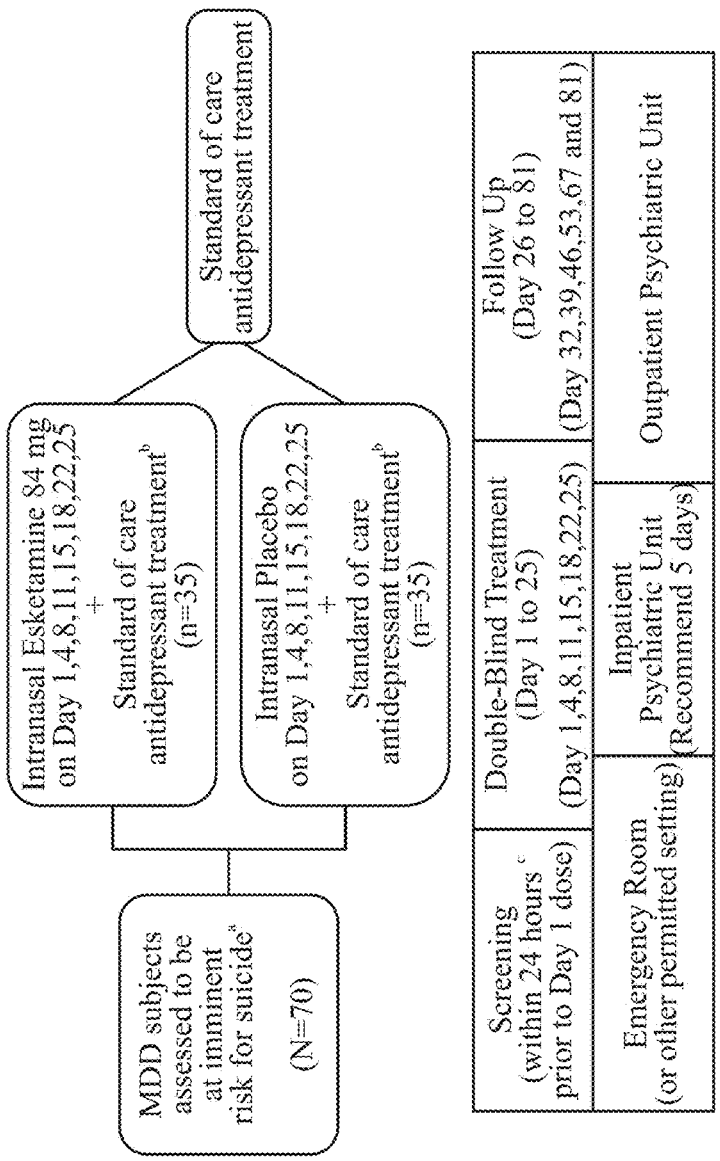

FIG. 37 shows the study design for evaluate the efficacy and safety of intranasal esketamine for the rapid reduction of the symptoms of major depressive disorder, including suicidal ideation, in subjects assessed to be at imminent risk for suicide.

Figure 38:
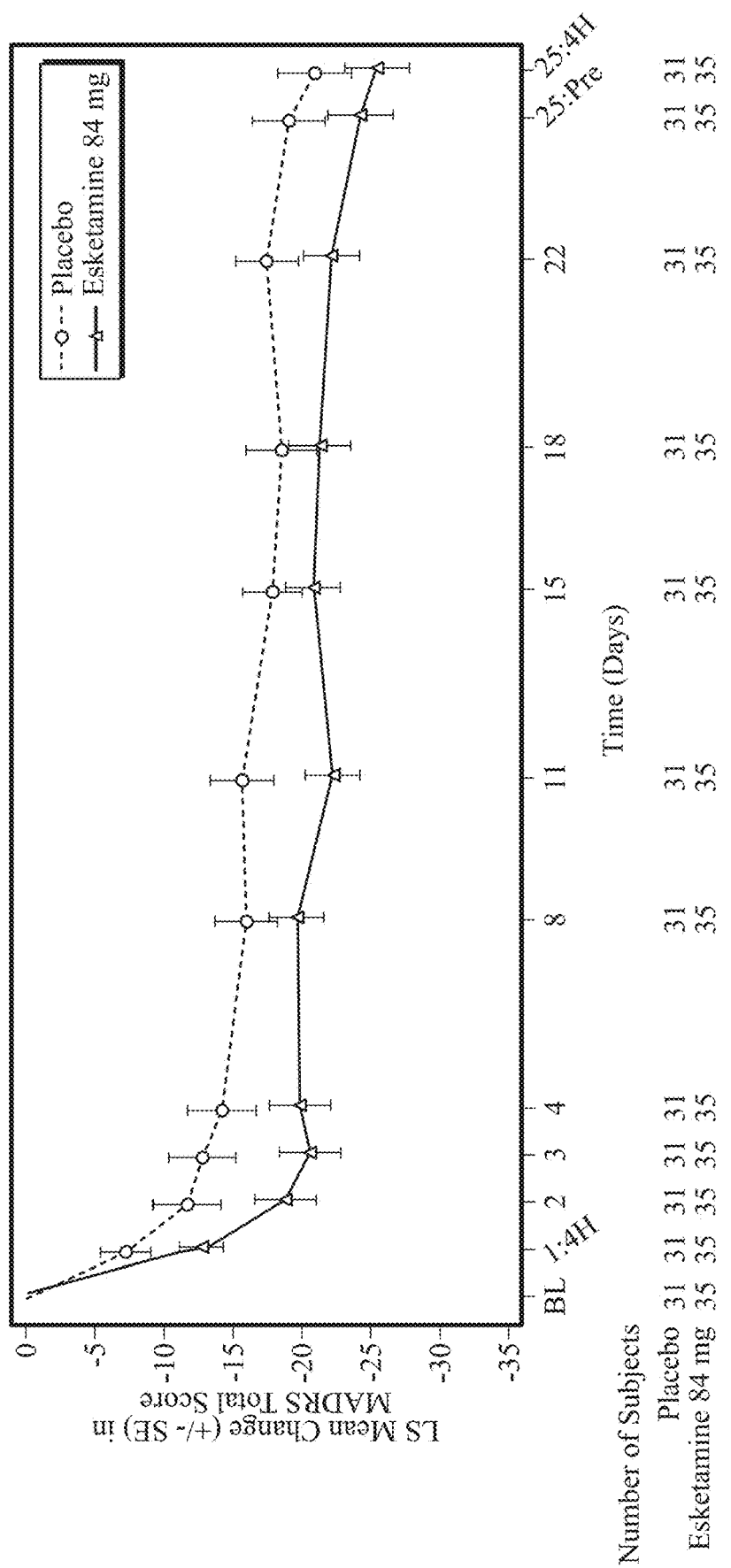

FIG. 38 shows least-square mean changes (±SE) from baseline for the MADRS total score over time in the double-blind phase using last observation carried forward data. LS Mean and SE was based on analysis of covariance (ANCOVA) model with treatment (placebo, esketamine 84 mg), antidepressant therapy (AD monotherapy, AD plus augmentation therapy) and analysis center as factors, and baseline value as a covariate.

Figure 39:
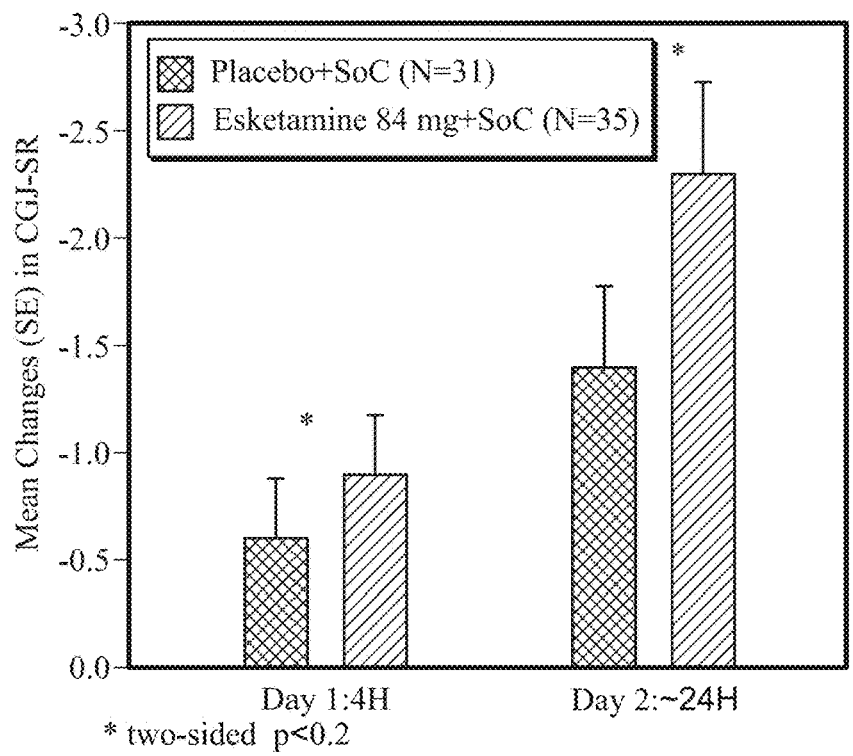

FIG. 39 shows the mean changes (SE) in CGJSR from baseline to 4 and 24 hours. Mean change and SE were based on ranks of change from baseline (LOCF) data and analyzed using an ANCOVA model with treatment, analysis center, and SoC as fixed effects and baseline value (unranked as a covariate).

Figure 40:
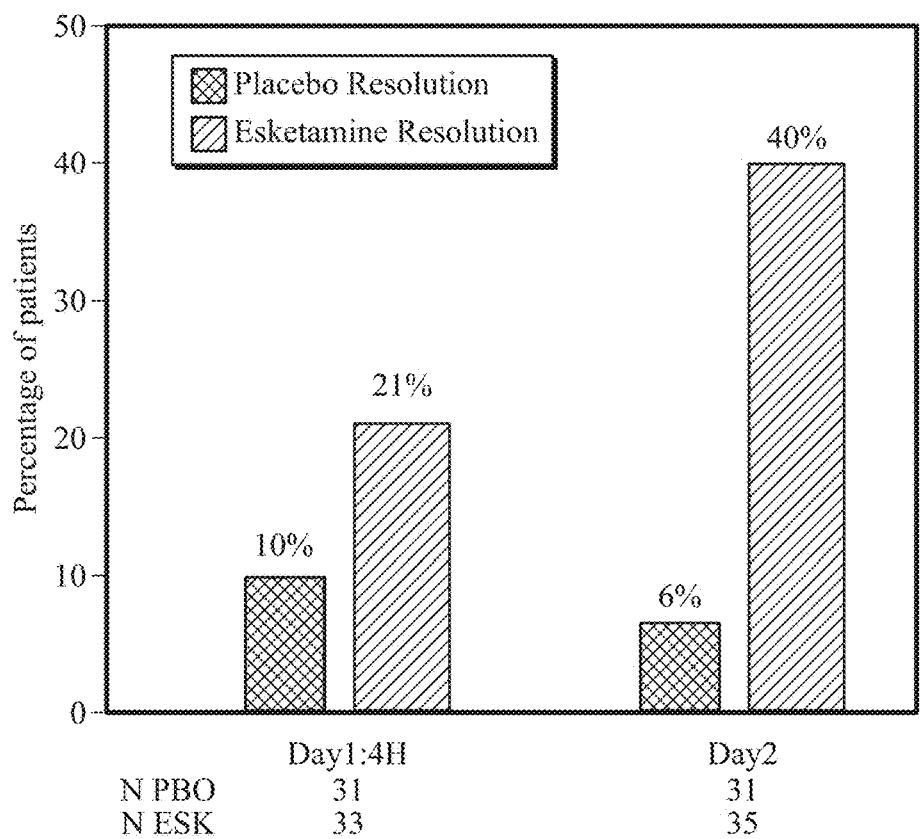

FIG. 40 correlates the percentage of patients with the resolution of suicide risk at 4 and 24 hours.

Figure 41:
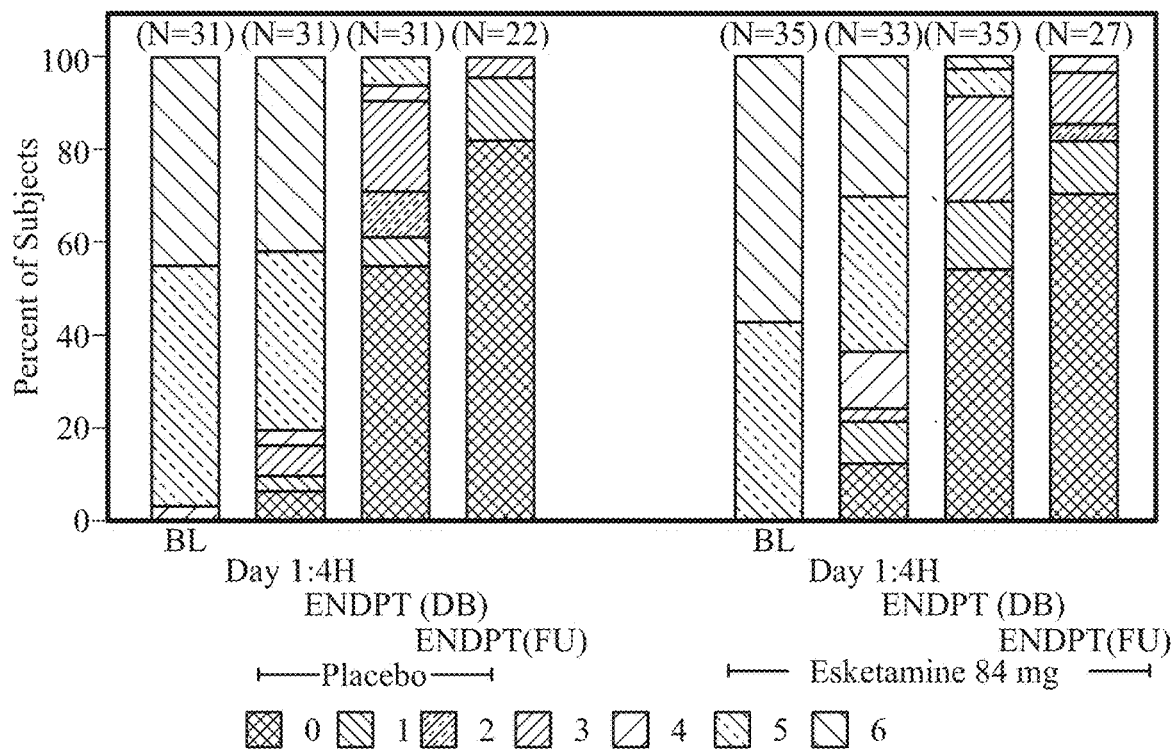

FIG. 41 shows the frequency distribution of SIBAT scores at double-blind baseline, Day 1:4-hours postdose, double-blind endpoint, and follow-up endpoint. Clinical global judgment of suicide risk scores range from 0 to 6. 0: Not suicidal; 1: Occasional suicidal ideas present, but no special intervention required; 2: Some clear suicidal ideas present; patient is encouraged to schedule professional contacts as needed; 3: Suicidal risk requires a scheduled outpatient follow-up; but no other immediate intervention: 4: Suicidal risk requires immediate intervention, but not hospitalization (e.g., medication, urgent outpatient follow-up); 5: Suicidal risk requires immediate hospitalization, but without suicide precautions; 6: Suicidal risk requires hospitalization with suicide precautions.

Figure 42:
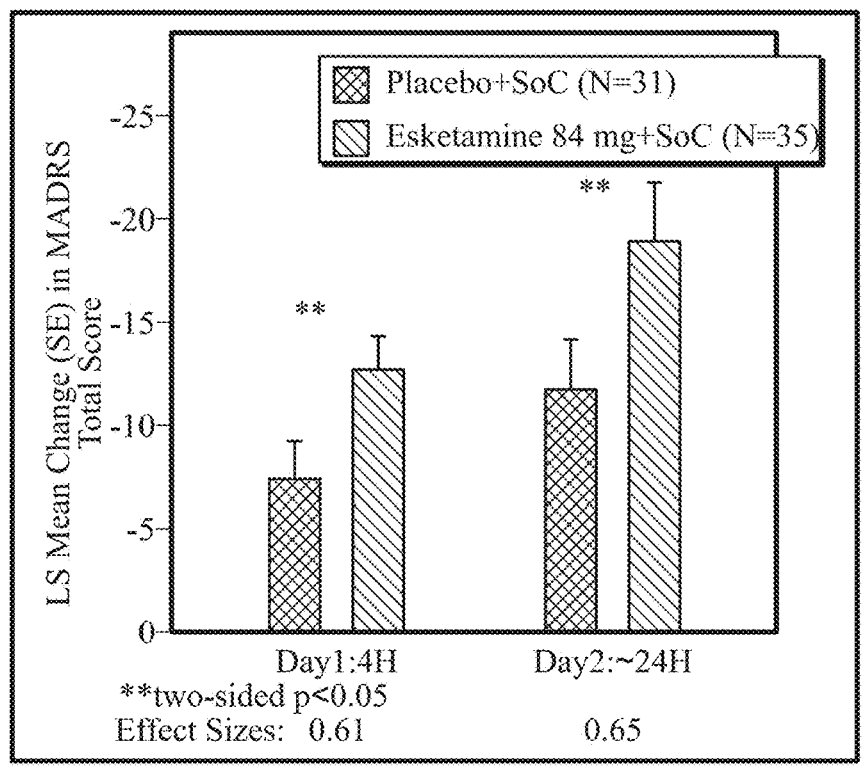

FIG. 42 shows the least-square mean changes (SE) from baseline in MADRS score to 4 hours (primary endpoint) and about 24 hours.

Figure 43:
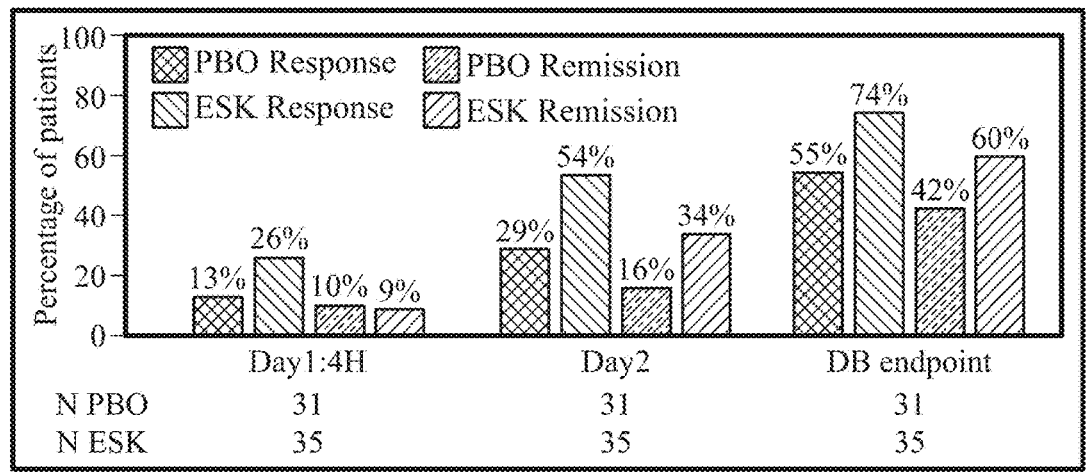

FIG. 43 correlates the percentage of patients with their respective MADRS response and remission at days 1, 2 and endpoint.

Figure 44:
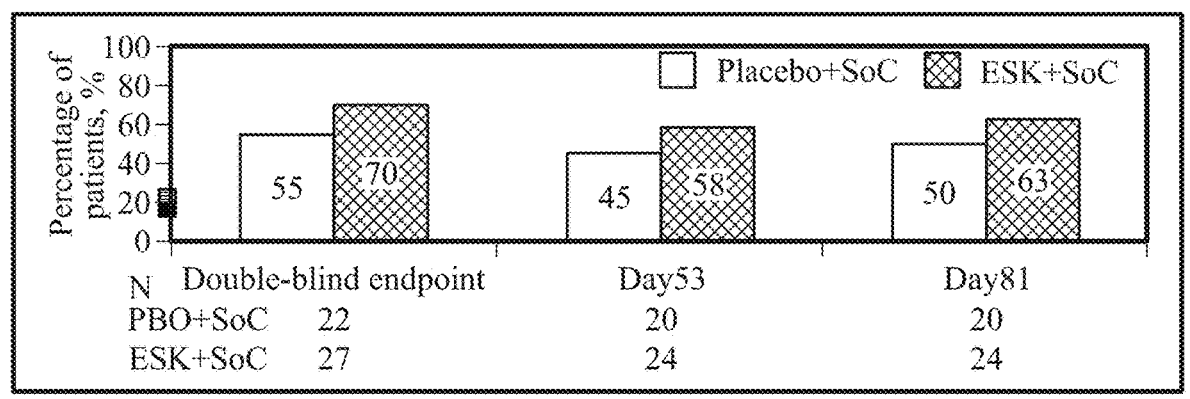

FIG. 44 correlates the percentage of patients having remission at DB endpoint and during follow-up.

Figure 45:
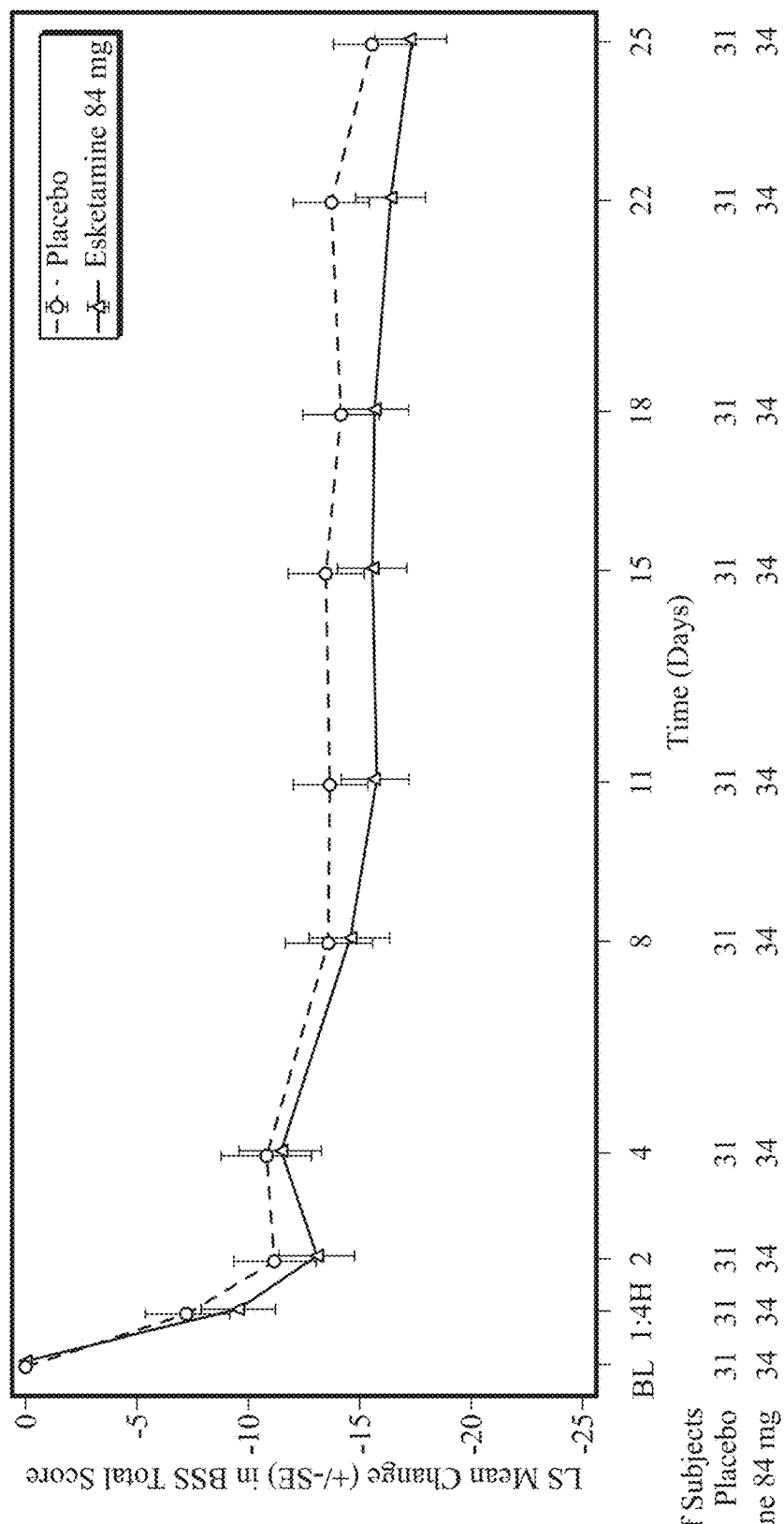

FIG. 45 shows least-square mean changes (t SE) from baseline for the BSS total score over time in the double-blind phase using last observation carried forward data.

Figure 46:
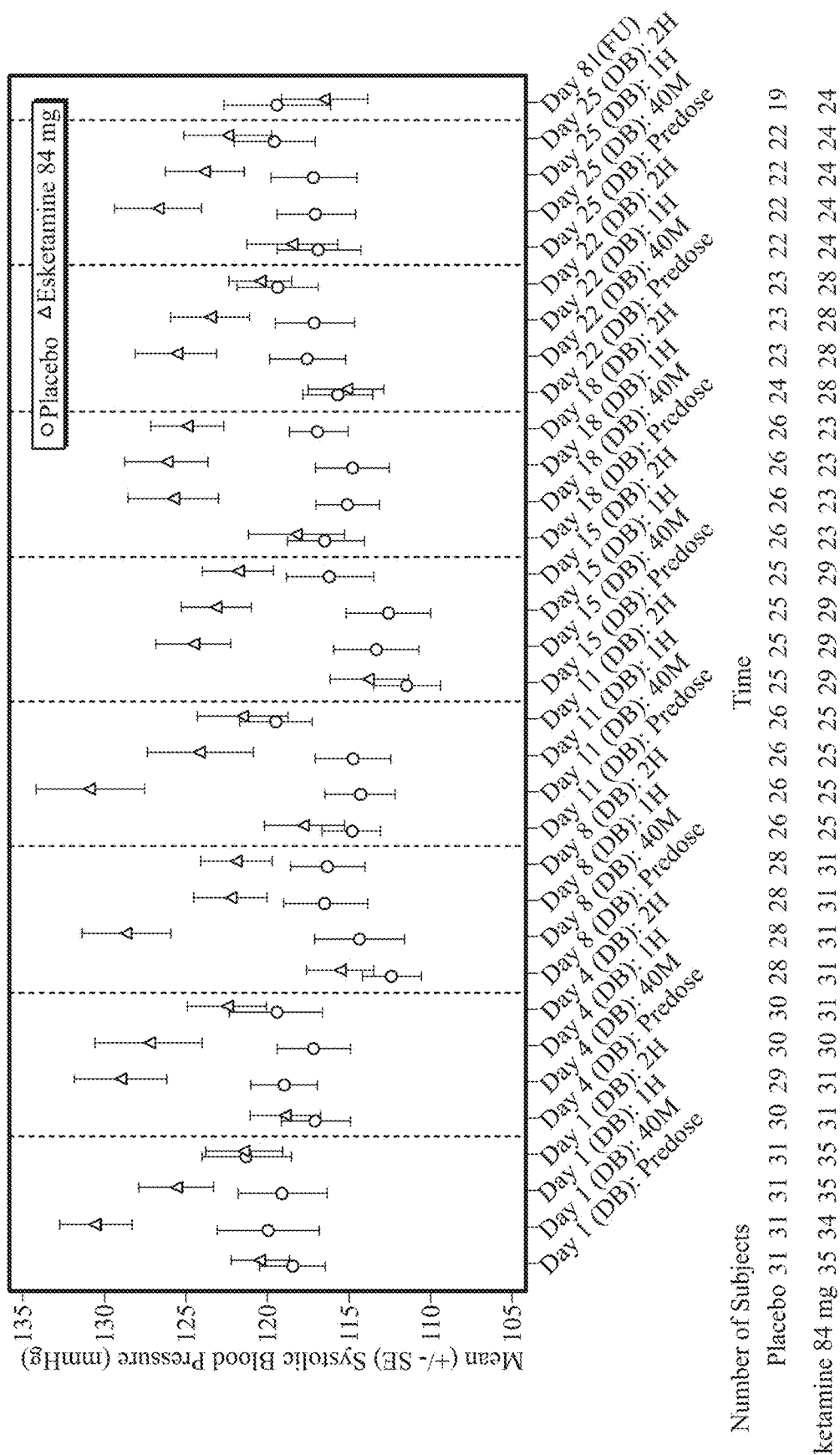
Figure 47:
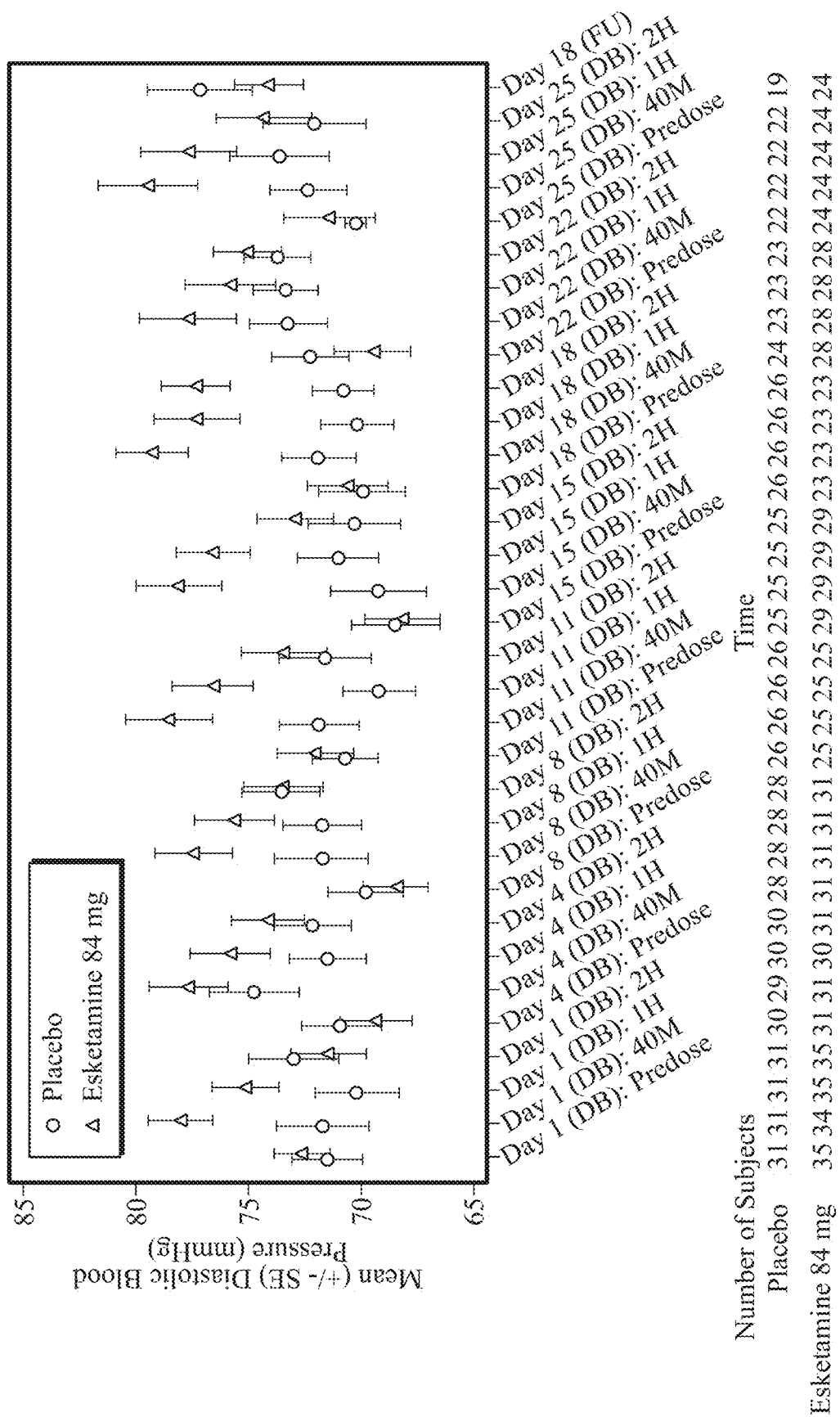

FIGS. 46 and 47 present means for blood pressure over time by treatment group in the double-blind phase.

Figure 48:
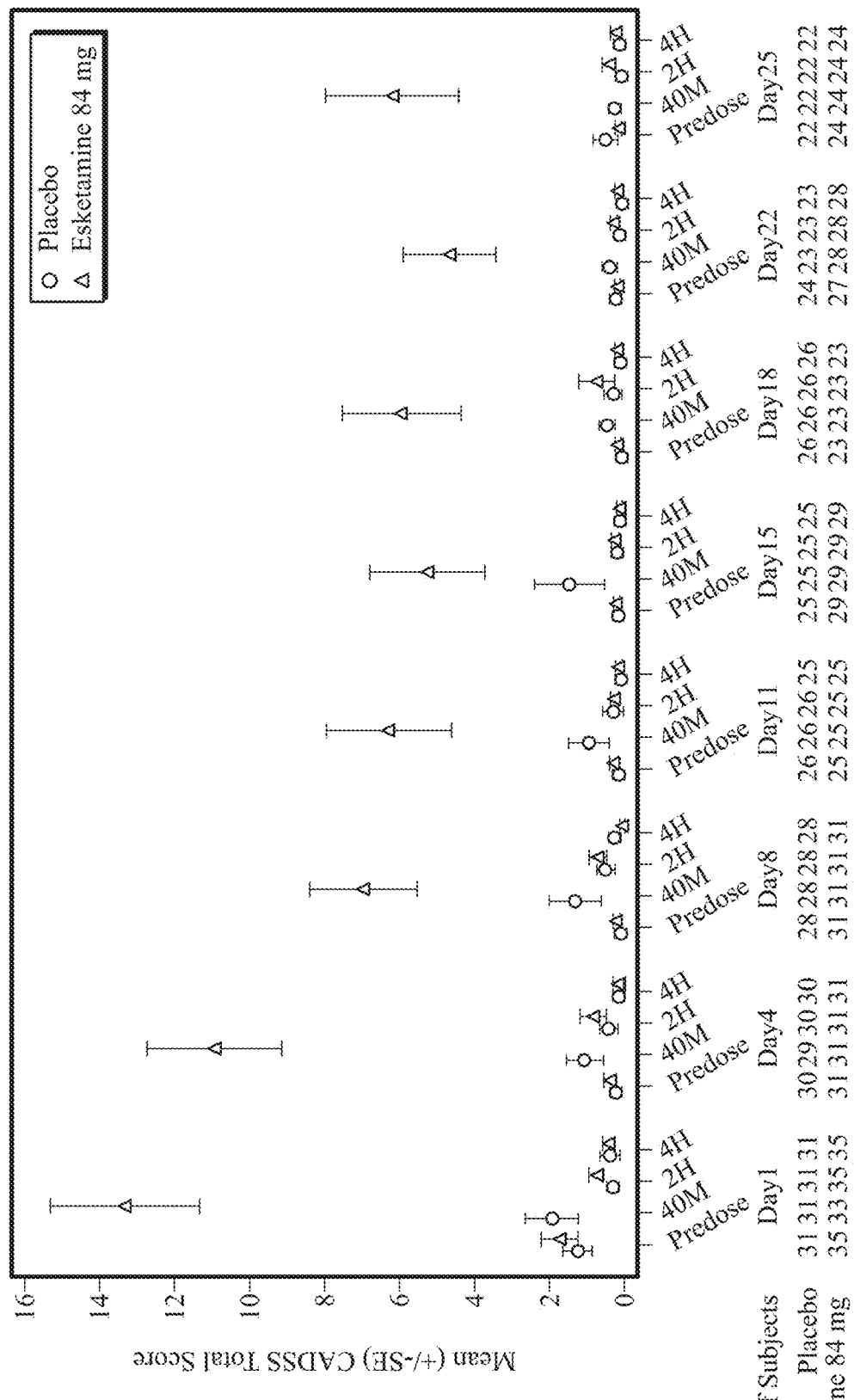

FIG. 48 is a plot of CADSS total score over time during the double-blind phase (Study ESKETINSUI2001: Safety Analysis Set).

Figure 49:
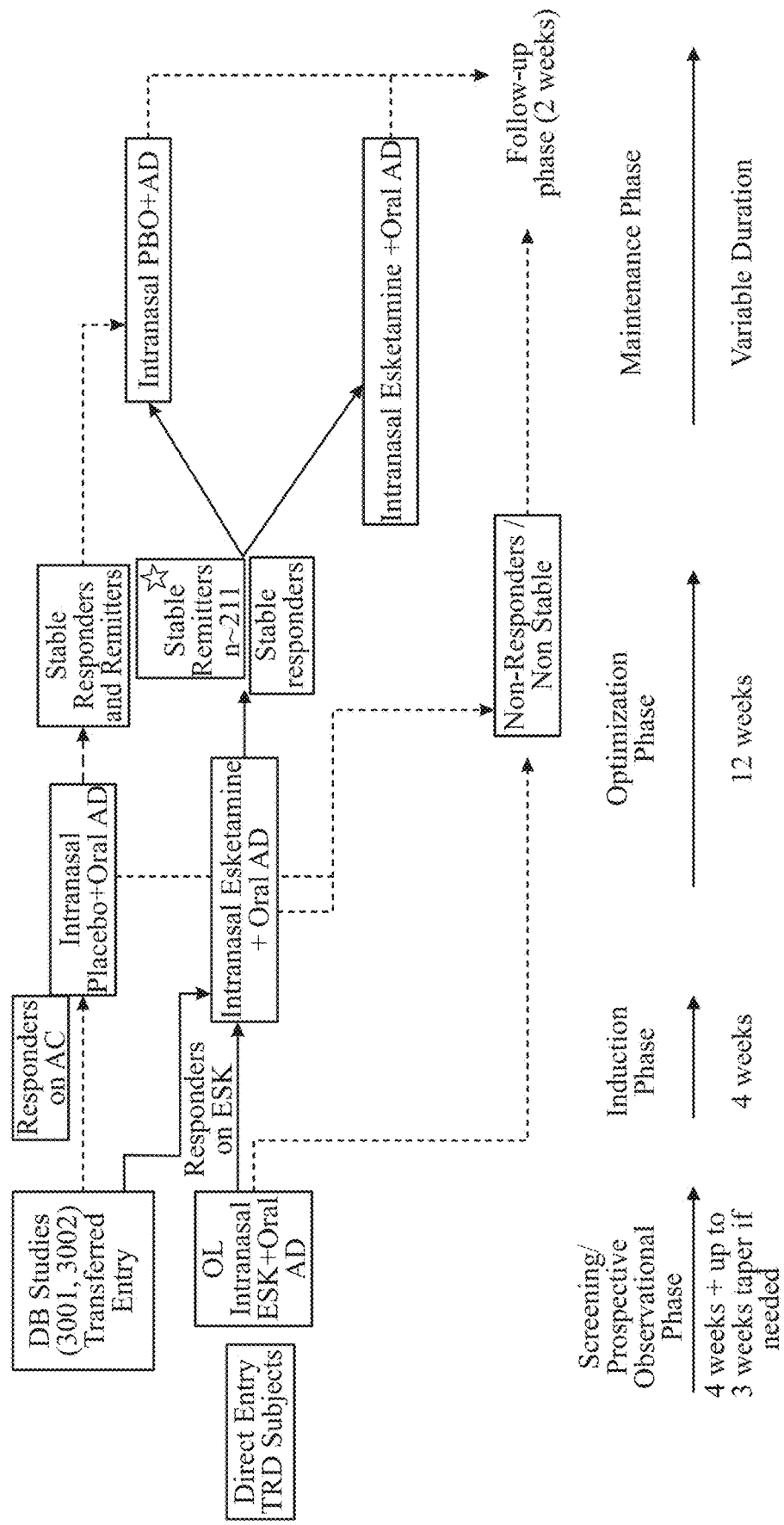

FIG. 49 is the trial design for Example 4.

Figure 50:
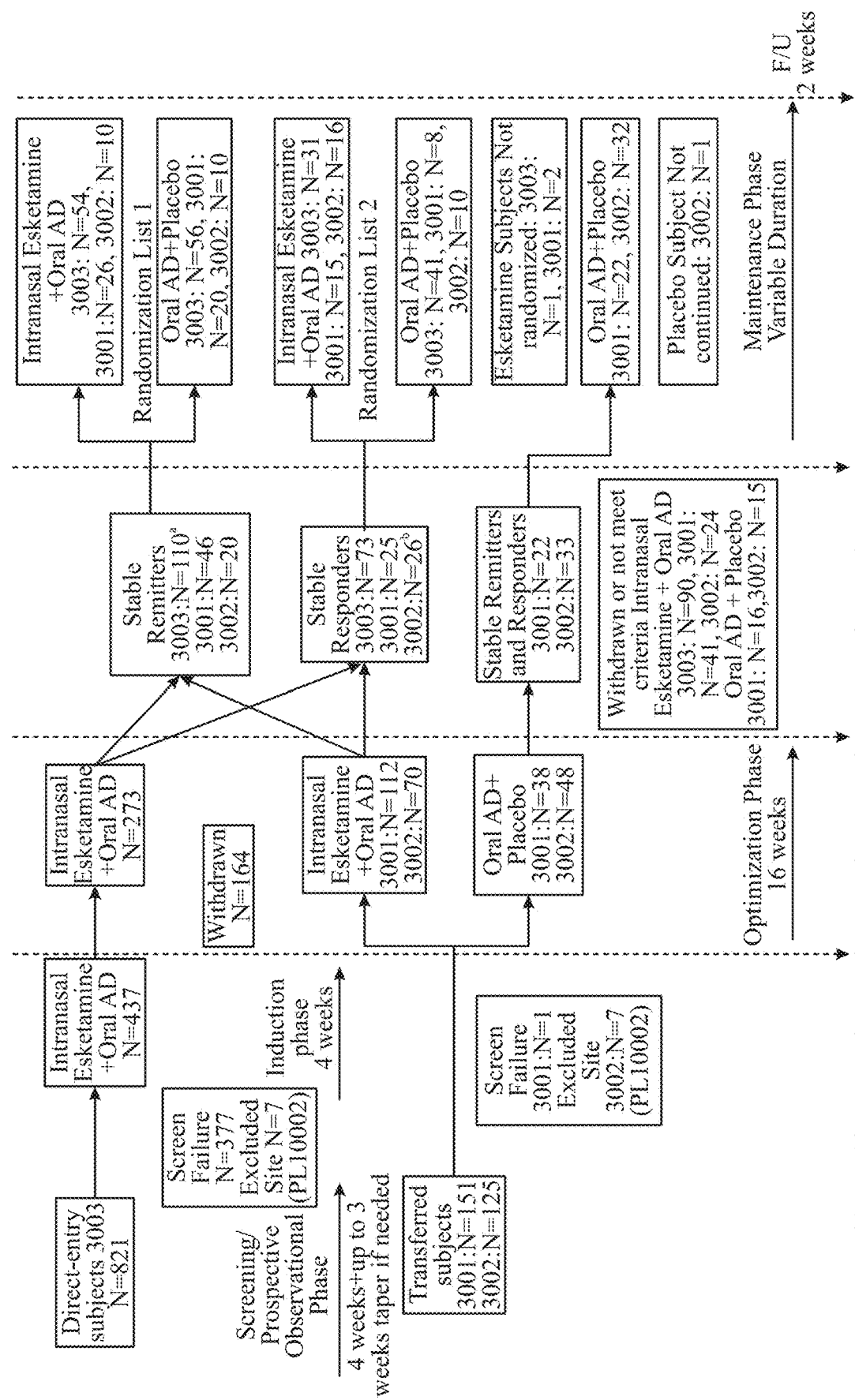

FIG. 50 is a flowchart summarizing the subject and treatment information of Example 4.

Figure 51:
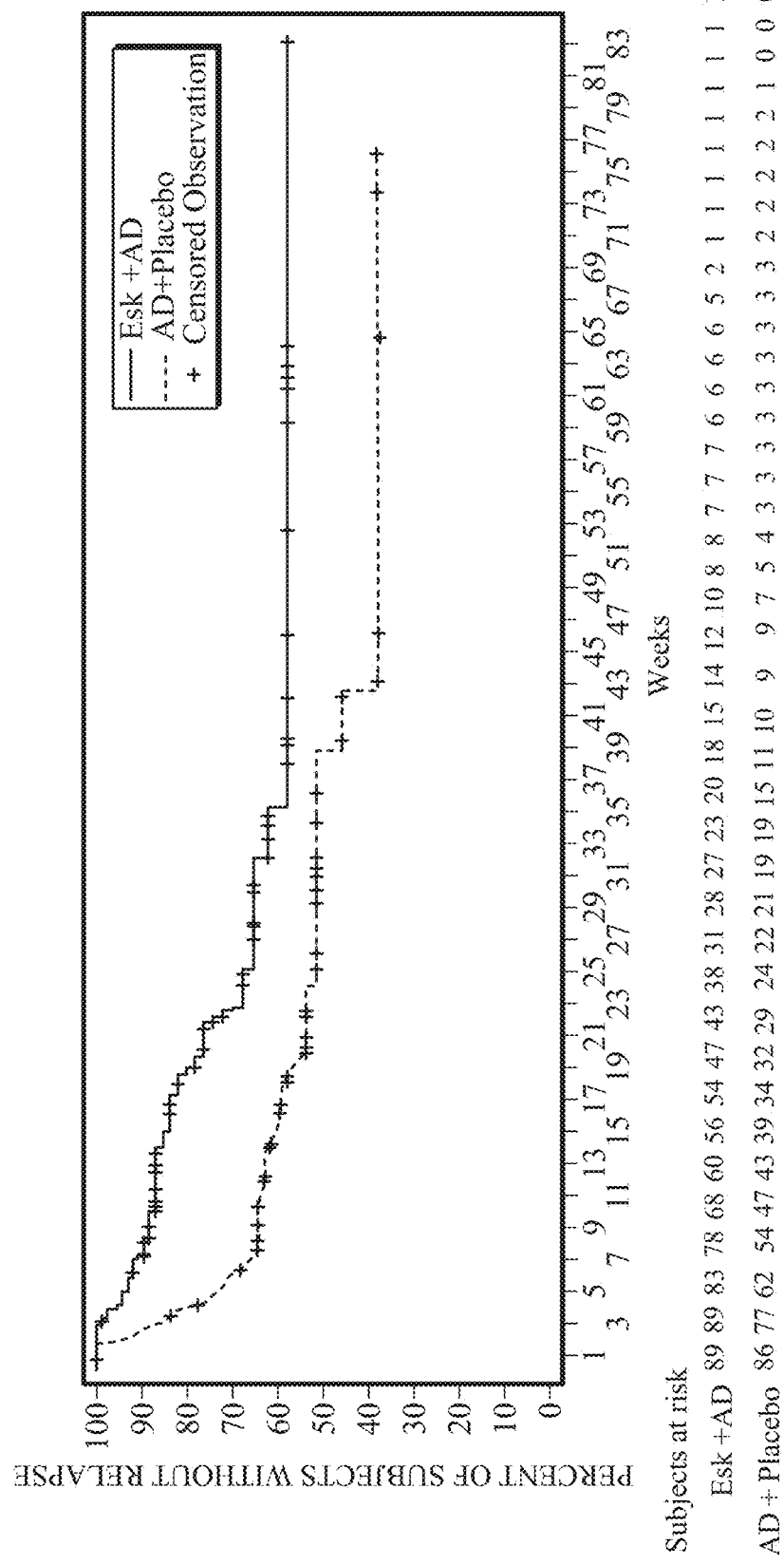

FIG. 51 shows the cumulative proportion of subjects who remained relapse free; maintenance phase (Kaplan-Meier estimates) (full (stable remitters) analysis set) for Example 4.

Figure 52:
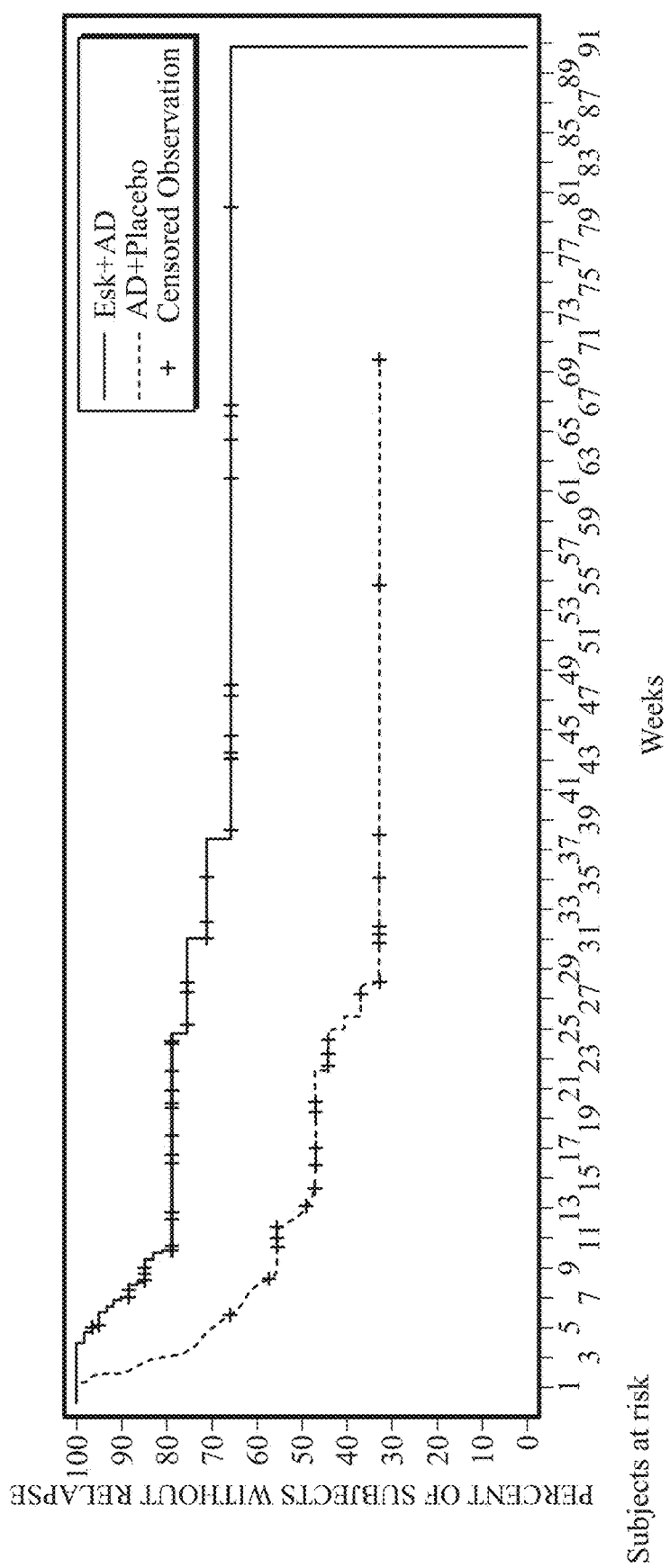

FIG. 52 shows the cumulative proportion of subjects who remained relapse free; maintenance phase (Kaplan-Meier estimates) (full (stable responders) analysis set) for Example 4.

Figure 53:
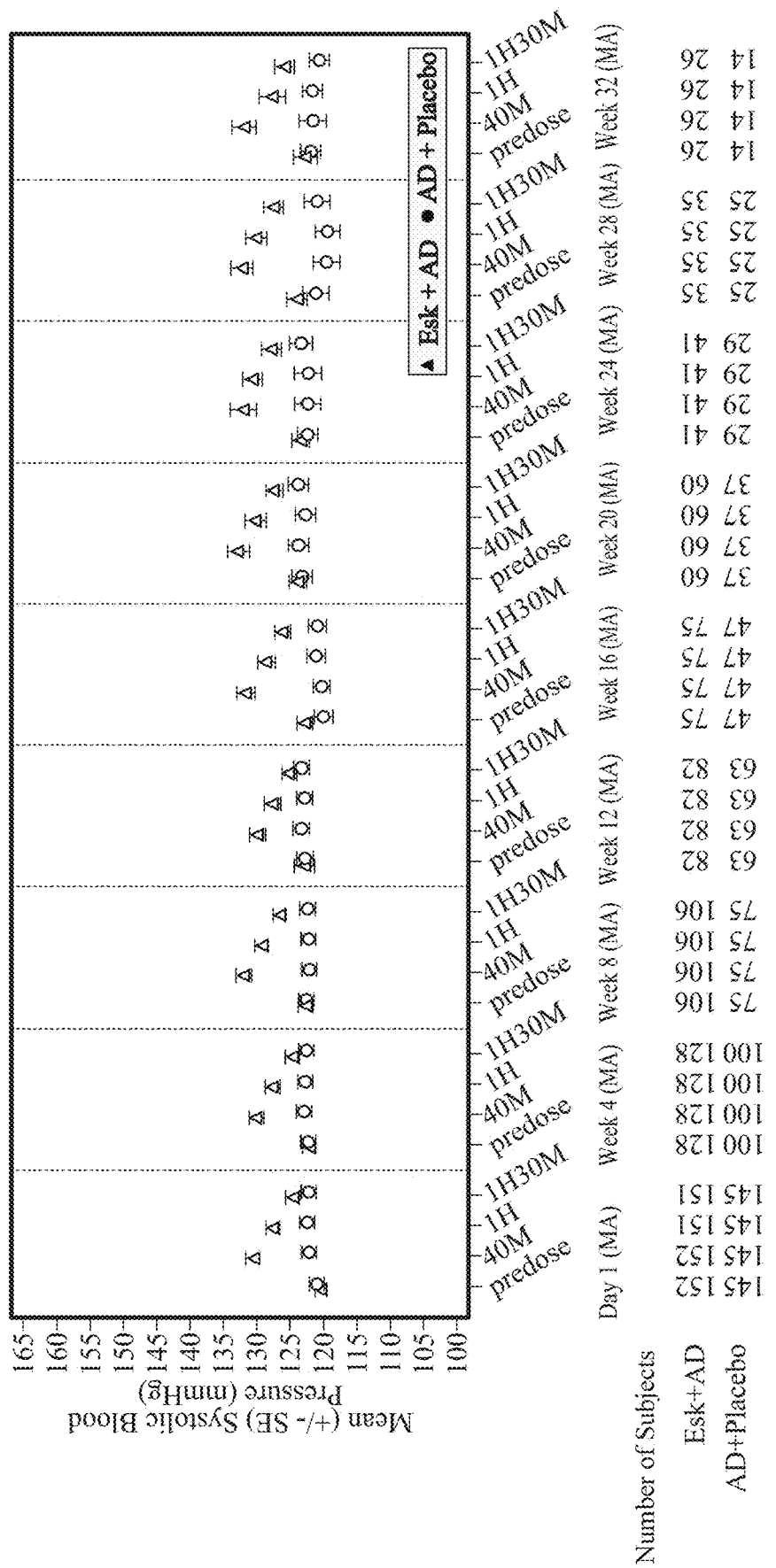

FIG. 53 shows the arithmetic mean (±SE) systolic blood pressure over time; maintenance phase (safety (MA) analysis set) for Example 4.

Figure 54:
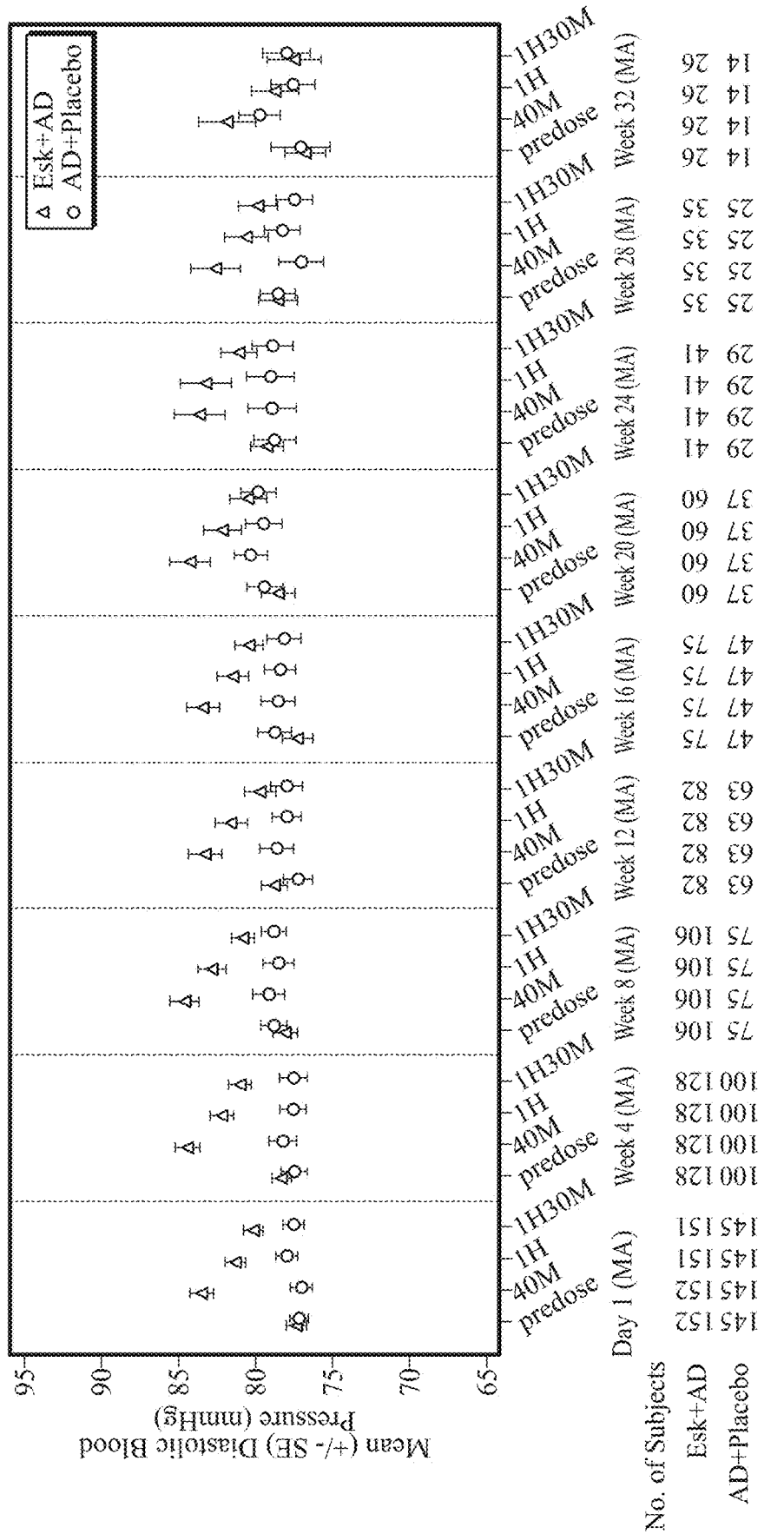

FIG. 54 shows the arithmetic mean (±SE) diastolic blood pressure over time; maintenance phase (safety (MA) analysis set) for Example 4.

Figure 55:
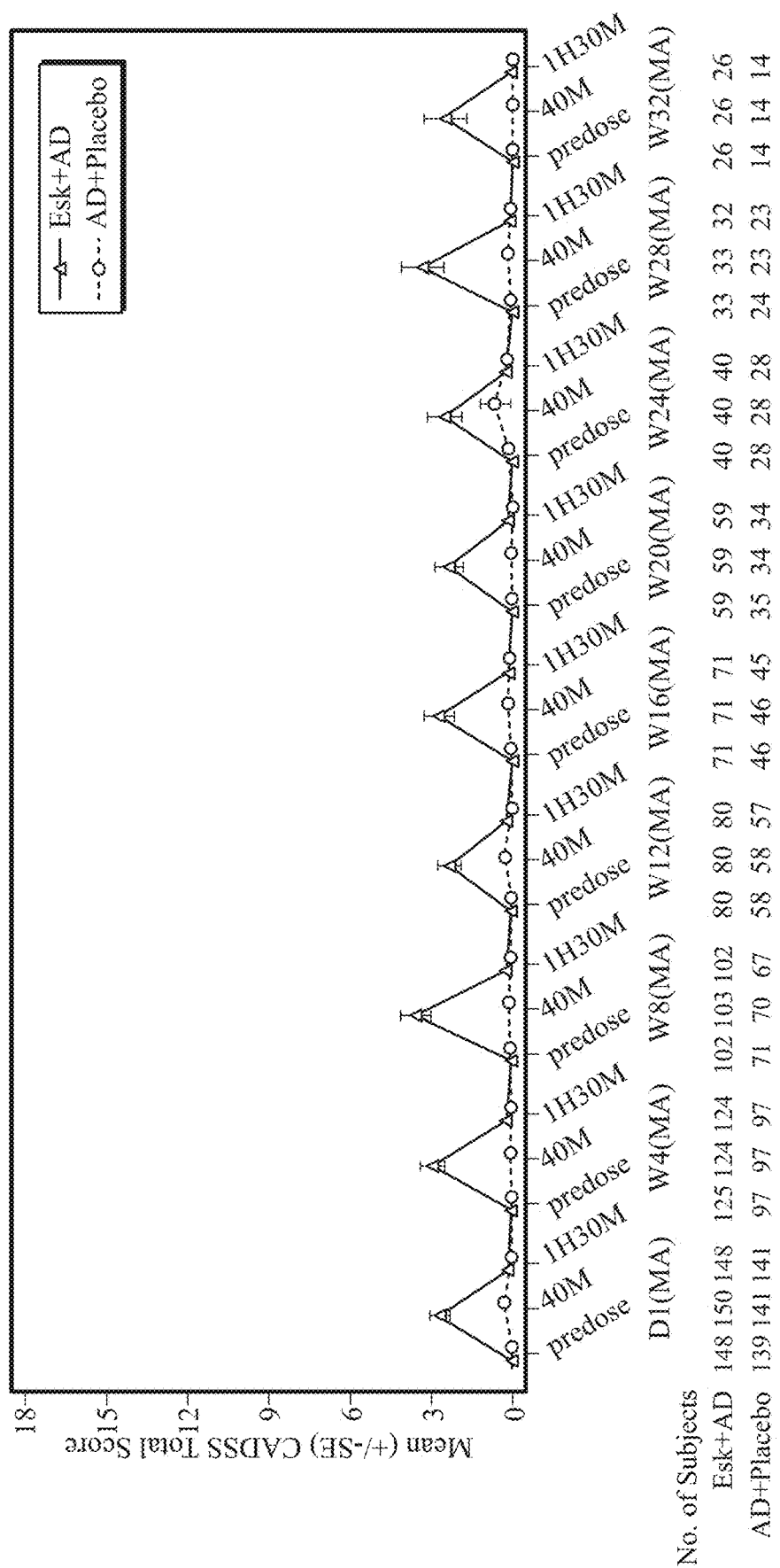

FIG. 55 shows the arithmetic mean (±SE) CADSS total score over time; maintenance phase (safety (MA) analysis set) for Example 4.

Figure 56:
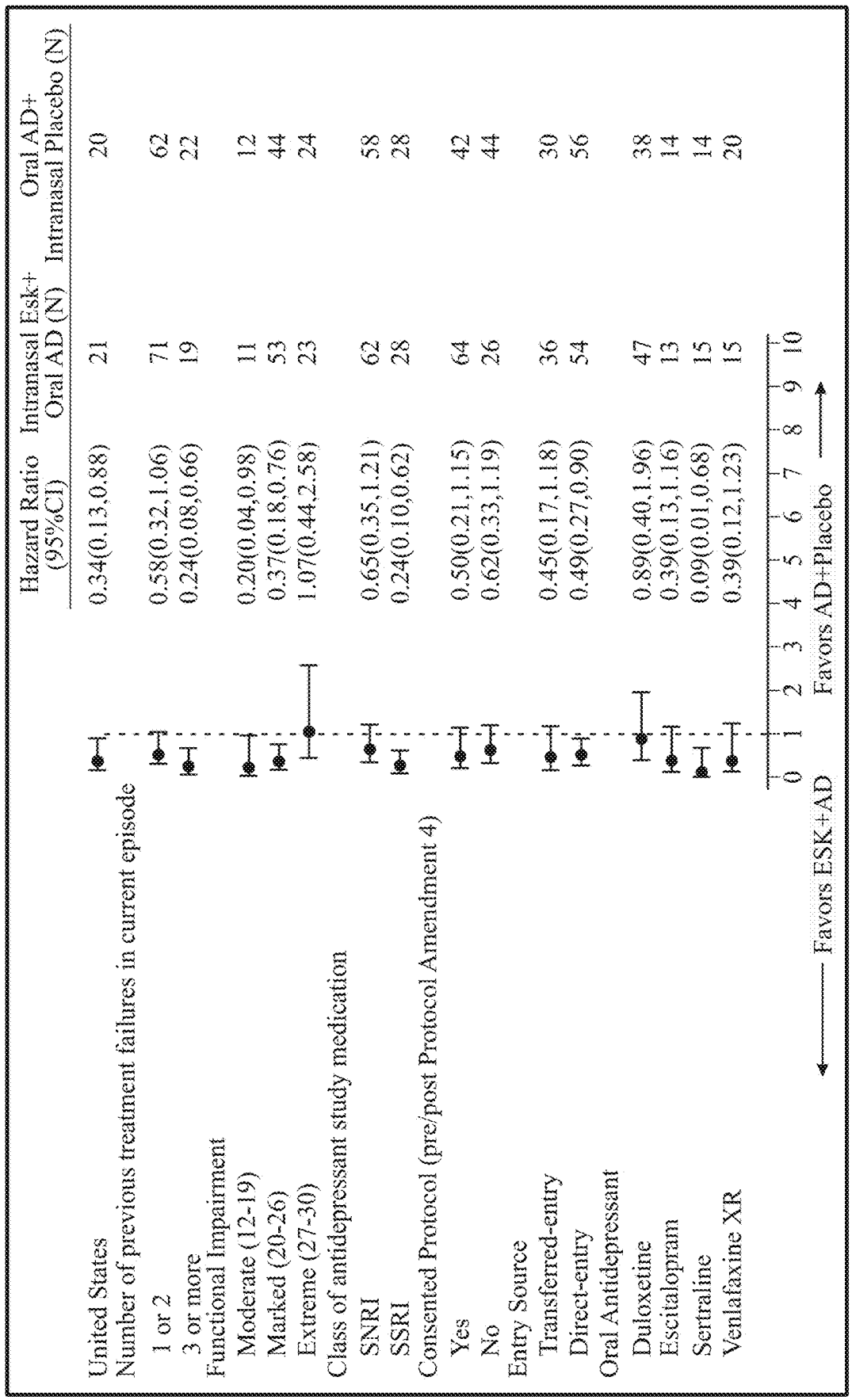

FIG. 56 is a forest plot of hazard ratio by subgroup: Cox Regression (full (stable remitters) analysis set) for Example 4. Hazard ratio estimates for subgroups with no event in either arm not displayed. Subgroups with fewer than 5 subjects not presented.

Figure 57:
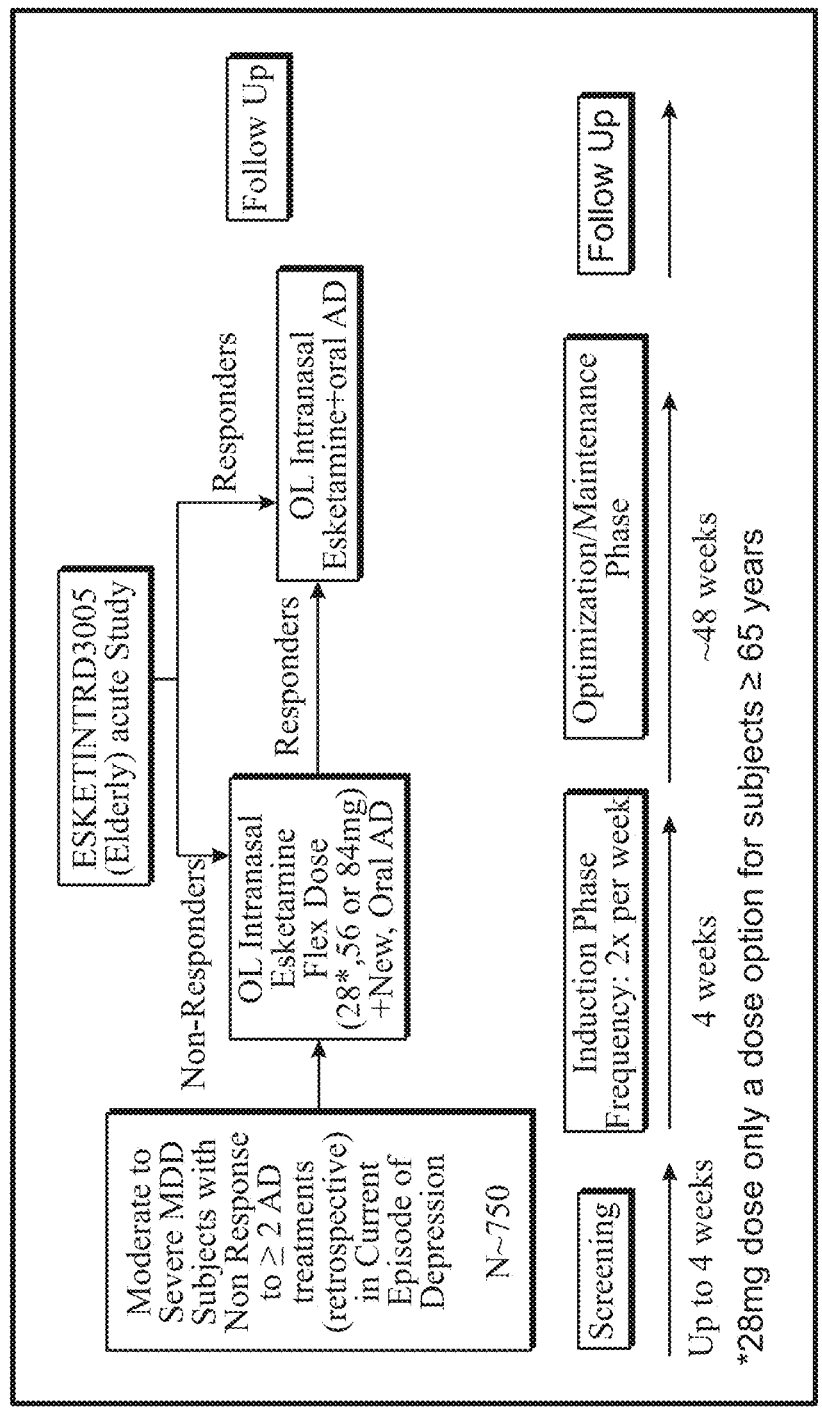

FIG. 57 is the trial design for Example 5. At entry to the trial, transferred entry non-responder subjects continued to receive the same oral antidepressant initiated in the ESKETINTRD3005 study. The new oral AD is for direct entry subjects only.

Figure 58:
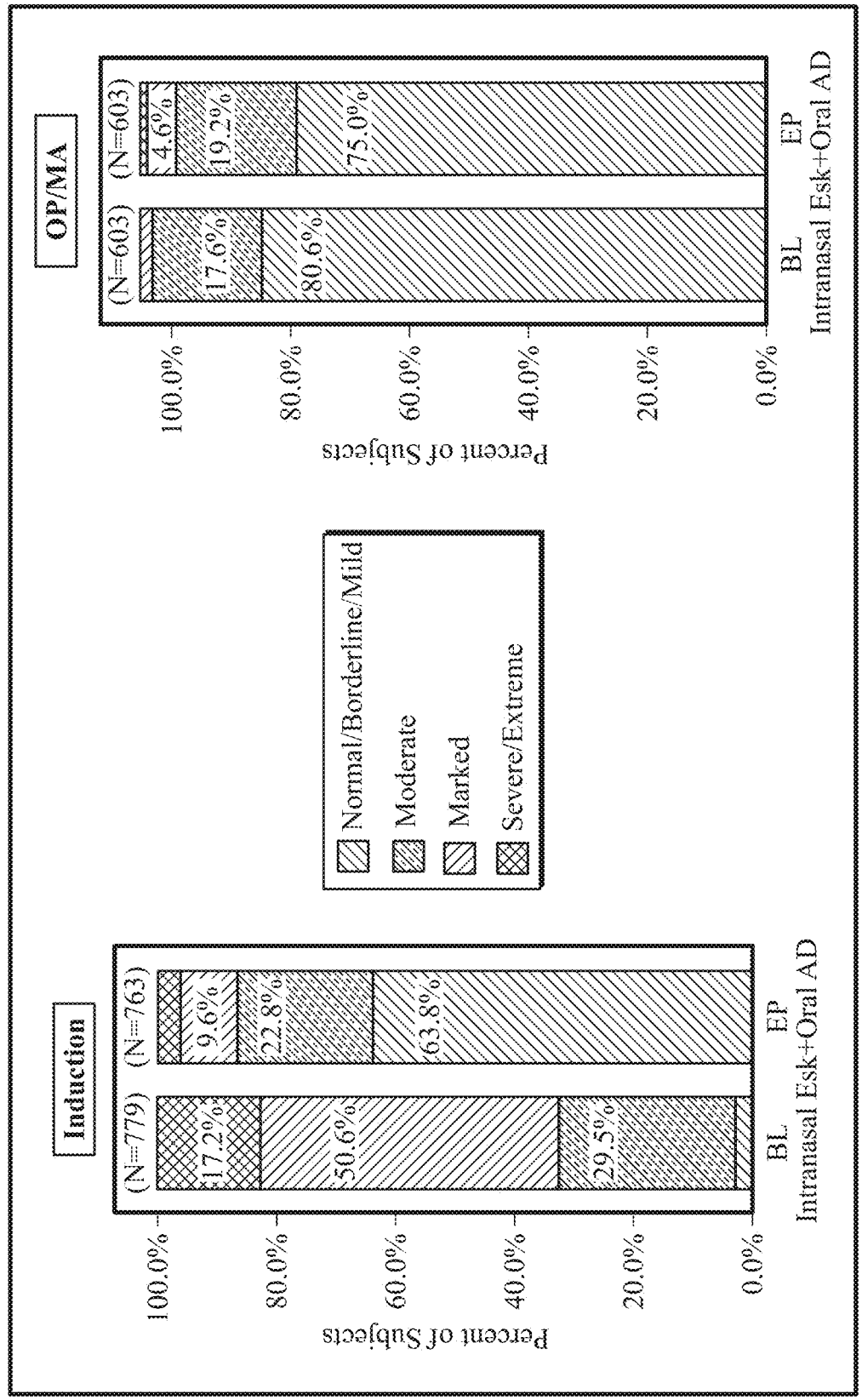

FIG. 58 is shows the frequency distribution for the CGI-S of Example 5.

Figure 59:
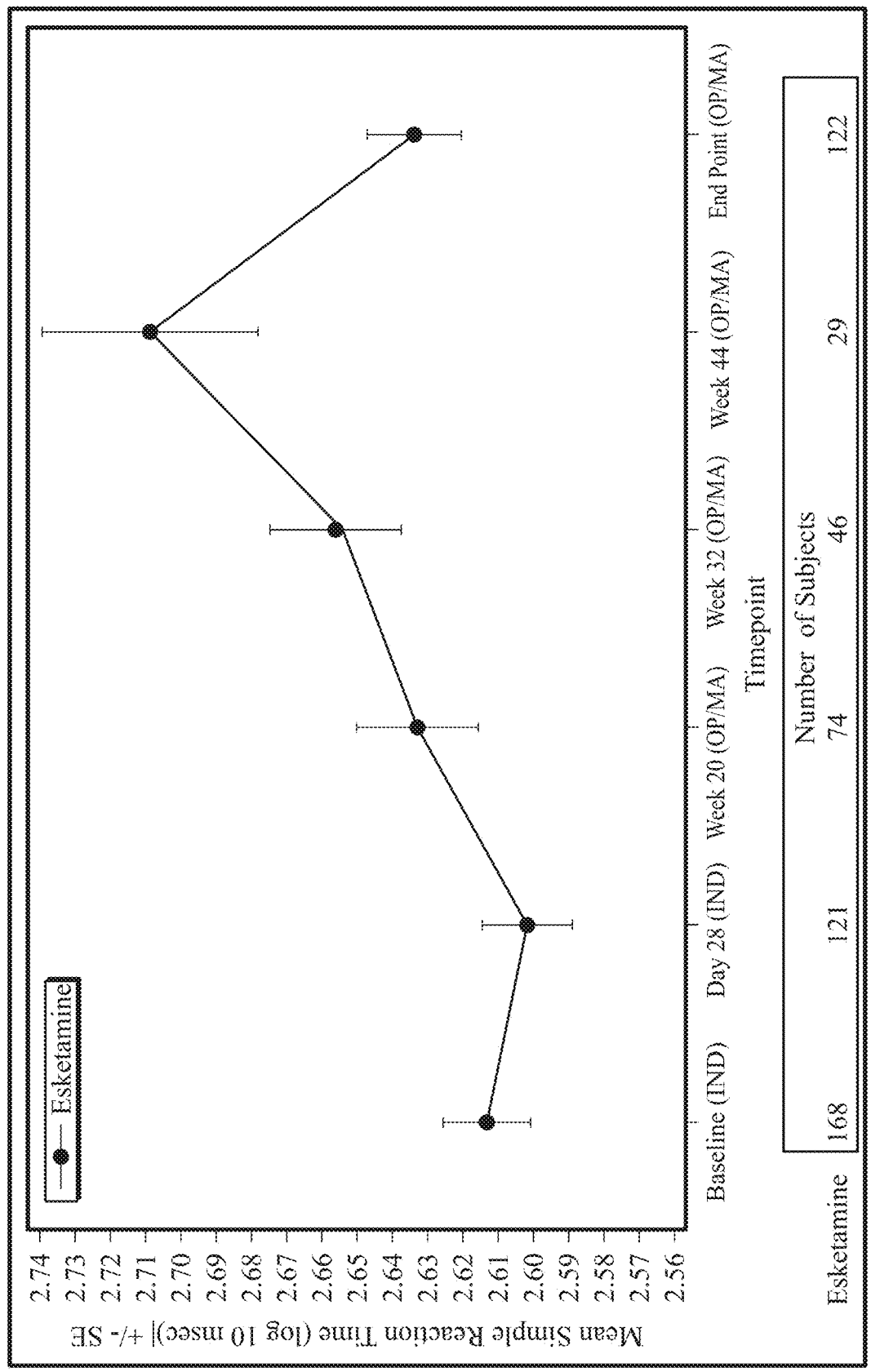

FIG. 59 shows the arithmetic mean (±SE) of detection—attention (simple reaction time) (all enrolled analysis set) for the age group ≥65 years in Example 5.

Figure 60:
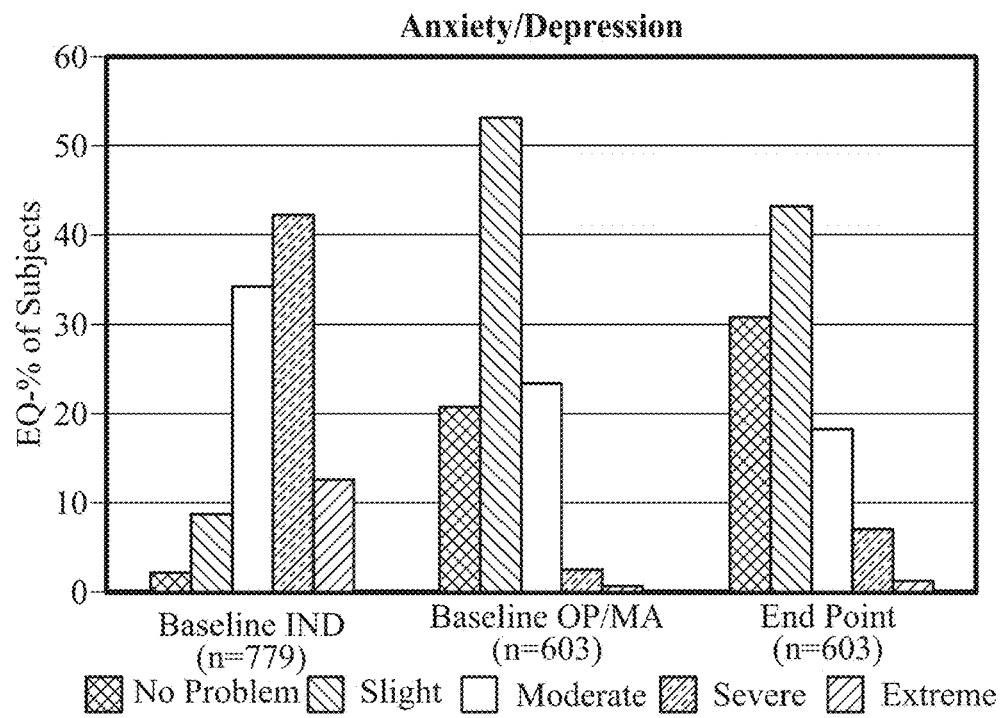
Figure 61:
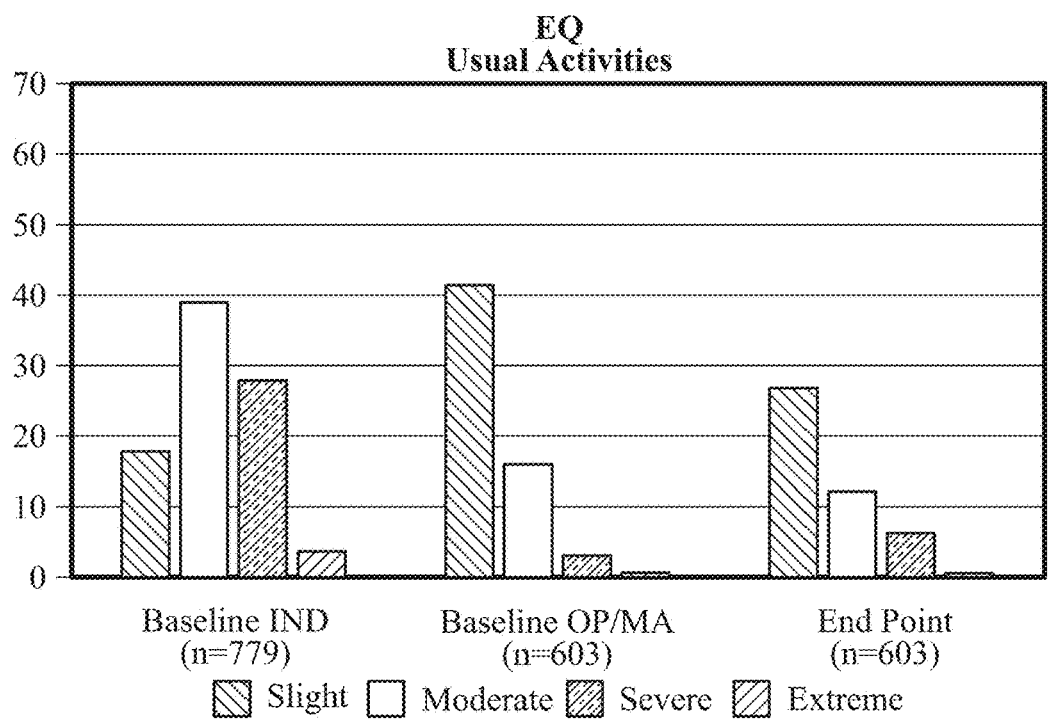
Figure 62:
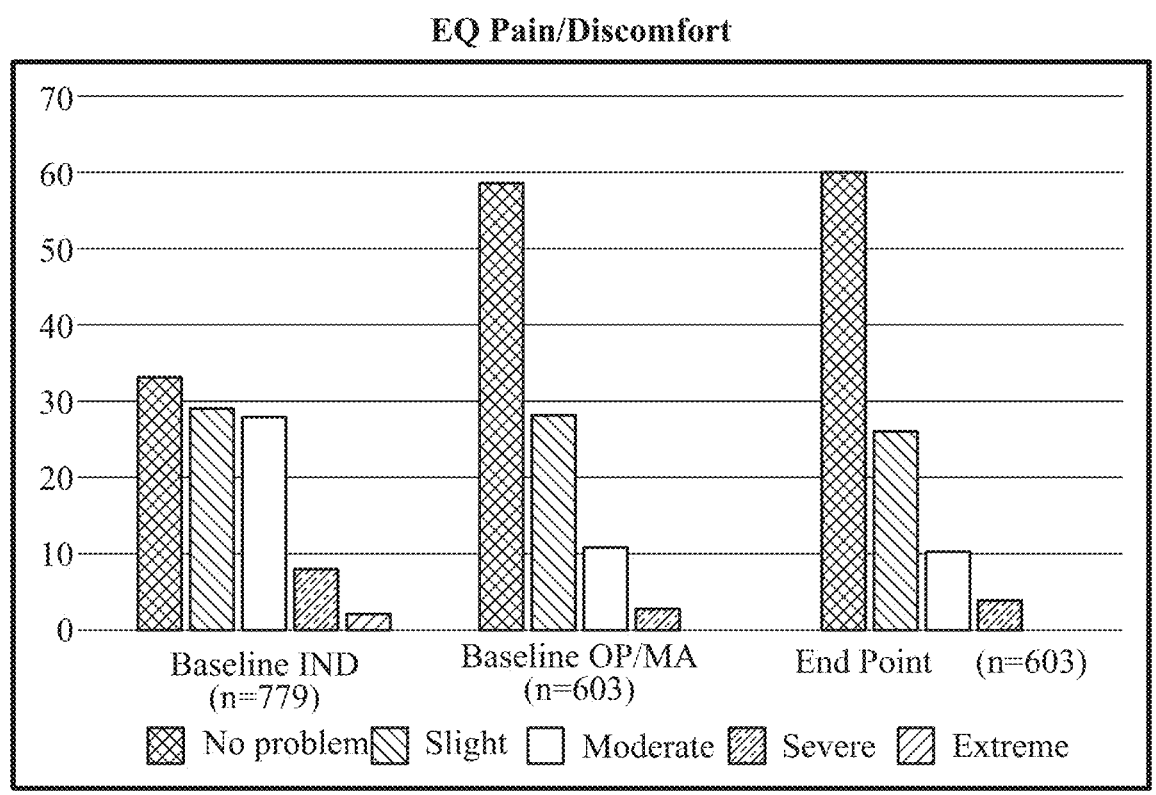

FIGS. 60-62 shows the level of impairment for the EQ-5D-5L by measuring anxiety/depression, usual activities, and pain/discomfort, respectively.

Figure 63:
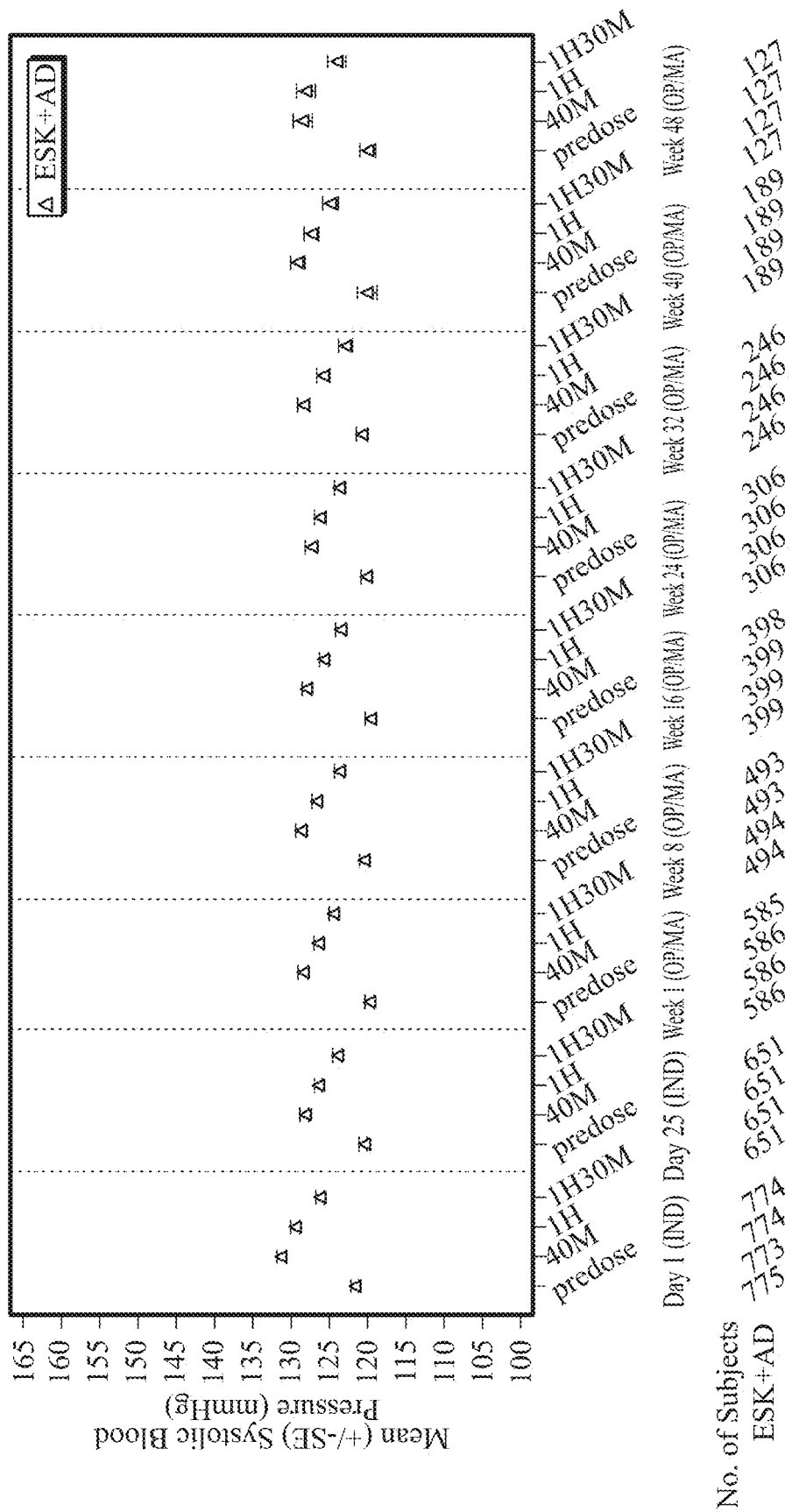

FIG. 63 shows the arithmetic mean (±SE) systolic blood pressure over time; induction and optimization/maintenance phases (all enrolled analysis set) for Example 5.

Figure 64:
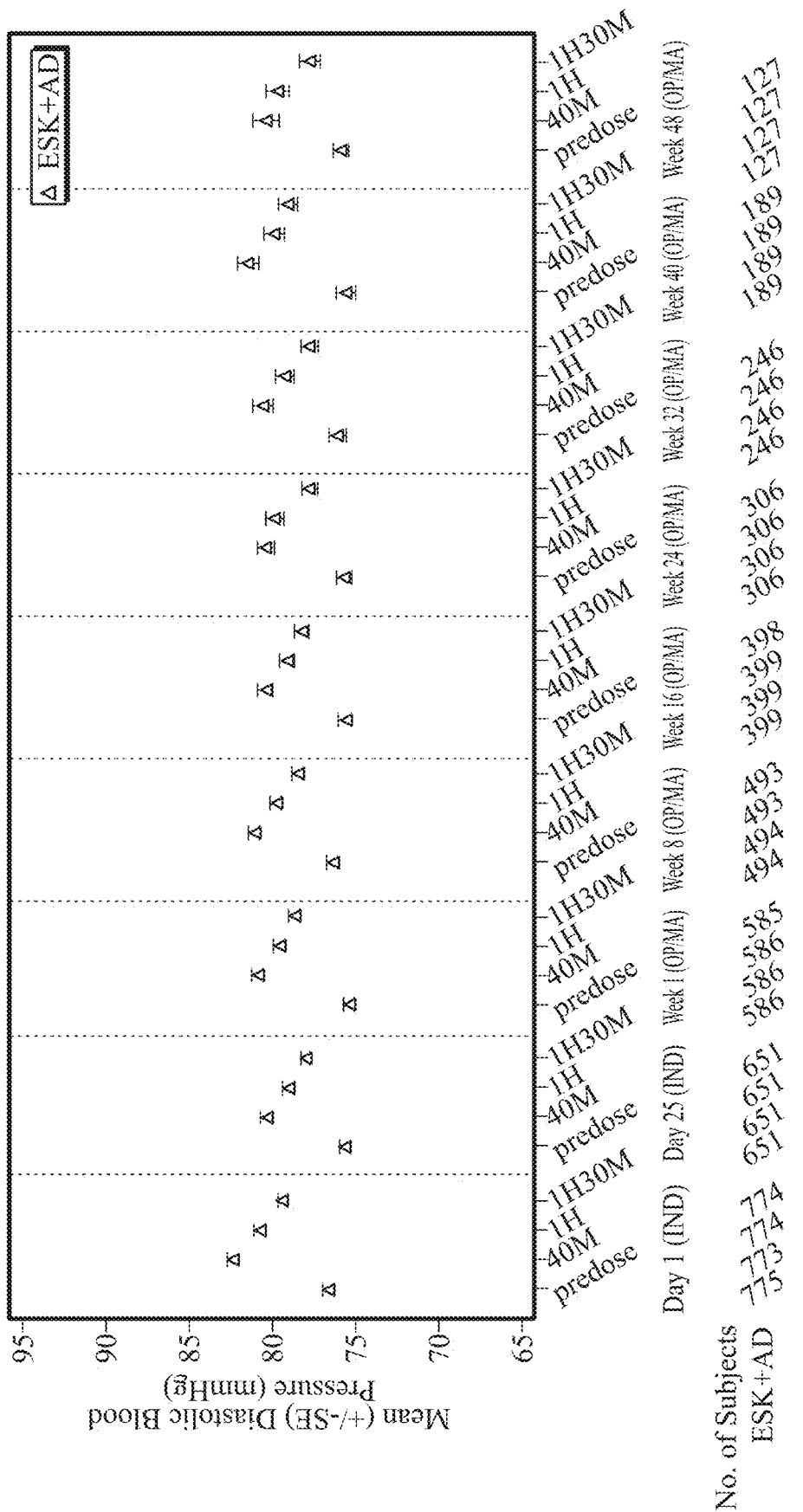

FIG. 64 shows the arithmetic mean (±SE) diastolic blood pressure over time; induction and optimization/maintenance phases (all enrolled analysis set) for Example 5.

Figure 65:
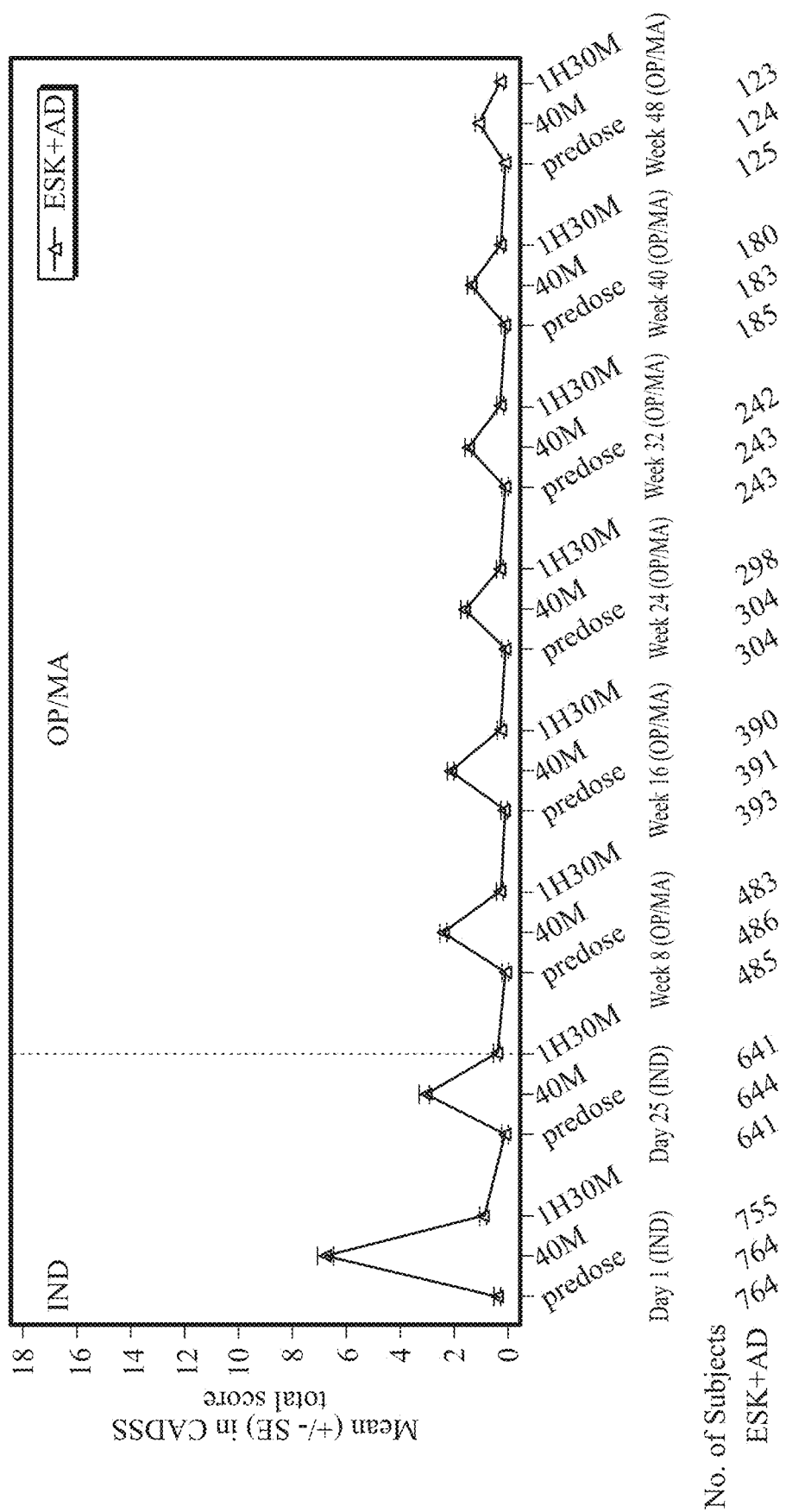

FIG. 65 is a plot of CADSS total score over time during the induction and optimization/maintenance phase (all enrolled analysis set) for Example 5.

Figure 66:
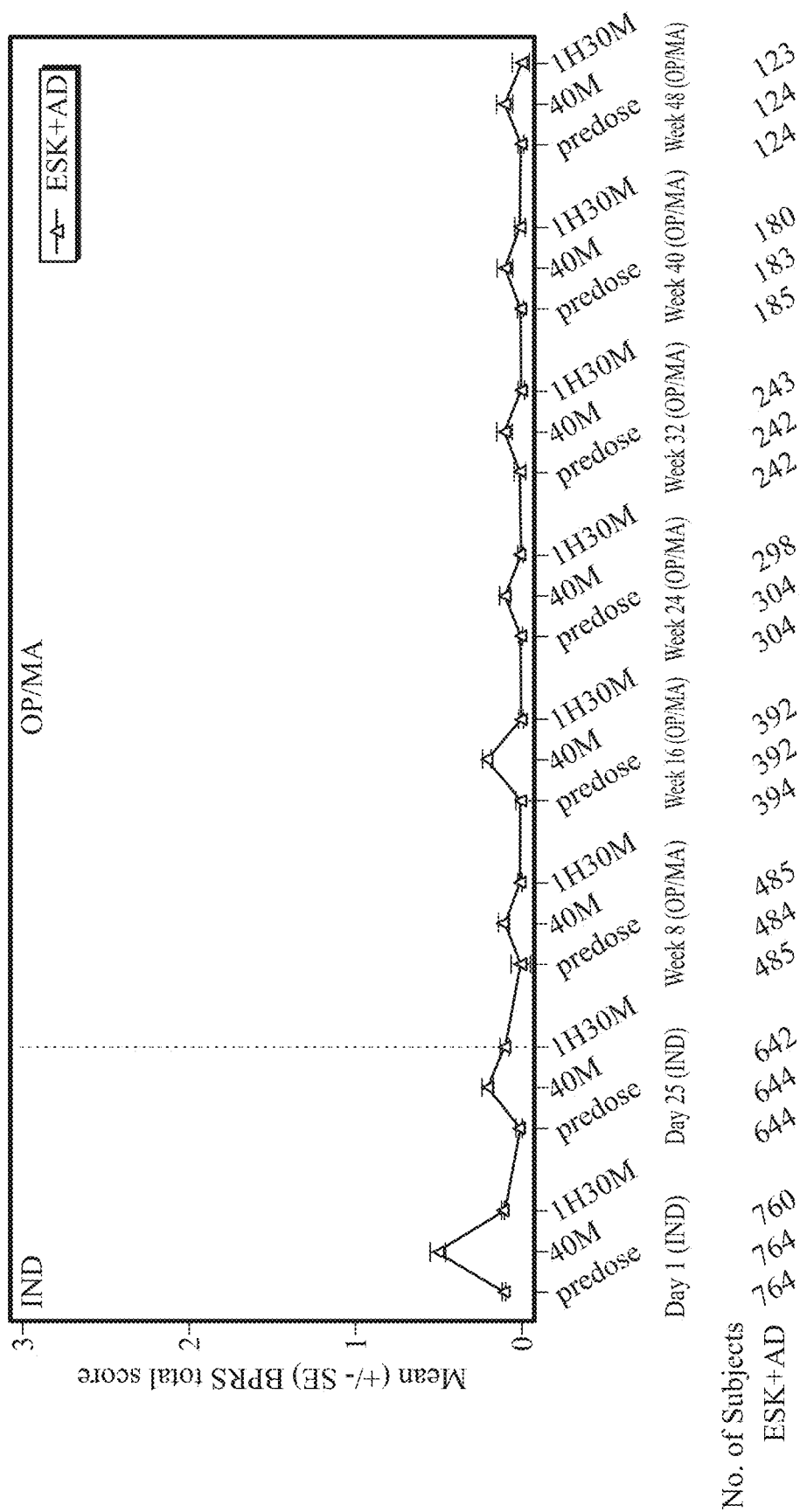

FIG. 66 is a plot showing the mean (t) SE for the of the brief psychiatric rating positive symptom subscale total score over time during the induction and optimization/maintenance phases (all enrolled analysis set) for Example 5.

Figure 67:
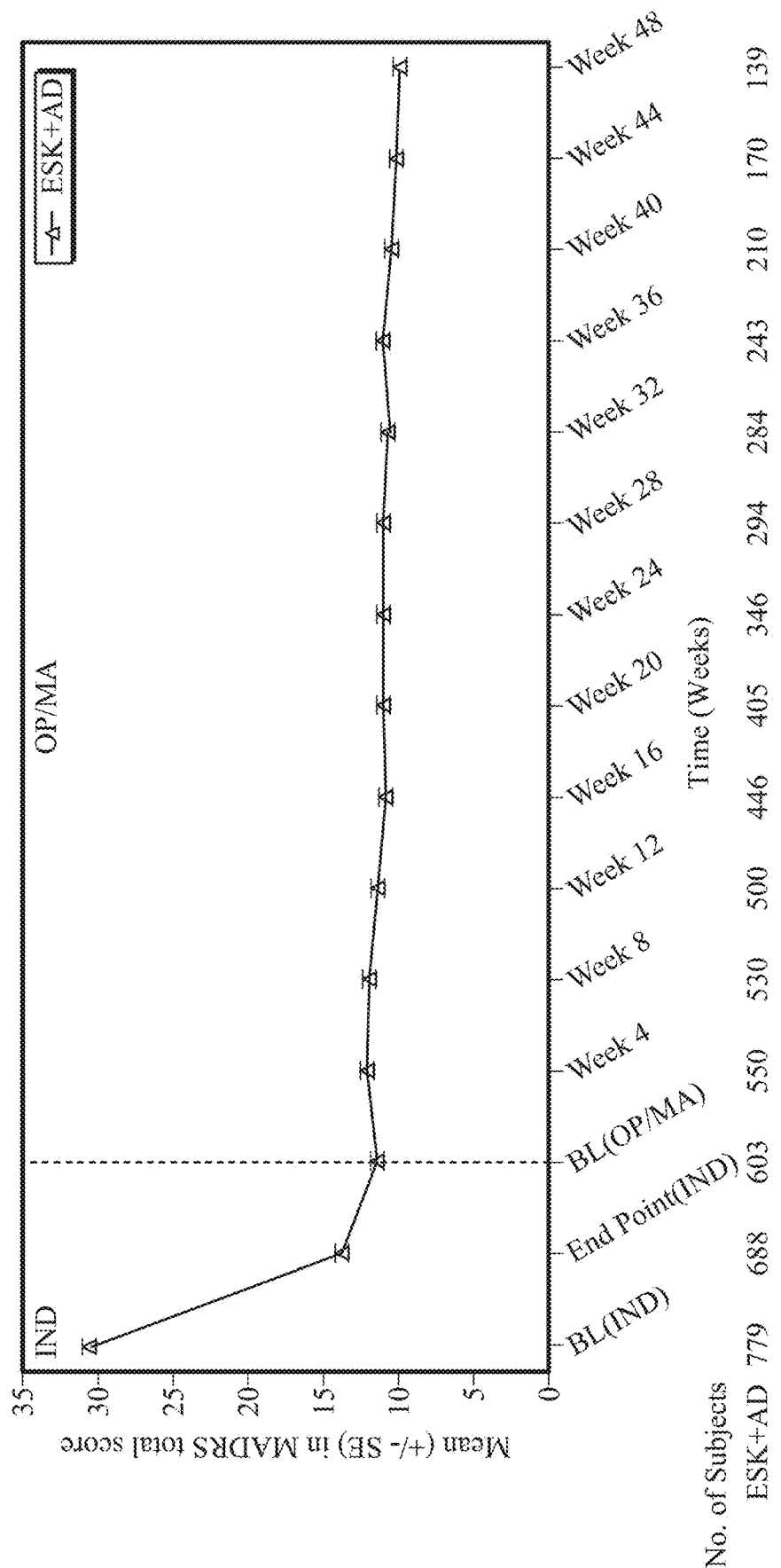

FIG. 67 shows means for the MADRS total score over time in the IND and OP/MA phases based on observed case data for Example 5.

Figure 68:
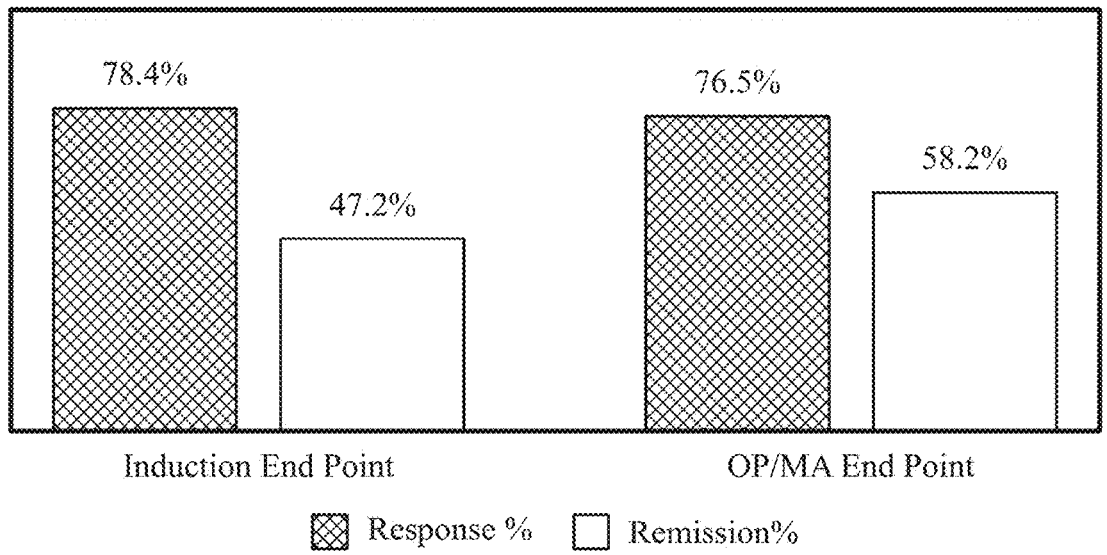

FIG. 68 shows the response for patients having a response with a ≤50% reduction from baseline and a remission with a MADRS of ≤12.

Figure 69:
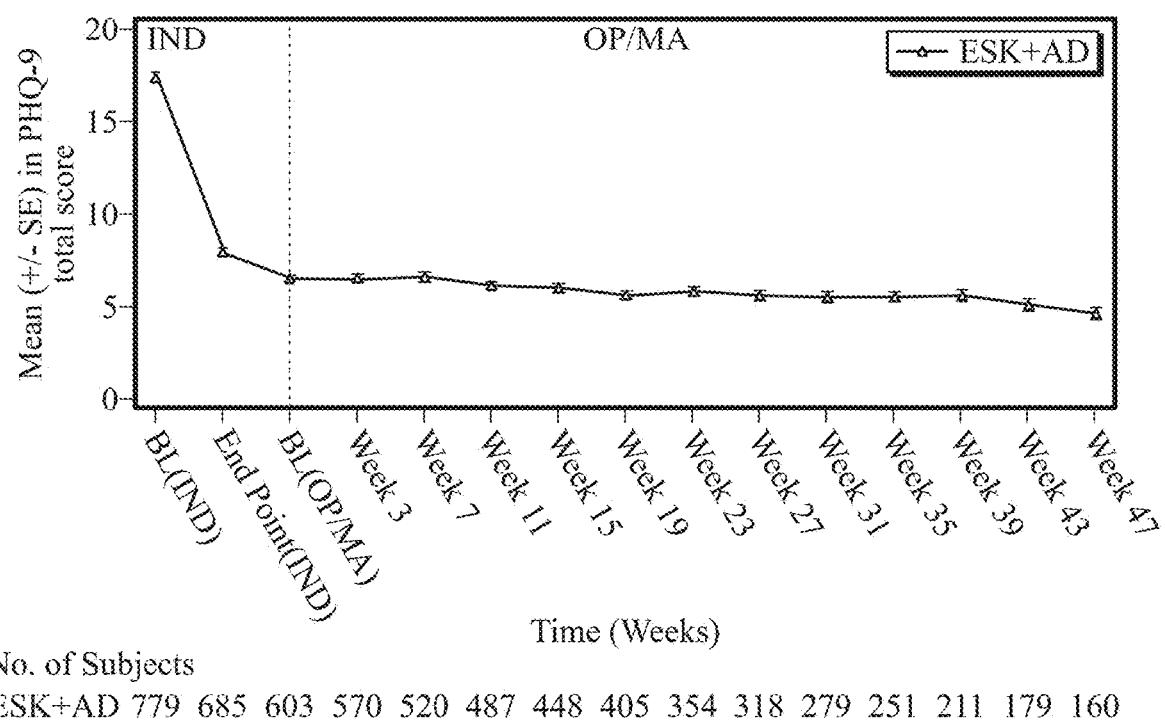

FIG. 69 shows means for the PHQ-9 total score over time in the IND and OP/MA phases based on observed case data for Example 5.

Figure 70:
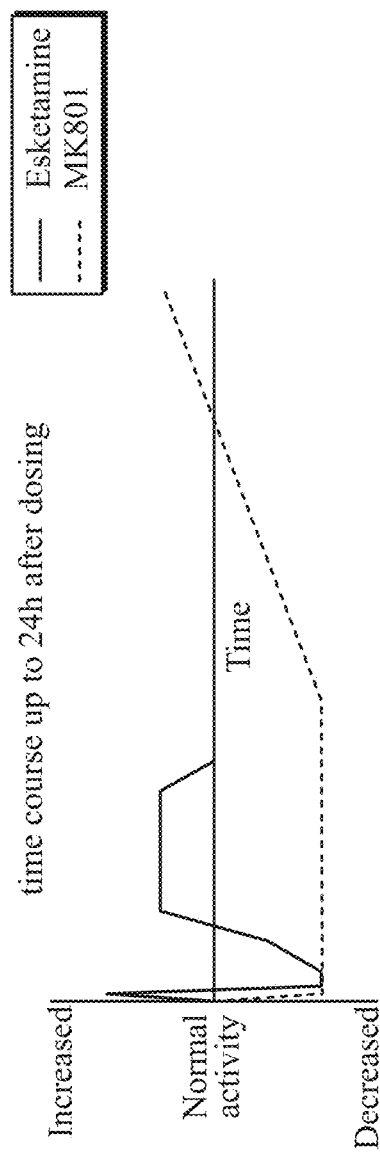

FIG. 70 is an illustration of decreased and increased activity. MK-801-induced changes in activity are described in Section 3.3 of Example 6. Gross pathology did not reveal any tissue changes.

Figure 71A:
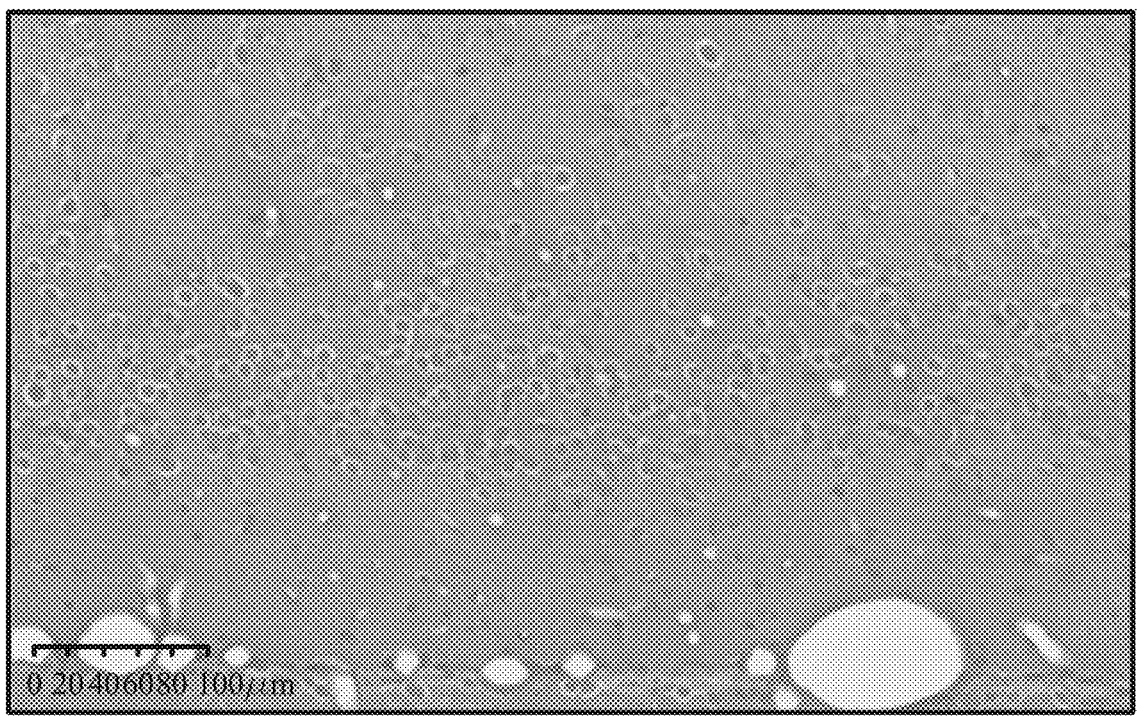
Figure 71B:
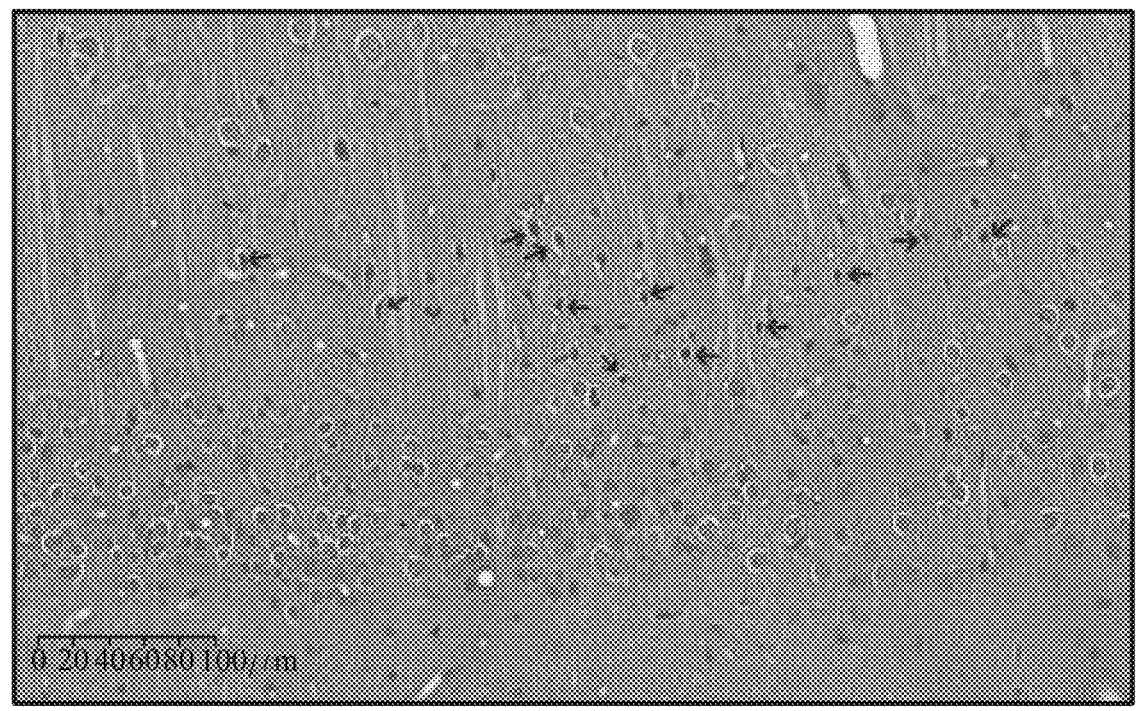
Figure 71C:
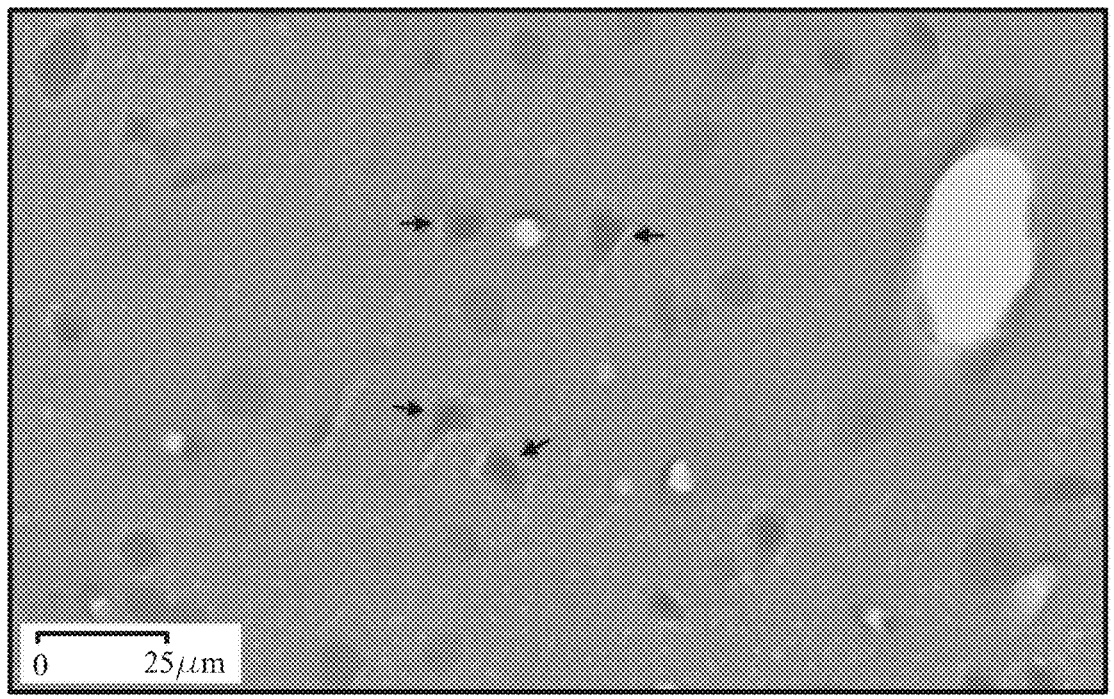

FIG. 71A to FIG. 71C shows a repeated dose neurotoxicity study. Haematoxylin-eosin (HE) stained retrosplenial cortex shows the absence of neuronal necrosis in an esketamine HCl-treated rat (54 mg/day) and its presence in an (+)MK-801 maleate-treated rat as described in Example 6. FIG. 71A is an image of the retrosplenial cortex of an esketamine HCl-treated rat (54 mg/day) showing the absence of neuronal necrosis. FIG. 71B is an image of the retrosplenial cortex from an (+)MK-801 maleate-treated animal. Arrows show necrotic neurons (shrunken, eosinophilic cytoplasm with condensed nuclei). FIG. 71C is an image of a higher power view of the necrotic neurons (arrows) in the retrosplenial cortex from an (+)MK-801maleate treated animal.

Figures 72A, 72B:
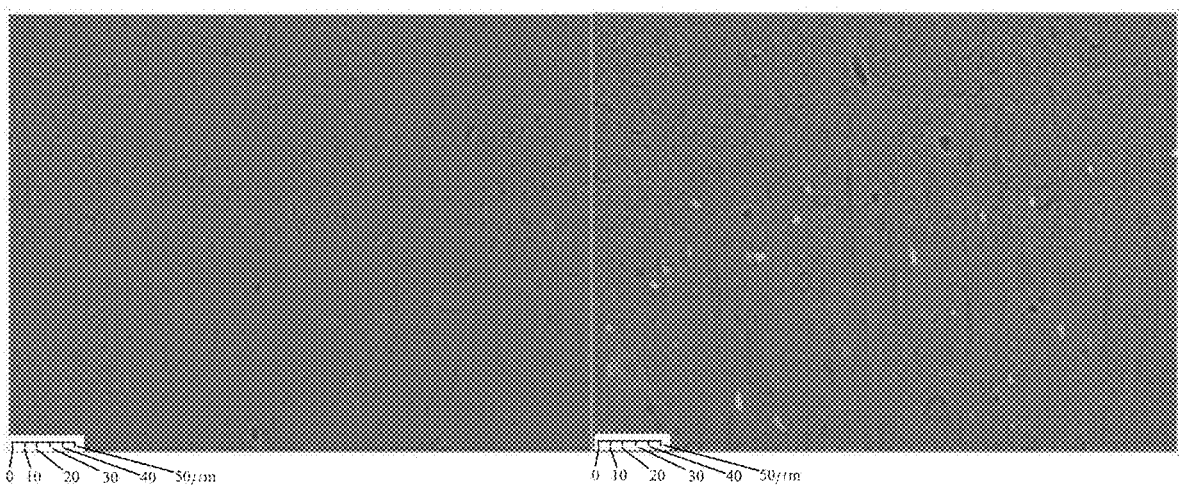

FIG. 72A and FIG. 72B illustrate[[s]] a repeated dose neurotoxicity study. Fluoro-Jade (FJ) stained retrosplenial cortex shows the absence of neuronal necrosis in an esketamine HCl-treated rat (54 mg/day) and its presence in an (+)MK-801 treated rat as described in Example 6. FIG. 72A is an image of the retrosplenial cortex of an esketamine HCl-treated rat (54 mg/day) showing the absence of neuronal necrosis. FIG. 72B is an image of the retrosplenial cortex from an (+)MK-801 maleate-treated animal.

Figure 73:
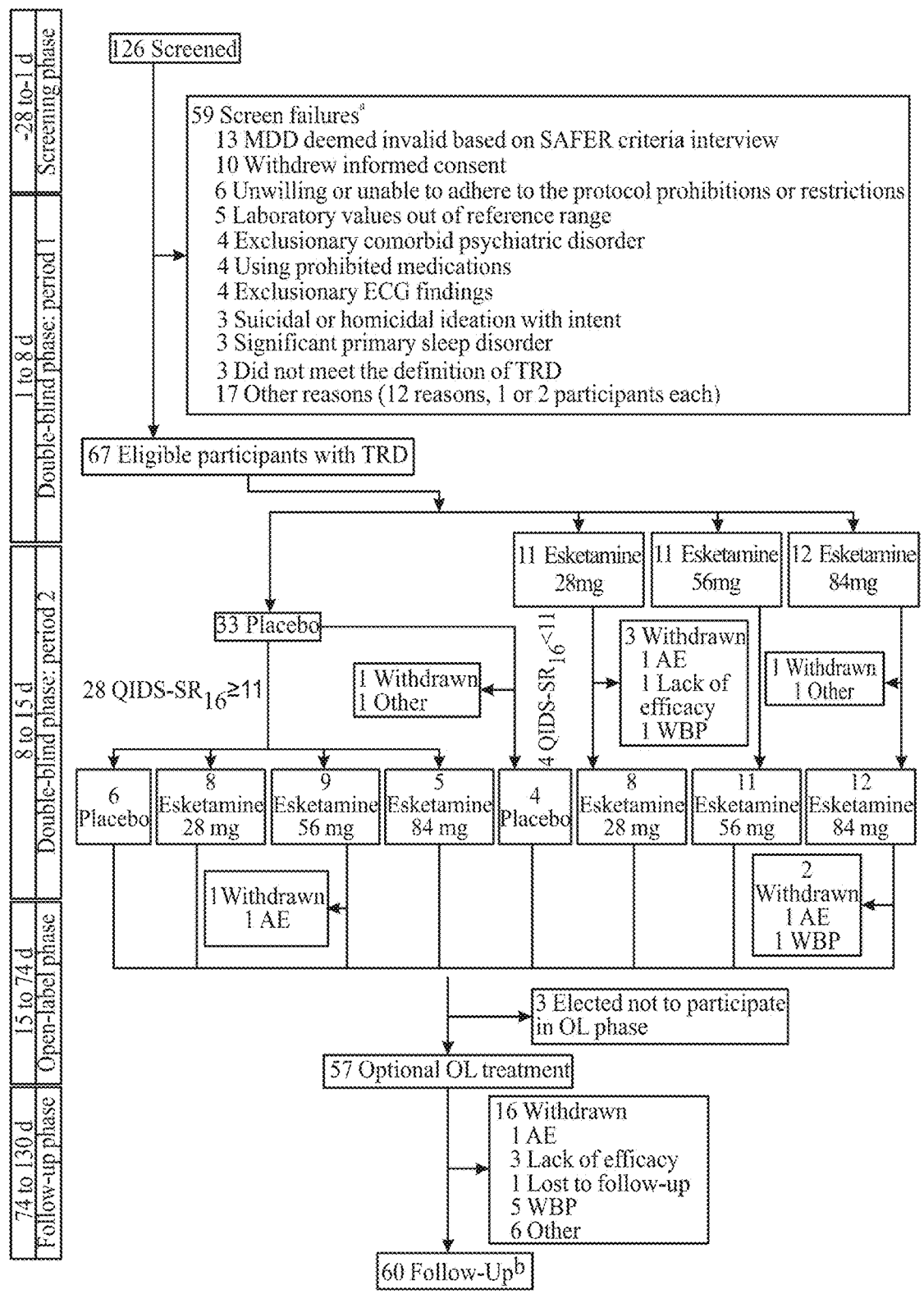

FIG. 73 is a flowchart showing the disposition of patients of Example 7. Seven participants started the follow-up phase earlier than day 74, having received 2 weeks of study drug during the open-label phase of the study.

Figures 74A, 74B:
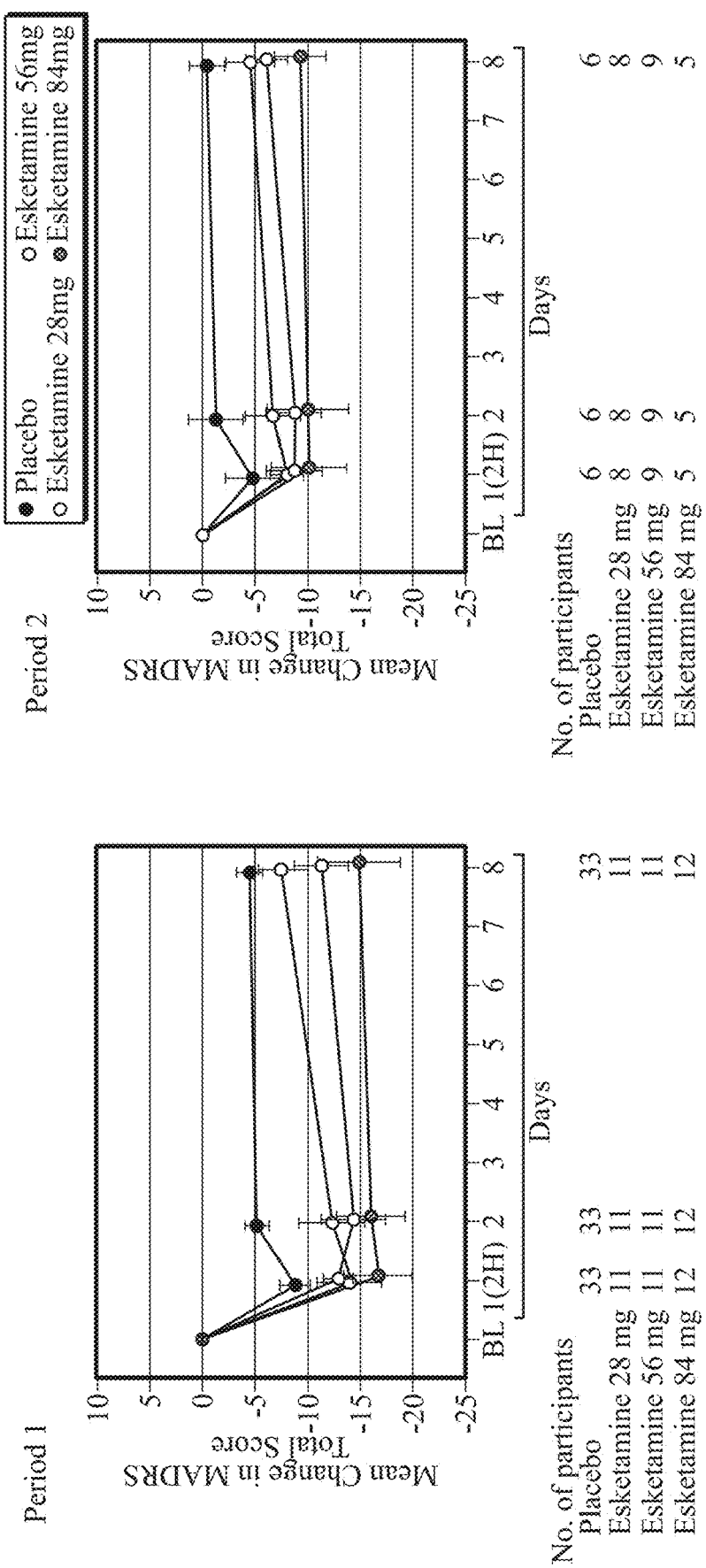

FIGS. 74A and 74B are line graphs showing the mean change (±SE) in MADRS total score over time in double blind phase of Example 7. Changes are shown in periods 1(A) and 2(B). Period 2 consisted only of participants who had received placebo in period 1 and had moderate to severe symptoms (n=28). Period 1 (days 1-8) and period 2 (days 8-15) are discussed in the Design section of the Methods and shown in the vertical axis of FIG. 73. BL indicates baseline; 2H, 2 hours post dose. Error bars indicate SE. Period 2 consists only of those participants who had been on placebo in Period 1 and had moderate-to-severe symptoms (n=28).

Figure 75:
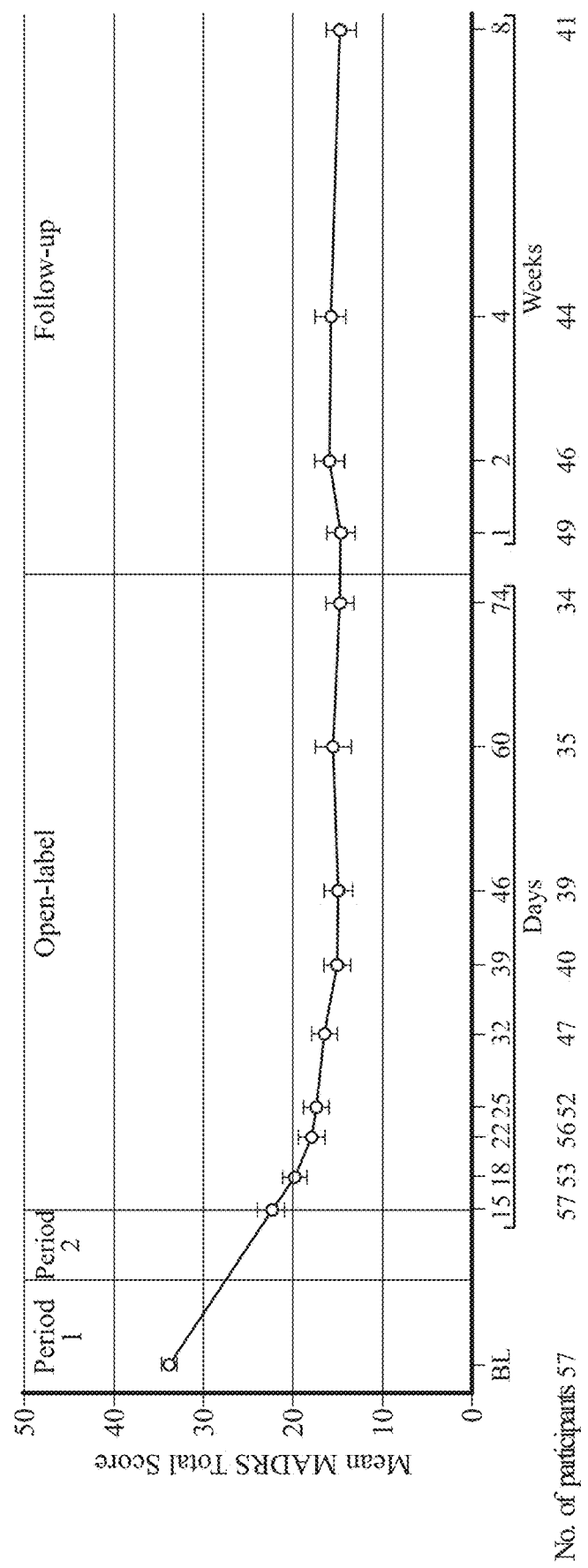

FIG. 75 is a line graph showing the MADRS total score mean change from baseline to follow-up endpoint for participants who entered the open-label phase of Example 7. Period 1 (days 1-8), period 2 (days 8-15), open-label period (days 15-74), and the follow-up period (days 74-130) are discussed in the Design section of the Methods and shown in the vertical axis of FIG. 73. BL indicates baseline; error bars, SE.

Figures 76A, 76B:
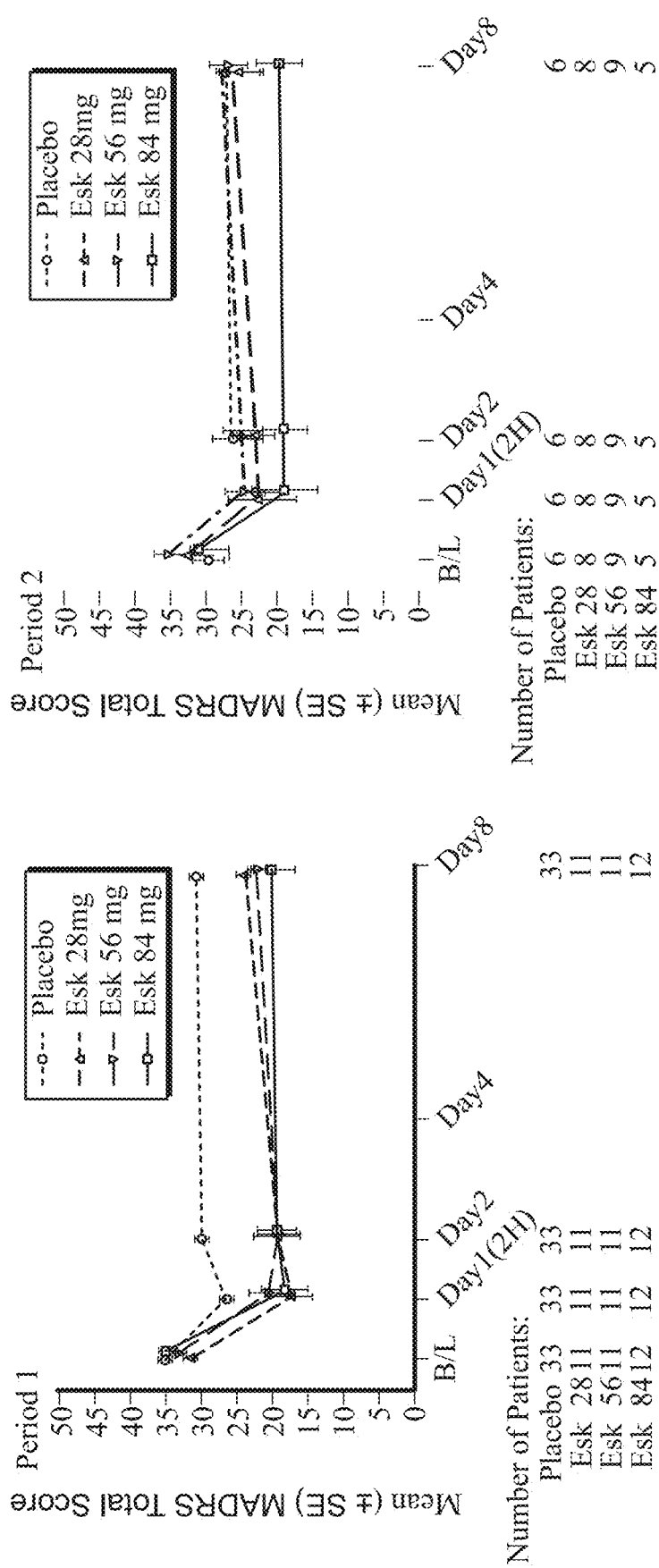

FIGS. 76A and 76B are line graphs showing the mean (±SE) MADRS total score over time in the double-blind phase of Example 7. Period 2 consists only of those participants who had been on placebo in Period 1 and had moderate-to-severe symptoms (n=28). At the 2-hour time point, modified MADRS was used, with baseline scores for sleep and appetite items carried forward.

Figure 77:
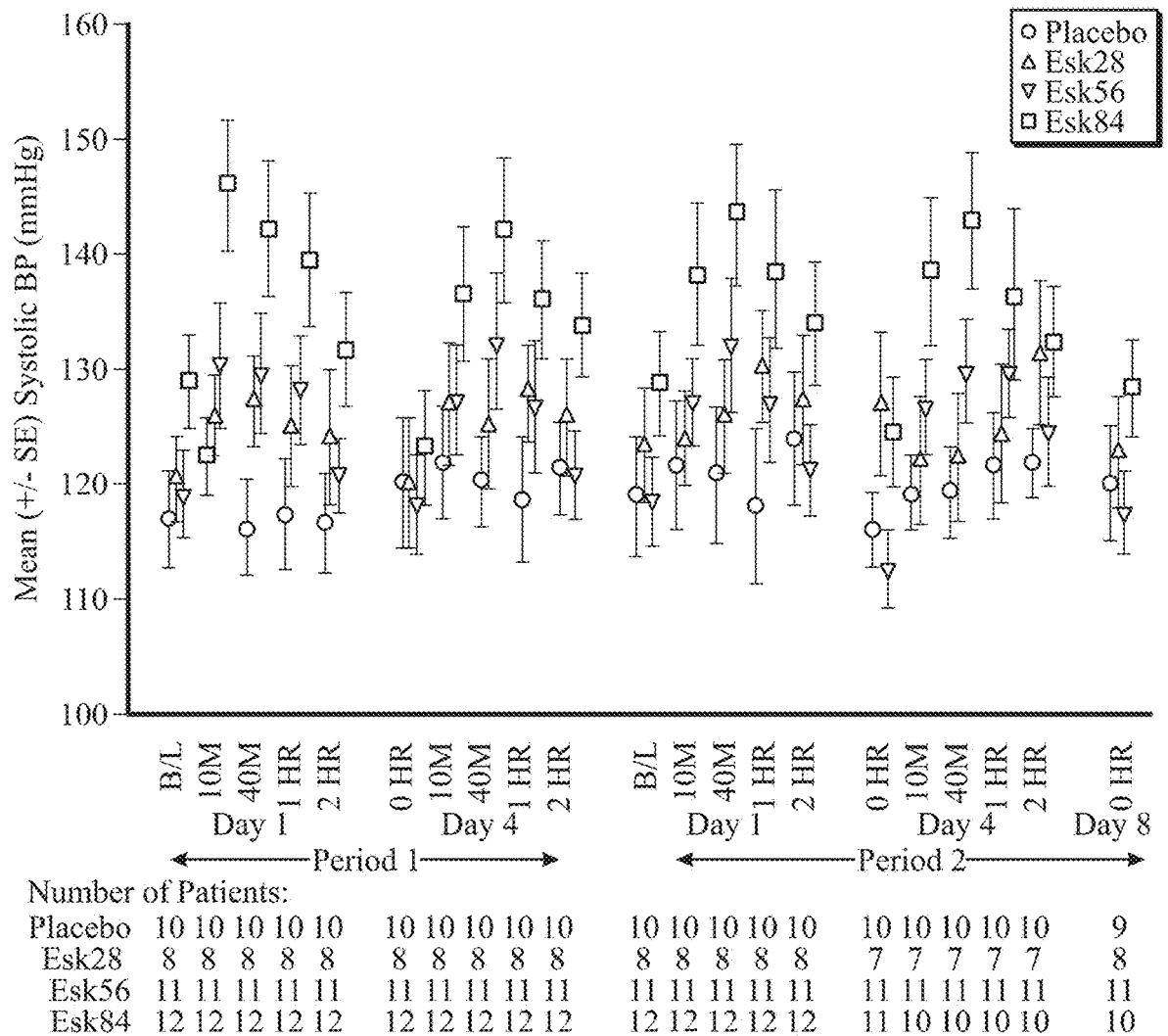

FIG. 77 is a plot of mean systolic blood pressure over time by period for participants who received the same treatment for both periods during the double-blind phase in Example 7.

Figure 78:
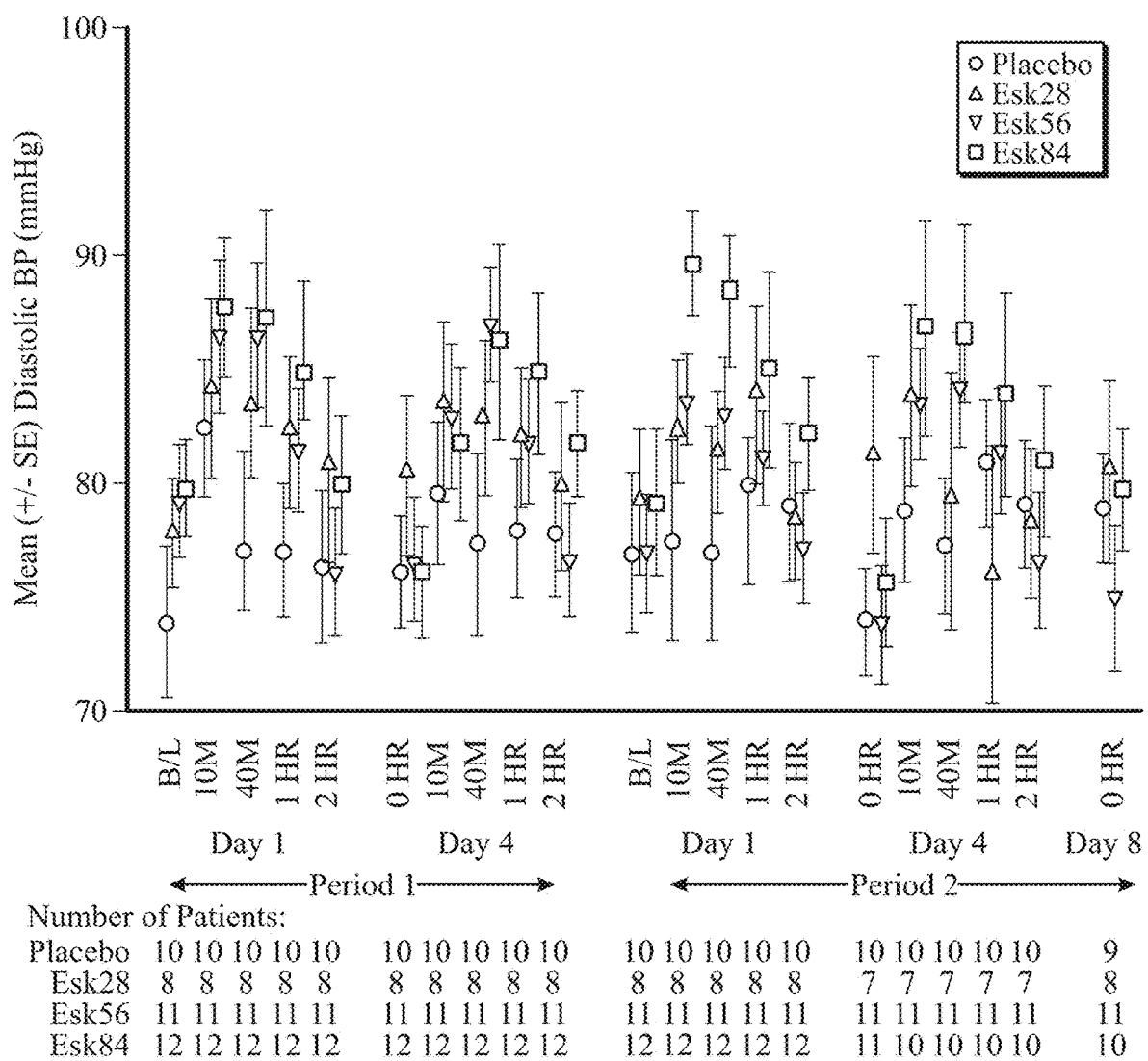

FIG. 78 is a plot of mean diastolic blood pressure over time by period for participants who received the same treatment for both periods during the double-blind phase in Example 7.

Figure 79:
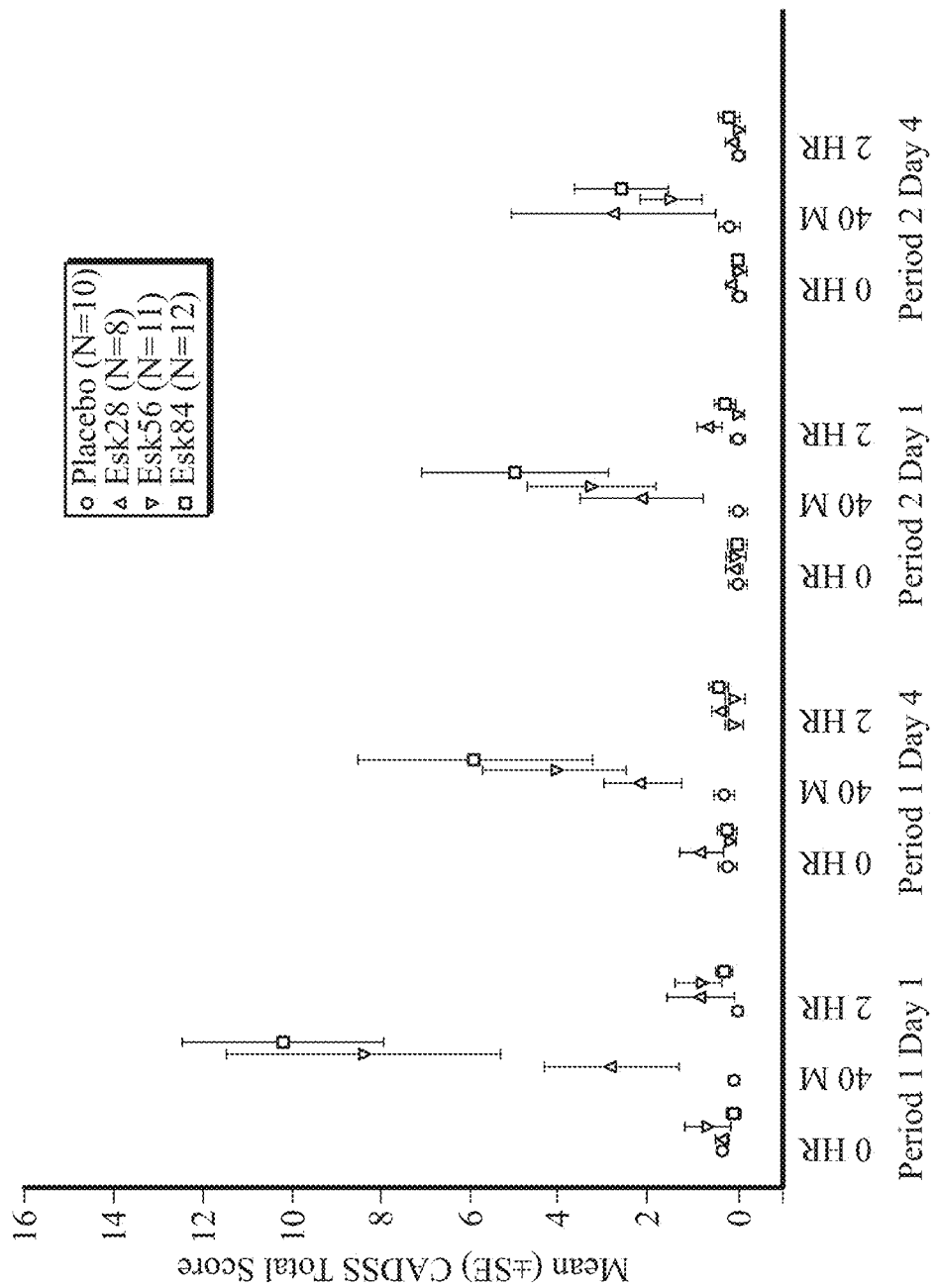

FIG. 79 is a plot of mean CADSS total score over time for participants who received the same treatment for both periods in Example 7.

Figure 80:
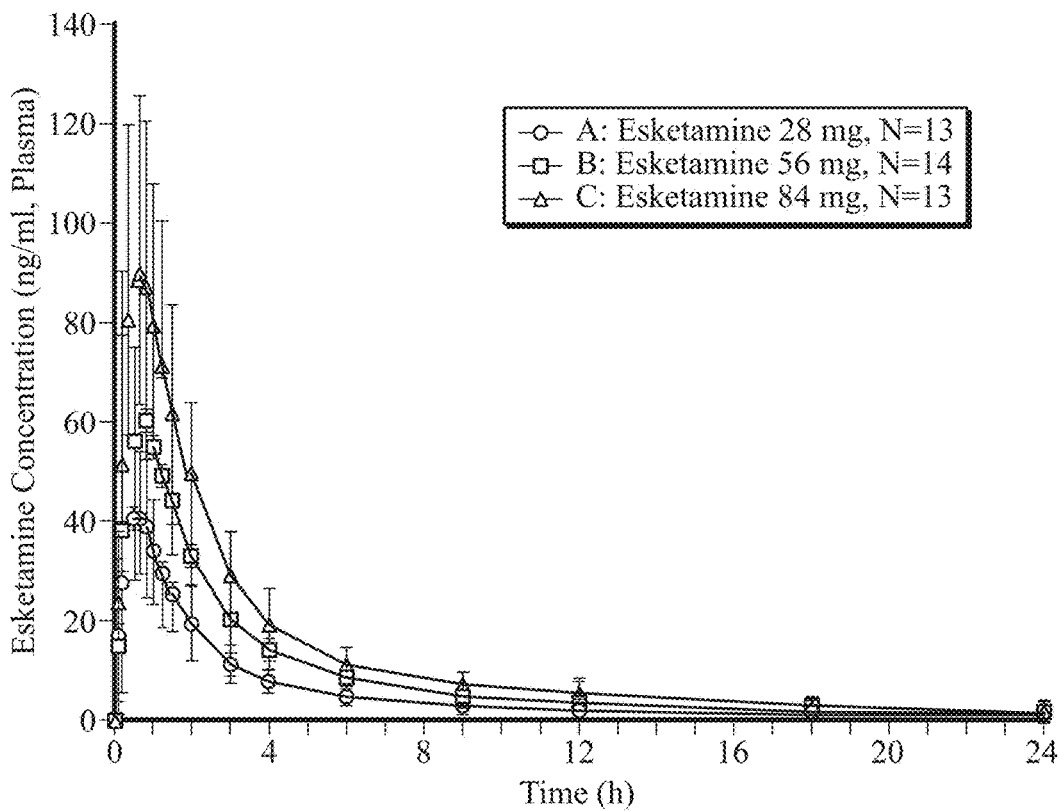

FIG. 80 is a plot of the mean plasma concentration-time profile of esketamine.

Figure 81:
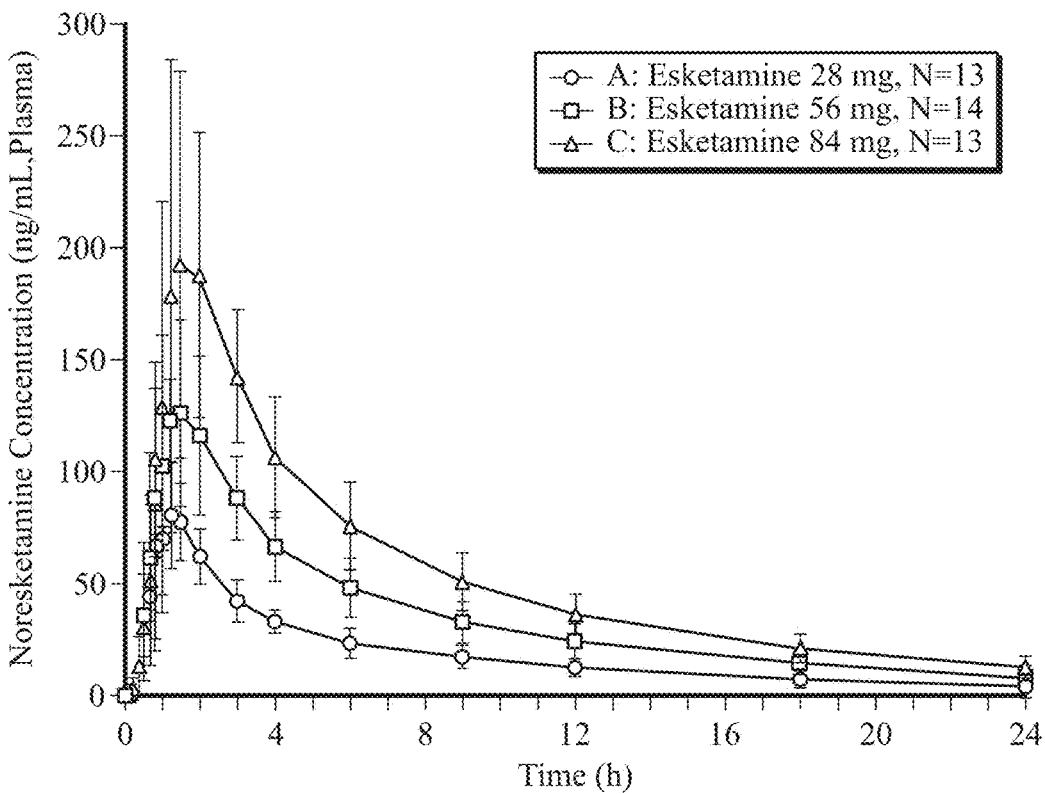

FIG. 81 is a plot of the mean plasma concentration-time profile of noresketamine.

Figure 82A:
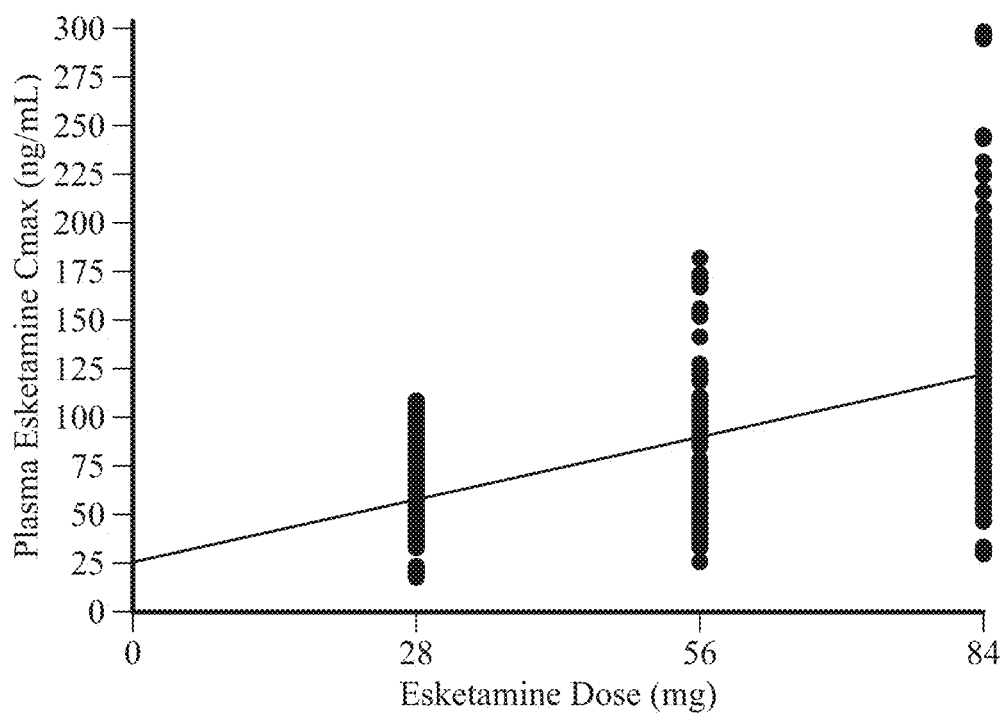
Figure 82B:
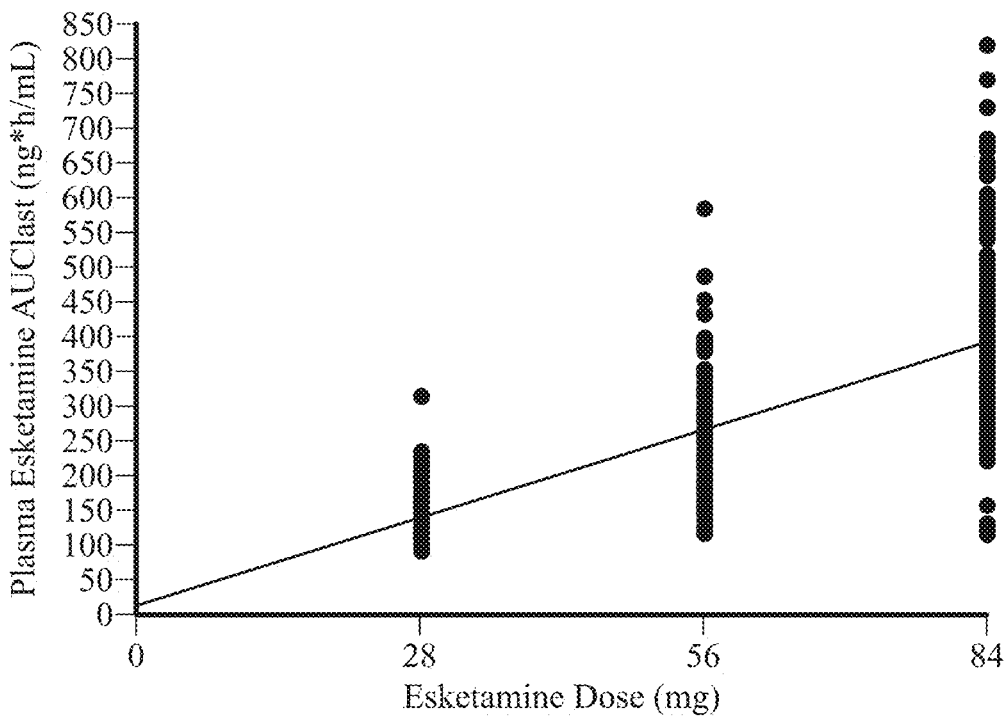
Figure 83E:
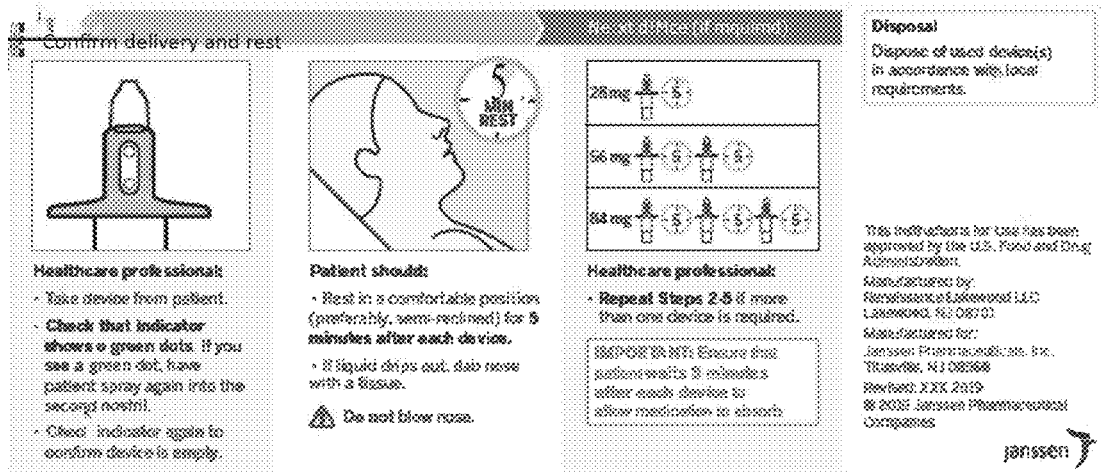

FIGS. 82A and 82B are $C_{max}$ vs. dose and $AUC_{last}$ vs. dose, respectively, for the data of Example 10. Line of regression shown for $C_{max}$ (r=0.53) and $AUC_{last}$ (r=0.70).

FIG. 83A to 83E depict instructions for use for an exemplary nasal spray device.

Figure 84:
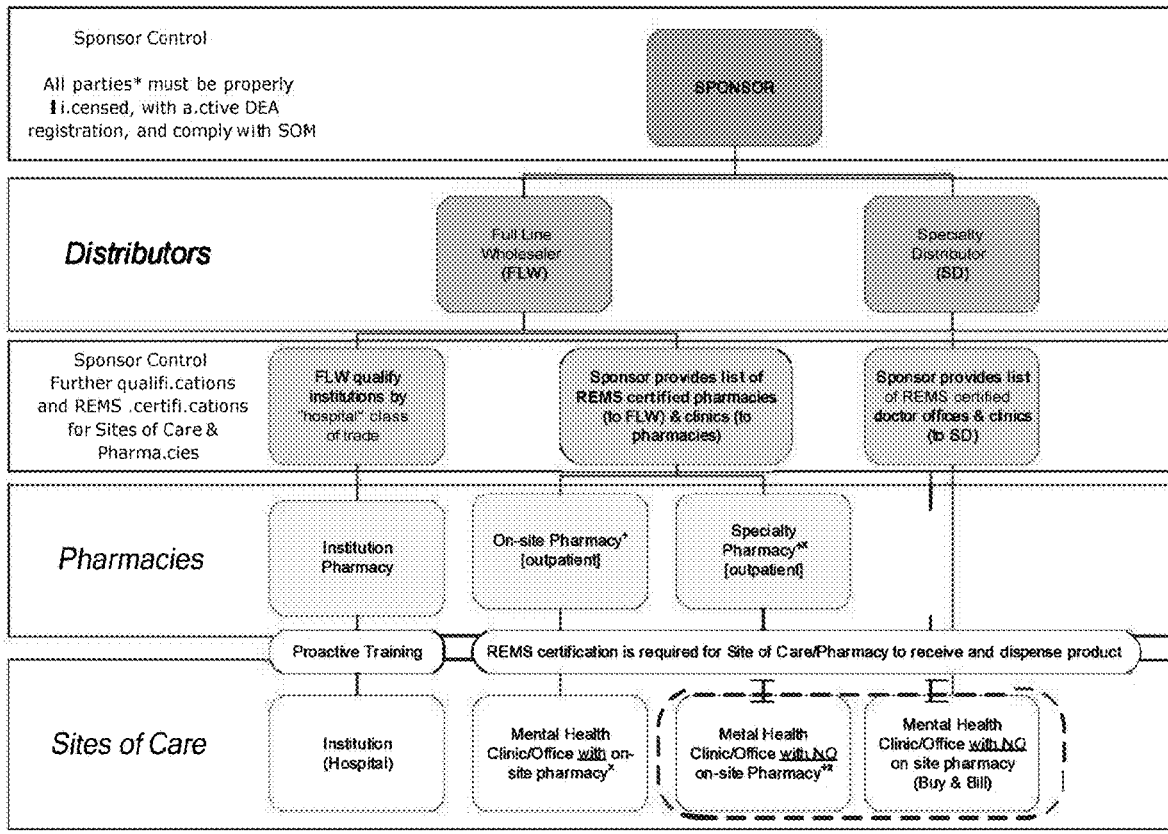

FIG. 84 is a flow diagram of an approved esketamine drug product through possible medical systems.

Figure 85:
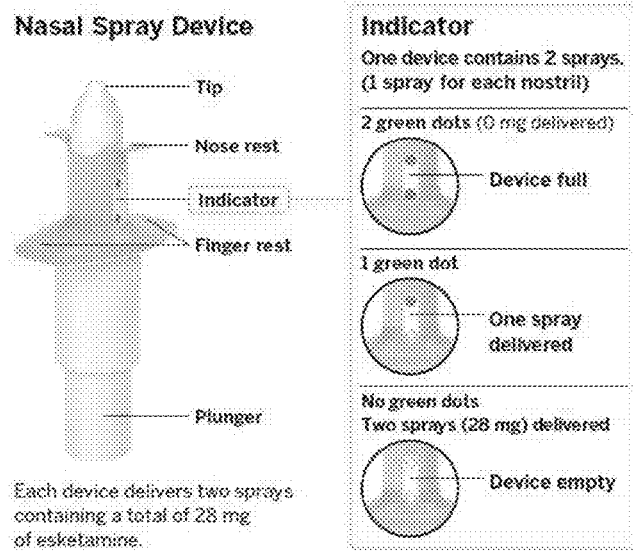

FIG. 85 are the administration instructions for Example 11.

Figure 86:
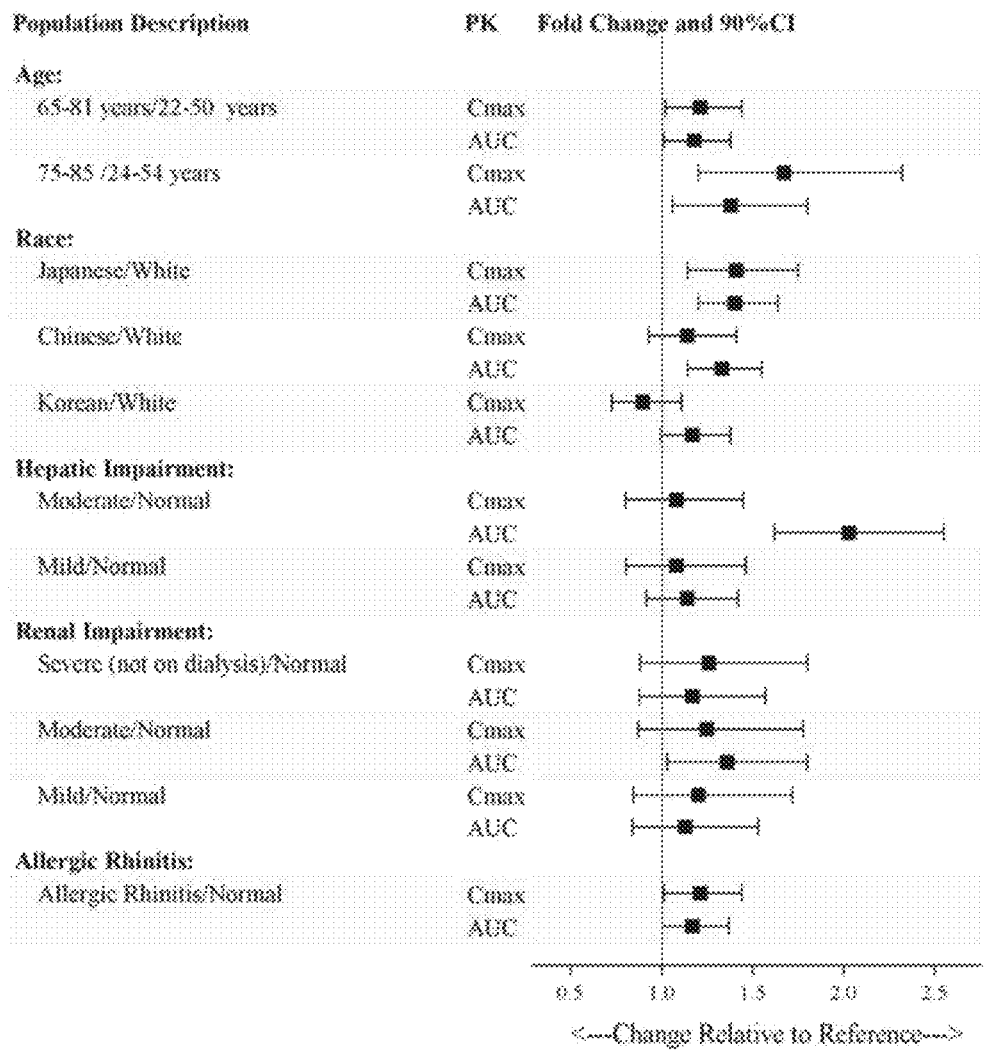

FIG. 86 shows the effect of specific populations on the pharmacokinetics of esketamine.

Figure 87:
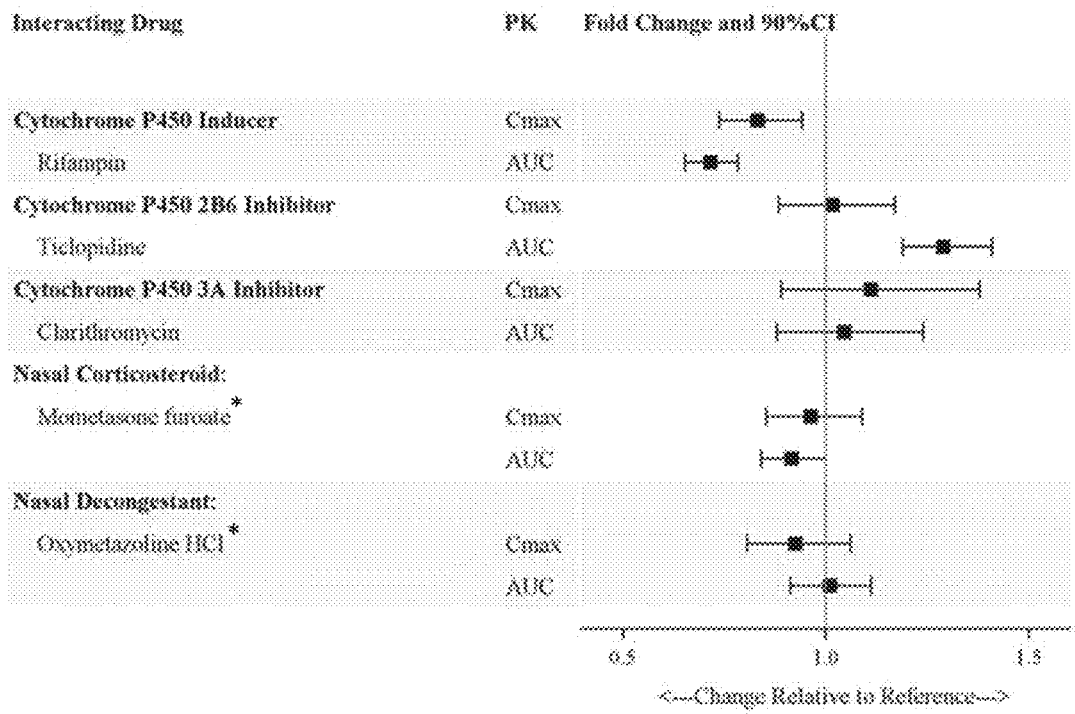

FIG. 87 shows the effect of co-administered drugs on the pharmacokinetics of esketamine.

Figure 88:
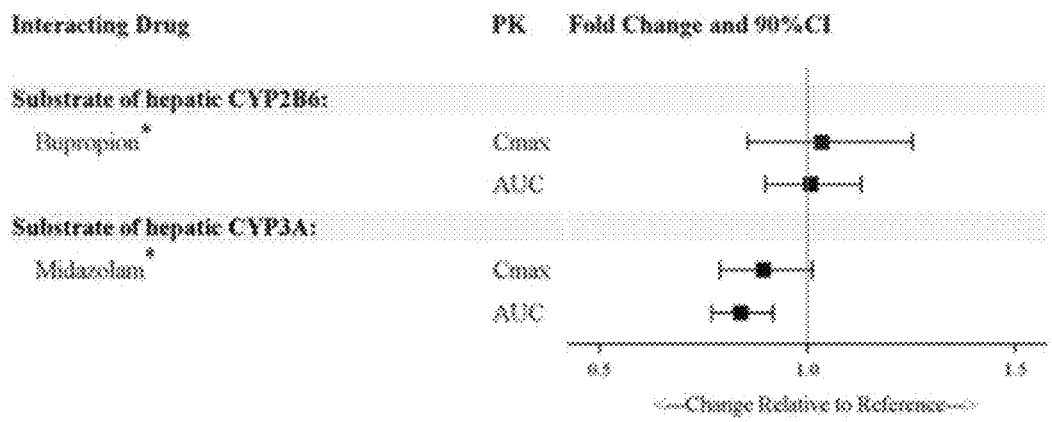

FIG. 88 shows the effect of esketamine on the pharmacokinetics of co-administered drugs.

Figure 89:
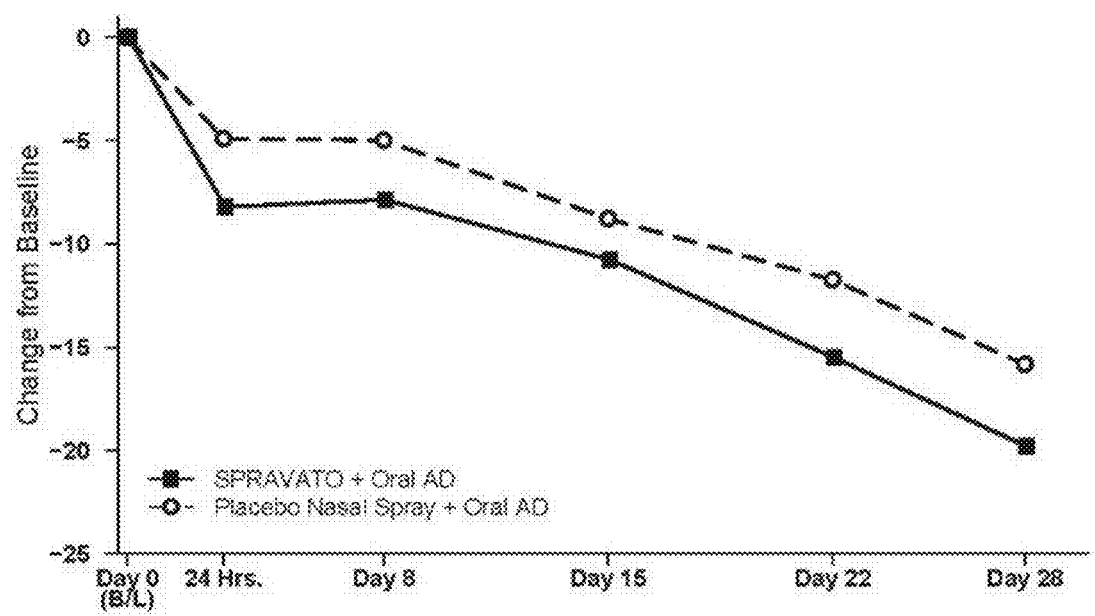

FIG. 89 is a line graph of the least squares mean change from baseline in MADRS total score over time in patients with TRD in study 1*(Full Analysis Set)–MMRM analysis. Note: In this flexible-dose study, dosing was individualized based on efficacy and tolerability. Few subjects (<10%) had reduction in SPRAVATO dosage from 84 mg to 56 mg twice weekly.

Figure 90:
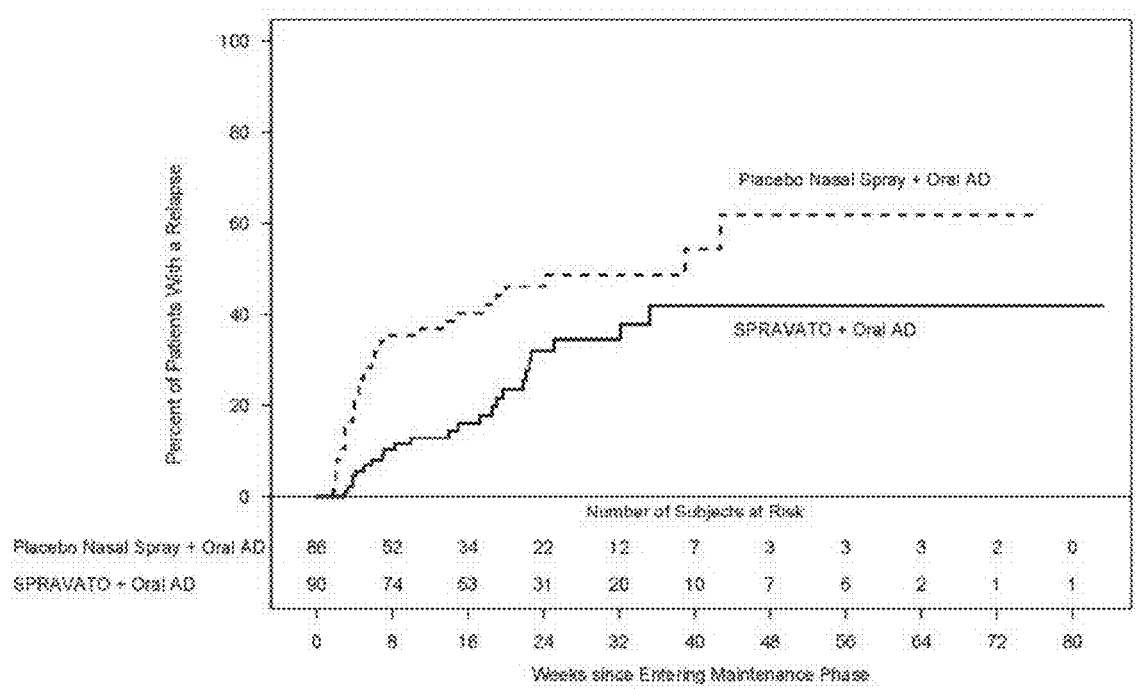

FIG. 90 is a plot of the time to relapse in patients with TRD in stable remission in study 2*(Full Analysis Set). Note: The estimated hazard ratio (95% CI) of SPRAVATO+ Oral AD relative to Placebo nasal spray+Oral AD based on weighted estimates was 0.49 (95% CI: 0.29, 0.84). However, the hazard ratio did not appear constant throughout the trial.

Figure 91:
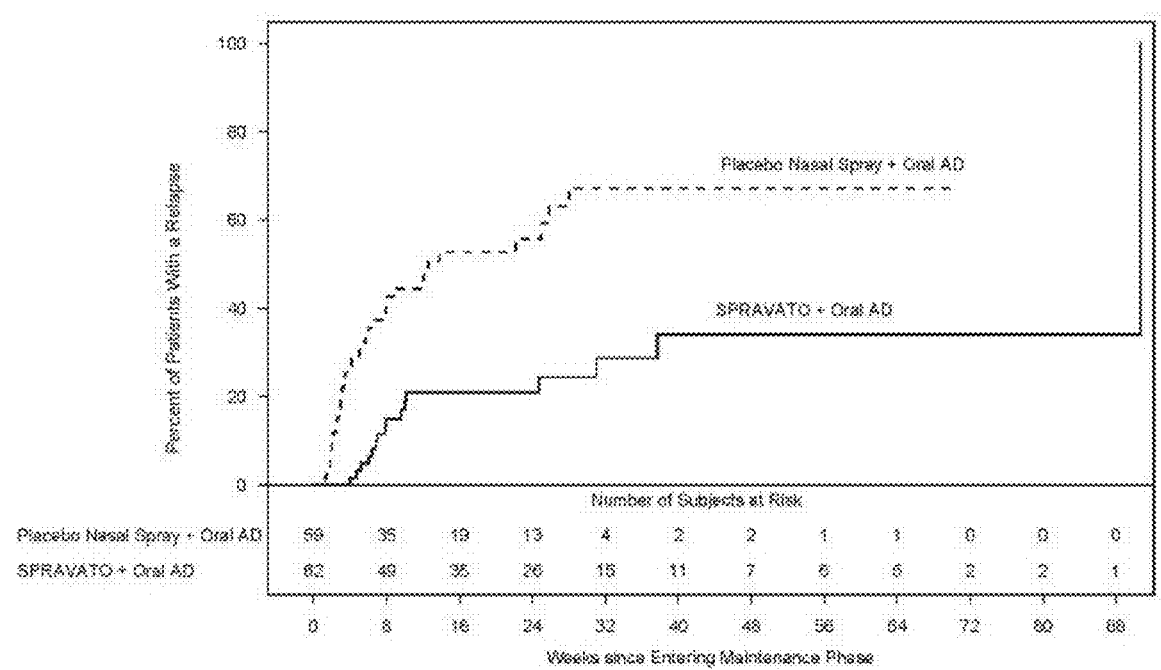

FIG. 91 is a plot of time to relapse in patients in stable response in TRD patients in study 2*(Full Analysis Set). Note: The estimated hazard ratio (95% CI) of SPRAVATO+ Oral AD relative to Placebo nasal spray+Oral AD based on Cox proportional hazards model was 0.30 (95% CI: 0.16, 0.55).

DETAILED DESCRIPTION OF THE INVENTION

The present invention is directed to methods for the treatment of depression (e.g., major depressive disorder), comprising administering to a patient in need thereof, a clinically proven safe and therapeutically effective amount of esketamine. In some embodiments, the methods are for the treatment of treatment refractory depression or treatment resistant depression. In other embodiments, the medicament is for treating suicidal ideation.

These methods advantageously permit tailoring an effective regimen to patients who have depression. Such patients include those who have already been diagnosed with MDD, TRD, are suicidal, or have otherwise been untreated for depression.

Methods of maintaining stable remission or stable response achieved by a patient with depression following administration of a therapeutically effective amount of esketamine during an initial administration phase also are described. Such methods include continuing administration of a therapeutically effective amount of esketamine for at least five months during a subsequent administration phase.

Thus, methods for the long term treatment of depression in a patient are also provided. These methods comprise administering to the patient in need of the treatment a clinically proven safe and clinically proven effective therapeutically effective amount of esketamine for at least six months. Desirably, cognitive performance of the patient remains stable, based on a baseline measurement, following six months of treatment. In some embodiments, the treatment may be a duration of at least about one year, at least about 18 months, or at least about two years. For example, long term treatment may include a duration range of about six months to about two years. Treatment may also be continued for longer periods of time including, without limitation, 4, 5, 6, 7, 8, 9, 10, or longer years, as determined by the attending physician. In some embodiments, the esketamine is initially dosed twice a week for up to four weeks during an induction phase, and, thereafter, dosed less frequently than twice a week.

In certain embodiments of the present invention, esketamine may be administered in combination with one or more antidepressants, as herein described, preferably in combination with one to three antidepressants, more preferably in combination with one to two antidepressants.

In certain embodiments of the present invention, esketamine may be administered in combination with one or more antidepressants, and further in combination with one or more atypical antipsychotics, herein described.

In an embodiment, the present invention is directed to combination therapy comprising esketamine and one or more antidepressants; wherein the esketamine is administered as acute treatment. In another embodiment, the present invention is directed to combination therapy comprising esketamine and one or more antidepressants wherein the esketamine is administered as acute treatment and wherein the one or more antidepressants are administered as chronic treatment.

In other embodiments, such as during an induction phase, the esketamine may be used as a mono-therapy and not in combination with any other active compounds.

Some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "esketamine" shall mean the (S)-enantiomer of ketamine, i.e., a compound of formula (I):

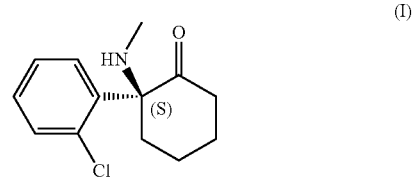

also known as (S)-2-(2-chlorophenyl)-2-(methylamino)cyclohexanone. "Esketamine" shall also mean a salt, e.g., a chloride salt such as the hydrochloride salt, of the (S)-enantiomer of ketamine, i.e., a compound of formula (II):

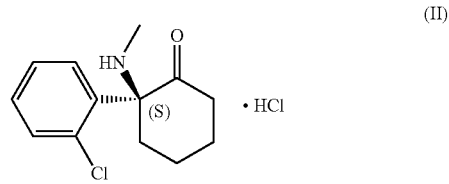

also known as (S)-2-(2-chlorophenyl)-2-(methylamino)cyclohexanone hydrochloride.

In some embodiments, the esketamine is substantially free of the (R)-enantiomer of ketamine, i.e. a compound of formula (III):

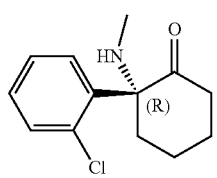

(III)

In other embodiments, the esketamine contains less than about 10% by weight, based on the weight of the esketamine sample, of the (R)-enantiomer of ketamine. In further embodiments, the esketamine contains less than about 10, 9, 8, 7, 6, 5, 4, 3, 2, 1, 0.5, 0.1, 0.005, or 0.001% by weight, based on the weight of the esketamine sample, of the (R)-enantiomer of ketamine. In yet other embodiments, the esketamine contains about 0.001 to about 10% by weight, based on the weight of the esketamine sample, of the (R)-enantiomer of ketamine. In still further embodiments, the esketamine contains about 0.001 to about 10%, about 0.001 to about 5%, about 0.001 to about 1, about 0.001 to about 0.5, about 0.001 to about 0.1, about 0.1 to about 5, about 0.1 to about 1, about 0.1 to about 5, or about 0.5 to about 5% by weight, based on the weight of the esketamine sample, of the (R)-enantiomer of ketamine.

The term "esketamine" may also include other pharmaceutically acceptable salts thereof, which may readily be selected by those skilled in the art. A "pharmaceutically acceptable salt" is intended to mean a salt of esketamine that is non-toxic, biologically tolerable, or otherwise biologically suitable for administration to the subject. See, generally, G. S. Paulekuhn, "Trends in Active Pharmaceutical Ingredient Salt Selection based on Analysis of the Orange Book Database", J. Med. Chem., 2007, 50:6665-72, S. M. Berge, "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for administration to patients without undue toxicity, irritation, or allergic response.

Examples of other pharmaceutically acceptable salts include sulfates, pyrosulfates, bisulfates, sulfites, bisulfites, phosphates, monohydrogen-phosphates, dihydrogenphosphates, metaphosphates, pyrophosphates, bromides (such as hydrobromides), iodides (such as hydroiodides), acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propane-sulfonates, naphthalene-1-sulfonates, naphthalene-2-sulfonates, and mandelates. In particular, the salt of esketamine is a hydrochloride salt.

In certain embodiments of the present invention, the esketamine is administered intranasally. In certain embodiments of the present invention, the esketamine is administered intranasally as its corresponding hydrochloride salt. In certain embodiments of the present invention, the esketamine is administered intranasally as its corresponding hydrochloride salt in an 16.14% weight/volume solution (equivalent to 14% weight/volume of esketamine base).

In certain embodiments of the present invention, the esketamine is administered intranasally as a solution comprising 161.4 mg/mL of esketamine hydrochloride (equivalent to 140 mg/mL of esketamine base), 0.12 mg/mL of ethylenediaminetetraacetic acid (EDTA) and 1.5 mg/mL citric acid, at a pH of 4.5 in water. In certain embodiments of the present invention, the esketamine is administered intranasally, wherein the intranasal delivery administers 100 µL of a solution comprising 161.4 mg/mL of esketamine hydrochloride (equivalent to 140 mg/mL of esketamine base), 0.12 mg/mL of ethylenediaminetetraacetic acid (EDTA) and 1.5 mg/mL citric acid, at a pH of 4.5 in water. In certain embodiments, the esketamine is delivered intranasally using a nasal spray pump, wherein the pump delivers 100 µL of a solution comprising 161.4 mg/mL of esketamine hydrochloride (equivalent to 140 mg/mL of esketamine base), 0.12 mg/mL of ethylenediaminetetraacetic acid (EDTA) and 1.5 mg/mL citric acid, at a pH of 4.5 in water.

In general, a single pump from a nasal spray device may be configured to deliver about 50 µL to about 200 µL of an esketamine solution to a nostril of the subject, including about 60 µL, about 70 µL, about 80 µL, about 90 µL, about 100 µL, about 110 µL, about 120 µL, about 130 µL, about 140 µL, about 150 µL, about 160 µL, about 170 µL, about 180 µL, and about 200 µL. Accordingly, two pumps deliver about 100 µL to about 400 µL to the subject.

In certain embodiments of the present invention, a patient in need of treatment with a clinically proven safe and therapeutically effective amount of esketamine, is a patient suffering from an episode of depression (e.g., major depressive disorder). In certain embodiments of the present invention, a patient in need thereof is suffering from an episode of depression (e.g., major depressive disorder), wherein the episode of depression (e.g., major depressive disorder) has not responded to treatment with at least two oral antidepressants (i.e. the patient has not responded to treatment with at least two oral antidepressants). In other embodiments, a geriatric patient in need thereof is suffering from an episode of depression (e.g., major depressive disorder), wherein the episode of depression (e.g., major depressive disorder) has not responded to treatment with two oral antidepressants (i.e. the geriatric patient has not responded to treatment with two oral antidepressants).

In certain embodiments of the present invention, a patient in need thereof is suffering from depression (e.g., major depressive disorder). For example, a patient as measured MADRS with a score of 18 or more or on the CGI scale a score of 4 or more.

As used herein, the term "depression" includes major depressive disorder, persistent depressive disorder, seasonal affective disorder, postpartum depression, premenstrual dysphoric disorder, situational depression, anhedonia, melancholy, mid-life depression, late-life depression, depression due to identifiable stressors, treatment resistant depression, or combinations thereof. In certain embodiments, the depression is major depressive disorder. In other embodiments, the major depressive disorder is with melancholic features or anxious distress. In further embodiments, the depression is treatment-resistant depression.

As used herein, the term "non-responder" means patients that do not recover fully on an antidepressant medication (e.g. 25% or less change from baseline in total MADRS score).

As used herein, the term "episode of major depressive disorder" means a continuous period (e.g., about 2 weeks or more) in which a patient has symptoms of a major depressive disorder sufficient to meet criteria for major depression as specified in the Diagnostic and statistical Manual of Mental Disorders, 5$^{th}$ Edition: DSM 5.

As used herein, "suicide" is the "act of taking one's own life". See, http://en.wikipedia.org/wiki/Suicide—cite_note-7. Suicide includes attempted suicide or non-fatal suicidal behavior, which is self-injury with the desire to end one's life that does not result in death. Suicide attempt is a self-initiated sequence of behaviors by an individual who, at the time of initiation, expected that the set of actions would lead to his or her own death.

As used herein, "suicidal ideation" refers to thoughts about or an unusual preoccupation with suicide, or thoughts of ending one's life or not wanting to live anymore but not necessarily taking any active efforts to do so. The range of suicidal ideation varies greatly from fleeting to chronic and progresses to detailed planning, role playing, and unsuccessful attempts, which may be deliberately constructed to fail or be discovered, or may be fully intended to result in death. In some embodiments, a patient is classified as being "suicidal" when the patient has a mean baseline MADRS total score of about 38 or greater. In other embodiments, a patient is classified as being suicidal when the patient has a mean baseline BBSS score of 22 or greater. In further embodiments, a patient is classified as being suicidal when the patient has a score of 6 or greater in the SIBAT clinical global judgement of suicide risk. In yet other embodiments, the patient has one or more combinations of these scores.

As used herein, the terms "co-therapy", "combination therapy", "adjunctive treatment", "adjunctive therapy", "combined treatment", and "co-administration" shall mean treatment of a patient in need thereof by administering esketamine in combination with one or more antidepressant(s), wherein the esketamine and the antidepressant(s) are administered by any suitable means. In some embodiments, esketamine is administered in a regimen with one to five antidepressants. In other embodiments, esketamine is administered in a regimen with one, two, three, four, or five antidepressants. In other embodiments, esketamine is administered in a regimen with one or two antidepressants. In further embodiments, the esketamine is administered in a regimen with the antidepressant currently being administered to the patient. In other embodiments, the esketamine is administered in a regimen with a different antidepressant. In yet further embodiments, the esketamine is administered in a regimen with an antidepressant not previously administered to the patient. In still other embodiments, the esketamine is administered in a regimen with an antidepressant previously administered to the patient. Where the esketamine and the antidepressant(s) are administered in separate dosage forms, the number of dosages administered per day for each compound may be the same or different and more typically different. The antidepressant may be dosed as prescribed by the attending physician and/or by its label and the esketamine is dosed as described herein. Typically, a patient is under concurrent treatment with both an antidepressant and esketamine, where both are administered by their prescribed dosing regimens.

The esketamine and the antidepressant(s) may be administered via the same or different routes of administration. Examples of suitable methods of administration include, but are not limited to, oral, intravenous (iv), intranasal (in) intramuscular (im), subcutaneous (sc), transdermal, buccal, or rectal. In some embodiments, esketamine is administered intranasally. As used herein, unless otherwise noted, the term "antidepressant" shall mean any pharmaceutical agent which can be used to treat depression. Suitable examples include, without limitation, a mono-amine oxidase inhibitor, tricyclic, serotonin reuptake inhibitor, serotonin noradrenergic reuptake inhibitor, noradrenergic and specific serotonergic agent, or atypical antipsychotic. Other examples include, but are not limited to mono-amine oxidase inhibitors such as phenelzine, tranylcypromine, moclobemide, and the like; tricyclics such as imipramine, amitriptyline, desipramine, nortriptyline, doxepin, protriptyline, trimipramine, domipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, citalopram, escitalopram, fluvoxamine, and the like; serotonin receptor antagonists such as nefazadone, and the like; serotonin noradrenergic reuptake inhibitors such as venlafaxine, milnacipran, desvenlafaxine, duloxetine, levomilnacipran and the like; noradrenergic and specific serotonergic agents such as mirtazapine, and the like; noradrenaline reuptake inhibitors such as reboxetine, edivoxetine and the like; atypical antipsychotics such as bupropion, and the like; natural products such as Kava-Kava, St. John's Wort, and the like; dietary supplements such as s-adenosylmethionine, and the like; and neuropeptides such as thyrotropin-releasing hormone and the like; compounds targeting neuropeptide receptors such as neurokinin receptor antagonists and the like; and hormones such as triiodothyronine, and the like. In some embodiments, the antidepressant is imipramine, amitriptyline, desipramine, nortriptyline, doxepin, protriptyline, trimipramine, maprotiline, amoxapine, trazodone, bupropion, domipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or triiodothyronine. Preferably, the antidepressant is selected from the group consisting of fluoxetine, imipramine, bupropion, venlafaxine and sertraline.

Therapeutically effective amounts/dosage levels and dosage regimens for antidepressants (for example, mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors, hormones and other pharmaceutical agents disclosed herein), may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) or other sources.

As used herein the term "antipsychotic" includes, but is not limited to:

(a) typical or traditional antipsychotics, such as phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like; and (b) atypical antipsychotics and mood stabilizers, such as paliperidone, clozapine, risperidone, olanzapine, quetiapine, zotepine, ziprasidone, iloperidone, perospirone, blonanserin, sertindole, ORG-5222 (Organon), and the like; and others such as sonepiprazole, aripiprazole, nemonapride, SR-31742 (Sanofi), CX-516 (Cortex), SC-111 (Scotia), NE-100 (Taisho), divalproate (mood stabilizer) and the like.

In an embodiment, the "atypical antipsychotic" is selected from the group consisting of aripiprazole, quetiapine, olanzapine, risperidone and paliperidone. In another embodiment, the atypical antipsychotic is selected from the group consisting of aripiprazole, quetiapine, olanzapine and risperidone; preferably, the atypical antipsychotic is selected from the group consisting of aripiprazole, quetiapine and olanzapine.

As used herein, the term "treatment-refractory or treatment-resistant depression" and the abbreviation "TRD" shall be defined as major depressive disorder in a patient that does not respond adequately to at least two different antidepressants, preferably between two and five antidepressants, in the current depressive episode. In other embodiments, TRD is defined as major depressive disorder in a patient that has not responded to at least two oral antidepressants of adequate dose and duration in the current depressive episode.

One skilled in the art will recognize that the failure to respond to an adequate course of a given antidepressant may be determined retrospectively or prospectively. In an embodiment, at least one of the failures to respond to an adequate course of antidepressant is determined prospectively. In another embodiment, at least two of the failures to respond to an adequate course of antidepressant are determined prospectively. In another embodiment, at least one of the failures to respond to an adequate course of antidepressant is determined retrospectively. In another embodiment, at least two of the failures to respond to an adequate course of antidepressant are determined retrospectively in a current depressive episode.

The "at least two oral antidepressants" or "at least two different oral depressants" has been administered to the patient at an adequate dose which may be determined by the attending physician. Similarly, the antidepressant has been administered for a suitable duration, as determined by the attending physician.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "clinically proven" (used independently or to modify the terms "safe" and/or "effective") shall mean that proof has been proven by a Phase III clinical trial that are sufficient to meet approval standards of U.S. Food and Drug Administration or similar study for market authorization by EMEA. Preferably for esketamine studies an adequately sized, randomized, double-blinded controlled study will be used to clinically prove the effects of esketamine. Most preferably to clinically prove the effects of esketamine to treat major depressive disorder, e.g., treatment resistant depression, this would be a randomized, double-blinded, active-controlled study of flexibly dosed intranasal esketamine (28 mg, 56 mg or 84 mg±20%) co-administered with a newly or currently initiated oral antidepressant as compared to a newly or currently initiated oral antidepressant (active comparator) plus intranasal placebo with the patient's condition assessed by techniques described herein, such as the MADRS, Hamilton, CGI, Beck's Depression Scale, QIDS or PHQ-9, including assessments from day 1 to day 28, as well as assessments during subsequent administration periods as described herein.

As used herein, unless otherwise noted, the term "clinically proven effective" means the efficacy of treatment has been proven by a Phase III clinical trial as statistically significant i.e., the results of the clinical trial are not likely to be due to chance with an alpha level less than 0.05 or the clinical efficacy results are sufficient to meet approval standards of U.S. Food and Drug Administration or similar study for market authorization by EMEA. For example, esketamine was clinically proven effective for the treatment for patients with major depressive disorder, e.g., treatment resistant depression, when flexibly dosed intranasally in a therapeutically effective dose of from 28 mg, 56 mg or 84 mg (±25%) and co-administered with a newly or currently initiated oral antidepressant in reducing patient MADRS scores by at least about 50% relative to the patients measured baseline MADRS score as part of a dosing regimen including induction and maintenance phases described herein, and as specifically set forth in the examples.

As used herein, unless otherwise noted, the term "safe" when referring to a pharmaceutical treatment (therapy) or combination therapy shall mean without undue adverse side effects (such as toxicity, irritation, or allergic response), commensurate with a reasonable benefit/risk ratio when used in the manner of this invention.

As used herein, unless otherwise noted, the term "clinically proven safe" means the safety of treatment has been proven by a Phase III clinical trial by analysis of the trial data and results establishing that the treatment is without undue adverse side effects and commensurate with the statistically significant clinical benefit (e.g. efficacy) sufficient to meet approval standards of U.S. Food and Drug Administration or similar study for market authorization by EMEA. For example, esketamine was clinically proven safe for the treatment for patients with major depressive disorder, e.g., treatment resistant depression, when flexibly dosed intranasally in a therapeutically effective dose of from 28 mg, 56 mg or 84 mg (±25%) and co-administered with a newly or currently initiated oral antidepressant as part of a dosing regimen including induction and maintenance phases described herein, and as specifically set forth in the examples.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Desirably, the therapeutically effective amount is a clinically proven safe and clinically proven effective amount. In some embodiments, the antidepressant is utilized in a therapeutically effective amount as determined by the attending physician. In other embodiments, esketamine is utilized in a therapeutically effective amount.

The therapeutically effective amount of esketamine and/or antidepressant may be administered during the initial phase(s) and/or subsequent phase(s) as described herein. In some embodiments, the therapeutically effective amount of esketamine is about 20 to about 100 mg. In other embodiments, the therapeutically effective amount of esketamine is about 30 to about 90 mg. In further embodiments, the therapeutically effective amount of esketamine is about 40 to about 80 mg. In yet other embodiments, the therapeutically effective amount of esketamine is about 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg. In further embodiments, the therapeutically effective amount is about 28 mg, about 56 mg, or about 84 mg. In other embodiments, the therapeutically effective amount is about 56 mg or about 84 mg. In yet further embodiments, the therapeutically effective amount of esketamine is about 28 mg. In other embodiments, the therapeutically effective amount of esketamine is about 56 mg. In still further embodiments, the therapeutically effective amount is of esketamine about 84 mg.

As used herein, unless otherwise noted, the terms "subject" and "patient" refer to an animal, preferably a mammal, most preferably a human, who has been the object of treatment, observation or experiment. Preferably, the subject or patient has experienced and/or exhibited at least one symptom of the disease or disorder to be treated and/or prevented.

In some embodiments, the subject or patient is an adult. As used herein, the term "adult" as used herein refers to a human that is about 18 years of age to about 65 years of age.

In other embodiments, the subject or patient is geriatric or elderly. As used herein, the terms "geriatric" and "elderly" are used interchangeably to refer to a human subject of about 65 years of age or older. Elderly patients between the ages of ≥65 to ≤75 appear to be more responsive to treatment than a patient of ≥75.

In further embodiments, the subject or patient is a pediatric subject. As used herein, the term "pediatric" refers to a human subject of younger than about 18 years of age.

As used herein, the term "composition" is intended to encompass a product comprising the specified ingredients in the specified amounts, as well as any product which results, directly or indirectly, from combinations of the specified ingredients in the specified amounts.

As used herein, "stable remission" refers to a patient having a MADRS total score of 12 or less for at least 3 of the last 4 weeks following the patient having achieved a substantially complete response to the esketamine during an induction phase. In certain exemplified embodiments herein, patients in "stable remission" include those having one excursion of a MADRS total score greater than 12 or one missing a MADRS assessment at week 13 or 14 following an induction phase. In other embodiments, patients in "stable remission" include those having a MADRS total score at weeks 15 and 16 of 12 or less following an induction phase.

As used herein, "stable response" refers to a patient having a 50% or greater reduction in the MADRS total score from baseline (Day 1 of induction phase; pre-randomization/prior to the first intranasal dose) in each of the last 2 weeks following the patient having achieved a substantially complete response to the esketamine during the induction phase, but does not meet criteria for stable remission.

As noted above, methods of treating depression in a patient are described. The methods include administering esketamine in one, two or optionally three phases, i.e., initial and subsequent administration phases. In some embodiments, the phases include an initial induction phase, an extended induction phase, a maintenance phase, or any combination thereof. Accordingly, an effective amount of esketamine is administered in each phase. A physician can assess the patient's condition to determine the most beneficial initiation/induction and maintenance doses for the patient from the dosage range and administration frequencies from those specified herein. The effective amount of esketamine may be the same in each phase or may differ.

The methods described herein permit optimizing dosages of esketamine for administration to a patient having or being predisposed to depression in an "optimization phase". Optimization may be considered part of the maintenance phase that follows the induction phase. In some embodiments, the methods described herein do not require adjustment of the esketamine dosage. In fact, esketamine may be administered during the phases discussed herein (e.g., induction and maintenance) at the lowest dosing frequency at which an esketamine response is observed and maintained in a patient. An effective amount of esketamine has been found to be from about 28 to about 84 mg.

As used herein, an "Induction phase" or "acute dosing phase" is a period of time that esketamine is initially administered to the patient. In some embodiments, the induction phase is sufficiently long as to achieve a robust, stable reduction of depressive symptoms. The induction phase may depend on factors including, without limitation, the particular patient and/or the patient's sex, age, weight, time of administration, administration frequency and concomitant diseases. The induction phase may include an initial induction phase and an extended induction phase. The totality of the induction phase (the initial and extended phases together) may be a period of about 4 to about 12 weeks, about 4 to about 11 weeks, about 4 to about 10 weeks, about 4 to about 9 weeks, about 4 to about 8 weeks, about 4 to about 7 weeks, about 4 to about 6 weeks, about 5 to about 12 weeks, about 5 to about 11 weeks, about to about 10 weeks, about 5 to about 9 weeks, about 5 to about 8 weeks, about 5 to about 7 weeks, about 5 to about 6 weeks, about 6 to about 12 weeks, about 6 to about 11 weeks, about 6 to about 10 weeks, about 6 to about 9 weeks, about 6 to about 8 weeks, about 7 to about 12 weeks, about 7 to about 11 weeks, about 7 to about 10 weeks, about 7 to about 9 weeks, about 8 to about 12 weeks, about 8 to about 11 weeks, or about 8 to about 10 weeks. In some embodiments, the entire induction period is about 4 to about 8 weeks.

In the initial induction period, a patient is administered a therapeutically effective amount of esketamine at a given frequency of at least twice a week. In some embodiments, a patient is administered a therapeutically effective amount of esketamine at a given frequency of 3 times a week. To the extent that the dosing is 3 times a week, the dosing is on days 1, 3, and 5 of the week±1 day. The initial induction phase is typically a period of time in which the patient is shown to be responsive to the treatment, but is not ready to progress to the maintenance phase. At timepoints therein, the patient's response is assessed by one skilled in the art. In some embodiments, the patient's response is assessed daily. In other embodiments, the patient's response is assessed twice weekly. In further embodiments, the patient's response is assessed every other day. In yet other embodiments, the patient's response is assessed at the end of the initial induction phase. Typically, the patient's response may be assessed using techniques and tests known to those skilled in the art. In some embodiments, the patient's MADRS score is determined and used as the determination as to whether the initial induction phase has concluded. The initial induction phase is desirably long as to achieve a reduction of depressive symptoms. In some embodiments, the initial induction phase is a period of about 1 to about 4 weeks. In other embodiments, the induction phase is a period of up to about 1 week, up to about 2 weeks, up to about 3 weeks, or up to about 4 weeks. In further embodiments, the initial induction period is about 1 to about 3 weeks, about 1 to about 2 weeks, about 2 to about 4 weeks, about 2 to about 3 weeks, about 3 to about 4 weeks, 1 week, 2 weeks, 3 weeks, 4 weeks, up to 1 week, up to 2 weeks, up to 3 weeks, or up to 4 weeks. The effective amount of esketamine administered during the initial induction phase may be determined by the attending physician. In some embodiments, the effective amount of esketamine administered during the initial induction phase is about 28 mg. In some embodiments, the effective amount of esketamine administered during the initial induction phase is about 56 mg. In other embodiments, the effective amount of esketamine administered during the initial induction phase is about 84 mg.

The term "twice weekly" as used herein refers to a frequency that is two times in a weekly (7-day) period. For example, "twice weekly" may refer herein to the administration of esketamine. "Twice weekly" may also refer to a frequency of monitoring a patient in one or more phases discussed herein. In some embodiments, twice weekly refers to a frequency that is day 1 and day 2 of a week. In other embodiments, twice weekly refers to a frequency that is day 1 and day 3 of a week. In further embodiments, twice weekly refers to a frequency that is day 1 and day 4 of a week. In still other embodiments, twice weekly refers to a frequency that is day 1 and day 5 of the week. The "day 1" may be any day of the week, including, Sunday, Monday, Tuesday, Wednesday, Thursday, Friday, or Saturday. Typically, with respect to administration of esketamine, twice weekly refers to a frequency that is day 1 and day 4 of a week. To the extent there is a mis-dose, the dose may be taken as soon as possible thereafter and the prescribed regimen thereafter continued.

In some patient populations (such as the elderly) the reduction of depressive symptoms during the initial induction phase is insufficient, and an extended induction phase is necessary. In an extended initial induction phase, continued administration of a therapeutically effective amount of esketamine at a given frequency of at least twice a week is performed. At timepoints therein, the patient's response is again assessed by one skilled in the art. In some embodiments, the patient's response is assessed daily. In other embodiments, the patient's response is assessed twice weekly. In further embodiments, the patient's response is assessed every other day. Typically, the patient's response may be assessed using techniques and tests known to those skilled in the art. In some embodiments, the patient's MADRS score is determined and used as the determination as to whether the extended induction period has concluded. The extended induction phase is desirably long as to achieve a substantial reduction of depressive symptoms, thus achieving a substantially complete response to esketamine.

The term "substantially complete response to esketamine" as used herein refers to a patient having a reduction of the MADRS score from baseline to at least a 50% improvement from baseline. In some embodiments, a substantially complete response to esketamine refers to a patient having either a MADRS score of at least 50% improvement from baseline or about −20 lower than the patients baseline score. In other embodiments, a substantially complete response includes a MADRS score of a reduction of about −20 or less, −19, or less, −18 or less, −17 or less, −16 or less, −15 or less, −14 or less, −13 or less, −12 or less, −11 or less, or −10 or less. In further embodiments, a substantially complete response results in a patient having a reduction from MADRS baseline score of about −15 to about −20. A substantially complete response to esketamine may also be obtained if the patient's MADRS scores is reduced by about 50% from the MADRS score at the start of the treatment. Such a substantially complete response may be observed at any point during esketamine treatment. In some embodiments, the substantially complete response is observed when the patient has a reduction of the MADRS total score from the baseline 4 hours following treatment. In other embodiments, the substantially complete response is observed where the patient has a reduction of the MADRS total score from the baseline 2 days following treatment.

The extended induction phase is a period of time that results in the substantially complete response to esketamine. In some embodiments, extended induction phase is about 1 to about 8 weeks. In other embodiments, the extended induction phase is a period of up to about 1 week, up to about 2 weeks, up to about 3 weeks, up to about 4 weeks, up to about 5 weeks, up to about 6 weeks, up to about 7 weeks, or up to about 8 weeks. In further embodiments, the extended induction period is about 1 to about 8 weeks, about 1 to about 7 weeks, about 1 to about 6 weeks, about 1 to about 5 weeks, about 1 to about 4 weeks, about 1 to about 3 weeks, about 2 to about 8 weeks, about 2 to about 7 weeks, about 2 to about 7 weeks, about 2 to about 6 weeks, about 2 to about weeks, about 2 to about 4 weeks, about 3 to about 8 weeks, about 3 to about 7 weeks, about 3 to about 6 weeks, about 3 to about 5 weeks, about 4 to about 8 weeks, about 4 to about 7 weeks, about 4 to about 6 weeks, about 5 to about 8 weeks, about 5 to about 7 weeks, about 1 week, about 2 weeks, about 3 weeks, about 4 weeks, about 5 weeks, about 6 weeks, about 7 weeks, or about 8 weeks. The effective amount of esketamine administered during the extended induction phase may be determined by the attending physician. In some embodiments, the effective amount of esketamine administered during the extended induction phase is about 56 mg. In other embodiments, the effective amount of esketamine administered during the extended induction phase is about 84 mg.

The administration may further comprise an optimization/maintenance phase that follows the induction phase and wherein after the patient achieves a substantially complete response to the esketamine during the induction phase, the esketamine is administered at a frequency of less than twice a week during the optimization/maintenance phase. In some embodiments, the frequency of administration during the optimization/maintenance phase is once every week, once every two weeks, once a month, or a combination thereof.

At any stage during one or more of an induction phase, optimization phase, or maintenance phase, the patient's response to the treatment may be assessed using techniques described herein. This assessment may be performed until the patient is considered by one skilled in the art to have achieved a suitable response to the treatment regimen. In some embodiments, the induction period may be said to have completed when a patient's MADRS score is reduced by ≥50% from baseline or from about 20 to about 13. In other embodiments, the patient's MADRS score may be about 19, about 18, about 17, about 16, about 15, about 14, or about 13. Patients with MADRS scores ≤12 are considered in remission and if stable for four weeks should be moved to or maintained in the maintenance phase.

At the end of the induction phase or extended induction phase, the treating physician should evaluate the patient to optimize the dosing amount and frequency for any subsequent administration phases such as the "maintenance phase" or "long-term therapy phase". It is anticipated that the intranasal treatment frequency during the subsequent administration such as the maintenance phase will be reduced from that in the induction phase or extended induction phase (at least twice weekly) to once weekly dosing for at least 4 weeks. In some embodiments, the subsequent administration such as the maintenance phase is at least about 4 weeks, about 5 weeks, about 6 weeks, about 7 weeks, about 8 weeks, about 9 week, about 10 weeks, about 11 weeks, about 12 weeks, about 13 weeks, about 17 weeks, about 18 weeks, about 19 weeks, about 20 weeks, about 6 months, about 7 months, about 8 months, about 9 months, about 10 months, about 11 months, 1 year, or about 2 years. In some embodiments, the continuing administration of the esketamine during the subsequent administration phase is for at least six months. In other embodiments, the continuing administration of the esketamine during the subsequent administration phase is at least one year. In further embodiments, the frequency of administration during the subsequent administration phase is once every week or once every two weeks, or a combination thereof. In yet other embodiments, the dosing frequency and effective amount of esketamine during the subsequent administration phase is the minimum frequency and amount to maintain the stable remission or stable response.

The subsequent administration, such as in a maintenance period, may include longer periods of time depending on the patient's condition. In some embodiments, those longer periods may be at least about 3 years, about 4 years, about 5 years, about 6 years, about 7 years, about 8 years, about 9 years, about 10 years, or more than about 10 years, including indefinitely. For example, for patients diagnosed with TRD, treatment may be indefinite. In other embodiments, the treatment frequency is reduced to biweekly. In further embodiments, the treatment frequency is reduced to every three weeks. In yet other embodiments, the treatment frequency is reduced to monthly. The patients will be maintained on schedule until the patient achieves remission, maintains a response, or fails treatment. If the patient achieves remission or maintains a response with the once a week treatment for at least 4 weeks, the frequency of intranasal treatment sessions may be decreased to a maintenance dose of once every other week based on the severity of depressive symptoms and for some patient populations the frequency of treatment may be reduced to about once every three or four weeks as discussed above.

One skilled in the art will recognize that the maintenance phase described herein may continue until further treatment is not required and as indicated by, for example, prolonged remission of the depression (including for example, the remission of one or more symptoms associated with depression), social and/or occupational functional improvement to normal or premorbid levels, or other known measures of depression.

An effective amount of esketamine is administered to the patient during the maintenance phase. As noted above, the amount of esketamine administered during the maintenance phase is an amount that elicits the biological or medicinal response in a tissue system discussed above for the induction phase. In certain embodiments, the effective amount of esketamine is the amount which maintains a pharmacodynamic steady state of esketamine attained in the induction phase. In other embodiments, if depressed symptoms begin to worsen with treatment every other week, every three weeks or every four weeks, the dosing of esketamine will be increased to stabilize the patient. For example if the patient is being dosed every other week and their symptoms begin to worsen, esketamine can be administered once per week to maintain response during the maintenance phase. Again, at any time during the maintenance phase the patient's response maybe reassessed.

For elderly patients, the recommended dose of esketamine is about 28 to about 84 mg. The initial dose (at the first treatment session) is recommended to be about 28 mg of esketamine. Based on efficacy and tolerability of the about 28 mg dose, the dose at the next treatment session may remain at about 28 mg or be increased to about 56 mg. Depending on efficacy and tolerability of the about 56 mg dose, the dose at subsequent treatment session may remain at about 56 mg or be increased to about 84 mg, or reduced to about 28 mg. Depending on tolerability of the about 84 mg dose, the dose at subsequent treatment sessions may remain at about 84 mg or be reduced to about 56 mg.

For hepatically impaired patients, the recommended dose of esketamine is about 28 to about 56 mg. The initial dose (at the first treatment session) is recommended to be about 28 mg of esketamine. Based on efficacy and tolerability of the about 28 mg dose, the dose at the next treatment session may remain at about 28 mg or be increased to about 56 mg. Physicians should regularly monitor the hepatically impaired patients for drug tolerability, because esketamine is extensively metabolized in the liver.

For the treatment of patients with major depressive disorder with suicidal ideation and at imminent risk for suicide, dosing is more aggressive because of the severity of the condition. The methods include administering esketamine in one or two phases, i.e., an initial induction phase, and optionally in certain circumstances a maintenance phase. Due to the imminent risk to the patient's life the initial dose of esketamine is dosed at the highest effective amount of esketamine that the patient may tolerate twice a week in the induction phase. In some embodiments, the patient continues on therapy with the existing (i.e. currently initiated) antidepressant agent simultaneously with the beginning of therapy on esketamine during the induction phase. In other embodiments, the patient is initiated on a new antidepressant agent simultaneously with the beginning of therapy on esketamine during the induction phase. In further embodiments, the patient continues on therapy with a previously administered antidepressant agent simultaneously with the beginning of therapy on esketamine during the induction phase.

The antidepressant should be dosed as labeled for the treatment of MDD, in a manner appropriate for the patient's condition/health. The induction phase should be about 4 to about 8 weeks, about 4 to about 7 weeks, about 4 to about 6 weeks, most preferably about 4 weeks. At the end of the induction phase the esketamine dosing should cease, if the patient adequately responds to treatment or is in remission. The patient should be monitored to ensure that the patient remains stable/or in remission on the antidepressant alone. Should the patient fail to stabilize on the first combination of esketamine and antidepressant or fail treatment on the antidepressant that was initiated with esketamine after the dosing with esketamine ceases, a second induction phase may be begun.

In the second induction phase, the patient would be reinitiated on esketamine at the highest tolerable dose and simultaneously with a second new antidepressant. Alternatively, the patient would be reinitiated on esketamine at the highest tolerable dose and simultaneously with the same antidepressant that was used during the previous induction phase. The esketamine being dosed twice a week. The antidepressant would be dosed as labeled for the treatment of MDD, in a manner appropriate for the patient's condition/ health. The second induction phase should be about 4 to about 8 weeks, about 4 to about 7 weeks, about 4 to about 6 weeks, most preferably about 4 weeks. At the end of the second induction phase, if the patient adequately responds to treatment or is in remission the esketamine dosing should cease and the patient should be monitored to ensure that the patient remains stable/or is in stable remission on the antidepressant alone. Should the patient fail to stabilize or fail treatment on the antidepressant that was initiated with esketamine after the dosing with esketamine ceases, a third induction phase may be begun.

In the third induction phase the patient would be reinitiated on esketamine at the highest tolerable dose and simultaneously with a third new antidepressant. Alternatively, the patient would be reinitiated on esketamine at the highest tolerable dose and simultaneously with the same antidepressant that was used during the second induction phase. The esketamine being dosed twice a week. The antidepressant would be dosed as labeled for the treatment of MDD in a manner appropriate for the patient's condition/health. The third induction phase should be about 4 to about 8 weeks, about 4 to about 7 weeks, about 4 to about 6 weeks, most preferably about 4 weeks. At the end of the third induction phase the patient would proceed to the maintenance phase specified for TRD, since the patient now qualifies as a TRD patient. The methods described herein permit optimizing dosages of esketamine for administration to a patient having or being predisposed to depression. In some embodiments, the methods described herein do not require adjustment of the esketamine dosage.

In general, the patient may be reinitiated on esketamine at the highest tolerable dose and simultaneously with the same antidepressant that was used during any previous induction phase, including with an antidepressant in which the patient failed to stabilize or otherwise failed treatment. For example, in a method for treating treatment-resistant depression in a patient wherein the patient has not responded to at least two oral antidepressants in the current depressive episode, the patient may be administered esketamine at least twice weekly solely with esketamine or along with a first oral antidepressant that is the same or different than the previously ineffective oral antidepressant in a first induction phase. To the extent the patient fails to achieve a substantially complete response to the esketamine, the patient can be reinitiated at the highest tolerable dose of esketamine alone or simultaneously with a second oral depressant that is the same or different than the first oral antidepressant in a second induction phase. To the extent the patient achieves a substantially complete response to the esketamine during the second induction phase, the patient can then be administered a therapeutically effective amount of esketamine less than twice weekly during a subsequent maintenance phase.

In the event that one or more (e.g., two) doses of esketamine in any of the phases described herein are missed, the next dose is scheduled when possible based on the dosing frequency regimen. If more than 2 doses are missed, per clinical judgement, adjustment of the dose or frequency of esketamine may be required.

The preferred pharmaceutical composition of the present invention, S-ketamine hydrochloride as the active ingredient is intimately admixed with a pharmaceutical carrier, preferably water, according to conventional pharmaceutical compounding techniques, which carrier may take a wide variety of forms depending on the form of preparation desired for administration. Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

One suitable aqueous formulation of S-ketamine, comprises water and S-ketamine; wherein the S-ketamine is present in an amount in the range of from about 25 mg/mL to about 250 mg/mL, preferably about 55 mg/mL to about 250 mg/mL or about 100 mg/mL to about 250 mg/mL, or any amount or range therein, based on the total volume of the pharmaceutical composition. Preferably, the S-ketamine is present in an amount in the range of from about 150 mg/ml to about 200 mg/mL, or any amount or range therein. More preferably, the S-ketamine is present in an amount in the range of from about 150 mg/mL to about 175 mg/mL, or any amount or range therein. More preferably, the S-Ketamine is present in an amount in the range of from about 160 mg/mL to about 163 mg/mL, for example, in an amount of about 161.4 mg/mL.

Another suitable aqueous formulation of S-ketamine comprises water and S-ketamine; wherein the S-ketamine is present in an amount in the range of from about eq. 100 mg/mL to about eq. 250 mg/mL, or any amount or range therein, based on the total volume of the pharmaceutical composition. Preferably, the S-ketamine is present in an amount in the range of from about eq. 125 mg/ml to about eq. 180 mg/mL, or any amount or range therein. More preferably, the S-ketamine is present in an amount in the range of from about eq. 140 mg/mL to about eq. 160 mg/mL, or any amount or range therein, for example, in an amount of about eq. 140 mg/mL.

Suitable pharmaceutical compositions for use in the present invention are preferably an aqueous formulation. As used herein, unless otherwise noted, the term "aqueous" shall mean that the primary liquid component of the formulation is water. Preferably, water constitutes greater than about 80 wt-% of the liquid component of the pharmaceutical composition, more preferably greater than about 90 wt-%, more preferably greater than about 95 wt-%, more preferably about 98 wt-%.

In suitable pharmaceutical compositions for use in the present invention, the water content of the composition is within the range of 85±14 wt.-%, more preferably 85±12 wt.-%, still more preferably 85±10 wt.-%, most preferably 85±7.5 wt-% and in particular 85±5 wt.-%, based on the total weight of the composition.

In suitable pharmaceutical compositions for use in the present invention, preferably the water content of the composition is within the range of 90±14 wt.-%, more preferably 90±12 wt.-%, still more preferably 90±10 wt.-%, most preferably 80±7.5 wt-% and in particular 90±5 wt.-%, based on the total weight of the composition.

In another pharmaceutical composition for use in the present invention, the water content of the composition is within the range of 95±4.75 wt.-%, more preferably 95±4.5 wt.-%, still more preferably 95±4 wt.-%, yet more preferably 95±3.5 wt.-%, most preferably 95±3 wt.-% and in particular 95±2.5 wt.-%, based on the total weight of the composition.

In another pharmaceutical composition for use in the present invention, the water content of the composition is within the range of from 75 to 99.99 wt.-%, more preferably 80 to 99.98 wt.-%, still more preferably 85 to 99.95 wt.-%, yet more preferably 90 to 99.9 wt.-%, most preferably 95 to 99.7 wt.-% and in particular 96.5 to 99.5 wt.-%, based on the total weight of the composition.

In another pharmaceutical composition for use in the present invention, the composition further comprises one or more buffers and/or buffer systems (i.e. conjugate acid-base-pairs).

As used herein, the term "buffer" shall mean any solid or liquid composition (preferably an aqueous, liquid composition) which when added to an aqueous formulation adjusts the pH of said formulation. One skilled in the art will recognize that a buffer may adjust the pH of the aqueous formulation in any direction (toward more acidic, more basic or more neutral pH). Preferably, the buffer is pharmaceutically acceptable.

Suitably examples of buffers which may be used in the aqueous formulations of the present invention include, but are not limited to citric acid, sodium dihydrogen phosphate, disodium hydrogen phosphate, acetic acid, boric acid, sodium borate, succinic acid, tartaric acid, malic acid, lactic acid, fumaric acid, and the like. Preferably, the buffer or buffer system is selected from the group consisting of NaOH, citric acid, sodium dihydrogen phosphate and disodium hydrogen phosphate.

In an embodiment, the buffer is selected to adjust the pH of the S-ketamine hydrochloride pharmaceutical compositions of the present invention (e.g. the aqueous formulations described herein) into a pH in the range of from about pH 3.5 to about pH 6.5, or any amount or range therein. Preferably, the buffer is selected to adjust the pH of the S-ketamine hydrochloride compositions of the present invention to about in the range of from about pH 4.0 to about pH 5.5, or any amount or range therein, more preferably, in the range of from about pH 4.5 to about pH 5.0, or any amount or range therein.

Preferably, the concentration of the buffer and buffer system, respectively, preferably NaOH, is adjusted to provide a sufficient buffer capacity.

In an embodiment, the present invention is directed to a pharmaceutical composition comprising S-ketamine hydrochloride, water, and a buffer or buffer system, preferably NaOH; wherein the buffer or buffer system is present in an amount sufficient to yield a formulation with a pH in the range of from about pH 4.0 to about pH 6.0, or any amount or range therein.

Optionally the pharmaceutical compositions of the present invention may contain a preservative.

As used herein, unless otherwise noted, the terms "antimicrobial preservative" and "preservative" preferably refer to any substance that is usually added to pharmaceutical compositions in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

The complete absence of preservatives in the pharmaceutical compositions used in the present invention is preferred when the content of S-ketamine hydrochloride is sufficiently high so that due to its preservative property the desired shelf life or in use stability can be achieved by the presence of the drug itself. Preferably, under these circumstances the concentration of S-ketamine hydrochloride is at least eq. 120 mg/mL, preferably in the range of from about eq. 120 mg/mL to about eq. 175 mg/ml, or any amount or range therein, more preferably in an amount in the range of from about eq. 125 mg/mL to about eq. 150 mg/mL, or any amount or range therein, for example at about eq. 126 mg/mL or at about eq. 140 mg/mL.

As used herein, the terms "penetration agent", "penetration enhancer", and "penetrant" refer to any substance that increases or facilitates absorption and/or bioavailability of the active ingredient (e.g. S-ketamine hydrochloride) of a pharmaceutical composition. Preferably, the penetration agents increases or facilitates absorption and/or bioavailability of the active ingredient (e.g. S-ketamine hydrochloride) of a pharmaceutical composition, following nasal administration (i.e. increases or facilitates absorption and/or bioavailability of the active ingredient through the mucosal membrane).

Suitable examples include, but are not limited to tetradecyl maltoside, sodium glycocholate, tauroursodeoxycholic acid (TUDCA), lecithines, and the like; and chitosan (and salts), and surface active ingredients such as benzalkonium chloride, sodium dodecyl sulfate, sodium docusate, polysorbates, laureth-9, oxtoxynol, sodium deoxycholate, polyarginine, and the like. Preferably, the penetration agent is tauroursodeoxycholic acid (TUDCA).

The penetration agent may work via any mechanism, including for example by increasing the membrane fluidity, creating transient hydrophilic pores in the epithelial cells, decreasing the viscosity of the mucus layer or opening up tight junctions. Some penetration agents (for example bile salts and fusidic acid derivatives) may also inhibit the enzymatic activity in the membrane, thereby improving bioavailability of the active ingredient.

Preferably, the penetration agent is selected to meet one or more, more preferably all, of the following general requirements:

(a) It is effective at increasing absorption (preferably nasal absorption) of the active ingredient, preferably in a temporary and/or reversible manner;
(b) It is pharmacologically inert;
(c) It is non-allergic, non-toxic and/or non-irritating;
(d) It is highly potent (effective in small amounts);
(e) It is compatible with the other components of the pharmaceutical composition;
(f) It is odorless, colorless and/or tasteless;
(g) It is accepted by regulatory agencies; and
(h) It is inexpensive and available in high purity.

In one embodiment of the present invention, the penetration agent is selected to increase penetration (absorption and/or bioavailability of the S-ketamine hydrochloride) without nasal irritation. In another embodiment of the present invention, the penetration agent is selected to improve absorption and/or bioavailability of the S-ketamine hydrochloride; and further selected to enhance uniform dosing efficacy.

In an embodiment, the present invention is directed to a pharmaceutical composition comprising S-ketamine and water; herein the pharmaceutical composition does not contain an antimicrobial preservative; and wherein the pharmaceutical compositions further contains a penetration enhancer, preferably TUDCA.

In another embodiment, the present invention is directed to a pharmaceutical composition comprising S-ketamine and water; herein the pharmaceutical composition does not contain an antimicrobial preservative; and wherein the pharmaceutical compositions further contains tauroursodeoxycholic acid (TUDCA); wherein the TUDCA is present in a concentration in the range of from about 1.0 mg/mL to about 25.0 mg/mL, or any amount or range therein, preferably in a concentration in the range of from about 2.5 mg/mL to about 15 mg/mL, or any amount or range therein, preferably in a concentration in the range of from about 5 mg/mL to about 10 mg/mL, or any amount or range therein. In another embodiment, the present invention is directed to pharmaceutical composition wherein the TUDCA is present at a concentration of about 5 mg/mL. In another embodiment, the present invention is directed to pharmaceutical composition wherein the TUDCA is present at a concentration of about 10 mg/mL.

The pharmaceutical compositions for use in the present invention may further contain one or more additional excipients for example, wetting agents, surfactant components, solubilizing agents, thickening agents, colorant agents, antioxidant components, and the like.

Examples of a suitable antioxidant component, if used, include, but are not limited to one or more of the following: sulfites; ascorbic acid; ascorbates, such as sodium ascorbate, calcium ascorbate, or potassium ascorbate; ascorbyl palmitate; fumaric acid; ethylene diamine tetraacetic acid (EDTA) or its sodium or calcium salts; tocopherol; gallates, such as propyl gallate, octyl gallate, or dodecyl gallate; vitamin E; and mixtures thereof. The antioxidant component provides long term stability to the liquid compositions. Addition of the antioxidant component can help enhance and ensure the stability of the compositions and renders the compositions stable even after six months at 40° C. A suitable amount of the antioxidant component, if present, is about 0.01 wt.-% to about 3 wt.-%, preferably about 0.05 wt.-% to about 2 wt.-%, of the total weight of the composition.

Solubilizing and emulsifying agents can be included to facilitate more uniform dispersion of the active ingredient or other excipient that is not generally soluble in the liquid carrier. Examples of a suitable emulsifying agent, if used, include, but are not limited to, for example, gelatin, cholesterol, acacia, tragacanth, pectin, methyl cellulose, carbomer, and mixtures thereof. Examples of a suitable solubilizing agent include polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

Preferably, the solubilizing agent includes glycerin. The solubilizing or emulsifying agent is/are generally present in an amount sufficient to dissolve or disperse the active ingredient, i.e. S-ketamine, in the carrier. Typical amounts when a solubilizing or an emulsifier are included are from about 1 wt.-% to about 80 wt.-%, preferably about 20 wt.-% to about 65 wt.-%, and more preferably about 25 wt.-% to about 55 wt.-%, of the total weight of the composition.

A suitable isotonizing agent, if used, includes sodium chloride, glycerin, D-mannitol, D-sorbitol, glucose, and mixtures thereof. A suitable amount of the isotonizing agent, when included, is typically about 0.01 wt.-% to about 15 wt.-%, more preferably about 0.3 wt.-% to about 4 wt.-%, and more preferably about 0.5 wt.-% to about 3 wt.-%, of the total weight of the composition.

A suspending agent or viscosity increasing agent can be added to the pharmaceutical compositions of the present invention, to for example, increase the residence time in the nose. Suitably examples include, but are not limited to, hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and the like.

Advantageously, esketamine may be administered in a single daily dose, or the total daily dosage may be administered in divided doses of two, three or four times daily, preferably two times daily. Typically, divided doses should be made closer in time. In some embodiments, divided doses are administered about within 20 minutes, about 15 minutes, about 10 minutes, about 5 minutes, about 4 minutes, about 3 minutes, about 2 minutes, about 1 minute, or less of each other. Additionally, in a flexible dosing regimen a patient could be dosed daily, twice a week, once a week, once every other week or once monthly. For example, one dose of the esketamine is administered on day 1 and another dose of the esketamine is administered on day 2, or one dose of the esketamine is administered on day 1 and another dose of the esketamine is administered on day 3, or one dose of the esketamine is administered on day 1 and another dose of the esketamine is administered on day 4, or one dose of the esketamine is administered on day 1 and another dose of the esketamine is administered on day 5. Furthermore, esketamine is preferably administered in intranasal form via topical use of suitable intranasal vehicles, such as a nasal spray pump.

As described, the methods of administering esketamine to a patient result in a pharmacokinetic profile that achieves a maximum plasma concentration ($C_{max}$) of esketamine of about 45 to about 165 ng/mL. One skilled in the art would understand that any of the ranges or individual $C_{max}$ values may vary by ±30%. In some embodiments, the $C_{max}$ is about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, or about 165 ng/mL. In other embodiments, the $C_{max}$ is about 50 to about 150, about 50 to about 125, about 50 to about 100, about 50 to about 75, about 75 to about 150, about 75 to about 125, or about 75 to about 100 ng/mL. In further embodiments, the $C_{max}$ is about to about 75, about 50 to about 70, about 55 to about 65, about 45 to about 70, about 45 to about 65, about 45 to about 60, about 45 to about 55, about 55 to about 75, or about 60 to about 70 ng/mL, when about 28 mg of esketamine is administered. In yet other embodiments, the $C_{max}$ is about 65 to about 120, about 70 to about 120, about 70 to about 110, about 70 to about 100, about 70 to about 90, about 70 to about 80, about 80 to about 120, about 80 to about 110, about 80 to about 90, about 90 to about 120, or about 90 to about 110 ng/mL, when about 56 mg of esketamine is administered. In still further embodiments, the $C_{max}$ is about 90 to about 165, about 95 to about 165, about 95 to about 155, about 95 to about 145, about 95 to about 135, about 95 to about 125, about 95 to about 115, about 105 to about 165, about 105 to about 155, about 105 to about 145, about 105 to about 135, about 105 to about 125, about 105 to about 115, about 115 to about 165, about 115 to about 155, about 115 to about 145, about 115 to about 135, about 115 to about 125, about 125 to about 165, about 125 to about 155, about 125 to about 145, about 125 to about 135, about 135 to about 165, about 135 to about 155, about 135 to about 145, or about 145 to about 165 ng/mL, when about 84 mg of esketamine is administered.

Similarly, the methods of administering esketamine to a patient results in a pharmacokinetic profile that achieves an area under the plasma concentration-time curve from time 0 to time of last quantifiable concentration ($AUC_{last}$) of about 125 to about 490 ng*h/mL. The term "$AUC_{last}$" as used herein refers to the area under the plasma concentration-time curve from time zero to time of last measurable concentration. "Time zero" in a general context refers to the start point of the intended dose. For example, in Example 1 regarding intranasal administration, time 0 is defined as the time of administration of the first intranasal spray to one nostril from the first intranasal device. To the extent the intended dose requires administration of two oral tablets, time 0 is the time of administration of the first tablet. One skilled in the art would understand that any of the ranges or individual $AUC_{last}$ values may vary by ±30%. In some embodiments, the $AUC_{last}$ is about 125, about 130, about 135, about 140, about 145, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, or about 490 ng*h/mL. In other embodiments, the $AUC_{last}$ is about 150 to about 450, about 200 to about 400, about 250 to about 350, about 150 to about 350, or about 200 to about 300 ng*h/mL. In further embodiments, the $AUC_{last}$ is about 125 to about 185, about 130 to about 180, about 135 to about 175, about 140 to about 170, about 145 to about 165, or about 150 to about 160 ng*h/mL, when about 28 mg of esketamine is administered. In yet other embodiments, the $AUC_{last}$ is about 210 to about 320, about 220 to about 310, about 230 to about 300, about 240 to about 290, about 250 to about 280, or about 260 to about 270 ng*h/mL, when about 56 mg of esketamine is administered. In still further embodiments, the $AUC_{last}$ is about 305 to about 490, about 310 to about 480, about 320 to about 470, about 330 to about 460, about 340 to about 450, about 350 to about 450, about 360 to about 440, about 370 to about 430, about 380 to about 420, or about 390 to about 410 ng*h/mL, when about 84 mg of esketamine is administered.

The methods of administering esketamine may also result in a pharmacokinetic profile that achieves combinations of the $C_{max}$ and $AUC_{last}$ individual values and ranges described above.

A representative nasal spray device is disclosed in U.S. Pat. No. 6,321,942, incorporated by reference herein. For example, a disposable atomizer for discharging successive partial discharge amounts as a spray may be utilized to carry out the methods discloses herein. Typically, such devices allow a medicament to be sprayed into both nostrils of a patient in two successive strokes. The device may be ready-to-use wherein the medicament is discharged from a medium container. The device is typically able to separate a first discharge stroke from a second discharge stroke to prevent complete emptying of the medium container in a single motion. The device may take the form of a double-stroke disposable pump, which is disposed of after a single use and enables individual partial discharges with high dosing precision and reliability.

In one embodiment, the nasal spray device is a single-use device that delivers a total of 28 mg of esketamine in two sprays, one spray per nostril. The device may be operated by the patient under the supervision of a healthcare professional. With respect to dosage amounts, one device may be used for a 28 mg dose, two devices for a 56 mg dose, or three devices for an 84 mg dose. It is also preferable to have a 5-minute interval between the use of each device. As described in Example 1, time 0 is defined as the time of administration of the first intranasal spray to one nostril from the first intranasal device.

As depicted in FIGS. 83A to 83E, instructions for use will accompany a esketamine nasal spray drug product according to the present disclosure. In one aspect, the instructions for use are on the drug product label of an approved drug product. In certain aspects, the drug product comprises one or more intranasal spray devices, with the one or more devices comprising esketamine. The one or more devices is configured to administer the esketamine in two or more sprays, preferably two sprays, 1 spray per nostril of the patient.

An exemplary device is illustrated in FIG. 83A and comprises a tip, a nose rest, an indicator, a finger rest, and a plunger. The indicator indicates if the device is full, how many sprays have been administered, and/or whether or not the device is empty. The indication may be accomplished, for example, by using colored dots, where two colored dots indicate a full device, one colored dot indicates one spray has been administered, and no colored dots signifies an empty device.

In certain aspects, the device is intended for administration by the patient under the supervision of a health care professional (HCP). The health care professional may be, for example, a doctor, psychiatrist, or nurse that preferably has completed an education and training program for informing healthcare professionals about the appropriate use of esketamine according to United States Prescribing Information (USPI). This may include an educational program with clinical educators, instructional materials, videos and web-based education.

In an exemplary use embodiment, a first step includes an instruction for the patient to blow their nose before using a first device. A device may be configured to administer from about 28 to about 84 mg of esketamine. In preferred embodiments, each device contains about 28 mg of esketamine, with additional devices utilized if administering 56 mg or 84 mg of esketamine. For example, three devices may be used to administer 84 mg of esketamine. Before use, the device should not be primed as this will result in loss of medication. At the start of use, the patient's head is preferably reclined at about 45 degrees to keep the medication inside the nose.

Typically, the tip of the device is inserted into a first nostril, and the patient should dose the opposite nostril and breathe through the nose while activating the plunger to release the medication. The tip of the device is then inserted into the second nostril to deliver the remaining amount of esketamine. At this point, the HCP may take the device from the patient and confirm that the device is empty. If not, the patient should spray again into the second nostril.

Before a next administration from a second device, the patient should rest, preferably in a reclined position, for about 5 minutes before administering additional esketamine from a second device. The steps may be repeated for the second device. If a third device is needed, the patient should again wait about 5 minutes following the second spray to the second nostril before administering additional esketamine to the first nostril from a third device. Having the patient wait about 5 minutes after each device allows the medication to absorb. A used device may be disposed in accordance with local requirements.

In certain aspects, methods of selling a drug product comprising esketamine are also provided. The terms "sale" or "selling" as used herein refers to transferring a drug product, e.g., a pharmaceutical composition or a dosage form, from a seller to a buyer. In some embodiments, a drug product label for a reference listed drug for the drug product includes instructions for treating depression, including treatment-resistant depression. The methods also include offering for sale a drug product comprising esketamine. The term "offering for sale," as used herein, refers to the proposal of a sale by a seller to a buyer for a drug product, e.g., a pharmaceutical composition or a dosage form. These methods comprise offering the drug product for sale.

The term "drug product" is product that contains an active pharmaceutical ingredient that has been approved for marketing by a governmental authority, e.g., the Food and Drug Administration or the similar authority in other countries.

Similarly, "label" or "drug product label" refers to information provided to a patient which provides relevant information regarding the drug product. Such information includes, without limitation, one or more of the description of the drug, clinical pharmacology, indications (uses for the drug product), contraindication (who should not take the drug product), warnings, precautions, adverse events (side effects), drug abuse and dependence, dosage and administration, use in pregnancy, use in nursing mothers, use in children and older patients, how the drug is supplied, safety information for the patient, or any combination thereof. In certain embodiments, the label or drug product label provides an instruction for use in a patient with treatment-resistant depression. In other embodiments, the drug product label comprises data directed to the reduction of depressive symptoms relative to a placebo and/or standard of care. In further embodiments, the label or drug product label identifies esketamine as a regulatory approved chemical entity. In still other embodiments, the label provides instructions for use in a patient with depression, including treatment-resistant depression.

The term "reference listed drug" or "RLD" as used herein refers to a drug product to which new generic versions are compared to show that they are bioequivalent. It is also a medicinal product that has been granted marketing authorization by a member state of the European Union or by the Commission on the basis of a completed dossier, i.e., with the submission of quality, pre-clinical and clinical data in accordance with Articles 8(3), 10a, 10b or 10c of Directive 2001/83/EC and to which the application for marketing authorization for a generic/hybrid medicinal product refers, by demonstration of bioequivalence, usually through the submission of the appropriate bioavailability studies.

In the United States, a company seeking approval to market a generic equivalent must refer to the RLD in its Abbreviated New Drug Application (ANDA). For example, an ANDA applicant relies on the FDA's finding that a previously approved drug product, i.e., the RLD, is safe and effective, and must demonstrate, among other things, that the generic drug product is the same as the RLD in certain ways. Specifically, with limited exceptions, a drug product for which an ANDA is submitted must have, among other things, the same active ingredient(s), conditions of use, route of administration, dosage form, strength, and (with certain permissible differences) labeling as the RLD. The RLD is the listed drug to which the ANDA applicant must show its ANDA drug product is the same with respect to active ingredient(s), dosage form, route of administration, strength, labeling and conditions of use, among other characteristics. In the electronic Orange Book, there is a column for RLDs and a column for reference standards. In the printed version of the Orange Book, the RLDs and reference standards are identified by specific symbol.

A reference standard is the drug product selected by FDA that an applicant seeking approval of an ANDA must use in conducting an in vivo bioequivalence study required for approval. FDA generally selects a single reference standard that ANDA applicants must use in in vivo bioequivalence testing. Ordinarily, FDA will select the reference listed drug as the reference standard. However, in some instances (e.g., where the reference listed drug has been withdrawn from sale and FDA has determined it was not withdrawn for reasons of safety or effectiveness, and FDA selects an ANDA as the reference standard), the reference listed drug and the reference standard may be different.

FDA identifies reference listed drugs in the Prescription Drug Product, OTC Drug Product, and Discontinued Drug Product Lists. Listed drugs identified as reference listed drugs represent drug products upon which an applicant can rely in seeking approval of an ANDA. FDA intends to update periodically the reference listed drugs identified in the Prescription Drug Product, OTC Drug Product, and Discontinued Drug Product Lists, as appropriate.

FDA also identifies reference standards in the Prescription Drug Product and OTC Drug Product Lists. Listed drugs identified as reference standards represent the FDA's best judgment at this time as to the appropriate comparator for purposes of conducting any in vivo bioequivalence studies required for approval.

In some instances when FDA has not designated a listed drug as a reference listed drug, such listed drug may be shielded from generic competition. If FDA has not designated a reference listed drug for a drug product the applicant intends to duplicate, the potential applicant may ask FDA to designate a reference listed drug for that drug product.

FDA may, on its own initiative, select a new reference standard when doing so will help to ensure that applications for generic drugs may be submitted and evaluated, e.g., in the event that the listed drug currently selected as the reference standard has been withdrawn from sale for other than safety and efficacy reasons.

In Europe, Applicants identify in the application form for its generic/hybrid medicinal product, which is the same as an ANDA or supplemental NDA (sNDA) drug product, the reference medicinal product (product name, strength, pharmaceutical form, marketing authorization holder (MAH, first authorization, Member State/Community), which is synonymous with a RLD, as follows:

1. The medicinal product that is or has been authorized in the European Economic Area (EEA), used as the basis for demonstrating that the data protection period defined in the European pharmaceutical legislation has expired. This reference medicinal product, identified for the purpose of calculating expiry of the period of data protection, may be for a different strength, pharmaceutical form, administration route or presentation than the generic/hybrid medicinal product.

2. The medicinal product, the dossier of which is cross-referred to in the generic/hybrid application (product name, strength, pharmaceutical form, MAH, marketing authorization number). This reference medicinal product may have been authorized through separate procedures and under a different name than the reference medicinal product identified for the purpose of calculating expiry of the period of data protection. The product information of this reference medicinal product will, in principle, serve as the basis for the product information claimed for the generic/hybrid medicinal product.

3. The medicinal product (product name, strength, pharmaceutical form, MAH, Member State of source) used for the bioequivalence study(ies) (where applicable).

The different abbreviated approval pathways for drug products under the Food, Drug, and Cosmetics (FD&C) Act are the abbreviated approval pathways described in sections 505(j) and 505(b)(2) of the FD&C Act (21 U.S.C. 355(j) and 21 U.S.C. 23 355(b)(2), respectively).

According to the FDA ("Determining Whether to Submit an ANDA or a 505(b)(2) Application Guidance for Industry," U.S. Department of Health and Human Services, October 2017, pp. 1-14, the contents of which is incorporated herein by reference), NDAs and ANDAs can be divided into the following four categories:

(1) A "stand-alone NDA" is an application submitted under section 505(b)(1) and approved under section 505(c) of the FD&C Act that contains full reports of investigations of safety and effectiveness that were conducted by or for the applicant or for which the applicant has a right of reference or use.

(2) A section 505(b)(2) application is an NDA submitted under section 505(b)(1) and approved under section 505(c) of the FD&C Act that contains full reports of investigations of safety and effectiveness, where at least some of the information required for approval comes from studies not conducted by or for the applicant and for which the applicant has not obtained a right of reference or use.

(3) An ANDA is an application for a duplicate of a previously approved drug product that was submitted and approved under section 505(j) of the FD&C Act. An ANDA relies on the FDA's finding that the previously approved drug product, i.e., the reference listed drug (RLD), is safe and effective. An ANDA generally must contain information to show that the generic product (a) is the same as the RLD with respect to the active ingredient(s), conditions of use, route of administration, dosage form, strength, and labeling (with certain permissible differences) and (b) is bioequivalent to the RLD. An ANDA may not be submitted if studies are necessary to establish the safety and effectiveness of the product.

(4) A petitioned ANDA is a type of ANDA for a drug product that differs from the RLD in its dosage form, route of administration, strength, or active ingredient (in a product with more than one active ingredient) and for which FDA has determined, in response to a petition submitted under section 505(j)(2)(C) of the FD&C Act (suitability petition), that studies are not necessary to establish the safety and effectiveness of the drug product.

A scientific premise underlying the Hatch-Waxman Act is that a drug product approved in an ANDA under section 505(j) of the FD&C Act is presumed to be therapeutically equivalent to its RLD. Products classified as therapeutically equivalent can be substituted with the full expectation that the substituted product will produce the same clinical effect and safety profile as the prescribed product when administered to patients under the conditions specified in the labeling. In contrast to an ANDA, a section 505(b)(2) application allows greater flexibility as to the characteristics of the product. A section 505(b)(2) application will not necessarily be rated therapeutically equivalent to the listed drug it references upon approval.

The term "therapeutically equivalent to a reference listed drug" is means that the drug product is a generic equivalent, i.e., pharmaceutical equivalents, of the reference listed drug product and, as such, is rated an AB therapeutic equivalent to the reference listed drug product by the FDA whereby actual or potential bioequivalence problems have been resolved with adequate in vivo and/or in vitro evidence supporting bioequivalence.

"Pharmaceutical equivalents" means drug products in identical dosage forms and route(s) of administration that contain identical amounts of the identical active drug ingredient as the reference listed drug.

FDA classifies as therapeutically equivalent those products that meet the following general criteria: (1) they are approved as safe and effective; (2) they are pharmaceutical equivalents in that they (a) contain identical amounts of the same active drug ingredient in the same dosage form and route of administration, and (b) meet compendial or other applicable standards of strength, quality, purity, and identity; (3) they are bioequivalent in that (a) they do not present a known or potential bioequivalence problem, and they meet an acceptable in vitro standard, or (b) if they do present such a known or potential problem, they are shown to meet an appropriate bioequivalence standard; (4) they are adequately labeled; and (5) they are manufactured in compliance with Current Good Manufacturing Practice regulations The term "bioequivalent" or "bioequivalence" is the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Section 505 (j)(8)(B) of the FD&C Act describes one set of conditions under which a test and reference listed drug shall be considered bioequivalent:

the rate and extent of absorption of the [test] drug do not show a significant difference from the rate and extent of absorption of the [reference] drug when administered at the same molar dose of the therapeutic ingredient under similar experimental conditions in either a single dose or multiple doses; or the extent of absorption of the [test] drug does not show a significant difference from the extent of absorption of the [reference] drug when administered at the same molar dose of the therapeutic ingredient under similar experimental conditions in either a single dose or multiple doses and the difference from the [reference] drug in the rate of absorption of the drug is intentional, is reflected in its labeling, is not essential to the attainment of effective body drug concentrations on chronic use, and is considered medically insignificant for the drug.

Where these above methods are not applicable (e.g., for drug products that are not intended to be absorbed into the bloodstream), other scientifically valid in vivo or in vitro test methods to demonstrate bioequivalence may be appropriate.

For example, bioequivalence may sometimes be demonstrated using an in vitro bioequivalence standard, especially when such an in vitro test has been correlated with human in vivo bioavailability data. In other situations, bioequivalence may sometimes be demonstrated through comparative clinical trials or pharmacodynamic studies.

The methods may also comprise, consist of, or consist essentially of placing esketamine into the stream of commerce. In certain embodiments, the esketamine drug product includes a package insert that contains instructions for safely and effectively treating depression, including treatment-resistant depression, using esketamine. In still further aspects, described herein are methods of offering for sale esketamine comprising, consisting of, or consisting essentially of offering an esketamine drug product into the stream of commerce. In certain embodiments, the esketamine drug product includes a package insert that contains instructions for safely and effectively treating depression, including treatment-resistant depression, using esketamine.

Aspects of the Disclosure

The present disclosure pertains to and includes at least the following aspects.

1. A method for treating major depressive disorder comprising intranasally administering to a patient in need thereof, a clinically proven safe and clinically proven effective therapeutically effective amount of esketamine;
wherein the patient in need thereof is a human patient having a major depressive episode and wherein the patient has not responded to at least two oral antidepressants in the current depressive episode.

2. A method of treating major depressive disorder comprising administering esketamine to a patient in need thereof;
wherein the patient in need thereof is having a major depressive episode and wherein the patient has not responded to at least two oral antidepressants in the current depressive episode;
wherein the esketamine is administered intranasally;
and wherein the therapeutically effective amount of esketamine administered to the patient is clinically proven safe and effective.

3. A method for treating major depressive disorder in a human patient comprising the steps of:
(a) diagnosing said human patient by measuring said human patient's baseline MADRS score;
(b) intranasally administering to said human patient a therapeutically effective amount of esketamine that is clinically proven safe and effective;
wherein the therapeutically effective amount improves said MADRS score of at least 50% relative to the measured baseline MADRS score;
and wherein the esketamine is administered at pre-determined intervals; and
(c) re-evaluating said human patient at regular intervals following step (b) to determine relative effectiveness;
wherein the re-evaluation comprises measurement of said human patient's MADRS score.

4. The method of aspects 1, 2 or 3 wherein the major depressive disorder is treatment refractory depression or treatment resistant depression.

5. The method of aspects 1, 2, 3 or 4 wherein a therapeutically effective amount of at least one antidepressant is co-administered with esketamine.

6. The method of aspect 5, wherein the combination therapy comprises esketamine and one to two antidepressants.

7. The method of aspect 5, wherein each antidepressant is independently selected from the group consisting of imipramine, amitriptyline, desipramine, nortriptyline, doxepin, protriptyline, trimipramine, maprotiline, amoxapine, trazodone, bupropion, clomipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, neurokinin receptor antagonists and triiodothyronine.

8. The method of aspect 5, wherein each antidepressant is independently selected from the group consisting of monoamine oxidase inhibitors, tricyclics, serotonin reuptake inhibitors, serotonin noradrenergic reuptake inhibitors; noradrenergic and specific serotonergic agents and atypical antidepressants.

9. The method of aspect 5, wherein each antidepressant is independently selected from the group consisting of phenelzine, tranylcypromine, moclobemide, imipramine, amitriptyline, desipramine, nortriptyline, doxepin, protriptyline, trimipramine, clomipramine, amoxapine, fluoxetine, sertraline, paroxetine, citalopram, fluvoxamine, venlafaxine, milnacipran, mirtazapine and bupropion.

10. The method of aspect 5, wherein the combination therapy comprises esketamine and one to two antidepressants independently selected from the group consisting of fluoxetine, imipramine, bupropion, venlafaxine and sertraline.

11. The method of aspect 5, wherein the combination therapy comprising esketamine and at least one antidepressant further comprises an atypical antidepressant.

12. The method of aspect 11, wherein the atypical antidepressant is selected from the group consisting of aripiprazole, quetiapine, olanzapine, risperidone and paliperidone.

13. The method of aspect 12, wherein the atypical antidepressant is selected from the group consisting of aripiprazole, quetiapine and olanzapine.

14. A pharmaceutical composition for the treatment of treatment-refractory or treatment-resistant depression comprising esketamine, optionally at least one antidepressant, and a at least one pharmaceutically acceptable carrier.

15. The use of esketamine in the preparation of a medicament for the treatment of treatment-refractory or treatment-resistant depression, in a patient in need thereof.

16. Esketamine for use in a method for the treatment of treatment-refractory or treatment-resistant depression, in a patient in need thereof.

17. A composition comprising esketamine for the treatment of treatment-refractory or treatment-resistant depression.

18. A pharmaceutical product comprising esketamine for administration to a patient suffering from treatment resistant depression wherein the esketamine is administered intranasally to said patient in a clinically proven safe and effective amount.

19. A method of maintaining stable remission or stable response achieved by a patient with depression following administration of a therapeutically effective amount of esketamine during an initial administration phase, comprising continuing administration of a therapeutically effective amount of esketamine for at least five months during a subsequent administration phase.

20. The method of aspect 19, wherein the depression is treatment resistant depression.

21. The method of aspect 19 or 20, wherein the therapeutically effective amount of esketamine is administered intranasally, intramuscularly, subcutaneously, transdermally, buccally, or rectally in the initial and subsequent administration phases.

22. The method of aspect 21, wherein the administration is intranasally.

23. The method of any one of aspects 19 to 22, wherein a therapeutically effective amount of at least one antidepressant is co-administered with the esketamine in the initial and subsequent administration phases.

24. The method of aspect 23, wherein the esketamine is co-administered with one to two antidepressants.

25. The method of aspect 24, wherein each antidepressant is, independently, imipramine, amitriptyline, desipramine, nortriptyline, doxepin, protriptyline, trimipramine, maprotiline, amoxapine, trazodone, bupropion, comipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or tiiodothyronine.

26. The method of any one of aspects 23-25, wherein each antidepressant is, independently, a mono-amine oxidase inhibitor, tricyclic, serotonin reuptake inhibitor, serotonin noradrenergic reuptake inhibitor, noradrenergic and specific serotonergic agent, or atypical antidepressant.

27. The method of any one of aspects 23-26, wherein each antidepressant is, independently, phenelzine, tranylcypromine, moclobemide, imipramine, amitriptyline, desipramine, nortriptyline, doxepin, protriptyline, trimipramine, clomipramine, amoxapine, fluoxetine, sertraline, paroxetine, citalopram, fluvoxamine, venlafaxine, milnacipran, mirtazapine, or bupropion.

28. The method of any one of aspects 23-27, wherein each antidepressant is, independently, fluoxetine, imipramine, bupropion, venlafaxine, or sertraline.

29. The method of aspect 23, wherein the at least one antidepressant is an atypical antidepressant.

30. The method of aspect 29, wherein the atypical antidepressant is aripiprazole, quetiapine, olanzapine, risperdone, or paliperidone.

31. The method of aspect 30, wherein the atypical antidepressant is aripiprazole, quetiapine, or olanzapine.

32. The method of any one of aspects 19 to 31, wherein the initial administration phase comprises an induction phase wherein the esketamine is administered at a frequency of at least twice a week.

33. The method of aspect 32, wherein the frequency is twice a week.

34. The method of aspect 32 or 33, further comprising assessing the patient response during the induction phase.

35. The method of any one of aspects 32-34, wherein the initial administration phase further comprises an optimization phase that follows the induction phase and wherein after the patient achieves a substantially complete response to the esketamine during the induction phase, the esketamine is administered at a frequency of less than twice a week during the optimization phase.

36. The method of aspect 35, further comprising assessing the patient response during the optimization phase and adjusting the frequency of the administration during the optimization phase based on the response in order to achieve stable remission or stable response.

37. The method of aspect 36, wherein the frequency of administration during the optimization phase is once every week, once every two weeks, or a combination thereof.

38. The method of any one of aspects 19 to 37, wherein the effective amount of esketamine is 28 mg, 56 mg, or 84 mg during the initial and subsequent administration phases.

39. The method of any one of aspects 32-38, wherein the continuing administration of the esketamine during the subsequent administration phase is for at least six months.

40. The method of any one of aspects 32-39, wherein the continuing administration of the esketamine during the subsequent administration phase is at least one year.

41. The method of any one of aspects 32-40, wherein the frequency of administration during the subsequent administration phase is once every week or once every two weeks, or a combination thereof.

42. The method of any one of aspects 32-41, wherein the effective amount of esketamine during the subsequent administration phase is 56 mg or 84 mg.

43. The method of any one of aspects 32-42, wherein the dosing frequency and effective amount of esketamine during the subsequent administration phase is the minimum frequency and amount to maintain the stable remission or stable response.

44. The method of any one of aspects 19 to 43, wherein the therapeutically effective amount of esketamine is a clinically proven safe and clinically proven effective amount.

45. A method for the long term treatment of depression in a patient, comprising administering to the patient in need of the treatment a clinically proven safe and clinically proven effective therapeutically effective amount of esketamine for at least six months.

46. The method of aspect 45, wherein the esketamine is administered for at least one year.

47. The method of aspect 45 or 46, wherein the esketamine is administered for up to two years.

48. The method of any one of aspects 45-47, wherein the depression is treatment resistant depression.

49. The method of any one of aspects 45-47, wherein the esketamine is administered intranasally.

50. The method of any one of aspects 45-48, wherein a therapeutically effective amount of at least one antidepressant is co-administered with the esketamine.

51. The method of aspect 50, wherein the esketamine is co-administered with one to two antidepressants.

52. The method of aspect 51, wherein each antidepressant is, independently, imipramine, amitriptyline, desipramine, nortriptyline, doxepin, protriptyline, trimipramine, maprotiline, amoxapine, trazodone, bupropion, domipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or triiodothyronine.

53. The method of any one of aspects 50-52, wherein each antidepressant is, independently, a mono-amine oxidase inhibitor, tricyclic, serotonin reuptake inhibitor, serotonin noradrenergic reuptake inhibitor, noradrenergic and specific serotonergic agent, or atypical antidepressant.

54. The method of any one of aspects 50-53, wherein each antidepressant is, independently, phenelzine, tranylcypromine, moclobemide, imipramine, amitriptyline, desipramine, nortriptyline, doxepin, protriptyline, trimipramine, domipramine, amoxapine, fluoxetine, sertraline, paroxetine, citalopram, fluvoxamine, venlafaxine, milnacipran, mirtazapine, or bupropion.

55. The method of any one of aspects 50-54, wherein each antidepressant is, independently, fluoxetine, imipramine, bupropion, venlafaxine, or sertraline.

56. The method of aspect 55, wherein the at least one antidepressant is an atypical antidepressant.

57. The method of aspect 56, wherein the atypical antidepressant is aripiprazole, quetiapine, olanzapine, risperidone, or paliperidone.

58. The method of aspect 57, wherein the atypical antidepressant is aripiprazole, quetiapine, or olanzapine.

59. The method of any one of aspects 45-58, wherein esketamine is initially dosed twice a week for up to four weeks during an induction phase, and, thereafter, dosed less frequently than twice a week.

60. The method of aspect 59, wherein the esketamine is dosed once a week or once every two weeks following the induction phase.

61. The method of any one of aspects 45-60, wherein the therapeutically effective amount of esketamine is 28 mg, 56 mg, or 84 mg.

62. The method of any one of aspects 45-61, wherein cognitive performance of the patient remains stable, based on a baseline measurement, following six months of treatment.

63. A method for treating major depressive disorder in an elderly patient comprising
administering to the patient in need of treatment for a major depressive disorder a therapeutically effective amount of esketamine at a frequency of at least twice a week during an initial induction phase of defined duration;
assessing the patient response following the initial induction phase; and
continuing administering, at the frequency of at least twice a week, during an extended induction phase based on the assessment of whether the patient had achieved a substantially complete response to esketamine.

64. The method of aspect 63, wherein the elderly patient had not responded to at least two oral antidepressants in the current depressive episode.

65. The method of aspect 64, wherein the therapeutically effective amount of esketamine is administered intranasally, intramuscularly, subcutaneously, transdermally, buccally or rectally.

66. The method of any one of aspects 63 to 65, wherein the administration is intranasally.

67. The method of any one of aspects 63 to 66, wherein the initial induction phase is up to 2 weeks.

68. The method of any one of aspects 63 to 66, wherein the initial induction phase is up to 3 weeks.

69. The method of any one of aspects 63 to 66, wherein the initial induction phase is up to 4 weeks 70. The method of any one of aspects 63 to 66, wherein the extended induction phase is up to 8 weeks.

71. The method of any one of aspects 63 to 70, wherein the effective amount 28 mg, 56 mg or 84 mg.

72. The method of any one of aspects 63 to 71, wherein after the elderly patient has achieved a substantially complete response to esketamine, thereafter administering esketamine at a frequency of not more than once a week during an optimization phase.

73. The method aspect 72, further comprising assessing the patient's response periodically during the optimization phase.

74. The method of any one of aspects 63 to 73, wherein the frequency in the initial induction phase, extended induction phase, or a combination thereof is twice weekly.

75. The method of any one of aspects 63 to 74, wherein the major depressive disorder is treatment refractory depression or treatment resistant depression.

76. The method of any one of aspects 63 to 75, wherein a therapeutically effective amount of at least one antidepressant is co-administered with esketamine.

77. The method of any one of aspects 63 to 76, wherein the combination therapy comprises esketamine and one to two antidepressants.

78. The method of aspect 77, wherein each antidepressant is, independently, imipramine, amitriptyline, desipramine, nortriptyline, doxepin, protriptyline, trimipramine, maprotiline, amoxapine, trazodone, bupropion, domipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or triiodothyronine.

79. The method of aspect 77 or 78, wherein each antidepressant is, independently, a mono-amine oxidase inhibitor, tricyclic, serotonin reuptake inhibitor, serotonin noradrenergic reuptake inhibitor, noradrenergic and specific serotonergic agent, or atypical antidepressant.

80. The method of any one of aspects 77 to 79, wherein each antidepressant is, independently, phenelzine, tranylcypromine, moclobemide, imipramine, amitriptyline, desipramine, nortriptyline, doxepin, protriptyline, trimipramine, domipramine, amoxapine, fluoxetine, sertraline, paroxetine, citalopram, fluvoxamine, venlafaxine, milnacipran, mirtazapine, or bupropion.

81. The method of any one of aspects 77 to 80, comprising one or two antidepressants that are, independently, fluoxetine, imipramine, bupropion, venlafaxine, or sertraline.

82. The method of aspect 79, wherein the at least one antidepressant is an atypical antidepressant.

83. The method of aspect 82, wherein the atypical antidepressant is aripiprazole, quetiapine, olanzapine, risperidone, or paliperidone.

84. The method of aspect 82 or 83, wherein the atypical antidepressant is aripiprazole, quetiapine, or olanzapine.

85. The method of any one of aspects 63 to 84, wherein the patient is at least 65 years of age.

86. A method for treating a patient with major depressive disorder, comprising administering to the patient in need of treatment for major depressive disorder a clinically proven safe and clinically proven effective therapeutically effective amount of esketamine.

87. The method of aspect 86, wherein the patient has not responded to at least two oral antidepressants of adequate dose and duration in the current depressive episode.

88. The method of aspect 86 or 87, wherein the patient has been diagnosed with treatment refractory depression or treatment resistant depression.

89. The method of aspect 86, wherein the patient has suicidal ideation as a symptom of major depressive disorder.

90. The method of aspect 89, wherein the patient is in imminent risk for suicide.

91. The method of any one of aspects 86 to 90, wherein the patient is an adult.

92. The method of any one of aspects 86 to 91, wherein the patient is an elderly patient.

93. The method of any one of aspects 86 to 92, wherein the esketamine is administered intranasally, intramuscularly, subcutaneously, transdermally, buccally or rectally.

94. The method of any one of aspects 86 to 93, wherein the esketamine is administered intranasally.

95. The method of any one of aspects 86 to 94, wherein a therapeutically effective amount of at least one antidepressant is co-administered with esketamine.

96. The method of aspect 95, wherein the esketamine is co-administered with one to two antidepressants.

97. The method of aspect 95 or 96, wherein each antidepressant is, independently, imipramine, amitriptyline, desipramine, nortriptyline, doxepin, protriptyline, trimipramine, maprotiline, amoxapine, trazodone, bupropion, clomipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or triiodothyronine.

98. The method of aspect 95 or 96, wherein each antidepressant is, independently, a mono-amine oxidase inhibitor, tricyclic, serotonin reuptake inhibitor, serotonin noradrenergic reuptake inhibitor, noradrenergic and specific serotonergic agent, or atypical antidepressant.

99. The method of any one of aspects 95 to 98, wherein each antidepressant is, independently, phenelzine, tranylcypromine, moclobemide, imipramine, amitriptyline, desipramine, nortriptyline, doxepin, protriptyline, trimipramine, domipramine, amoxapine, fluoxetine, sertraline, paroxetine, citalopram, fluvoxamine, venlafaxine, milnacipran, mirtazapine, or bupropion.

100. The method of any one of aspects 96 to 99, wherein each antidepressant is, independently, fluoxetine, imipramine, bupropion, venlafaxine, or sertraline.

101. The method of aspect 95, wherein the at least one antidepressant is an atypical antidepressant.

102. The method of aspect 101, wherein the atypical antidepressant is aripiprazole, quetiapine, olanzapine, risperidone, or paliperidone.

103. The method of aspect 101 or 102, wherein the atypical antidepressant is aripiprazole, quetiapine, or olanzapine.

104. A pharmaceutical composition for the treatment of major depressive disorder, comprising esketamine, optionally at least one antidepressant, and at least one pharmaceutically acceptable carrier.

105. A pharmaceutical composition for the treatment of treatment refractory depression or treatment resistant depression, comprising esketamine, optionally at least one antidepressant, and at least one pharmaceutically acceptable carrier.

106. A pharmaceutical composition for the treatment of suicidal ideation, comprising esketamine, optionally at least one antidepressant, and at least one pharmaceutically acceptable carrier.

107. Use of esketamine in the preparation of a medicament for the treatment of major depressive disorder in a patient in need thereof.

108. Use of aspect 107, wherein the patient is suffering from treatment refractory depression or treatment resistant depression.

109. Use of aspect 107, wherein the patient is suffering from suicidal ideation.

110. Esketamine for use in a method for the treatment of major depressive disorder in a patient in need thereof.

111. Esketamine of aspect 110, wherein the patient is suffering from treatment refractory depression or treatment resistant depression.

112. Esketamine of aspect 110, wherein the patient is suffering from suicidal ideation.

113. A composition comprising esketamine for the treatment of major depressive disorder.

114. A composition comprising esketamine for the treatment of treatment refractory depression or treatment resistant depression.

115. A composition comprising esketamine for the treatment of suicidal ideation.

116. A pharmaceutical product comprising esketamine for administration to a patient suffering from major depressive disorder, wherein the esketamine is administered intranasally to said patient in a clinically proven safe and effective amount.

117. The pharmaceutical product of aspect 116, wherein the patient is suffering from treatment refractory depression or treatment resistant depression.

118. The pharmaceutical product of aspect 116, wherein the patient is suffering from suicidal ideation.

119. A method of administering esketamine to a patient, comprising a first phase, of a duration of about one week to about four weeks, wherein about 28 mg to about 84 mg of esketamine is administered to the patient at a frequency of twice per week, and wherein the method is clinically proven safe.

120. The method of aspect 119, wherein about 28 mg of esketamine is administered.

121. The method of aspect 119 or 120, wherein the administration of the esketamine achieves a maximum plasma concentration (Cmax) of esketamine of about 45 to about 75 ng/mL, an area under the plasma concentration-time curve from time 0 to time of last quantifiable concentration (AUClast) of about 125 to about 185 ng*h/mL, or a combination thereof.

122. The method of any one of aspects 119-121, wherein the esketamine is administered intranasally.

123. The method of aspect 122, wherein the about 28 mg of esketamine is administered in at least two sprays.

124. The method of aspect 123, wherein the about 28 mg of esketamine is administered via one spray in each nostril.

125. The method of aspect 119, wherein about 56 mg of esketamine is administered.

126. The method of aspect 119 or 125, wherein the administration of the esketamine achieves a maximum plasma concentration (Cmax) of esketamine of about 65 to about 120 ng/mL, an area under the plasma concentration-time curve from time 0 to time of last quantifiable concentration (AUClast) of about 210 to about 320 ng*h/mL, or a combination thereof.

127. The method of aspect 125 or 126, wherein the esketamine is administered intranasally.

128. The method of aspect 127, wherein the about 56 mg of esketamine is administered in at least 4 sprays.

129. The method of aspect 128, wherein the esketamine is administered via one spray in each nostril at time 0 for a total of about 28 mg, and repeated after about 5 minutes for the total of about 56 mg.

130. The method of aspect 119, wherein about 84 mg of esketamine is administered.

131. The method of aspect 119 or 130, wherein the administration of the esketamine achieves a maximum plasma concentration (Cmax) of esketamine of about 90 to about 165 ng/mL, an area under the plasma concentration-time curve from time 0 to time of last quantifiable concentration (AUClast) of about 305 to about 490 ng*h/mL, or a combination thereof.

132. The method of aspect 130 or 131, wherein the esketamine is administered intranasally.

133. The method of aspect 132, wherein the about 84 mg of esketamine is administered in at least 6 sprays.

134. The method of aspect 133, wherein the esketamine is administered via one spray in each nostril at time 0 for a total of about 28 mg, repeated after about 5 minutes for a total of about 56 mg, and repeated again after about 5 minutes for the total of about 84 mg in about 10 minutes.

135. The method of any one of aspects 119 to 134, wherein the first phase is a duration of about 4 weeks.

136. The method of any one of aspects 119 to 135, further comprising a second phase, of a duration of about 1 to about 4 weeks, following the first phase, wherein about 56 mg to about 84 mg of esketamine is administered to the patient at a frequency of once per week.

137. The method of aspect 136, wherein about 56 mg of esketamine is administered to the patient at a frequency of once per week during the second phase.

138. The method of aspect 136, wherein about 84 mg of esketamine is administered to the patient at a frequency of once per week during the second phase.

139. The method of any one of aspects 136-138, wherein the esketamine is administered intranasally in the second phase.

140. The method of any one of aspects 136-139, wherein the second phase is a duration of about 4 weeks.

141. The method of any one of aspects 119 to 140, further comprising a third phase, of a duration of about at least one week, following the second phase, wherein about 56 mg to about 84 mg of esketamine is administered to the patient at a frequency of every 2 weeks or once per week.

142. The method of aspect 141, wherein about 56 mg of esketamine is administered to the patient at a frequency of every 2 weeks or once per week during the third phase.

143. The method of aspect 141, wherein about 84 mg of esketamine is administered to the patient at a frequency of every 2 weeks or once per week during the third phase.

144. The method of any one of aspects 141-143, wherein the esketamine is administered intranasally in the third phase.

145. The method of any one of aspects 141-144, wherein the third phase is a duration of about at least one month.

146. The method of any one of aspects 141-144, wherein the third phase is a duration of about at least two months.

147. The method of any one of aspects 141-144, wherein the third phase is a duration of about at least three months.

148. The method of any one of aspects 141-144, wherein the third phase is a duration of about at least four months.

149. The method of any one of aspects 141-144, wherein the third phase is a duration of about at least five months.

150. The method of any one of aspects 141-144, wherein the third phase is a duration of about at least six months.

151. The method of any one of aspects 141-144, wherein the third phase is a duration of at least about a year.

152. The method of any one of aspects 141-144, wherein the third phase is a duration of at least about two years.

153. The method of any one of aspects 119 to 152, wherein the method further comprises co-administering an antidepressant, and wherein the method is clinically proven effective to treat a major depressive disorder.

154. The method of aspect 153, wherein the antidepressant is administered orally.

155. The method of aspects 153 or 154, wherein the major depressive disorder is treatment resistant depression.

156. A pharmaceutical product comprising one or more intranasal spray devices, wherein the one or more devices comprise an esketamine composition and the one or more devices is configured to administer from about 28 to about 84 mg of esketamine, and wherein the pharmaceutical product is clinically proven safe and/or clinically proven effective to treat a major depressive disorder.

157. The pharmaceutical product of aspect 156, wherein the major depressive disorder is treatment resistant depression.

158. The pharmaceutical product of aspect 156 or 157, wherein the product comprises one device.

159. The pharmaceutical product of aspect 156, wherein the device is configured to administer the esketamine in two or more sprays.

160. The pharmaceutical product of aspect 158 or 159, wherein the device comprises about 28 mg of esketamine.

161. The pharmaceutical product of aspect 156, wherein the product comprises more than one device and each device comprises about 28 mg of esketamine.

162. The pharmaceutical product of aspect 161, wherein each device is a single use device.

163. The pharmaceutical product of aspect 162, comprising three devices.

164. The pharmaceutical product of any one of aspects 156-163, further comprising instructions for performing any one of the methods of aspects 119-155.

165. A method of treating major depressive disorder with suicidal ideation, comprising
administering esketamine at a highest tolerable dose twice weekly during a first induction phase of a defined duration;
administering a first oral antidepressant simultaneously with the esketamine; and
evaluating the patient to determine if a substantially complete response to esketamine is achieved.

166. The method of aspect 165, wherein the treatment ceases if the patient achieves a substantially complete response to the esketamine.

167. The method of aspect 166, wherein the patient is monitored to ensure the patient remains stable or in remission on the first oral antidepressant alone.

168. The method of aspect 165, wherein a second induction phase is initiated if a substantially complete response is not achieved during the first induction phase.

169. The method of aspect 168, wherein the patient is reinitiated on esketamine at the highest tolerable dose and simultaneously with a second oral antidepressant during the second induction phase.

170. The method of aspect 169, wherein the second oral antidepressant is the same as the first oral antidepressant.

171. The method of aspect 169, wherein the second oral antidepressant is different than the first oral antidepressant.

172. The method of any one of aspects 169-171, wherein the patient is monitored to ensure the patient remains stable or in remission on the second oral antidepressant alone.

173. The method of any one of aspects 169-172, wherein a third induction phase is initiated if a substantially complete response is not achieved during the second induction phase.

174. The method of aspect 173, wherein the patient is reinitiated on esketamine at the highest tolerable dose and simultaneously with a third oral antidepressant during the third induction phase.

175. The method of aspect 174, wherein the third oral antidepressant is the same as the second oral antidepressant.

176. The method of aspect 174, wherein the third oral antidepressant is different than the second oral antidepressant.

177. The method of any one of aspects 165-176, further comprising administering a therapeutically effective amount of esketamine to the patient less than twice a week in a subsequent maintenance phase.

178. The method of any one of aspects 165-177, wherein the first, second, and third induction phase are, independently, at least 4 weeks.

179. A method for treating treatment-resistant depression in a patient wherein the patient has not responded to at least two oral antidepressants in the current depressive episode, the method comprising:
administering a first oral antidepressant to the patient, and
administering esketamine to the patient at least twice weekly during a first induction phase of a defined duration;
evaluating the patient during the first induction phase; and
wherein the patient fails to achieve a substantially complete response to the esketamine, reinitiating the patient on the highest tolerable dose of esketamine and simultaneously with a second oral depressant in a second induction phase of a defined duration.

180. The method of aspect 179, wherein the first oral antidepressant is the same as at least one of the at least two oral antidepressants.

181. The method of aspect 179, wherein the first oral antidepressant is different than at least one of the at least two oral antidepressants.

182. The method of aspect 179, wherein the first oral antidepressant is different than the at least two oral antidepressants.

183. The method of any one of aspects 179-182, wherein if the patient fails to achieve a substantially complete response to the esketamine during the second induction phase, reinitiating the patient on esketamine and simultaneously with a third oral depressant in a third induction phase of a defined duration.

184. The method of aspect 183, wherein the third oral antidepressant is the same as the second oral antidepressant.

185. The method of aspect 183, wherein the third oral antidepressant is different than the second oral antidepressant.

186. The method of any one of aspects 179-185, further comprising that when the patient achieves a substantially complete response to the esketamine, administering a therapeutically effective amount of esketamine to the patient at most once weekly during a subsequent maintenance phase.

187. The method of any one of aspects 179-186, wherein the first, second, and third induction phase are, independently, at least 4 weeks.

188. A method of treating treatment-resistant depression in a patient, said method comprising:
administering a therapeutically effective amount of an oral antidepressant to said patient; and
intranasally administering a therapeutically effective amount of esketamine to said patient at least twice weekly during an induction phase of at least 4 weeks; and
intranasally administering a therapeutically effective amount of esketamine to the patient at most once weekly during a subsequent maintenance phase,
wherein the method is clinically proven safe and/or clinically proven effective.

189. The method of aspect 188, wherein the esketamine is administered once every two weeks during the subsequent maintenance phase.

190. The method of aspect 188, wherein the frequency of administration may be adjusted during the induction phase and/or maintenance phase.

191. The method of aspect 188, wherein the therapeutically effective amount of esketamine administered during the induction phase is from about 28 mg to about 84 mg.

192. The method of aspect 191, wherein the therapeutically effective amount of esketamine is about 28 mg.

193. The method of aspect 191, wherein the therapeutically effective amount of esketamine is about 56 mg.

194. The method of aspect 191, wherein the therapeutically effective amount of esketamine is about 84 mg.

195. The method of aspect 191, wherein the therapeutically effective amount of esketamine is about 56 mg at the start of the induction phase and is adjusted to about 84 mg during the induction phase.

196. The method of aspect 192, wherein the patient is 65 years or older.

197. The method of aspect 188, wherein the therapeutically effective amount of esketamine administered during the maintenance phase is about 56 mg or about 84 mg.

198. The method of any one of aspects 188-197, wherein the therapeutically effective amount of esketamine during the induction and maintenance phase is delivered from an intranasal administration device in 2 or more sprays.

199. The method of any one of aspects 188-198, wherein the treatment continues for at least six months.

200. The method of any one of aspects 188-198, wherein the treatment continues for up to two years.

As used herein, AD=antidepressant; AE=adverse event; ESK=esketamine nasal spray; PBO=placebo nasal spray; PHQ-9=Patient Adherence Questionnaire; SDS=Sheehan Disability Scale; CGI-S=Clinical Global Impression-Severity; MADRS=Montgomery-Åsberg Depression Rating Scale; SD=standard deviation: SNRI=serotonin and norepinephrine reuptake inhibitors; SSRI=selective serotonin reuptake inhibitors: LS=least square; SE=standard error; BMI=body mass index; BPIC-SS=Bladder Pain/Interstitial Cystitis Symptom Score; BPRS+=4-item positive symptom subscale of the Brief Psychiatric Rating Scale; C=clinic visit; CADSS=Clinician Administered Dissociative States Scale; CGADR=Clinical Global Assessment of Discharge Readiness; C-SSRS=Columbia Suicide Severity Rating Scale; DNA=deoxyribonucleic acid; ECG=electrocardiogram; EQ-5D-5L=EuroQol-5 dimension-5-level; EW=early withdrawal; GAD-7=Generalized Anxiety Disorder, 7-item scale; HE=haematoxylin and eosin stain; HbA1c test, glycated hemoglobin test; HRUQ=Healthcare Resource Use Questionnaire; HVLT-R=Hopkins Verbal Learning Test-Revised; IDS-$C_{30}$=Inventory of Depressive Symptomatology Clinician-rated, 30-item scale; LOE=lack of efficacy; MDD—major depressive disorder; LTF=lost to follow-up; MGH-ATRQ=Massachusetts General Hospital-Antidepressant Treatment History Questionnaire; MGH-Female RLHQ=Massachusetts General Hospital-Female Reproductive Lifecyde and Hormones Questionnaire; MINI=Mini-International Neuropsychiatric Interview; MOAA/S=Modified Observer's Assessment of Alertness/Sedation; NS=not statistically significant; OL=open-label; OTH=other reason for withdrawal; PAQ, Patient Adherence Questionnaire; PHQ-9=Patient Health Questionnaire—9; PWC-20=Physician Withdrawal Checklist, 20-item scale; QIDS=16-item Quick Inventory of Depressive Symptoms—Self-Report; RNA=ribonudeic acid; SDS, Sheehan Disability Scale; SAFER=State vs. Trait, Assessibility, Face Validity, Ecological Validity, Rule of Three P's; STOP-Bang=Snoring, Tired, Observed Apnea, High Blood Pressure, Body mass index, Age, Neck Size, Gender (a questionnaire); TRD=treatment resistant depression; TSH=thyroid-stimulating hormone; RA=remote assessments only; LOCF=last observation carried forward; WBP=withdrawal by patient; WD=withdrawn.

The following Examples are set forth to aid in the understanding of the invention, and are not intended and should not be construed to limit in any way the invention set forth in the claims which follow thereafter.

Example 1

Efficacy of Intranasal Esketamine for Treating Treatment Resistance Depression (TRD), Phase 3 Clinical Trial The ability of esketamine to treat treatment-refractory or treatment-resistant depression (TRD) was evaluated via the clinical study described below, which was conducted to evaluate the efficacy, safety, and tolerability of flexibly dosed intranasal esketamine plus a newly initiated oral antidepressant in adult subjects with TRD. The study served as a pivotal Phase 3 short-term efficacy and safety study in support of regulatory agency requirements for registration of intranasal esketamine for the treatment of TRD.

The hypothesis for this study was that, in adult subjects with TRD, switching from a failed antidepressant treatment to intranasal esketamine plus a newly initiated oral antidepressant would be superior to switching to a newly initiated oral antidepressant treatment (active comparator) plus intranasal placebo in improving depressive symptoms.

The primary objective of this study was to evaluate the efficacy of switching adult subjects with TRD from a prior antidepressant treatment (to which they have not responded) to flexibly dosed intranasal esketamine (28 mg, 56 mg or 84 mg) plus a newly initiated oral antidepressant compared with switching to a newly initiated oral antidepressant (active comparator) plus intranasal placebo, in improving depressive symptoms, as assessed by the change from baseline in the MADRS total score from Day 1 (pre-randomization) to the end of the 4-week double-blind induction phase.

The key secondary objectives were to assess the effect of intranasal esketamine plus a newly initiated oral antidepressant compared with a newly initiated oral antidepressant (active comparator) plus intranasal placebo on the following parameters in adult subjects with TRD: (a) Depressive symptoms (subject-reported), (b) Onset of clinical response by Day 2, and (c) Functioning and associated disability. Additional secondary objectives included (a) Depression response rates, (b) Depression remission rates, (c) Overall severity of depressive illness, (d) Anxiety symptoms and (e) Health-related quality of life and health status.

To investigate the safety and tolerability of intranasal esketamine plus a newly initiated oral antidepressant compared with a newly initiated oral antidepressant (active comparator) plus intranasal placebo in adult subjects with TRD, the following parameters were also measured: (a) TEAEs, including AEs of special interest, (b) Local nasal tolerability, (c) Effects on heart rate, blood pressure, respiratory rate, and blood oxygen saturation, (d) Effects on alertness and sedation, (e) Potential psychosis-like effects, (f) Dissociative symptoms, (g) Potential effects on cognitive function, (h) Potential effects on suicidal ideation/behavior, (i) Potential treatment-emergent symptoms of cystitis and/or lower urinary tract symptoms, (j) Potential withdrawal and/or rebound symptoms following cessation of intranasal esketamine treatment, and (k) Potential effects on sense of smell.

The PK of intranasal esketamine in adult subjects with TRD receiving intranasal esketamine plus a newly-initiated oral antidepressant was also assessed as part of the secondary objectives.

Study Drug Information

Esketamine was supplied as a clear, colorless intranasal solution of esketamine hydrochloride (16.14% weight/volume [w/v]; equivalent to 14% w/v of esketamine base) in a nasal spray pump. The solution consisted of 161.4 mg/mL esketamine hydrochloride (equivalent to 140 mg of esketamine base) formulated in 0.12 mg/mL ethylenediaminetetraacetic acid (EDTA) and 1.5 mg/mL citric acid at a pH of 4.5 in water for injection. It is provided in a nasal spray pump, which delivered 16.14 mg esketamine hydrochloride (14 mg esketamine base) per 100-μL spray. Each individual nasal spray pump (device) contained a total of 28 mg (i.e., 2 sprays).

The placebo solution was supplied as a clear, colorless intranasal solution of water for injection, with a bittering agent (denatonium benzoate [Bitrex®] at a final concentration of 0.001 mg/mL) added to simulate the taste of the intranasal solution with active drug. The placebo solution was provided in matching nasal spray pump devices. Benzalkonium chloride was added as a preservative at a concentration of 0.3 mg/mL. Each individual nasal spray pump (device) contained 2 sprays.

Oral Antidepressant Medications

Duloxetine 30 mg was obtained from commercial stock and provided under the responsibility of the sponsor. Please refer to the package insert/SmPC for the physical description and a list of excipients.

Escitalopram 10 mg was obtained from commercial stock and provided under the responsibility of the sponsor. Please refer to the package insert/SmPC for the physical description and a list of excipients.

Sertraline 50 mg and 25 mg (as applicable) were obtained from commercial stock and provided under the responsibility of the sponsor. Please refer to the package insert/SmPC for the physical description and a list of excipients.

Venlafaxine 75 mg and 37.5 mg (as applicable) were obtained from commercial stock and provided under the responsibility of the sponsor. Please refer to the package insert/SmPC for the physical description and a list of excipients.

Overview of Study Design

Figure 1:
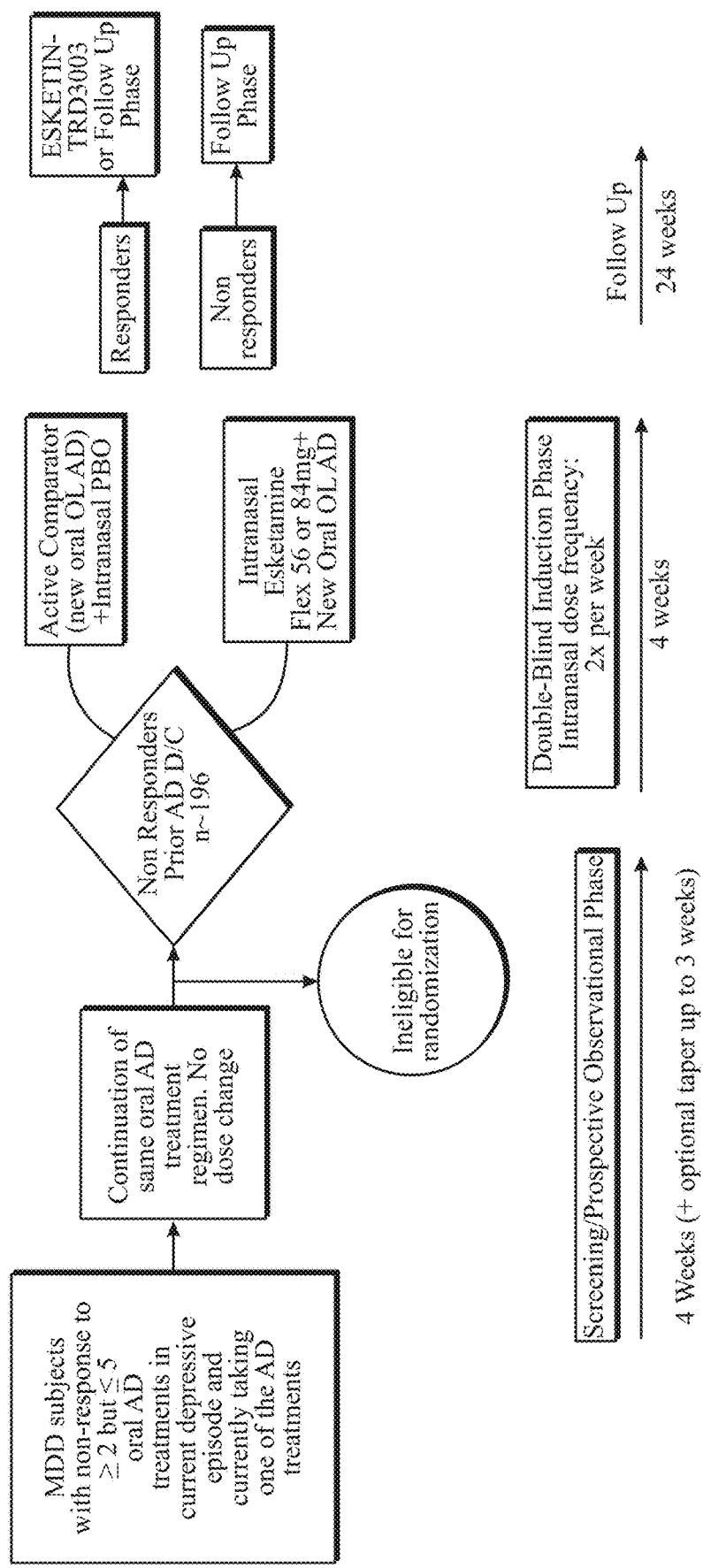
FIG. 1 illustrates a schematic of the study design of the ESKETINTRD3002 Phase 3 clinical trial.

This was a randomized, double-blind, active-controlled, multicenter study in male and female adult subjects with TRD to assess the efficacy, safety, and tolerability of flexibly dosed intranasal esketamine (28 mg, 56 mg or 84 mg) plus a newly initiated oral antidepressant compared with a newly initiated oral antidepressant (active comparator) plus intranasal placebo. The study had 3 phases which are briefly described below. A diagram of the study design is provided in FIG. 1.

Screening/Prospective Observational Phase (4-Week Duration)

This phase prospectively assessed treatment response to the subject's current oral antidepressant treatment regimen. After 4 weeks of continuing the same treatment regimen (at the same dosage), subjects who were non-responders to their current oral antidepressant treatment (as assessed by independent, remote raters) were eligible to proceed to the double-blind induction phase. The site investigators were blinded to the study criteria for non-response.

Eligible subjects who entered the double-blind induction phase discontinued their current oral antidepressant medication(s). If clinically indicated, a subject's current antidepressant medication(s) could be tapered and discontinued over an additional, optional period of up to 3 weeks per the local prescribing information or clinical judgment.

As a new oral antidepressant was initiated on Day 1 of the double-blind induction phase, eligible subjects who did not require a tapered discontinuation of their antidepressant medication(s) proceeded immediately into the double-blind induction phase.

Double-Blind Induction Phase (4-Week Duration)

The study included 227 randomized subjects (4 of whom did not receive intranasal and/or oral AD study drug and were therefore not included in the analysis sets), who were randomly assigned at a 1:1 ratio (n=98 subjects per treatment arm) to receive double-blind treatment with either intranasal esketamine or intranasal placebo. The intranasal treatment sessions (esketamine or placebo) occurred twice weekly. In addition, all subjects initiated a new open-label oral antidepressant on Day 1 that was taken daily for the duration of this phase. The assigned oral antidepressant was 1 of 4 oral antidepressant medications (duloxetine, escitalopram, sertraline, or venlafaxine extended release [XR]), that the subject had not previously had a nonresponse to in the current depressive episode, had not been previously intolerant to (lifetime), and was available in the participating country.

At the end of the induction phase, subjects who were responders (defined as ≥50% reduction in the MADRS total score from baseline [Day 1 pre-randomization] to the end of the 4-week double-blind induction phase) were eligible to participate in the subsequent study ESKETINTRD3003 if they met all other study entry criteria (ESKETINTRD3003 is a longer-term efficacy maintenance study involving repeated treatment sessions of intranasal esketamine).

If a subject withdrew from the study before the end of the double-blind induction phase for reasons other than withdrawal of consent, an Early Withdrawal visit was conducted within 1 week of the date of discontinuation, followed by the follow-up phase.

Follow-Up Phase (24-Week Duration)

This phase included all subjects who were not eligible or who chose to not participate in the maintenance of effect study ESKETINTRD3003 and had received at least 1 dose of intranasal study medication in the double-blind induction phase. There were no intranasal treatment sessions administered during this phase.

At the start of the follow-up phase, further clinical/standard of care for the treatment of depression were arranged by the study investigator and/or the subject's treating physician. The decision to continue the oral antidepressant in this phase was at the discretion of the investigator, however, in order to better assess potential withdrawal symptoms from intranasal study medication, it was recommended that the oral antidepressant medication be continued for at least the first 2 weeks of the follow-up phase unless determined as not clinically appropriate.

The follow-up phase also allowed collection of additional informative data to assess the course of the subject's major depressive episode over a 6-month period.

Taking into consideration the optional taper period of up to 3 weeks, the duration of a subject's study participation was 11 weeks (for subjects continuing into ESKETINTRD3003) or 35 weeks (for subjects completing the follow-up phase).

Study Population

The inclusion criteria for enrolling subjects in this study were as follows. Each potential subject satisfied all of the following criteria to be enrolled in the study.

1. At the time of signing the informed consent form (ICF), subject was a man or woman 18 (or older if the minimum legal age of consent in the country in which the study is taking place is >18) to 64 years of age, inclusive.
2. At the start of the screening/prospective observational phase, subject met the DSM-5 diagnostic criteria for single-episode MDD (if single-episode MDD, the duration was ≥2 years) or recurrent MDD, without psychotic features, based upon clinical assessment and confirmed by the MINI.
3. At the start of the screening/prospective observational phase, subject had a history of nonresponse to ≥2 but ≤5 oral antidepressant treatments in the current episode of depression, assessed using the MGH-ATRQ and confirmed by documented medical history and pharmacy/prescription records. Subject was taking an oral antidepressant treatment with nonresponse at the start of the screening/prospective observational phase. Subjects were adherent to the continued oral antidepressant treatment medication(s) (without adjustment in dosage) through the screening/prospective observational phase, as documented on the PAQ. Missing ≥4 days of antidepressant medication in the prior 2-week period was considered as inadequate adherence. Subjects who were non-responders to their current oral antidepressant medication(s) from the screening/prospective observational phase (as assessed by independent, remote raters) were eligible for randomization if all other entry criteria are met.
4. At the start of the screening/prospective observational phase, subject had an IDS-$C_{30}$ total score of ≥34.
5. The subject's current major depressive episode, and antidepressant treatment response in the current depressive episode, was confirmed using a Site Independent Qualification Assessment.
6. Subject was medically stable on the basis of physical examination, medical history, vital signs (including blood pressure), pulse oximetry, and 12-lead ECG performed in the screening/prospective observational phase. If there were any abnormalities that were not specified in the inclusion and exclusion criteria, the determination of their clinical significance was determined by the investigator and recorded in the subject's source documents and initialed by the investigator.
7. Subject was medically stable on the basis of clinical laboratory tests performed in the screening/prospective observational phase. If the results of the serum chemistry panel, hematology, or urinalysis were outside the normal reference ranges, the subject was included only if the investigator judged the abnormalities or deviations from normal to not be clinically significant or to be appropriate and reasonable for the population under study. This determination was recorded in the subject's source documents and initialed by the investigator. Subjects with a pre-existing history of thyroid disease/disorder who were treated with thyroid hormones were on a stable dosage for 3 months prior to the start of the screening/prospective observational phase and had thyroid-stimulating hormone (TSH) within normal range in the screening/prospective observational phase.
8. Subject were comfortable with self-administration of intranasal medication and able to follow the intranasal administration instructions provided.
9. Before the start of the screening/prospective phase, a female subject was either (a) Not of childbearing potential: Postmenopausal (>45 years of age with amenorrhea for at least 12 months or any age with amenorrhea for at least 6 months and a serum follicle stimulating hormone (FSH) level >40 IU/L); permanently sterilized (e.g., tubal occlusion, hysterectomy, bilateral salpingectomy); or otherwise be incapable of pregnancy; or (b) Of childbearing potential and practicing a highly effective method of birth control consistent with local regulations regarding the use of birth control methods for subjects participating in clinical studies, e.g., established use of oral, injected, or implanted hormonal methods of contraception; placement of an intrauterine device (IUD) or intrauterine system (IUS); barrier methods (e.g., condom with spermicidal foam/gel/film/cream/suppository or occlusive cap [diaphragm or cervical/vault caps] with spermicidal foam/gel/film/cream/suppository); male partner sterilization (the vasectomized partner should be the sole partner for that subject); or true abstinence (when this is in line with the preferred and usual lifestyle of the subject). If the childbearing potential changed after start of the study (e.g., woman who was not heterosexually active became active), the female subject began a highly effective method of birth control, as described above. Women agreed to continue using these methods of contraception throughout the study and for at least 6 weeks after the last dose of intranasal study drug.

10. A woman of childbearing potential had a negative serum (β-human chorionic gonadotropin [β-hCG]) at the start of the screening/prospective observational phase and a negative urine pregnancy test on Day 1 of the double-blind induction phase prior to randomization.

11. A man who was sexually active with a woman of childbearing potential and had not had a vasectomy agreed to use a barrier method of birth control e.g., either condom with spermicidal foam/gel/film/cream/suppository or partner with occlusive cap (diaphragm or cervical/vault caps) with spermicidal foam/gel/film/cream/suppository from Day 1 of the double-blind induction phase (prior to randomization) through 3 months after the last dose of intranasal study medication. Alternatively, female partners of childbearing potential could practice a highly effective method of birth control, e.g., established use of oral, injected, or implanted hormonal methods of contraception; placement of an intrauterine device (IUD) or intrauterine system (IUS); or male partner sterilization. If the childbearing potential changed after start of the study, a female partner of a male study subject, began a highly effective method of birth control, as described above.

12. Subject was willing and able to adhere to the prohibitions and restrictions specified in the clinical trial protocol.

13. Each subject signed an ICF indicating that he or she understood the purpose of and procedures required for the study and was willing to participate in the study.

The exclusion criteria for enrolling subjects in this study were as follows. Any potential subject who met any of the following criteria was excluded from participating in the study.

1. The subjects depressive symptoms had previously demonstrated nonresponse to: (a) Esketamine or ketamine in the current major depressive episode per clinical judgment, or (b) All of the oral antidepressant treatment options available in the respective country for the double-blind induction phase (i.e., duloxetine, escitalopram, sertraline, and venlafaxine XR) in the current major depressive episode (based on MGH-ATRQ), or (c) An adequate course of treatment with electroconvulsive therapy (ECT) in the current major depressive episode, defined as at least 7 treatments with unilateral ECT.

2. Subject has an implant for vagal nerve stimulation (VNS) or had received deep brain stimulation (DBS) in the current episode of depression.

3. Subject had a current or prior DSM-5 diagnosis of a psychotic disorder or MDD with psychosis, bipolar or related disorders (confirmed by the MINI), comorbid obsessive compulsive disorder, intellectual disability (only DSM-5 diagnostic code 319), borderline personality disorder, antisocial personality disorder, histrionic personality disorder, or narcissistic personality disorder.

4. Subject had homicidal ideation/intent, per the investigator's clinical judgment, or had suicidal ideation with some intent to act within 6 months prior to the start of the screening/prospective observational phase, per the investigator's clinical judgment or based on the C-SSRS, corresponding to a response of "Yes" on Item 4 (active suicidal ideation with some intent to act, without specific plan) or Item 5 (active suicidal ideation with specific plan and intent) for suicidal ideation on the C-SSRS, or a history of suicidal behavior within the past year prior to the start of the screening/prospective observational phase. Subjects reporting suicidal ideation with intent to act or suicidal behavior prior to the start of the double-blind induction phase were excluded.

5. Subject had a history of moderate or severe substance or alcohol use disorder according to DSM-5 criteria, except nicotine or caffeine, within 6 months before the start of the screening/prospective observational phase. A history (lifetime) of ketamine, phencyclidine (PCP), lysergic acid diethylamide (LSD), or 3, 4-methylene-dioxy-methamphetamine (MDMA) hallucinogen-related use disorder was exclusionary.

6. Subject had a current or past history of seizures (uncomplicated childhood febrile seizures with no sequelae are not exclusionary).

7. Subject had an UPSIT total score ≤18, indicative of anosmia, during the screening/prospective observational phase.

8. Subject had one of the following cardiovascular-related conditions: (a) Cerebrovascular disease with a history of stroke or transient ischemic attack, (b) Aneurysmal vascular disease (including intracranial, thoracic, or abdominal aorta, or peripheral arterial vessels), (c) Coronary artery disease with myocardial infarction, unstable angina, revascularization procedure (e.g., coronary angioplasty or bypass graft surgery) within 12 months before the start of the screening/prospective observational phase, or planned revascularization procedure, (d) Hemodynamically significant valvular heart disease such as mitral regurgitation, aortic stenosis, or aortic regurgitation or (e) New York Heart Association (NYHA) Class III-IV heart failure of any etiology.

9. Subject had a history of uncontrolled hypertension despite diet, exercise, or antihypertensive therapy at the start of the screening/prospective observational phase or any past history of hypertensive crisis or ongoing evidence of uncontrolled hypertension defined as a supine systolic blood pressure (SBP) >140 mmHg or diastolic blood pressure (DBP) >90 mmHg during screening/prospective observational phase which continues to be above this range with repeated testing during this phase. On Day 1 of the double-blind induction phase prior to randomization a supine SBP >140 mmHg or DBP >90 mmHg was also exclusionary.

A potential subject may have had his/her current antihypertensive medication regimen adjusted during the screening/prospective observational phase and then re-evaluated to assess their blood pressure control. The subject was on a stable regimen for at least 2 weeks before Day 1 of the double-blind induction phase.

10. Subject had a current or past history of significant pulmonary insufficiency/condition or with an arterial blood oxygen saturation ($SpO_2$) of <93% at the start of the screening/prospective observational phase or Day 1 prior to randomization.

11. Subject had clinically significant ECG abnormalities at the start of the screening/prospective observational phase or on Day 1 of the double-blind induction phase prior to randomization, defined as: (a) QT interval corrected according to Fridericia's formula (QTcF): ≥450 msec, (b) Evidence of 2nd and 3rd degree AV block, or 1st degree AV block with PR interval >200 msec, left bundle branch block (LBBB), or right bundle branch block (RBBB), (c) Features of new ischemia, (d) Arrhythmia (except premature atrial contractions [PACs] and premature ventricular contractions [PVCs]).

12. Subject had a history of additional risk factors for Torsades des Pointes (e.g., heart failure, hypokalemia, family history of Long QT Syndrome), or the use of concomitant medications that prolong the QT interval/corrected QT (QTc) interval 13. Subject had a history of, or symptoms and signs suggestive of, liver cirrhosis (e.g., esophageal varices, ascites, and increased prothrombin time) OR alanine aminotransferase (ALT) or aspartate aminotransferase (AST) values ≥2× the upper limit of normal or total bilirubin >1.5 times the ULN in the screening/prospective observational phase. For elevations in bilirubin if, in the opinion of the investigator and agreed upon by the sponsor's medical officer, the elevation in bilirubin was consistent with Gilbert's disease, the subject was able to participate in the study.

14. Subject had positive test result(s) for drugs of abuse (including barbiturates, methadone, opiates, cocaine, phencyclidine, and amphetamine/methamphetamine) at the start of the screening/prospective observational phase or Day 1 of the double-blind induction phase prior to randomization. Subjects who had a positive test result at screening due to prescribed/over-the-counter opiates, barbiturates, or amphetamines were permitted to continue in the screening/prospective observational phase if the medication was discontinued at least 1 week or 5 half-lives, whichever was longer, before Day 1 of the double-blind induction phase (prior to randomization) in accordance with restrictions as presented to the investigator and reproduced in Table 6, below. The result of the Day 1 (prior to randomization) test for drugs of abuse had to be negative for the subject to be randomized. Retesting was not permitted for positive test result(s), except for reasons stated above. Prior intermittent use of cannabinoids prior to the start of the screening/prospective observational phase was not exclusionary as long as the subject did not meet the criteria for substance use disorder. However, a positive test result for cannabinoids pre-dose on Day 1 of the double-blind induction phase was exclusionary.

15. Subject had uncontrolled diabetes mellitus or secondary diabetes, as evidenced by HbA1c>9% in the screening/prospective observational phase or history in the prior 3 months prior to the start of the screening/prospective observational phase of diabetic ketoacidosis, hyperglycemic coma, or severe hypoglycemia with loss of consciousness.

16. Subject had untreated glaucoma, current penetrating or perforating eye injury, brain injury, hypertensive encephalopathy, intrathecal therapy with ventricular shunts, or any other condition associated with increased intracranial pressure or increased intraocular pressure or planned eye surgery.

17. Subject had any anatomical or medical condition that may impede delivery or absorption of intranasal study drug (e.g., significant structural or functional abnormalities of the nose or upper airway; obstructions or mucosal lesions of the nostrils or nasal passages; undergone sinus surgery in the previous 2 years).

18. Subject had an abnormal or unrepaired deviated nasal septum with any 1 or more of the following symptoms: (a) Blockage of 1 or both nostrils in the past few months that can impact study participation, (b) nasal congestion (especially 1-sided), (c) frequent nosebleeds, (d) frequent sinus infections, or (e) noisy breathing during sleep.

19. Subject had a history of malignancy within 5 years before the start of the screening/prospective observational phase (exceptions were squamous and basal cell carcinomas of the skin and carcinoma in situ of the cervix, or malignancy that, in the opinion of the investigator, with concurrence with the sponsor's medical monitor, was considered cured with minimal risk of recurrence).

20. Subject had known allergies, hypersensitivity, intolerance, or contraindications to esketamine/ketamine and/or its excipients or all of the available oral antidepressant treatment options for the double-blind induction phase.

21. Subject had taken any prohibited therapies that would not permit dosing on Day 1, as outlined in the section headed Pre-study and Concomitant Therapy and Table 6.

22. Subject was taking a total daily dose of benzodiazepines greater than the equivalent of 6 mg/day of lorazepam at the start of the screening/prospective observational phase.

23. Subject had a score of ≥5 on the STOP-Bang questionnaire, in which case obstructive sleep apnea needed to be ruled out (e.g., apnea-hypopnea index [AHI]<30). A subject with obstructive sleep apnea could be included if he or she was using a positive airway pressure device or other treatment/therapy that was effectively treating his or her sleep apnea.

24. Subject had received an investigational drug (including investigational vaccines) or used an invasive investigational medical device within 60 days before the start of the screening/prospective observational phase, or had participated in 2 or more MDD or other psychiatric condition clinical interventional studies in the previous 1 year before the start of the screening/prospective observational phase, or was currently enrolled in an investigational study.

25. Subject was a woman who was pregnant, breastfeeding, or planning to become pregnant while enrolled in this study or within 6 weeks after the last dose of intranasal study drug.

26. Subject had a diagnosis of acquired immunodeficiency syndrome (AIDS). Human immunodeficiency virus (HIV) testing was not required for this study.

27. Subject had any condition or situation/circumstance for which, in the opinion of the investigator, participation would not be in the best interest of the subject (e.g., compromise the well-being) or that could prevent, limit, or confound the protocol-specified assessments.

28. Subject had major surgery, (e.g., requiring general anesthesia) within 12 weeks before the start of the screening/prospective observational phase, or would not have fully recovered from surgery, or had surgery planned during the time the subject was expected to participate in the study. Subjects with planned surgical procedures to be conducted under local anesthesia were allowed to participate.

29. Subject was an employee of the investigator or study site, with direct involvement in the proposed study or other studies under the direction of that investigator or study site, as well as family members of the employees or the investigator.

Investigators ensured that all study enrollment criteria were met. If a subject's status changed (including laboratory results or receipt of additional medical records) before the first dose of study drug was given such that he or she no longer met all eligibility criteria, then the subject would be excluded from participation in the study.

Additionally, potential subjects had to be willing and able to adhere to the following prohibitions and restrictions during the course of the study to be eligible for participation:
1. Inclusion and Exclusion Criteria;
2. Pre-Study and Concomitant Therapy Restrictions, including list of Prohibited Concomitant Medications for Intranasal Study Medication.
3. A positive urine drug screen for use of phencyclidine (PCP), 3, 4-methylenedioxy-methamphetamine (MDMA), or cocaine from Day 1 of the induction phase through the final visit in the double-blind induction phase will lead to discontinuation.
4. Subjects had to abstain from using alcohol within 24 hours before and after each intranasal treatment session. If a subject appeared intoxicated, dosing should not occur.
5. On all intranasal study drug dosing days, all subjects had to remain at the clinical study site until study procedures were completed and the subject was ready for discharge, and had to be accompanied by a responsible adult when released from the clinical study site. Subjects were not to drive a car or work with machines for 24 hours after study drug dosing.
6. Subjects were not to ingest grapefruit juice, Seville oranges, or quinine for 24 hours before an intranasal dose of study medication was to be administered.
7. ECT, DBS, transcranial magnetic stimulation (TMS), and VNS were prohibited from study entry through the end of the double-blind induction phase.
8. Subjects receiving psychotherapy were able to continue receiving psychotherapy provided this therapy had been stable in terms of frequency for the last 6 months prior to the screening/prospective observational phase and remained unchanged until the end of the double-blind induction phase.

Treatment Allocation, Randomization and Blinding

Central randomization was implemented in this study. Subjects were randomly assigned to 1 of 2 treatment groups in a 1:1 ratio based on a computer-generated randomization schedule prepared before the study by or under the supervision of the sponsor. The randomization was balanced by using randomly permuted blocks and was stratified by country and class of oral antidepressant (SNRI or SSRI) to be initiated in the double-blind induction phase. The interactive web response system (IWRS) was assigned a unique treatment code, which dictated the treatment assignment and matching study drug kits for the subject. After the investigator selected the oral antidepressant treatment for the double-blind induction phase, the site entered this information into IWRS. The requestor used his or her own user identification and personal identification number when contacting the IWRS, and was then given the relevant subject details to uniquely identify the subject.

The investigator was not provided with randomization codes. The codes were maintained within the IWRS, which had the functionality to allow the investigator to break the blind for an individual subject.

Data that could potentially unblind the treatment assignment (e.g., intranasal study drug plasma concentrations, treatment allocation) was handled with special care to ensure that the integrity of the blind was maintained and the potential for bias was minimized. This could include making special provisions, such as segregating the data in question from view by the investigators, clinical team, or others as appropriate until the time of database was lock and unblinding.

Under normal circumstances, the blind should not be broken until all subjects had completed the study and the database was finalized. Otherwise, the blind could be broken only if specific emergency treatment/course of action was dictated by knowing the treatment status of the subject. In such cases, the investigator could in an emergency determine the identity of the treatment by contacting the IWRS. It was recommended that the investigator contact the sponsor or its designee, if possible, to discuss the particular situation, before breaking the blind. Telephone contact with the sponsor or its designee was available 24 hours per day, 7 days per week. In the event the blind was broken, the sponsor was informed as soon as possible. The date and time of the unblinding was documented by the IWRS, and reason for the unblinding documented by the electronic case report form (eCRF) and in the source document. The documentation received from the IWRS indicating the code break was retained with the subject's source documents in a secure manner.

Subjects who had their treatment assignment unblinded were to continue to return for scheduled early withdrawal and follow up visits.

In general, randomization codes were disclosed fully only if the study was completed and the clinical database was closed. For interim analysis, the randomization codes and, if required, the translation of randomization codes into treatment and control groups were disclosed to those authorized and only for those subjects included in the interim analysis.

At the end of the double-blind induction phase the database was locked for the analysis and reporting of this phase. The subject treatment assignment was revealed only to sponsor's study staff. The investigators and the site personnel were blinded to the treatment assignment until all subjects had completed study participation through the follow-up phase.

To maintain the blinding of intranasal study medication, the esketamine and placebo intranasal devices were indistinguishable.

A total of 227 subjects were randomized in the study. Of these, 3 subjects did not receive any study drug (intranasal or oral AD) and 1 subject did not receive both the intranasal and oral AD study drug.

Demographic and baseline characteristics for the subjects in the study were as listed in Table 1, below. In general, the treatment groups were similar with respect to the baseline characteristics. The majority of subjects entering the study were female, with a mean age of all subjects of 45.7 years, ranging from 19 to 64 years.

TABLE 1

Demographic and Baseline Characteristics of Study Subjects

|  | Intranasal Esk + Oral AD (N = 114) | Oral AD + Intranasal Placebo (N = 109) | Total (N = 223) |
|---|---|---|---|
| Age (years) | | | |
| N | 114 | 109 | 223 |
| Mean (SD) | 44.9 (12.58) | 46.4 (11.14) | 45.7 (11.89) |
| Median | 45.0 | 47.0 | 47.0 |
| Range | (19; 64) | (20; 64) | (19; 64) |
| Age category (years), n (%) | | | |
| N | 114 | 109 | 223 |
| 18-44 | 54 (47.4%) | 40 (36.7%) | 94 (42.2%) |
| 45-64 | 60 (52.6%) | 69 (63.3%) | 129 (57.8%) |
| Sex, n (%) | | | |
| N | 114 | 109 | 223 |
| Male | 39 (34.2%) | 46 (42.2%) | 85 (38.1%) |
| Female | 75 (65.8%) | 63 (57.8%) | 138 (61.9%) |
| Race, n (%) | | | |
| N | 114 | 109 | 223 |
| Asian | 1 (0.9%) | 1 (0.9%) | 2 (0.9%) |
| Black or African American | 6 (5.3%) | 5 (4.6%) | 11 (4.9%) |
| White | 106 (93.0%) | 102 (93.6%) | 208 (93.3%) |
| Multiple | 1 (0.9%) | 1 (0.9%) | 2 (0.9%) |
| Ethnicity, n (%) | | | |
| N | 114 | 109 | 223 |
| Hispanic or Latino | 5 (4.4%) | 7 (6.4%) | 12 (5.4%) |
| Not Hispanic or Latino | 108 (94.7%) | 99 (90.8%) | 207 (92.8%) |
| Not Reported | 0 | 1 (0.9%) | 1 (0.4%) |
| Unknown | 1 (0.9%) | 2 (1.8%) | 3 (1.3%) |
| Baseline weight (kg) | | | |
| N | 114 | 109 | 223 |
| Mean (SD) | 79.30 (20.140) | 82.67 (19.468) | 80.95 (19.842) |
| Median | 73.10 | 84.90 | 79.70 |
| Range | (48.9; 162.8) | (45.3; 147.0) | (45.3; 162.8) |
| Baseline height (cm) | | | |
| N | 114 | 109 | 223 |
| Mean (SD) | 169.23 (10.179) | 169.81 (9.953) | 169.51 (10.051) |
| Median | 168.15 | 167.00 | 168.00 |
| Range | (148.5; 193.0) | (151.0; 194.0) | (148.5; 194.0) |
| Baseline body mass index (kg/m$^2$) | | | |
| N | 114 | 109 | 223 |
| Mean (SD) | 27.5 (5.84) | 28.6 (6.24) | 28.1 (6.05) |
| Median | 26.9 | 28.2 | 27.3 |
| Range | (16; 56) | (18; 53) | (16; 56) |
| BMI category (kg/m$^2$), n (%) | | | |
| N | 114 | 109 | 223 |
| Underweight <18.5 | 1 (0.9%) | 2 (1.8%) | 3 (1.3%) |
| Normal 18.5-<25 | 41 (36.0%) | 28 (25.7%) | 69 (30.9%) |
| Overweight 25-<30 | 41 (36.0%) | 36 (33.0%) | 77 (34.5%) |
| Obese 30-<40 | 28 (24.6%) | 39 (35.8%) | 67 (30.0%) |
| Morbidly obese ≥40 | 3 (2.6%) | 4 (3.7%) | 7 (3.1%) |
| Employment status, n (%) [a] | | | |
| N | 114 | 109 | 223 |
| Any type of employment | 68 (59.6%) | 63 (57.8%) | 131 (58.7%) |
| Any type of unemployment | 34 (29.8%) | 35 (32.1%) | 69 (30.9%) |
| Other | 12 (10.5%) | 11 (10.1%) | 23 (10.3%) |
| Hypertension status, n (%) [b] | | | |
| N | 114 | 109 | 223 |
| Yes | 18 (15.8%) | 27 (24.8%) | 45 (20.2%) |
| No | 96 (84.2%) | 82 (75.2%) | 178 (79.8%) |
| Country, n (%) | | | |
| N | 114 | 109 | 223 |
| Czech Republic | 30 (26.3%) | 28 (25.7%) | 58 (26.0%) |
| Germany | 10 (8.8%) | 10 (9.2%) | 20 (9.0%) |

TABLE 1-continued

Demographic and Baseline Characteristics of Study Subjects

| | Intranasal Esk + Oral AD (N = 114) | Oral AD + Intranasal Placebo (N = 109) | Total (N = 223) |
|---|---|---|---|
| Poland | 20 (17.5%) | 18 (16.5%) | 38 (17.0%) |
| Spain | 9 (7.9%) | 9 (8.3%) | 18 (8.1%) |
| United States | 45 (39.5%) | 44 (40.4%) | 89 (39.9%) |
| Region, n (%) | | | |
| N | 114 | 109 | 223 |
| Europe | 69 (60.5%) | 65 (59.6%) | 134 (60.1%) |
| North America | 45 (39.5%) | 44 (40.4%) | 89 (39.9%) |
| Class of oral antidepressant, n (%) | | | |
| N | 114 | 109 | 223 |
| SNRI | 77 (67.5%) | 75 (68.8%) | 152 (68.2%) |
| SSRI | 37 (32.5%) | 34 (31.2%) | 71 (31.8%) |
| Oral antidepressant, n (%) | | | |
| N | 114 | 109 | 223 |
| Duloxetine | 60 (52.6%) | 61 (56.0%) | 121 (54.3%) |
| Escitalopram | 21 (18.4%) | 17 (15.6%) | 38 (17.0%) |
| Sertraline | 16 (14.0%) | 16 (14.7%) | 32 (14.3%) |
| Venlafaxine extended release (XR) | 17 (14.9%) | 15 (13.8%) | 32 (14.3%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

Of the 227 randomized subjects, 197 completed the 28-day double-blind induction phase. The most frequent reason for withdrawal was adverse event. Subsequently 86 subjects entered the follow-up phase and 118 subjects continued into the ESKETINTRD3003 clinical study. Table 2 below presents the numbers and reasons for withdrawal from the study.

TABLE 2

Study Completion/Withdrawal Information; Double-blind Induction Phase

| | Intranasal Esk + Oral AD (N = 116) | Oral AD + Intranasal Placebo (N = 111) | Total (N = 227) |
|---|---|---|---|
| Completed | 98 (84.5%) | 99 (89.2%) | 197 (86.8%) |
| Withdrawn | 18 (15.5%) | 12 (10.8%) | 30 (13.2%) |
| Adverse event | 9 (7.8%) | 1 (0.9%) | 10 (4.4%) |
| Lack of efficacy | 2 (1.7%) | 0 | 2 (0.9%) |
| Lost to follow-up | 1 (0.9%) | 1 (0.9%) | 2 (0.9%) |
| Protocol violation | 2 (1.7%) | 2 (1.8%) | 4 (1.8%) |
| Withdrawal by subject | 4 (3.4%) | 7 (6.3%) | 11 (4.8%) |
| Other | 0 | 1 (0.9%) | 1 (0.4%) |

Baseline psychiatric history was as presented in table 3, below. The mean (SD) baseline MADRS total score was 37.1, ranging from 21 to 52.

TABLE 3

Baseline Psychiatric History

| | Intranasal Esk + Oral AD (N = 114) | Oral AD + Intranasal Placebo (N = 109) | Total (N = 223) |
|---|---|---|---|
| Age when diagnosed with MDD (years) | | | |
| N | 114 | 109 | 223 |
| Mean (SD) | 32.1 (12.53) | 35.3 (13.04) | 33.7 (12.86) |
| Median | 30.5 | 36.0 | 33.0 |
| Range | (8; 60) | (5; 64) | (5; 64) |
| Baseline MADRS total score | | | |
| N | 114 | 109 | 223 |
| Mean (SD) | 37.0 (5.69) | 37.3 (5.66) | 37.1 (5.67) |
| Median | 37.0 | 37.0 | 37.0 |
| Range | (22; 48) | (21; 52) | (21; 52) |

TABLE 3-continued

| Baseline Psychiatric History | | | |
|---|---|---|---|
| | Intranasal Esk + Oral AD (N = 114) | Oral AD + Intranasal Placebo (N = 109) | Total (N = 223) |
| Screening IDS-C30 total score | | | |
| N | 114 | 109 | 223 |
| Mean (SD) | 46.0 (6.26) | 45.7 (5.89) | 45.9 (6.07) |
| Median | 46.0 | 46.0 | 46.0 |
| Range | (34; 60) | (35; 63) | (34; 63) |
| Baseline CGI-S | | | |
| N | 114 | 109 | 223 |
| Mean (SD) | 5.0 (0.83) | 5.1 (0.67) | 5.1 (0.75) |
| Median | 5.0 | 5.0 | 5.0 |
| Range | (0; 7) | (4; 7) | (0; 7) |
| Baseline CGI-S category, n (%) | | | |
| N | 114 | 109 | 223 |
| Normal, not at all ill | 0 | 0 | 0 |
| Borderline mentally ill | 0 | 0 | 0 |
| Mildly ill | 0 | 0 | 0 |
| Moderately ill | 21 (18.4%) | 19 (17.4%) | 40 (17.9%) |
| Markedly ill | 64 (56.1%) | 63 (57.8%) | 127 (57.0%) |
| Severely ill | 27 (23.7%) | 26 (23.9%) | 53 (23.8%) |
| Among the most extremely ill patients | 1 (0.9%) | 1 (0.9%) | 2 (0.9%) |
| Not assessed | 1 (0.9%) | 0 | 1 (0.4%) |
| Baseline PHQ-9 total score | | | |
| N | 114 | 109 | 223 |
| Mean (SD) | 20.2 (3.63) | 20.4 (3.74) | 20.3 (3.68) |
| Median | 20.0 | 21.0 | 20.0 |
| Range | (5; 27) | (10; 27) | (5; 27) |
| Screening C-SSRS lifetime $^a$, n (%) | | | |
| N | 114 | 109 | 223 |
| No event | 65 (57.0%) | 61 (56.0%) | 126 (56.5%) |
| Suicidal ideation | 40 (35.1%) | 34 (31.2%) | 74 (33.2%) |
| Suicidal behavior | 9 (7.9%) | 14 (12.8%) | 23 (10.3%) |
| Screening C-SSRS past 6 or 12 months $^a$, n (%) | | | |
| N | 114 | 109 | 223 |
| No event | 77 (67.5%) | 74 (67.9%) | 151 (67.7%) |
| Suicidal ideation (past 6 months) | 37 (32.5%) | 34 (31.2%) | 71 (31.8%) |
| Suicidal behavior (past 12 months) | 0 | 1 (0.9%) | 1 (0.4%) |
| Duration of current episode (wks) | | | |
| N | 114 | 109 | 223 |
| Mean (SD) | 111.4 (124.28) | 118.0 (187.37) | 114.6 (157.96) |
| Median | 63.5 | 52.0 | 0.0 |
| Range | (9; 649) | (8; 1196) | (8; 1196) |
| No. of previous antidepressant medications $^b$, n (%) | | | |
| N | 114 | 109 | 223 |
| 1 | 9 (7.9%) | 18 (16.5%) | 27 (12.1%) |
| 2 | 69 (60.5%) | 54 (49.5%) | 123 (55.2%) |
| 3 | 24 (21.1%) | 22 (20.2%) | 46 (20.6%) |
| 4 | 7 (6.1%) | 13 (11.9%) | 20 (9.0%) |
| 5 | 3 (2.6%) | 1 (0.9%) | 4 (1.8%) |
| 6 | 1 (0.9%) | 1 (0.9%) | 2 (0.9%) |
| 9 | 1 (0.9%) | 0 | 1 (0.4%) |
| Family history of depression, n (%) | | | |
| N | 114 | 109 | 223 |
| Yes | 51 (44.7%) | 56 (51.4%) | 107 (48.0%) |
| No | 63 (55.3%) | 53 (48.6%) | 116 (52.0%) |
| Family history of anxiety disorder, n (%) | | | |
| N | 114 | 109 | 223 |
| Yes | 10 (8.8%) | 16 (14.7%) | 26 (11.7%) |
| No | 104 (91.2%) | 93 (85.3%) | 197 (88.3%) |
| Family history of bipolar disorder, n (%) | | | |
| N | 114 | 109 | 223 |
| Yes | 8 (7.0%) | 11 (10.1%) | 19 (8.5%) |
| No | 106 (93.0%) | 98 (89.9%) | 204 (91.5%) |

TABLE 3-continued

Baseline Psychiatric History

|  | Intranasal Esk + Oral AD (N = 114) | Oral AD + Intranasal Placebo (N = 109) | Total (N = 223) |
|---|---|---|---|
| Family history of schizophrenia, n (%) | | | |
| N | 114 | 109 | 223 |
| Yes | 6 (5.3%) | 4 (3.7%) | 10 (4.5%) |
| No | 108 (94.7%) | 105 (96.3%) | 213 (95.5%) |
| Family history of alcohol abuse, n (%) | | | |
| N | 114 | 109 | 223 |
| Yes | 18 (15.8%) | 20 (18.3%) | 38 (17.0%) |
| No | 96 (84.2%) | 89 (81.7%) | 185 (83.0%) |
| Family history of substance abuse, n (%) | | | |
| N | 114 | 109 | 223 |
| Yes | 8 (7.0%) | 4 (3.7%) | 12 (5.4%) |
| No | 106 (93.0%) | 105 (96.3%) | 211 (94.6%) |

$^a$ C-SSRS category: No event = 0; Suicidal ideation = 1, 2, 3, 4, 5; Suicidal behavior = 6, 7, 8, 9, 10.
$^b$ Number of antidepressant medications with non-response (defined as ≤25% improvement) taken for at least 6 weeks during the current episode as obtained from MGH-ATRQ.

Dosage and Administration

Screening/Prospective Observational Phase

At the start of screening/prospective observational phase, subjects were taking an oral antidepressant treatment with non-response at the start of the screening/prospective observational phase and continued this same treatment for the duration of the phase to confirm nonresponse. The site and investigators were blinded to the study criteria for non-response. During this phase, antidepressant treatment adherence was assessed using the PAQ.

After completion of 4 weeks of prospective antidepressant treatment and assessment of the antidepressant treatment response, the antidepressant medication could be tapered and discontinued over a period of up to 3 weeks per the local prescribing information or clinical judgment (e.g., antidepressant treatments with short half-lives, such as paroxetine and venlafaxine XR; or tolerability concerns).

Double-Blind Induction Phase

During this phase, subjects self-administered double-blind intranasal treatment with esketamine (56 mg or 84 mg) or placebo twice per week for 4 weeks as a flexible dose regimen at the study site. In addition, subjects simultaneously initiated a new, open-label oral antidepressant (i.e., duloxetine, escitalopram, sertraline, or venlafaxine XR) on Day 1 that was continued for the duration of this phase.

Intranasal Study Drug

On all intranasal treatment sessions, a physician, nurse, or other appropriate member of the site staff with recent training (i.e., within 1 year) for cardiopulmonary resuscitation (CPR) was present with the subject during the intranasal treatment session and the post-dose observation period. In addition, equipment for supportive ventilation and resuscitation was present. Table 4, below describes how each intranasal treatment session was to be administered in the double-blind induction phase.

TABLE 4

Intranasal Treatment Administration during the Double-blind Induction Phase

| Intranasal Treatment | Time of Intranasal Device Administration | | |
|---|---|---|---|
| | $0^a$ | 5 minutes | 10 minutes |
| Intranasal Device$^b$ | $1^{st}$ | $2^{nd}$ | $3^{rd}$ |
| Placebo | 1 spray of placebo to each nostril | 1 spray of placebo to each nostril | 1 spray of placebo to each nostril |
| Esketamine 56 mg | 1 spray of esketamine to each nostril | 1 spray of esketamine to each nostril | 1 spray of placebo to each nostril |
| Esketamine 84 mg | 1 spray of esketamine to each nostril | 1 spray of esketamine to each nostril | 1 spray of esketamine to each nostril |

$^a$Time 0 was defined as the time of administration of the first intranasal spray to one nostril from the first intranasal device.
$^b$One device was used at each time point. Each individual intranasal device contained 2 sprays. The intranasal devices containing esketamine delivered 14 mg per spray, for a total of 28 mg per individual device (i.e., 2 sprays).

Prior to the first intranasal dose on Day 1, subjects practiced spraying (into the air, not intranasally) a demonstration intranasal device that was filled with placebo solution.

All subjects self-administered the intranasal study drug (esketamine or placebo) at treatment sessions twice a week for 4 weeks at the study site. The first treatment session was on Day 1. Intranasal treatment sessions did not take place on consecutive days.

On Day 1, subjects randomized to intranasal esketamine started with a dose of 56 mg. On Day 4, the dose was increased to 84 mg or remained at 56 mg, as determined by the investigator based on efficacy and tolerability. On Day 8, the dose was increased to 84 mg (if Day 4 dose was 56 mg), remained the same, or was reduced to 56 mg (if Day 4 dose was 84 mg), as determined by the investigator based on efficacy and tolerability. On Day 11, the dose was increased to 84 mg (if Day 8 dose was 56 mg), remained the same, or was reduced to 56 mg (if Day 8 dose was 84 mg), as determined by the investigator based on efficacy and tolerability. On Day 15, a dose reduction from 84 mg to 56 mg was permitted, if required for tolerability; no dose increase was permitted on Day 15. After Day 15, the dose remained stable (unchanged).

Food was restricted for at least 2 hours before each administration of study drug. Drinking of any fluids was restricted for at least 30 minutes before the first nasal spray.

If the subject had nasal congestion on the dosing day, it was recommended that the dosing day be delayed (per the permitted visit window). Doses were not to be given on consecutive days. If an intranasal decongestant was used to reduce congestion, it could not be used within 1 hour prior to intranasal study drug dosing.

On all intranasal treatment sessions, subjects remained at the clinical site until study procedures had been completed and the subject was ready for discharge and was accompanied by a responsible adult when released from the clinical study site. Subjects were not to drive a car or work with machines for 24 hours after the last dose of intranasal study drug on each dosing day.

Oral Antidepressant Medication

Starting on Day 1, a new, open-label oral antidepressant treatment was initiated in all subjects and continued for the duration of this phase. The oral antidepressant was 1 of 4 oral antidepressant medications (duloxetine, escitalopram, sertraline, or venlafaxine XR). The antidepressant medication was assigned by the investigator based on a review of the MGH-ATRQ and relevant information regarding prior antidepressant treatments, and was one that the subject has not previously had a non-response to in the current depressive episode, had not been previously intolerant to (lifetime), and was available in the participating country.

Dosing of the oral antidepressant began on Day 1 and followed the local prescribing information for the respective product, with a forced titration to the maximum tolerated dose. The protocol-specified titration schedule was as presented in Table 5 below.

TABLE 5

Global titration schedule (except for Japan, Taiwan, South Korea, and Malaysia):

| Active Comparator Oral Antidepressant | Titration Schedule | | | |
|---|---|---|---|---|
| | Week 1 (Starting Day 1) | Week 2 (Starting Day 8) | Week 3 (Starting Day 15) | Week 4 (Starting Day 22) |
| Duloxetine | 60 mg | 60 mg | 60 mg | 60 mg |
| Escitalopram | 10 mg | 20 mg | 20 mg | 20 mg |
| Sertraline | 50 mg | 100 mg | 150 mg | 150 mg |
| Venlafaxine XR | 75 mg | 150 mg | 225 mg | 225 mg |

If higher doses were not tolerated, a down-titration was permitted based on clinical judgment. However, the subject's maximum tolerated dose should not be lower than the following minimum therapeutic doses: Sertraline (50 mg/day), venlafaxine XR (150 mg/day), escitalopram (10 mg/day), and duloxetine (60 mg/day). While subjects requiring lower doses could continue in the study and complete the double-blind induction phase, such subjects were not eligible to participate in the maintenance of effect study ESKETINTRD3003 and proceeded to the follow-up phase after completion of the double-blind induction phase.

All subjects were provided with an additional 4-week supply of the oral antidepressant medication to ensure there was no interruption of antidepressant therapy during the transition to further clinical/standard of care.

Study-site personnel instructed subjects on how to administer and store the oral antidepressant treatments supplied during the double-blind induction phase for at-home use.

On intranasal treatment sessions, it was recommended that oral antidepressant treatment be taken in the evening and at the same time of day during the double-blind induction phase. In addition, on intranasal dosing days, if the oral antidepressant medication frequency was greater than once daily (e.g., twice a day), it was recommended that the dose should not be taken until at least 3 hours after the intranasal treatment session.

Guidance on Blood Pressure Monitoring on Intranasal Dosing Days:

Given the potential for treatment emergent transient elevation in systolic and diastolic blood pressure, the following guidance was followed on intranasal dosing days:

If subsequent to fulfilling the inclusion and exclusion criteria on Day 1, a subject's pre-dose systolic blood pressure (SBP) was ≥160 mmHg and/or diastolic blood pressure (DBP) was ≥100 mmHg, it was recommended to repeat the blood pressure measurement after subject rested for 10 minutes in sitting or recumbent position. If repeated pre-dose SBP was ≥160 mmHg and/or DBP is ≥100 mmHg, then dosing was postponed and the subject scheduled to return on the following day or within the given visit window. If the blood pressure elevation persisted on the next visit, the subject was scheduled for a consultation by cardiologist or primary care physician, prior to further dosing.

If at any post-dose time point on the dosing day, the SBP was ≥180 mmHg but <200 mmHg and/or the DBP was ≤110 mmHg but <120 mmHg, further intranasal dosing was interrupted and the subject was referred to a cardiologist or primary care physician for a follow-up assessment.

After the assessment by a cardiologist or primary care physician, and provided the subject was given approval to continue in the study, the subject could continue with intranasal dosing if the pre-dose blood pressure at the next scheduled visit was within the acceptable range.

If at any post-dose time point on the dosing day the SBP was ≥200 mmHg and/or the DBP was ≥120 mmHg, the subject was to discontinue from further dosing and the subject referred to a cardiologist or primary care physician for a follow-up assessment.

During the double-blind induction phase, at 1.5 hours post-dose, if the SBP was ≥160 mmHg and/or the DBP was ≥100 mmHg, assessments should continue every 30 minutes until the blood pressure was <160 mmHg SBP and <100 mmHg DBP or until the subject was referred for appropriate medical care, if clinically indicated.

Follow-Up Phase

Subjects who received at least 1 dose of intranasal study medication in the double-blind induction phase, but did not enter the subsequent maintenance clinical study ESKETINTRD3003, proceeded into the 24-week follow-up phase. No intranasal study medication was administered during this phase.

At the start of the follow-up phase, further clinical/standard of care for the treatment of depression were arranged by the study investigator and/or the subject's treating physician. The decision to continue the oral antidepressant medication in this phase was at the discretion of the investigator; however, in order to better assess potential withdrawal symptoms from intranasal study medication, it was recommended that the oral antidepressant medication be continued for at least the first 2 weeks of the follow-up phase unless determined as not clinically appropriate.

Treatment Compliance

The investigator or designated study-site personnel were required to maintain a log of all intranasal study drug and oral antidepressant medication dispensed and returned. Drug supplies for each subject were inventoried and accounted for throughout the study.

Subjects received instructions on compliance with the oral antidepressant treatment. During the course of the study, the investigator or designated study-site personnel were responsible for providing additional instruction to re-educate any subject to ensure compliance with taking the oral antidepressant.

Antidepressant treatment adherence during the screening/prospective observational phase was assessed using the PAQ. Missing 24 days of antidepressant medication in the prior 2-week period was considered as inadequate adherence.

Antidepressant treatment compliance during the double-blind induction phase was assessed by performing pill counts (i.e., compliance check) and drug accountability.

All doses of intranasal study drug was self-administered by the subjects at the investigative site under the direct supervision of the investigator or designee, and will be recorded.

Pre-Study and Concomitant Therapy

Pre-study non-antidepressant therapies administered up to 30 days before the start of the screening/prospective observational phase were recorded at the start of this phase.

All antidepressant treatment(s), including adjunctive treatment for MDD, taken during the current depressive episode (i.e., including those taken more than 30 days prior to the start of the screening/prospective observational phase) were recorded at the start of the screening/prospective observational phase. In addition, information was also obtained regarding any history of intolerance to any of the 4 antidepressant choices (i.e., duloxetine, escitalopram, sertraline, and venlafaxine XR).

Concomitant therapies were recorded throughout the study, beginning with signing of the informed consent and continuing up to the last follow-up visit. Information on concomitant therapies were also obtained beyond this time only in conjunction with new or worsening adverse events until resolution of the event.

Subjects continued to take their permitted concomitant medications (e.g., antihypertensive medications) at their regular schedule; however, subject to restrictions and Table 6, below were to taken into account. Of note, if oral antihypertensive medications were taken in the morning, the morning dose was to be taken on intranasal dosing days.

Subjects receiving psychotherapy could continue receiving psychotherapy provided this therapy had been stable in terms of frequency for the last 6 months prior to the start of the screening/prospective observational phase and remained unchanged until after completion of the double-blind induction phase.

All therapies (prescription or over-the-counter medications, including vaccines, vitamins, herbal supplements; nonpharmacologic therapies, such as psychotherapy, electrical stimulation, acupuncture, special diets, and exercise regimens) different from the study drug were recorded. Modification of an effective preexisting therapy should not be made for the explicit purpose of entering a subject into the study, unless permitted by protocol (e.g., adjustment of blood pressure medications).

Rescue Medications

Rescue medications were not supplied by the sponsor. In case of treatment-emergent adverse events that could not be resolved by stopping further administration of intranasal esketamine/placebo, the following rescue medications could be considered:

For agitation or anxiety: As required, midazolam (maximum dose 2.5 mg orally or IM) or short acting benzodiazepine For nausea: As required, ondansetron 8 mg sublingually, metoclopramide (10 mg orally or IV or IM) or dimenhydrinate (25 to 50 mg, IV or IM)

It was recommended that transient increases in blood pressure not be treated, as the blood pressure returns to pre-dose values typically in 2 hours. The effect of any treatment may result in hypotension.

Prohibited Medications

A list of prohibited medications (not all inclusive) was provided as general guidance for the investigator and is reproduced in Table 6, below. The sponsor was notified in advance (or as soon as possible thereafter) of any instances in which prohibited therapies were administered.

TABLE 6

Prohibited Concomitant Medications with Intranasal Study Medication

| Drug Class | Episodic Use (as needed) | Continuous Use | Comments | Reason for Prohibition |
|---|---|---|---|---|
| Amantadine | N | N | | PD interaction |
| Anorexiants (eg, phentermine) | N | N | | Safety |
| Anticholinesterase inhibitors | N | N | | Subject population is excluded |
| Anticonvulsants | N | N | Subjects with seizures are excluded. Use as adjunctive treatment for major depressive disorder (MDD) is prohibited. Note: Anticonvulsants used for indications other than seizures may be allowed (eg, valproate for migraine) | Safety and PD interaction |
| Antidepressants (other than the specific antidepressant started in the induction phase of the study) | N | N | Only 1 of the 4 predefined oral antidepressant treatment options are permitted. If a subject is taking a monoamine oxidase inhibitor (MAOI) during the screening/prospective observational phase, there must be a minimum washout interval of 2 weeks prior to the first dose of intranasal study medication. | Safety and PD interaction |

TABLE 6-continued

Prohibited Concomitant Medications with Intranasal Study Medication

| Drug Class | Episodic Use (as needed) | Continuous Use | Comments | Reason for Prohibition |
|---|---|---|---|---|
| Antipsychotics | N | N | | PD interaction |
| Benzodiazepines and non-benzodiazepine sleeping medication (including: zolpidem, zaleplon, eszopiclone, and ramelteon) | Y | Y | Benzodiazepines are prohibited within 12 hours prior to the start of each intranasal treatment session or cognition testing Non-benzodiazepine sleeping medications are prohibited within 12 hours prior to the start of cognition testing but are permitted the night before dosing if no cognitive testing is scheduled. | Safety and PD interaction |
| Benztropine | Y | N | Prohibited if use is continuous and prohibited within 12 hours prior to the start of cognition testing | Safety and PD interaction. |
| Chloral hydrate, melatonin, valerian | N | N | | Safety and PD interaction |
| Clonidine | N | N | | Safety and PD interaction |
| Corticosteroids (oral) | N | N | Inhaled, intranasal, topical, and ophthalmic steroids are not prohibited. | PD interaction |
| Cough/cold preparations/nasal solutions containing vasoconstrictors, decongestants | Y | Y | Intranasally-administered decongestants (vasoconstrictors) should not be used from 1 hour prior to each intranasal study medication administration. | |
| CYP3A4 inhibitors Potent | N | N | Subjects may not take a known potent inhibitor of hepatic CYP3A activity within 1 week or within a period less than 5 times the drug's half-life, whichever is longer, before the first administration of study medication until at least 24 hours after the last intranasal dose of study medication Examples (not all-inclusive): Indinavir, nelfinavir, ritonavir, clarithromycin, itraconazole, ketoconazole, nefazodone, saquinavir, and telithromycin | PK |
| CYP3A4 inducers Potent | N | N | Subjects may not take a known potent inducer of hepatic CYP3A activity within 2 weeks of the first administration of intranasal study medication until at least 24 hours after the last intranasal dose of study medication. Examples (not all-inclusive): Efavirenz, nevirapine, barbiturates, carbamazepine, glucocorticoids, modafinil, oxcarbazepine, phenobarbital, phenytoin, rifabutin, rifampin, and St. John's wort | PK |
| Dextromethorphan | N | N | | PD interaction |
| Diphenhydramine | Y | N | Prohibited within 12 hours prior to the start of each intranasal treatment session | Safety |
| Ketanserin | N | N | | Safety |
| Lithium | N | N | | PD interaction |
| Memantine | N | N | | PD interaction |
| Methyldopa | N | N | | Safety and PD Interaction |
| Metyrosine | N | N | | Safety and PD interaction |

TABLE 6-continued

Prohibited Concomitant Medications with Intranasal Study Medication

| Drug Class | Episodic Use (as needed) | Continuous Use | Comments | Reason for Prohibition |
|---|---|---|---|---|
| Opioids | N | N | | PD interaction |
| Psychostimulants (eg, amphetamines) | N | N | | Cardiovascular safety |
| Reserpine | N | N | | PD interaction |
| Scopolamine | N | N | | PD interaction |
| St. John's Wort | N | N | | PD interaction and PK |
| Thyroid hormone supplement for treatment of thyroid condition only (not for depression) | N | Y | Subjects needing supplements must be on a stable thyroid supplement dose for at least 6 weeks prior to the first intranasal treatment session | Safety |
| Thyroxine/ triiodothyronine (T3), thyroid hormone prescribed for depression | N | N | | PD interaction |
| Warfarin | N | N | | Primary condition where used is excluded |

Abbreviations: N, Prohibited; PD, pharmacodynamics; PK, pharmacokinetics; Y, Permitted, with restrictions (please refer to the column labeled "Comments" for additional guidance).

The number of doses of intranasal study medication is summarized in Table 7, below.

TABLE 7

Number of Days Dosed with Intranasal Study Medication; Double-blind Induction Phase (Study ESKETINTRD3002: Safety Analysis Set)

| Number of days dosed | Intranasal Esk + Oral AD (N = 115) | Oral AD + Intranasal Placebo (N = 109) |
|---|---|---|
| 1 | 6 (5.2%) | 1 (0.9%) |
| 2 | 0 | 2 (1.8%) |
| 3 | 2 (1.7%) | 1 (0.9%) |
| 4 | 2 (1.7%) | 2 (1.8%) |
| 5 | 2 (1.7%) | 2 (1.8%) |
| 6 | 0 | 2 (1.8%) |
| 7 | 9 (7.8%) | 6 (5.5%) |
| 8 | 94 (81.7%) | 93 (85.3%) |

A summary of mean, mode and final dose of intranasal study medication is summarized in Table 8, below.

TABLE 8

Mean, Mode, and Final Daily Dose of Intranasal Study Medication; Double-blind Induction Phase (Study ESKETINTRD3002: Safety Analysis Set)

| | Intranasal Esk + Oral AD (N = 115) |
|---|---|
| Mean daily dose (mg) | |
| N | 115 |
| Mean (SD) | 70.7 (10.64) |
| Median | 77.0 |
| Range | (56; 81) |
| Mode daily dose (mg) | |
| N | 109 |
| Mean (SD) | 74.5 (13.32) |
| Median | 84.0 |
| Range | (56; 84) |
| Final daily dose (mg) | |
| N | 115 |
| Mean (SD) | 73.7 (13.51) |
| Median | 84.0 |
| Range | (56; 84) |

The calculation of mean, mode, and final daily dose excludes days off intranasal study medication. The final dose is the last non-zero dose received during the double-blind induction phase.

On Day 25 of the Double-blind Induction phase 66/99 (66/7%) subjects were receiving the 84 mg dose of esketamine. Of the 115 subjects treated with intranasal esketamine, 11 (9.6%) of subjects decreased their dose during the double-blind phase. Duration of exposure to oral antidepressant study medication was as summarized in Table 9, below.

TABLE 9

Extent of Exposure to Oral Antidepressant; Double-blind Induction Phase (Study ESKETINTRD3002: Safety Analysis Set)

Serotonin and Norepinephrine Reuptake Inhibitors (SNRI)

| | Duloxetine | Venlafaxine XR | Total |
|---|---|---|---|
| Intranasal esk + oral AD Total duration, days | (N = 60) | (N = 17) | (N = 77) |

TABLE 9-continued

Extent of Exposure to Oral Antidepressant; Double-blind Induction Phase (Study ESKETINTRD3002: Safety Analysis Set)

| Category, n (%) | | | |
|---|---|---|---|
| ≤7 | 1 (1.7%) | 0 | 1 (1.3%) |
| 8-14 | 2 (3.3%) | 1 (5.9%) | 3 (3.9%) |
| 15-21 | 1 (1.7%) | 0 | 1 (1.3%) |
| 22-28 | 37 (61.7%) | 7 (41.2%) | 44 (57.1%) |
| >28 | 19 (31.7%) | 9 (52.9%) | 28 (36.4%) |
| Mean (SD) | 26.8 (4.91) | 27.6 (4.73) | 27.0 (4.85) |
| Median | 28.0 | 29.0 | 28.0 |
| Range | (1; 30) | (10; 32) | (1; 32) |
| Oral AD + intranasal placebo Total duration, days Category, n (%) | (N = 61) | (N = 15) | (N = 76) |
| ≤7 | 2 (3.3%) | 0 | 2 (2.6%) |
| 8-14 | 0 | 0 | 0 |
| 15-21 | 1 (1.6%) | 0 | 1 (1.3%) |
| 22-28 | 30 (49.2%) | 8 (53.3%) | 38 (50.0%) |
| >28 | 28 (45.9%) | 7 (46.7%) | 35 (46.1%) |
| Mean (SD) | 28.0 (5.99) | 28.6 (1.12) | 28.2 (5.38) |
| Median | 28.0 | 28.0 | 28.0 |
| Range | (4; 48) | (27; 31) | (4; 48) |

Selective Serotonin Reuptake Inhibitors (SSRI)

| | Escitalopram | Sertraline | Total |
|---|---|---|---|
| Intranasal esk + oral AD Total duration, days | (N = 21) | (N = 16) | (N = 37) |

TABLE 9-continued

Extent of Exposure to Oral Antidepressant; Double-blind Induction Phase (Study ESKETINTRD3002: Safety Analysis Set)

| Category, n (%) | | | |
|---|---|---|---|
| ≤7 | 1 (4.8%) | 2 (12.5%) | 3 (8.1%) |
| 8-14 | 0 | 1 (6.3%) | 1 (2.7%) |
| 15-21 | 0 | 1 (6.3%) | 1 (2.7%) |
| 22-28 | 12 (57.1%) | 3 (18.8%) | 15 (40.5%) |
| >28 | 8 (38.1%) | 9 (56.3%) | 17 (45.9%) |
| Mean (SD) | 26.8 (4.74) | 23.8 (9.50) | 25.5 (7.24) |
| Median | 28.0 | 29.0 | 28.0 |
| Range | (7; 29) | (1; 30) | (1; 30) |
| Oral AD + intranasal placebo Total duration, days Category, n (%) | (N = 17) | (N = 16) | (N = 33) |
| ≤7 | 0 | 0 | 0 |
| 8-14 | 1 (5.9%) | 1 (6.3%) | 2 (6.1%) |
| 15-21 | 0 | 0 | 0 |
| 22-28 | 10 (58.8%) | 8 (50.0%) | 18 (54.5%) |
| >28 | 6 (35.3%) | 7 (43.8%) | 13 (39.4%) |
| Mean (SD) | 27.8 (4.27) | 27.3 (4.99) | 27.5 (4.56) |
| Median | 28.0 | 28.0 | 28.0 |
| Range | (14; 37) | (9; 31) | (9; 37) |

Percentages are calculated with the number of subjects in each treatment group as the denominator. The duration of exposure is defined as the duration between the date of the first antidepressant exposure and the date of the last antidepressant exposure. It includes days on which subjects did not actually take medication.

Study Evaluations

The Time and Events Schedule was as presented in Table 10 and Table 11 below, summarizes the frequency and timing of efficacy, PK, biomarker, pharmacogenomic, medical resource utilization, health economic, and safety measurements applicable to this study.

TABLE 10

Time and Events Schedule
(SCREENING/PROSPECTIVE OBSERVATIONAL PHASE AND DOUBLE-BLIND INDUCTION PHASE)

| | Screening/Prospective Observational Phase | | | Double-blind Induction Phase | | | | | | | | | | |
|---|---|---|---|---|---|---|---|---|---|---|---|---|---|---|
| Visit number | 1.1 | 1.2 | 1.3 [a] | 2.1 [a] | 2.2 | 2.3 | 2.4 | 2.5 | 2.6 | 2.7 | 2.8 | 2.9 | 2.10 | EW [b] |
| Week | Week 1 | Week 2 | End of Week 4 | 1 | | 2 | | 3 | | 4 | | | | — |
| Study day | — | — | — | 1 (baseline) | 2 | 4 | 8 | 11 | 15 | 18 | 22 | 25 | 28 | EW |
| Clinic visit window (in days) | — | ±2 | ±2 | — | — | ±1 | ±1 | ±1 | ±1 | ±1 | ±1 | +1 | −1 | — |
| Remote MADRS interview window (in days) | — | −2 | −2 | −2 [d] | — | — | −2 [c] | — | −2 [c] | — | −2 [c] | — | −1 | — |
| Clinic visit (C) or remote MADRS interview only (RM) | C | C | C | C | RM | C | C | C | C | C | C | C | C | C |
| | | | | Screening/Administrative | | | | | | | | | | |
| Informed consent (ICF) | X | | | | | | | | | | | | | |
| Medical history, psychiatric history, demographics, employment status | X | | | | | | | | | | | | | |
| MINI | X | | | | | | | | | | | | | |
| MGH-ATRQ | X | | | | | | | | | | | | | |
| Site Independent Qualification Assessment | X | | | | | | | | | | | | | |
| Height | X | | | | | | | | | | | | | |
| Inclusion/exclusion criteria | X | | | X | | | | | | | | | | |
| Pre-study therapy | X | | | | | | | | | | | | | |
| Preplanned surgery/procedures | X | | | | | | | | | | | | | |

TABLE 10-continued

Time and Events Schedule
(SCREENING/PROSPECTIVE OBSERVATIONAL PHASE AND DOUBLE-BLIND INDUCTION PHASE)

| | Screening/Prospective Observational Phase | | | Double-blind Induction Phase | | | | | | | | | | |
|---|---|---|---|---|---|---|---|---|---|---|---|---|---|---|
| Visit number | 1.1 | 1.2 | 1.3 [a] | 2.1 [a] | 2.2 | 2.3 | 2.4 | 2.5 | 2.6 | 2.7 | 2.8 | 2.9 | 2.10 | EW [b] |
| STOP-Bang questionnaire (including assessment of BMI and neck circumference) | X | | | | | | | | | | | | | |
| MGH-Female RLHQ: Module I | X | | | | | | | | | | | | | |
| IDS-$C_{30}$ | X | | | | | | | | | | | | | |
| Study Drug | | | | | | | | | | | | | | |
| Randomization | | | | X | | | | | | | | | | |
| Dispensing of new oral antidepressant (duloxetine, escitalopram, sertraline, or venlafaxine XR) | | | | X | | | | | | | | | | |
| Practice session for use of intranasal device | | | | X [c] | | | | | | | | | | |
| Intranasal esketamine or placebo | | | | X | | X | X | X | X | X | X | X | | |
| Drug accountability (intranasal study medication) | | | | X | | X | X | X | X | X | X | X | | X |
| Drug accountability (oral antidepressant study medication) | | | | X | | | | | | | | | X | X |
| Oral antidepressant compliance check | | | | | | | X | | X | | X | | X | X |
| Safety Assessments (Clinician) | | | | | | | | | | | | | | |
| Physical examination | X | | | X | | | | | | | | | X | X |
| Nasal examination [c] | X | | | X | | | | | | | | | X | X |
| Vital signs: blood pressure, pulse, respiratory rate, temperature [c] | X | | | X | X | X | X | X | X | X | X | X | | X |
| Vital signs (postdose): blood pressure, pulse, respiratory rate [e] | | | | X | X | X | X | X | X | X | X | X | | |
| Weight | X | | | X | | | | | | | | | X | X |
| 12-lead ECG [f] | X | | | X | | | X | | X | | | X | | X |
| C-SSRS: Baseline/Screening version | X | | | | | | | | | | | | | |
| C-SSRS: Since last visit version | | X | X | X | X | X | X | X | X | X | X | X | X | X |
| MOAA/S and pulse oximetry [g] | X | | | X | X | X | X | X | X | X | X | X | | |
| BPRS+ [h] | | | | X | X | X | X | X | X | X | X | X | | |
| CADSS [h] | | | | X | X | X | X | X | X | X | X | X | | |
| CGADR [i] | | | | X | X | X | X | X | X | X | X | X | | |
| PWC-20 | | | | | | | | | | | | | X [j] | X |
| Safety Assessments (Subject-completed) | | | | | | | | | | | | | | |
| Nasal symptom questionnaire [k] | | | | X | | X | | X | | X | | X | | |
| BPIC-SS [c] | | | | X | | | | X | | | | | X | X |
| Assessment of Sense of Smell | | | | | | | | | | | | | | |
| UPSIT [c] | | X | | | | | | X | | | | | X | X |
| Smell Threshold Test [c] | | X | | | | | | | | | | | X | X |
| Efficacy Assessments (Clinician) | | | | | | | | | | | | | | |
| MADRS (7-day recall; performed by independent, remote raters) | X | X | X | X [d] | | X | | X | | | X | | X | X |
| MADRS (24-hr recall; performed by independent, remote raters) | | | | | | X | | | | | | | | |
| CGI-S [c] | X | | | X | | X | X | X | X | | X | | X | X |

TABLE 10-continued

Time and Events Schedule
(SCREENING/PROSPECTIVE OBSERVATIONAL PHASE AND DOUBLE-BLIND INDUCTION PHASE)

| | Screening/Prospective Observational Phase | | | Double-blind Induction Phase | | | | | | | | | | |
|---|---|---|---|---|---|---|---|---|---|---|---|---|---|---|
| Visit number | 1.1 | 1.2 | 1.3 [a] | 2.1 [a] | 2.2 | 2.3 | 2.4 | 2.5 | 2.6 | 2.7 | 2.8 | 2.9 | 2.10 | EW [b] |
| Subject-completed Assessments | | | | | | | | | | | | | | |
| PAQ | X | X | X | | | | | | | | | | | |
| PHQ-9 [c] | X | | | X | | | | | X | | | | X | X |
| SDS [c] | X | | | X | | | | | | | | | X | X |
| GAD-7 [c] | X | | | X | | | | | | | | | X | X |
| EQ-5D-5L [c] | X | | | X | | | | | X | | | | X | X |
| Cognition Testing | | | | | | | | | | | | | | |
| Practice sessions | | X | | | | | | | | | | | | |
| Computerized test battery and HVLT-R | | | | X | | | | | | | | | X | X |
| Clinical Laboratory Assessments | | | | | | | | | | | | | | |
| TSH, HbA1c | X | | | | | | | | | | | | | |
| Lipid panel (fasting) | | X | | | | | | | | | | | | |
| Hematology, chemistry [c] | X | | | X | | | | | | | | | X | X |
| Urine drug screen [c] | X | | | X | | | | | X | | | X | | |
| Alcohol breath test | X | | | X | | | | | | | | | | |
| Urinalysis [c] | X | | | X | | | | | X | | | | X | X |
| Serum pregnancy test | X | | | | | | | | | | | | | |
| Urine pregnancy test [c] | | | | X | | | | | X | | | | X | X |
| Pharmacokinetics | | | | | | | | | | | | | | |
| Blood collection [l] | | | | | | | X | | | | X | | | |
| Biomarker, Pharmacogenomic (DNA), and Expression (RNA) Evaluations | | | | | | | | | | | | | | |
| Blood sample collection (protein) [c, m] | X | | | X | | | X | | | | | | X | X |
| Blood sample collection (DNA) [c, m] | X | | | | | | | | | | | | X | X |
| Blood sample collection (RNA) [c, m] | X | | | X | | | X | | | | | | X | X |
| Ongoing Subject Review | | | | | | | | | | | | | | |
| Concomitant therapy | | | | | | | | | Ongoing | | | | | |
| Adverse events | | | | | | | | | Ongoing | | | | | |
| Other | | | | | | | | | | | | | | |
| Menstrual cycle tracking (start date of last menstrual period prior to study visit) | X | | | X | | | | | | | | | X | |
| Additional supply of oral antidepressant | | | | | | | | | | | | | X | X |

On intranasal dosing days, time 0 was defined as the time of the first intranasal spray. Therefore, postdose time points were referenced from this.

[a] An additional, optional period of up to 3 weeks was permitted to taper and discontinue current antidepressant medication(s) after completion of the Week 4 (Visit 1.3) assessments, per the local prescribing information or clinical judgment. Subjects who did not require a taper and were thus eligible to immediately proceed to the double-blind induction phase will have Visit 1.3 and Visit 2.1 occurring on the same day.

[b] If a subject withdrew before the end of the double-blind induction phase (i.e., before completing Visit 2.10/Day 28) for reasons other than withdrawal of consent, an early withdrawal visit was conducted within 1 week of the date of discontinuation, followed by the follow-up phase. If the early withdrawal visit was conducted on the same day as a scheduled visit, duplicate assessments were not required.

[c] Pre-dose (if/when performed on intranasal dosing days). With the exception of post-dose assessments, subject-reported outcome assessments were administered before all other study-related procedures during a clinic visit.

[d] Performed only for subjects requiring a taper period during the screening/prospective observational phase; the result was considered as the subject's baseline MADRS for the double-blind induction phase. For all other subjects, the baseline MADRS for the double-blind induction phase was the MADRS performed at the end of Week 4 of the screening/prospective observational phase.

[e] Post-dose vital signs were performed at 40 minutes, 1 hour, and 1.5 hours post-dose.

[f] Twelve-lead ECG was performed pre-dose and at t = 1 hour post-dose at Visit 2.1. Twelve-lead ECG were performed at t = 1 hour post-dose at Visits 2.3 to 2.9, but no pre-dose ECGs were required at Visits 2.3 to 2.9. A time window of ±15 minutes was permitted.

[g] The MOAA/S was not performed at Visit 1.1 (pulse oximetry only). The MOAA/S was performed every 15 minutes from pre-dose to t = +1.5 hours post-dose. Pulse oximetry was performed every 15 minutes from pre-dose to t = 1.5 hours post-dose.

[h] The BPRS+ and CADSS were performed pre-dose and at 40 minutes and 1.5 hours post-dose.

[i] CGADR was performed at 1 hour and 1.5 hour post-dose; if the response is not "Yes" at 1.5 hour post-dose, the assessment was repeated every 15 minutes until a "Yes" response was achieved or until the subject was referred for appropriate medical care if clinically indicated. A subject was not to be discharged prior to the 1.5 hour time point.

[j] PWC-20 was performed only if the subject was not continuing into Study ESKETINTRD3003.

[k] Nasal symptom questionnaire was performed pre-dose and at 1 hour post-dose.

[l] PK blood collection was performed at t = 40 minutes and t = 2 hours post-dose (where time = 0 was defined as the time of the first intranasal spray).

[m] Blood samples were collected prior to dosing. It was preferred that subjects adhere to a low fat diet on the day of sample collection.

TABLE 11

Time and Events Schedule (FOLLOW-UP PHASE)

| | Follow-up Phase | | | | | | | | | | | | |
|---|---|---|---|---|---|---|---|---|---|---|---|---|---|
| Visit number | 3.1 | 3.2 | 3.3 | 3.4 | 3.5 | 3.6 | 3.7 | 3.8 | 3.9 | 3.10 | 3.11 | 3.12 | 3.13 |
| Weeks after last intranasal dose | 1 | 2 | 4 | 6 | 8 | 10 | 12 | 14 | 16 | 18 | 20 | 22 | 24 |
| Visit window for clinic visit or remote assessments only (days) | ±3 | ±3 | ±3 | ±3 | ±3 | ±3 | ±3 | ±3 | ±3 | ±3 | ±3 | ±3 | ±3 |
| Clinic visit (C) or remote assessments only (RA) | RA | C | RA | RA | RA | RA | C | RA | RA | RA | RA | RA | C |
| Oral antidepressant compliance [a] | | | | | | | | | | | | | |
| Oral antidepressant compliance check | | X | | | | | | | | | | | |
| Safety Assessments (Clinician-completed) | | | | | | | | | | | | | |
| Physical examination | | X | | | | | | | | | | | X |
| Nasal examination | | X | | | | | | | | | | | |
| Vital signs: Blood pressure, pulse, respiratory rate, temperature | | X | | | | | | | | | | | X |
| 12-lead ECG | | X | | | | | | | | | | | |
| C-SSRS: Since last visit version | | X | | | | | X | | | | | | X |
| PWC-20 | X [c] | X | | | | | | | | | | | |
| Safety Assessments (Subject-completed) | | | | | | | | | | | | | |
| BPIC-SS | | X | | | | | | | | | | | |
| Efficacy Assessments (Clinician-completed) | | | | | | | | | | | | | |
| MADRS (performed by independent, remote raters) | | | | | | | | | | | | | X |
| CGI-S | | X | | | | | X | | | | | | X |
| Efficacy Assessments (Subject-completed) | | | | | | | | | | | | | |
| PHQ-9 | | X | X | | X | | X | | X | | X | | X |
| SDS | | X | X | | X | | X | | X | | X | | X |
| GAD-7 | | X | X | | X | | X | | X | | X | | X |
| EQ-5D-5L | | X | X | | X | | X | | X | | X | | X |
| Cognition testing | | | | | | | | | | | | | |
| Computerized test battery and HVLT-R | | X | | | | | | | | | | | |
| Medical Resource Utilization | | | | | | | | | | | | | |
| HRUQ [b] | | X | X | X | X | X | X | X | X | X | X | X | X |
| Clinical Laboratory Assessments | | | | | | | | | | | | | |
| Hematology, chemistry | | X | | | | | | | | | | | |
| Urinalysis | | X | | | | | | | | | | | |
| Serum pregnancy test | | X | | | | | | | | | | | |
| Biomarker and Expression (RNA) Evaluations | | | | | | | | | | | | | |
| Blood sample collection (protein) [d] | | X | | | | | | | | | | | |
| Blood sample collection (RNA) [d] | | X | | | | | | | | | | | |

TABLE 11-continued

Time and Events Schedule (FOLLOW-UP PHASE)

| | Follow-up Phase |
|---|---|
| Visit number | 3.1  3.2  3.3  3.4  3.5  3.6  3.7  3.8  3.9  3.10  3.11  3.12  3.13 |

| Ongoing Subject Review | |
|---|---|
| Concomitant therapy | Ongoing |
| Adverse events | Ongoing |

No intranasal study medication was administered during the follow-up phase.
[a] In order to better assess potential withdrawal symptoms from intranasal study medication, it was recommended that the oral antidepressant medication be continued for at least the first 2 weeks of the follow-up phase unless determined to be not clinically appropriate.
[b] For the HRUQ, a clinician-completed assessment was required (based on subject-responses).
[c] Performed by telephone by qualified site staff.
[d] It was preferred that subjects adhere to a low fat diet the day of sample collection.

With the exception of post-dose assessments, visit-specific subject-reported outcomes assessments were conducted or completed before any tests, procedures, or other consultations for that clinic visit to prevent influencing subject perceptions. A recommended order of study procedures was provided. Actual dates and times of assessments were recorded in the source documentation and eCRF.

The approximate total blood volume to be collected from each subject was 123.5 mL (See Table 12, below). Repeat or unscheduled samples could be taken for safety reasons or for technical issues with the samples. Additional serum or urine pregnancy tests could be performed, as determined necessary by the investigator or required by local regulation, to establish the absence of pregnancy at any time during the subject's participation in the study.

TABLE 12

Volume of Blood to Be Collected From Each Subject

| Type of Sample | Volume per Sample (mL) | No. of Samples per Subject | Total Volume of Blood (mL)[a] |
|---|---|---|---|
| Screening/Prospective Observational Phase | | | |
| Serum chemistry [b] | 5 | 1 | 5 |
| TSH | 3.5 | 1 | 3.5 |
| Hematology [c] | 2 | 1 | 2 |
| Biomarker: protein [d] | 13 | 1 | 13 |
| Biomarker: DNA | 8.5 | 1 | 8.5 |
| Biomarker: RNA | 2.5 | 1 | 2.5 |
| Double-blind Induction Phase | | | |
| Serum chemistry | 2.5 | 2 | 5 |
| Hematology | 2 | 2 | 4 |
| Pharmacokinetics | 2 | 4 | 8 |
| Biomarker: protein (at Visits 2.1 and 2.9) [d] | 13 | 2 | 26 |
| Biomarker: protein (at Visit 2.4) | 10 | 1 | 10 |
| Biomarker: DNA | 8.5 | 1 | 8.5 |
| Biomarker: RNA | 2.5 | 3 | 7.5 |
| Follow-up Phase | | | |
| Serum chemistry | 2.5 | 1 | 2.5 |
| Hematology | 2 | 1 | 2 |
| Biomarker: protein [d] | 13 | 1 | 13 |
| Biomarker: RNA | 2.5 | 1 | 2.5 |
| Approximate volume of blood collected during the study: | | | 123.5 mL |

[a] Calculated as number of samples multiplied by amount of blood per sample.
[b] Serum chemistry includes serum β-hCG pregnancy tests (for women of childbearing potential) and lipid panel.
[c] As needed, HbA1c will be measured from the sample collected for hematology.
[d] Blood volume listed under protein biomarkers represents the combined volume of several different collection tubes.
An indwelling IV cannula may be used for blood sample collection.
Repeat or unscheduled samples may be taken for safety reasons or technical issues with the samples.

Screening/Prospective Observational Phase

Prior to conducting any study procedure, the investigator (or designated study personnel) reviewed and explained the written ICF to each subject. After signing the ICF, subjects who were 18 (or older if the minimum legal age of consent in the country in which the study is taking place is >18) to 64 years of age (inclusive) were screened to determine eligibility for study participation.

Subjects had to meet DSM-5 diagnostic criteria for single-episode MDD (if single-episode MDD, the duration must be ≥2 years) or recurrent MDD, without psychotic features, based upon clinical assessment and confirmed by the MINI. In addition, at the start of the screening/prospective observational phase, the subject must have had an IDS-$C_{30}$ total score ≥34.

At the start of this phase, subjects must been nonresponse to ≥2 but ≤5 oral antidepressant treatments in the current episode of depression, assessed using the MGH-ATRQ and confirmed by documented medical history and pharmacy/prescription records. The subject was taking an oral antidepressant treatment with nonresponse at entry and continued this treatment at the same dosage for the duration of this phase to confirm nonresponse prospectively. Antidepressant treatment adherence was assessed using the PAQ. Missing ≥4 days of antidepressant medication in the prior 2-week period was considered as inadequate adherence.

The subject's current major depressive episode and antidepressant treatment response to antidepressant therapies used during the current depressive episode were confirmed using the Site Independent Qualification Assessment.

An independent, blinded rater performed remote MADRS assessments to assess depressive symptoms during this phase. The investigator and study site were blinded to specific details regarding the response criteria for entry into the double-blind induction phase. Eligible non-responders (determined by remote blinded rater) discontinued their current antidepressant medication(s) and any other prohibited psychotropic medications, including adjunctive atypical antipsychotics. Benzodiazepines or nonbenzodiazepine sleep medications were allowed to continue but had specific restrictions regarding the administration time relative to the intranasal treatment sessions.

All other subjects who did not proceed to the double-blind induction phase ended study participation at this time. No further study visits or follow-up were required.

Optional Antidepressant Taper Period

Since all nonresponder subjects were starting a new oral antidepressant during the double-blind induction phase, no washout or drug-free period was required after discontinuing the current antidepressant treatment. However, an additional, optional period of up to 3 weeks was permitted to taper and discontinue the current oral antidepressant medication per the local prescribing information or clinical judgment.

The taper period did not start until after the completion of 4 weeks of prospective antidepressant treatment and assessment of the antidepressant treatment response.

Double-Blind Induction Phase

During this phase, subjects self-administered double-blind intranasal treatment with esketamine (56 mg or 84 mg) or placebo twice per week for 4 weeks as a flexible dose regimen. In addition, subjects simultaneously initiated a new, open-label oral antidepressant.

Study subjects (with TRD) were randomly assigned to 1 of the following 2 double-blind treatment groups at a 1:1 ratio (approximately 98 subjects per group): 1. Intranasal placebo or 2. Intranasal esketamine (56 mg or 84 mg). On the same day (i.e., Day 1), subjects were switched to a new, open-label oral antidepressant treatment. The oral antidepressant was 1 of 4 oral antidepressant medications (duloxetine, escitalopram, sertraline, or venlafaxine XR). The antidepressant medication was assigned by the investigator (based on review of the MGH-ATRQ and relevant prior antidepressant treatment information) and was one that the subject had not previously had a nonresponse to in the current depressive episode, had not been previously intolerant to (lifetime), and was available in the participating country. Dosing of the oral antidepressant began on Day 1 and followed the local prescribing information for the respective product, with a forced titration to the maximally tolerated dose. The titration schedule for the selected oral antidepressant was as presented in Table 5, above.

For information obtained via telephone contact, written documentation of the communication was made available for review in the source documents. During telephone contact visits with the subject by site personnel, adverse event and concomitant therapy information were obtained. In addition, specified clinician-administered assessments were performed by appropriately qualified staff.

At the end of the double-blind induction phase, subjects who were responders (defined as ≥50% reduction in the MADRS total score from baseline [Day 1 pre-randomization] to the end of the 4-week double-blind induction phase) were eligible to enter the subsequent maintenance clinical study (Study ESKETINTRD3003). To maintain study blinding, all responder subjects, including responders to the active comparator (i.e., oral antidepressant plus intranasal placebo), were eligible to enter Study ESKETINTRD3003. Participation in ESKETINTRD3003 began immediately after the completion of the double-blind induction phase. Subjects received oral antidepressant medication and were instructed to continue taking their oral antidepressant medication through their next study visit (i.e., first study visit of the stabilization phase in Study ESKETINTRD3003).

Those subjects who did not enter Study ESKETINTRD3003 proceeded into the follow-up phase.

Early Withdrawal

If a subject withdrew before the end of the double-blind induction phase for reasons other than withdrawal of consent, the Early Withdrawal visit was conducted within 1 week of the date of discontinuation, followed by the follow up phase. If the Early Withdrawal visit occurred on the same day as a scheduled visit, the early withdrawal visit was performed on the same day and duplicate assessments were not required.

Further clinical/standard of care for the treatment of depression were arranged by the study investigator and/or the subject's treating physician. The study investigator and/or treating physician determined whether or not the current oral antidepressant medication would continue.

If applicable, subjects who withdrew early received additional oral antidepressant medication and it was recommended that they continue taking the oral antidepressant medication for at least the first 2 weeks of the follow-up phase unless determined as not clinically appropriate.

Follow-up Phase

All subjects who received at least 1 dose of intranasal study medication in the double-blind induction phase and were not participating in the subsequent ESKETINTRD3003 study proceeded into the 24-week follow-up phase. Clinic visits and remote assessment visits were performed as specified in the Time and Events Schedule. During this phase, safety and tolerability, including potential withdrawal symptoms, following discontinuation of intranasal esketamine were assessed. In addition, data was collected to assess the course of the subject's current major depressive episode over a 6-month period.

Further clinical/standard of care for the treatment of depression were arranged by the study investigator and/or the subject's treating physician. No intranasal study medication was administered during this phase. In order to better assess potential withdrawal symptoms from the intranasal medication it was recommended that the oral antidepressant medication be continued for at least the first 2 weeks of the follow up phase unless determined as not clinically appropriate. The decision to continue the antidepressant was at the discretion of the investigator.

If information was obtained via telephone contact, written documentation of the communication was to be available for review in the source documents.

Any clinically significant abnormalities persisting at the end of the study were followed by the investigator until resolution or until a clinically stable endpoint was reached. All adverse events and special reporting situations, whether serious or non-serious, were reported until completion of the subject's last study-related procedure.

Efficacy Evaluations

It was recommended that the various subject-reported outcome assessments be completed prior to other procedures.

Primary Efficacy Evaluation

The primary efficacy evaluation was the MADRS total score. The MADRS was performed by independent remote raters during the study. The 10-item clinician-administered, clinician-rated scale MADRS was designed to be used in subjects with MDD to measure the overall severity of depressive symptoms, including depression severity and to detect changes due to antidepressant treatment. The MADRS scale was used as the primary efficacy measure for this study because it is validated, reliable, and acceptable to regulatory health authorities as a primary scale to determine efficacy in major depression.

The MADRS scale consists of 10 items, each of which is scored from 0 (item not present or normal) to 6 (severe or continuous presence of the symptoms), for a total possible score of 60. Higher scores represent a more severe condition. The MADRS evaluates apparent sadness, reported sadness, inner tension, sleep, appetite, concentration, lassitude, interest level, pessimistic thoughts, and suicidal thoughts. The test exhibits high inter-rater reliability.

The primary efficacy endpoint was a change in the MADRS total score from baseline (Day 1 prior to randomization) to the end of the 4-week double-blind induction phase.

In this study, subjects in any of the 2 treatment groups who responded to the study medication (i.e., responders) were defined as subjects who met the criterion for response defined as 250% reduction in the MADRS total score from baseline (Day 1 pre-randomization) to the end of the 4-week double-blind induction phase.

In addition to being the primary efficacy measure, the MADRS was also used to evaluate the key secondary efficacy endpoint of onset of clinical response (i.e., antidepressant effect) by Day 2 that was maintained for the duration of the double-blind induction phase. Onset of clinical response was defined as ≥50% improvement in MADRS total score by Day 2 (i.e., the day after taking the first dose of double-blind intranasal medication) that continued through the end of the double-blind phase.

MADRS was also used to evaluate a secondary objective assessing proportion of subjects with response and those in remission (defined as subjects with a MADRS total score ≤12) at the end of the 4-week double-blind induction phase.

Key Secondary Efficacy Evaluation (Clinician-Completed)

The MADRS was administered using a modified recall period of 24 hours for the key secondary efficacy evaluation related to onset of clinical response by Day 2 that was maintained for the duration of the double-blind induction phase.

The MADRS with a 24-hour recall period was used on Day 2. The feasibility of this shortened recall period has been confirmed with patients, and physicians, and there are data supporting the psychometric properties of this shortened recall period. The MADRS with a 7-day recall was used for all subsequent MADRS assessments used for the key secondary efficacy evaluation (maintenance of clinical response achieved on Day 2 for duration of double-blind induction phase).

Key Secondary Efficacy Evaluation (Patient-Reported Outcome)

The Patient Health Questionnaire (PHQ-9) is a 9-item, subject-reported outcome measure that was used to assess depressive symptoms. The scale scores each of the 9 symptom domains of the DSM-5 MDD criteria and has been used both as a screening tool and a measure of response to treatment for depression. Each item was rated on a 4-point scale (0=not at all, 1=several days, 2=more than half the days, and 3=nearly every day). The subject's item responses were summed to provide a total score (range of 0 to 27) with higher scores indicating greater severity of depressive symptoms. The recall period was 2 weeks.

The Sheehan Disability Scale (SDS) was used to assess the secondary objective of functional impact and associated disability. The SDS is a subject-reported outcome measure and is a 5-item questionnaire which has been widely used and accepted for assessment of functional impairment and associated disability. The first three items assess disruption of (1) work/school, (2) social life, and (3) family life/home responsibilities using a 0-10 rating scale. The score for the first three items were summed to create a total score of 0-30 where a higher score indicated greater impairment. The SDS also has one item on days lost from school or work and one item on days when underproductive. The recall period for this study was 7 days.

The Clinical Global Impression-Severity (CGI-S) provides an overall clinician-determined summary measure of the severity of the subject's illness that takes into account all available information, including knowledge of the subject's history, psychosocial circumstances, symptoms, behavior, and the impact of the symptoms on the subject's ability to function. The CGI-S evaluates the severity of psychopathology on a scale of 0 to 7. Considering total clinical experience, a subject was assessed on severity of mental illness at the time of rating according to: 0=not assessed; 1=normal (not at all ill); 2=borderline mentally ill; 3=mildly ill; 4=moderately ill; 5=markedly ill; 6=severely ill; 7=among the most extremely ill patients. The CGI-S permits a global evaluation of the subject's condition at a given time.

The 7-item subject-reported Generalized Anxiety Disorder 7-item Scale (GAD-7) was used to measure the secondary objective of symptoms of anxiety. The GAD-7 is a brief and validated measure of overall anxiety. Each item was rated on a 4-point scale (0=not at all; 1=several days; 2=more than half the days; and 3=nearly every day). Item responses were summed to yield a total score with range of 0 to 21, where higher scores indicated more anxiety. The recall period was 2 weeks.

The Euro-Qol-5 Dimention-5 Level (EQ-5D-5L) is a standardized instrument for use as a measure of health outcome, primarily designed for self-completion by respondents. It consists of the EQ-5D-5L descriptive system and the EQ visual analogue scale (EQ-VAS). The EQ-5D-5L descriptive system comprises the following 5 dimensions: Mobility, self-care, usual activities, pain/discomfort and anxiety/depression. Each of the 5 dimensions is divided into 5 levels of perceived problems (Level 1 indicating no problem, Level 2 indicating slight problems, Level 3 indicating moderate problems, Level 4 indicating severe problems, and Level 5 indicating extreme problems).

The subject selected an answer for each of the 5 dimensions considering the response that best matches his or her health "today." The descriptive system was used to represent a health state. The EQ-VAS self-rating recorded the respondent's own assessment of his or her overall health status at the time of completion, on a scale of 0 to 100.

Primary Endpoint

The primary efficacy endpoint was the change in the MADRS total score as measured by the change from baseline (Day 1 prior to randomization) to the end of the 4-week double-blind induction phase.

Primary Endpoint Results:

A serial gatekeeping (fixed sequence) approach was applied to adjust for multiplicity and to strongly control type I error across the primary and the 3 key secondary efficacy endpoints (onset of clinical response, change in SDS total score, and change in PHQ-9 total score). The 3 key secondary endpoints were analyzed sequentially and were considered statistically significant at the 1-sided 0.025 level only if the endpoint was individually significant at the 1-sided 0.025 level and previous endpoints in the hierarchy were significant at the 1-sided 0.025 level, including the primary endpoint. If the primary endpoint was statistically significant, the selected secondary endpoints were assessed in the following order: onset of clinical response, change in SDS total score, change in PHQ-9 total score.

Figure 2:
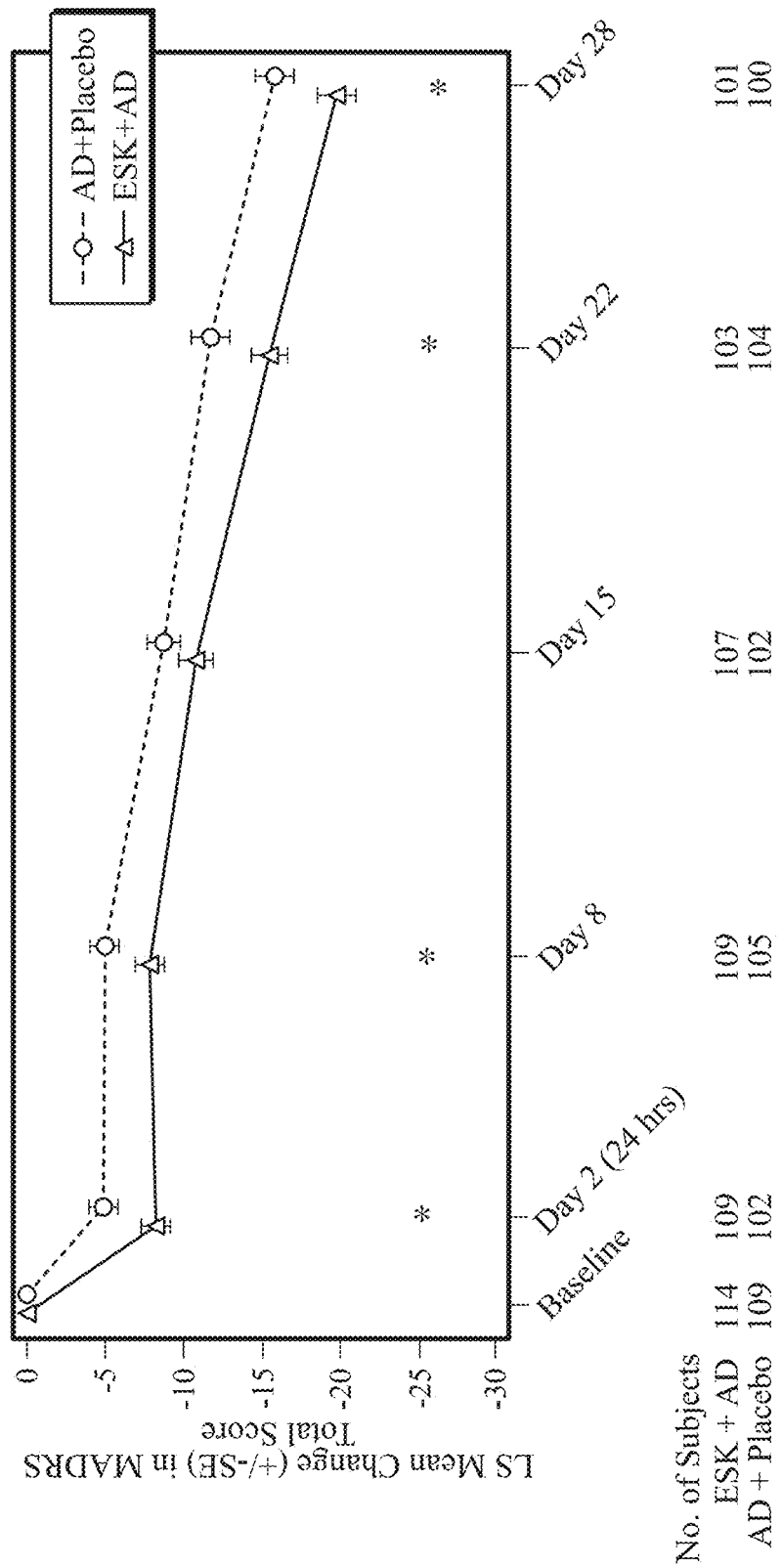
FIG. 2 illustrates the least squares mean changes (±SE) in MADRS total score over time observed case MMRM during the double-blind induction phase. LS mean and SE were based on MMRM with change from baseline as the response variable and the fixed effect model terms for treatment (intranasal esketamine+oral AD, oral AD+intranasal placebo), day, country, class or oral antidepressant (SNRI or SSRI), and treatment-by-day, and baseline value as a covariate. Negative change in score indicated improvement. *1-sided p<0.025.

The primary efficacy endpoint was the change in MADRS total score from baseline to Day 28. MADRS total scores range from 0 to 60. The primary efficacy analysis was performed on the full analysis set, which included all randomized subjects who received at least 1 dose of intranasal study medication and 1 dose of oral antidepressant study medication. As shown in Table 13 below, results for the change in MADRS total score favored intranasal esketamine+oral AD over oral AD+intranasal placebo. (FIG. 2 presents the least-square mean changes (±SE) from baseline for the MADRS total score over time in the double-blind phase based on the MMRM analysis.) The mean change from baseline (SD) at Day 28 was −21.4 (12.32) for esketamine+oral AD and −17.0 (13.88) for the active comparator. Based on an MMRM model with treatment, day, country, class of oral antidepressant and treatment by day as factors and baseline value as a covariate, the least-square mean difference (SE) between esketamine+oral AD and active comparator was −4.0 (1.69). The difference between treatment groups was statistically significant (one-sided p=0.010). The MMRM analysis was considered the primary analysis for all dossiers except the EU.

Results based on an ANCOVA model for the change in MADRS total score from baseline to End Point (DB) with factors for treatment, country and class of oral antidepressant and baseline value as a covariate were consistent with the MMRM analysis (least-square mean difference (SE) between esketamine+oral AD and active comparator was −3.5 (1.63), one-sided p=0.017.

TABLE 13

Montgomery-Asberg Depression Rating Scale (MADRS) Total Score: Change From Baseline to Day 28 MMRM; Double-blind Induction Phase (Study ESKETINTRD3002: Full Analysis Set)

|  | Intranasal Esk + Oral AD (N = 114) | Oral AD + Intranasal Placebo (N = 109) |
|---|---|---|
| Baseline |  |  |
| N | 114 | 109 |
| Mean (SD) | 37.0 (5.69) | 37.3 (5.66) |
| Median (Range) | 37.0 (22; 48) | 37.0 (21; 52) |
| Day 28 |  |  |
| N | 101 | 100 |
| Mean (SD) | 15.5 (10.67) | 20.6 (12.70) |
| Median (Range) | 12.0 (1; 49) | 19.0 (0; 49) |
| Change from baseline to day 28 |  |  |
| N | 101 | 100 |
| Mean (SD) | −21.4 (12.32) | −17.0 (13.88) |
| Median (Range) | −24.0 (−44; 13) | −18.5 (−43; 8) |
| MMRM analysis $^a$ |  |  |
| Diff. of LS means (SE) (Esk + AD minus AD + Placebo) | −4.0 (1.69) |  |
| 95% confidence interval on diff. | −7.31; −0.64 |  |
| 1-sided p-value | 0.010 |  |

$^a$ Test for treatment effect is based on mixed model for repeated measures (MMRM) with change from baseline as the response variable and the fixed effect model terms for treatment (intranasal esk + oral AD, oral AD + intranasal placebo), day, country, class of oral antidepressant (SNRI or SSRI), and treatment-by-day, and baseline value as a covariate. A negative difference favors esketamine.
MADRS Total score ranges from 0 to 60; a higher score indicates a more severe condition.
Negative change in score indicates improvement.

Secondary Endpoints

The first key secondary endpoint was the change from baseline (Day 1 prior to randomization) to the end of the 4-week double-blind induction phase in subject-reported depressive symptoms, using the PHQ-9 total score.

The second key secondary endpoint was the proportion of subjects showing onset of clinical response by Day 2 that was maintained through the end of the 4-week double-blind induction phase. Onset of clinical response was defined as 250% reduction in the MADRS total score by the day after taking the first dose of double-blind medication [Day 2] that continued through the end of the 4-week double-blind induction phase). Subjects who discontinued the study prior to the end of the double-blind induction phase were not considered to have maintained clinical response.

The third key secondary endpoint was the change in SDS total score as measured by the change from baseline (Day 1 prior to randomization) to the end of the 4-week double-blind induction phase.

Other secondary efficacy endpoints included: (a) Proportion of responders (≥50% reduction from baseline in MADRS total score) at the end of the 4-week double-blind induction phase, (b) Proportion of subjects in remission (MADRS≤12) at the end of the 4-week double-blind induction phase, and (c) Change from baseline (Day 1 prior to randomization) to the end of the 4-week double-blind induction phase in: Severity of depressive illness, using the CGI-S, Anxiety symptoms, as measured by the GAD-7, Health-related quality of life and health status, as assessed by the EQ-5D-5L.

Secondary Endpoint Results
Onset of Clinical Response

A subject was defined as having a clinical response if there was at least 50% improvement from baseline in the MADRS total score with onset by Day 2 that was maintained to Day 28 at each visit. Subjects were allowed one excursion (non-response) on Days 8, 15 or 22, however the score must have shown at least 25% improvement. Subjects who do not meet such criterion, or discontinue during the study before Day 28 for any reason were considered as non-responders and were assigned the value of no, meaning they did not meet the criteria for Onset of Clinical Response.

As shown in Table 14 below, 7.9% of subjects in the esketamine+oral AD group achieved clinical response compared to 4.6% of subjects in the active comparator group. The difference between treatment groups was not statistically significant at the 1-sided 0.025 level. Hence, based on the predefined testing sequence of key secondary endpoints, SDS total score and PHQ-9 total score could not be formally evaluated.

TABLE 14

Onset of Clinical Response Based on Montgomery-Asberg Depression Rating Scale (MADRS) Total Score CMH Analysis; Double-blind Induction Phase (Study ESKETINTRD3002: Full Analysis Set)

|  | Intranasal Esk + Oral AD (N = 114) | Oral AD + Intranasal Placebo (N = 109) |
|---|---|---|
| Onset of clinical response, n (%) $^a$ |  |  |
| N | 114 | 109 |
| Yes | 9 (7.9%) | 5 (4.6%) |
| No | 105 (92.1%) | 104 (95.4%) |

TABLE 14-continued

Onset of Clinical Response Based on Montgomery-Asberg Depression Rating Scale (MADRS) Total Score CMH Analysis; Double-blind Induction Phase (Study ESKETINTRD3002: Full Analysis Set)

|  | Intranasal Esk + Oral AD (N = 114) | Oral AD + Intranasal Placebo (N = 109) |
|---|---|---|
| Generalized Cochran-Mantel-Haenszel test [b] | | |
| 1-sided p-value (esk + AD vs. AD + placebo) [c] | 0.161 | |
| Odds ratio (95% CI) [d] | 1.79 (0.57, 5.67) | |

[a] Onset of clinical response was defined as at least 50% improvement from baseline in MADRS total score with onset by Day 2 that is maintained to Day 28. Subjects are allowed one excursion (non-response) on Days 8, 15 or 22, provided the score is at least 25% improvement. Subjects with missed assessments or discontinued early were not considered to have onset of clinical response.
[b] Generalized Cochran-Mantel-Haenszel (CMH) test for mean score difference between treatments adjusting for country and class of oral antidepressant (SNRI or SSRI).
[c] The analysis was considered statistically significant at the 1-sided 0.025 level only if the MADRS total score analysis is also significant.
[d] Odds of achieving onset of clinical response on intranasal esketamine + oral AD divided by the odds of achieving onset of clinical response on oral AD + intranasal placebo.

Response and Remission Rates Based on MADRS Total Score

Figure 3:
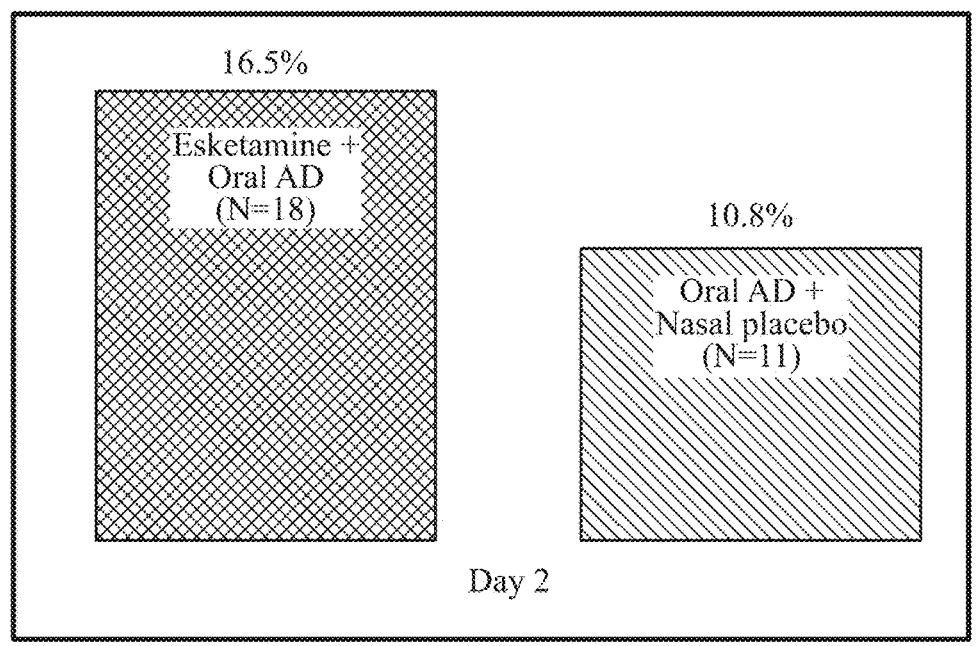
FIG. 3 is a bar graph of the response rates on day 2; a response is a ≤50% improvement on MADRS from baseline for patients taking esketamine and an oral antidepressant.
Figure 4:
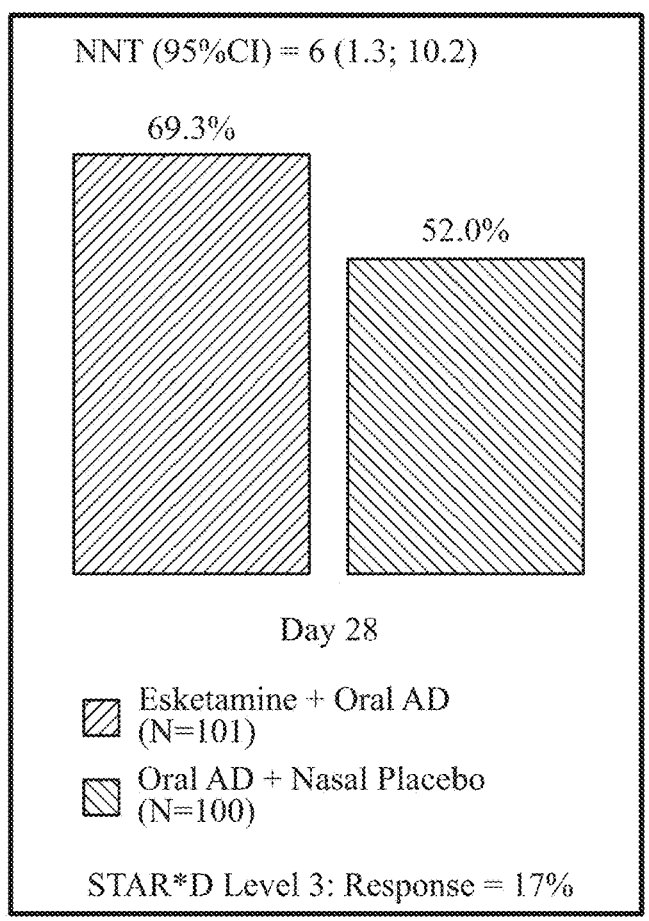
FIG. 4 is a bar graph of the response rates on day 28; a response is a ≤50% improvement on MADRS from baseline for patients taking esketamine and an oral antidepressant.
Figure 5:
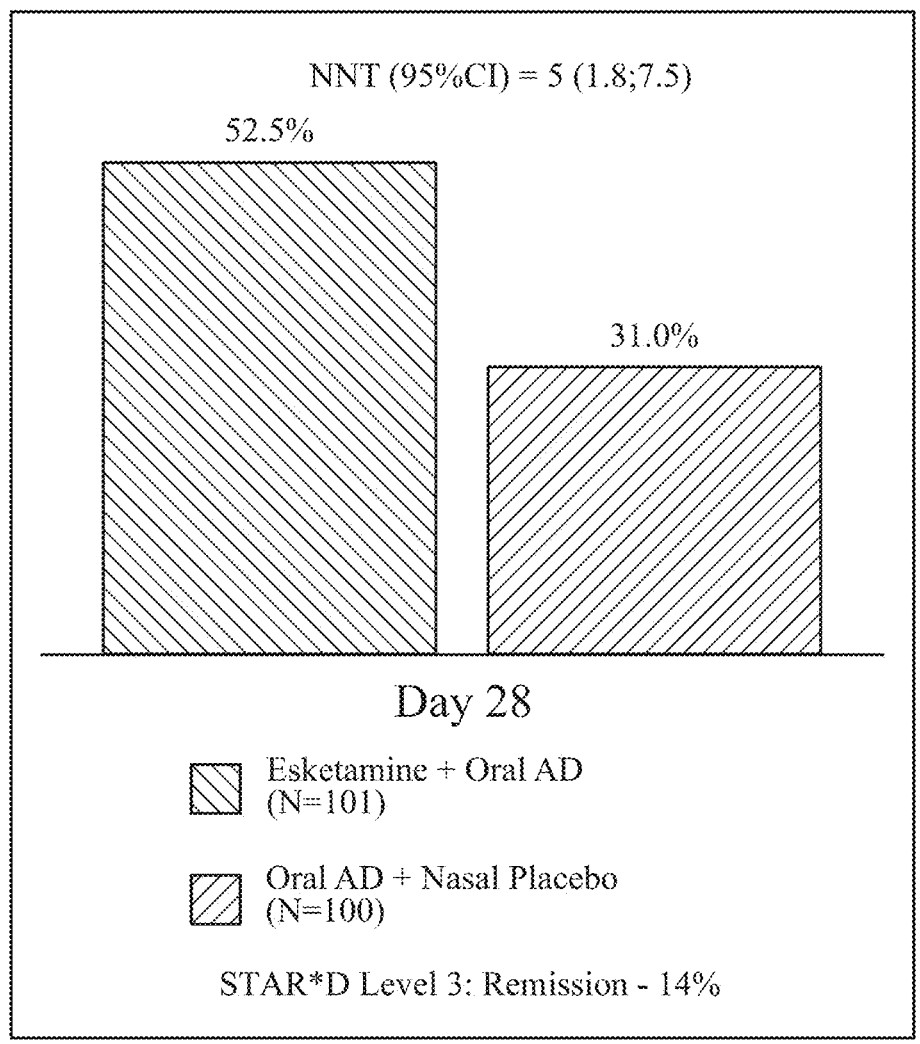
FIG. 5 is a bar graph of the remission rates on day 28; remission is a MADRS total score of ≤12.

Response (≥50% improvement from baseline in the MADRS total score) and Remission (MADRS total score is ≤12) rates were as presented in Table 15 and FIGS. 3-5.

TABLE 15

Response and Remission Rates Based on Montgomery-Asberg Depression Rating Scale (MADRS); Double-blind Induction Phase (Study ESKETINTRD3002: Full Analysis Set)

|  | Response | | Remission | |
|---|---|---|---|---|
|  | Intranasal Esk + Oral AD | Oral AD + Intranasal Placebo | Intranasal Esk + Oral AD | Oral AD + Intranasal Placebo |
| Day 2 (24 hrs.) | 18/109 (16.5%) | 11/102 (10.8%) | 10/109 (9.2%) | 6/102 (5.9%) |
| Day 8 | 15/109 (13.8%) | 13/105 (12.4%) | 8/109 (7.3%) | 7/105 (6.7%) |
| Day 15 | 29/107 (27.1%) | 23/102 (22.5%) | 13/107 (12.1%) | 13/102 (12.7%) |
| Day 22 | 54/103 (52.4%) | 35/104 (33.7%) | 32/103 (31.1%) | 20/104 (19.2%) |
| Day 28 | 70/101 (69.3%) | 52/100 (52.0%) | 53/101 (52.5%) | 31/100 (31.0%) |

A subject was defined as a responder at a given time point if the percent improvement from baseline in MADRS total score was at least 50%. A subject was in remission at a given time point if the MADRS total score was ≤12.

Sheehan Disability Scale (SDS)

The SDS is a subject-reported outcome measure and is a 5-item questionnaire which has been widely used and accepted for assessment of functional impairment and associated disability. The first three items assess disruption of (1) work/school, (2) social life, and (3) family life/home responsibilities using a 0-10 rating scale. The score for the first three items are summed to create a total score of 0-30 where a higher score indicates greater impairment.

As shown in Table 16 below, results for the change in SDS total score favored intranasal esketamine+oral AD over oral AD+intranasal placebo. The mean change from baseline (SD) at Day 28 was −13.3 (8.22) for esketamine+oral AD and −9.5 (8.38) for the active comparator. Based on an MMRM model with treatment, day, country, class of oral antidepressant and treatment by day as factors and baseline value as a covariate, the least-square mean difference (SE) between esketamine+oral AD and active comparator was −3.6(1.18). Based on the pre-defined testing sequence of key secondary endpoints, SDS total score could not be formally evaluated because there was not a statistically significant difference between treatment groups for onset of clinical response. The nominal one-sided p-value=0.001.

Results based on an ANCOVA model for the change in SDS total score from baseline to End Point (DB) with factors for treatment, country and class of oral antidepressant and baseline value as a covariate were consistent with the MMRM analysis.

TABLE 16

Sheehan Disability Scale (SDS) Total Score: Change From Baseline to Day 28 MMRM; Double-blind Induction Phase (Study ESKETINTRD3002: Full Analysis Set)

|  | Intranasal Esk + Oral AD (N = 114) | Oral AD + Intranasal Placebo (N = 109) |
|---|---|---|
| Baseline | | |
| N | 111 | 104 |
| Mean (SD) | 24.0 (4.07) | 24.2 (4.38) |
| Median (Range) | 25.0 (11; 30) | 25.0 (11; 30) |
| Day 28 | | |
| N | 84 | 85 |
| Mean (SD) | 10.3 (7.73) | 14.6 (9.06) |
| Median (Range) | 9.0 (0; 29) | 15.0 (0; 30) |
| Change from baseline to day 28 | | |
| N | 84 | 84 |
| Mean (SD) | −13.3 (8.22) | −9.5 (8.38) |
| Median (Range) | −14.0 (−30; 6) | −9.5 (−29; 6) |
| MMRM analysis [a] | | |
| Diff. of LS means (SE) (Esk + AD minus AD + Placebo) | −3.6 (1.18) | |

TABLE 16-continued

Sheehan Disability Scale (SDS) Total Score: Change
From Baseline to Day 28 MMRM; Double-blind Induction
Phase (Study ESKETINTRD3002: Full Analysis Set)

|  | Intranasal Esk + Oral AD (N = 114) | Oral AD + Intranasal Placebo (N = 109) |
|---|---|---|
| 95% confidence interval on diff. | −5.94; −1.27 | |
| 1-sided p-value [b] | 0.001 | |

[a] Test for treatment effect was based on mixed model for repeated measures (MMRM) with change from baseline as the response variable and the fixed effect model terms for treatment (intranasal esketamine + oral AD, oral AD + intranasal placebo), day, country, class of oral antidepressant (SNRI or SSRI), and treatment-by-day, and baseline value as a covariate. A negative difference favored esketamine.
[b] The analysis was considered statistically significant at the 1-sided 0.025 level only if the MADRS total score and the onset of clinical response analyses are also significant. Negative change in SDS score indicates improvement.

Patient Health Questionnaire—9 Item (PHQ-9)

The PHQ-9 is a 9-item, self-report scale assessing depressive symptoms. Each item is rated on a 4-point scale (0=Not at all, 1=Several Days, 2=More than half the days, and 3=Nearly every day), with a total score range of 0-27. A higher score indicates greater severity of depression.

As shown in Table 17 below, results for the change in PHQ-9 total score favored intranasal esketamine+oral AD over oral AD+ intranasal placebo. The mean change from baseline (SD) at Day 28 was −12.8 (6.43) for esketamine+oral AD and −10.2(7.84) for the active comparator. Based on an MMRM model with treatment, day, country, class of oral antidepressant and treatment by day as factors and baseline value as a covariate, the least-square mean difference (SE) between esketamine+oral AD and active comparator was −2.2(0.89). Based on the predefined testing sequence of key secondary endpoints, PHQ-9 total score cannot be formally evaluated because there was not a statistically significant difference between treatment groups for onset of clinical response. The nominal one-sided p-value=0.006.

Results based on an ANCOVA model for the change in PHQ-9 total score from baseline to End Point (DB) with factors for treatment, country and class of oral antidepressant and baseline value as a covariate were consistent with the MMRM analysis (see Attachment 3).

TABLE 17

Patient Health Questionnaire (PHQ-9) Total Score: Change
From Baseline to Day 28 MMRM Double-blind Induction
Phase (Study ESKETINTRD3002: Full Analysis Set)

|  | Intranasal Esk + Oral AD (N = 114) | Oral AD + Intranasal Placebo (N = 109) |
|---|---|---|
| Baseline | | |
| N | 114 | 109 |
| Mean (SD) | 20.2 (3.63) | 20.4 (3.74) |
| Median (Range) | 20.0 (5; 27) | 21.0 (10; 27) |
| Day 28 | | |
| N | 101 | 99 |
| Mean (SD) | 7.4 (5.76) | 10.1 (7.71) |
| Median (Range) | 6.0 (0; 27) | 8.0 (0; 26) |
| Change from baseline to day 28 | | |
| N | 101 | 99 |
| Mean (SD) | −12.8 (6.43) | −10.2 (7.84) |
| Median (Range) | −14.0 (−26; 3) | −9.0 (−25; 6) |
| MMRM analysis [a] | | |
| Diff. of LS means (SE) (Esk + AD minus AD + Placebo) | −2.2 (0.89) | |
| 95% confidence interval on diff. | −3.99; −0.48 | |
| 1-sided p-value [b] | 0.006 | |

[a] Test for treatment effect was based on mixed model repeated measures (MMRM) with change from baseline as the response variable and the fixed effect model terms for treatment (intranasal esketamine + oral AD, oral AD + intranasal placebo), day, country, class of oral antidepressant (SNRI or SSRI), and treatment-by-day, and baseline value as a covariate. A negative difference favored esketamine.
[b] The analysis was considered statistically significant at the 1-sided 0.025 level only if the MADRS total score, onset of clinical response, and SDS total score analyses are also significant.
Negative change in PHQ-9 score indicates improvement.

Safety Evaluations

Any clinically relevant changes occurring during the study were recorded on the Adverse Event section of the eCRF. Any clinically significant abnormalities persisting at the end of the study/early withdrawal were followed by the investigator until resolution or until a clinically stable endpoint was reached. The study included the following evaluations of safety and tolerability according to the time points provided in the Time and Events Schedule.

Adverse Events

Adverse events were reported by the subject (or, when appropriate, by a caregiver, surrogate, or the subject's legally acceptable representative) for the duration of the study. Adverse events were followed by the investigator. TEAEs of special interest were examined separately.

Clinical Laboratory Tests

Blood samples for serum chemistry and hematology and a urine sample for urinalysis were collected. The investigator reviewed the laboratory report, documented this review, and recorded any clinically relevant changes occurring during the study in the adverse event section of the eCRF. The laboratory reports were filed with the source documents. The use of local laboratories was allowed in cases where initiation of treatment or safety follow-up was time-critical and the central laboratory results were not expected to be available before the need to begin dosing or if actions need to be taken for safety reasons.

The following tests were performed by the central laboratory, unless noted otherwise:

| Hematology Panel | |
|---|---|
| hemoglobin | platelet count |
| hematocrit | |
| red blood cell (RBC) count | |
| white blood cell (WBC) count with differential | |

| Serum Chemistry Panel | |
|---|---|
| sodium | alkaline phosphatase |
| potassium | creatine phosphokinase (CPK) |
| chloride | calcium |
| bicarbonate | phosphate |
| blood urea nitrogen (BUN) | albumin |
| creatinine | total protein |
| glucose | |
| aspartate aminotransferase (AST) | |
| alanine aminotransferase (ALT) | |
| gamma-glutamyltransferase (GGT) | |

| Urinalysis | |
|---|---|
| Dipstick | Sediment (if dipstick result is abnormal) |
| specific gravity | red blood cells |
| pH | white blood cells |
| glucose | epithelial cells |
| protein | crystals |
| blood | casts |
| ketones | bacteria |
| bilirubin | |
| urobilinogen | |
| nitrite | |
| leukocyte esterase | |

If dipstick result was abnormal, flow cytometry or microscopy was used to measure sediment. In case of discordance between the dipstick results and the flow cytometric results, the sediment was examined microscopically.

The following tests were done at time points specified in the Time and Events Schedule:
1. Lipid panel: Total cholesterol, low density lipoprotein (LDL)-cholesterol, low density lipoprotein (HDL)-cholesterol, and triglycerides
2. Serum and urine pregnancy testing (for women of childbearing potential only)
3. Urine Drug Screen: Barbiturates, methadone, opiates, cocaine, cannabinoids (cannabinoids are only tested at Day 1 predose), phencyclidine, and amphetamine/methamphetamine
4. Alcohol breath test
5. Thyroid-stimulating hormone (TSH)
6. Glycated hemoglobin (HbA1c) test
7. A serum follicle stimulating hormone (FSH) level test, only if required for documentation that a female subject is not of childbearing potential (refer to Inclusion Criteria No. 0)

Single, 12-Lead ECG

During the collection of ECGs, subjects should be in a quiet setting without distractions (e.g., television, cell phones). Subjects should rest in a supine position for at least 5 minutes before ECG collection and should refrain from talking or moving arms or legs.

All ECG tracings were sent to a central ECG laboratory. The ECGs were read at the scheduled time points and summarized by a central ECG laboratory. The investigator or sub-investigator was required to review all ECGs at the study visit to assess for any potential safety concerns or evidence of exclusionary conditions.

Vital Signs (Temperature, Pulse/Heart Rate, Respiratory Rate, Blood Pressure)

Blood pressure and pulse/heart rate measurements were assessed supine with a completely automated device. Manual techniques were used only if an automated device is not available. Blood pressure and pulse/heart rate measurements were preceded by at least 5 minutes of rest in a quiet setting without distractions (e.g., television, cell phones).

Tympanic temperature was recommended. An automated device was used for measurement of respiratory rate.

Pulse Oximetry

Pulse oximetry was used to measure arterial oxygen saturation. On each dosing day, the device was attached to the finger, toe, or ear before the first nasal spray and then, after the first spray it was monitored and documented. Any arterial blood oxygen saturation ($SpO_2$)<93% and lasting for more than 2 minutes, and confirmed by an additional manual measurement on another part of the body, was reported as an adverse event.

On intranasal treatment session days, pulse oximetry was performed every 15 minutes from pre-dose to t=1.5 hours post-dose. If ≤93% at any time during the 1.5 hours post-dose interval, pulse oximetry was performed every 5 minutes until returned to ≥93% or until the subject was referred for appropriate medical care, if clinically indicated.

Physical Examination, Height, Body Weight, and Neck Circumference

Physical examinations, body weight, and height were performed or measured as per the Time and Events Schedule. In addition, body mass index (BMI) was calculated and neck circumference measured as part of the information required for the STOP-Bang questionnaire.

Nasal Examinations

Nasal examinations (including the upper respiratory tract/throat) were conducted by a qualified healthcare practitioner. The objective of the examination at screening was to rule out any subjects with anatomical or medical conditions that may impede drug delivery or absorption.

Subsequent examinations consisted of a visual inspection of the nostrils, nasal mucosa, and throat for nasal erythema, rhinorrhea, rhinitis, capillary/blood vessel disruption, and epistaxis, and were graded as absent, mild, moderate, or severe. Any treatment-emergent change or worsening from the baseline examination was recorded as an adverse event.

Nasal Symptom Questionnaire

Subjects completed a nasal symptom questionnaire. The nasal symptom questionnaire was developed to assess nasal tolerability following intranasal administration of study drug. The questionnaire asks about nasal symptoms, which were rated by the subject as none, mild, moderate, or severe, based on how he or she feels at the time of the assessment.

C-SSRS

The C-SSRS was performed to assess potential suicidal ideation and behavior. The C-SSRS is a low-burden measure of the spectrum of suicidal ideation and behavior that was developed in the National Institute of Mental Health Treatment of Adolescent Suicide Attempters Study to assess severity and track suicidal events through any treatment. It is a clinical interview providing a summary of both suicidal ideation and behavior that can be administered during any evaluation or risk assessment to identify the level and type of suicidality present. The C-SSRS can also be used during treatment to monitor for clinical worsening.

Two versions of the C-SSRS were used in this study, the Baseline/Screening version, and the Since Last Visit version. The Baseline/Screening version of the C-SSRS was used in the screening/prospective observational phase. In this version, suicidal ideation was assessed at 2 time points ("lifetime" and "in the past 6 months") and suicidal behavior was assessed at 2 time points ("lifetime" and "in the past year"). All subsequent C-SSRS assessments in this study used the Since Last Visit version, which assessed suicidal ideation and behavior since the subject's last visit.

CADSS

The CADSS is an instrument for the measurement of present-state dissociative symptoms, and was administered to assess treatment-emergent dissociative symptoms. The CADSS consists of 23 subjective items, divided into 3 components: Depersonalization (Items 3 to 7, 20, and 23), derealization (Items 1, 2, 8 to 13, 16 to 19, and 21) and amnesia (Items 14, 15, and 22). Participant's responses were coded on a 5-point scale (0=not at all through to 4=extremely). CADSS has excellent inter-rater reliability and internal consistency.

BPR+

Four items of the BPRS were administered to assess potential treatment-emergent psychotic symptoms. The BPRS is an 18-item rating scale that is used to assess a range of psychotic and affective symptoms, rated from both observation of the subject and the subject's own report. It reportedly provides a rapid and efficient evaluation of treatment response in clinic drug studies and in clinical settings. Only the 4-item positive symptom subscale BPRS+(i.e., suspiciousness, hallucinations, unusual thought content, and conceptual disorganization) were used in this study. It is highly sensitive to change, and excellent inter-rater reliability can be achieved with training and a standard interview procedure.

MQAA/S

The MOAA/S was used to measure treatment-emergent sedation, with correlation to levels of sedation defined by the American Society of Anesthesiologists (ASA) continuum. The MOAA/S scores range from 0=no response to painful stimulus (corresponds to ASA continuum for general anesthesia) to 5=readily responds to name spoken in normal tone (awake; corresponds to ASA continuum for minimal sedation).

On each intranasal dosing day, the MOAA/S was performed every 15 minutes from pre-dose to t=+1.5 hours post-dose. If the score was ≤3 at any time during the 1.5 hours post-dose interval, the MOAA/S was performed every 5 minutes until a score of 4 is reached (at which point a frequency of every 15 minutes can be resumed until t=+1.5 hours post dose). If a subject did not have a score of at least 5 at t=+1.5 hours post-dose, they were monitored further. For subjects with a score of 4, the assessment was repeated every 15 minutes. And for subjects with a score of ≤3, the assessment was repeated every 5 minutes until the score returns to 5 or the subject was referred for appropriate medical care, if clinically indicated.

CGADR

The CGADR was used to measure the subject's current clinical status and was the clinician's assessment of the readiness to be discharged from the study site. The clinician answered "Yes" or "No" to the question "Is the subject considered ready to be discharged based on their overall clinical status (e.g., sedation, blood pressure, and other adverse events)?"

On each intranasal dosing day, the CGADR was performed at 1 hour and 1.5 hours post-dose; if the response was not "Yes" at 1.5 hours post-dose, the assessment was repeated every 15 minutes until a "Yes" response was achieved or until the subject was referred for appropriate medical care, if clinically indicated. A subject was not discharged prior to the 1.5-hour time point. On all intranasal treatment session days, subjects remained at the clinical site until study procedures were completed and the subject was ready for discharge.

PWC-20

The PWC-20 was administered to assess potential withdrawal symptoms following cessation of intranasal esketamine treatment. An assessment was performed on Day 25 to establish a baseline prior to discontinuation of intranasal esketamine treatment. In order to better assess potential withdrawal symptoms from the intranasal medication it was recommended that the oral antidepressant medication be continued for at least the first 2 weeks of the follow up phase unless determined as not clinically appropriate.

The PWC-20 is a 20-item simple and accurate method to assess potential development of discontinuation symptoms after stopping of study drug. The PWC-20 is a reliable and sensitive instrument for the assessment of discontinuation symptoms. Discontinuation symptoms occur early and disappear rather swiftly, depending upon speed of taper, daily medication dose, and drug elimination half-life.

BPIC-SS

The BPIC-SS is a subject-reported outcome measure that was developed to identify an appropriate bladder pain syndrome/interstitial cystitis population for clinical studies evaluating new treatments for bladder pain syndrome.

The BPIC-SS was used to monitor subjects for potential symptoms of cystitis, bladder pain, and interstitial cystitis. The BPIC-SS includes 8 questions with a recall period of the past 7 days, and addresses key symptoms identified by subjects with BPS including symptom concepts of pain and/or pressure of the bladder and urinary frequency. Subjects responded to items using a 5-point scale (0=never, 1=rarely, 2=sometimes, 3=most of the time, 4=always for frequency-based questions, and 0=not at all, 1=a little, 2=somewhat, 3=moderately, and 4=a great deal for items related to bother associated with symptoms). Question 8 records the worst bladder pain in the last 7 days using a 0-10 numerical rating scale. A total score was calculated by adding up the numbers beside the response options chosen by the subject. The range of possible scores for the scale is 0 to 38. A total score of 19 or more demonstrated good sensitivity/specificity and was considered a relevant cut-off to distinguish those with significant bladder symptoms or cystitis.

If any items were missing, a total score could not be calculated.

In the current study, if a subject had a score >18 on the BPIC-SS scale and there was no evidence of urinary tract infection based on urinalysis and microscopy, he or she was referred to a specialist for further evaluation. As such, in addition to urinalysis, a urine culture was obtained if BPIC-SS score was >18 on applicable study day.

Cognition Testing: Computerized Cognitive Battery and HVLT-R

The computerized cognitive battery provides assessment of multiple cognitive domains, including attention, visual learning and memory, and executive function. The tests use culture-neutral stimuli, enabling use in multilingual/multi-cultural settings. The computerized battery includes:

Simple and choice reaction time tests; scored for speed of response (mean of the log 10-transformed reaction times for correct responses)

Visual episodic memory; visual recall test scored using arcsine transformation of the proportion of correct responses Working memory (n back); scored for speed of correct response (mean of the log 10-transformed reaction times for correct responses)

Executive function; maze/sequencing test, scored for total number of errors

All measures have been validated against traditional neuropsychological tests and are sensitive to the effects of various drugs on cognitive performance, including alcohol and benzodiazepines. Completing the cognitive battery requires approximately 25 minutes.

The HVLT-R, a measure of verbal learning and memory, is a 12-item word list recall test. Administration includes 3 learning trials, a 24-word recognition list (including 12 target and 12 foil words), and a delayed recall (20-minute) trial. Administration is computer-assisted; instructions and word lists appear on-screen. The test administrator records each word correctly recalled, and scores for learning, short-term, and delayed recall are generated via the test software. The HVLT-R is a well-validated and widely used measure of verbal episodic memory.

The tests were administered in the following order HVLT-R, computerized cognitive test battery, and HVLT-R Delayed.

UPSIT and Smell Threshold Test

To assess any potential treatment-emergent effects on the sense of smell, olfactory function was qualitatively and quantitatively assessed using validated standardized olfactory tests prior to and at specified time points during the study. The 2 tests administered were:

The UPSIT assesses a subject's ability to identify odors. This standardized test, the most widely used olfactory test in the world, is derived from basic psychological test measurement theory and focuses on the comparative ability of subjects to identify odorants at the suprathreshold level. The UPSIT consists of 4 envelope-sized booklets, each containing 10 "scratch and sniff" odorants embedded in 10- to 50-μm polymer microcapsules positioned on brown strips at the bottom of the pages of the booklets. The internal consistency and test-retest reliability coefficients of this instrument are >0.90. Numerous studies have shown this and related tests to be sensitive to subtle changes in smell function associated with multiple etiologies, including those due to viruses, head trauma, and a number of neurodegenerative diseases.

The Smell Threshold Test assesses the smell threshold using a forced-choice single staircase threshold procedure. This test quantifies a detection threshold for the rose-like smelling odorant phenyl ethyl alcohol (PEA). This odorant is used because it has little propensity to stimulate the trigeminal nerve within the nose. This test is sensitive to olfactory deficits from a wide range of disorders.

These tests were administered bilaterally (i.e., both nostrils at the same time). Testing occurred during the screening/prospective observational phase to establish a subject's baseline sensitivity. The degree of change from this baseline was determined subsequently over time. The percent change from baseline served as the dependent measure for each subject for each test.

MINI

Subjects underwent MINI (a brief, structured diagnostic interview) to confirm the diagnosis of MDD and to determine if there are other psychiatric conditions present. It has an administration time of approximately 15 minutes.

MGH-ATRQ

The MGH-ATRQ was used to determine treatment resistance in MDD. The MGH-ATRQ evaluates the adequacy of duration and dosage of all antidepressant medications used for the current major depressive episode. In addition, the MGH-ATRQ assesses the degree of improvement on a scale from 0% (not improved at all) to 100% (completely improved). The MGH-ATRQ was completed by the clinician in collaboration with the subject.

STOP-Bang Questionnaire

The STOP-Bang Questionnaire is a concise, easy-to-use, validated, and sensitive screening tool for obstructive sleep apnea (OSA). This questionnaire has 8 items which address key risk factors for obstructive sleep apnea: snoring, tiredness, observed breathing interruption during sleep, high blood pressure, body mass index, age, neck size, and gender. The STOP-Bang questions do not specify a recall period. Subjects answer yes or no to questions about snoring, tiredness, observed breathing interruption, and high blood pressure (these are the "STOP" items in the STOP-BANG acronym); this takes approximately 1 minute.

Study site staff answered yes or no to questions about body mass index (more than 35 kg/m$^2$?), age (older than 50 years?), neck circumference (larger than 17 inches [43 cm] in men, or larger than 16 inches [41 cm] in women?), and gender (male?).

The total STOP-BANG score was calculated by summing the number of positive responses, yielding a score range of 0 to 8. A score of ≥5 on the STOP-Bang indicates a moderate to severe risk for Obstructive Sleep Apnea (apnea hypopnea index of >30).

Site Independent Qualification Assessment

Independent psychiatrists/psychologists performed the Site Independent Qualification Assessment by telephone in the screening/prospective observational phase for all subjects to confirm diagnosis of depression and eligibility for the study.

IDS-C$_{30}$

The 30-item IDS-C$_{30}$ is designed to assess the severity of depressive symptoms. The IDS assesses all the criterion symptom domains designated by the DSM-5 to diagnose a major depressive episode. These assessments can be used to screen for depression, although they have been used predominantly as measures of symptom severity. The 7-day period prior to assessment is the usual time frame for assessing symptom severity. The psychometric properties of the IDS-Cao have been established in various study samples.

Massachusetts General Hospital Female Reproductive Lifecycle and Hormones Questionnaire (MGH-Female RLHQ): Module I and Menstrual Cycle Tracking The MGH-Female RLHQ Module I (childbearing potential, menopausal status, and menstrual cycle) is a brief questionnaire aimed at standardizing the minimal collection of relevant information about reproductive hormones and status. It was completed by a clinician. This information may facilitate exploratory analyses of the impact of endogenous and exogenous reproductive hormones on the course of treatment of MDD and potentially inform care of women with MDD in the future.

Menstrual cycle tracking (start date of last menstrual period) was documented at the study visits specified in the Time and Events Schedule.

PAQ

Subjects' adherence to their oral antidepressant treatment regimen during the screening/prospective observational phase was assessed using the PAQ. It is a brief, 2-item subject-report outcome measure that was developed at the University of Texas Southwestern Medical Center to assess how often the subject has taken, and whether he or she has made any changes to his/her antidepressant treatment regimen in the last 2 weeks. The total score was calculated by adding response choices for questions 1c through 1f, with 0=adherent and 1 or more=nonadherent.

Sample Collection and Handling

The actual dates and times of sample collection were recorded in the eCRF or laboratory requisition form. If blood samples were collected via an indwelling cannula, an appropriate amount (1 mL) of serosanguineous fluid slightly greater than the dead space volume of the lock was removed from the cannula and discarded before each blood sample is taken. After blood sample collection, the cannula was flushed with 0.9% sodium chloride, United States Pharmacopeia (USP) (or equivalent) and charged with a volume equal to the dead space volume of the lock.

Subject Completion/Withdrawal

Completion

A subject was considered to have completed the double-blind induction phase of the study if he or she completed the MADRS assessment at the end of the 4-week double-blind induction phase (i.e., Day 28 MADRS). Subjects who prematurely discontinued study treatment for any reason before completion of the double-blind induction phase were not considered to have completed the double-blind induction phase of the study. Subjects who entered the follow-up phase were considered to have completed this phase of the study if he or she had completed the MADRS assessment at Week 24 of the follow-up phase.

Withdrawal from the Study

A subject was withdrawn from the study for any of the following reasons:
1. Lost to follow-up
2. Withdrawal of consent
3. Violation of protocol procedures (determined on a case-by-case basis)
4. Blind was broken (double-blind induction phase)
5. Lack of efficacy
6. The investigator or sponsor believed (e.g., that for safety or tolerability reasons such as an adverse event) it was in the best interest of the subject to discontinue the study.
7. Subject became pregnant
8. Study was terminated by sponsor for futility
9. Death If a subject was lost to follow-up, every reasonable effort was made by the study site personnel to contact the subject and determine the reason for discontinuation/withdrawal.

When a subject withdrew before completing the study, the reason for withdrawal was documented. Study drug assigned to the withdrawn subject was not assigned to another subject. If a subject withdrew from the study before the end of the double-blind induction phase for reasons other than withdrawal of consent, an early withdrawal visit was conducted within 1 week of the date of discontinuation, followed by the follow-up phase.

Safety Analyses

Safety data was analyzed for the double-blind induction phase using the safety analysis set.

Adverse Events

The verbatim terms used in the eCRF by investigators to identify adverse events were coded using the MedDRA. All reported adverse events with onset during the double-blind induction phase (i.e., TEAEs, and adverse events that have worsened since baseline) were included in the analysis. For each adverse event, the percentage of subjects who experience at least 1 occurrence of the given event was summarized by treatment group. Adverse events occurring during the follow-up phase were summarized separately.

TEAEs of special interest were examined separately. AEs of special interest were listed in the SAP. Subjects who died, who discontinued treatment due to an adverse event, or who experienced a severe or a serious adverse event were summarized separately.

Clinical Laboratory Tests

Laboratory data were summarized by type of laboratory test. Reference ranges and markedly abnormal results (specified in the Statistical Analysis Plan) were used in the summary of laboratory data. Descriptive statistics were calculated for each laboratory analyte at baseline and at each scheduled time point in each phase of the study. Changes from baseline results were presented. Frequency tabulations of the abnormalities were provided. Listings of subjects with laboratory results outside the reference ranges and markedly abnormal results were provided.

ECG

The effects on cardiovascular variables were evaluated by means of descriptive statistics and frequency tabulations. These tables include observed values and change from baseline values.

Electrocardiogram data was summarized by ECG parameter. Descriptive statistics were calculated at baseline and for observed values and changes from baseline at each scheduled time point. Frequency tabulations of the abnormalities were made.

The ECG variables that were analyzed were heart rate, PR interval, QRS interval, QT interval, and QTc interval using the following correction methods: QT corrected according to Bazett's formula (QTcB) and QTcF.

Descriptive statistics of QTc intervals and changes from double-blind baseline were summarized at each scheduled time point. The percentage of subjects with QTc interval >450 msec, >480 msec, or >500 msec were summarized, as will the percentage of subjects with QTc interval increases from baseline <30 msec, 30-60 msec, or >60 msec.

All important abnormalities in ECG waveform that were changes from the baseline readings were reported (e.g., changes in T-wave morphology or the occurrence of U-waves).

Vital Signs

Descriptive statistics of temperature, pulse/heart rate, respiratory rate, pulse oximetry, and blood pressure (systolic and diastolic) (supine) values and changes from baseline were summarized at each scheduled time point. The percentage of subjects with values beyond clinically important limits were summarized.

Nasal Examination

Changes in findings from the baseline nasal examination (including the upper respiratory tract/throat) were listed by treatment group. Examinations provided ratings (absent, mild, moderate, or severe) that were based on a visual inspection of the nostrils, nasal mucosa, and throat for nasal erythema, rhinorrhea, rhinitis, capillary/blood vessel disruption and epistaxis. A shift table for changes from double-blind baseline in ratings for each examination was presented by treatment group.

Nasal Symptom Questionnaire

Scoring from the nasal symptom questionnaire was summarized descriptively for each scheduled time point by treatment group.

C-SSRS

Suicide-related thoughts and behaviors based on the C-SSRS were summarized by treatment group in incidence and shift tables. Separate endpoints for suicidal ideation and suicidal behavior were defined and summarized descriptively by treatment group. Missing scores were not imputed.

CADSS, BPRS+, and MOAA/S

Descriptive statistics of each score and changes from pre-dose were summarized at each scheduled time point.

Clinical Global Assessment of Discharge Readiness, PWC-20, BPIC-SS, UPSIT, and Smell Threshold Test Descriptive statistics of each score and changes and/or percent changes from baseline were summarized at each scheduled time point.

Cognition Testing

Descriptive statistics of the cognitive domain scores and changes from baseline were summarized at each scheduled time point.

Adverse Event Definitions and Classifications

An adverse event is any untoward medical occurrence in a clinical study subject administered a medicinal (investigational or non-investigational) product. An adverse event does not necessarily have a causal relationship with the treatment. An adverse event can therefore be any unfavorable and unintended sign (including an abnormal finding), symptom, or disease temporally associated with the use of a medicinal (investigational or non-investigational) product, whether or not related to that medicinal (investigational or non-investigational) product (definition per International Conference on Harmonisation [ICH]). This includes any occurrence that is new in onset or aggravated in severity or frequency from the baseline condition, or abnormal results of diagnostic procedures, including laboratory test abnormalities.

A serious adverse event based on ICH and EU Guidelines on Pharmacovigilance for Medicinal Products for Human Use is any untoward medical occurrence that at any dose:
  Results in death
  Is life-threatening (for example, the subject was at risk of death at the time of the event. "Life threatening" does not refer to an event that hypothetically might have caused death if it were more severe.)
  Requires inpatient hospitalization or prolongation of existing hospitalization
  Results in persistent or significant disability/incapacity
  Is a congenital anomaly/birth defect
  Is a suspected transmission of any infectious agent via a medicinal product
  Is medically important*
  *Medical and scientific judgment should be exercised in deciding whether expedited reporting is also appropriate in other situations, such as important medical events that may not be immediately life threatening or result in death or hospitalization but may jeopardize the subject or may require intervention to prevent one of the other outcomes listed in the definition above. These should usually be considered serious.

If a serious and unexpected adverse event occurred for which there is evidence suggesting a causal relationship between the study drug and the event (e.g., death from anaphylaxis), the event was reported as a serious and unexpected suspected adverse reaction even if it was a component of the study endpoint (e.g., all-cause mortality).

An adverse event was considered unlisted if the nature or severity was not consistent with the applicable product reference safety information. For esketamine, the expectedness of an adverse event was determined by whether or not it was listed in the Reference Safety Information Section of the Investigator's Brochure.

For duloxetine, escitalopram, sertraline, and venlafaxine XR, the expectedness of an adverse event was determined by whether or not it is listed in the SmPC or US prescribing information.

An adverse event was considered associated with the use of the drug if the attribution was possible, probable, or very likely by the attribution definitions listed below.

Not Related: An adverse event that was not related to the use of the drug.

Doubtful: An adverse event for which an alterative explanation was more likely, e.g., concomitant drug(s), concomitant disease(s), or the relationship in time suggests that a causal relationship is unlikely.

Possible: An adverse event that might be due to the use of the drug. An alternative explanation, e.g., concomitant drug(s), concomitant disease(s), was inconclusive. The relationship in time was reasonable; therefore, the causal relationship could not be excluded.

Probable: An adverse event that might be due to the use of the drug. The relationship in time was suggestive (e.g., confirmed by dechallenge). An alternative explanation was less likely, e.g., concomitant drug(s), concomitant disease(s).

Very Likely: An adverse event that was listed as a possible adverse reaction and could not be reasonably explained by an alternative explanation, e.g., concomitant drug(s), concomitant disease(s). The relationship in time was very suggestive (e.g., it is confirmed by dechallenge and rechallenge).

An assessment of severity grade was made using the following general categorical descriptors:
  Mild: Awareness of symptoms that were easily tolerated, causing minimal discomfort and not interfering with everyday activities.
  Moderate: Sufficient discomfort was present to cause interference with normal activity.
  Severe: Extreme distress, causing significant impairment of functioning or incapacitation. Prevented normal everyday activities.

The investigator used clinical judgment in assessing the severity of events not directly experienced by the subject (e.g., laboratory abnormalities).

Special Reporting Situations

Safety events of interest on a sponsor study drug that may require expedited reporting and/or safety evaluation included, but were not limited to:
  Overdose of a sponsor study drug
  Suspected abuse/misuse of a sponsor study drug
  Inadvertent or accidental exposure to a sponsor study drug
  Medication error involving a sponsor product (with or without subject/patient exposure to the sponsor study drug, e.g., name confusion)

Special reporting situations were recorded in the eCRF. Any special reporting situation that met the criteria of a serious adverse event was recorded on the serious adverse event page of the eCRF.

Procedures: All Adverse Events

All adverse events and special reporting situations, whether serious or non-serious, were reported from the time a signed and dated ICF was obtained until completion of the subject's last study-related procedure (which may include contact for follow-up of safety). Serious adverse events, including those spontaneously reported to the investigator within 30 days after the last dose of study drug, were reported using the Serious Adverse Event Form. The sponsor evaluated any safety information that was spontaneously reported by an investigator beyond the time frame specified in the protocol.

All events that met the definition of a serious adverse event were reported as serious adverse events, regardless of whether they were protocol-specific assessments. Anticipated events were recorded and reported.

All adverse events, regardless of seriousness, severity, or presumed relationship to study drug, were recorded using medical terminology in the source document and the eCRF. Whenever possible, diagnoses were given when signs and symptoms were due to a common etiology (e.g., cough, runny nose, sneezing, sore throat, and head congestion should be reported as "upper respiratory infection"). Investigators recorded in the eCRF their opinion concerning the relationship of the adverse event to study therapy. All measures required for adverse event management were recorded in the source document and reported.

The sponsor assumed responsibility for appropriate reporting of adverse events to the regulatory authorities.

For all studies with an outpatient phase, including open-label studies, the subject was provided with a "Wallet (study) card" and instructed to carry this card with them for the duration of the study indicating the following:
  Study number
  Statement, in the local language(s), that the subject is participating in a clinical study
  Investigators name and 24-hour contact telephone number
  Local sponsor's name and 24-hour contact telephone number (for medical staff only)
  Site number
  Subject number
  Any other information that is required to do an emergency breaking of the blind Serious Adverse Events All serious adverse events occurring during the study were reported to the appropriate sponsor contact person by study-site personnel within 24 hours of their knowledge of the event.

All serious adverse events that were not resolved by the end of the study, or that were not resolved upon discontinuation of the subject's participation in the study, were followed until any of the following occurs:

The event resolved

The event stabilized

The event returned to baseline, if a baseline value/status is available

The event could be attributed to agents other than the study drug or to factors unrelated to study conduct It became unlikely that any additional information could be obtained (subject or health care practitioner refusal to provide additional information, lost to follow-up after demonstration of due diligence with follow-up efforts)

Suspected transmission of an infectious agent by a medicinal product was reported as a serious adverse event. Any event requiring hospitalization (or prolongation of hospitalization) that occurred during the course of a subject's participation in a study was reported as a serious adverse event, except hospitalizations for the following:

Hospitalizations not intended to treat an acute illness or adverse event (e.g., social reasons such as pending placement in long-term care facility)

Surgery or procedure planned before entry into the study (must be documented in the eCRF). Hospitalizations that were planned before the signing of the ICF, and where the underlying condition for which the hospitalization was planned had not worsened, were not considered serious adverse events. Any adverse event that resulted in a prolongation of the originally planned hospitalization was to be reported as a new serious adverse event.

For convenience the investigator was able to choose to hospitalize the subject for the duration of the treatment period.

The cause of death of a subject in a study, whether or not the event was expected or associated with the study drug, was considered a serious adverse event.

Pregnancy

All initial reports of pregnancy were to be reported to the sponsor by the study-site personnel within 24 hours of their knowledge of the event using the appropriate pregnancy notification form. Abnormal pregnancy outcomes (e.g., spontaneous abortion, stillbirth, and congenital anomaly) were considered serious adverse events and were to be reported using the Serious Adverse Event Form. Any subject who became pregnant during the study was to promptly withdraw from the study and discontinue further study treatment.

Because the effect of the study drug on sperm is unknown, pregnancies in partners of male subjects included in the study was to be reported by the study-site personnel within 24 hours of their knowledge of the event using the appropriate pregnancy notification form.

Follow-up information regarding the outcome of the pregnancy and any postnatal sequelae in the infant was required.

Summary of all Adverse Events

An overall summary of all treatment-emergent adverse events (TEAEs) during the double-blind phase is presented in Table 18. Overall, 84.3% of subjects in the esketamine+ oral AD group and 60.6% of subjects in the active comparator group experienced at least one TEAE during the double-blind phase.

TABLE 18

Overall Summary of Treatment-emergent Adverse Events; Double-blind Induction Phase (Study ESKETINTRD3002: Safety Analysis Set)

|  | Intranasal Esk + Oral AD (N = 115) | Oral AD + Intranasal Placebo (N = 109) |
|---|---|---|
| TEAE | 97 (84.3%) | 66 (60.6%) |
| TEAE possibly related to intranasal drug [a] | 90 (78.3%) | 39 (35.8%) |
| TEAE possibly related to oral antidepressant [a] | 37 (32.2%) | 26 (23.9%) |
| TEAE leading to death | 0 | 0 |
| 1 or more serious TEAE | 1 (0.9%) | 1 (0.9%) |
| TEAE leading to intranasal drug withdrawn [b] | 8 (7.0%) | 1 (0.9%) |
| TEAE leading to oral antidepressant withdrawn [b] | 4 (3.5%) | 0 |

[a] Study drug relationships of possible, probable, and very likely are included in this category.
[b] An adverse event that started in the double-blind induction phase and resulted in discontinuation in the follow-up phase was counted as treatment-emergent in the double-blind induction phase.
Incidence was based on the number of subjects experiencing at least one adverse event, not the number of events.

Figure 6:
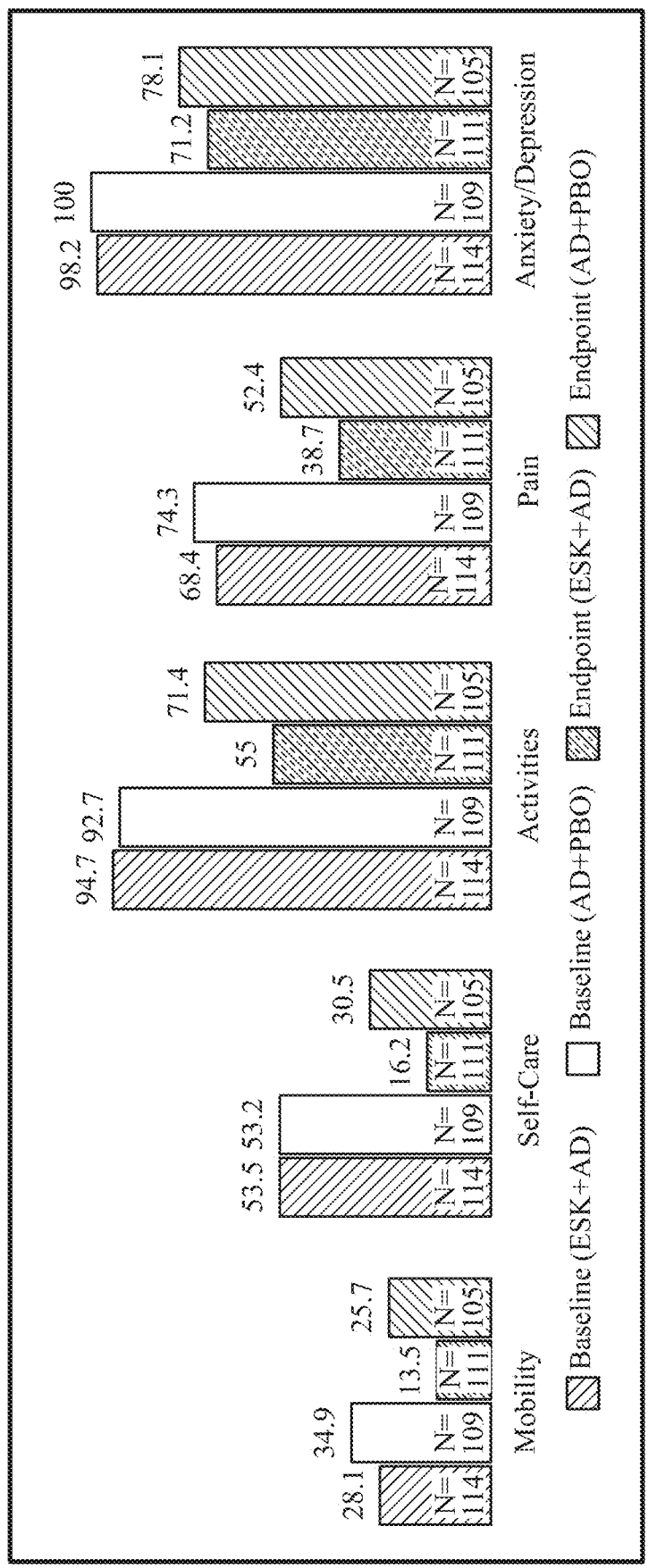
FIG. 6 is a bar graph showing the percent of subjects reporting problems (levels 2 through 5) with mobility, self-care, activities, pain, and anxiety/depression.

FIG. 6 shows the percentage of subjects reporting problems at baseline and endpoint as determined by EQ-5D-% L individual dimensions.

Treatment-emergent adverse events occurring during the double-blind phase (≥5% of subjects in either treatment group) are summarized by treatment group for the safety analysis set in Table 19, below. The most common (≥20%) TEAEs in the esketamine+oral AD group during the double-blind phase were nausea (26.1%), vertigo (26.1%), dysgeusia (24.3%), and dizziness (20.9%). The most common TEAE in the active comparator group was headache (17.4%).

TABLE 19

Treatment-emergent Adverse Events in at Least 5% of Subjects in Either Treatment Group; Double-blind Induction Phase (Study ESKETINTRD3002: Safety Analysis Set)

|  | Intranasal Esk + Oral AD (N = 115) | Oral AD + Intranasal Placebo (N = 109) |
|---|---|---|
| Total no. subjects with TEAE | 97 (84.3%) | 66 (60.6%) |
| Nervous system disorders | 72 (62.6%) | 38 (34.9%) |
| Dysgeusia | 28 (24.3%) | 13 (11.9%) |
| Dizziness | 24 (20.9%) | 5 (4.6%) |
| Headache | 21 (18.3%) | 19 (17.4%) |
| Somnolence | 15 (13.0%) | 7 (6.4%) |
| Paresthesia | 13 (11.3%) | 1 (0.9%) |
| Dizziness postural | 8 (7.0%) | 1 (0.9%) |
| Hypoesthesia | 8 (7.0%) | 1 (0.9%) |
| Gastrointestinal disorders | 52 (45.2%) | 26 (23.9%) |
| Nausea | 30 (26.1%) | 7 (6.4%) |
| Vomiting | 11 (9.6%) | 2 (1.8%) |
| Diarrhea | 10 (8.7%) | 10 (9.2%) |
| Dry mouth | 9 (7.8%) | 3 (2.8%) |
| Hypoesthesia oral | 9 (7.8%) | 1 (0.9%) |
| Paresthesia oral | 9 (7.8%) | 1 (0.9%) |
| Psychiatric disorders | 52 (45.2%) | 20 (18.3%) |
| Dissociation | 14 (12.2%) | 2 (1.8%) |
| Anxiety | 12 (10.4%) | 5 (4.6%) |
| Insomnia | 11 (9.6%) | 6 (5.5%) |

TABLE 19-continued

Treatment-emergent Adverse Events in at Least 5% of Subjects
in Either Treatment Group; Double-blind Induction Phase
(Study ESKETINTRD3002: Safety Analysis Set)

|  | Intranasal Esk + Oral AD (N = 115) | Oral AD + Intranasal Placebo (N = 109) |
|---|---|---|
| Derealisation | 9 (7.8%) | 2 (1.8%) |
| Delusional perception | 6 (5.2%) | 0 |
| Illusion | 6 (5.2%) | 1 (0.9%) |
| Ear and labyrinth disorders | 34 (29.6%) | 6 (5.5%) |
| Vertigo | 30 (26.1%) | 3 (2.8%) |
| General disorders and administration site conditions | 34 (29.6%) | 14 (12.8%) |
| Feeling abnormal | 10 (8.7%) | 1 (0.9%) |
| Feeling drunk | 8 (7.0%) | 1 (0.9%) |
| Fatigue | 5 (4.3%) | 6 (5.5%) |
| Respiratory, thoracic and mediastinal disorders | 25 (21.7%) | 15 (13.8%) |
| Throat irritation | 9 (7.8%) | 5 (4.6%) |
| Nasal discomfort | 8 (7.0%) | 2 (1.8%) |
| Eye disorders | 18 (15.7%) | 3 (2.8%) |
| Vision blurred | 14 (12.2%) | 3 (2.8%) |
| Investigations | 14 (12.2%) | 4 (3.7%) |
| Blood pressure increased | 11 (9.6%) | 0 |

Incidence was based on the number of subjects experiencing at least one adverse event, not the number of events.

Adverse Events Leading to Study Drug Withdrawal

There were 9 subjects (8 subjects in the esketamine+oral AD group and 1 subject in the active comparator group) who discontinued the double-blind induction phase intranasal study medication due to treatment-emergent adverse events (Table 20). There were 4 subjects in the esketamine+oral AD group who discontinued the double-blind induction phase oral antidepressant study medication due to treatment-emergent adverse events (Table 21). Three subjects in the esketamine+oral AD group discontinued the double-blind phase due to both intranasal and oral AD medications. (Summarized in both Table 20 and 21).

TABLE 20

Treatment-emergent Adverse Events Leading to Discontinuation
of Intranasal Study Medication; Double-blind Induction
Phase (Study ESKETINTRD3002: Safety Analysis Set)

|  | Intranasal Esk + Oral AD (N = 115) | Oral AD + Intranasal Placebo (N = 109) |
|---|---|---|
| Total no. subjects with TEAE leading to discontinuation [a] | 8 (7.0%) | 1 (0.9%) |
| Psychiatric disorders | 4 (3.5%) | 0 |
| Anxiety | 1 (0.9%) | 0 |
| Depression | 1 (0.9%) | 0 |
| Depressive symptom | 1 (0.9%) | 0 |
| Panic attack | 1 (0.9%) | 0 |
| General disorders and administration site conditions | 2 (1.7%) | 0 |
| Drug intolerance | 1 (0.9%) | 0 |
| Feeling drunk | 1 (0.9%) | 0 |
| Nervous system disorders | 2 (1.7%) | 0 |
| Dizziness | 1 (0.9%) | 0 |
| Headache | 1 (0.9%) | 0 |
| Ear and labyrinth disorders | 1 (0.9%) | 0 |
| Vertigo | 1 (0.9%) | 0 |
| Gastrointestinal disorders | 1 (0.9%) | 0 |
| Nausea | 1 (0.9%) | 0 |
| Injury, poisoning and procedural complications | 1 (0.9%) | 0 |
| Multiple injuries | 1 (0.9%) | 0 |

TABLE 20-continued

Treatment-emergent Adverse Events Leading to Discontinuation
of Intranasal Study Medication; Double-blind Induction
Phase (Study ESKETINTRD3002: Safety Analysis Set)

|  | Intranasal Esk + Oral AD (N = 115) | Oral AD + Intranasal Placebo (N = 109) |
|---|---|---|
| Skin and subcutaneous tissue disorders | 0 | 1 (0.9%) |
| Rash generalized | 0 | 1 (0.9%) |

[a] An adverse event that started in the double-blind induction phase and resulted in discontinuation in the follow-up phase was counted as treatment-emergent in the double-blind induction phase. Incidence was based on the number of subjects experiencing at least one adverse event, not the number of events.

TABLE 21

Treatment-emergent Adverse Events Leading to Discontinuation
of Oral Antidepressant; Double-blind Induction Phase
(Study ESKETINTRD3002: Safety Analysis Set)

|  | Intranasal Esk + Oral AD (N = 115) | Oral AD + Intranasal Placebo (N = 109) |
|---|---|---|
| Total no. subjects with TEAE leading to discontinuation [a] | 4 (3.5%) | 0 |
| Psychiatric disorders | 2 (1.7%) | 0 |
| Depressive symptom | 2 (1.7%) | 0 |
| General disorders and administration site conditions | 1 (0.9%) | 0 |
| Drug intolerance | 1 (0.9%) | 0 |
| Injury, poisoning and procedural complications | 1 (0.9%) | 0 |
| Multiple injuries | 1 (0.9%) | 0 |

[a] An adverse event that started in the double-blind induction phase and resulted in discontinuation in the follow-up phase was counted as treatment-emergent in the double-blind induction phase. Incidence was based on the number of subjects experiencing at least one adverse event, not the number of events.

Serious Adverse Events

Two subjects experienced a serious treatment-emergent adverse event during the double-blind phase. One subject in the active comparator group experienced positional vertigo which was consider of doubtful relationship to both intranasal placebo and oral AD. One subject in the esketamine+oral AD group experienced multiple injuries due to a motorbike accident (and subsequently died after formal database lock). This event was considered not related to esketamine and of doubtful relationship to the oral AD.

One subject in the esketamine+oral AD group experienced a cerebral hemorrhage during the follow up phase 83 days after the last intranasal administration of esketamine. This was considered of doubtful relationship to esketamine and not related to the oral AD.

Blood Pressure

Figure 7:
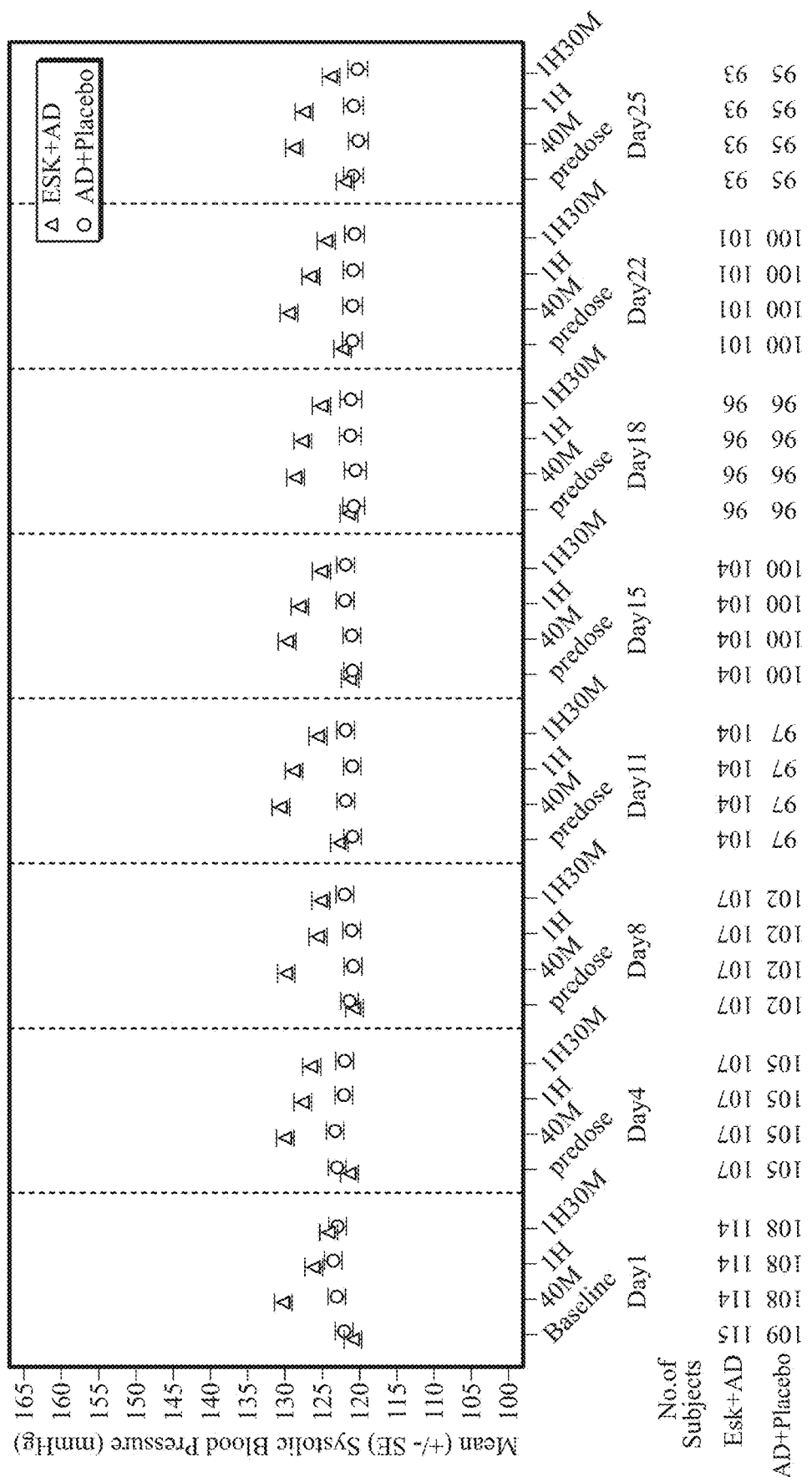
FIG. 7 illustrates the arithmetic mean (±SE) for systolic blood pressure over time during the double-blind induction phase using the safety analysis set.
Figure 8:
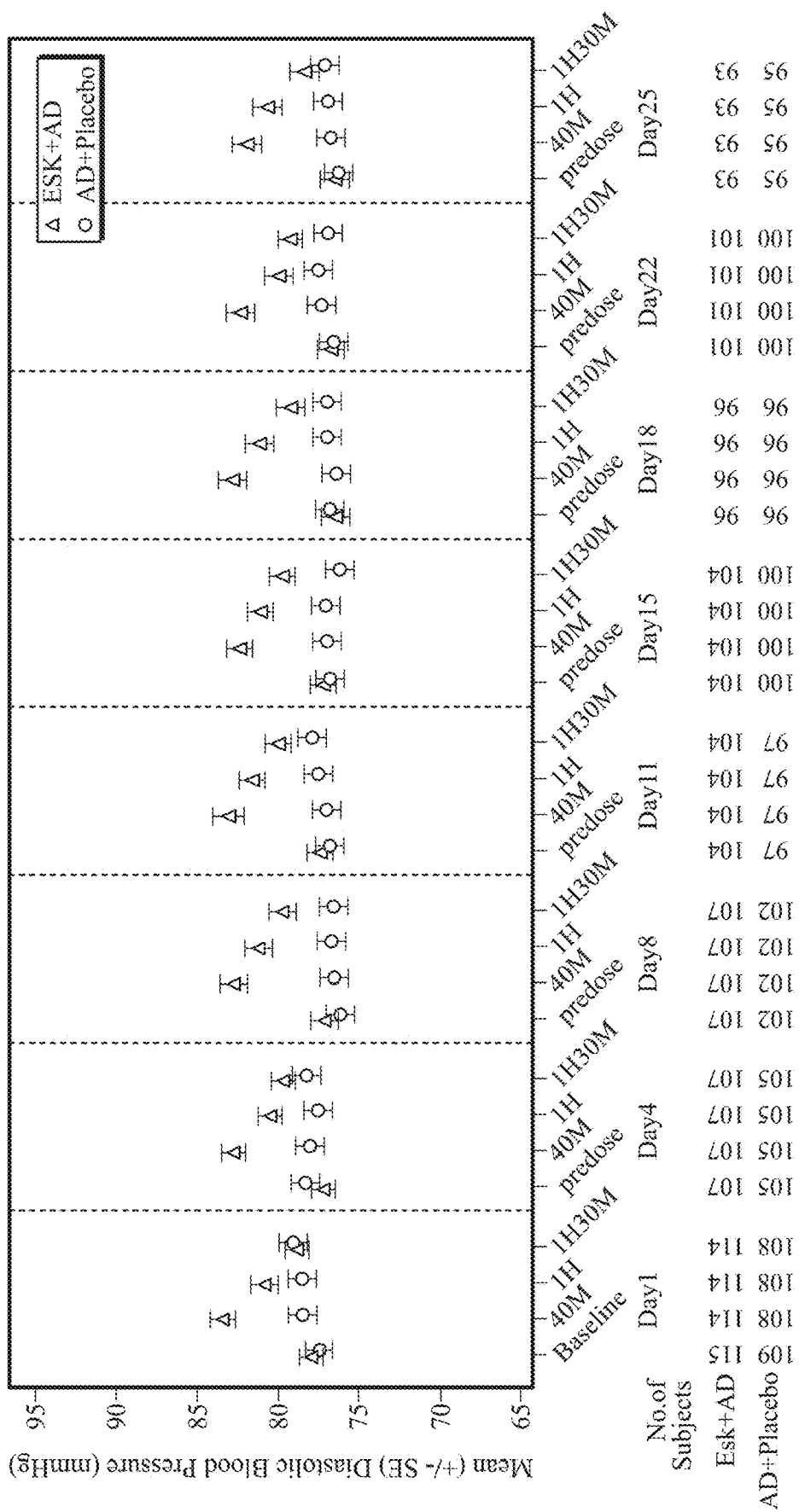
FIG. 8 illustrates the arithmetic mean (±SE) for diastolic blood pressure over time; double-blind induction phase using the safety analysis set.

Transient blood pressure increases peaked for the esketamine group at approximately 40 minutes post dose and returned to normal range at 90 minutes. The maximum mean increases (across all dosing days) in systolic BP was 11.6 in the esketamine+oral AD group and 5.0 in the active comparator group. The maximum mean increase (across all dosing days) in diastolic BP were 8.1 in the esketamine group and 4.5 in the active comparator group. FIGS. 7 and 8 present the means for measured blood pressure over time by treatment group in the double-blind phase.

Clinician-Assessed Dissociative Symptom Scale (CADSS)

Figure 9:
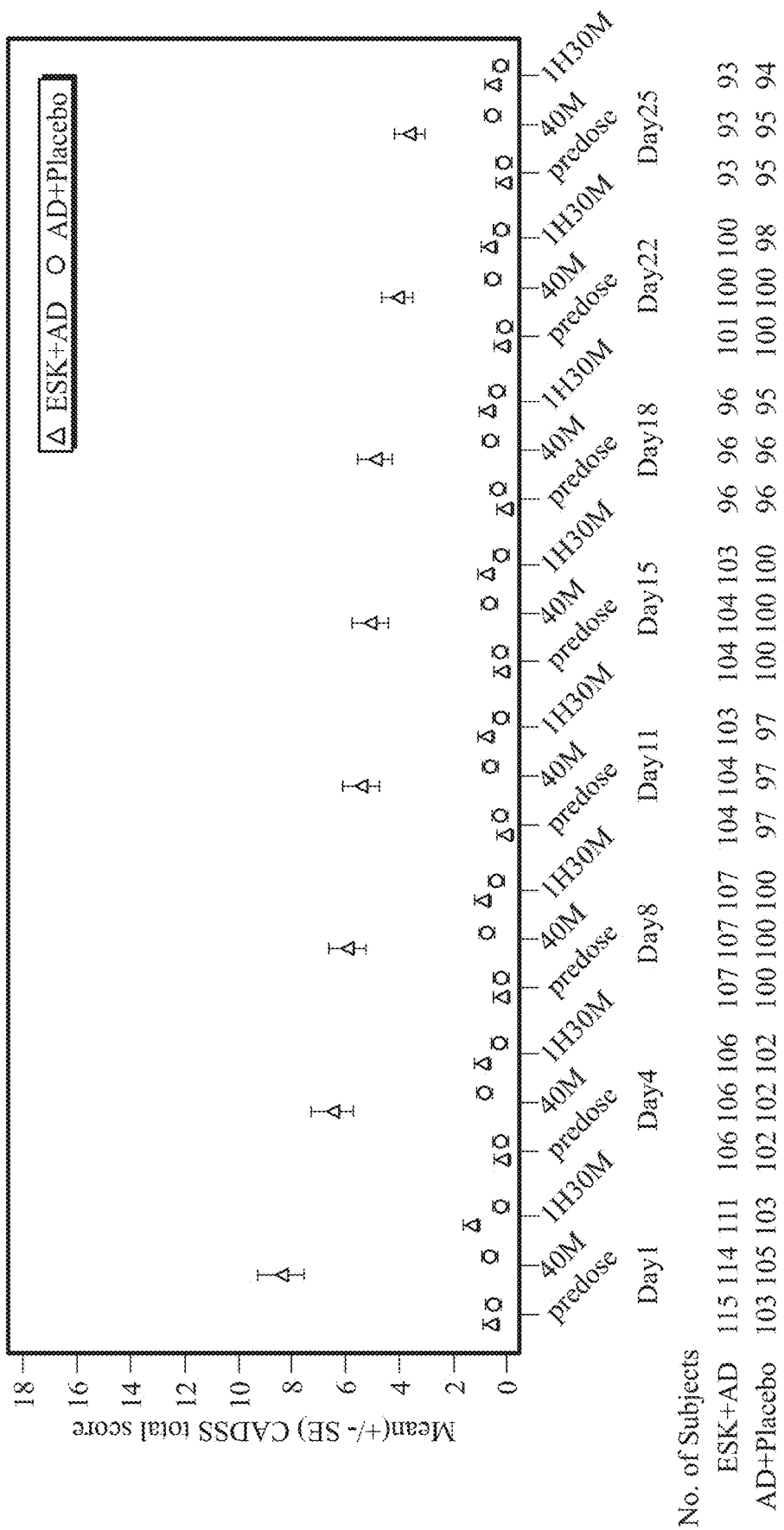
FIG. 9 illustrates the clinician-assessed dissociative symptom scale (CADSS), total score over time during the double-blind phase using the safety analysis set.

The Clinician Administered Dissociative States Scale (CADSS) was measured prior to the start of each dose, at 40 minutes, and 1.5 hours postdose. The CADSS was used to assess treatment emergent dissociative symptoms and perceptual changes and the total score ranged from 0 to 92 with a higher score representing a more severe condition. The dissociative and perceptual change symptoms measured by the CADSS, suggest these symptoms had an onset shortly after the start of the dose and resolved by 1.5 hours postdose (as shown in FIG. 9).

Modified Observer's Assessment of Alertness/Sedation (MOAA/S)

Figure 10:
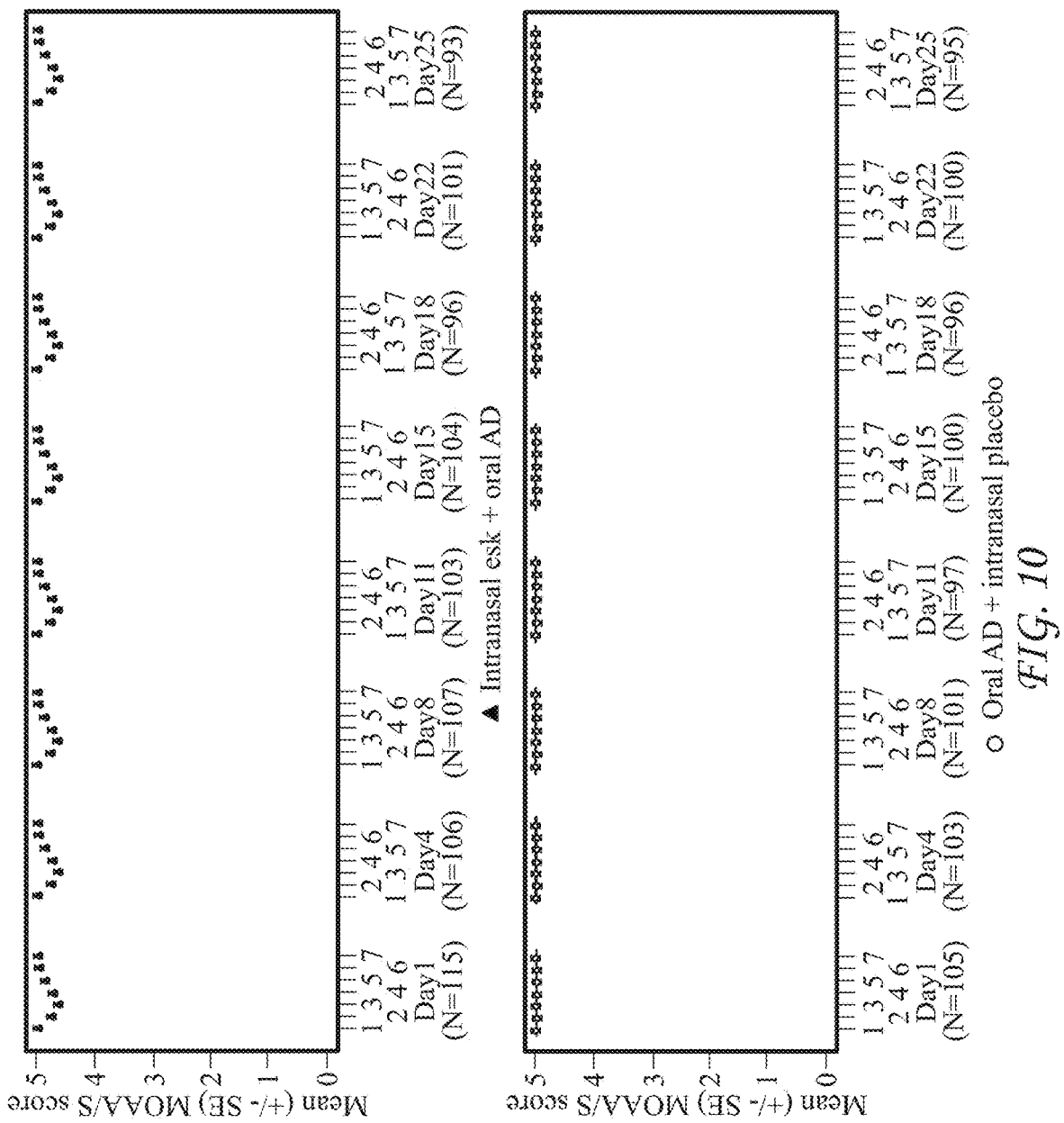
FIG. 10 illustrates the arithmetic mean (±SE) modified observer's assessment of alertness/sedation (MOAA/S) score over time; double-blind induction phase using the safety analysis set.

The Modified Observer's Assessment of Alertness/Sedation (MOAA/S) was used to measure treatment-emergent sedation with correlation to levels of sedation defined by the American Society of Anesthesiologists (ASA) continuum. The MOAA/S scores ranged from 0 (No response to painful stimulus; corresponds to ASA continuum for general anesthesia) to 5 (Readily responds to name spoken in normal tone [awake]; corresponding to ASA continuum for minimal sedation). Sedation as measured by the MOAA/S, suggests that sedation resolved by 1.5 hours postdose (as shown in FIG. 10).

Pharmacokinetics

Venous blood samples of approximately 2 mL were collected for measurement of plasma concentrations of esketamine, noresketamine, and other metabolites (if warranted) at the time points specified in the Time and Events Schedule. The exact dates and times of PK blood sampling were recorded.

Plasma samples were analyzed to determine concentrations of esketamine (and noresketamine, if warranted) using a validated, specific, achiral, and sensitive liquid chromatography-tandem mass spectrometry (LC-MS/MS) method by or under the supervision of the sponsor. If required, some plasma samples were analyzed to document the presence of other analytes (e.g., circulating metabolites or denatonium) using a qualified research method. In addition, plasma PK samples could be stored for future analysis of the metabolite profile.

Pharmacokinetic Parameters

The plasma concentration-time data of esketamine (and noresketamine, if warranted) was analyzed using population PK modeling. Typical population values of basic PK parameters (e.g., esketamine clearance distribution volume) were estimated together with the inter-individual variability. Effects of subject demographics, laboratory parameter values, and other covariates on the PK of esketamine were explored.

Pharmacokinetic/Pharmacodynamic Evaluations

The relationship between MADRS total score (and possibly selected adverse events as additional PD parameters) and PK metrics of esketamine were evaluated. If there was any visual trend in graphical analysis, suitable models were applied to describe the exposure-effect relationships.

Biomarker, Pharmacogenomic (DNA), and Expression (RNA) Evaluations

During the study, blood was collected for the assessment of biomarkers at the time points indicated in the Time and Events schedule. The biomarker blood samples were collected prior to dosing. It was preferred that subjects adhere to a low fat diet on the day of sample collection.

In blood, biomarkers (protein, metabolite, and ribonucleic acid [RNA]) related to (but not limited to) the immune system activity, hypothalamus pituitary adrenal (HPA) axis activation, neurotrophic factors, and metabolic factors were investigated. Biomarkers were added or deleted based on scientific information or technical innovations under the condition that the total volume of blood collected was not increased.

Blood samples for DNA analyses were collected at the time points indicated in the Time and Events Schedule for the assessment of genetic and epigenetic variation in genes in pathways relevant to depression (e.g., HPA axis, inflammation, growth factors, monoamine transporters, ion channels, and circadian rhythm). Genotyping was conducted only on the screening sample; pharmacogenomic and epigenetic evaluations could be performed on any/all collected samples.

DNA samples were used for research related to esketamine, oral antidepressants, TRD, or MDD. They could also be used to develop tests/assays related to esketamine, oral antidepressants, TRD, or MDD. Pharmacogenomic research consisted of the analysis of 1 or more candidate genes or of the analysis of genetic markers throughout the genome (as appropriate) in relation to esketamine, oral antidepressants, TRD, or MDD clinical endpoints.

Medical Resource Utilization

Medical resource utilization data, associated with medical encounters, were collected during the follow-up phase of the study. Protocol-mandated procedures, tests, and encounters were excluded. The data collected could be used to conduct exploratory economic analyses and include: (a) Number and duration of medical care encounters, including surgeries, and other selected procedures (inpatient and outpatient), (b) Duration of hospitalization (total days length of stay, including duration by wards; e.g., intensive care unit), (c) Number and character of diagnostic and therapeutic tests and procedures, and/or (d) Outpatient medical encounters and treatments (including physician or emergency room visits, tests and procedures, and medications).

Pharmacokinetic Analyses

Plasma esketamine (and noresketamine, if warranted) concentrations were listed for all subjects. The plasma concentration-time data of esketamine (and noresketamine, if warranted) was analyzed using population PK modeling. Data may have been combined with those of other selected studies to support a relevant structural model. Typical population values of basic PK parameters were estimated together with the inter-individual variability. Effects of subject demographics, laboratory parameter values, and other covariates on the PK of esketamine were explored.

Pharmacokinetic/Pharmacodynamic Analyses

The relationship between MADRS total score (and possibly selected adverse events as additional PD parameters) and PK metrics of esketamine were evaluated. If there was any visual trend in graphical analysis, suitable models were applied to describe the exposure-effect relationships.

Biomarker and Pharmacogenomic Analyses

Baseline biomarker values and changes from baseline biomarker values to the time points specified in the Time and Events Schedule were summarized. Exploratory analyses may have included comparison of biomarker measures between the treatment groups and correlation with baseline and change from baseline biomarker values in the efficacy and other measures. Additional exploratory analyses may have also included relationship of baseline and change from baseline in biomarker measures to clinical response, maintenance/stabilization of response, relapse, and non-response.

Pharmacogenomic analyses may also have included candidate gene analyses or genome-wide association analyses in relation to treatment response, maintenance/stabilization of response, relapse, non-response, and MDD/TRD. Expression analyses may include testing of known messenger RNA/microRNA (mRNA/miRNA) transcripts or transcriptome-wide analysis in relationship to antidepressant treatment response and MDD/TRD.

Statistical Methods Used in Analysis

A general description of the statistical methods used to analyze the efficacy and safety data is outlined below. At the end of the double-blind induction phase the database was locked for the analysis and reporting of this phase. The subject treatment assignment was revealed only to sponsor's study staff. The investigators and the site personnel were blinded to the treatment assignment until all subjects had completed study participation through the follow-up phase.

The primary efficacy and safety analysis sets were as follows:

Full Analysis Set: All randomized subjects who received at least 1 dose of intranasal study medication and 1 dose of oral antidepressant in the double-blind induction phase.

Safety Analysis Set: All randomized subjects who received at least 1 dose of intranasal study medication or 1 dose of oral antidepressant in the double-blind induction phase.

The maximum sample size planned for this study was calculated assuming a treatment difference for the double-blind induction phase of 6.5 points in MADRS total score between esketamine and the active comparator, a standard deviation of 12, a 1-sided significance level of 0.0125, and a drop-out rate of 25%. A maximum of about 98 subjects would need to be randomized to each treatment group to achieve 90% power using a fixed design with no interim analysis. The treatment difference and standard deviation used in this calculation were based on results of Panel A of the ESKETINTRD2003 study and on clinical judgment.

Interim Analysis for Sample Size Re-Estimation or Stopping for Futility

One unblinded interim analysis was performed 4 weeks after randomizing 66 subjects in the study (approximately 33 subjects per treatment arm). It was projected that at that time approximately 50 subjects in the full analysis set would have completed the double-blind induction phase of the study (approximately 25 subjects per treatment group). The drop-out rate was monitored to ensure a sufficient number of subjects were included in the interim analysis. The purpose of the interim analysis was to either re-estimate sample size or to stop the study due to futility. The sample size could be adjusted to achieve the desired power while maintaining control of the overall Type I error. The maximum sample size planned for this study was 98 per treatment group.

A rigorous interim statistical analysis plan (SAP) and charter was developed detailing the algorithm for a sample size re-estimation based on the interim data and how the analysis was executed. An IDMC performed the interim analysis and made recommendations for any sample size adjustment based on the rules defined in the interim SAP. Any changes to sample size were communicated IDMC (or the statistician from the Statistical Support Group) to the IWRS vendor to ensure that the appropriate number of subjects were enrolled in the study. None of the esketamine team members or staff members at the investigational sites conducting the clinical study were informed of the results of the interim analysis and any adjustments that were made to the sample size.

Procedures were in place to ensure that the results of the interim analysis did not influence the conduct of the study, investigators, or subjects.

Efficacy Analyses

Efficacy analyses were performed on the full analysis set, which included all randomized subjects who received at least 1 dose of intranasal study drug and 1 dose of oral antidepressant medication in the double-blind induction phase.

The primary efficacy variable, change from baseline in MADRS total score at Week 4 in the double-blind induction phase, was analyzed using MMRM. The model included baseline MADRS total score as a covariate, and treatment, country, class of antidepressant (SNRI or SSRI), day, and day-by-treatment interaction as fixed effects, and a random subject effect. Comparison of the esketamine plus oral antidepressant arm versus oral antidepressant plus intranasal placebo was performed using the appropriate contrast.

For the EU dossier, the primary efficacy analysis was based on an analysis of covariance (ANCOVA) model using last observation carried forward (LOCF) data. The model included factors for treatment, country, and class of oral antidepressant (SNRI or SSRI) and baseline MADRS total score as a covariate. Comparison of the esketamine plus oral antidepressant arm versus intranasal placebo plus oral antidepressant was performed using the appropriate contrast.

Subject to regulatory acceptance of PHQ-9 as a key secondary endpoint, the first of 3 key secondary efficacy endpoints, change from baseline in PHQ-9 total score at Week 4 in the double-blind induction phase, were analyzed using the same models described above for the MADRS total score.

For the analysis of the second key secondary efficacy endpoints, the proportion of subjects showing onset of clinical response by Day 2 that is maintained for the duration of the double-blind induction phase in the esketamine plus oral antidepressant arm was compared with the oral antidepressant plus intranasal placebo arm using a Cochran-Mantel-Haenszel chi-square test adjusting for country and class of antidepressant (SNRI or SSRI). Clinical response was defined as ≥50% improvement in MADRS total score by Day 2 (i.e., the day after taking the first dose of double-blind intranasal medication) that continues through the end of the double-blind phase. Subjects who discontinued the study prior to end of the double-blind induction phase were not considered to have maintained clinical response.

The third key secondary efficacy endpoint, change from baseline in SDS total score at Week 4 in the double-blind induction phase, was analyzed using ANCOVA. The model included factors for treatment, country, and class of oral antidepressant (SNRI or SSRI) and baseline SDS total score as a covariate. Comparison of each intranasal esketamine plus oral antidepressant arm versus oral antidepressant plus intranasal placebo was performed using the appropriate contrast. Responses to questions H1 to H3 was summarized separately.

A serial gatekeeping (fixed sequence) approach was applied to adjust for multiplicity and to strongly control type I error across the primary and the 3 key secondary efficacy endpoints (change in PHQ-9 total score, onset of clinical response, and change in SDS total score).

Response and remission rates were summarized at each visit.

Change from baseline in GAD-7 total scores and ranks of change from baseline in CGI-S scores at the end of the double-blind induction phase were analyzed based on LOCF data using an ANCOVA model, with country and class of antidepressant (SNRI or SSRI) as factors, and the respective baseline score (unranked score in the case of CGI-S) as the covariate.

Dimension scores of EQ-5D-5L data, health status index, and the overall health status score were summarized over time.

Additionally, scores of all efficacy endpoints were summarized for all visits in the double-blind induction phase. Summaries were provided to show consistency of effect among relevant subgroups (e.g., antidepressant class SNRI and SSRI).

Analysis of the US Subpopulation—Clinical Efficacy and Safety

In the overall analysis, ESK+AD demonstrated statistically significant and clinically meaningful superiority compared with AD+PBO in primary efficacy endpoint (i.e., change from baseline in the MADRS total score (Montgomery, British Journal of Psychiatry. 1979; 134:382-389)). In this analysis, the efficacy and safety of these treatment groups were analyzed in only US patients and to assess for differences in efficacy and safety between the US population and the overall study population.

A. Outcomes

For the clinician-rated assessments, MADRS was administered at baseline; and days 2 (~24 hours post dose), 8, 15, 22, and 28. Similarly, the Clinical Global Impressions-Severity (CGI-S) scale (Guy W. ECDEU Assessment Manual for Psychopharmacology (028 Clinical Global Impressions [CGI]). 1976:218-222) administered at baseline; days 4, 8, 11, 15, 22; and at the 4-week double blind end point.

For the patient-rated assessments, a 9-item Patient Health Questionnaire-9 (PHQ-9) (Spitzer, JAMA. 1999; 282(18): 1737-1744) and Sheehan Disability Scale (SDS) (Sheehan DV. The Anxiety Disease. A Leading Psychiatrist Offers New Hope for Victims of Severe Anxiety. New York, N.Y.: Charles Scribner & Sons; 1983) were administered at baseline, day 15 and day 28.

B. Patient Demographics/Disease Characteristics

Inclusion criteria included adults, aged 18 to 64 years (inclusive), who met DSM-diagnostic criteria for MDD confirmed by Mini-International Neuropsychiatric Interview, and Inventory of Depressive Symptomatology-Clinician rated, 30-item total score of ≥34 (moderate to severe depression)

Patients must have had TRD and non-response at the end of the screening phase, defined as ≤25% improvement in MADRS total score from Week 1 to Week 4 and a MADRS total score of ≥28 on Week 2 and Week 4.

Of the 91 US patients, 46 received ESK+AD, 44 received AD+PBO, and one did not dose. The baseline patient demographics and disease characteristics were generally similar between the 2 treatment groups. See, Table 22. The overall mean age was 44.1 year, and approximately two-thirds (61.1%) of patients were women and most (83.3%) patients were Caucasian. The mean age of MDD diagnosis was 27.5 years, indicating on average, a >15-year history of depression. The baseline MADRS, CGI-S and PHQ-9 scores were consistent with a population with TRD.

TABLE 22

Baseline patient demographics and disease characteristics

| Parameter | ESK + AD (n = 46) | AD + PBO (n = 44) |
|---|---|---|
| Age, y, mean (SD) | 43.4 (13.5) | 44.7 (12.4) |
| Sex, n (%) | | |
| Male | 17 (37.0) | 18 (40.9) |
| Female | 29 (63.0) | 26 (59.1) |

TABLE 22-continued

Baseline patient demographics and disease characteristics

| Parameter | ESK + AD (n = 46) | AD + PBO (n = 44) |
|---|---|---|
| Race, n (%) | | |
| Caucasian | 38 (82.6) | 37 (84.1) |
| Black or African American | 6 (13.0) | 5 (11.4) |
| Asian | 1 (2.2) | 1 (2.3) |
| Multiple | 1 (2.2) | 1 (2.3) |
| Class of oral antidepressants, n (%)† | | |
| SNRI | 27 (58.7) | 26 (59.1) |
| SSRI | 19 (41.3) | 18 (40.9) |
| Duration of current episode, weeks, mean (SD) | 132.2 (109.8) | 177.6 (252.4) |
| Age at MDD diagnosis, y, mean (SD) | 25.5 (11.8) | 29.5 (14.0) |
| MADRS total score,$^a$ mean (SD) | 36.6 (5.9) | 36.0 (6.0) |
| CGI-S,$^b$ mean (SD) | 4.8 (0.6) | 4.8 (0.7) |
| SDS derived total score,$^c$ mean (SD) | 23.4 (4.5) | 24.1 (4.9) |
| PHQ-9 total score,$^d$ mean (SD) | 20.2 (3.3) | 20.9 (3.8) |

$^a$MADRS total score ranges from 0 to 60; a higher score indicates a more severe condition.
$^b$CGI-S score ranges from 1 (normal, not at all ill) to 7 (among the most extremely ill patients).
$^c$SDS total scores range from 0 to 30, where 0 = unimpaired and 30 = highly impaired.
$^d$PHQ-9 total score ranges from 0 to 27; a higher score indicates greater depression.

C. Efficacy

Efficacy was determined by measuring MADRS total scores, SDS scores, PHQ-9 scores and CGI-S scores. For the MADRS total scores, SDS scores, and PHQ-9 scores, the test for treatment effect was based on mixed model for repeated measures (MMRM) with change from baseline as the response variable and the fixed effect model terms for treatment (ESK+AD, AD+PBO), day, class of oral antidepressant (serotonin and norepinephrine reuptake inhibitor [SNRI] or selective serotonin reuptake inhibitor [SSRI]), treatment-by-day, and baseline value as a covariate. For the CGI-S scores, the test for treatment effect was based on analysis of covariance (ANCOVA) model last observation carried forward (LOCF) on ranks of change from baseline as the response variable and factors for treatment (ESK+AD, AD+PBO) and class of oral antidepressant (SNRI or SSRI), and baseline value (unranked) as a covariate. For each analysis, a negative difference favors esketamine nasal spray plus new oral AD.

Figure 11:
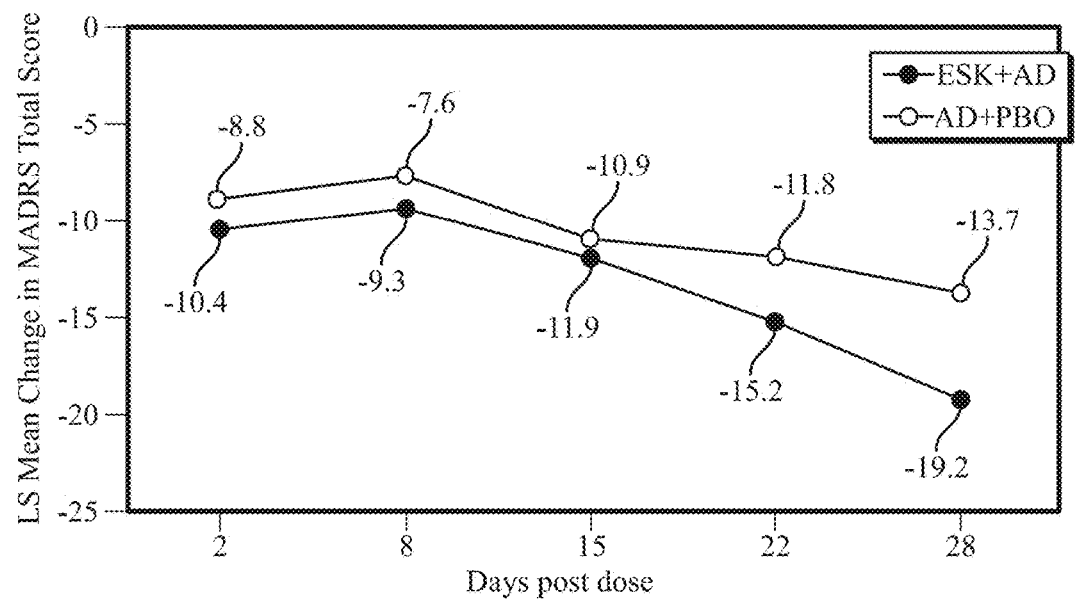
FIG. 11 illustrates the Least Square mean change in total MADRS score over time (observed cases) in US patients with TRD.

The results illustrate that the least square (LS) mean changes in MADS total score decreased in both treatment groups during the 4-week double-blind induction phase. See, FIG. 11.

The treatment effect favored the ESK+AD group at about 24-hours post dose (day 2) and on day 28, with the difference reaching statistical significance at day 28. See, Table 23. The LS mean difference (SE) was −1.6 (2.15; P=0.225) at about 24-hours post dose (day 2) and −5.5 (2.58; P=0.017) at day 28.

TABLE 23

Change from Baseline in MADRS total score (observed cases) in US patients with TRD

| MADRS parameter | ESK + AD (n = 46) | AD + PBO (n = 44) |
|---|---|---|
| Total score at baseline | 36.6 (5.9) | 36.0 (6.0) |
| Change at day 2 (~24 hours post-initial dose) | | |
| LS mean change | −10.4 | −8.8 |
| LS mean difference from placebo nasal spray plus new oral AD (SE) | | −1.6 (2.15) |

TABLE 23-continued

Change from Baseline in MADRS total score
(observed cases) in US patients with TRD

| MADRS parameter | ESK + AD (n = 46) | AD + PBO (n = 44) |
|---|---|---|
| P value |  | .225 |
| Change at day 28 |  |  |
| LS mean change | −19.2 | −13.7 |
| LS mean difference from placebo nasal spray plus new oral AD (SE) |  | −5.5 (2.58) |
| P value |  | 017 |

MADRS total score ranges from 0 to 60; a higher score indicates a more severe condition. AD, antidepressant; ESK, esketamine nasal spray; LS, least square; MADRS, Montgomery-Åsberg Depression Rating Scale; PBO, placebo nasal spray; SE, standard error.

A statistically significant difference in improvement of severity of depressive illness, as measured by the CGI-S, was observed between the 2 treatment groups at day 4 (P=0.015). The difference approached significance at 4-weeks post-initial dose (P=0.070). See, Table 24.

TABLE 24

Change in clinician-rated severity of depressive illness (LOCF) in US patients with TRD, as assessed with CGI-S.

| CGI-S Parameter | ESK + AD (n = 46) | AD + PBO (n = 44) |
|---|---|---|
| Baseline | | |
| N | 45 | 44 |
| Median (range) | 5.0 (4, 6) | 5.0 (4, 6) |
| Day 4 post-initial dose | | |
| N | 42 | 38 |
| Median (range) | 4.0 (2, 6) | 4.0 (3, 6) |
| Change from baseline at day 4 post-initial dose | | |
| N | 42 | 38 |
| Median (range) | 0.0 (−3, 0) | 0.0 (−2, 1) |
| 1-sided P value | 0.015 | |
| 4-week double blind end point | | |
| N | 44 | 44 |
| Median (range) | 3.0 (1, 6) | 4.0 (1, 6) |
| Change from baseline to 4-week double blind end point | | |
| N | 44 | 44 |
| Median (range) | −1.5 (−5, 1) | −1.0 (−4, 1) |
| 1-sided P value | 0.070 | |

CGI-S score ranges from 1 (normal, not at all ill) to 7 (among the most extremely ill patients). AD, antidepressant; Clinical Global Impression - Severity; ESK, esketamine nasal spray; LOCF, last observation carried forward; Max, maximum; Min, minimum; PBO, placebo nasal spray.

Figure 12:
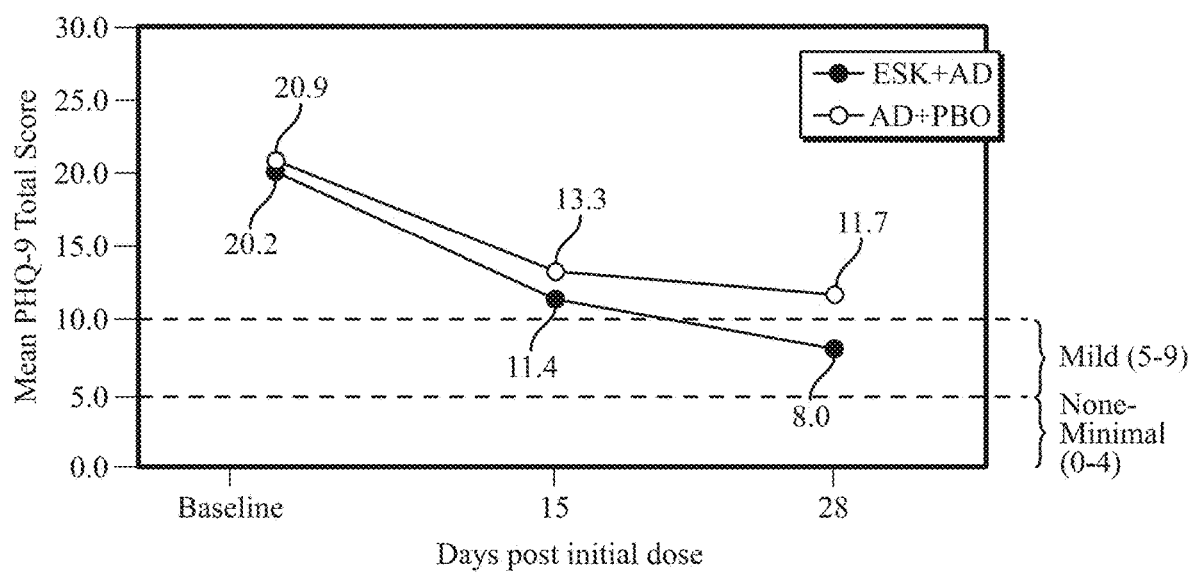
FIG. 12 illustrates patient-rated severity of depressive illness (observed cases) in US patients with TRD, as assessed with the PHQ-9.

The Patient-rated severity of depressive illness decreased in both treatment groups, but the magnitude of decrease was greater in the ESK+AD group at day 28. See, FIG. 12. The mean PHQ-9 scores at baseline were 20.2 in the ESK+AD group and 20.9 in the AD+PBO group. On day 28, mean PHQ-9 total scores were 8.0 and 11.7, respectively. LS mean difference (SE) in PHQ-9 was −3.1 (1.52; P=0.024).

Figure 13:
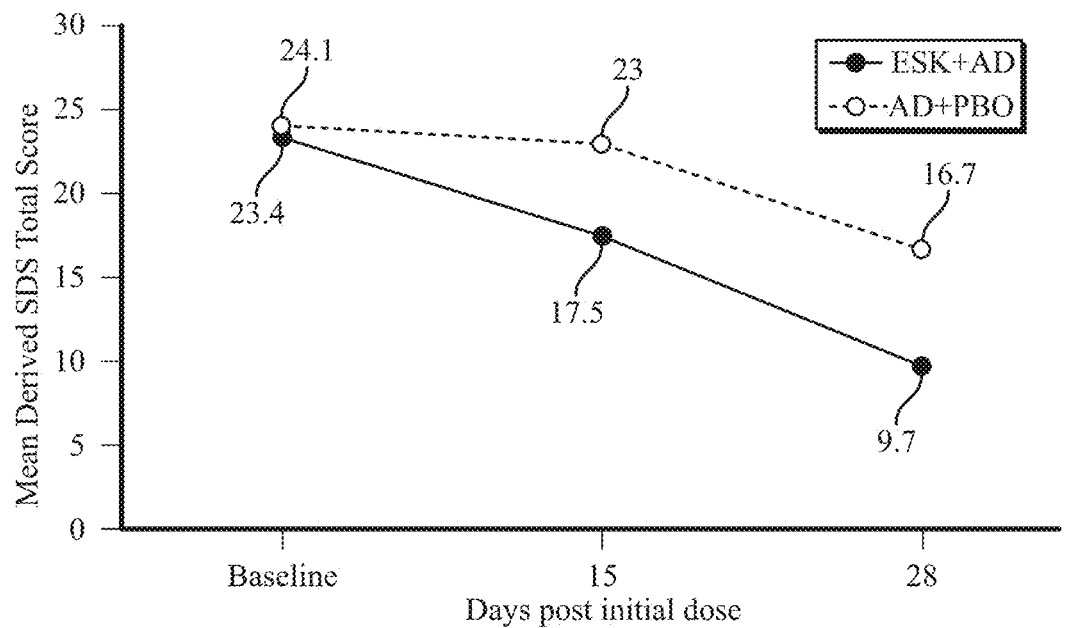
FIG. 13 illustrates functional impairment (observed case) in US patients with TRD, as assessed with SDS.

Functional impairment decreased in both treatment groups, but the magnitude of improvement was greater in the ESK+AD group at day 28. See, FIG. 13. The mean SDS scores at baseline were 23.4 in the ESK+AD group and 24.1 in the AD+PBO group. n day 28, mean derived SDS total scores were 9.7 and 16.7, respectively. LS mean difference (SE) in SDS total score was −5.2 (2.13; P=0.009).

D. Safety

Safety was assessed via treatment emergent adverse events (TEAEs), serious AEs, vital signs, psychiatric symptoms as assessed by Brief Psychiatric Rating Scale (BPRS), dissociation as measured by Clinician Administered Dissociative States Scale (CADSS), and discharge readiness.

Overall, TEAEs were observed in 91.3% of patients in the ESK+AD group and 77.3% of patients in the AD+PBO group. See, Table 25A. There were no deaths. One patient in the ESK+AD group experienced a SAE during the follow-up phase (cerebral hemorrhage on day 98). Four patients withdrew from nasal spray drug (n=3 ESK; n=1 PBO); no patient withdrew new oral AD.

The most common TEAEs (≥5% in either treatment group) are shown in Table 4. The incidence of TEAEs was similar between the US patients and the overall study population. AEs observed during the study were mostly mild to moderate in severity and transient in nature.

As observed in the overall population, present-state dissociative symptoms and transient perceptual effects as measured by the CADSS total score resolved spontaneously during the post dose observation period prior to discharge (within 60-90 minutes post dose). Most (>90%) patients in each treatment group were ready for discharge by 1.5 hours post dose. Vital sign and BPRS findings were consistent with the overall population.

TABLE 25A

Overview of treatment-emergent adverse events

| Parameter | ESK + AD (n = 46) | AD + PBO (n = 44) |
|---|---|---|
| Overall TEAE, n (%) | 42 (91.3) | 34 (77.3) |
| Possibly related to nasal spray drug | 38 (82.6) | 22 (50.0) |
| Possibly related to oral AD | 23 (50.0) | 15 (34.1) |
| Leading to death | 0 | 0 |
| 1 or more serious TEAE | 0 | 0 |
| Leading to nasal spray drug withdrawal | 3 (6.5) | 1 (2.3) |
| Leading to oral AD withdrawal | 0 | 0 |
| Most common (≥5%) TEAEs in either treatment group | | |
| Dizziness | 15 (32.6) | 4 (9.1) |
| Nausea | 14 (30.4) | 2 (4.5) |
| Headache | 13 (28.3) | 8 (18.2) |
| Dysgeusia | 11 (23.9) | 3 (6.8) |
| Throat irritation | 9 (19.6) | 5 (11.4) |
| Vertigo | 9 (19.6) | 1 (2.3) |
| Nasal discomfort | 8 (17.4) | 2 (4.5) |
| Feeling abnormal | 7 (15.2) | 1 (2.3) |
| Dissociation | 6 (13.0) | 1 (2.3) |
| Hypoesthesia | 6 (13.0) | 0 |
| Insomnia | 6 (13.0) | 4 (9.1) |
| Paresthesia | 6 (13.0) | 1 (2.3) |
| Anxiety | 5 (10.9) | 4 (9.1) |
| Delusional perception | 5 (10.9) | 0 |
| Illusion | 5 (10.9) | 0 |
| Hypoesthesia oral | 5 (10.9) | 1 (2.3) |
| Vomiting | 5 (10.9) | 1 (2.3) |
| Dizziness postural | 4 (8.7) | 0 |
| Diarrhea | 4 (8.7) | 4 (9.1) |
| Feeling drunk | 4 (8.7) | 1 (2.3) |
| Rhinorrhea | 4 (8.7) | 0 |
| Dysarthria | 3 (6.5) | 1 (2.3) |
| Tunnel vision | 3 (6.5) | 1 (2.3) |
| Derealization | 3 (6.5) | 0 |
| Euphoric mood | 3 (6.5) | 0 |
| Dry mouth | 3 (6.5) | 2 (4.5) |
| Blood pressure increased | 3 (6.5) | 0 |
| Somnolence | 2 (4.3) | 3 (6.8) |
| Fatigue | 2 (4.3) | 5 (11.4) |

E. Summary

These results demonstrated that ESK+AD provided a rapid onset of effect that continued for 4 weeks and was generally well tolerated in US patients with TRD. These observations agree with those from the overall study population, indicating that the US population had no significant differences in efficacy. In STAR-D level 3 (i.e., patients with MDD who did not remit with level 1 or level 2 treatment) attainment of the primary outcome (17-item Hamilton Rating Scale of Depression score ≤7) occurred in 8-12% of patients in ~6 weeks' time. See, Rush, CNS Drugs. 2009; 23(8):627-647. By comparison, at 4 weeks past-initial dose, ESK+AD resulted in improvements in LS mean change in MADRS total score, patient-rated severity of depressive illness, and functional impairment.

Moreover, a statistically significant improvement in clinician-rated severity of depressive illness was observed 24 hours after ESK+AD dosing. Improvements in clinician- and patient-rated efficacy measures were noted in ESK+AD and AD+PBO treatment groups.

ESK+AD compared with AD+PBO (active comparator) in US patients with TRD provided evidence for clinically meaningful, statistically significant, and rapid reduction of depressive symptoms. Significant improvements in clinician-rated severity of depressive illness were observed as early as 24 hours after dosing in some patients. Improvements in LS mean change in MADRS total score, patient-rated severity of depressive illness, and functional impairment were observed at 4 weeks post-initial dose.

Overall, safety and response/remission results of US patients were similar to those found for the overall population.

Final Analysis of the US Subpopulation—Response, Remission, and Safety

As discussed above for the overall analysis, ESK+AD demonstrated statistically significant and clinically meaningful superiority compared with AD+PBO in primary efficacy endpoint (i.e., change from baseline in the MADRS total score. See, Montgomery cited above. In this analysis, the response, remission, and safety of these treatment groups were analyzed in only US patients and to assess for differences in efficacy and safety between the US population and the overall study population.

A. Outcomes

For the clinician-rated assessments, MADRS was administered at baseline; and days 2 (~24 hours post dose), 8, 15, 22, and 28. Similarly, the Clinical Global Impressions-Severity (CGI-S) scale (Guy W. ECDEU Assessment Manual for Psychopharmacology (028 Clinical Global Impressions [CGI]). 1976:218-222) administered at baseline; days 4, 8, 11, 15, 22; and at the 4-week double blind end point.

For the patient-rated assessments, a 9-item Patient Health Questionnaire-9 (PHQ-9) (Spitzer, JAMA. 1999; 282(18): 1737-1744) and Sheehan Disability Scale (SDS) (Sheehan DV. The Anxiety Disease. A Leading Psychiatrist Offers New Hope for Victims of Severe Anxiety. New York, N.Y.: Charles Scribner & Sons; 1983) were administered at baseline, day 15 and day 28.

B. Patient Demographics/Disease Characteristics

Inclusion criteria included adults, aged 18 to 64 years (inclusive), who met DSM-diagnostic criteria for MDD confirmed by Mini-International Neuropsychiatric Interview, and Inventory of Depressive Symptomatology-Clinician rated, 30-item total score of 234 (moderate to severe depression).

Patients must have had TRD and non-response at the end of the screening phase, defined as ≤25% improvement in MADRS total score from Week 1 to Week 4 and a MADRS total score of ≥28 on Week 2 and Week 4.

Of the 91 US patients, 46 received ESK+AD, 44 received AD+PBO, and one did not dose. The baseline patient demographics and disease characteristics were generally similar between the 2 treatment groups. See, Table 22. The overall mean age was 44.1 years, and approximately two-thirds (61.1%) of patients were women and most (83.3%) patients were Caucasian. The mean age of MDD diagnosis was 27.5 years, indicating on average, a >15-year history of depression. The baseline MADRS, CGI-S and PHQ-9 scores were consistent with a population with TRD.

C. Efficacy

Efficacy was assessed by measuring response, remission and change in clinician-rated symptom severity. A patient was considered responsive if there was a ≥50% decrease in MADRS baseline score. A patient was classified to be "in remission" if the clinician-rated MADRS score was ≤12 and the patient-rated PHQ-9 score was <5. Finally, a patient was considered to have a change in clinician-rated symptom severity if there was a ≥1-point decrease in the CGI-S and a ≥2-point decrease on the CGI-S.

Figure 14:
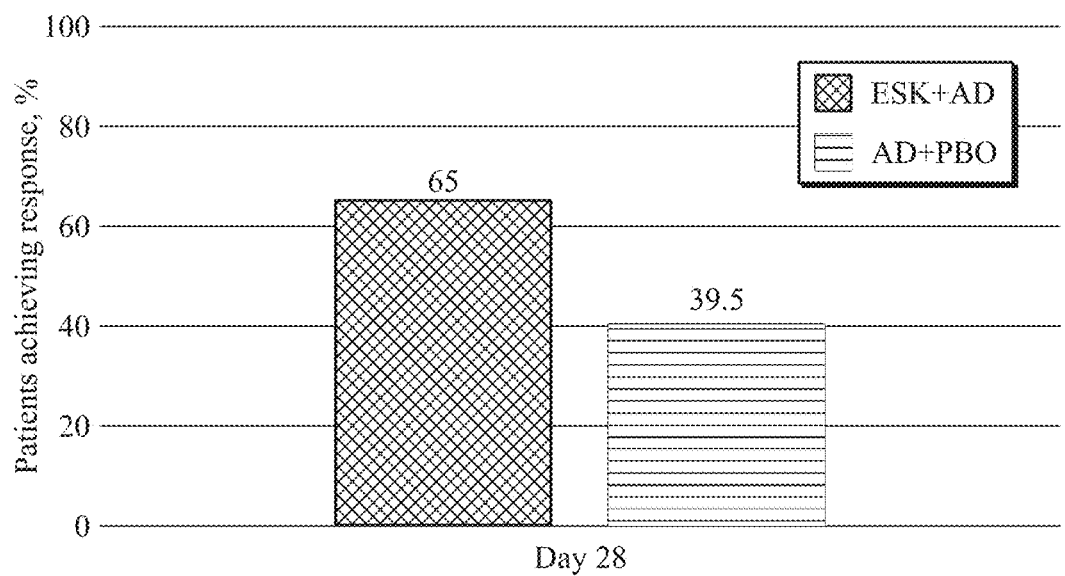
FIG. 14 illustrates the percentage of US patients with TRD achieving a response 4 weeks post initial dose (observed case).

Approximately 24-hours post dose (day 2), 11/43 (25.6%) patients in the ESK+AD and 9/40 (22.5%) patients in the AD+PBO achieved a response. Responses at day 28 were 26/40 (65.0%) for patients in the ESK+AD vs 15/38 (39.5%) in the AD+PBO group. See, FIG. 14. Similarly, approximately 24-hours post dose (day 2), 6/43 (14.0%) patients in the ESK+PBO group and 4/40 (10.0%) patients in the AD+PBO group achieved clinician-rated remission.

Figure 15:
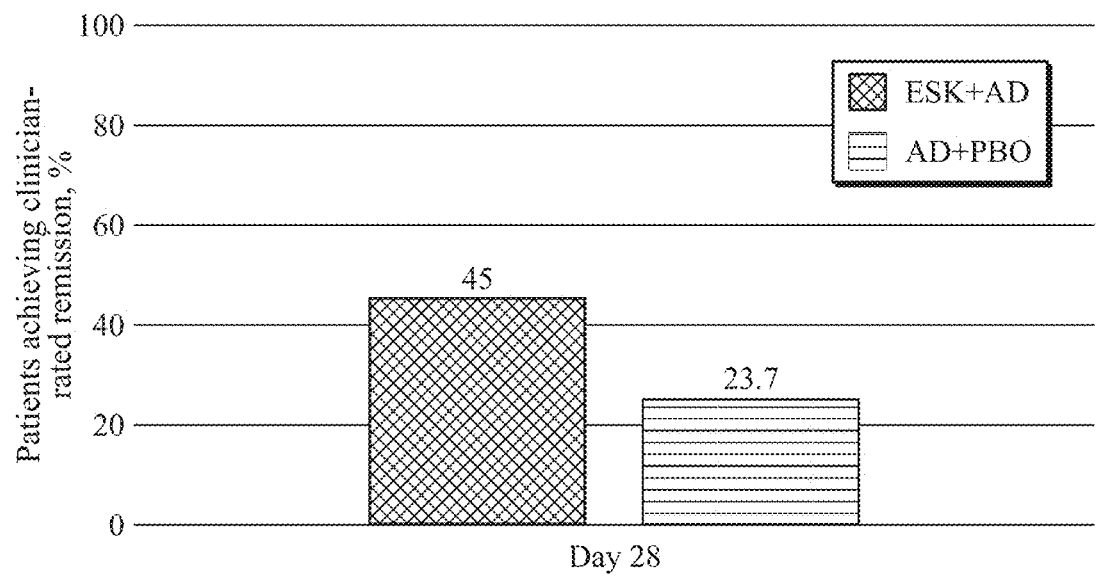
FIG. 15 illustrates the percentage of US patients with TRD achieving clinician-rated remission 4-weeks post initial dose.

Clinician-rated remission rates at day 28 were 18/40 (45.0%) patients in the ESK+AD group and 9/38 (23.7%) patients in the AD+PBO group. See, FIG. 15.

Figure 16:
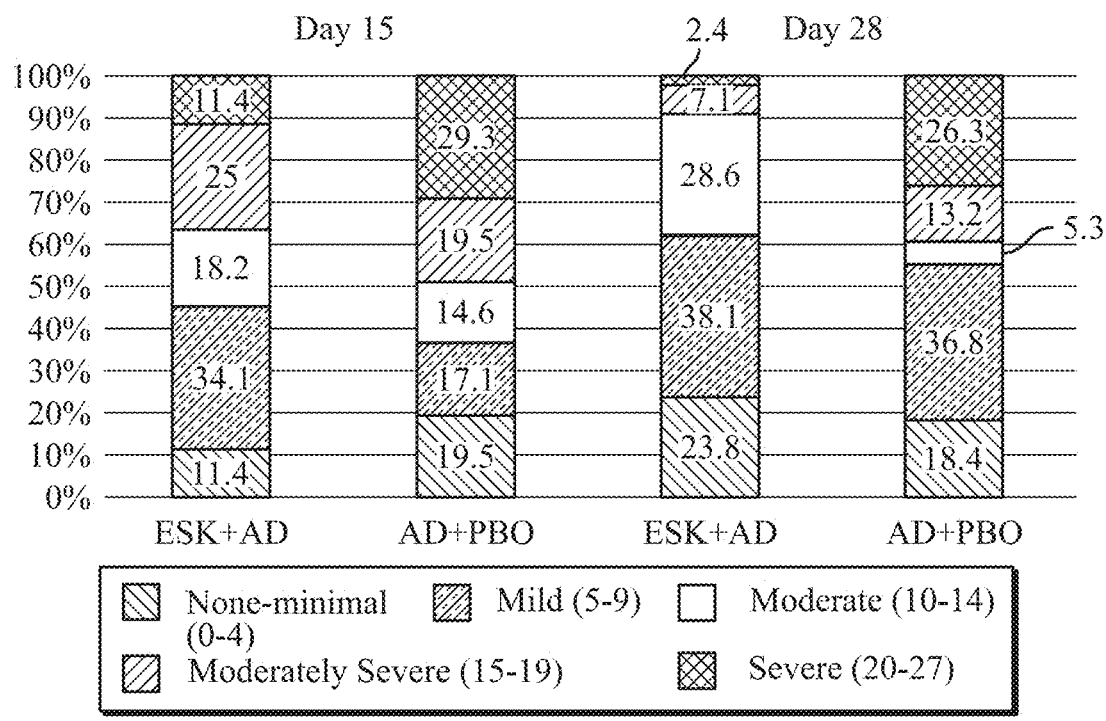
FIG. 16 illustrates the frequency distribution of PHQ-9 severity categories (observed case) in US patients with TRD.

The frequency distribution of PHQ-9 severity categories at day 15 and day 28 is shown in FIG. 16. At day 15, the percentage of patients with remission (i.e., score <5) was 11.4% in the ESK+AD group and 19.5% in the AD+PBO group. At 4 weeks post-initial dose, the percentage of patients with remission (i.e., score <5) was 23.8% in the ESK+AD group and 18.4% in the AD+PBO group. Further, at 4 weeks post-initial dose, the percentage of patients with severe depression (i.e., score 20-27), was more than 10-fold higher in the AD+PBO group (26.3%) than in the ESK+AD group (2.4%).

Figure 17:
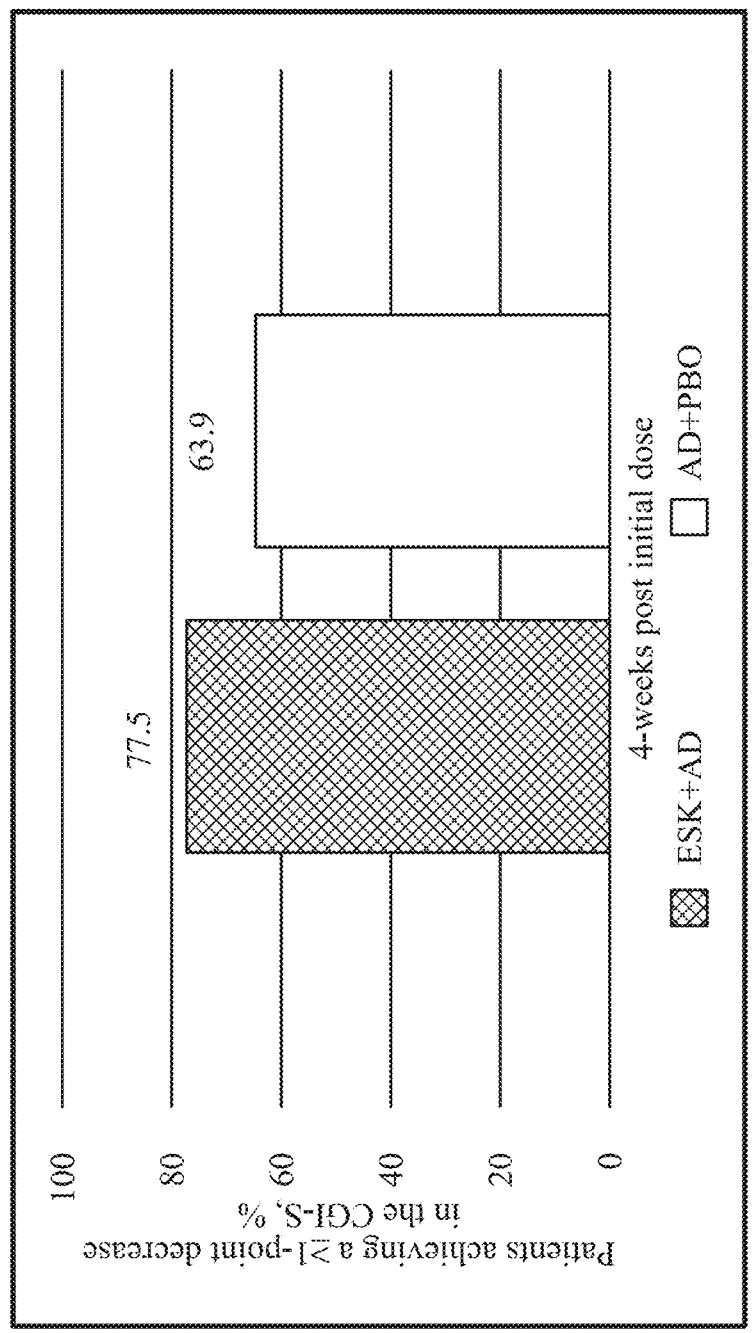
FIG. 17 illustrates the percentage of US patients with TRD who had 21-point decrease in the CGI-S (observed case) 4-weeks post initial dose.

Further, at day 4, a 21-point decrease in the CGI-S was observed in nearly twice as many patients in the ESK+AD group compared with those in the PBO+AD group (47.6 vs 26.3%); at day 28, the percentages were 77.5 and 63.9%, respectively. See, FIG. 17. The percentage of patients with 22-point decrease in the CGI-S was nearly 2-fold greater in the ESK+AD group compared with the PBO+AD group (14.3 vs 7.9%) at day 4; at day 28, the percentages were 52.5 vs 44.4%, respectively.

D. Safety

Safety was assessed via treatment emergent adverse events (TEAEs), serious AEs, vital signs, psychiatric symptoms as assessed by Brief Psychiatric Rating Scale (BPRS), dissociation as measured by Clinician Administered Dissociative States Scale (CADSS), and discharge readiness. See, Table 25B which shows the clinical global assessment of discharge readiness which was assessed based on overall clinical states (including sedation, perceptual changes, blood pressure, and other adverse events).

TABLE 25B

| Discharge Ready on each dosing day (% patients) | esketamine + Oral AD | oral AD + Nasal placebo |
| --- | --- | --- |
| 1 hour post dose | ≥44.3% | 92.0% |
| 1.5 hour post dose | ≥93.2% | 98.9% |

Overall, TEAEs were observed in 91.3% of patients in the ESK+AD group and 77.3% of patients in the AD+PBO group. See, Table 23. There were no deaths. One patient in the ESK+AD group experienced a SAE during the follow-up phase (cerebral hemorrhage on day 98). Four patients withdrew from the nasal spray drug (n=3 ESK; n=1 PBO), but no patients withdrew new oral AD.

The most common TEAEs (25% in either treatment group) are shown in Table 23. The incidence of TEAEs was similar between the US patients and the overall study population. AEs observed during the study were mostly mild to moderate in severity and transient in nature.

As observed in the overall population, present-state dissociative symptoms and transient perceptual effects as measured by the CADSS total score resolved spontaneously during the post dose observation period prior to discharge (within 60-90 minutes post dose). Most (>90%) patients in each treatment group were ready for discharge by 1.5 hours post dose. Vital sign and BPRS findings were consistent with the overall population.

E. Conclusions

These results demonstrated that ESK+AD, compared with AD+PBO, provided a rapid onset of effect that continued for 4 weeks and was generally well tolerated in US patients with TRD. These results also showed that that ESK+AD showed clinically meaningful improvements in depressive-symptom response and remission and had a favorable safety profile in US patients with TRD. Specifically, ESK+AD demonstrated improvement in clinician-rated (CGI-S) and patient-rated (PHQ-9) assessments. Again, these observations agree with those from the overall study population, indicating that the US population has no significant differences in efficacy.

However, in the STAR-D level 3, which included patients with MDD who did not remit with level 1 or level 2 treatment, the overall acute response rate (based on Quick Inventory of Depressive Symptomatology-Self Report, which was administered at each acute treatment clinic visit) was 16.8% and the overall acute remission rate was 13.7%. See, Rush, American Journal of Psychiatry. 2006; 163(11): 1905-1917 and Howland RH. Journal of Psychosocial Nursing and Mental Health Services. 2008; 46(10):21-24. By comparison, the response and remission rates observed with ESK+AD at 4 weeks post-initial dose were much higher (45 and 65.0%, respectively, as assessed with MADRS).

Example 2

Figure 18:
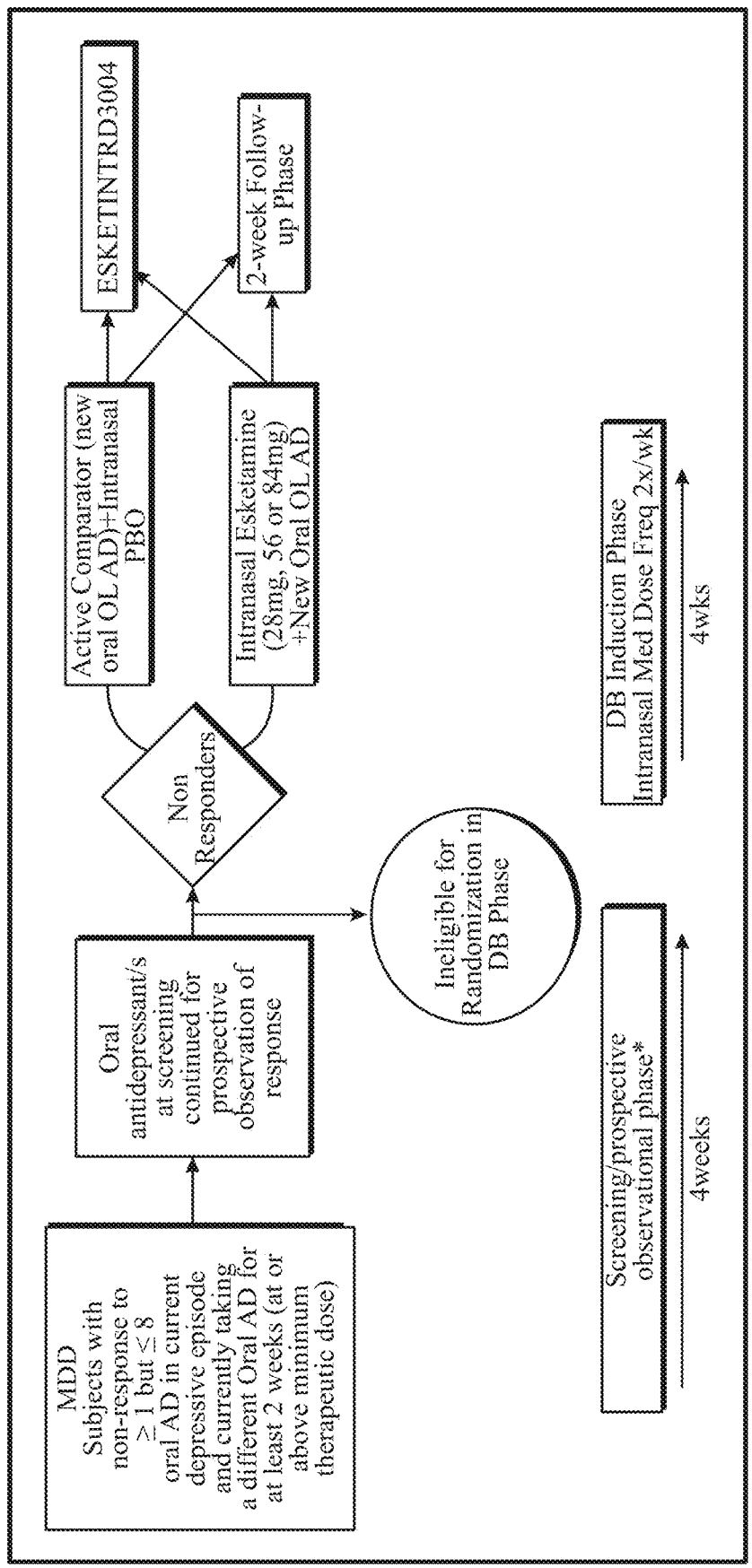
FIG. 18 illustrates a schematic to the study design of the ESKETINTRD3005 Phase 3 clinical trial.

Efficacy of Intranasal Esketamine for Treating Treatment Resistance Depression (TRD) in Geriatric Patients, Phase 3 Clinical Trial The ability of esketamine to treat treatment-refractory or treatment-resistant depression (TRD) was evaluated via the clinical study described below, which was conducted to evaluate the efficacy, safety, and tolerability of flexibly dosed intranasal esketamine plus a newly initiated oral antidepressant in elderly subjects with TRD. The study served as a pivotal Phase 3 short-term efficacy and safety study in support of regulatory agency requirements for registration of intranasal esketamine for the treatment of TRD. A diagram of the study design is provided in FIG. 18.

The hypothesis for this study was that, in elderly subjects with TRD, switching from a failed antidepressant treatment to intranasal esketamine plus a newly initiated oral antidepressant would be superior to switching to a newly initiated oral antidepressant treatment (active comparator) plus intranasal placebo in improving depressive symptoms.

The primary objective of this study was to evaluate the efficacy of switching elderly subjects with treatment-resistant depression (TRD) from a prior antidepressant treatment (to which they have not responded) to flexibly dosed intranasal esketamine (28 mg, 56 mg or 84 mg) plus a newly initiated oral antidepressant compared with switching to a newly initiated oral antidepressant plus intranasal placebo, in improving depressive symptoms, as assessed by the change from baseline in the Montgomery-Asberg Depression Rating Scale (MADRS) total score from Day 1 (pre-randomization) to the end of the 4-week double-blind induction phase.

The key secondary objectives were to assess the effect of intranasal esketamine plus a newly initiated oral antidepressant compared with a newly initiated oral antidepressant (active comparator) plus intranasal placebo on the following parameters in elderly subjects with TRD: (a) Depressive symptoms (subject-reported), (b) Onset of clinical response by Day 2, and (c) Functioning and associated disability. Additional secondary objectives included (a) Depression response rates, (b) Depression remission rates, (c) Overall severity of depressive illness, (d) Anxiety symptoms and (e) Health-related quality of life and health status.

To investigate the safety and tolerability of intranasal esketamine plus a newly initiated oral antidepressant compared with a newly initiated oral antidepressant (active comparator) plus intranasal placebo in elderly subjects with TRD, the following parameters were also measured: (a) TEAEs, including AEs of special interest, (b) Local nasal tolerability, (c) Effects on heart rate, blood pressure, respiratory rate, and blood oxygen saturation, (d) Effects on alertness and sedation, (e) Potential psychosis-like effects, (f) Dissociative symptoms, (g) Potential effects on cognitive function, (h) Potential effects on suicidal ideation/behavior, (i) Potential treatment-emergent symptoms of cystitis and/or lower urinary tract symptoms, (j) Potential withdrawal and/or rebound symptoms following cessation of intranasal esketamine treatment, and (k) Potential effects on sense of smell.

Esketamine, the placebo solutions, and the oral antidepressant medications were provided as described in Example 1 in "STUDY DRUG INFORMATION".

Overview of Study Design

This was a randomized, double-blind, active-controlled, multicenter study that included 138 randomized elderly subjects with TRD. The study had 3 phases which are briefly described below.

The screening/prospective observational phase (4-week duration) was the same as described in Example 1.

Double-Blind Induction Phase (4-Week Duration)

The study included 138 randomized subjects (one subject did not receive any study drug (intranasal or oral AD) and is therefore not included in the safety analysis and full analysis sets). The other 137 subjects received both the intranasal and oral AD study drug and are included in the full analysis set (FAS). The intranasal treatment sessions (esketamine or placebo) occurred twice weekly. In addition, all subjects initiated a new open-label oral antidepressant on Day 1 that was taken daily for the duration of this phase. The assigned oral antidepressant was 1 of 4 oral antidepressant medications (duloxetine, escitalopram, sertraline, or venlafaxine extended release [XR]), that the subject had not previously had a nonresponse to in the current depressive episode, had not been previously intolerant to (lifetime), and was available in the participating country.

At the end of the induction phase, subjects who were responders (defined as ≥50% reduction in the MADRS total score from baseline [Day 1 pre-randomization] to the end of the 4-week double-blind induction phase) were eligible to participate in the subsequent study ESKETINTRD3003 if they met all other study entry criteria (ESKETINTRD3003 is a longer-term efficacy maintenance study involving repeated treatment sessions of intranasal esketamine).

If a subject withdrew from the study before the end of the double-blind induction phase for reasons other than withdrawal of consent, an Early Withdrawal visit was conducted within 1 week of the date of discontinuation, followed by the follow-up phase.

The Follow-Up Phase (24-Week Duration) was the Same as Described in Example 1.

Study Population

The inclusion and exclusion criteria for enrolling subjects in this study were as described in Example 1 under "Study Population" with the exception that at the time of signing the informed consent form (ICF), the subject was a man or woman ≥65 years of age, inclusive. Each potential subject satisfied all of the criteria to be enrolled in the study.

Additionally, potential subjects had to be willing and able to adhere to the prohibitions and restrictions as described in Example 1 under "Study Population".

Treatment Allocation, Randomization and Blinding

The treatment allocation, randomization and blinding was performed as described in Example 1.

In the FAS, 130/137 (94.9%) of the subjects were white and 85/137 (62.0%) of the subjects were female. The mean age was 70.0 years, ranging from 65 to 86 years. Out of 138 subjects in the all randomized analysis set, 122 (88.4%) completed the double-blind phase and 16 withdrew early, of which 6 withdrew due to 'adverse events', 3 due to 'withdrawal by subject', 4 due to 'lack of efficacy', 1 for 'loss to follow-up', 1 due to protocol violation and 1 due to 'other' reasons. Subsequently, 15 subjects entered the follow-up phase, 111 subjects continued into the ESKETINTRD3004 study and 2 subjects continued to 54135419TRD3008.

Subject and Treatment Information

A total of 302 subjects were screened across 57 sites in 13 countries (Belgium, Brazil, Bulgaria, Finland, France, Italy, Lithuania, Poland, South Africa, Spain, Sweden, UK and the US). Excluding 3 subjects from a US site due to GCP issues, 138 subjects with a DSM-5 (Diagnostic and Statistical Manual of Mental Disorders, 5th Edition) diagnosis of MDD (aged 65 or older) were randomized to two groups in a ratio of 1:1 (72 in intranasal esketamine plus oral AD and 66 in oral AD plus intranasal placebo).

Of the 138 randomized subjects, 1 subject did not receive any study drug (intranasal or oral AD) and are therefore not included in the safety analysis and full analysis sets. The other 137 subjects received both the intranasal and oral AD study drug and are included in the full analysis set.

TABLE 26

Number of Subjects in Each Analysis Set (Study ESKETINTRD3005: All Randomized Analysis Set)

|  | Intranasal Esk + Oral AD (N = 72) | Oral AD + Intranasal Placebo (N = 66) | Total (N = 138) |
| --- | --- | --- | --- |
| All randomized | 72 (100.0%) | 66 (100.0%) | 138 (100.0%) |
| Full | 72 (100.0%) | 65 (98.5%) | 137 (99.3%) |
| Safety | 72 (100.0%) | 65 (98.5%) | 137 (99.3%) |
| Follow-up | 12 (16.7%) | 3 (4.5%) | 15 (10.9%) |

Of the 138 randomized subjects, 122 (88.4%) subjects completed the 28-day double-blind induction phase. Results are presented in Table 27. The most frequent reason for withdrawal was adverse event. Subsequently, 15 subjects entered the follow-up phase, 111 subjects continued into the ESKETINTRD3004 study and 2 subjects continued to 54135419TRD3008 after ESKETINTRD3004 was dosed.

TABLE 27

Study Completion/Withdrawal Information; Double-blind Induction Phase (Study ESKETINTRD3005: All Randomized Analysis Set)

|  | Intranasal Esk + Oral AD (N = 72) | Oral AD + Intranasal Placebo (N = 66) | Total (N = 138) |
| --- | --- | --- | --- |
| Completed | 62 (86.1%) | 60 (90.9%) | 122 (88.4%) |
| Withdrawn | 10 (13.9%) | 6 (9.1%) | 16 (11.6%) |
| Adverse event | 4 (5.6%) | 2 (3.0%) | 6 (4.3%) |
| Lack of efficacy | 3 (4.2%) | 1 (1.5%) | 4 (2.9%) |
| Lost to follow-up | 1 (1.4%) | 0 | 1 (0.7%) |
| Protocol violation | 0 | 1 (1.5%) | 1 (0.7%) |
| Withdrawal by subject | 1 (1.4%) | 2 (3.0%) | 3 (2.2%) |
| Other | 1 (1.4%) | 0 | 1 (0.7%) |

Demographic and baseline characteristics are displayed in Table 28 for the full analysis set. In general, the treatment groups were similar with respect to the baseline characteristics. The majority of subjects entering the study were female (62.0%). The mean (SD) age of all subjects was 70.0 (4.52) years, ranging from 65 to 86 years. See, FIG. 26.

TABLE 28

Demographic and Baseline Characteristics (Study ESKETINTRD3005: Full Analysis Set)

|  | Intranasal Esk + Oral AD (N = 72) | Oral AD + Intranasal Placebo (N = 65) | Total (N = 137) |
| --- | --- | --- | --- |
| Age (years) |  |  |  |
| N | 72 | 65 | 137 |
| Mean (SD) | 70.6 (4.79) | 69.4 (4.15) | 70.0 (4.52) |
| Median | 70.0 | 68.0 | 69.0 |
| Range | (65; 86) | (65; 82) | (65; 86) |
| Age category (years), n (%) |  |  |  |
| N | 72 | 65 | 137 |
| 65-74 | 59 (81.9%) | 57 (87.7%) | 116 (84.7%) |
| ≥75 | 13 (18.1%) | 8 (12.3%) | 21 (15.3%) |

TABLE 28-continued

Demographic and Baseline Characteristics (Study ESKETINTRD3005: Full Analysis Set)

| | Intranasal Esk + Oral AD (N = 72) | Oral AD + Intranasal Placebo (N = 65) | Total (N = 137) |
|---|---|---|---|
| Sex, n (%) | | | |
| N | 72 | 65 | 137 |
| Male | 27 (37.5%) | 25 (38.5%) | 52 (38.0%) |
| Female | 45 (62.5%) | 40 (61.5%) | 85 (62.0%) |
| Race, n (%) | | | |
| N | 72 | 65 | 137 |
| White | 66 (91.7%) | 64 (98.5%) | 130 (94.9%) |
| Multiple | 4 (5.6%) | 0 | 4 (2.9%) |
| Not Reported | 1 (1.4%) | 1 (1.5%) | 2 (1.5%) |
| Unknown | 1 (1.4%) | 0 | 1 (0.7%) |
| Ethnicity, n (%) | | | |
| N | 72 | 65 | 137 |
| Hispanic or Latino | 10 (13.9%) | 5 (7.7%) | 15 (10.9%) |
| Not Hispanic or Latino | 59 (81.9%) | 59 (90.8%) | 118 (86.1%) |
| Not Reported | 2 (2.8%) | 1 (1.5%) | 3 (2.2%) |
| Unknown | 1 (1.4%) | 0 | 1 (0.7%) |
| Baseline weight (kg) | | | |
| N | 72 | 65 | 137 |
| Mean (SD) | 78.44 (16.665) | 81.70 (18.948) | 79.99 (17.794) |
| Median | 76.25 | 77.60 | 77.50 |
| Range | (44.0; 113.5) | (43.0; 134.8) | (43.0; 134.8) |
| Baseline height (cm) | | | |
| N | 72 | 65 | 137 |
| Mean (SD) | 165.46 (10.951) | 166.79 (10.346) | 166.09 (10.650) |
| Median | 162.80 | 165.00 | 164.00 |
| Range | (139.7; 191.0) | (149.9; 193.0) | (139.7; 193.0) |
| Baseline body mass index (kg/m2) | | | |
| N | 72 | 65 | 137 |
| Mean (SD) | 28.6 (5.17) | 29.3 (6.14) | 28.9 (5.64) |
| Median | 27.6 | 28.3 | 27.8 |
| Range | (20; 45) | (16; 45) | (16; 45) |
| BMI category (kg/m$^2$), n (%) | | | |
| N | 72 | 65 | 137 |
| Underweight <18.5 | 0 | 1 (1.5%) | 1 (0.7%) |
| Normal 18.5-<25 | 18 (25.0%) | 14 (21.5%) | 32 (23.4%) |
| Overweight 25-<30 | 28 (38.9%) | 21 (32.3%) | 49 (35.8%) |
| Obese 30-<40 | 23 (31.9%) | 24 (36.9%) | 47 (34.3%) |
| Morbidly obese ≥40 | 3 (4.2%) | 5 (7.7%) | 8 (5.8%) |
| Employment status, n (%) [a] | | | |
| N | 72 | 65 | 137 |
| Any type of employment | 11 (15.3%) | 13 (20.0%) | 24 (17.5%) |
| Any type of unemployment | 2 (2.8%) | 6 (9.2%) | 8 (5.8%) |
| Other | 59 (81.9%) | 46 (70.8%) | 105 (76.6%) |
| Hypertension status, n (%) [b] | | | |
| N | 72 | 65 | 137 |
| Yes | 41 (56.9%) | 32 (49.2%) | 73 (53.3%) |
| No | 31 (43.1%) | 33 (50.8%) | 64 (46.7%) |
| Country, n (%) | | | |
| N | 72 | 65 | 137 |
| Belgium | 2 (2.8%) | 4 (6.2%) | 6 (4.4%) |
| Brazil | 1 (1.4%) | 0 | 1 (0.7%) |
| Bulgaria | 3 (4.2%) | 0 | 3 (2.2%) |
| Finland | 1 (1.4%) | 1 (1.5%) | 2 (1.5%) |
| France | 4 (5.6%) | 3 (4.6%) | 7 (5.1%) |
| Italy | 6 (8.3%) | 3 (4.6%) | 9 (6.6%) |
| Lithuania | 2 (2.8%) | 0 | 2 (1.5%) |
| Poland | 4 (5.6%) | 3 (4.6%) | 7 (5.1%) |
| South Africa | 2 (2.8%) | 5 (7.7%) | 7 (5.1%) |
| Spain | 4 (5.6%) | 4 (6.2%) | 8 (5.8%) |
| Sweden | 8 (11.1%) | 6 (9.2%) | 14 (10.2%) |
| United Kingdom | 1 (1.4%) | 0 | 1 (0.7%) |
| United States | 34 (47.2%) | 36 (55.4%) | 70 (51.1%) |

TABLE 28-continued

Demographic and Baseline Characteristics (Study ESKETINTRD3005: Full Analysis Set)

|  | Intranasal Esk + Oral AD (N = 72) | Oral AD + Intranasal Placebo (N = 65) | Total (N = 137) |
|---|---|---|---|
| Region, n (%) |  |  |  |
| N | 72 | 65 | 137 |
| Europe | 35 (48.6%) | 24 (36.9%) | 59 (43.1%) |
| North America | 34 (47.2%) | 36 (55.4%) | 70 (51.1%) |
| Other | 3 (4.2%) | 5 (7.7%) | 8 (5.8%) |
| Class of oral antidepressant, n (%) |  |  |  |
| N | 72 | 65 | 137 |
| SNRI | 31 (43.1%) | 30 (46.2%) | 61 (44.5%) |
| SSRI | 41 (56.9%) | 35 (53.8%) | 76 (55.5%) |
| Oral antidepressant, n (%) |  |  |  |
| N | 72 | 65 | 137 |
| Duloxetine | 25 (34.7%) | 23 (35.4%) | 48 (35.0%) |
| Escitalopram | 25 (34.7%) | 25 (38.5%) | 50 (36.5%) |
| Sertraline | 15 (20.8%) | 10 (15.4%) | 25 (18.2%) |
| Venlafaxine extended release (XR) | 7 (9.7%) | 7 (10.8%) | 14 (10.2%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

Baseline psychiatric history for the full analysis set is presented in Table 29. The mean (SD) baseline MADRS total score was 35.2 (6.16), ranging from 19 to 51. 84.7% of subjects documented non-response to 2 or more antidepressant treatments taken for at least 6 weeks on the MGH-ATRQ at screening. The remaining 15.3% subjects documented non-response to 1 antidepressant at screening, and non-response to a second antidepressant was confirmed prospectively during the screening/prospective observational phase.

TABLE 29

Baseline Psychiatric History (Study ESKETINTRD3005: Full Analysis Set)

|  | Intranasal Esk + Oral AD (N = 72) | Oral AD + Intranasal Placebo (N = 65) | Total (N = 137) |
|---|---|---|---|
| Age when diagnosed with MDD (years) |  |  |  |
| N | 72 | 65 | 137 |
| Mean (SD) | 42.6 (16.18) | 43.7 (16.28) | 43.1 (16.18) |
| Median | 43.0 | 45.0 | 44.0 |
| Range | (10; 75) | (11; 77) | (10; 77) |
| Baseline MADRS total score |  |  |  |
| N | 72 | 65 | 137 |
| Mean (SD) | 35.5 (5.91) | 34.8 (6.44) | 35.2 (6.16) |
| Median | 36.0 | 35.0 | 36.0 |
| Range | (23; 50) | (19; 51) | (19; 51) |
| Screening IDS-C30 total score |  |  |  |
| N | 71 | 63 | 134 |
| Mean (SD) | 44.2 (6.50) | 43.1 (6.71) | 43.7 (6.60) |
| Median | 45.0 | 43.0 | 44.0 |
| Range | (33; 60) | (31; 67) | (31; 67) |
| Baseline CGI-S |  |  |  |
| N | 72 | 65 | 137 |
| Mean (SD) | 5.1 (0.76) | 4.8 (0.80) | 5.0 (0.79) |
| Median | 5.0 | 5.0 | 5.0 |
| Range | (3; 7) | (3; 6) | (3; 7) |
| Baseline CGI-S category, n (%) |  |  |  |
| N | 72 | 65 | 137 |
| Normal, not at all ill | 0 | 0 | 0 |
| Borderline mentally ill | 0 | 0 | 0 |
| Mildly ill | 2 (2.8%) | 2 (3.1%) | 4 (2.9%) |
| Moderately ill | 10 (13.9%) | 20 (30.8%) | 30 (21.9%) |
| Markedly ill | 39 (54.2%) | 29 (44.6%) | 68 (49.6%) |
| Severely ill | 20 (27.8%) | 14 (21.5%) | 34 (24.8%) |
| Among the most extremely ill patients | 1 (1.4%) | 0 | 1 (0.7%) |

TABLE 29-continued

Baseline Psychiatric History (Study ESKETINTRD3005: Full Analysis Set)

| | Intranasal Esk + Oral AD (N = 72) | Oral AD + Intranasal Placebo (N = 65) | Total (N = 137) |
|---|---|---|---|
| Baseline PHQ-9 total score | | | |
| N | 72 | 65 | 137 |
| Mean (SD) | 17.6 (4.99) | 17.4 (6.33) | 17.5 (5.65) |
| Median | 19.0 | 18.0 | 19.0 |
| Range | (2; 27) | (0; 27) | (0; 27) |
| Screening C-SSRS lifetime [a], n (%) | | | |
| N | 70 | 64 | 134 |
| No event | 38 (54.3%) | 34 (53.1%) | 72 (53.7%) |
| Suicidal ideation | 24 (34.3%) | 19 (29.7%) | 43 (32.1%) |
| Suicidal behavior | 8 (11.4%) | 11 (17.2%) | 19 (14.2%) |
| Screening C-SSRS past 6 or 12 months [a], n (%) | | | |
| N | 70 | 64 | 134 |
| No event | 42 (60.0%) | 43 (67.2%) | 85 (63.4%) |
| Suicidal ideation (past 6 months) | 28 (40.0%) | 20 (31.3%) | 48 (35.8%) |
| Suicidal behavior (past 12 months) | 0 | 1 (1.6%) | 1 (0.7%) |
| Duration of current episode (wks) | | | |
| N | 72 | 65 | 137 |
| Mean (SD) | 163.1 (277.04) | 274.1 (395.47) | 215.8 (341.71) |
| Median | 83.5 | 104.0 | 92.0 |
| Range | (8; 1700) | (8; 2184) | (8; 2184) |
| No. of previous antidepressant medications [b], n (%) | | | |
| N | 72 | 65 | 137 |
| 1 | 15 (20.8%) | 6 (9.2%) | 21 (15.3%) |
| 2 | 31 (43.1%) | 32 (49.2%) | 63 (46.0%) |
| 3 | 13 (18.1%) | 17 (26.2%) | 30 (21.9%) |
| 4 | 12 (16.7%) | 4 (6.2%) | 16 (11.7%) |
| 5 | 1 (1.4%) | 4 (6.2%) | 5 (3.6%) |
| 7 | 0 | 1 (1.5%) | 1 (0.7%) |
| 8 | 0 | 1 (1.5%) | 1 (0.7%) |
| Family history of depression, n (%) | | | |
| N | 72 | 65 | 137 |
| Yes | 30 (41.7%) | 26 (40.0%) | 56 (40.9%) |
| No | 42 (58.3%) | 39 (60.0%) | 81 (59.1%) |
| Family history of anxiety disorder, n (%) | | | |
| N | 72 | 65 | 137 |
| Yes | 6 (8.3%) | 5 (7.7%) | 11 (8.0%) |
| No | 66 (91.7%) | 60 (92.3%) | 126 (92.0%) |
| Family history of bipolar disorder, n (%) | | | |
| N | 72 | 65 | 137 |
| Yes | 3 (4.2%) | 4 (6.2%) | 7 (5.1%) |
| No | 69 (95.8%) | 61 (93.8%) | 130 (94.9%) |
| Family history of schizophrenia, n (%) | | | |
| N | 72 | 65 | 137 |
| Yes | 2 (2.8%) | 4 (6.2%) | 6 (4.4%) |
| No | 70 (97.2%) | 61 (93.8%) | 131 (95.6%) |
| Family history of alcohol abuse, n (%) | | | |
| N | 72 | 65 | 137 |
| Yes | 3 (4.2%) | 7 (10.8%) | 10 (7.3%) |
| No | 69 (95.8%) | 58 (89.2%) | 127 (92.7%) |
| Family history of substance abuse, n (%) | | | |
| N | 72 | 65 | 137 |
| Yes | 1 (1.4%) | 0 | 1 (0.7%) |
| No | 71 (98.6%) | 65 (100.0%) | 136 (99.3%) |

[a] C-SSRS category: No event = 0; Suicidal ideation = 1, 2, 3, 4, 5; Suicidal behavior = 6, 7, 8, 9, 10;

[b] Number of antidepressant medications with non-response (defined as ≤25% improvement) taken for at least 6 weeks during the current episode as obtained from MGH-ATRQ.

Dosage and Administration

Screening/Prospective Observational Phase: The Screening/Prospective Observational Phase was the same as that described in Example 1.

Double-Blind Induction Phase: The double-blind induction phase was the same as that described in Example 1.

Intranasal Study Drug: The intranasal study drug was the same as that described in Example 1. See, Table 4.

Oral Antidepressant Medication: The oral antidepressant medication treatment was the same as that described in Example 1. See, Table 5.

Guidance on Blood Pressure Monitoring on Intranasal Dosing Days: The guidance on blood pressure monitoring on intranasal dosing days was the same as described in Example 1.

Follow-up Phase: The follow-up phase was the same as that described in Example 1.

Treatment Compliance: The treatment compliance was the same as that described in Example 1.

Pre-Study and Concomitant Therapy: The pre-study and concomitant therapy was the same as that described in Example 1.

Rescue Medications: Rescue medication use is described in Example 1.

Prohibited Medications: A list of prohibited medications is the same as those listed in Table 6 of Example 1.

The number of doses of intranasal study medication was the same as described in Table 7 of Example 1.

A summary of mean, mode and final dose of intranasal study medication is summarized in Table 30. On Day 15 of the Double-blind Induction phase 49/65 (75.4%) were receiving the 84 mg dose of esketamine. Of the 72 subjects treated with intranasal esketamine, 17 (23.6%) of subjects decreased their dose during the double-blind phase.

TABLE 30

Mean, Mode, and Final Daily Dose of Intranasal Study Medication; Double-blind Induction Phase Study ESKETINTRD3005: Safety Analysis Set)

| | Intranasal Esk + Oral AD (N = 72) |
|---|---|
| Mean daily dose (mg) | |
| N | 72 |
| Mean (SD) | 59.8 (15.40) |
| Median | 66.5 |
| Range | (28; 74) |
| Mode daily dose (mg) | |
| N | 71 |
| Mean (SD) | 68.6 (22.09) |
| Median | 84.0 |
| Range | (28; 84) |
| Final daily dose (mg) | |
| N | 72 |
| Mean (SD) | 68.1 (21.45) |
| Median | 84.0 |
| Range | (28; 84) |

The calculation of mean, mode, and final daily dose excludes days off intranasal study medication. The final dose is the last non-zero dose received during the double-blind induction phase.

A summary of mean, mode and final dose of oral AD by each type of oral AD is summarized in Table 31.

TABLE 31

Mean, Mode and Final Daily Dose of Oral Antidepressant; Double-blind Induction Phase (Study ESKETINTRD3005: Safety Analysis Set)

| | Intranasal Esk + Oral AD (N = 72) | Oral AD + Intranasal Placebo (N = 65) |
|---|---|---|
| Duloxetine | | |
| Mean daily dose (mg) | | |
| N | 25 | 23 |
| Mean (SD) | 49.8 (7.42) | 50.3 (7.65) |
| Median | 52.2 | 52.2 |
| Range | (30; 60) | (30; 60) |
| Mode daily dose (mg) | | |
| N | 25 | 23 |
| Mean (SD) | 52.8 (13.08) | 56.1 (10.33) |
| Median | 60.0 | 60.0 |
| Range | (30; 60) | (30; 60) |
| Final daily dose (mg) | | |
| N | 25 | 23 |
| Mean (SD) | 57.6 (8.31) | 57.4 (8.64) |
| Median | 60.0 | 60.0 |
| Range | (30; 60) | (30; 60) |
| Escitalopram | | |
| Mean daily dose (mg) | | |
| N | 25 | 25 |
| Mean (SD) | 10.2 (0.89) | 9.9 (0.58) |
| Median | 10.0 | 10.0 |
| Range | (10; 14) | (7; 10) |
| Mode daily dose (mg) | | |
| N | 25 | 25 |
| Mean (SD) | 10.2 (1.00) | 9.8 (1.00) |
| Median | 10.0 | 10.0 |
| Range | (10; 15) | (5; 10) |
| Final daily dose (mg) | | |
| N | 25 | 25 |
| Mean (SD) | 10.2 (1.00) | 9.8 (1.00) |
| Median | 10.0 | 10.0 |
| Range | (10; 15) | (5; 10) |
| Sertraline | | |
| Mean daily dose (mg) | | |
| N | 15 | 10 |
| Mean (SD) | 70.7 (18.54) | 80.6 (18.70) |
| Median | 74.1 | 82.4 |
| Range | (40; 100) | (38; 108) |
| Mode daily dose (mg) | | |
| N | 15 | 10 |
| Mean (SD) | 81.7 (49.52) | 90.0 (55.53) |
| Median | 50.0 | 75.0 |
| Range | (25; 150) | (25; 150) |
| Final daily dose (mg) | | |
| N | 15 | 10 |
| Mean (SD) | 110.0 (42.05) | 127.5 (41.58) |
| Median | 100.0 | 150.0 |
| Range | (50; 150) | (25; 150) |
| Venlafaxine XR | | |
| Mean daily dose (mg) | | |
| N | 7 | 8 |
| Mean (SD) | 92.7 (29.05) | 86.3 (29.60) |
| Median | 102.2 | 94.1 |
| Range | (49; 140) | (38; 131) |
| Mode daily dose (mg) | | |
| N | 7 | 8 |
| Mean (SD) | 112.5 (48.41) | 107.8 (46.74) |
| Median | 150.0 | 112.5 |
| Range | (38; 150) | (38; 150) |

TABLE 31-continued

Mean, Mode and Final Daily Dose of Oral Antidepressant;
Double-blind Induction Phase (Study ESKETINTRD3005:
Safety Analysis Set)

|  | Intranasal Esk +<br>Oral AD<br>(N = 72) | Oral AD +<br>Intranasal Placebo<br>(N = 65) |
|---|---|---|
| Final daily dose (mg) | | |
| N | 7 | 8 |
| Mean (SD) | 117.9 (40.09) | 117.2 (46.74) |
| Median | 150.0 | 150.0 |
| Range | (75; 150) | (38; 150) |

The calculation of mean, mode, and final daily dose excludes days off oral antidepressant. The final dose is the last non-zero dose received during the double-blind induction phase.

Duration of exposure to oral antidepressant study medication is Summarized in Table 32 and 33.

TABLE 32

Extent of Exposure to Oral Antidepressant; Double-blind Induction
Phase (Study ESKETINTRD3005: Safety Analysis Set)

|  | Serotonin and Norepinephrine Reuptake Inhibitors (SNRI) | | |
|---|---|---|---|
|  | Duloxetine | Venlafaxine XR | Total |
| Intranasal esk + oral AD<br>Total duration, days<br>Category, n (%) | (N = 25) | (N = 7) | (N = 32) |
| ≤7 | 1 (4.0%) | 0 | 1 (3.1%) |
| 8-14 | 2 (8.0%) | 0 | 2 (6.3%) |
| 15-21 | 1 (4.0%) | 2 (28.6%) | 3 (9.4%) |
| 22-28 | 12 (48.0%) | 2 (28.6%) | 14 (43.8%) |
| >28 | 9 (36.0%) | 3 (42.9%) | 12 (37.5%) |
| Mean (SD) | 25.6 (6.70) | 25.6 (5.32) | 25.6 (6.34) |
| Median | 27.0 | 28.0 | 28.0 |
| Range | (5; 31) | (16; 29) | (5; 31) |
| Oral AD + intranasal placebo<br>Total duration, days<br>Category, n (%) | (N = 23) | (N = 8) | (N = 31) |
| ≤7 | 1 (4.3%) | 1 (12.5%) | 2 (6.5%) |
| 8-14 | 0 | 0 | 0 |
| 15-21 | 1 (4.3%) | 0 | 1 (3.2%) |
| 22-28 | 9 (39.1%) | 5 (62.5%) | 14 (45.2%) |
| >28 | 12 (52.2%) | 2 (25.0%) | 14 (45.2%) |
| Mean (SD) | 27.2 (5.52) | 26.3 (8.31) | 26.9 (6.22) |
| Median | 29.0 | 28.0 | 28.0 |
| Range | (5; 35) | (7; 36) | (5; 36) |

Percentages are calculated with the number of subjects in each treatment group as the denominator. The duration of exposure is defined as the duration between the date of the first antidepressant exposure and the date of the last antidepressant exposure. It includes days on which subjects did not actually take medication.

TABLE 33

Extent of Exposure to Oral Antidepressant; Double-blind Induction
Phase (Study ESKETINTRD3005: Safety Analysis Set)

|  | Selective Serotonin Reuptake Inhibitors (SSRI) | | |
|---|---|---|---|
|  | Escitalopram | Sertraline | Total |
| Intranasal esk + oral AD<br>Total duration, days<br>Category, n (%) | (N = 25) | (N = 15) | (N = 40) |
| ≤7 | 0 | 0 | 0 |
| 8-14 | 0 | 0 | 0 |
| 15-21 | 0 | 1 (6.7%) | 1 (2.5%) |
| 22-28 | 11 (44.0%) | 7 (46.7%) | 18 (45.0%) |
| >28 | 14 (56.0%) | 7 (46.7%) | 21 (52.5%) |
| Mean (SD) | 28.9 (2.14) | 28.0 (2.39) | 28.6 (2.25) |
| Median | 29.0 | 28.0 | 29.0 |
| Range | (26; 37) | (21; 32) | (21; 37) |
| Oral AD + intranasal placebo<br>Total duration, days<br>Category, n (%) | (N = 25) | (N = 10) | (N = 35) |
| ≤7 | 0 | 0 | 0 |
| 8-14 | 1 (4.0%) | 0 | 1 (2.9%) |
| 15-21 | 1 (4.0%) | 1 (10.0%) | 2 (5.7%) |
| 22-28 | 11 (44.0%) | 5 (50.0%) | 16 (45.7%) |
| >28 | 12 (48.0%) | 4 (40.0%) | 16 (45.7%) |
| Mean (SD) | 27.8 (4.93) | 31.2 (9.47) | 28.7 (6.59) |
| Median | 28.0 | 28.0 | 28.0 |
| Range | (11; 35) | (20; 49) | (11; 49) |

Percentages are calculated with the number of subjects in each treatment group as the denominator. The duration of exposure is defined as the duration between the date of the first antidepressant exposure and the date of the last antidepressant exposure. It includes days on which subjects did not actually take medication.

Study Evaluations

The study evaluations were performed as described in Example 1. The time and events schedule was the same as described in Example 1 in Tables 10 and 11. The approximate total blood volume to be collected from each subject was the same as described in Example 1. See, Table 12.

Screening/Prospective Observational Phase

The screening/prospective observational phase was the same as described in Example 1. After signing the ICF, subjects who were ≥65 years of age (inclusive) were screened to determine eligibility for study participation.

Optional Antidepressant Taper Period: The optional antidepressant taper period was performed as described in Example 1.

Double-Blind Induction Phase: The double-blind induction phase was performed as described in Example 1.

Early Withdrawal: The early withdrawal of patient was followed according to the procedure in Example 1.

Follow-up Phase: The follow-up phase was performed as described in Example 1.

Efficacy Evaluations

Efficacy evaluations were performed as described in Example 1.

Primary Efficacy Evaluation: The primary efficacy evaluation is described in Example 1.

Key Secondary Efficacy Evaluation (Clinician-completed): The key secondary efficacy evaluation (clinician-completed) is described in Example 1.

Key Secondary Efficacy Evaluation (Patient-reported Outcome): The key secondary efficacy evaluation (patient-reported outcome) is described in Example 1.

Primary Endpoint: The primary efficacy endpoint is described in Example 1.

Figure 19:
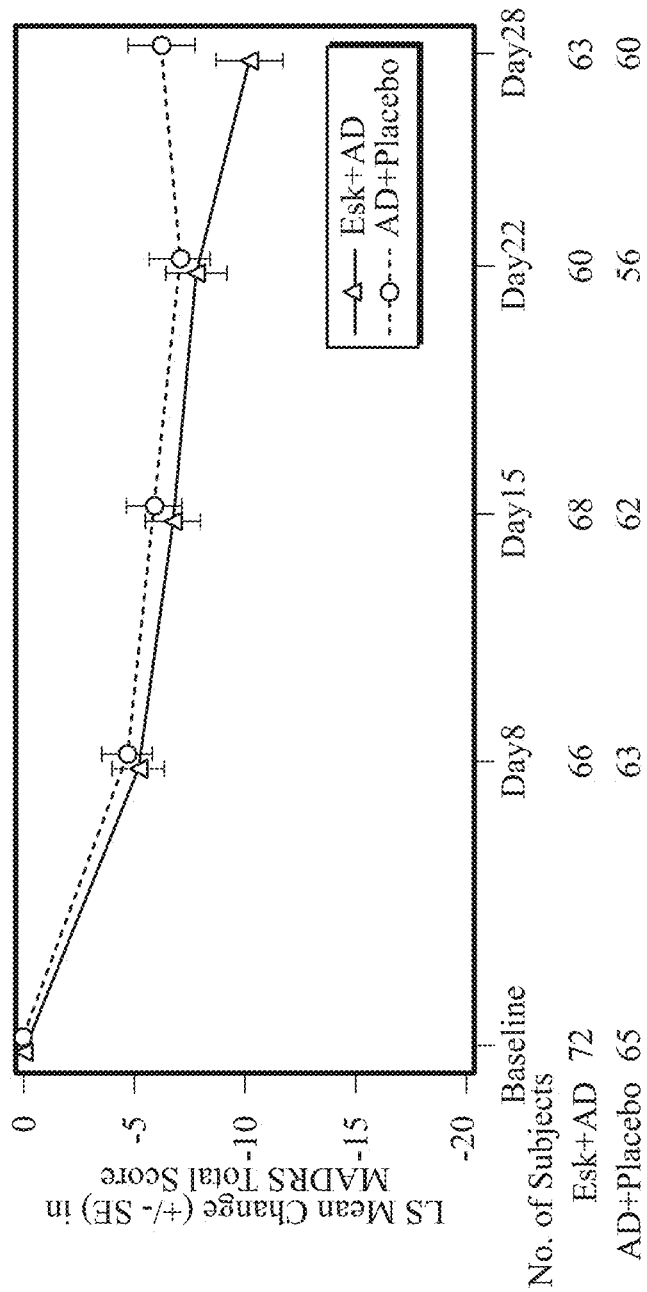
FIG. 19 illustrates the least squares mean changes (±SE) in MADRS total score over time observed case MMRM; double-blind induction phase (study ESKETINTRD3005: full analysis set).

Primary Endpoint Results: The primary endpoint results are the same as described in Example 1. See, Table 34 and FIG. 19.

TABLE 34

MADRS Total Score: Change From Baseline to
Day 28 MMRM; Double-blind Induction Phase
(Study ESKETINTRD3005: Full Analysis Set)

|  | Intranasal Esk + Oral AD (N = 72) | Oral AD + Intranasal Placebo (N = 65) |
|---|---|---|
| Baseline | | |
| N | 72 | 65 |
| Mean (SD) | 35.5 (5.91) | 34.8 (6.44) |
| Median (Range) | 36.0 (23; 50) | 35.0 (19; 51) |
| Day 28 | | |
| N | 63 | 60 |
| Mean (SD) | 25.4 (12.70) | 28.7 (10.11) |
| Median (Range) | 25.0 (0; 47) | 30.0 (2; 44) |
| Change from baseline to day 28 | | |
| N | 63 | 60 |
| Mean (SD) | −10.0 (12.74) | −6.3 (8.86) |
| Median (Range) | −5.0 (−42; 10) | −4.5 (−33; 11) |
| MMRM analysis [a] | | |
| Diff. of LS means (Esk + AD minus AD + Placebo) [b] | −3.6 | |
| 95% confidence interval on diff. [c] | −7.20; 0.07 | |
| 1-sided p-value [d] | 0.029 NS | |

[a] Test for treatment effect is based on mixed model for repeated measures (MMRM) with change from baseline as the response variable and the fixed effect model terms for treatment (intranasal esk + oral AD, oral AD + intranasal placebo), day, region, class of oral antidepressant (SNRI or SSRI), and treatment-by-day, and baseline value as a covariate. A negative difference favors esketamine.
[b] Difference from placebo is the median unbiased estimate, which is a weighted combination of the least squares means of the difference from placebo
[c] 2-sided flexible confidence interval
[d] P-value is based on the weighted combination test statistics
MADRS Total score ranges from 0 to 60; a higher score indicates a more severe condition. Negative change in score indicates improvement.

Figure 23:
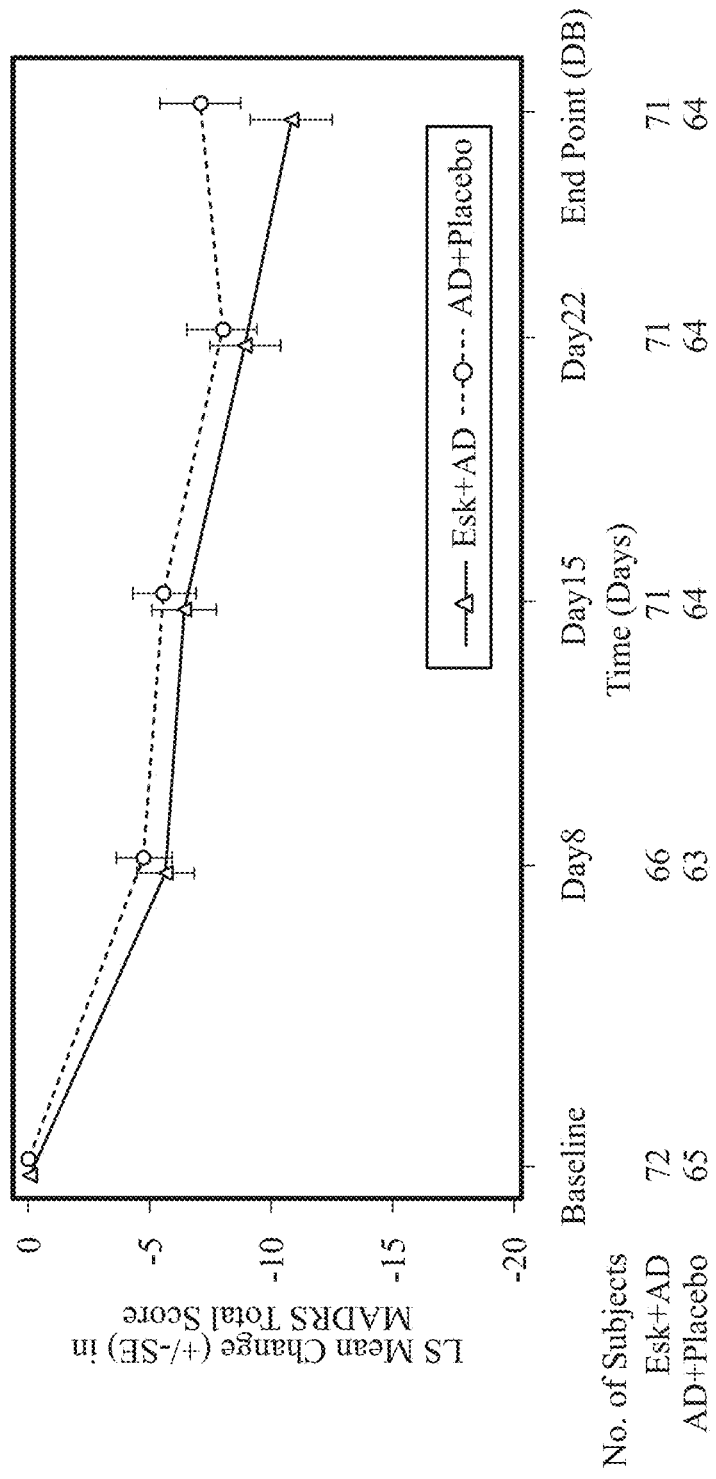
FIG. 23 illustrates the least squares mean changes (t SE) in MADRS total score over time LOCF ANCOVA during the double-blind induction phase using the full analysis set. LS Mean and SE were based on analysis of covariance (ANCOVA) model with change from baseline as the response variable and factors for treatment (intranasal esk+oral AD, oral AD+intranasal placebo), region, and class of oral antidepressant (SNRI or SSRI), and baseline value as a covariate. Results are not adjusted for sample size re-estimation. Negative change in score indicates improvement.
Figure 24:
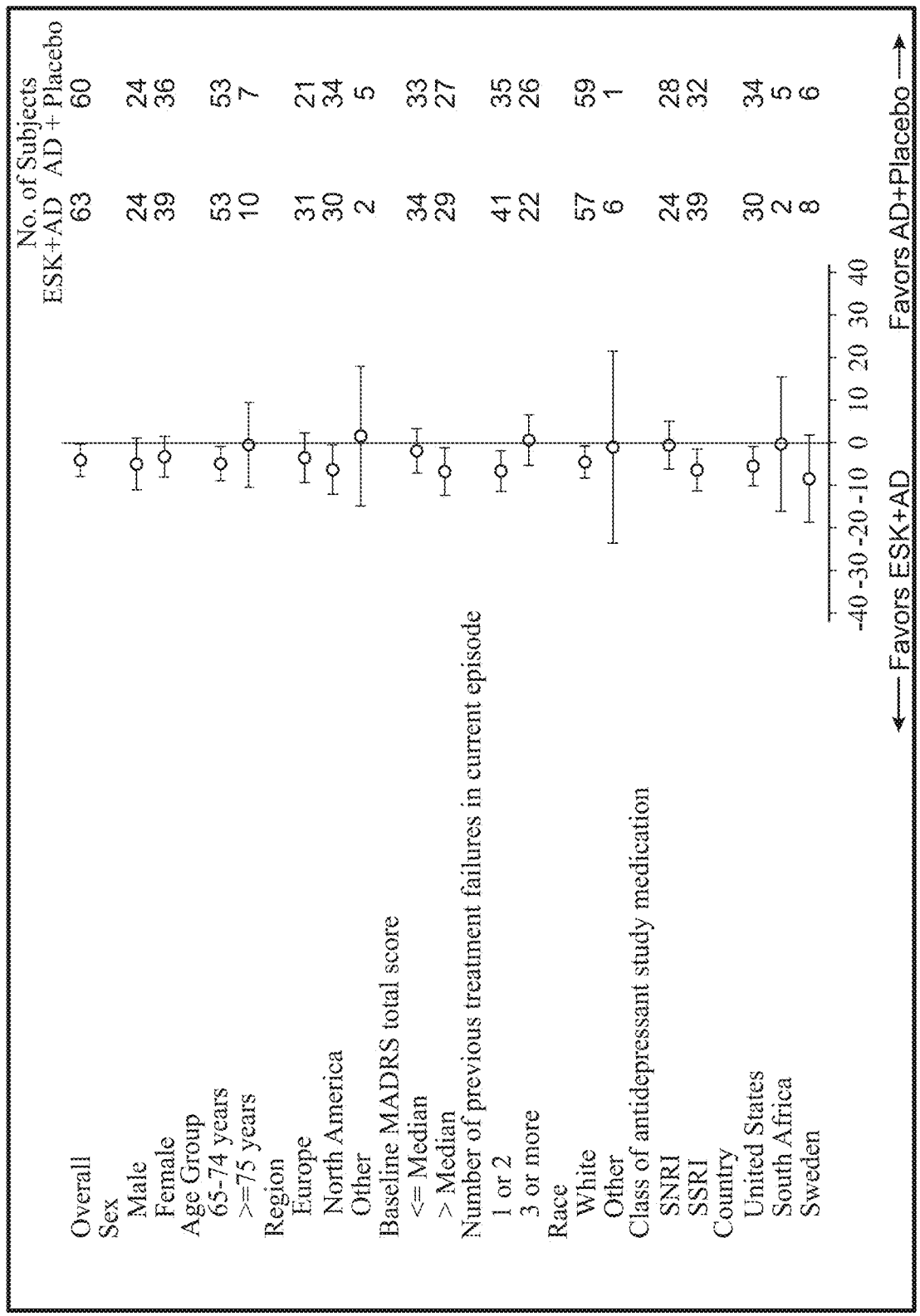
FIG. 24 illustrates the forest plot for MADRS total score showing the least squares mean treatment difference of change from baseline (95% Confidence Interval) to day 28

FIG. 23 shows the least square mean changes (t) from baseline for the MADRS total score over time in the double-blind phase based on the MMRM analysis. This data shows that, when compared to a younger population, a longer induction period is required to achieve the desired response. See, FIG. 2 which shows the response for the corresponding younger population (-▲-).
Secondary Endpoints: The secondary endpoints were the same as described in Example 1.
Subgroup Analyses
A forest plot showing the treatment differences based on an MMRM analysis for the preplanned subgroups are shown in FIG. 24. There was a notable difference by age subgroup. The arithmetic mean changes over time for the MADRS total score are presented by age group in FIGS. 25 and 26. The difference in LS mean change (SE) based on the MMRM analysis at Day 28 was −4.9 (2.04) for subjects aged 65-74 and −0.4 (5.02) for subjects aged 75 and above. However, the number of subjects in the higher age group was low.
Post-Hoc Analyses for Primary Endpoint
As specified in the SAP, the weighted combination test was the primary analysis for the primary efficacy endpoint since an interim analysis for sample size re-estimation was conducted. A post-hoc analysis using an unweighted MMRM analysis (essentially disregarding the interim analysis) was performed and the one-sided p-value was 0.018 using this approach. The post-hoc one-sided p-value was 0.017 using the unweighted ANCOVA analysis.
In addition, a treatment by stage (before and after IA was performed) interaction was explored. A differential treatment effect was seen for Stage 1 (those subjects enrolled prior to when the IA was performed) and Stage 2 (those subjects enrolled after the IA was performed). The LS mean (SE) treatment difference was −1.6 (2.62) for Stage 1 and −5.6 (2.63) for Stage 2. See, FIG. 27 (Stage 1) and FIG. 28 (Stage 2) for the LS mean changes over time for each treatment group.
Response and Remission Rates Based on MADRS Total Score
Response (≥50% improvement from baseline in the MADRS total score) and Remission (MADRS total score is ≤12) rates are presented in Table 35.

TABLE 35

Response and Remission Rates Based on MADRS; Double-blind
Induction Phase (Study ESKETINTRD3005: Full Analysis Set)

|  | Response | | Remission | |
|---|---|---|---|---|
|  | Intranasal Esk + Oral AD | Oral AD + Intranasal Placebo | Intranasal Esk + Oral AD | Oral AD + Intranasal Placebo |
| Day 8 | 4/66 (6.1%) | 3/63 (4.8%) | 4/66 (6.1%) | 1/63 (1.6%) |
| Day 15 | 4/68 (5.9%) | 8/62 (12.9%) | 2/68 (2.9%) | 5/62 (8.1%) |
| Day 22 | 9/60 (15.0%) | 8/56 (14.3%) | 4/60 (6.7%) | 4/56 (7.1%) |
| Day 28 | 17/63 (27.0%) | 8/60 (13.3%) | 11/63 (17.5%) | 4/60 (6.7%) |

A subject is defined as a responder at a given time point if the percent improvement from baseline in MADRS total score is at least 50%. A subject is in remission at a given time point if the MADRS total score is ≤12.

The response rates (≥50% improvement from baseline) at Day 28 based on the MADRS total score were 17/63 (27.0%) and 8/60 (13.3%) for the intranasal esketamine+oral AD and oral AD+ intranasal placebo groups, respectively. The remission rates (MADRS total score ≤12) at Day 28 were 11/63 (17.5%) and 4/60 (6.7%) for the intranasal esketamine+oral AD and oral AD+ intranasal placebo groups, respectively.
Safety Evaluations: Safety evaluations were performed as described in Example 1.
Adverse Events: Adverse events were followed as described in Example 1.
Clinical Laboratory Tests: Clinical laboratory tests were performed as described in Example 1.
Subject Completion/Withdrawal
Completion
A subject was considered to have completed the double-blind induction phase of the study if he or she completed the MADRS assessment at the end of the 4-week double-blind induction phase (i.e., Day 28 MADRS) as described in Example 1.
Withdrawal from the Study: A subject was withdrawn from the study for any of the nine reasons provided in Example 1.
Safety Analyses: Safety data was analyzed for the double-blind induction phase using the safety analysis set.
Adverse Events: The verbatim terms used in the eCRF by investigators to identify adverse events were coded using the MedDRA as described in Example 1.
Clinical Laboratory Tests: Clinical laboratory tests were performed as described in Example 1.
ECG: The effects on cardiovascular variables were evaluated by means of descriptive statistics and frequency tabulations. These tables include observed values and change from baseline values. Electrocardiogram data was summarized by ECG parameter as described in Example 1.
Vital Signs: Vital signs were obtained as described in Example 1.
Nasal Examination: Nasal examinations were performed as described in Example 1.

Nasal Symptom Questionnaire: Scoring from the nasal symptom questionnaire was summarized descriptively for each scheduled time point by treatment group as described in Example 1.

C-SSRS: Suicide-related thoughts and behaviors based on the C-SSRS were summarized by treatment group in incidence and shift tables as described in Example 1. Separate endpoints for suicidal ideation and suicidal behavior were defined and summarized descriptively by treatment group. Missing scores were not imputed.

CADSS, BPRS+, and MOAA/S: Descriptive statistics of each score and changes from pre-dose were summarized at each scheduled time point as described in Example 1.

Clinical Global Assessment of Discharge Readiness, PWC-20, BPIC-SS, UPSIT, and Smell Threshold Test Descriptive statistics of each score and changes and/or percent changes from baseline were summarized at each scheduled time point as described in Example 1.

Cognition Testing: Descriptive statistics of the cognitive domain scores and changes from baseline were summarized at each scheduled time point.

Adverse Event Definitions and Classifications: Adverse event definitions and classifications were performed as described in Example 1.

Special Reporting Situations: Special reporting situations were discussed in Example 1

Procedures: All Adverse Events

All adverse events and special reporting situations, whether serious or non-serious, were reported from the time a signed and dated ICF was obtained until completion of the subject's last study-related procedure (which may include contact for follow-up of safety) as described in Example 1.

Serious Adverse Events: Serious adverse event studies were performed as described in Example 1.

Pregnancy: Pregnancy was assessed as described in Example 1.

Summary of all Adverse Events

An overall summary of all treatment-emergent adverse events (TEAEs) during the double-blind phase is presented in Table 36. Overall, 70.8% of subjects in the esketamine+oral AD group and 60.0% of subjects in the oral AD+placebo group experienced at least one TEAE during the double-blind phase.

TABLE 36

Overall Summary of Treatment-emergent Adverse Events (TEAE); Double-blind Induction Phase (Study ESKETINTRD3005: Safety Analysis Set)

| | Intranasal Esk + Oral AD (N = 72) | Oral AD + Intranasal Placebo (N = 65) |
|---|---|---|
| TEAE | 51 (70.8%) | 39 (60.0%) |
| TEAE possibly related to intranasal drug [a] | 42 (58.3%) | 22 (33.8%) |
| TEAE possibly related to oral antidepressant [a] | 13 (18.1%) | 11 (16.9%) |
| TEAE leading to death | 0 | 0 |
| 1 or more serious TEAE | 3 (4.2%) | 2 (3.1%) |
| TEAE leading to intranasal drug withdrawn [b] | 4 (5.6%) | 2 (3.1%) |
| TEAE leading to oral antidepressant withdrawn [b] | 1 (1.4%) | 1 (1.5%) |

[a] Study drug relationships of possible, probable, and very likely are included in this category.
[b] An adverse event that started in the double-blind induction phase and resulted in discontinuation in the follow-up phase is counted as treatment-emergent in the double-blind induction phase.
Incidence is based on the number of subjects experiencing at least one adverse event, not the number of events. Adverse events are coded using MedDRA version 20.0.

Treatment-emergent adverse events occurring during the double-blind phase (>5% of subjects in either treatment group) are summarized by treatment group for the safety analysis set in Table 37. The most common (>10%) TEAEs in the esketamine+oral AD group during the double-blind phase were dizziness (20.8%), nausea (18.1%), headache (12.5%), fatigue (12.5%), blood pressure increased (12.5%), vertigo (11.1%) and dissociation (11.1%). The most common TEAE in the oral AD+placebo group were anxiety (7.7%), dizziness (7.7%) and fatigue (7.7%). There were no deaths.

TABLE 37

Treatment-emergent Adverse Events in at Least 5% of Subjects in Either Treatment Group; Double-blind Induction Phase (Study ESKETINTRD3005: Safety Analysis Set)

| | Intranasal Esk + Oral AD (N = 72) | Oral AD + Intranasal Placebo (N = 65) |
|---|---|---|
| Total no. subjects with TEAE | 51 (70.8%) | 39 (60.0%) |
| Psychiatric disorders | 26 (36.1%) | 11 (16.9%) |
| Dissociation | 8 (11.1%) | 1 (1.5%) |
| Dysphoria | 4 (5.6%) | 0 |
| Insomnia | 4 (5.6%) | 3 (4.6%) |
| Anxiety | 2 (2.8%) | 5 (7.7%) |
| Nervous system disorders | 24 (33.3%) | 15 (23.1%) |
| Dizziness | 15 (20.8%) | 5 (7.7%) |
| Headache | 9 (12.5%) | 2 (3.1%) |
| Dysgeusia | 4 (5.6%) | 3 (4.6%) |
| Hypoesthesia | 4 (5.6%) | 1 (1.5%) |
| Paresthesia | 4 (5.6%) | 2 (3.1%) |
| Gastrointestinal disorders | 19 (26.4%) | 8 (12.3%) |
| Nausea | 13 (18.1%) | 3 (4.6%) |
| Hypoesthesia oral | 5 (6.9%) | 0 |
| Vomiting | 5 (6.9%) | 1 (1.5%) |
| General disorders and administration site conditions | 14 (19.4%) | 9 (13.8%) |
| Fatigue | 9 (12.5%) | 5 (7.7%) |
| Investigations | 14 (19.4%) | 6 (9.2%) |
| Blood pressure increased | 9 (12.5%) | 3 (4.6%) |
| Ear and labyrinth disorders | 10 (13.9%) | 4 (6.2%) |
| Vertigo | 8 (11.1%) | 2 (3.1%) |
| Infections and infestations | 8 (11.1%) | 6 (9.2%) |
| Urinary tract infection | 6 (8.3%) | 1 (1.5%) |

Incidence is based on the number of subjects experiencing at least one adverse event, not the number of events. Adverse events are coded using MedDRA version 20.0.

Adverse Events Leading to Study Drug Withdrawal

There were 6 subjects (4 subjects in the esketamine+oral AD group and 2 subject in the oral AD+placebo group) who discontinued the double-blind induction phase intranasal study medication due to treatment-emergent adverse events. See, Table 19. There were 2 subjects (1 subject in the esketamine+oral AD group and 1 subject in the oral AD+placebo group) who discontinued the double-blind phase due to TEAEs. See, Tables 38 and 39.

TABLE 38

Treatment-emergent Adverse Events Leading to Discontinuation of Intranasal Study Medication; Double-blind Induction Phase (Study ESKETINTRD3005: Safety Analysis Set)

| | Intranasal Esk + Oral AD (N = 72) | Oral AD + Intranasal Placebo (N = 65) |
|---|---|---|
| Total no. subjects with TEAE leading to discontinuation [a] | 4 (5.6%) | 2 (3.1%) |
| Investigations | 2 (2.8%) | 0 |
| Blood pressure increased | 1 (1.4%) | 0 |
| Blood pressure systolic increased | 1 (1.4%) | 0 |

TABLE 38-continued

Treatment-emergent Adverse Events Leading to Discontinuation of Intranasal Study Medication; Double-blind Induction Phase (Study ESKETINTRD3005: Safety Analysis Set)

|  | Intranasal Esk + Oral AD (N = 72) | Oral AD + Intranasal Placebo (N = 65) |
| --- | --- | --- |
| Injury, poisoning and procedural complications | 1 (1.4%) | 0 |
| Hip fracture | 1 (1.4%) | 0 |
| Psychiatric disorders | 1 (1.4%) | 1 (1.5%) |
| Anxiety disorder | 1 (1.4%) | 0 |
| Anxiety | 0 | 1 (1.5%) |
| Feeling of despair | 0 | 1 (1.5%) |
| Eye disorders | 0 | 1 (1.5%) |
| Dry eye | 0 | 1 (1.5%) |
| Eye color change | 0 | 1 (1.5%) |
| Eye inflammation | 0 | 1 (1.5%) |
| Eye pruritus | 0 | 1 (1.5%) |
| General disorders and administration site conditions | 0 | 1 (1.5%) |
| Gait disturbance | 0 | 1 (1.5%) |

[a] An adverse event that started in the double-blind induction phase and resulted in discontinuation in the follow-up phase is counted as treatment-emergent in the double-blind induction phase.
Incidence is based on the number of subjects experiencing at least one adverse event, not the number of events. Adverse events are coded using MedDRA version 20.0.

TABLE 39

Treatment-emergent Adverse Events Leading to Discontinuation of Oral Antidepressant; Double-blind Induction Phase (Study ESKETINTRD3005: Safety Analysis Set)

|  | Intranasal Esk + Oral AD (N = 72) | Oral AD + Intranasal Placebo (N = 65) |
| --- | --- | --- |
| Total no. subjects with TEAE leading to discontinuation [a] | 1 (1.4%) | 1 (1.5%) |
| Psychiatric disorders | 1 (1.4%) | 0 |
| Anxiety disorder | 1 (1.4%) | 0 |
| Eye disorders | 0 | 1 (1.5%) |
| Dry eye | 0 | 1 (1.5%) |
| Eye color change | 0 | 1 (1.5%) |
| Eye inflammation | 0 | 1 (1.5%) |
| Eye pruritus | 0 | 1 (1.5%) |
| Skin and subcutaneous tissue disorders | 0 | 1 (1.5%) |
| Pruritus | 0 | 1 (1.5%) |

[a] An adverse event that started in the double-blind induction phase and resulted in discontinuation in the follow-up phase is counted as treatment-emergent in the double-blind induction phase.
Incidence is based on the number of subjects experiencing at least one adverse event, not the number of events. Adverse events are coded using MedDRA version 20.0.

Serious Adverse Events

Five subjects experienced serious treatment-emergent adverse events during the double-blind phase. One subject in the esketamine+oral AD group experienced anxiety disorder which was considered as of possible relationship to both intranasal esketamine and oral AD. One subject in the esketamine+oral AD group experienced blood pressure increased which was considered as of probable relationship to intranasal esketamine and not related to oral AD. In addition, one subject in the esketamine+oral AD group experienced hip fracture which was considered not related to both intranasal esketamine and oral AD. One subject in the oral AD+placebo group experienced feelings of despair and gait disturbance. The first event was considered as of possible relationship to intranasal placebo and not related to oral AD. The second event was considered as of possible relationship to intranasal placebo and very likely relationship to oral AD. One subject in the oral AD+placebo group experienced dizziness which was considered as of doubtful relationship to both intranasal placebo and oral AD.

Blood Pressure

Figure 20:
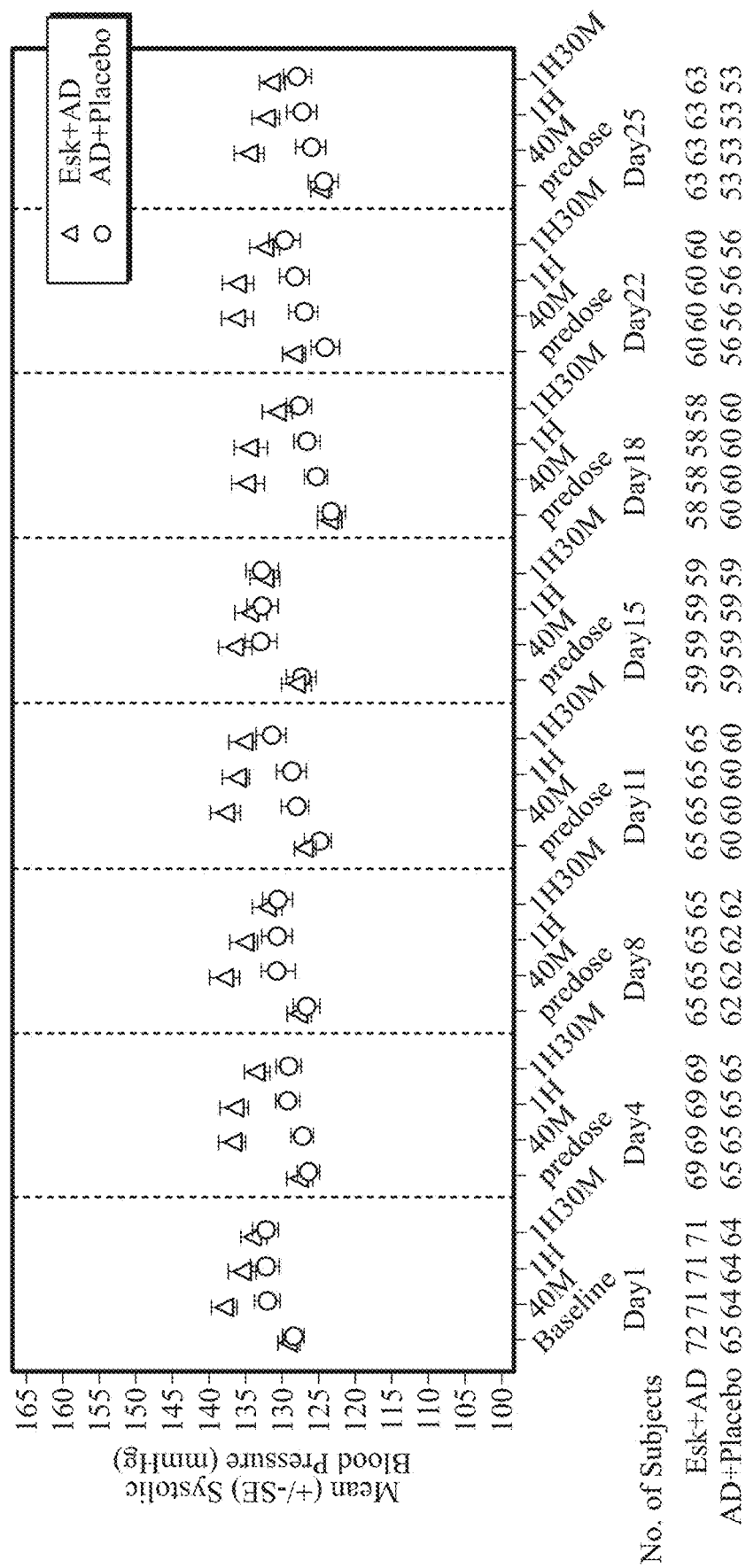
FIG. 20 illustrates that arithmetic mean (±SE) systolic blood pressure over time during the double-blind induction phase using the ESKETINTRD3005 safety analysis set.
Figure 21:
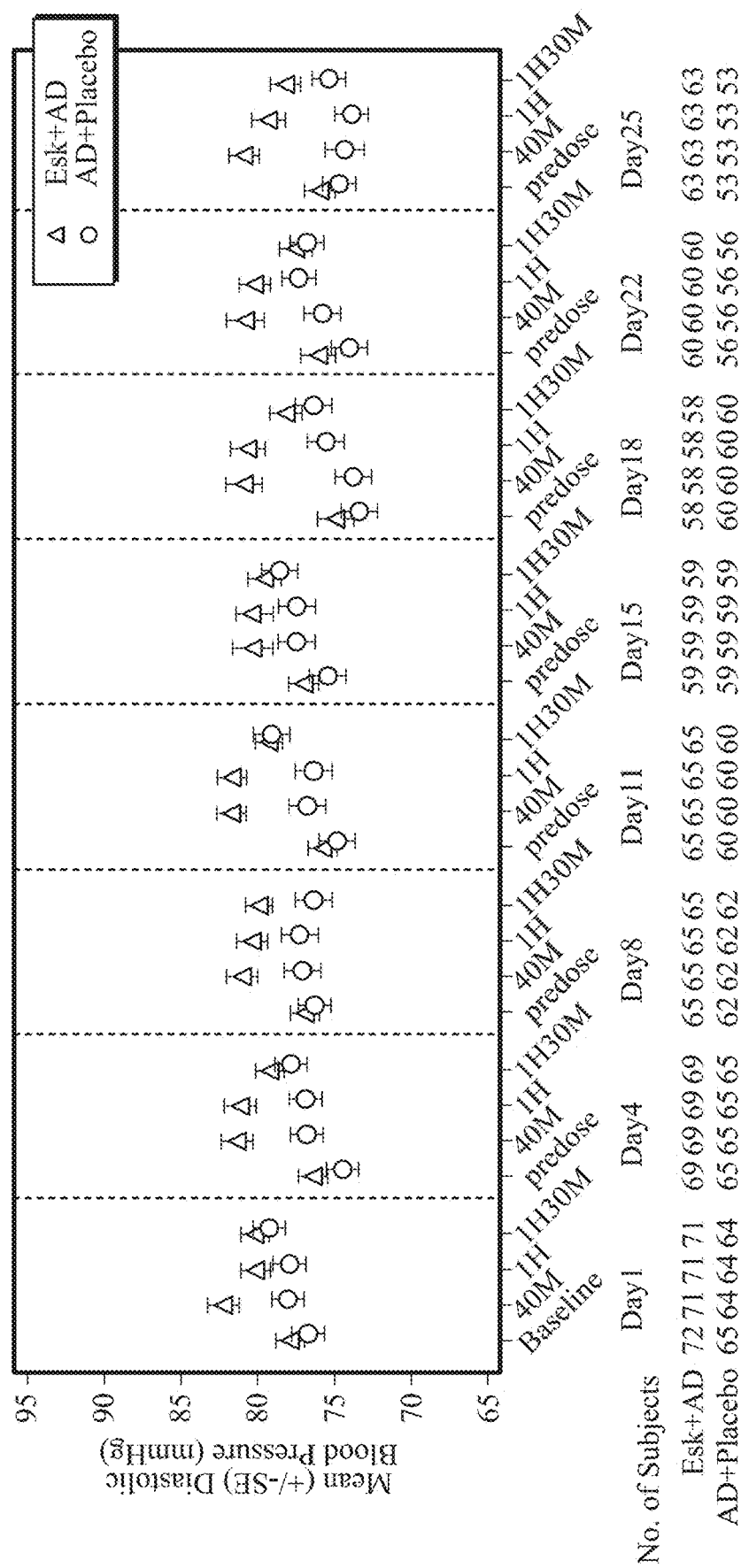
FIG. 21 illustrates that arithmetic mean (±SE) diastolic blood pressure over time during the double-blind induction phase using the ESKETINTRD3005 safety analysis set.

Transient blood pressure increases peaked for the esketamine+oral AD group peaked at approximately 40 minutes post dose and returned to normal range at 90 minutes. The maximum mean increases (across all dosing days) in systolic BP was 16.0 mm Hg in the esketamine+oral AD group and 11.1 mm Hg in the oral AD+placebo group. The maximum mean increases (across all dosing days) in diastolic BP were 9.5 mm Hg in the esketamine+oral AD group and 6.8 mm Hg in the oral AD+placebo group. FIGS. 20 and 21 present means for blood pressure over time by treatment group in the double-blind phase.

Clinician-Assessed Dissociative Symptom Scale (CADSS)

The Clinician Administered Dissociative States Scale (CADSS) was measured prior to the start of each dose, at 40 minutes, and 1.5 hours postdose. The CADSS is used to assess treatment emergent dissociative symptoms and perceptual changes and the total score ranges from 0 to 92 with a higher score representing a more severe condition.

Figure 22:
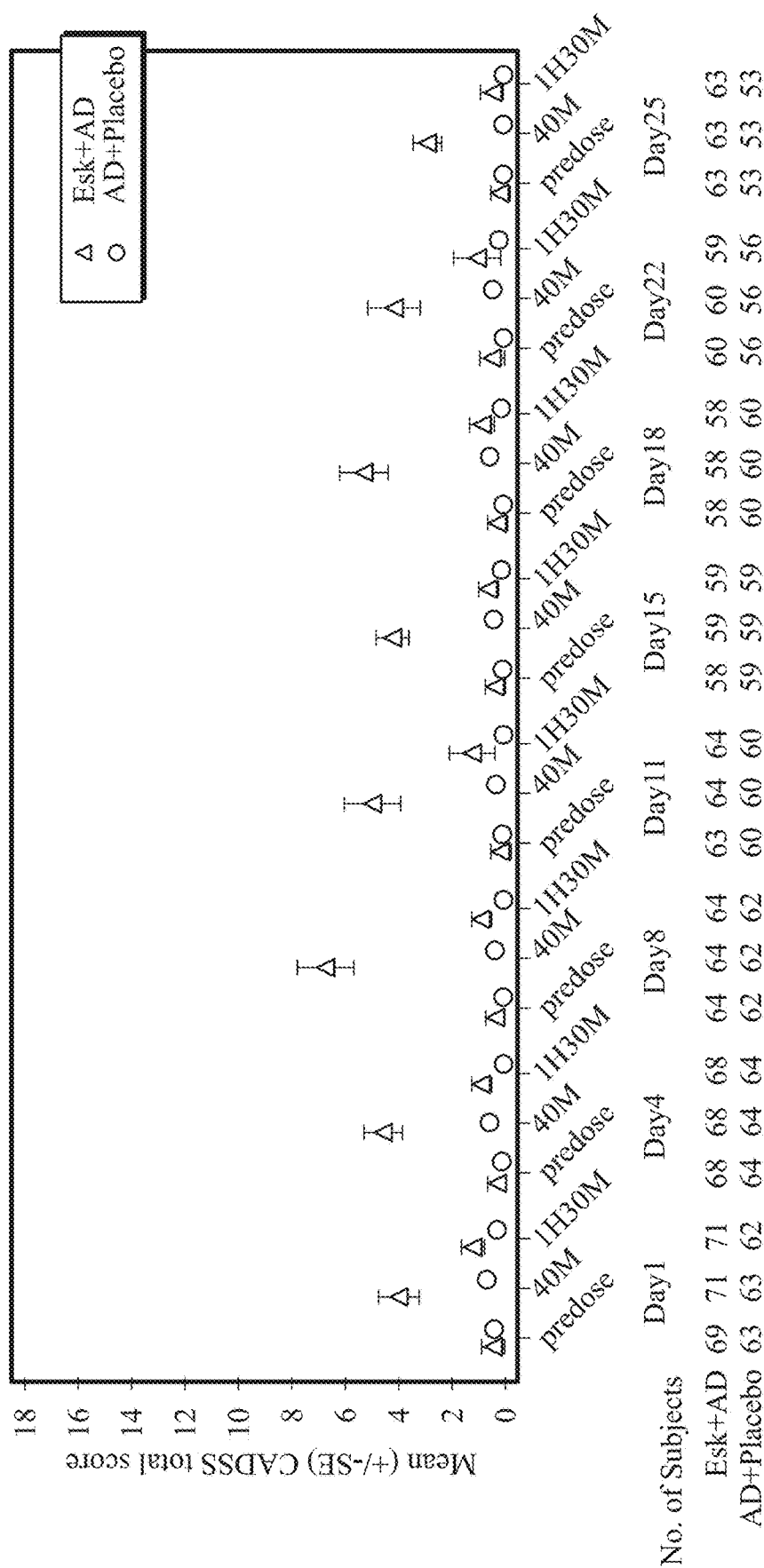
FIG. 22 is a plot of CADSS total score over time during the double-blind phase using the safety analysis set.

The dissociative and perceptual change symptoms measured by the CADSS, suggest these symptoms had an onset shortly after the start of the dose and resolved by 1.5 hours postdose. See, FIG. 22. The proportion of subjects with sedation (post dose MOAA/S score of ≤3) was <4% for the esketamine group for each dosing day.

Modified Observer's Assessment of Alertness/Sedation (MOAA/S)

The Modified Observer's Assessment of Alertness/Sedation (MOAA/S) was used to measure treatment-emergent sedation with correlation to levels of sedation defined by the American Society of Anesthesiologists (ASA) continuum. The MOAA/S scores range from 0 (No response to painful stimulus; corresponds to ASA continuum for general anesthesia) to 5 (Readily responds to name spoken in normal tone [awake]; corresponds to ASA continuum for minimal sedation). The proportion of subjects experienced MOAN/S scores ≤3 post dose by dose day is presented in Table 40. The proportion of subjects with sedation was <4% for the esketamine group for each dosing day.

TABLE 40

Modified Observer's Assessment of Alertness/Sedation (MOAA/S): Frequency of Subjects with a Score of 3 or Less by Dose Day; Double-blind Induction Phase (Study ESKETINTRD3005: Safety Analysis Set)

|  | Intranasal Esk + Oral AD (N = 72) | Oral AD + Intranasal Placebo (N = 65) |
| --- | --- | --- |
| Score ≤3 on Day 1, n (%) | 70 | 64 |
| Yes | 0 | 0 |
| No | 70 (100.0%) | 64 (100.0%) |
| Score ≤3 on Day 4, n (%) | 67 | 65 |
| Yes | 2 (3.0%) | 1 (1.5%) |
| No | 65 (97.0%) | 64 (98.5%) |
| Score ≤3 on Day 8, n (%) | 63 | 62 |
| Yes | 2 (3.2%) | 0 |
| No | 61 (96.8%) | 62 (100.0%) |
| Score ≤3 on Day 11, n (%) | 65 | 60 |
| Yes | 2 (3.1%) | 0 |
| No | 63 (96.9%) | 60 (100.0%) |
| Score ≤3 on Day 15, n (%) | 60 | 59 |
| Yes | 1 (1.7%) | 0 |
| No | 59 (98.3%) | 59 (100.0%) |
| Score ≤3 on Day 18, n (%) | 58 | 60 |
| Yes | 2 (3.4%) | 0 |
| No | 56 (96.6%) | 60 (100.0%) |

TABLE 40-continued

Modified Observer's Assessment of Alertness/Sedation (MOAA/S): Frequency of Subjects with a Score of 3 or Less by Dose Day; Double-blind Induction Phase (Study ESKETINTRD3005: Safety Analysis Set)

|  | Intranasal Esk + Oral AD (N = 72) | Oral AD + Intranasal Placebo (N = 65) |
|---|---|---|
| Score ≤3 on Day 22, n (%) | 60 | 56 |
| Yes | 1 (1.7%) | 0 |
| No | 59 (98.3%) | 56 (100.0%) |
| Score ≤3 on Day 25, n (%) | 63 | 54 |
| Yes | 0 | 0 |
| No | 63 (100.0%) | 54 (100.0%) |

MOAA/S score ranges from 0 (no response to painful stimulus) to 5 (readily responds to name spoken in normal tone [awake]).

Pharmacokinetics

Venous blood samples of approximately 2 mL were collected for measurement of plasma concentrations of esketamine, noresketamine, and other metabolites (if warranted) at the time points specified in the Time and Events Schedule as described in Example 1. Plasma samples were analyzed as described in Example 1.

Pharmacokinetic Parameters: The plasma concentration-time data of esketamine (and noresketamine, if warranted) was analyzed as described in Example 1.

Pharmacokinetic/Pharmacodynamic Evaluations: The relationship between MADRS total score (and possibly selected adverse events as additional PD parameters) and PK metrics of esketamine were evaluated as described in Example 1.

Biomarker, Pharmacogenomic (DNA), and Expression (RNA) Evaluations

During the study, blood was collected for the assessment of biomarkers at the time points indicated in the Time and Events schedule as described in Example 1.

In blood, biomarkers (protein, metabolite, and ribonucleic acid [RNA]) related to (but not limited to) the immune system activity, hypothalamus pituitary adrenal (HPA) axis activation, neurotrophic factors, and metabolic factors were investigated as described in Example 1.

Blood samples for DNA analyses were collected at the time points indicated in the Time and Events Schedule for the assessment of genetic and epigenetic variation in genes in pathways relevant to depression (e.g., HPA axis, inflammation, growth factors, monoamine transporters, ion channels, and circadian rhythm) as described in Example 1.

Medical Resource Utilization: Medical resource utilization data, associated with medical encounters, were collected during the follow-up phase of the study as described in Example 1.

Pharmacokinetic Analyses: Pharmacokinetic analyses were performed as described in Example 1.

Pharmacokinetic/Pharmacodynamic Analyses: The relationship between MADRS total score (and possibly selected adverse events as additional PD parameters) and PK metrics of esketamine were evaluated as described in Example 1.

Biomarker and Pharmacogenomic Analyses: Biomarker and pharmacogenomics analyses were performed as described in Example 1.

Statistical Methods Used in Analysis

A general description of the statistical methods used to analyze the efficacy and safety data is outlined in Example 1.

Interim Analysis for Sample Size Re-estimation or Stopping for Futility: An interim analysis for sample size re-estimation or stopping for futility was performed as described in Example 1.

Efficacy Analyses: Efficacy analyses were performed as described in Example 1.

Analysis of the US Subpopulation—Clinical Efficacy and Safety

Although the primary efficacy analysis using the weighted combination test was not statistically significant, treatment differences were clinically meaningful for ESK+AD change compared to AD+PBO for improving depressive symptoms, as assessed by change in MADRS total score after 28 days in elderly subjects with TRD. Based on MMRM analysis, the median-unbiased estimate of the difference between ESK+AD and AD+PBO was −3.6 (95% CI: −7.20, 0.07). The differences were similar to those seen in studies that assessed SSRI/SNRI oral ADs against placebo in adults with depression.

The greater numerical improvement in depression response (approximately 2 times greater) and remission rates (approximately 3 times greater) for ESK+AD compared to AD+PBO at Day 28 suggested a true clinical benefit of treatment with esketamine nasal spray plus an oral antidepressant in elderly subjects with TRD.

There was also a clinically meaningful treatment difference for improvement in the overall severity of depressive illness based on CGI-S score for ESK+AD over AD+PBO.

A. Outcomes

For the clinician-rated assessments, MADRS was administered at baseline and days 8, 15, 22 and 28. MADRS scores were obtained remotely by telephone by independent raters blinded to subject's treatment response. Similarly, the Clinical Global Impressions-Severity (CGI-S) scale was administered at baseline: days 4, 8, 11, 15, 18, 22, 25; and at the 4-week double-blind end point.

For the patient-rated assessments, a 9-item Patient Adherence Questionnaire-9 (PHQ-9) and Sheehan Disability Scale (SDS) were administered at baseline, day 15, and day 28. Although PHQ-9 and SDS assessments were eliminated by study amendment, site pads were not modified, therefore data were collected.

B. Patient Demographics/Disease Characteristics

Inclusion criteria included adults, aged ≥65 years, who met DSM-5 diagnostic criteria for recurrent MDD without psychotic features or single episode MDD (with duration of episode >2 years) and Inventory of Depressive Symptoms-Clinician rated, 30-item score of ≥31.

Inclusion criteria also included nonresponsive (≤25% improvement in the MADRS) to ≥1 but ≤8 AD treatments in the current episode of depression taken for at least 6 weeks at a therapeutic dose (based on the Massachusetts General Hospital Antidepressant Treatment Response Questionnaire-geriatric version).

Patients must have had a current major depressive episode, depression symptom severity (Week 1 MADRS total score ≥24), and AD treatment response in the current depressive episode, confirmed using a Site Independent Qualification Assessment Of the 70 US patients aged ≥65 years, 34 received ESK+AD and 36 received AD+PBO. The baseline patient demographics and disease characteristics were generally similar between the 2 treatment groups (Table 41). The overall mean age was 70.0 years, 57.1% were women, and most patients were white (98.6%). The mean age at MDD diagnosis was 42.5 years, indicating on average, a >27-year history of depression in this population. The baseline MADRS, CGI-S and PHQ-9 scores were consistent with an adult population with TRD.

TABLE 41

Baseline patient demographics and disease characteristics in US patients

| Parameter | ESK + AD (n = 34) | AD + PBO (n = 36) |
|---|---|---|
| Age, y, mean (SD) | 70.7 (4.5) | 69.3 (4.1) |
| Sex, n (%) | | |
| Male | 15 (44.1) | 15 (41.7) |
| Female | 19 (55.9) | 21 (58.3) |
| Race, n (%) | | |
| White | 33 (97.1) | 36 (100.0) |
| Multiple | 1 (2.9) | 0 |
| Class of oral ADs, n (%)† | | |
| SNRI | 16 (47.1) | 17 (47.2) |
| SSRI | 18 (52.9) | 19 (52.8) |
| Duration of current episode, weeks, mean (SD) | 187.6 (283.4) | 420.9 (480.7) |
| Age at MDD diagnosis, yr, mean (SD) | 42.1 (15.3) | 43.0 (15.1) |
| MADRS total score,[a] mean (SD) | 35.5 (5.5) | 35.7 (6.0) |
| CGI-S,[b] mean (SD) | 5.0 (0.6) | 4.7 (0.6) |
| PHQ-9 total score,[c] mean (SD) | 15.2 (5.6) | 18.2 (5.6) |
| SDS total score,[d] mean (SD) | 20.9 (6.19) | 22.1 (4.72) |

C. Efficacy

Efficacy was determined by measuring MADRS total scores, SDS scores, PHQ-9 scores, and CGI-S scores. The primary efficacy endpoint, compared between treatment groups, was the change in the MADRS total score from baseline to day 28. Other efficacy measures were changes in CGI-S scores, SDS total scores, and PHQ-9 total scores, which assessed changes in general clinical condition and function. Efficacy analysis was conducted at a one-sided 0.025 level of significance.

For the MADRS, PHQ-9, and SDS total scores, the test for treatment effect was based on mixed model for repeated measures (MMRM) on observed case data with change from baseline as the response variable and the fixed effect model terms for treatment (ESK+AD, AD+PBO), day, class of oral AD (SNRI or SSRI), and treatment-by-day, and baseline value as a covariate. For the CGI-S scores, the test for treatment effect was based on analysis of covariance (ANCOVA) model on last observation carried forward (LOCF) data on ranks of change from baseline as the response variable and factors for treatment (ESK+AD, AD+PBO), and class of oral AD (SNRI or SSRI), and baseline value (unranked) as a covariate.

The results illustrate that the least square (LS) mean changes in MADRS total score decreased in both treatment groups during the 4-week double-blind induction phase. See, FIG. 29. Statistically significant improvement in MADRS total score was observed with ESK+AD vs AD+PBO at day 28 (LS mean difference [SE]: −5.4 [2.48]; 1-sided P=0.016). See, Table 42.

In summary, ESK+AD compared with AD+PBO (active comparator) demonstrated a clinically meaningful, statistically significant reduction of depressive symptoms and an improvement in overall severity of depressive illness and in health-related quality of life and functioning in US patients aged ≥65 years with TRD at 4 weeks.

TABLE 42

Change from baseline in MADRS total score (observed case) in US patients aged ≥65 years with TRD

| MADRS parameter | ESK + AD (n = 34) | AD + PBO (n = 36) |
|---|---|---|
| Total score at baseline, mean (SD) | 35.5 (5.5) | 35.7 (6.0) |
| Change at day 8 | | |
| N | 32 | 35 |
| LS mean change | −6.3 | −4.7 |
| LS mean difference from AD + PBO (SE) | −1.6 (1.71) | |
| P value | .176 | |
| Change at day 28 (4-weeks post-initial dose) | | |
| N | 30 | 34 |
| LS mean change | −11.9 | −6.5 |
| LS mean difference from AD + PBO (SE) | −5.4 (2.48) | |
| P value | .016 | |

MADRS total score ranges from 0 to 60; a higher score indicated a more severe condition.

Clinician-rated severity of depressive illness as assessed by CGI-S was similar 4 days post-initial dose. However, a statistically significant difference in improvement of severity of depressive illness as measured by CGI-S was observed between the two treatment groups 4 weeks post-initial dose (1-sided P=0.005). See, Table 43.

TABLE 43

Change from baseline in PHQ-9 and SDS total scores (observed case) in US patients aged ≥65 years with TRD

| Parameter | ESK + AD (n = 34) | AD + PBO (n = 36) |
|---|---|---|
| PHQ-9 total score | | |
| Baseline, mean (SD) | 15.2 (5.6) | 18.2 (5.6) |
| Change at day 15 | | |
| N | 25 | 23 |
| LS mean change | −6.1 | −3.0 |
| LS mean difference from AD + PBO (SE) | | −3.1 (1.38) |
| P value | | 0.015 |
| Change at day 28 | | |
| N | 31 | 32 |
| LS mean change | −7.4 | −3.0 |
| LS mean difference from AD + PBO (SE) | | −4.4 (1.68) |
| P value | | 0.006 |
| SDS total score | | |
| Baseline, mean | 20.9 (6.19) | 22.1 (4.72) |
| Change at day 15 | | |
| N | 9 | 12 |
| LS mean change | −5.5 | −9.0 |
| LS mean difference from AD + PBO (SE) | | 3.5 (4.15) |
| P value | | 0.794 |
| Change at day 28 | | |
| N | 11 | 19 |
| LS mean change | −10.8 | −3.2 |
| LS mean difference from AD + PBO (SE) | | −7.6 (2.68) |
| P value | | 0.004 |

PHQ-9 total score ranges from 0 to 27; a higher score indicates greater depression. SDS total scores range from 0 to 30, where 0 = unimpaired and 30 = highly impaired.

The frequency distribution of illness severity based on CGI-S scores at baseline and the double-blind phase endpoint are shown in FIG. 30. At baseline, the percentage of patients with normal/borderline/mild illness was similar in the ESK+AD and AD+PBO groups (2.9% and 2.8%, respectively). At the double-blind endpoint, the percentage of patients with normal/borderline/mild illness was 3.8-fold higher in the ESK+AD group compared with the AD+PBO group (42.4% and 11.2%, respectively).

The patient-rated severity of depressive illness, as assessed by PHQ-9 total scores, and functional impairment, as assessed by SDS total scores, decreased in both treatment groups, but the magnitude of difference was significantly greater in the ESK+AD group at day 28. See, Table 24. For PHQ-9, the LS mean difference (SE) was −4.4 (1.68; 1-sided P=0.006). For SDS, the LS mean difference (SE) was −7.6 [2.68; 1-sided P=0.004].

D. Safety

Safety evaluation included reported adverse events, clinical laboratory tests, vital sign measurements, physical examinations, electrocardiograms and nasal examinations. Safety was assessed via treatment emergent AEs (TEAEs). Overall, TEAEs were observed in 64.7% of US patients in the ESK+AD group and 58.3% of patients in the AD+PBO group. See, Table 25. There were no deaths. One serious AE was observed in each group. Three patients withdrew the nasal spray (n=2 ESK [systolic BP increase >180; hip fracture], n=1 PBO) and one patient in the AD+PBO group withdrew oral AD (elevated BP, dizziness, and peripheral edema). Most TEAEs were mild or moderate in severity, and no new or unexpected safety signals were observed.

The most common (25% in either treatment group) TEAEs are shown in Table 44. TEAEs tended to be mild to moderate in severity and transient in nature. The incidence of AEs in the US patients was similar to that observed in the overall study population. Results show that ESK+AD showed statistically significant, clinically meaningful AD efficacy in patients aged ≥65 years with a safety profile similar to that observed in younger patients. These observations are similar to the global analysis, which shows clinically meaningful AD efficacy and were similar to those found for the younger population in the ESK phase 3 study and in the phase 2 studies.

TABLE 44

Overview of treatment-emergent adverse events in US patients aged ≥65 years

| Parameter | ESK + AD (n = 34) | PBO + AD (n = 36) |
|---|---|---|
| Overall TEAE, n (%) | 22 (64.7) | 21 (58.3) |
| Possibly related to nasal spray | 15 (44.1) | 10 (27.8) |
| Possibly related to oral AD | 7 (20.6) | 7 (19.4) |
| Leading to death | 0 | 0 |
| 1 or more serious TEAE | 1 (2.9) | 1 (2.8) |
| Leading to nasal spray withdrawal | 2 (5.9) | 1 (2.8) |
| Leading to oral AD withdrawal | 0 | 1 (2.8) |
| Most common (≥5% in either treatment group) TEAEs | | |
| Dysphoria | 4 (11.8) | 0 |
| Fatigue | 4 (11.8) | 3 (8.3) |
| Headache | 4 (11.8) | 1 (2.8) |
| Insomnia | 4 (11.8) | 2 (5.6) |
| Nausea | 4 (11.8) | 0 |
| Abdominal discomfort | 2 (5.9) | 1 (2.8) |
| Cough | 2 (5.9) | 0 |
| Dizziness | 2 (5.9) | 2 (5.6) |
| Erythema | 2 (5.9) | 1 (2.8) |
| Nasal congestion | 2 (5.9) | 0 |
| Urinary tract infection | 2 (5.9) | 0 |
| Vomiting | 2 (5.9) | 0 |
| Anxiety | 1 (2.9) | 2 (5.6) |
| Viral upper respiratory tract infection | 1 (2.9) | 2 (5.6) |
| Muscle strain | 0 | 2 (5.6) |

Analysis of the US Subpopulation—Response, Remission, and Safety

As discussed above for the overall analysis, ESK+AD demonstrated statistically significant and clinically meaningful superiority compared with AD+PBO in primary efficacy endpoint (i.e., change from baseline in the MADRS total score in geriatric patients. See, Montgomery cited above. In this analysis, the response, remission, and safety of these treatment groups were analyzed in only US geriatric patients and to assess for differences in efficacy and safety between the US population and the overall study population.

A. Outcomes

For the clinician-rated assessments, MADRS was administered at baseline and days 8, 15, 22, and 28. Similarly, the Clinical Global Impressions-Severity (CGI-S) scale was administered at baseline and days 4, 8, 11, 15, 18, 22, 25 and 28.

For the patient-rated assessment, a 9-item Patient Adherence Questionnaire-9 (PHQ-9) was administered at baseline, day 15, and day 28.

B. Patient Demographics/Disease Characteristics

Inclusion criteria included adults, aged ≥65 years, who met Diagnostic and Statistical Manual of Mental Disorders, Fifth Edition (DSM-5) diagnostic criteria for recurrent MDD without psychotic features or single episode MDD (with duration of episode >2 years). Nonresponsive (≤25% improvement in the Montgomery-Åsberg Depression Rating Scale [MADRS]) to ≥1 but ≤8 AD treatments in the current episode of depression taken for at least 6 weeks at a therapeutic dose (based on the Massachusetts General Hospital Antidepressant Treatment Response Questionnaire—geriatric version). Inventory of Depressive Symptoms-Clinician rated, 30-item score of ≤31. Current major depressive episode, depression symptom severity (Week 1 MADRS total score ≥24), and AD treatment response in the current depressive episode, confirmed using a Site Independent Qualification Assessment.

Of 70 US patients aged ≥65 years, 34 received ESK+AD and 36 received AD+PBO. The baseline patient demographics and disease characteristics were generally similar between the 2 treatment groups. See, Table 45. Overall mean age was 70.0 years, 57.1% were women, and most patients were white (98.6%). The mean age at MDD diagnosis was 42.5 years, indicating on average, a >27-year history of depression in this population. The baseline MADRS, CGI-S and PHQ-9 scores were consistent with an adult population with TRD.

TABLE 45

Baseline patient demographics and disease characteristics

| Parameter | ESK + AD (n = 34) | AD + PBO (n = 36) |
|---|---|---|
| Age, y, mean (SD) | 70.7 (4.5) | 69.3 (4.1) |
| Sex, n (%) | | |
| Male | 15 (44.1) | 15 (41.7) |
| Female | 19 (55.9) | 21 (58.3) |
| Race, n (%) | | |
| White | 33 (97.1) | 36 (100.0) |
| Multiple | 1 (2.9) | 0 |
| Class of oral ADs, n (%)† | | |
| SNRI | 16 (47.1) | 17 (47.2) |
| SSRI | 18 (52.9) | 19 (52.8) |
| Duration of current episode, weeks, mean (SD) | 187.6 (283.4) | 420.9 (480.7) |

TABLE 45-continued

Baseline patient demographics and disease characteristics

| Parameter | ESK + AD (n = 34) | AD + PBO (n = 36) |
|---|---|---|
| Age at MDD diagnosis, y, mean (SD) | 42.1 (15.3) | 43.0 (15.1) |
| MADRS total score,[a] mean (SD) | 35.5 (5.5) | 35.7 (6.0) |
| CGI-S,[b] mean (SD) | 5.0 (0.6) | 4.7 (0.6) |
| PHQ-9 total score,[c] mean (SD) | 15.2 (5.6) | 18.2 (5.6) |

[a] MADRS total score ranged from 0 to 60; a higher score indicates a more severe condition.
[b] CGI-S score ranges from 1 (normal, not at all ill) to 7 (among the most extremely ill patients).
[c] PHQ-9 total score ranges from 0 to 27; a higher score indicates greater depression.

C. Efficacy

Efficacy was determined by measuring MADRS total scores, SDS scores, PHQ-9 scores and CGI-S scores. A patient was considered responsive if there was a ≥50% decrease in MADRS baseline score. A patient was classified to be "in remission" if the clinician-rated: MADRS score was ≤12 and the patient-rated PHQ-9 score was <5. A patient was considered to have a change in clinician-rate symptom severity if there was a clinically meaningful response with a ≥1-point decrease in the CGI-S and a clinically significant response with a ≥2-point decrease on the CGI-S.

Approximately, eight days post initial dose, response rates based on MADRS were 6.3% (2/32) and 0% (0/35) in ESK+AD and AD+PBO, respectively.

Twenty-eight days post-initial dose, response rates based on MADRS were nearly 2-fold higher in patients treated with ESK+AD compared with patients treated with AD+PBO (8/30 [26.7%] vs 5/34 [14.7%]). See, FIG. 31. Twenty-eight days post-initial dose, remission rates based on MADRS were approximately 5-fold greater in patients treated with ESK+AD compared with patients treated with AD+PBO (5/30 [16.7%] vs 1/34 [2.9%]). See, FIG. 32. At day 28 post-initial dose, patient-rated remission was almost 2.5-fold higher in the ESK+AD group compared with AD+PBO group (22.6% [7/31] vs 9.4% [3/32]). See, FIG. 33.

At day 15 post-initial dose, patient-rated remission rates based on PHQ-9 were similar between treatment groups (8.0% [2/25] vs 8.7% [2/23]).

At 4 weeks post-initial dose, clinically meaningful response was nearly 2-fold higher, and clinically significant response was nearly 4-fold higher, in the ESK+AD group compared with the AD+PBO group (63.3% vs 29.4% and 43.2% vs 11.8%, respectively). See, FIGS. 34 and 35.

D. Safety

Safety was assessed via treatment emergent AEs (TE-AEs). Overall, TEAEs were observed in 64.7% of US patients in the ESK+AD group and 58.3% of patients in the AD+PBO group. See, Table 27. There were no deaths; one serious AE was observed in each group. Three patients withdrew nasal spray (n=2 ESK [systolic BP increase >180; hip fracture], n=1 PBO) and one patient in the AD+PBO group withdrew oral AD (elevated BP, dizziness, and peripheral edema).

The most common (≥5% in either treatment group) TEAEs are shown in Table 46. TEAEs tended to be mild to moderate in severity and transient in nature. The incidence of TEAEs in the US patients was similar to that observed in the overall study population.

TABLE 46

Overview of treatment-emergent adverse events in US patients aged ≥65 years

| Parameter | ESK + AD (n = 34) | AD + PBO (n = 36) |
|---|---|---|
| Overall TEAE, n (%) | 22 (64.7) | 21 (58.3) |
| Possibly related to nasal spray | 15 (44.1) | 10 (27.8) |
| Possibly related to oral AD | 7 (20.6) | 7 (19.4) |
| Leading to death | 0 | 0 |
| 1 or more serious TEAE | 1 (2.9) | 1 (2.8) |
| Leading to nasal spray withdrawal | 2 (5.9) | 1 (2.8) |
| Leading to oral AD withdrawal | 0 | 1 (2.8) |
| Most common (≥5% in either treatment group) TEAEs | | |
| Dysphoria | 4 (11.8) | 0 |
| Fatigue | 4 (11.8) | 3 (8.3) |
| Headache | 4 (11.8) | 1 (2.8) |
| Insomnia | 4 (11.8) | 2 (5.6) |
| Nausea | 4 (11.8) | 0 |
| Abdominal discomfort | 2 (5.9) | 1 (2.8) |
| Cough | 2 (5.9) | 0 |
| Dizziness | 2 (5.9) | 2 (5.6) |
| Erythema | 2 (5.9) | 1 (2.8) |
| Nasal congestion | 2 (5.9) | 0 |
| Urinary tract infection | 2 (5.9) | 0 |
| Vomiting | 2 (5.9) | 0 |
| Anxiety | 1 (2.9) | 2 (5.6) |
| Viral upper respiratory tract infection | 1 (2.9) | 2 (5.6) |
| Muscle strain | 0 | 2 (5.5) |

E. Conclusions

These results demonstrated that, in this subpopulation of US patients aged ≥65 years with TRD from a larger, multinational study, almost twice as many patients attained response (i.e., ≥50% decrease in MADRS baseline score) when treated with ESK+AD compared with those treated with AD+PBO. In addition, remission rates (i.e., MADRS score ≤12) were approximately 5-fold greater in patients treated with ESK+AD compared with patients treated with AD+PBO.

Thus, ESK+AD demonstrated clinically meaningful and clinically significant improvement in clinician-rated (CGI-S) and patient-rated (PHQ-9) remission. The safety, response, and remission results of US patients were similar to those found for the total population studied.

Example 3

This was a randomized, double-blind, placebo-controlled, multicenter study. See, Camusso, "Efficacy and Safety of Intranasal Esketamine for the Rapid Reduction of Symptoms of Depression and Suicidality in Patients at Imminent Risk for Suicide: Results of a Double-Blind, Randomized Placebo-Controlled Study," Am. J. Psych., 2018, 1-11, which is herein incorporated by reference. Approximately 70 male and female subjects, 19 to 64 years of age, with MDD at imminent risk for suicide presenting to an emergency room (ER) or other permitted setting and assessed to be at imminent risk for suicide were enrolled. The majority of subjects were female, and the mean age of all subjects was approximately 36 years. The mean baseline Montgomery-Asberg Depression Rating Scale (MADRS) total score was over 38 (corresponding to severe depression), and the mean baseline Beck Scale for Suicidal Ideation (BSS) score was over 22. Over half of the subjects had a score of 6 on the Suicide Ideation and Behavior Assessment Tool (SIBAT) Clinical Global Judgment of Suicide Risk, corresponding to suicidal risk requiring hospitalization with suicide precautions. A diagram of the study design is provided in FIG. 37.

The study consisted of a screening evaluation performed within 24 hours (or up to 48 hours upon consultation with the Sponsor's medical monitor) prior to Day 1 dose, immediately followed by a 25-day double-blind treatment phase (Day 1 to 25) with twice a week dosing, and a 56-day follow up phase (Day 26 to Day 81). The study was designed as a POC study and therefore a two-sided 0.20 significance level was used.

Randomization: 68 subjects were randomized in a 1:1 ratio to 1 of the 2 treatments: intranasal esketamine 84 mg (N=36) or intranasal placebo (N=32). The randomization was stratified by study center and by the physician's assessment of the subject's need of standard of care antidepressant treatment prior to randomization on Day 1 (i.e., antidepressant monotherapy or antidepressant plus augmentation therapy). In addition, all subjects received aggressive clinical care, including hospitalization and the initiation or optimization of standard antidepressant medication (determined by the treating physician based on clinical judgment and practice guidelines).

Primary analysis set for efficacy: The primary efficacy analyses was based on the intent-to-treat (ITT) analysis set which was defined to include all randomized subjects who receive at least 1 dose of study medication during the double-blind phase and have both baseline and the Day 1, 4-hour postdose evaluation for the MADRS total score.

Primary efficacy variable/Primary Time point: Change from baseline (Day 1, predose) to Day 1, 4-hours postdose in MADRS total score. The MADRS consists of 10 items that cover all of the core depressive symptoms, with each item scoring from 0 (item is not present or is normal) to 6 (severe or continuous presence of the symptom). A higher score represents a more severe condition.

Secondary efficacy variables:
  a. Changes from baseline to Day 2 and Day 25 for the MADRS total score
  b. Changes from baseline to Day 1 4-hours postdose, Day 2 and Day 25 for the MADRS Suicide Item
  c. Changes from baseline to Day 1 4-hours postdose, Day 2, and Day 25 for the clinical global judgment of suicide risk from the Suicide Ideation and Behavior Assessment Tool (SIBAT)
  d. Sustained response (Onset of Clinical Response) defined as at least 50% reduction from baseline in MADRS total score with onset on Day 1 that is maintained through the end of the double-blind phase (Day 25)
  e. Changes from baseline to Day 1 4-hours postdose, Day 2, and Day 25 for the Beck Scale for Suicidal Ideation (BSS)
  f. Changes from baseline to Day 1 4-hours postdose and Day 25 for the Beck Hopelessness Scale Expected effect size and planned sample size: The sample size was based on the assumption of a treatment difference of at least 6 points in the mean change from baseline to Day 1 (4 hours postdose) in MADRS total score between the esketamine and placebo groups. A standard deviation of 9 was used for both groups. Using a 2-sample t-test, 32 subjects in each group were required to detect the treatment difference of 6 points with a power of 91% at an overall 1-sided significance level of 0.10 (which is the same as a 2-sided significance level 0.20). Assuming 8% of randomized subjects discontinue before providing post-baseline efficacy measurements, the total number of subjects required for each treatment group is 35. The goal of sample size selection for this Phase 2a proof-of-concept study was to increase sensitivity for detecting a therapeutic signal while also maintaining a modest sample size. Thus, power was set to a high value ($\geq 90\%$; $\beta \leq 0.1$) but the type 1 error rate was specified at 1-sided $\alpha = 0.10$.

Primary Objective: The primary objective is to evaluate the efficacy of intranasal esketamine 84 mg compared with intranasal placebo in reducing the symptoms of MDD, including suicidal ideation, in subjects who are assessed to be at imminent risk for suicide, as measured by the change from baseline on the Montgomery-Asberg Depression Rating Scale (MADRS) total score at 4 hours postdose on Day 1.

Subject and Treatment Information:

This was a randomized, double-blind, placebo-controlled study that included 68 randomized subjects with a diagnosis of MDD at imminent risk for suicide without psychotic features, based upon clinical assessment (DSM-IV 296.22, 296.23, 296.32, or 296.33) and confirmed by the Mini International Psychiatric Interview (MINI). Subjects must have had current suicidal ideation with intent, confirmed by a "Yes" response to Question B5 [Think about suicide (killing yourself)?] and Question B9 [Intend to act on thoughts of killing yourself?] obtained from the MINI; and subjects must have had a MADRS total score of $\leq 22$ predose on Day 1. Due to the lower than assumed dropout rate at the time of the primary endpoint (Day 1: 4 hours postdose), study recruitment was discontinued at 68 subjects which is a sufficient number of evaluable subjects. Of the 68 randomized subjects, 2 subjects did not receive study drug and are therefore not included in the safety or ITT analysis sets. In the ITT analysis set, 35/66 (53.0%) of the subjects were white and 43/66 (65.2%) of the subjects were female. The mean age was 35.8 years, ranging from 19 to 64 years. Out of 68 subjects in the all randomized analysis set, 49 (72.1%) completed the double-blind phase and 19 withdrew early, of which 6 withdrew due to adverse events, 5 due to lack of efficacy, 2 for loss to follow-up, 2 due to withdrawal of consent and 4 due to other reasons. Subsequently, 49 subjects entered into the 56-day follow-up phase.

Efficacy:

Primary Efficacy Endpoint

Based on an ANCOVA model, results for the change from baseline to Day 1, 4-hours postdose in MADRS total score favored esketamine 84 mg with a least-square mean difference (SE) from placebo of −5.3 (2.10). The difference between treatment groups was statistically significant (two-sided p=0.015), using a two-sided significance level of 0.20.

Secondary Efficacy Endpoints

Table 47 below summarizes the results of the secondary efficacy endpoints.

TABLE 47

| Assessment | Time | Two-sided p-value |
| --- | --- | --- |
| MADRS | Day 2 (DB) | 0.015 |
|  | End Point (DB) | 0.159 |
| MADRS Suicide Item | Day 1: 4-hours postdose | 0.002 |
|  | Day 2 (DB) | 0.129 |
|  | End Point (DB) | 0.143 |
| SIBAT Clinical Global Judgment of Suicide Risk | Day 1: 4-hours postdose | 0.112 |
|  | Day 2 (DB) | 0.150 |
|  | End Point (DB) | 0.922 |
| Sustained Response (Onset of Clinical Response) | Day 1 until the end of DB phase | 0.608 |
| BSS | Day 1: 4-hours postdose | 0.326 |
|  | Day 2 (DB) | 0.415 |
|  | End Point (DB) | 0.431 |

TABLE 47-continued

| Assessment | Time | Two-sided p-value |
|---|---|---|
| BHS | Day 1: 4-hours postdose | 0.297 |
|  | End Point (DB) | 0.165 |

Statistical significance for this proof-of-concept study was based on a two-sided 0.20 significance level.

Safety

The most common (≥20%) TEAEs in the esketamine 84 mg group during the double-blind phase were nausea (37.1%), dizziness (34.3%), dysgeusia (31.4%), headache (31.4%), dissociation (31.4%) and vomiting (20.0%). The most common (≥20%) TEAE in the placebo group was headache (25.8%).

Four subjects experienced a serious treatment-emergent adverse event during the double-blind phase and all were in the esketamine 84 mg group. Two subjects experienced suicidal ideation, 1 subject experienced agitation, and 1 subject experienced depressive symptoms. Six subjects experienced a serious adverse event during the follow up phase (5 in the placebo group and 1 in the esketamine 84 mg group). The SAEs in the placebo group included 3 suicide attempts (non-fatal), 1 subject who experienced suicidal ideation, and 1 subject with cellulitis. The SAE in the subject from the esketamine group was suicidal ideation.

There were 6 subjects (1 subject in the placebo group and 5 subjects in the esketamine 84 mg group), who discontinued from the double-blind phase due to treatment-emergent adverse events.

Transient blood pressure increases for the esketamine 84 mg group peaked at 40 minutes post dose with the maximum mean increases (across all dosing days) in systolic BP being 8.7 and 16.7 in the placebo and esketamine 84 mg groups, respectively. The maximum mean increases (across all dosing days) in diastolic BP were 7.6 and 11.9 in the placebo and esketamine 84 mg groups, respectively.

The dissociative and perceptual change symptoms measured by the CADSS, suggest onset of these symptoms occurred shortly after the start of the dose and resolved by 2 hours post dose.

Results

Subject and Treatment Information

In total, 68 subjects with a DSM-IV-TR (Diagnostic and Statistical Manual, 4th Edition—Text Revised) diagnosis of MDD (aged 19-64 years) were randomized to two groups in a ratio of 1:1 (32 in placebo and 36 in esketamine 84 mg). The number of subjects included in each analysis set is included in Table 48. All subjects enrolled were from the US.

Among 68 randomized subjects, 66 were included in the safety analysis set (defined as receiving at least one dose of study medication in the double-blind phase). Two subjects were randomized but did not receive study medication. All safety subjects (N=66) were included in the intent-to-treat (ITT) analysis set (defined as receiving at least one dose of study medication during the double-blind phase and having both the baseline and the Day 1, 4-hour postdose evaluation for the MADRS total score). Forty-nine subjects were included in the safety (FU) analysis set (defined as all subjects who have at least 1 visit during the follow up phase).

TABLE 48

Number of Subjects in Each Analysis Set (Study ESKETINSUI2001: All Randomized Analysis Set)

|  | Placebo (N = 32) | Esketamine 84 mg (N = 36) | Total (N = 68) |
|---|---|---|---|
| All randomized | 32 (100.0%) | 36 (100.0%) | 68 (100.0%) |
| ITT | 31 (96.9%) | 35 (97.2%) | 66 (97.1%) |
| Safety | 31 (96.9%) | 35 (97.2%) | 66 (97.1%) |
| ITT (FU) | 22 (68.8%) | 27 (75.0%) | 49 (72.1%) |
| Safety (FU) | 22 (68.8%) | 27 (75.0%) | 49 (72.1%) |

Percentages calculated with the number of subjects in each group as denominator.

Study Completion/Withdrawal Information

Of the 68 subjects in the all randomized analysis set, 19 (27.9%) subjects discontinued from the double-blind phase. The completion and withdrawal information for subjects in the double-blind phase is provided in Table 49. More subjects in the esketamine 84 mg group discontinued due to adverse events (5 subjects in the esketamine 84 mg group versus 1 subject in the placebo group) whereas more subjects in the placebo group discontinued due to lack of efficacy (4 subjects in the placebo group versus 1 subject in the esketamine 84 mg group).

Four subjects withdrew due to other reasons during the double-blind phase. The details are provided below.

1) One subject (in the esketamine 84 mg group) experienced elevated blood pressure after randomization but prior to dosing and was thus withdrawn.

2) One subject (in the esketamine 84 mg group) withdrew due to lack of transportation.

3) One subject (in the placebo group) changed her mind and decided not to participate in the trial. However, the study coordinator mistakenly randomized her into the trial.

4) One subject (in the placebo group) had no dose on Day 22 due to lack of clinician availability, then the subject did not show up for Day 25. The subject returned for the early withdrawal visit but did not return for the follow up phase.

TABLE 49

Study Completion/Withdrawal Information for Double-Blind Phase (Study ESKETINSUI2001: All Randomized Analysis Set)

|  | Placebo (N = 32) | Esketamine 84 mg (N = 36) | Total (N = 68) |
|---|---|---|---|
| Completed | 22 (68.8%) | 27 (75.0%) | 49 (72.1%) |
| Withdrawn | 10 (31.3%) | 9 (25.0%) | 19 (27.9%) |
| Adverse event | 1 (3.1%) | 5 (13.9%) | 6 (8.8%) |
| Lack of Efficacy | 4 (12.5%) | 1 (2.8%) | 5 (7.4%) |
| Lost to follow-up | 2 (6.3%) | 0 | 2 (2.9%) |
| Withdrawal of consent | 1 (3.1%) | 1 (2.8%) | 2 (2.9%) |
| Other | 2 (6.3%) | 2 (5.6%) | 4 (5.9%) |

Demographic and Baseline Characteristics

Demographic and baseline characteristics are displayed in Table 50 for the ITT analysis set. In general, the treatment groups were similar with respect to the baseline characteristics. The majority of subjects entering the double-blind phase were female (65.2%). The mean (SD) age of all subjects was 35.8 (13.03) years, ranging from 19 to 64 years. 75.8% of subjects were to receive antidepressant monotherapy; 24.2% of subjects were to receive antidepressant plus augmentation therapy.

Baseline psychiatric history for the ITT analysis set is presented in Table 51. The mean (SD) baseline MADRS total score was 38.6 (6.53), ranging from 20 to 52. A majority of subjects had a score of 6 on the clinical global judgment of suicide risk as assessed by the SIBAT Module 8 (51.5%). Values of 6 correspond to suicidal risk requiring hospitalization with suicide precautions.

TABLE 50

| Demographic and Baseline Characteristics (Study ESKETINSUI2001: ITT Analysis Set) | | | |
|---|---|---|---|
| | Placebo (N = 31) | Esketamine 84 mg (N = 35) | Total (N = 66) |
| Age (years) | | | |
| N | 31 | 35 | 66 |
| Mean (SD) | 36.0 (12.82) | 35.7 (13.40) | 35.8 (13.03) |
| Median | 31.0 | 32.0 | 31.5 |
| Range | (19; 64) | (19; 64) | (19; 64) |
| Age Category, n (%) | | | |
| 18-34 | 18 (58.1%) | 18 (51.4%) | 36 (54.5%) |
| 35-54 | 10 (32.3%) | 12 (34.3%) | 22 (33.3%) |
| 55-64 | 3 (9.7%) | 5 (14.3%) | 8 (12.1%) |
| Sex, n (%) | | | |
| N | 31 | 35 | 66 |
| Male | 10 (32.3%) | 13 (37.1%) | 23 (34.8%) |
| Female | 21 (67.7%) | 22 (62.9%) | 43 (65.2%) |
| Race, n (%) | | | |
| N | 31 | 35 | 66 |
| White | 15 (48.4%) | 20 (57.1%) | 35 (53.0%) |
| Black or African American | 13 (41.9%) | 12 (34.3%) | 25 (37.9%) |
| Asian | 0 | 1 (2.9%) | 1 (1.5%) |
| Multiple | 1 (3.2%) | 0 | 1 (1.5%) |
| Other | 2 (6.5%) | 0 | 2 (3.0%) |
| Not Reported | 0 | 2 (5.7%) | 2 (3.0%) |
| Ethnicity, n (%) | | | |
| N | 31 | 35 | 66 |
| Not Hispanic or Latino | 29 (93.5%) | 31 (88.6%) | 60 (90.9%) |
| Hispanic or Latino | 1 (3.2%) | 4 (11.4%) | 5 (7.6%) |
| Not Reported | 1 (3.2%) | 0 | 1 (1.5%) |
| Baseline Weight (kg) | | | |
| N | 31 | 35 | 66 |
| Mean (SD) | 76.1 (18.83) | 83.5 (23.86) | 80.0 (21.79) |
| Median | 75.0 | 77.1 | 75.4 |
| Range | (48; 110) | (51; 149) | (48; 149) |
| Baseline Height (cm) | | | |
| N | 31 | 35 | 66 |
| Mean (SD) | 168.6 (7.15) | 167.9 (15.64) | 168.2 (12.31) |
| Median | 167.1 | 167.6 | 167.6 |
| Range | (156; 182) | (108; 203) | (108; 203) |
| Baseline Body Mass Index (kg/m2) | | | |
| N | 31 | 35 | 66 |
| Mean (SD) | 26.8 (6.62) | 30.1 (9.49) | 28.5 (8.37) |
| Median | 25.0 | 28.6 | 26.6 |
| Range | (18; 41) | (17; 60) | (17; 60) |
| BMI Category (kg/m2), n (%) | | | |
| N | 31 | 35 | 66 |
| Underweight <18.5 | 2 (6.5%) | 1 (2.9%) | 3 (4.5%) |
| Normal 18.5-<25 | 13 (41.9%) | 12 (34.3%) | 25 (37.9%) |
| Overweight 25-<30 | 6 (19.4%) | 6 (17.1%) | 12 (18.2%) |
| Obese ≥30 | 10 (32.3%) | 16 (45.7%) | 26 (39.4%) |
| Standard of Care Antidepressant Treatment as Randomized, n (%) | | | |
| N | 31 | 35 | 66 |
| Antidepressant monotherapy | 25 (80.6%) | 25 (71.4%) | 50 (75.8%) |
| Antidepressant plus augmentation therapy | 6 (19.4%) | 10 (28.6%) | 16 (24.2%) |
| Standard of Care Antidepressant Treatment as Actually Received, n (%) | | | |
| N | 31 | 35 | 66 |
| Monotherapy | 22 (71.0%) | 24 (68.6%) | 46 (69.7%) |
| Augmentation | 5 (16.1%) | 9 (25.7%) | 14 (21.2%) |
| Both | 4 (12.9%) | 2 (5.7%) | 6 (9.1%) |

TABLE 51

Baseline Psychiatric History by Treatment: (Study ESKETINSUI2001: ITT Analysis Set)

| | Placebo (N = 31) | Esketamine 84 mg (N = 35) | Total (N = 66) |
|---|---|---|---|
| Baseline MADRS Total Score | | | |
| N | 31 | 35 | 66 |
| Mean (SD) | 38.8 (7.02) | 38.5 (6.17) | 38.6 (6.53) |
| Median | 40.0 | 38.0 | 38.5 |
| Range | (20; 52) | (27; 49) | (20; 52) |
| Hx of Suicide Attempt | | | |
| Lifetime (%) | 21 (67.7%) | 20 (57.1%) | 41 (62.1%) |
| Within last 30 Days (%) | 13 (41.9%) | 11 (31.4%) | 24 (36.4%) |
| Baseline SIBAT (Module 2): Prior Thought on Suicide, n (%) | | 4 | |
| N | 31 | 34 | 65 |
| Yes | 31 (100.0%) | 34 (100.0%) | 65 (100.0%) |
| No | 0 | 0 | 0 |
| Baseline SIBAT (Module 6): My Self-Assessment of Suicide Risk: Which rating best describes your intent for suicide right now, n (%) | | | |
| N | 31 | 35 | 66 |
| None | 3 (9.7%) | 3 (8.6%) | 6 (9.1%) |
| Very weak/Weak/Moderately weak | 8 (25.8%) | 7 (20.0%) | 15 (22.7%) |
| Mild | 6 (19.4%) | 6 (17.1%) | 12 (18.2%) |
| Moderate/Moderately strong | 9 (29.0%) | 10 (28.6%) | 19 (28.8%) |
| Strong | 3 (9.7%) | 5 (14.3%) | 8 (12.1%) |
| Extremely strong/Extremely strong and constant | 2 (6.5%) | 4 (11.4%) | 6 (9.1%) |
| Baseline SIBAT (Module 8): Clinical Global Judgment of Suicide Risk, n (%) | | | |
| N | 31 | 35 | 66 |
| 0 | 0 | 0 | 0 |
| 1 | 0 | 0 | 0 |
| 2 | 0 | 0 | 0 |
| 3 | 0 | 0 | 0 |
| 4 | 1 (3.2%) | 0 | 1 (1.5%) |
| 5 | 16 (51.6%) | 15 (42.9%) | 31 (47.0%) |
| 6 | 14 (45.2%) | 20 (57.1%) | 34 (51.5%) |
| MINI B5: Think about suicide (killing yourself): Y/N, n (%) | | | |
| N | 31 | 35 | 66 |
| Yes | 31 (100.0%) | 35 (100.0%) | 66 (100.0%) |
| No | 0 | 0 | 0 |
| MINI B5: Think about suicide (killing yourself): frequency, n (%) | | | |
| N | 31 | 35 | 66 |
| Occasionally | 5 (16.1%) | 5 (14.3%) | 10 (15.2%) |
| Often | 9 (29.0%) | 11 (31.4%) | 20 (30.3%) |
| Very Often | 17 (54.8%) | 19 (54.3%) | 36 (54.5%) |
| MINI B5: Think about suicide (killing yourself): Intensity, n (%) | | | |
| N | 31 | 35 | 66 |
| Mild | 1 (3.2%) | 0 | 1 (1.5%) |
| Moderate | 9 (29.0%) | 12 (34.3%) | 21 (31.8%) |
| Severe | 21 (67.7%) | 23 (65.7%) | 44 (66.7%) |
| MINI B9: Intent to act on thoughts of killing yourself (Y/N), n (%) | | | |
| N | 31 | 35 | 66 |
| Yes | 31 (100.0%) | 35 (100.0%) | 66 (100.0%) |
| No | 0 | 0 | 0 |
| Baseline BSS Total Score | | | |
| N | 31 | 34 | 65 |
| Mean (SD) | 21.4 (8.28) | 24.0 (5.45) | 22.8 (7.01) |
| Median | 23.0 | 25.0 | 24.0 |
| Range | (1; 38) | (8; 33) | (1; 38) |

TABLE 51-continued

Baseline Psychiatric History by Treatment: (Study ESKETINSUI2001: ITT Analysis Set)

|  | Placebo (N = 31) | Esketamine 84 mg (N = 35) | Total (N = 66) |
|---|---|---|---|
| Baseline BSS-5 | | | |
| N | 31 | 35 | 66 |
| Mean (SD) | 6.2 (2.61) | 7.3 (2.11) | 6.8 (2.41) |
| Median | 7.0 | 8.0 | 7.0 |
| Range | (1; 10) | (2; 10) | (1; 10) |
| Baseline BHS Total Score | | | |
| N | 30 | 35 | 65 |
| Mean (SD) | 15.5 (4.59) | 16.5 (2.91) | 16.0 (3.79) |
| Median | 16.0 | 17.0 | 17.0 |
| Range | (0; 20) | (9; 20) | (0; 20) |

Baseline is defined as the last predose value on Day 1.
SIBAT (Module 8) scores are as follows: 0 = Not suicidal, 1 = Occasional suicidal ideas present, but no special intervention required, 2 = Some clear suicidal ideas present, patient is encouraged to schedule professional contacts as needed 3 = Suicidal risk requires a scheduled outpatient follow up; but no other immediate intervention, 4 = Suicidal risk requires immediate intervention, but not hospitalization (e.g., medication, urgent outpatient follow up), 5 = Suicidal risk requires immediate hospitalization, but without suicide precautions, 6 = Suicidal risk requires hospitalization with suicide precautions.

Extent of Exposure

The number of days dosed is presented in Table 52. More subjects in the esketamine 84 mg group than in the placebo group had all 8 dosing sessions (74.3% vs. 64.5%). The duration of exposure to double-blind medication is summarized in Table 53. Five subjects reduced their dose of esketamine from 84 mg to 56 mg. Of these, 3 reduced their dose due to an adverse event and 2 had their dose reduced in error and were considered major protocol deviations. In addition, 1 subject had an incorrect med kit number recorded for device 2 on Day 15 so it appears that the dose was reduced but in actuality it was not (Table 54).

TABLE 52

Number of Days Dosed with Double-Blind Study Medication (Study ESKETINSUI2001: ITT Analysis Set)

| Number of Days Dosed | Placebo (N = 31) | Esketamine 84 mg (N = 35) |
|---|---|---|
| 1 | 1 (3.2%) | 4 (11.4%) |
| 2 | 2 (6.5%) | 0 |
| 3 | 0 | 2 (5.7%) |
| 4 | 1 (3.2%) | 0 |
| 5 | 1 (3.2%) | 1 (2.9%) |
| 6 | 3 (9.7%) | 1 (2.9%) |
| 7 | 3 (9.7%) | 1 (2.9%) |
| 8 | 20 (64.5%) | 26 (74.3%) |

TABLE 53

Extent of Exposure During the Double-Blind Phase (Study ESKETINSUI2001: Safety Analysis Set)

|  | Placebo (N = 31) | Esketamine 84 mg (N = 35) |
|---|---|---|
| Total Duration, Days | | |
| N | 31 | 35 |
| Category, n (%) | | |
| ≤7 | 3 (9.7%) | 5 (14.3%) |
| 8-14 | 1 (3.2%) | 2 (5.7%) |
| 15-21 | 5 (16.1%) | 1 (2.9%) |
| 22-25 | 14 (45.2%) | 21 (60.0%) |
| >25 | 8 (25.8%) | 6 (17.1%) |
| Mean (SD) | 21.5 (7.22) | 20.7 (8.49) |
| Median | 25.0 | 25.0 |
| Range | (1; 28) | (1; 27) |

The duration of exposure is defined as the duration between the date of the first exposure and the last date of exposure. It includes days on which subjects did not actually take study medication.

TABLE 54

Number of Subjects who Decreased Their Dose During the Double-Blind Phase (Study ESKETINSUI2001: Safety Analysis Set)

| Dose Decreased During Double-Blind | Esketamine 84 mg (N = 35) |
|---|---|
| Yes | 6 (17.1%) |
| No | 29 (82.9%) |

Primary Endpoint Analysis—Change from Baseline to Day 1 4-Hours Postdose in MADRS Total Score The primary efficacy endpoint is the change in MADRS total score from baseline to Day 1: 4-hours postdose. MADRS total scores range from 0 to 60. The primary efficacy analysis was performed on the intent-to-treat (ITT) analysis set, which included all randomized subjects who received at least 1 dose of study medication during the double-blind phase and had both the baseline and the Day 1: 4-hour postdose evaluation for the MADRS total score. As this is a phase 2a proof-of-concept study, statistical significance is based on a two-sided alpha level of 0.20. All p-values presented in this document are two-sided.

As shown in Table 55 below, results for the change in MADRS total score favored esketamine 84 mg over placebo. The mean change from baseline (SD) at Day 1: 4-hours postdose was −13.4 (9.03) for esketamine 84 mg and −9.1 (8.38) for placebo. Based on an ANCOVA model with treatment, antidepressant therapy and analysis center as factors and baseline value as a covariate, the least-square mean difference (SE) between esketamine 84 mg and placebo was −5.3 (2.10). The difference between treatment groups was statistically significant (two-sided p=0.015) using a two-sided significance level of 0.20.

TABLE 55

MADRS Total Score: Change from Baseline to Day 1, 4-Hour Postdose ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 31 | 35 |
| Mean (SD) | 38.8 (7.02) | 38.5 (6.17) |
| Median (Range) | 40.0 (20; 52) | 38.0 (27; 49) |
| Day 1(DB): 4 H | | |
| N | 31 | 35 |
| Mean (SD) | 29.7 (11.28) | 25.1 (9.67) |
| Median (Range) | 30.0 (3; 52) | 23.0 (7; 48) |
| Change from Baseline to Day 1 (DB): 4 H | | |
| N | 31 | 35 |
| Mean (SD) | −9.1 (8.38) | −13.4 (9.03) |
| Median (Range) | −6.0 (−25; 0) | −14.0 (−32; 1) |
| Two-sided p-value (minus Placebo) [a] | | 0.015 |
| Diff. of LS Means (SE) | | −5.3 (2.10) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

Secondary Endpoint Analyses

MADRS Total Score: Change from Baseline to Day 2 (DB) and to End Point (DB)

The results for the change in MADRS total score at Day 2 (DB) are shown in Table 56. The mean change from baseline (SD) was −19.3 (12.02) for esketamine 84 mg and −12.8 (9.77) for placebo. Based on an ANCOVA model with treatment, antidepressant therapy and analysis center as factors and baseline value as a covariate, the esketamine 84 mg group was statistically superior to the placebo group (two-sided p-value=0.015) using a two-sided significance level of 0.20. Thus, the changes in MADRS total score at Day 2 and the Day 25 DB endpoint were statistically superior in the esketamine group compared to the placebo group (two-sided p=0.015 and p=0.159, respectively).

TABLE 56

MADRS Total Score: Change from Baseline to Day 2(DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 31 | 35 |
| Mean (SD) | 38.8 (7.02) | 38.5 (6.17) |
| Median (Range) | 40.0 (20; 52) | 38.0 (27; 49) |
| Day 2(DB) | | |
| N | 31 | 35 |
| Mean (SD) | 26.0 (12.85) | 19.2 (11.23) |
| Median (Range) | 25.0 (4; 49) | 18.0 (3; 42) |
| Change from Baseline to Day 2(DB) | | |
| N | 31 | 35 |
| Mean (SD) | −12.8 (9.77) | −19.3 (12.02) |
| Median (Range) | −10.0 (−33; 1) | −19.0 (−41; 1) |
| Two-sided p-value (minus Placebo) [a] | | 0.015 |
| Diff. of LS Means (SE) | | −7.2 (2.85) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

As shown in Table 57 below, results for the change in MADRS total score at End Point (DB) favored esketamine 84 mg over placebo. The mean change from baseline (SD) was −26.4 (14.52) for esketamine 84 mg and −23.0 (10.83) for placebo. Based on the same ANCOVA model mentioned above, the esketamine 84 mg group was statistically superior to the placebo group (two-sided p-value=0.159) using a two-sided significance level of 0.20. See, FIG. 38.

TABLE 57

MADRS Total Score: Change from Baseline to End Point (DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 31 | 35 |
| Mean (SD) | 38.8 (7.02) | 38.5 (6.17) |
| Median (Range) | 40.0 (20; 52) | 38.0 (27; 49) |
| End Point(DB) | | |
| N | 31 | 35 |
| Mean (SD) | 15.8 (12.59) | 12.1 (11.90) |
| Median (Range) | 14.0 (0; 39) | 8.0 (0; 44) |
| Change from Baseline to End Point(DB) | | |
| N | 31 | 35 |
| Mean (SD) | −23.0 (10.83) | −26.4 (14.52) |
| Median (Range) | −21.0 (−42; 1) | −25.0 (−46; 13) |
| Two-sided p-value (minus Placebo) [a] | | 0.159 |
| Diff. of LS Means (SE) | | −4.5 (3.14) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

MADRS Suicide Item: Change from Baseline Over Time

Results of the change from baseline over time for the suicide item from the MADRS assessment can be found in Attachment 1. Statistically significant differences favoring esketamine 84 mg were found at Day 1: 4-hours postdose (two-sided p=0.002), Day 2 (DB) (two-sided p=0.129) and End Point (DB) (two-sided p=0.143).

SIBAT-Clinical Global Judgment of Suicide Risk: Change from Baseline to Day 1: 4-Hours Post Dose, Day 2(DB), and End Point (DB)

The clinical global judgment of suicide risk (Module 8) summarizes clinician overall judgment of suicide risk as derived from information gathered from the full SIBAT tool. It operates like numerous other CGI-severity scales that have been used in other psychiatric studies. Change in the clinical global judgment of suicide risk is designed to directly identify clinical meaningful changes in suicidal ideation and to permit classification of suicide risk.

The analysis of the change in SIBAT score was based on an ANCOVA model on ranks of change in SIBAT with treatment, antidepressant therapy, and analysis center as factors, and baseline value (unranked) as a covariate. There was a significant difference (two-sided p-value=0.112) between the two treatment groups when comparing the mean rank of change from baseline at Day 1: 4-hours postdose in favor of esketamine 84 mg See, Table 58. See, FIG. 39. Specifically, the changes in the SIBAT Clinical Global Judgment of Suicide Risk were statistically superior (i.e., two-sided p<0.2) at Day 1: 4-hours postdose and Day 2 in the esketamine group compared to the placebo group. This difference was not evident at the Day 25 DB endpoint. See, FIG. 40, which is based on LOCF data and analyzed using Cochran-Mantel-Haenszel test controlling for analysis center and antidepressant therapy.

TABLE 58

SIBAT Clinical Global Judgment of Suicide Risk: Change from Baseline to Day 1 4-Hour Post Dose ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 31 | 35 |
| Median (Range) | 5.0 (4; 6) | 6.0 (5; 6) |
| Day 1(DB): 4 H | | |
| N | 31 | 33 |
| Median (Range) | 5.0 (0; 6) | 5.0 (0; 6) |
| Change from Baseline to Day 1 (DB): 4 H | | |
| N | 31 | 33 |
| Median (Range) | 0.0 (−5; 1) | 0.0 (−6; 1) |
| Two-sided p-value (minus Placebo) [a] | | 0.112 |

[a] Based on analysis of covariance (ANCOVA) model on ranks of change with treatment (placebo, esketamine 84 mg), antidepressant therapy (AD monotherapy, AD plus augmentation therapy) and analysis center as factors, and baseline value (unranked) as a covariate.
Negative change in score indicates improvement. Baseline is the predose, Day 1 value.

As shown in Table 59, similar results were seen for the change from baseline to Day 2 (DB). Although not shown, at End Point (DB) there was no statistically significant difference between the treatment groups (two-sided p=0.922).

TABLE 59

SIBAT Clinical Global Judgment of Suicide Risk: Change from Baseline to Day 2(DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 31 | 35 |
| Median (Range) | 5.0 (4; 6) | 6.0 (5; 6) |
| Day 2(DB) | | |
| N | 31 | 35 |
| Median (Range) | 5.0 (0; 6) | 5.0 (0; 6) |

TABLE 59-continued

SIBAT Clinical Global Judgment of Suicide Risk: Change from Baseline to Day 2(DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Change from Baseline to Day 2(DB) | | |
| N | 31 | 35 |
| Median (Range) | 0.0 (−6; 0) | −1.0 (−6; 1) |
| Two-sided p-value (minus Placebo) [a] | | 0.150 |

[a] Based on analysis of covariance (ANCOVA) model on ranks of change with treatment (placebo, esketamine 84 mg), antidepressant therapy (AD monotherapy, AD plus augmentation therapy) and analysis center as factors, and baseline value (unranked) as a covariate.
Negative change in score indicates improvement. Baseline is the predose, Day 1 value.

For the ITT subjects, the percentage of subjects with a baseline SIBAT score of 5 (Suicidal risk requires immediate hospitalization, but without suicide precautions) or 6 (Suicidal risk requires hospitalization with suicide precautions) was 96.8% and 100% for placebo and esketamine 84 mg groups, respectively. At Day 1: 4-hour postdose the percentage of subjects with a score of 5 or 6 was 80.6% for the placebo group and 63.6% for the esketamine 84 mg group. The bar chart in FIG. 41 shows the frequency distribution of SIBAT scores at double-blind baseline, Day 1:4-hours postdose, double-blind endpoint, and follow-up endpoint. The bar chart in FIG. 42 shows the least-square mean changes (SE) from baseline in MADRS score to 4 hours (primary endpoint) and about 24 hours.

Sustained Response (Onset of Clinical Response) in MADRS Total Score

The results for sustained response are shown in Table 60. Sustained response is defined as at least 50% reduction from baseline in MADRS total score with onset on Day 1: 4 hours postdose that is maintained through the end of the double-blind phase (Day 25). Four subjects in the esketamine 84 mg group and 2 subjects in the placebo group had sustained response throughout the double-blind phase. There was no statistically significant difference between treatment groups (two-sided p=0.608).

TABLE 60

Sustained Response Based on MADRS Total Score (Study ESKETINSUI2001: ITT Analysis Set)

| Day 25 sustained response | Placebo (N = 31) | Esketamine 84 mg (N = 35) |
|---|---|---|
| Yes | 2 (6.7%) | 4 (11.8%) |
| No | 28 (93.3%) | 30 (88.2%) |
| Two-sided p-value (vs. Placebo) [a] | | 0.608 |

Percentages calculated with the number of subjects in each group as denominator.
Sustained response is defined as at least 50 percent reduction from baseline in MADRS total score with onset on Day 1 that is maintained through the end of the double-blind phase (Day 25).
[a] Generalized Cochran-Mantel-Haenszel test for mean score difference in being a sustained responder controlling for analysis center and antidepressant therapy (AD monotherapy, AD plus augmentation therapy).

FIG. 43 is a bar graph that correlates the percentage of patients with their respective MADRS response and remission at days 1, 2 and endpoint.

FIG. 44 is a bar graph that correlates the percentage of patients having remission at DB endpoint and during follow-up at days 53 and 81.

Beck Scale of Suicidal Ideation (BSS): Change from Baseline to Day 1: 4-Hours Post Dose, Day 2 (DB), and End Point (DB)

The BSS is a 21-item self-reported instrument to detect and measure the severity of suicidal ideation in adults and adolescents aged 17 years and older. The BSS total score represents the severity of suicide ideation, and it is calculated by summing the ratings of the first 19 items; the total score ranges from 0 to 38, with a higher score representing greater suicide ideation. Increasing scores reflect increases in suicidal risk.

As shown in Tables 61-63, there were no statistically significant differences between esketamine 84 mg and placebo for the change in BSS total score at Day 1: 4-hours postdose, Day 2 (DB), or End Point (DB), using the same ANCOVA model as described above for MADRS total score. See, FIG. 45.

TABLE 61

BSS Total Score: Change from Baseline to Day 1, 4-Hour Postdose ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) |  |  |
| N | 31 | 34 |
| Mean (SD) | 21.4 (8.28) | 24.0 (5.45) |
| Median (Range) | 23.0 (1; 38) | 25.0 (8; 33) |
| Day 1 (DB): 4 H |  |  |
| N | 31 | 34 |
| Mean (SD) | 13.1 (10.12) | 13.8 (10.26) |
| Median (Range) | 13.0 (0; 36) | 16.5 (0; 31) |
| Change from Baseline to Day 1 (DB): 4 H |  |  |
| N | 31 | 34 |
| Mean (SD) | −8.3 (7.12) | −10.2 (9.74) |
| Median (Range) | −9.0 (−27; 2) | −8.0 (−33; 8) |
| Two-sided p-value (minus Placebo) [a] |  | 0.326 |
| Diff. of LS Means (SE) |  | −2.3 (2.29) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

TABLE 62

BSS Total Score: Change from Baseline to Day 2(DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) |  |  |
| N | 31 | 34 |
| Mean (SD) | 21.4 (8.28) | 24.0 (5.45) |
| Median (Range) | 23.0 (1; 38) | 25.0 (8; 33) |
| Day 2(DB) |  |  |
| N | 31 | 34 |
| Mean (SD) | 10.6 (9.71) | 11.1 (10.12) |
| Median (Range) | 9.0 (0; 36) | 13.0 (0; 34) |
| Change from Baseline to Day 2(DB) |  |  |
| N | 31 | 34 |
| Mean (SD) | −10.7 (7.73) | −12.9 (9.63) |
| Median (Range) | −10.0 (−31; 0) | −11.5 (−33; 2) |

TABLE 62-continued

BSS Total Score: Change from Baseline to Day 2(DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Two-sided p-value (minus Placebo) [a] |  | 0.415 |
| Diff. of LS Means (SE) |  | −1.9 (2.30) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

TABLE 63

BSS Total Score: Change from Baseline to End Point (DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) |  |  |
| N | 31 | 34 |
| Mean (SD) | 21.4 (8.28) | 24.0 (5.45) |
| Median (Range) | 23.0 (1; 38) | 25.0 (8; 33) |
| End Point(DB) |  |  |
| N | 31 | 34 |
| Mean (SD) | 5.4 (7.74) | 4.7 (9.03) |
| Median (Range) | 0.0 (0; 23) | 0.0 (0; 34) |
| Change from Baseline to End Point(DB) |  |  |
| N | 31 | 34 |
| Mean (SD) | −16.0 (10.54) | −19.3 (9.61) |
| Median (Range) | −17.0 (−38; 3) | −21.0 (−33; 8) |
| Two-sided p-value (minus Placebo) [a] |  | 0.431 |
| Diff. of LS Means (SE) |  | −1.7 (2.15) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

Beck Hopelessness Scale (BHS): Change from Baseline to Day 1: 4-Hours Post Dose and End Point (DB)

The BHS is a self-reported measure to assess one's level of negative expectations or pessimism regarding the future. It consists of 20 true-false items that examine the respondent's attitude over the past week by either endorsing a pessimistic statement or denying an optimistic statement. For every statement, each response is assigned a score of 0 or 1. The total BHS score is a sum of item responses and ranges from 0 to 20, with a higher score representing a higher level of hopelessness.

As shown in Table 64, there was no statistically significant difference between esketamine 84 mg and placebo for the change in BHS total score at Day 1: 4-hours postdose (two-sided p=0.297). However, at End Point (DB) esketamine 84 mg was statistically superior (two-sided p=0.165) to placebo using a two-sided significance level of 0.20. (Table 65).

TABLE 64

BHS Total Score: Change from Baseline to Day 1, 4-Hour Postdose ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 30 | 35 |
| Mean (SD) | 15.5 (4.59) | 16.5 (2.91) |
| Median (Range) | 16.0 (0; 20) | 17.0 (9; 20) |
| Day 1(DB): 4 H | | |
| N | 30 | 35 |
| Mean (SD) | 12.4 (7.12) | 12.3 (6.95) |
| Median (Range) | 14.5 (0; 20) | 14.0 (0; 20) |
| Change from Baseline to Day 1 (DB): 4 H | | |
| N | 30 | 35 |
| Mean (SD) | −3.1 (5.71) | −4.1 (5.63) |
| Median (Range) | 0.0 (−18; 4) | −2.0 (−16; 2) |
| Two-sided p-value (minus Placebo) [a] | | 0.297 |
| Diff. of LS Means (SE) | | −1.5 (1.47) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

TABLE 65

BHS Total Score: Change from Baseline to End Point (DB) ANCOVA LOCF Analysis: Double-Blind Phase (Study ESKETINSUI2001: ITT Analysis Set)

|  | Placebo (N = 31) | Esketamine 84 mg (N = 35) |
|---|---|---|
| Baseline(DB) | | |
| N | 30 | 35 |
| Mean (SD) | 15.5 (4.59) | 16.5 (2.91) |
| Median (Range) | 16.0 (0; 20) | 17.0 (9; 20) |
| End Point(DB) | | |
| N | 30 | 35 |
| Mean (SD) | 7.8 (7.16) | 6.2 (5.96) |
| Median (Range) | 4.5 (0; 20) | 4.0 (0; 20) |
| Change from Baseline to End Point(DB) | | |
| N | 30 | 35 |
| Mean (SD) | −7.7 (7.81) | −10.3 (5.51) |
| Median (Range) | −9.0 (−20; 8) | −11.0 (−19; 0) |
| Two-sided p-value (minus Placebo) [a] | | 0.165 |
| Diff. of LS Means (SE) | | −2.3 (1.66) |

[a] Based on analysis of covariance (ANCOVA) model with treatment (placebo, esketamine 84 mg), antidepressant therapy (AD monotherapy, AD plus augmentation therapy) and analysis center as factors, and baseline value as a covariate.
Negative change in score indicates improvement. Baseline is the predose, Day 1 value.

Safety
Summary of all Adverse Events

An overall summary of all treatment-emergent adverse events (TEAEs) during the double-blind phase is presented in Table 66. Overall, 80.6% of subjects in the placebo group and 94.3% of subjects in the esketamine 84 mg group experienced at least one TEAE during the double-blind phase.

Overall, 33/35 (94.3%) of subjects who received esketamine 84 mg and 25/31 (80.6%) of subjects who received placebo experienced at least one treatment-emergent adverse event (TEAE) during the double-blind phase.

TABLE 66

Overall Summary of Treatment-Emergent Adverse Events Double-Blind Phase (Study ESKETINSUI2001: Safety Analysis Set)

|  | Placebo (N = 31) | Esketamine 84 mg (N = 35) |
|---|---|---|
| TEAE | 25 (80.6%) | 33 (94.3%) |
| Possibly related TEAE [a] | 12 (38.7%) | 29 (82.9%) |
| TEAE leading to death | 0 | 0 |
| 1 or more serious TEAE | 0 | 4 (11.4%) |
| TEAE leading to drug withdrawn | 1 (3.2%) | 5 (14.3%) |

[a] Study drug relationships of possible, probable, and very likely are included in this category.
Incidence is based on the number of subjects experiencing at least one adverse event, not the number of events.
Adverse events are coded using MedDRA version 18.0

Treatment-emergent adverse events occurring during the double-blind phase (≥5% of subjects in any treatment group) are summarized by treatment group for safety analysis set in Table 67. The most common (≥20%) TEAEs in the esketamine 84 mg group during the double-blind phase were nausea (37.1%), dizziness (34.3%), dysgeusia (31.4%), headache (31.4%), dissociation (31.4%) and vomiting (20.0%). The most common TEAE in the placebo group was headache (25.8%).

TABLE 67

Treatment-Emergent Adverse Events in ≥5% of Subjects in Any Treatment Group: Double-Blind Phase (Study ESKETINSUI2001: Safety Analysis Set)

|  | Placebo (N = 31) | Esketamine 84 mg (N = 35) |
|---|---|---|
| Total no. subjects with TEAE | 25 (80.6%) | 33 (94.3%) |
| Nervous system disorders | 16 (51.6%) | 25 (71.4%) |
| Dizziness | 4 (12.9%) | 12 (34.3%) |
| Dysgeusia | 5 (16.1%) | 11 (31.4%) |
| Headache | 8 (25.8%) | 11 (31.4%) |
| Paresthesia | 1 (3.2%) | 6 (17.1%) |
| Sedation | 2 (6.5%) | 6 (17.1%) |
| Somnolence | 2 (6.5%) | 4 (11.4%) |
| Hypoesthesia | 0 | 3 (8.6%) |
| Dizziness postural | 0 | 2 (5.7%) |
| Psychiatric disorders | 10 (32.3%) | 20 (57.1%) |
| Dissociation | 4 (12.9%) | 11 (31.4%) |
| Anxiety | 1 (3.2%) | 6 (17.1%) |
| Euphoric mood | 2 (6.5%) | 4 (11.4%) |
| Agitation | 0 | 3 (8.6%) |
| Insomnia | 2 (6.5%) | 3 (8.6%) |
| Suicidal ideation | 0 | 2 (5.7%) |
| Panic attack | 2 (6.5%) | 0 |
| Gastrointestinal disorders | 11 (35.5%) | 19 (54.3%) |
| Nausea | 1 (3.2%) | 13 (37.1%) |
| Vomiting | 0 | 7 (20.0%) |
| Diarrhea | 0 | 3 (8.6%) |
| Dry mouth | 0 | 3 (8.6%) |
| Hypoesthesia oral | 0 | 2 (5.7%) |
| Paresthesia oral | 0 | 2 (5.7%) |
| Flatulence | 2 (6.5%) | 1 (2.9%) |
| Abdominal pain | 2 (6.5%) | 0 |
| Constipation | 3 (9.7%) | 0 |
| Toothache | 2 (6.5%) | 0 |
| General disorders and administration site conditions | 2 (6.5%) | 10 (28.6%) |
| Feeling abnormal | 0 | 3 (8.6%) |
| Fatigue | 1 (3.2%) | 2 (5.7%) |
| Feeling cold | 0 | 2 (5.7%) |
| Ear and labyrinth disorders | 1 (3.2%) | 9 (25.7%) |
| Vertigo | 0 | 4 (11.4%) |
| Hyperacusis | 0 | 2 (5.7%) |
| Tinnitus | 0 | 2 (5.7%) |
| Respiratory, thoracic and mediastinal disorders | 8 (25.8%) | 9 (25.7%) |
| Nasal discomfort | 1 (3.2%) | 3 (8.6%) |
| Throat irritation | 0 | 3 (8.6%) |

TABLE 67-continued

Treatment-Emergent Adverse Events in ≥5% of Subjects in Any Treatment Group: Double-Blind Phase (Study ESKETINSUI2001: Safety Analysis Set)

| | Placebo (N = 31) | Esketamine 84 mg (N = 35) |
|---|---|---|
| Oropharyngeal pain | 1 (3.2%) | 2 (5.7%) |
| Pharyngeal hypoesthesia | 0 | 2 (5.7%) |
| Nasal congestion | 2 (6.5%) | 1 (2.9%) |
| Epistaxis | 2 (6.5%) | 0 |
| Intranasal paranesthesia | 2 (6.5%) | 0 |
| Rhinalgia | 2 (6.5%) | 0 |
| Rhinorrhoea | 2 (6.5%) | 0 |
| Eye disorders | 2 (6.5%) | 7 (20.0%) |
| Vision blurred | 0 | 3 (8.6%) |
| Diplopia | 0 | 2 (5.7%) |
| Blepharospasm | 2 (6.5%) | 0 |
| Investigations | 1 (3.2%) | 5 (14.3%) |
| Blood pressure increased | 0 | 2 (5.7%) |
| Weight increased | 0 | 2 (5.7%) |
| Skin and subcutaneous tissue disorders | 4 (12.9%) | 5 (14.3%) |
| Acne | 0 | 2 (5.7%) |
| Hyperhidrosis | 0 | 2 (5.7%) |
| Rash | 3 (9.7%) | 1 (2.9%) |
| Infections and infestations | 4 (12.9%) | 1 (2.9%) |
| Upper respiratory tract infection | 2 (6.5%) | 0 |
| Renal and urinary disorders | 2 (6.5%) | 1 (2.9%) |
| Pollakiuria | 2 (6.5%) | 0 |

Incidence is based on the number of subjects experiencing at least one adverse event, not the number of events. Adverse events are coded using MedDRA version 18.0

Adverse events occurring during the follow up phase are summarized in Table 68. In total, 77.3% subjects in the placebo group and 48.1% subjects in the esketamine 84 mg group experienced at least one adverse event during the follow u phase.

TABLE 68

Adverse Events by MedDRA System Organ Class and Preferred Term: Follow up Phase (Study ESKETINSUI2001: Safety (FU) Analysis Set)

| | Placebo (N = 22) | Esketamine 84 mg (N = 27) |
|---|---|---|
| Total no. subjects with adverse events | 17 (77.3%) | 13 (48.1%) |
| Gastrointestinal disorders | 4 (18.2%) | 6 (22.2%) |
| Dry mouth | 0 | 2 (7.4%) |
| Abdominal pain | 0 | 1 (3.7%) |
| Abdominal tenderness | 0 | 1 (3.7%) |
| Diarrhea | 0 | 1 (3.7%) |
| Vomiting | 0 | 1 (3.7%) |
| Aphthous ulcer | 1 (4.5%) | 0 |
| Nausea | 1 (4.5%) | 0 |
| Tooth impacted | 1 (4.5%) | 0 |
| Toothache | 1 (4.5%) | 0 |
| Nervous system disorders | 3 (13.6%) | 6 (22.2%) |
| Headache | 2 (9.1%) | 2 (7.4%) |
| Tremor | 0 | 2 (7.4%) |
| Cogwheel rigidity | 0 | 1 (3.7%) |
| Dizziness | 0 | 1 (3.7%) |
| Dysgeusia | 0 | 1 (3.7%) |
| Loss of consciousness | 0 | 1 (3.7%) |
| Migraine | 0 | 1 (3.7%) |
| Sedation | 0 | 1 (3.7%) |
| Somnolence | 1 (4.5%) | 0 |
| Psychiatric disorders | 8 (36.4%) | 5 (18.5%) |
| Insomnia | 0 | 3 (11.1%) |
| Depression | 1 (4.5%) | 1 (3.7%) |
| Intentional self-injury | 0 | 1 (3.7%) |
| Restlessness | 0 | 1 (3.7%) |
| Suicidal ideation | 1 (4.5%) | 1 (3.7%) |
| Depressed mood | 1 (4.5%) | 0 |
| Panic reaction | 1 (4.5%) | 0 |
| Self-injurious ideation | 1 (4.5%) | 0 |

TABLE 68-continued

Adverse Events by MedDRA System Organ Class and Preferred Term: Follow up Phase (Study ESKETINSUI2001: Safety (FU) Analysis Set)

| | Placebo (N = 22) | Esketamine 84 mg (N = 27) |
|---|---|---|
| Suicide attempt | 3 (13.6%) | 0 |
| Infections and infestations | 8 (36.4%) | 3 (11.1%) |
| Pharyngitis | 0 | 2 (7.4%) |
| Ear infection | 0 | 1 (3.7%) |
| Nasopharyngitis | 1 (4.5%) | 1 (3.7%) |
| Upper respiratory tract infection | 1 (4.5%) | 1 (3.7%) |
| Vulvovaginal mycotic infection | 0 | 1 (3.7%) |
| Bronchitis | 1 (4.5%) | 0 |
| Cellulitis | 3 (13.6%) | 0 |
| Folliculitis | 1 (4.5%) | 0 |
| Influenza | 1 (4.5%) | 0 |
| Viral upper respiratory tract infection | 1 (4.5%) | 0 |
| Injury, poisoning and procedural complications | 1 (4.5%) | 2 (7.4%) |
| Contusion | 0 | 1 (3.7%) |
| Road traffic accident | 0 | 1 (3.7%) |
| Procedural pain | 1 (4.5%) | 0 |
| Musculoskeletal and connective tissue disorders | 1 (4.5%) | 2 (7.4%) |
| Back pain | 0 | 1 (3.7%) |
| Flank pain | 0 | 1 (3.7%) |
| Musculoskeletal chest pain | 0 | 1 (3.7%) |
| Musculoskeletal pain | 0 | 1 (3.7%) |
| Neck pain | 1 (4.5%) | 1 (3.7%) |
| Respiratory, thoracic and mediastinal disorders | 0 | 2 (7.4%) |
| Epistaxis | 0 | 1 (3.7%) |
| Nasal congestion | 0 | 1 (3.7%) |
| Reproductive system and breast disorders | 1 (4.5%) | 1 (3.7%) |
| Pelvic pain | 0 | 1 (3.7%) |
| Sexual dysfunction | 1 (4.5%) | 0 |
| Skin and subcutaneous tissue disorders | 1 (4.5%) | 1 (3.7%) |
| Night sweats | 0 | 1 (3.7%) |
| Rash | 1 (4.5%) | 0 |
| Ear and labyrinth disorders | 1 (4.5%) | 0 |
| Meniere's disease | 1 (4.5%) | 0 |
| Immune system disorders | 1 (4.5%) | 0 |
| Drug hypersensitivity | 1 (4.5%) | 0 |
| Metabolism and nutrition disorders | 1 (4.5%) | 0 |
| Polydipsia | 1 (4.5%) | 0 |
| Renal and urinary disorders | 1 (4.5%) | 0 |
| Renal failure | 1 (4.5%) | 0 |

Incidence is based on the number of subjects experiencing at least one adverse event, not the number of events. Adverse events are coded using MedDRA version 18.0

Deaths

There were no deaths.

Adverse Events Leading to Study Drug Withdrawal

There were 6 subjects (1 subject in the placebo group and 5 subjects in the esketamine 84 mg group) who discontinued from the double-blind phase due to treatment-emergent adverse events. See, Table 69.

TABLE 69

Treatment-Emergent Adverse Events Leading to Study Discontinuation: Double-Blind Phase (Study ESKETINSUI2001: Safety Analysis Set)

| | Placebo (N = 31) | Esketamine 84 mg (N = 35) |
|---|---|---|
| Total no. subjects with TEAE leading to study discontinuation | 1 (3.2%) | 5 (14.3%) |
| Nervous system disorders | 0 | 2 (5.7%) |
| Dizziness | 0 | 1 (2.9%) |
| Dysgeusia | 0 | 1 (2.9%) |
| Psychiatric disorders | 1 (3.2%) | 2 (5.7%) |
| Aggression | 0 | 1 (2.9%) |

TABLE 69-continued

Treatment-Emergent Adverse Events Leading to
Study Discontinuation: Double-Blind Phase
(Study ESKETINSUI2001: Safety Analysis Set)

|  | Placebo (N = 31) | Esketamine 84 mg (N = 35) |
|---|---|---|
| Agitation | 0 | 1 (2.9%) |
| Dissociative disorder | 1 (3.2%) | 0 |
| Panic attack | 1 (3.2%) | 0 |
| Cardiac disorders | 0 | 1 (2.9%) |
| Ventricular extrasystoles | 0 | 1 (2.9%) |
| Gastrointestinal disorders | 0 | 1 (2.9%) |
| Nausea | 0 | 1 (2.9%) |
| Respiratory, thoracic and mediastinal disorders | 0 | 1 (2.9%) |
| Dyspnea | 0 | 1 (2.9%) |

Incidence is based on the number of subjects experiencing at least one adverse event, not the number of events. Adverse events are coded using MedDRA version 18.0

Serious Adverse Events

Four subjects experienced a serious treatment-emergent adverse event during the double-blind phase and all were in the esketamine 84 mg group (Table 70). Two subjects experienced suicidal ideation, 1 subject experienced agitation, and 1 subject experienced depressive symptoms. One placebo subject experienced serious major depressive disorder aggravated post double-blind phase after discontinuing from the study. This subject did not participate in the follow up phase.

TABLE 70

Treatment-Emergent Serious Adverse Events: Double-Blind
Phase (Study ESKETINSUI2001: Safety Analysis Set)

|  | Placebo (N = 31) | Esketamine 84 mg (N = 35) |
|---|---|---|
| Total no. subjects with a serious TEAE | 0 | 4 (11.4%) |
| Psychiatric disorders | 0 | 4 (11.4%) |
| Suicidal ideation | 0 | 2 (5.7%) |
| Agitation | 0 | 1 (2.9%) |
| Depressive symptom | 0 | 1 (2.9%) |

Incidence is based on the number of subjects experiencing at least one adverse event, not the number of events. Adverse events are coded using MedDRA version 18.0

As shown in Table 71, 6 subjects experienced a serious adverse event in the follow up phase (5 in the placebo group and 1 in the esketamine 84 mg group).

TABLE 71

Serious Adverse Events: Follow up Phase (Study
ESKETINSUI2001: Safety (FU) Analysis Set)

|  | Placebo (N = 22) | Esketamine 84 mg (N = 27) |
|---|---|---|
| Total no. subjects with a serious adverse event | 5 (22.7%) | 1 (3.7%) |
| Psychiatric disorders | 4 (18.2%) | 1 (3.7%) |
| Suicidal ideation | 1 (4.5%) | 1 (3.7%) |
| Suicide attempt | 3 (13.6%) | 0 |
| Infections and infestations | 1 (4.5%) | 0 |
| Cellulitis | 1 (4.5%) | 0 |

Incidence is based on the number of subjects experiencing at least one adverse event, not the number of events. Adverse events are coded using MedDRA version 18.0

Vital Signs

Transient blood pressure increases peaked for the esketamine group at approximately 40 minutes post dose with the maximum mean increases (across all dosing days) in systolic BP being 8.7 in the placebo group and 16.7 in the esketamine 84 mg group. The maximum mean increases (across all dosing days) in diastolic BP were 7.6 in the placebo group and 11.9 in the esketamine 84 mg group. In summary, transient blood pressure increases, typically returning to normal range by 2 hours post dose, were observed in the esketamine group. See, FIGS. 46 and 47.

Other Safety Observations

Clinician-Assessed Dissociative Symptom Scale (CADSS)

The CADSS was measured prior to the start of each dose, at 40 minutes, 2 hours, and 4 hours postdose. The CADSS is used to assess treatment emergent dissociative symptoms and perceptual changes and the total score ranges from 0 to 92 with a higher score representing a more severe condition.

The dissociative and perceptual change symptoms measured by the CADSS, suggest these symptoms had an onset shortly after the start of the dose and resolved by 2 hours postdose (FIG. 55). See, Tables 72A and 72B.

TABLE 72A

MADRS Suicide Item: Medians and Median Changes
Over Time During the Double-Blind and Follow up
Phases (Study ESKETINSUI2001: ITT Analysis Set)

|  |  | Placebo |  |  | Change from Baseline |  |  |
|---|---|---|---|---|---|---|---|
| Suicidal Thoughts | N | Med | Min | Max | Med | Min | Max |
| Baseline(DB) | 31 | 5.0 | 3 | 6 |  |  |  |
| Day 1(DB): 4 H | 31 | 4.0 | 0 | 6 | −1.0 | −6 | 0 |
| Day 2(DB) | 31 | 2.0 | 0 | 5 | −2.0 | −6 | 0 |
| Day 3(DB) | 31 | 2.0 | 0 | 5 | −3.0 | −6 | 0 |
| Day 4(DB) | 25 | 2.0 | 0 | 5 | −2.0 | −6 | 0 |
| Day 5(DB) | 10 | 1.5 | 0 | 5 | −4.0 | −6 | 0 |
| Day 8(DB) | 29 | 2.0 | 0 | 5 | −3.0 | −6 | 1 |
| Day 11(DB) | 26 | 1.5 | 0 | 4 | −4.0 | −6 | 0 |
| Day 15(DB) | 25 | 1.0 | 0 | 4 | −4.0 | −6 | −1 |
| Day 18(DB) | 26 | 1.0 | 0 | 5 | −4.0 | −6 | 0 |
| Day 22(DB) | 25 | 1.0 | 0 | 5 | −4.0 | −6 | 2 |
| Day 25(DB): Predose | 22 | 1.0 | 0 | 4 | −4.0 | −6 | −1 |
| Day 25(DB): 4 H | 24 | 0.0 | 0 | 4 | −4.0 | −6 | −1 |
| Day 32(FU) | 22 | 0.0 | 0 | 5 | −4.0 | −6 | 0 |
| Day 39(FU) | 21 | 0.0 | 0 | 4 | −4.0 | −6 | −1 |
| Day 46(FU) | 20 | 0.5 | 0 | 4 | −4.0 | −6 | −1 |
| Day 53(FU) | 20 | 0.0 | 0 | 4 | −4.0 | −6 | −2 |
| Day 67(FU) | 19 | 0.0 | 0 | 2 | −5.0 | −6 | −3 |
| Day 81 (FU) | 20 | 0.5 | 0 | 3 | −4.0 | −6 | −2 |
| Day 1(DB): 4 H LOCF | 31 | 4.0 | 0 | 6 | −1.0 | −6 | 0 |
| Day 2(DB) LOCF | 31 | 2.0 | 0 | 5 | −2.0 | −6 | 0 |
| Day 3(DB) LOCF | 31 | 2.0 | 0 | 5 | −3.0 | −6 | 0 |
| Day 4(DB) LOCF | 31 | 2.0 | 0 | 5 | −3.0 | −6 | 0 |
| Day 5(DB) LOCF | 31 | 2.0 | 0 | 5 | −2.0 | −6 | 0 |
| Day 8(DB) LOCF | 31 | 2.0 | 0 | 5 | −3.0 | −6 | 1 |
| Day 11(DB) LOCF | 31 | 2.0 | 0 | 4 | −4.0 | −6 | 0 |
| Day 15(DB) LOCF | 31 | 1.0 | 0 | 4 | −4.0 | −6 | 0 |
| Day 18(DB) LOCF | 31 | 2.0 | 0 | 5 | −4.0 | −6 | 0 |
| Day 22(DB) LOCF | 31 | 2.0 | 0 | 5 | −4.0 | −6 | 2 |
| Day 25(DB): Predose LOCF | 31 | 1.0 | 0 | 5 | −4.0 | −6 | 2 |
| End Point(DB) | 31 | 0.0 | 0 | 4 | −4.0 | −6 | 0 |
| Day 32(FU) LOCF | 22 | 0.0 | 0 | 5 | −4.0 | −6 | 0 |
| Day 39(FU) LOCF | 22 | 0.0 | 0 | 4 | −4.0 | −6 | −1 |
| Day 46(FU) LOCF | 22 | 0.0 | 0 | 4 | −4.0 | −6 | −1 |
| Day 53(FU) LOCF | 22 | 0.0 | 0 | 4 | −4.0 | −6 | −2 |
| Day 67(FU) LOCF | 22 | 0.0 | 0 | 2 | −4.5 | −6 | −3 |
| End Point(FU) | 22 | 0.5 | 0 | 3 | −4.0 | −6 | −2 |

[a] Test for no difference between treatments from ANCOVA model on ranks of change with factor(s) for treatment, antidepressant therapy (AD monotherapy, AD plus augmentation therapy) and analysis center with baseline value (unranked) as a covariate.

TABLE 72B

MADRS Suicide Item: Medians and Median Changes Over Time During the Double-Blind and Follow up Phases (Study ESKETINSUI2001: ITT Analysis Set)

| Suicidal Thoughts | Esketamine 84 mg | | | Change from Baseline | | | Esketamine 84 mg-Placebo |
|---|---|---|---|---|---|---|---|
| | N | Med | Min | Max | Med | Min | Max | P-value |
| Baseline(DB) | 35 | 5.0 | 3 | 6 | | | | |
| Day 1(DB): 4 H | 35 | 2.0 | 0 | 6 | −3.0 | −5 | 1 | 0.002 |
| Day 2(DB) | 35 | 2.0 | 0 | 6 | −3.0 | −6 | 1 | 0.129 |
| Day 3(DB) | 32 | 2.0 | 0 | 6 | −4.0 | −6 | 1 | 0.183 |
| Day 4(DB) | 24 | 1.0 | 0 | 5 | −4.0 | −6 | 1 | 0.010 |
| Day 5(DB) | 21 | 0.0 | 0 | 6 | −4.0 | −6 | 1 | 0.423 |
| Day 8(DB) | 31 | 1.0 | 0 | 6 | −4.0 | −6 | 1 | 0.205 |
| Day 11(DB) | 25 | 0.0 | 0 | 6 | −4.0 | −6 | 1 | 0.077 |
| Day 15(DB) | 29 | 1.0 | 0 | 5 | −4.0 | −6 | 1 | 0.440 |
| Day 18(DB) | 23 | 1.0 | 0 | 6 | −4.0 | −6 | 1 | 0.583 |
| Day 22(DB) | 28 | 0.0 | 0 | 5 | −4.0 | −6 | 1 | 0.328 |
| Day 25(DB): Predose | 24 | 0.0 | 0 | 6 | −4.5 | −6 | 2 | 0.260 |
| Day 25(DB): 4 H | 24 | 0.0 | 0 | 6 | −4.5 | −6 | 2 | 0.426 |
| Day 32(FU) | 26 | 0.0 | 0 | 6 | −4.0 | −6 | 2 | 0.635 |
| Day 39(FU) | 26 | 0.0 | 0 | 5 | −5.0 | −6 | 1 | 0.274 |
| Day 46(FU) | 25 | 0.0 | 0 | 5 | −4.0 | −6 | 1 | 0.830 |
| Day 53(FU) | 24 | 0.0 | 0 | 5 | −5.0 | −6 | 1 | 0.933 |
| Day 67(FU) | 26 | 0.0 | 0 | 5 | −4.0 | −6 | 1 | 0.323 |
| Day 81(FU) | 24 | 0.0 | 0 | 5 | −5.0 | −6 | 1 | 0.527 |
| Day 1(DB): 4 H LOCF | 35 | 2.0 | 0 | 6 | −3.0 | −5 | 1 | 0.002 |
| Day 2(DB) LOCF | 35 | 2.0 | 0 | 6 | −3.0 | −6 | 1 | 0.129 |
| Day 3(DB) LOCF | 35 | 2.0 | 0 | 6 | −4.0 | −6 | 1 | 0.136 |
| Day 4(DB) LOCF | 35 | 1.0 | 0 | 6 | −4.0 | −6 | 1 | 0.049 |
| Day 5(DB) LOCF | 35 | 1.0 | 0 | 6 | −4.0 | −6 | 1 | 0.003 |
| Day 8(DB) LOCF | 35 | 1.0 | 0 | 6 | −4.0 | −6 | 1 | 0.170 |
| Day 11(DB) LOCF | 35 | 1.0 | 0 | 6 | −4.0 | −6 | 1 | 0.037 |
| Day 15(DB) LOCF | 35 | 1.0 | 0 | 5 | −4.0 | −6 | 1 | 0.128 |
| Day 18(DB) LOCF | 35 | 1.0 | 0 | 6 | −4.0 | −6 | 1 | 0.093 |
| Day 22(DB) LOCF | 35 | 0.0 | 0 | 5 | −4.0 | −6 | 1 | 0.059 |
| Day 25(DB): Predose LOCF | 35 | 0.0 | 0 | 6 | −4.0 | −6 | 2 | 0.058 |
| End Point(DB) | 35 | 0.0 | 0 | 6 | −4.0 | −6 | 2 | 0.143 |
| Day 32(FU) LOCF | 26 | 0.0 | 0 | 6 | −4.0 | −6 | 2 | 0.635 |
| Day 39(FU) LOCF | 27 | 0.0 | 0 | 5 | −5.0 | −6 | 1 | 0.211 |
| Day 46(FU) LOCF | 27 | 0.0 | 0 | 5 | −4.0 | −6 | 1 | 0.589 |
| Day 53(FU) LOCF | 27 | 0.0 | 0 | 5 | −4.0 | −6 | 1 | 0.959 |
| Day 67(FU) LOCF | 27 | 0.0 | 0 | 5 | −4.0 | −6 | 1 | 0.296 |
| End Point(FU) | 27 | 0.0 | 0 | 5 | −5.0 | −6 | 1 | 0.497 |

[a] Test for no difference between treatments from ANCOVA model on ranks of change with factor(s) for treatment, antidepressant therapy (AD monotherapy, AD plus augmentation therapy) and analysis center with baseline value (unranked) as a covariate.

In summary, dissociative symptoms, as measured on the CADSS, observed in the esketamine group were consistent with prior studies. These symptoms were transient (resolved within 2 hrs) and attenuated with repeated dosing.

Summary

Intranasal esketamine 84 mg, compared to placebo, demonstrated a clinically meaningful and statistically significant rapid reduction of depressive symptoms in subjects with MDD who are assessed to be at imminent risk for suicide, as demonstrated by change from baseline in the MADRS total score at both 4 hours and Day 2. Significant improvement in suicidality was also observed at 4 hours and Day 2 as measured by both the MADRS suicide item and the SIBAT Clinical Global Judgment of Suicide Risk. There was no difference detected on the BSS at any of these time points. As observed in previous esketamine studies in TRD, the perceptual (dissociative) symptoms measured by the CADSS and BP elevation, appear to occur shortly after the start of the administration and resolved by 2 hours post administration. Additionally, perceptual symptoms attenuated with repeated dosing. Of note, during the follow up period 3 subjects in the placebo group, but none in the esketamine group, made suicide attempts (non-fatal).

The results of the Phase 2a POC study supports the hypothesis that intranasal esketamine is an efficacious treatment for the rapid reduction of the symptoms of MDD, including suicidal ideation, in patients assessed to be at imminent risk for suicide. The subjects included in this study were severely depressed and suicidal as evidenced by their high baseline MADRS and BSS scores. All subjects were treated aggressively with initial hospitalization and optimized standard of care antidepressant medication. Therefore, it is not surprising that, subjects in both treatment groups experienced clinically meaningful improvement in all efficacy measures over the course of the double-blind period. Despite the non-specific improvement in the placebo group, the beneficial effect of esketamine on the symptoms of MDD, as measured by the MADRS total score and the MADRS suicide item, could be distinguished at early time points and at the double-point end-point.

Example 4

The primary objective of this study is to assess the efficacy of intranasal esketamine plus an oral antidepressant compared with an oral antidepressant plus intranasal placebo in delaying relapse of depressive symptoms in subjects with TRD who have achieved stable remission (primary) or stable response (secondary) after an induction and optimization course of intranasal esketamine plus an oral antidepressant (AD), to assess the efficacy of esketamine plus an oral AD compared with an oral AD plus intranasal placebo in delaying relapse of depressive symptoms. A key question addressed was whether in the stable remitter/responder groups, esketamine could be stopped and longer-term maintenance be achieved with the oral AD alone. A relapse adjudication committee reviewed events that were considered clinically relevant to determine if a relapse occurred.

Together with the 3 short-term efficacy and safety studies and the long term open label safety study, this study supports regulatory agency requirements for registration of esketamine nasal spray for the treatment of TRD.

Subject and Treatment Information

This was a randomized, double-blind, parallel-group, active-controlled, multicenter study that included 705 enrolled subjects with TRD. This study evaluated the efficacy, safety, and tolerability of intranasal esketamine plus an oral antidepressant compared with an oral antidepressant plus intranasal placebo in delaying relapse of depressive symptoms in adult men and women with TRD who are in stable remission after an induction and optimization phase treatment with intranasal esketamine plus an oral antidepressant. See, FIG. 49 for the trial design.

Of the 705 enrolled subjects, 437 (62.0%) were directly enrolled into the 3003 study, 150 (21.3%) were transferred from the ESKETINTRD3001 study, and 118 (16.7%) were transferred from the ESKETINTRD3002 study. See, FIG. 50. In the all enrolled analysis set, 635 (90.1%) of the subjects were white and 457 (64.8%) of the subjects were female. The mean age was 46.1 years, ranging from 18 to 64 years. Of the 437 safety (IND) analysis set subjects (direct-entry subjects only), 273 (62.5%) subjects completed the 28-day IND phase and 164 (37.5%) withdrew. The majority of subjects were discontinued from the IND phase due to subjects who did not meet criteria for continuing into the next phase' (114 subjects).

Of the 455 esketamine-treated subjects entering the OP phase (including 182 esketamine-treated transferred-entry subjects from the TRD3001 or TRD3002 study), 297 (65.3%) subjects completed the 12-week OP phase and 158 (34.7%) subjects withdrew. The most frequent reasons for discontinuation were due to subject did not meet criteria for continuing into the next phase (107 subjects).

Of the 176 subjects in the full (stable remitters) analysis set, 159 (90.3%) subjects completed the MA phase (of those, 63 (35.8%) had a relapse event and 96 (54.5%) remained relapse-free at the time of the study termination). The most frequent reason for withdrawal was 'other' (8 subjects).

Of the 121 subjects in the full (stable responders) analysis set, 113 (93.4%) subjects completed the MA phase (of those, 50 (41.3%) had a relapse event and 63 (52.1%) remained relapse-free at the time of the study termination). The most frequent reason for withdrawal was 'withdrawal by subject' (3 subjects). A total of 545 subjected entered the follow-up phase and 532 (97.6%) completed the follow-up phase.

Subjects presented at baseline (IND) with a median MADRS total score of 38, (severe depression) and the median duration of the current depressive episode was 64 weeks, with 27.4% having a lifetime history of suicidal ideation (29.1% in the past 6 months) and a 14.9% lifetime history of suicidal behavior. Over 89.0% of subjects had received 3 or more ADs with non-response (defined as ≤25% improvement) prior to starting the Induction phase. Subjects reported a family history of depression (45.1%), anxiety disorder (9.1%), and alcohol abuse (13.5%).

Treatment duration/Trial duration: Each subject participated in up to 5 phases: a screening prospective observational phase (direct-entry subjects only) of 4 weeks+an optional up to 3-week taper period, a 4-week open-label induction phase (direct-entry subjects only), a 12-week optimization phase (open-label for direct-entry subjects and double-blind for transferred-entry subjects), a double-blind maintenance phase of variable duration and a 2-week follow-up phase. The maximum duration of a subject's participation was variable, depending on whether he or she entered the study directly or was transferred from one of the double-blind short-term studies, and whether he or she met phase-specific criteria (e.g., met criteria for response at the end of the induction phase, was in stable remission/response at the end of the optimization phase, and when and if he or she relapsed in the maintenance phase). Direct-entry subjects participated in up to 5 phases and transferred-entry subjects participated in up to 3 phases in the current study after having participated in the screening prospective observational and Induction phases in the studies they transferred from. The inclusion/exclusion criteria were the same for direct and transfer entry subjects.

Efficacy

Level of Significance

A pre-planned interim analysis of efficacy data was conducted when 33 relapse events occurred in stable remitters with at least 30 relapses (31 were actually included in the interim analysis) from randomized stable remitters treated with intranasal esketamine plus an oral antidepressant in the optimization phase (List 1). The objectives of the interim analysis were to re-estimate sample size or to stop the study for efficacy. An independent external statistical support group (Cytel) conducted the analysis and the IDMC reviewed unblinded results and recommended to continue the study. Based on the predefined rules, the final sample size determined from the sample size re-estimation was 59. The Janssen team and the sites remained blinded to the IDMC sample size recommendation until 59 relapses had occurred in the List 1 subjects.

The interim efficacy analysis was performed at a significance level of 0.0097 (two-sided). As the study was not stopped for efficacy at the interim analysis, the final efficacy analysis was to be performed at a significance level of 0.046 (two-sided).

Primary Endpoint

The primary efficacy analysis was performed on the full (stable remitters) analysis set, which included 175 stable remitters and 1 stable responder (who was incorrectly randomized as a stable remitter) which is defined as randomized subjects who were in stable remission at the end of the optimization phase after treatment with intranasal esketamine plus an oral antidepressant. The subjects were randomized as stable remitters (List 1) in a 1:1 ratio to continue on intranasal esketamine plus oral AD (N=90) or to discontinue esketamine and receive oral AD plus intranasal placebo (N=86); These subjects received at least 1 dose of intranasal study drug and 1 dose of oral antidepressant during the maintenance phase.

Results for the time to relapse in the maintenance phase favored intranasal esketamine+oral AD in delaying relapse compared to oral AD+ intranasal placebo. Overall, 24 (26.7%) subjects in the intranasal esketamine+oral AD group and 39 (45.3%) subjects in the oral AD+ intranasal placebo group experienced a relapse event during the maintenance phase. Based on the weighted combination test, the difference between treatment groups was statistically significant (two-sided p=0.003), which was below the threshold of statistical significance (0.046). The estimated hazard ratio of intranasal esketamine+oral AD relative to oral AD+ intranasal placebo based on weighted estimates was 0.49 (95% CI: 0.29, 0.84) using ADDPLAN. The most common reason for relapse was a MADRS total score ≥22 for 2 consecutive assessments separated by 5 to 15 days.

No major differences in efficacy were seen by region, gender, age, direct or transfer entry, or oral AD group (SNRIs and SSRIs).

Other Secondary Efficacy Endpoints

Secondary efficacy variables included:
The time between subject randomization and the first documentation (earliest date) of a relapse in the maintenance phase for subjects with stable response (but who were not in remission) at the end of the optimization phase after treatment with intranasal esketamine plus an oral antidepressant.
Change in MADRS from Baseline (MA) to End Point (MA)
Proportion of subjects with response and remission based on MADRS
Change in PHQ-9 from Baseline (MA) to End Point (MA)
Change in CGI-S from Baseline (MA) to End Point (MA)
Change in GAD-7 from Baseline (MA) to End Point (MA)
Change in EQ-5D-5L from Baseline (MA) to End Point (MA)
Change in SDS from Baseline (MA) to End Point (MA)

Results for the time between subject randomization and the first documentation (earliest date) of a relapse in the maintenance phase for subjects in the full (stable responders) analysis set (including 121 subjects: 120 stable responders and 1 subject not meeting either stable remission or stable response criteria at the end of the optimization phase) after treatment with intranasal esketamine plus an oral antidepressant favored intranasal esketamine+oral AD in delaying relapse compared to oral AD+ intranasal placebo. Overall, 16 (25.8%) subjects in the intranasal esketamine+ oral AD group and 34 (57.6%) subjects in the oral AD+ intranasal placebo group experienced a relapse event during maintenance phase. The difference between treatment groups was statistically significant (two-sided p<0.001) using a two-sided log-rank test. The estimated hazard ratio of intranasal esketamine+oral AD relative to oral AD+ intranasal placebo based on the Cox proportional hazards model with treatment as a factor was 0.30 (95% CI: 0.16, 0.55).

The subjects were randomized as stable responders (List 2) in a 1:1 ratio to continue on intranasal esketamine plus oral AD (N=62) or to discontinue esketamine and receive oral AD plus intranasal placebo (N=59). Both randomization lists were stratified by country.

Safety

Overall, 76.9% of subjects experienced at least one TEAE during the IND phase. In the safety (OP) analysis set (safety (OP) and safety (MA) analysis sets do not include the transferred-entry subjects who continued to receive oral AD+placebo (TEP) during the subsequent phases), 73.6% of subjects experienced at least one TEAE during the OP phase. In the safety (MA) analysis set, 82.2% of subjects in the esketamine+oral AD group and 45.5% of subjects in the oral AD+placebo group experienced at least one TEAE during the MA phase. For the TEP subjects, 61.6% of subjects experienced at least one TEAE during the OP phase and 68.5% experienced at least one TEAE during the MA phase.

The most common TEAEs (≥10%) during the IND phase were vertigo (22.7%), dizziness (22.2%), nausea (21.5%), dysgeusia (20.6%), somnolence (14.9%), headache (13.7%), paranesthesia (11.0%), dissociation (11.0%), feeling abnormal (10.8%), vision blurred (10.3%) and sedation (10.1%). In the safety (OP) analysis set, the most common TEAEs during the OP phase were vertigo (20.0%), dysgeusia (17.4%), somnolence (13.8%), dizziness (13.4%), headache (12.5%) and nausea (10.5%). In the safety (MA) analysis set, the most common TEAEs in esketamine+oral AD during the double-blind MA phase were dysgeusia (26.3%), vertigo (25.0%), somnolence (21.1%), dizziness (20.4%), headache (17.8%), nausea (16.4%), vision blurred (15.8%), dissociation (13.8%) and hypoesthesia oral (13.2%). There was no TEAE in ≥10% of subjects with oral AD+placebo in the safety (MA) analysis set. For the TEP subjects, the most common TEAE was headache (18.6%) during the OP phase, and viral upper respiratory tract infection (24.1%), headache (22.2%) and dysgeusia (14.8%) during the MA phase.

There were no deaths reported in this study.

There were 32 subjects with 39 serious adverse events (SAEs) reported in this study. A total of 13 subjects experienced serious treatment-emergent adverse events (TEAEs) during the IND phase in the safety (IND) analysis set. Three subjects had serious TEAEs considered as of very likely relationship to intranasal esketamine by the investigators: disorientation (Day 1), suicidal ideation (Day 8), sedation (Day 22), and one subject had two serious TEAEs on the same day (Day 5) considered as of very likely relationship to intranasal esketamine: autonomic nervous system imbalance and simple partial seizures. One subject had a serious TEAE considered by the investigator as probably related to intranasal esketamine: lacunar stroke (Day 1). One subject had a serious TEAE considered possibly related to intranasal esketamine: hypothermia (Day 10). Eleven subjects experienced serious treatment-emergent adverse events during the OP phase in the safety (OP) analysis set. No serious TEAEs were considered to be possibly, probably or very likely related to esketamine. Five subjects (4 in esketamine+oral AD, 1 in oral AD+placebo) in the safety (MA) analysis set experienced serious treatment-emergent adverse events during the MA phase. All the events were considered as not related to intranasal medication or oral AD. Two subjects had serious AEs considered not related to oral AD in the follow-up phase. One subject experienced two serious AEs considered to be possibly related to oral AD. No TEP subject experienced a serious treatment-emergent adverse event during the OP phase. One TEP subject experienced a serious TEAE during the MA phase which was considered not related to intranasal medication or oral AD.

There were 22 subjects who discontinued the IND phase intranasal study medication due to treatment-emergent adverse events in the safety (IND) analysis set and 5 subjects who discontinued the OP phase intranasal study medication due to treatment-emergent adverse events in the safety (OP) analysis set. Per study design, these subjects could continue the oral AD in the follow-up phase if appropriate. Eight subjects discontinued the IND phase oral AD medication and 2 subjects discontinued the OP phase oral AD medication due to treatment-emergent adverse events. There were 7 subjects (4 subjects in esketamine+oral AD, 3 subjects in oral AD+placebo) who discontinued the MA phase intranasal study medication due to treatment-emergent adverse events in the safety (MA) analysis set. Per study design, these subjects could continue the oral AD in the follow-up phase if appropriate. Three subjects in esketamine+oral AD arm discontinued the MA phase oral AD study medication due to treatment-emergent adverse events; no subjects in oral AD+ intranasal placebo arm discontinued the MA phase oral AD study medication due to treatment-emergent adverse events. No TEP subjects discontinued the OP phase intranasal study medication or oral AD due to treatment-emergent adverse events in the safety (OP_TEP) analysis set. There were 2 TEP subjects who discontinued the MA phase intranasal study medication in the safety (MA_TEP) analysis set. One of these subjects discontinued the MA phase due to both intranasal and oral AD medications.

Other Safety Observations

Transient blood pressure increases for the esketamine+ oral AD group peaked at 40 minutes post dose and returned closer to predose levels by 1.5 hours post dose.

Dissociative/perceptual change symptoms measured by the CADSS, suggest onset of these symptoms occurred shortly after the start of the intranasal dosing session and resolved by 1.5 hours post dose.

The proportion of subjects with sedation (as measured by the MOAA/S scale ≤3) was ≤3.9% for esketamine+oral AD for each dosing day in all phases.

Subject and Treatment Information

A total of 1097 subjects were enrolled across 164 sites in 16 countries (Belgium, Brazil, Canada, Czech Republic, Estonia, France, Germany, Hungary, Italy, Mexico, Poland, Slovakia, Spain, Sweden, Turkey, and United States). Excluding 378 screen failures and 14 subjects from site PL10002 due to GCP issues, 705 subjects with a DSM-5 (Diagnostic and Statistical Manual of Mental Disorders, 5th Edition) diagnosis of MDD were enrolled.

Four hundred thirty-seven subjects were directly enrolled into the 3003 study, 150 subjects were transferred from the ESKETINTRD3001 study, and 118 subjects were transferred from the ESKETINTRD3002 study. Results are presented in Table 73.

TABLE 73

Number of Direct-entry and Transferred-entry Subjects Enrolled in Study (Study ESKETINTRD3003: All Enrolled Analysis Set)

| | Total (N = 705) |
|---|---|
| Direct-entry subjects in study | |
| ESKETINTRD3003 | 437 (62.0%) |
| Transferred-entry subjects from: | |
| Study ESKETINTRD3001 | 150 (21.3%) |
| Transfer-entry Placebo | 38 (5.4%) |
| Transfer-entry Esketamine | 112 (15.9%) |
| Study ESKETINTRD3002 | 118 (16.7%) |
| Transfer-entry Placebo | 48 (6.8%) |
| Transfer-entry Esketamine | 70 (9.9%) |

TABLE 74

Number of Subjects in Each Phase and Analysis Set (Study ESKETINTRD3003: All Enrolled Analysis Set)

| | Intranasal Esk + Oral AD | Oral AD + Intranasal Placebo | Total |
|---|---|---|---|
| Open-label induction phase | | | |
| Full (IND) | 430 | N/A | 430 |
| Safety (IND) | 437 | N/A | 437 |
| Optimization phase | | | |
| Full (OP) | 452 | 0 | 452 |
| Safety (OP) | 455 | 0 | 455 |
| Safety transfer-entry placebo (OP) [a] | 0 | 86 | 86 |
| Maintenance phase | | | |
| Interim full (stable remitters) [b] | 49 | 47 | 96 |
| Full (stable remitters) | 90 | 86 | 176 |
| Full (stable responders) | 62 | 59 | 121 |
| Safety (MA) | 152 | 145 | 297 |
| Safety (stable remitters) | 90 | 86 | 176 |
| Safety transfer-entry placebo (MA) [a] | 0 | 54 | 54 |
| Follow-up phase | | | |
| Follow-up | 481 | 64 | 545 |

[a] Transferred entry subjects who continued to receive an oral antidepressant plus intranasal Placebo.
[b] Full (Stable Remitters) analysis set at the time of Interim analysis. Stable Remission: MADRS total score ≤12 for at least 3 of the last 4 weeks of the optimization phase, but one excursion of a MADRS total score >12 or one missing MADRS assessment is permitted at Optimization week 13 or 14 only. The MADRS total score at weeks 15 and 16 must be ≤12. Stable Response: ≥50% reduction in the MADRS total score from baseline (Day 1 of induction phase; pre-randomization/prior to the first intranasal dose) in each of the last 2 weeks of the optimization phase, but does not meet criteria for stable remission. For transferred-entry subjects, Day 1 of the open-label induction phase will take place in studies ESKETINTRD3001 or ESKETINTRD3002.

Study Completion/Withdrawal Information

Of the 437 safety (IND) analysis set subjects (direct-entry subjects only), 273 (62.5%) subjects completed the 28-day IND phase and 164 (37.5%) withdrew. Results are presented in Table 75. The majority of subjects were discontinued from the IND phase due to subject 'did not meet criteria for continuing into the next phase' (114 subjects).

TABLE 75

Study Completion/Withdrawal Information; Open-label Induction Phase (Study ESKETINTRD3003: Safety (IND) Analysis Set)

| | Intranasal Esk + Oral AD (N = 437) |
|---|---|
| Continued to optimization phase | 273 (62.5%) |
| Withdrawn during open-label induction phase | 164 (37.5%) |
| Adverse event | 22 (5.0%) |
| Lack of efficacy | 2 (0.5%) |
| Lost to follow-up | 1 (0.2%) |
| Protocol violation | 2 (0.5%) |
| Subject does not meet criteria for continuing into the next phase | 114 (26.1%) |
| Withdrawal by subject | 15 (3.4%) |
| Other | 8 (1.8%) |

Of the 455 subjects entering the OP phase (including 182 esketamine-treated transferred-entry subjects from the TRD3001 or TRD3002 study) in the safety (OP) analysis set, 297 (65.3%) subjects completed the 12-week OP phase and 158 (34.7%) subjects withdrew. Results are presented in Table 76.

TABLE 76

Study Completion/Withdrawal Information; Optimization Phase (Study ESKETINTRD3003: Safety (OP) Analysis Set)

| | Intranasal Esk + Oral AD (N = 455) |
|---|---|
| Continued to maintenance phase | 297 (65.3%) |
| Withdrawn during optimization phase | 158 (34.7%) |
| Adverse event | 5 (1.1%) |
| Lack of efficacy | 8 (1.8%) |
| Lost to follow-up | 2 (0.4%) |
| MADRS total score ≥22 for 2 consecutive visit [a] | 14 (3.1%) |
| Protocol violation | 4 (0.9%) |
| Subject does not meet criteria for continuing into the next phase | 107 (23.5%) |
| Subject does not meet criteria for stable remission or stable response | 106 (23.3%) |
| Subject missed ≥3 MADRS assessments [b] | 1 (0.2%) |
| Withdrawal by subject | 8 (1.8%) |
| Other | 10 (2.2%) |

[a] This criterion applies to subjects prior to Protocol Amendment 3.
[b] This criterion applies to subjects prior to Protocol Amendment 4.

The most frequent reasons for discontinuation were due to subject 'did not meet criteria for continuing into the next phase' (107 subjects). Note that the safety (OP) and safety (MA) analysis sets do not include the transferred-entry subjects who continued to receive oral AD+placebo (TEP) during the subsequent phases, see Tables 77 and 78 for Study Completion/Withdrawal Information for these analysis sets.

TABLE 77

Study Completion/Withdrawal Information; Optimization Phase (Study ESKETINTRD3003: Safety (OP_TEP) Analysis Set)

| | Oral AD + Intranasal Placebo (N = 86) |
|---|---|
| Continued to maintenance phase | 54 (62.8%) |
| Withdrawn during optimization phase | 32 (37.2%) |
| Lost to follow-up | 1 (1.2%) |

TABLE 77-continued

Study Completion/Withdrawal Information; Optimization Phase (Study ESKETINTRD3003: Safety (OP_TEP) Analysis Set)

| | Oral AD + Intranasal Placebo (N = 86) |
|---|---|
| MADRS total score ≥22 for 2 consecutive visit [a] | 5 (5.8%) |
| Protocol violation | 1 (1.2%) |
| Subject does not meet criteria for continuing into the next phase | 20 (23.3%) |
| Subject does not meet criteria for stable remission or stable response | 18 (20.9%) |
| Subject missed ≥3 MADRS assessments [b] | 2 (2.3%) |
| Withdrawal by subject | 3 (3.5%) |
| Other | 2 (2.3%) |

[a] This criterion applies to subjects prior to Protocol Amendment 3.
[b] This criterion applies to subjects prior to Protocol Amendment 4.

TABLE 78

Study Completion/Withdrawal Information; Maintenance Phase (Study ESKETINTRD3003: Safety (MA_TEP) Analysis Set)

| | Oral AD + Intranasal Placebo (N = 54) |
|---|---|
| Completed maintenance phase | 44 (81.5%) |
| Subjects who relapsed | 13 (24.1%) |
| Subjects who remained relapse-free[a] | 31 (57.4%) |
| Withdrawn during maintenance phase | 10 (18.5%) |
| Adverse event | 2 (3.7%) |
| Protocol violation | 1 (1.9%) |
| Withdrawal by subject | 3 (5.6%) |
| Other | 4 (7.4%) |

[a] Subjects were considered completers if they were relapse-free at the time of the study termination Of the 176 subjects in the full (stable remitters) analysis set, 159 (90.3%) subjects completed the MA phase (of those, 63 (35.8%) had a relapse event and 96 (54.5%) remained relapse-free at the time of the study termination). Results are presented in Table 79. The most frequent reason for withdrawal was 'other' (8 subjects).

TABLE 79

Study Completion/Withdrawal Information; Maintenance Phase (Study ESKETINTRD3003: Full (Stable Remitters) Analysis Set)

| | Intranasal Esk + Oral AD (N = 90) | Oral AD + Intranasal Placebo (N = 86) | Total (N = 176) |
|---|---|---|---|
| Completed maintenance phase | 82 (91.1%) | 77 (89.5%) | 159 (90.3%) |
| Subjects who relapsed | 24 (26.7%) | 39 (45.3%) | 63 (35.8%) |
| Subjects who remained relapse-free [a] | 58 (64.4%) | 38 (44.2%) | 96 (54.5%) |
| Withdrawn during maintenance phase | 8 (8.9%) | 9 (10.5%) | 17 (9.7%) |
| Adverse event | 1 (1.1%) | 1 (1.2%) | 2 (1.1%) |
| Pregnancy | 1 (1.1%) | 0 | 1 (0.6%) |
| Withdrawal by subject | 3 (3.3%) | 3 (3.5%) | 6 (3.4%) |
| Other | 3 (3.3%) | 5 (5.8%) | 8 (4.5%) |

[a] Subjects were considered completers if they were relapse-free at the time of the study termination Of the 121 subjects in the full (stable responders) analysis set, 113 (93.4%) subjects completed the MA phase (of those, 50 (41.3%) had a relapse event and 63 (52.1%) remained relapse-free at the time of the study termination). Results are presented in Table 80. The most frequent reason for withdrawal was 'withdrawal by subject' (3 subjects).

TABLE 80

Study Completion/Withdrawal Information; Maintenance Phase (Study ESKETINTRD3003: Full (Stable Responders) Analysis Set)

|  | Intranasal Esk + Oral AD (N = 62) | Oral AD + Intranasal Placebo (N = 59) | Total (N = 121) |
|---|---|---|---|
| Completed maintenance phase | 57 (91.9%) | 56 (94.9%) | 113 (93.4%) |
| Subjects who relapsed | 16 (25.8%) | 34 (57.6%) | 50 (41.3%) |
| Subjects who remained relapse-free [a] | 41 (66.1%) | 22 (37.3%) | 63 (52.1%) |
| Withdrawn during maintenance phase | 5 (8.1%) | 3 (5.1%) | 8 (6.6%) |
| Adverse event | 0 | 1 (1.7%) | 1 (0.8%) |
| Lost to follow-up | 1 (1.6%) | 0 | 1 (0.8%) |
| Noncompliance with study drug | 0 | 1 (1.7%) | 1 (0.8%) |
| Protocol violation | 1 (1.6%) | 0 | 1 (0.8%) |
| Withdrawal by subject | 2 (3.2%) | 1 (1.7%) | 3 (2.5%) |
| Other | 1 (1.6%) | 0 | 1 (0.8%) |

[a] Subjects were considered completers if they were relapse-free at the time of the study termination Subjects could enter the follow-up phase from the IND phase, OP phase or MA phase. A total of 545 subjects entered the follow-up phase and 532 (97.6%) completed the follow-up phase.

Demographic and Baseline Characteristics

Demographic and baseline characteristics are displayed in Table 81 for the all enrolled analysis set. The majority of subjects enrolled were female (64.8%).

TABLE 81

Demographic and Baseline (IND) Characteristics (Study ESKETINTRD3003: All Enrolled Analysis Set)

|  | Total (N = 705) |
|---|---|
| Age (years) | |
| N | 705 |
| Mean (SD) | 46.1 (11.10) |
| Median | 47.0 |
| Range | (18; 64) |
| Age category (years), n (%) | |
| N | 705 |
| 18-44 | 292 (41.4%) |
| 45-64 | 413 (58.6%) |
| Sex, n (%) | |
| N | 705 |
| Male | 248 (35.2%) |
| Female | 457 (64.8%) |
| Race, n (%) | |
| N | 705 |
| American Indian or Alaskan native | 1 (0.1%) |
| Asian | 3 (0.4%) |
| Black or African American | 31 (4.4%) |
| White | 635 (90.1%) |
| Other | 22 (3.1%) |
| Multiple | 4 (0.6%) |
| Not Reported | 9 (1.3%) |
| Ethnicity, n (%) | |
| N | 705 |
| Hispanic or Latino | 94 (13.3%) |
| Not Hispanic or Latino | 600 (85.1%) |
| Not Reported | 10 (1.4%) |
| Unknown | 1 (0.1%) |
| Baseline weight (kg) | |
| N | 705 |
| Mean (SD) | 81.61 (19.408) |
| Median | 80.00 |
| Range | (44.1; 179.0) |

TABLE 81-continued

Demographic and Baseline (IND) Characteristics (Study ESKETINTRD3003: All Enrolled Analysis Set)

|  | Total (N = 705) |
|---|---|
| Baseline height (cm) | |
| N | 705 |
| Mean (SD) | 168.88 (10.185) |
| Median | 168.00 |
| Range | (136.0; 210.3) |
| Baseline body mass index (kg/m$^2$) | |
| N | 705 |
| Mean (SD) | 28.6 (6.23) |
| Median | 27.6 |
| Range | (17; 67) |
| BMI category (kg/m$^2$), n (%) | |
| N | 705 |
| Underweight <18.5 | 6 (0.9%) |
| Normal 18.5-<25 | 195 (27.7%) |
| Overweight 25-<30 | 259 (36.7%) |
| Obese 30-<40 | 212 (30.1%) |
| Morbidly obese ≥40 | 33 (4.7%) |
| Employment status, n (%) [a] | |
| N | 705 |
| Any type of employment | 448 (63.5%) |
| Any type of unemployment | 180 (25.5%) |
| Other | 77 (10.9%) |
| Hypertension status, n (%) [b] | |
| N | 705 |
| Yes | 147 (20.9%) |
| No | 558 (79.1%) |
| Country, n (%) | |
| N | 705 |
| Belgium | 14 (2.0%) |
| Brazil | 64 (9.1%) |
| Canada | 5 (0.7%) |
| Czech Republic | 99 (14.0%) |
| Estonia | 1 (0.1%) |
| France | 10 (1.4%) |
| Germany | 7 (1.0%) |
| Hungary | 35 (5.0%) |
| Italy | 21 (3.0%) |
| Mexico | 35 (5.0%) |
| Poland | 132 (18.7%) |
| Slovakia | 7 (1.0%) |
| Spain | 16 (2.3%) |
| Sweden | 16 (2.3%) |
| Turkey | 53 (7.5%) |
| United States | 190 (27.0%) |

TABLE 81-continued

Demographic and Baseline (IND) Characteristics (Study ESKETINTRD3003: All Enrolled Analysis Set)

| | Total (N = 705) |
|---|---|
| Region, n (%) | |
| N | 705 |
| Europe | 411 (58.3%) |
| North America | 195 (27.7%) |
| Other | 99 (14.0%) |
| Class of oral antidepressant, n (%) | |
| N | 699 |
| SNR | 440 (62.9%) |
| SSRI | 259 (37.1%) |
| Oral antidepressant, n (%) | |
| N | 699 |
| Duloxetine | 323 (46.2%) |
| Escitalopram | 128 (18.3%) |
| Sertraline | 130 (18.6%) |
| Venlafaxine extended release (XR) | 118 (16.9%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

The mean (SD) age was 46.1 (11.10) years, ranging from 18 to 64 years. Baseline psychiatric history for the all enrolled analysis set is presented in Table 82. The mean (SD) baseline (IND) MADRS total score was 37.9 (5.50), ranging from 4 to 53.

TABLE 82

Baseline (IND) Psychiatric History (Study ESKETINTRD3003: All Enrolled Analysis Set)

| | Total (N = 705) |
|---|---|
| Age when diagnosed with MDD (years) | |
| N | 705 |
| Mean (SD) | 32.7 (11.70) |
| Median | 32.0 |
| Range | (5; 64) |
| Baseline MADRS total score | |
| N | 705 |
| Mean (SD) | 37.9 (5.50) |
| Median | 38.0 |
| Range | (4; 53) |
| Screening IDS-C30 total score | |
| N | 705 |
| Mean (SD) | 47.2 (7.26) |
| Median | 47.0 |
| Range | (34; 76) |
| Baseline CGI-S | |
| N | 705 |
| Mean (SD) | 5.1 (0.66) |
| Median | 5.0 |
| Range | (3; 7) |
| Baseline CGI-S category, n (%) | |
| N | 705 |
| Normal, not at all ill | 0 |
| Borderline mentally ill | 0 |
| Mildly ill | 2 (0.3%) |
| Moderately ill | 98 (13.9%) |
| Markedly ill | 412 (58.4%) |
| Severely ill | 187 (26.5%) |
| Among the most extremely ill patients | 6 (0.9%) |

TABLE 82-continued

Baseline (IND) Psychiatric History (Study ESKETINTRD3003: All Enrolled Analysis Set)

| | Total (N = 705) |
|---|---|
| Baseline PHQ-9 total score | |
| N | 705 |
| Mean (SD) | 19.9 (4.18) |
| Median | 20.0 |
| Range | (3; 27) |
| Screening C-SSRS lifetime [a], n (%) | |
| N | 705 |
| No event | 407 (57.7%) |
| Suicidal ideation | 193 (27.4%) |
| Suicidal behavior | 105 (14.9%) |
| Screening C-SSRS past 6 or 12 months [a], n (%) | |
| N | 705 |
| No event | 499 (70.8%) |
| Suicidal ideation (past 6 months) | 205 (29.1%) |
| Suicidal behavior (past 12 months) | 1 (0.1%) |
| Duration of current episode (wks) | |
| N | 705 |
| Mean (SD) | 132.2 (209.18) |
| Median | 64.0 |
| Range | (4; 2288) |
| Previous antidepressant medications [b], n (%) | |
| N | 702 |
| 1 | 77 (11.0%) |
| 2 | 394 (56.1%) |
| 3 | 150 (21.4%) |
| 4 | 59 (8.4%) |
| 5 | 20 (2.8%) |
| 8 | 1 (0.1%) |
| 9 | 1 (0.1%) |
| Family history of depression, n (%) | |
| N | 705 |
| Yes | 318 (45.1%) |
| No | 387 (54.9%) |
| Family history of anxiety disorder, n (%) | |
| N | 705 |
| Yes | 64 (9.1%) |
| No | 641 (90.9%) |
| Family history of bipolar disorder, n (%) | |
| N | 705 |
| Yes | 46 (6.5%) |
| No | 659 (93.5%) |
| Family history of schizophrenia, n (%) | |
| N | 705 |
| Yes | 28 (4.0%) |
| No | 677 (96.0%) |
| Family history of alcohol abuse, n (%) | |
| N | 705 |
| Yes | 95 (13.5%) |
| No | 610 (86.5%) |
| Family history of substance abuse, n (%) | |
| N | 705 |
| Yes | 29 (4.1%) |
| No | 676 (95.9%) |

[a] C-SSRS category: No event = 0; Suicidal ideation = 1, 2, 3, 4, 5; Suicidal behavior = 6, 7, 8, 9, 10
[b] Number of antidepressant medications with non-response (defined as ≤25% improvement) taken for at least 6 weeks during the current episode as obtained from MGH-ATRQ at the time of first screening visit.

Demographic and baseline characteristics, and baseline psychiatric history for the safety (IND) analysis set are displayed in the Tables 83 and 84. The majority of subjects enrolled were female (61.3%). The mean (SD) age was 46.5

(10.96) years, ranging from 19 to 64 years. The mean (SD) baseline (IND) MADRS total score was 37.8 (5.51), ranging from 4 to 53.

TABLE 83

Demographic and Baseline (IND) Characteristics (Study ESKETINTRD3003: Safety (IND) Analysis Set)

| | Total (N = 437) |
|---|---|
| Age (years) | |
| N | 437 |
| Mean (SD) | 46.5 (10.96) |
| Median | 48.0 |
| Range | (19; 64) |
| Age category (years), n (%) | |
| N | 437 |
| 18-44 | 173 (39.6%) |
| 45-64 | 264 (60.4%) |
| Sex, n (%) | |
| N | 437 |
| Male | 169 (38.7%) |
| Female | 268 (61.3%) |
| Race, n (%) | |
| N | 437 |
| Asian | 1 (0.2%) |
| Black or African American | 18 (4.1%) |
| White | 413 (94.5%) |
| Other | 1 (0.2%) |
| Multiple | 4 (0.9%) |
| Ethnicity, n (%) | |
| N | 437 |
| Hispanic or Latino | 31 (7.1%) |
| Not Hispanic or Latino | 406 (92.9%) |
| Baseline weight (kg) | |
| N | 437 |
| Mean (SD) | 81.53 (19.305) |
| Median | 80.00 |
| Range | (47.2; 179.0) |
| Baseline height (cm) | |
| N | 437 |
| Mean (SD) | 169.22 (10.016) |
| Median | 168.20 |
| Range | (136.0; 210.3) |
| Baseline body mass index (kg/m$^2$) | |
| N | 437 |
| Mean (SD) | 28.5 (6.35) |
| Median | 27.4 |
| Range | (18; 67) |
| BMI category (kg/m$^2$), n (%) | |
| N | 437 |
| Underweight <18.5 | 4 (0.9%) |
| Normal 18.5-<25 | 128 (29.3%) |
| Overweight 25-<30 | 159 (36.4%) |
| Obese 30-<40 | 124 (28.4%) |
| Morbidly obese ≥40 | 22 (5.0%) |
| Employment status, n (%) [a] | |
| N | 437 |
| Any type of employment | 280 (64.1%) |
| Any type of unemployment | 109 (24.9%) |
| Other | 48 (11.0%) |
| Hypertension status, n (%) [b] | |
| N | 437 |
| Yes | 94 (21.5%) |
| No | 343 (78.5%) |
| Country, n (%) | |
| N | 437 |
| Brazil | 28 (6.4%) |
| Czech Republic | 59 (13.5%) |
| Hungary | 33 (7.6%) |
| Italy | 21 (4.8%) |
| Poland | 106 (24.3%) |
| Spain | 10 (2.3%) |
| Sweden | 16 (3.7%) |
| Turkey | 53 (12.1%) |
| United States | 111 (25.4%) |
| Region, n (%) | |
| N | 437 |
| Europe | 298 (68.2%) |
| North America | 111 (25.4%) |
| Other | 28 (6.4%) |
| Class of oral antidepressant, n (%) | |
| N | 431 |
| SNRI | 266 (61.7%) |
| SSRI | 165 (38.3%) |
| Oral antidepressant, n (%) | |
| N | 431 |
| Duloxetine | 195 (45.2%) |
| Escitalopram | 76 (17.6%) |
| Sertraline | 89 (20.6%) |
| Venlafaxine extended release (XR) | 71 (16.5%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

TABLE 84

Baseline (IND) Psychiatric History (Study ESKETINTRD3003: Safety (IND) Analysis Set)

| | Total (N = 437) |
|---|---|
| Age when diagnosed with MDD (years) | |
| N | 437 |
| Mean (SD) | 32.3 (11.35) |
| Median | 31.0 |
| Range | (5; 61) |
| Baseline MADRS total score | |
| N | 437 |
| Mean (SD) | 37.8 (5.51) |
| Median | 38.0 |
| Range | (4; 53) |
| Screening IDS-C30 total score | |
| N | 437 |
| Mean (SD) | 47.4 (7.36) |
| Median | 47.0 |
| Range | (34; 76) |
| Baseline CGI-S | |
| N | 437 |
| Mean (SD) | 5.2 (0.65) |
| Median | 5.0 |
| Range | (3; 7) |
| Baseline CGI-S category, n (%) | |
| N | 437 |
| Normal, not at all ill | 0 |

TABLE 84-continued

Baseline (IND) Psychiatric History (Study ESKETINTRD3003: Safety (IND) Analysis Set)

| | Total (N = 437) |
|---|---|
| Borderline mentally ill | 0 |
| Mildly ill | 2 (0.5%) |
| Moderately ill | 54 (12.4%) |
| Markedly ill | 258 (59.0%) |
| Severely ill | 119 (27.2%) |
| Among the most extremely ill patients | 4 (0.9%) |
| Baseline PHQ-9 total score | |
| N | 437 |
| Mean (SD) | 19.6 (4.32) |
| Median | 20.0 |
| Range | (3; 27) |
| Screening C-SSRS lifetime [a], n (%) | |
| N | 437 |
| No event | 252 (57.7%) |
| Suicidal ideation | 118 (27.0%) |
| Suicidal behavior | 67 (15.3%) |
| Screening C-SSRS past 6 or 12 months [a], n (%) | |
| N | 437 |
| No event | 320 (73.2%) |
| Suicidal ideation (past 6 months) | 117 (26.8%) |
| Suicidal behavior (past 12 months) | 0 |
| Duration of current episode (wks) | |
| N | 437 |
| Mean (SD) | 117.3 (186.94) |
| Median | 59.0 |
| Range | (4; 1560) |
| Previous antidepressant medications [b], n (%) | |
| N | 436 |
| 1 | 46 (10.6%) |
| 2 | 243 (55.7%) |
| 3 | 92 (21.1%) |
| 4 | 39 (8.9%) |
| 5 | 15 (3.4%) |
| 8 | 1 (0.2%) |
| Family history of depression, n (%) | |
| N | 437 |
| Yes | 174 (39.8%) |
| No | 263 (60.2%) |
| Family history of anxiety disorder, n (%) | |
| N | 437 |
| Yes | 40 (9.2%) |
| No | 397 (90.8%) |
| Family history of bipolar disorder, n (%) | |
| N | 437 |
| Yes | 24 (5.5%) |
| No | 413 (94.5%) |
| Family history of schizophrenia, n (%) | |
| N | 437 |
| Yes | 17 (3.9%) |
| No | 420 (96.1%) |
| Family history of alcohol abuse, n (%) | |
| N | 437 |
| Yes | 58 (13.3%) |
| No | 379 (86.7%) |
| Family history of substance abuse, n (%) | |
| N | 437 |
| Yes | 14 (3.2%) |
| No | 423 (96.8%) |

[a] C-SSRS category: No event = 0; Suicidal ideation = 1, 2, 3, 4, 5; Suicidal behavior = 6, 7, 8, 9, 10
[b] Number of antidepressant medications with non-response (defined as ≤25% improvement) taken for at least 6 weeks during the current episode as obtained from MGH-ATRQ at the time of first screening visit.

Demographic and baseline characteristics, and baseline psychiatric history for the full (stable remitters) analysis set are displayed in the Tables 85 and 86. The majority of the stable remitters randomized to the MA phase were female (66.5%). The mean (SD) age was 45.8 (11.64) years, ranging from 19 to 64 years. The mean (SD) baseline (IND) MADRS total score was 37.5 (4.93), ranging from 26 to 49.

TABLE 85

Demographic and Baseline (IND) Characteristics (Study ESKETINTRD3003: Full (Stable Remitters) Analysis Set)

| | Intranasal Esk + Oral AD (N = 90) | Oral AD + Intranasal Placebo (N = 86) | Total (N = 176) |
|---|---|---|---|
| Age (years) | | | |
| N | 90 | 86 | 176 |
| Mean (SD) | 45.4 (12.12) | 46.2 (11.16) | 45.8 (11.64) |
| Median | 47.5 | 45.0 | 46.5 |
| Range | (19; 64) | (19; 64) | (19; 64) |
| Age category (years), n (%) | | | |
| N | 90 | 86 | 176 |
| 18-44 | 38 (42.2%) | 37 (43.0%) | 75 (42.6%) |
| 45-64 | 52 (57.8%) | 49 (57.0%) | 101 (57.4%) |
| Sex, n (%) | | | |
| N | 90 | 86 | 176 |
| Male | 32 (35.6%) | 27 (31.4%) | 59 (33.5%) |
| Female | 58 (64.4%) | 59 (68.6%) | 117 (66.5%) |
| Race, n (%) | | | |
| N | 90 | 86 | 176 |
| Black or African American | 4 (4.4%) | 6 (7.0%) | 10 (5.7%) |

TABLE 85-continued

Demographic and Baseline (IND) Characteristics (Study ESKETINTRD3003: Full (Stable Remitters) Analysis Set)

|  | Intranasal Esk + Oral AD (N = 90) | Oral AD + Intranasal Placebo (N = 86) | Total (N = 176) |
| --- | --- | --- | --- |
| White | 80 (88.9%) | 76 (88.4%) | 156 (88.6%) |
| American Indian or Alaskan native | 0 | 1 (1.2%) | 1 (0.6%) |
| Other | 2 (2.2%) | 1 (1.2%) | 3 (1.7%) |
| Multiple | 1 (1.1%) | 0 | 1 (0.6%) |
| Not Reported | 3 (3.3%) | 2 (2.3%) | 5 (2.8%) |
| Ethnicity, n (%) | | | |
| N | 90 | 86 | 176 |
| Hispanic or Latino | 14 (15.6%) | 12 (14.0%) | 26 (14.8%) |
| Not Hispanic or Latino | 73 (81.1%) | 72 (83.7%) | 145 (82.4%) |
| Not Reported | 3 (3.3%) | 2 (2.3%) | 5 (2.8%) |
| Baseline weight (kg) | | | |
| N | 90 | 86 | 176 |
| Mean (SD) | 82.78 (19.554) | 84.21 (20.781) | 83.48 (20.118) |
| Median | 82.05 | 81.05 | 82.00 |
| Range | (47.0; 147.0) | (44.1; 179.0) | (44.1; 179.0) |
| Baseline height (cm) | | | |
| N | 90 | 86 | 176 |
| Mean (SD) | 169.05 (11.330) | 168.60 (9.673) | 168.83 (10.525) |
| Median | 167.55 | 166.00 | 167.00 |
| Range | (150.0; 210.3) | (150.0; 192.0) | (150.0; 210.3) |
| Baseline body mass index (kg/m$^2$) | | | |
| N | 90 | 86 | 176 |
| Mean (SD) | 28.9 (5.75) | 29.5 (6.26) | 29.2 (6.00) |
| Median | 28.4 | 28.70 | 28.6 |
| Range | (18; 47) | (20; 54) | (18; 54) |
| BMI category (kg/m$^2$), n (%) | | | |
| N | 90 | 86 | 176 |
| Underweight <18.5 | 2 (2.2%) | 0 | 2 (1.1%) |
| Normal 18.5-<25 | 19 (21.1%) | 18 (20.9%) | 37 (21.0%) |
| Overweight 25-<30 | 32 (35.6%) | 33 (38.4%) | 65 (36.9%) |
| Obese 30-<40 | 33 (36.7%) | 30 (34.9%) | 63 (35.8%) |
| Morbidly obese ≥40 | 4 (4.4%) | 5 (5.8%) | 9 (5.1%) |
| Employment status, n (%) [a] | | | |
| N | 90 | 86 | 176 |
| Any type of employment | 57 (63.3%) | 54 (62.8%) | 111 (63.1%) |
| Any type of unemployment | 23 (25.6%) | 19 (22.1%) | 42 (23.9%) |
| Other | 10 (11.1%) | 13 (15.1%) | 23 (13.1%) |
| Hypertension status, n (%) [b] | | | |
| N | 90 | 86 | 176 |
| Yes | 23 (25.6%) | 19 (22.1%) | 42 (23.9%) |
| No | 67 (74.4%) | 67 (77.9%) | 134 (76.1%) |
| Country, n (%) | | | |
| N | 90 | 86 | 176 |
| Belgium | 1 (1.1%) | 1 (1.2%) | 2 (1.1%) |
| Brazil | 11 (12.2%) | 11 (12.8%) | 22 (12.5%) |
| Canada | 1 (1.1%) | 0 | 1 (0.6%) |
| Czech Republic | 14 (15.6%) | 14 (16.3%) | 28 (15.9%) |
| France | 3 (3.3%) | 3 (3.5%) | 6 (3.4%) |
| Germany | 0 | 1 (1.2%) | 1 (0.6%) |
| Hungary | 2 (2.2%) | 2 (2.3%) | 4 (2.3%) |
| Italy | 2 (2.2%) | 1 (1.2%) | 3 (1.7%) |
| Mexico | 5 (5.6%) | 5 (5.8%) | 10 (5.7%) |
| Poland | 19 (21.1%) | 18 (20.9%) | 37 (21.0%) |
| Slovakia | 2 (2.2%) | 1 (1.2%) | 3 (1.7%) |
| Spain | 2 (2.2%) | 3 (3.5%) | 5 (2.8%) |
| Sweden | 3 (3.3%) | 3 (3.5%) | 6 (3.4%) |
| Turkey | 4 (4.4%) | 3 (3.5%) | 7 (4.0%) |
| United States | 21 (23.3%) | 20 (23.3%) | 41 (23.3%) |
| Region, n (%) | | | |
| N | 90 | 86 | 176 |
| Europe | 52 (57.8%) | 50 (58.1%) | 102 (58.0%) |
| North America | 22 (24.4%) | 20 (23.3%) | 42 (23.9%) |
| Other | 16 (17.8%) | 16 (18.6%) | 32 (18.2%) |

TABLE 85-continued

Demographic and Baseline (IND) Characteristics (Study ESKETINTRD3003: Full (Stable Remitters) Analysis Set)

| | Intranasal Esk + Oral AD (N = 90) | Oral AD + Intranasal Placebo (N = 86) | Total (N = 176) |
|---|---|---|---|
| Class of oral antidepressant, n (%) | | | |
| N | 90 | 86 | 176 |
| SNRI | 62 (68.9%) | 58 (67.4%) | 120 (68.2%) |
| SSRI | 28 (31.1%) | 28 (32.6%) | 56 (31.8%) |
| Oral antidepressant, n (%) | | | |
| N | 90 | 86 | 176 |
| Duloxetine | 47 (52.2%) | 38 (44.2%) | 85 (48.3%) |
| Escitalopram | 13 (14.4%) | 14 (16.3%) | 27 (15.3%) |
| Sertraline | 15 (16.7%) | 14 (16.3%) | 29 (16.5%) |
| Venlafaxine extended release (XR) | 15 (16.7%) | 20 (23.3%) | 35 (19.9%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

TABLE 86

Baseline (IND) Psychiatric History (Study ESKETINTRD3003: Full (Stable Remitters) Analysis Set)

| | Intranasal Esk + Oral AD (N = 90) | Oral AD + Intranasal Placebo (N = 86) | Total (N = 176) |
|---|---|---|---|
| Age when diagnosed with MDD (years) | | | |
| N | 90 | 86 | 176 |
| Mean (SD) | 32.5 (11.42) | 33.4 (11.41) | 32.9 (11.39) |
| Median | 33.0 | 32.0 | 32.5 |
| Range | (5; 55) | (10; 60) | (5; 60) |
| Baseline MADRS total score | | | |
| N | 90 | 86 | 176 |
| Mean (SD) | 37.4 (5.20) | 37.6 (4.66) | 37.5 (4.93) |
| Median | 37.0 | 37.5 | 37.0 |
| Range | (26; 49) | (28; 47) | (26; 49) |
| Screening IDS-C30 total score | | | |
| N | 90 | 86 | 176 |
| Mean (SD) | 46.9 (6.24) | 47.7 (7.77) | 47.3 (7.02) |
| Median | 46.0 | 48.0 | 47.0 |
| Range | (36; 64) | (34; 73) | (34; 73) |
| Baseline CGI-S | | | |
| N | 90 | 86 | 176 |
| Mean (SD) | 5.1 (0.69) | 5.1 (0.71) | 5.1 (0.70) |
| Median | 5.0 | 5.0 | 5.0 |
| Range | (4; 6) | (3; 7) | (3; 7) |
| Baseline CGI-S category, n (%) | | | |
| N | 90 | 86 | 176 |
| Normal, not at all ill | 0 | 0 | 0 |
| Borderline mentally ill | 0 | 0 | 0 |
| Mildly ill | 0 | 1 (1.2%) | 1 (0.6%) |
| Moderately ill | 18 (20.0%) | 13 (15.1%) | 31 (17.6%) |
| Markedly ill | 47 (52.2%) | 51 (59.3%) | 98 (55.7%) |
| Severely ill | 25 (27.8%) | 19 (22.1%) | 44 (25.0%) |
| Among the most extremely ill patients | 0 | 2 (2.3%) | 2 (1.1%) |
| Baseline PHQ-9 total score | | | |
| N | 90 | 86 | 176 |
| Mean (SD) | 19.2 (4.16) | 19.8 (3.43) | 19.5 (3.82) |
| Median | 19.0 | 20.0 | 20.0 |
| Range | (5; 27) | (10; 27) | (5; 27) |

TABLE 86-continued

Baseline (IND) Psychiatric History (Study ESKETINTRD3003: Full (Stable Remitters) Analysis Set)

|  | Intranasal Esk + Oral AD (N = 90) | Oral AD + Intranasal Placebo (N = 86) | Total (N = 176) |
|---|---|---|---|
| Screening C-SSRS lifetime [a], n (%) |  |  |  |
| N | 90 | 86 | 176 |
| No event | 64 (71.1%) | 62 (72.1%) | 126 (71.6%) |
| Suicidal ideation | 19 (21.1%) | 17 (19.8%) | 36 (20.5%) |
| Suicidal behavior | 7 (7.8%) | 7 (8.1%) | 14 (8.0%) |
| Screening C-SSRS past 6 or 12 months [a], n (%) |  |  |  |
| N | 90 | 86 | 176 |
| No event | 72 (80.0%) | 72 (83.7%) | 144 (81.8%) |
| Suicidal ideation (past 6 months) | 18 (20.0%) | 14 (16.3%) | 32 (18.2%) |
| Suicidal behavior (past 12 months) | 0 | 0 | 0 |
| Duration of current episode (wks) |  |  |  |
| N | 90 | 86 | 176 |
| Mean (SD) | 112.2 (171.30) | 110.5 (147.41) | 111.4 (159.62) |
| Median | 51.5 | 58.0 | 54.0 |
| Range | (12; 1040) | (9; 884) | (9; 1040) |
| Previous antidepressant medications [b], n (%) |  |  |  |
| N | 90 | 84 | 174 |
| 1 | 10 (11.1%) | 10 (11.9%) | 20 (11.5%) |
| 2 | 61 (67.8%) | 52 (61.9%) | 113 (64.9%) |
| 3 | 11 (12.2%) | 15 (17.9%) | 26 (14.9%) |
| 4 | 6 (6.7%) | 7 (8.3%) | 13 (7.5%) |
| 5 | 2 (2.2%) | 0 | 2 (1.1%) |
| Family history of depression, n (%) |  |  |  |
| N | 90 | 86 | 176 |
| Yes | 39 (43.3%) | 36 (41.9%) | 75 (42.6%) |
| No | 51 (56.7%) | 50 (58.1%) | 101 (57.4%) |
| Family history of anxiety disorder, n (%) |  |  |  |
| N | 90 | 86 | 176 |
| Yes | 5 (5.6%) | 4 (4.7%) | 9 (5.1%) |
| No | 85 (94.4%) | 82 (95.3%) | 167 (94.9%) |
| Family history of bipolar disorder, n (%) |  |  |  |
| N | 90 | 86 | 176 |
| Yes | 7 (7.8%) | 5 (5.8%) | 12 (6.8%) |
| No | 83 (92.2%) | 81 (94.2%) | 164 (93.2%) |
| Family history of schizophrenia, n (%) |  |  |  |
| N | 90 | 86 | 176 |
| Yes | 4 (4.4%) | 1 (1.2%) | 5 (2.8%) |
| No | 86 (95.6%) | 85 (98.8%) | 171 (97.2%) |
| Family history of alcohol abuse, n (%) |  |  |  |
| N | 90 | 86 | 176 |
| Yes | 7 (7.8%) | 9 (10.5%) | 16 (9.1%) |
| No | 83 (92.2%) | 77 (89.5%) | 160 (90.9%) |
| Family history of substance abuse, n (%) |  |  |  |
| N | 90 | 86 | 176 |
| Yes | 2 (2.2%) | 6 (7.0%) | 8 (4.5%) |
| No | 88 (97.8%) | 80 (93.0%) | 168 (95.5%) |

[a] C-SSRS category: No event = 0; Suicidal ideation = 1, 2, 3, 4, 5; Suicidal behavior = 6, 7, 8, 9, 10

[b] Number of antidepressant medications with non-response (defined as ≤25% improvement) taken for at least 6 weeks during the current episode as obtained from MGH-ATRQ at the time of first screening visit.

Extent of Exposure

The extent of exposure to intranasal study medication during the MA phase for the full (stable remitters) analysis set and full (stable responders) analysis set are displayed in Tables 87 and 88.

TABLE 87

Extent of Exposure to Intranasal Study Medication; Maintenance Phase
(Study ESKETINTRD3003: Full (Stable Remitters) Analysis Set)

|  | Intranasal Esk + Oral AD | | Oral AD + Intranasal Placebo | |
| --- | --- | --- | --- | --- |
|  | Total Duration (N = 90) | Cumulative Duration (N = 90) | Total Duration (N = 86) | Cumulative Duration (N = 86) |
| Duration, weeks | | | | |
| N | 90 | 90 | 86 | 86 |
| Category, n (%) | | | | |
| ≤Week 4 (≤28 days) | 7 (7.8%) | 7 (7.8%) | 23 (26.7%) | 23 (26.7%) |
| Week 4-8 (Days 29-56) | 10 (11.1%) | 17 (18.9%) | 12 (14.0%) | 35 (40.7%) |
| Week 8-12 (Days 57-84) | 15 (16.7%) | 32 (35.6%) | 10 (11.6%) | 45 (52.3%) |
| Week 12-16 (Days 85-112) | 7 (7.8%) | 39 (43.3%) | 8 (9.3%) | 53 (61.6%) |
| Week 16-20 (Days 113-140) | 12 (13.3%) | 51 (56.7%) | 7 (8.1%) | 60 (69.8%) |
| Week 20-24 (Days 141-168) | 9 (10.0%) | 60 (66.7%) | 4 (4.7%) | 64 (74.4%) |
| Week 24-28 (Days 169-196) | 7 (7.8%) | 67 (74.4%) | 4 (4.7%) | 68 (79.1%) |
| Week 28-32 (Days 197-224) | 4 (4.4%) | 71 (78.9%) | 7 (8.1%) | 75 (87.2%) |
| Week 32-36 (Days 225-252) | 5 (5.6%) | 76 (84.4%) | 2 (2.3%) | 77 (89.5%) |
| Week 36-40 (Days 253-280) | 4 (4.4%) | 80 (88.9%) | 2 (2.3%) | 79 (91.9%) |
| Week 40-44 (Days 281-308) | 2 (2.2%) | 82 (91.1%) | 3 (3.5%) | 82 (95.3%) |
| Week 44-48 (Days 309-336) | 1 (1.1%) | 83 (92.2%) | 1 (1.2%) | 83 (96.5%) |
| >Week 48 (>Day 336) | 7 (7.8%) | 90 (100.0%) | 3 (3.5%) | 86 (100.0%) |
| Mean (SD) | 21.1 (16.25) | | 16.0 (16.12) | |
| Median | 17.7 | | 10.2 | |
| Range | (0; 83) | | (0; 76) | |

The duration of exposure is defined as the duration between the date of the first exposure and the last date of exposure to intranasal study medication in the Maintenance Phase. It includes days on which subjects did not actually take intranasal study medication.

TABLE 88

Extent of Exposure to Intranasal Study Medication; Maintenance Phase
(Study ESKETINTRD3003: Full (Stable Responders) Analysis Set)

|  | Intranasal Esk + Oral AD | | Oral AD + Intranasal Placebo | |
| --- | --- | --- | --- | --- |
|  | Total Duration (N = 62) | Cumulative Duration (N = 62) | Total Duration (N = 59) | Cumulative Duration (N = 59) |
| Duration, weeks | | | | |
| N | 62 | 62 | 59 | 59 |
| Category, n (%) | | | | |
| ≤Week 4 (≤28 days) | 3 (4.8%) | 3 (4.8%) | 18 (30.5%) | 18 (30.5%) |
| Week 4-8 (Days 29-56) | 13 (21.0%) | 16 (25.8%) | 9 (15.3%) | 27 (45.8%) |
| Week 8-12 (Days 57-84) | 9 (14.5%) | 25 (40.3%) | 8 (13.6%) | 35 (59.3%) |
| Week 12-16 (Days 85-112) | 4 (6.5%) | 29 (46.8%) | 5 (8.5%) | 40 (67.8%) |
| Week 16-20 (Days 113-140) | 3 (4.8%) | 32 (51.6%) | 2 (3.4%) | 42 (71.2%) |
| Week 20-24 (Days 141-168) | 7 (11.3%) | 39 (62.9%) | 5 (8.5%) | 47 (79.7%) |
| Week 24-28 (Days 169-196) | 4 (6.5%) | 43 (69.4%) | 5 (8.5%) | 52 (88.1%) |
| Week 28-32 (Days 197-224) | 4 (6.5%) | 47 (75.8%) | 4 (6.8%) | 56 (94.9%) |
| Week 32-36 (Days 225-252) | 2 (3.2%) | 49 (79.0%) | 1 (1.7%) | 57 (96.6%) |
| Week 36-40 (Days 253-280) | 2 (3.2%) | 51 (82.3%) | 0 | 57 (96.6%) |
| Week 40-44 (Days 281-308) | 3 (4.8%) | 54 (87.1%) | 0 | 57 (96.6%) |
| Week 44-48 (Days 309-336) | 2 (3.2%) | 56 (90.3%) | 0 | 57 (96.6%) |
| >Week 48 (>Day 336) | 6 (9.7%) | 62 (100.0%) | 2 (3.4%) | 59 (100.0%) |
| Mean (SD) | 23.4 (20.31) | | 13.3 (13.53) | |
| Median | 19.4 | | 10.1 | |
| Range | (3; 91) | | (0; 70) | |

The duration of exposure is defined as the duration between the date of the first exposure and the last date of exposure to intranasal study medication in the Maintenance Phase. It includes days on which subjects did not actually take intranasal study medication.

On Day 1 of the MA phase, 40/90 (44.4%) of the subjects who received intranasal esketamine in the full (stable remitters) analysis set were receiving the 56 mg dose of esketamine and 50/90 (55.6%) were receiving the 84 mg dose of esketamine. In the full (stable responders) analysis set, 20/61 (32.8%) of the subjects were receiving the 56 mg dose of esketamine and 41/61 (67.2%) of the subjects were receiving the 84 mg dose of esketamine. Starting from Week 4 (MA), the intranasal treatment session frequency could be adjusted (if applicable) at fixed, 4-week intervals. Tables 89 and 90 display the dosing regimen subjects were on at least 50% of the time during the MA phase for the full (stable remitters) analysis set and full (stable responders) analysis set. Of the 90 randomized stable remitters treated with intranasal esketamine during the MA phase, 62 (68.9%) subjects used an "every other week" dosing schedule the majority of the time. Of the 62 randomized stable responders treated with intranasal esketamine during the MA phase, 21 (33.9%) subjects used an "every other week" dosing schedule the majority of the time.

TABLE 89

Frequency of Dosing Frequency (Weekly or Every Other Week) Used the Majority of the Time; Maintenance Phase (Study ESKETINTRD3003: Full (Stable Remitters) Analysis Set)

| Majority dosing frequency | Intranasal Esk + Oral AD (N = 90) | Oral AD + Intranasal Placebo (N = 86) |
|---|---|---|
| Weekly | 21 (23.3%) | 27 (31.4%) |
| Every other week | 62 (68.9%) | 48 (55.8%) |
| Weekly or every other week | 7 (7.8%) | 11 (12.8%) |

Majority dosing frequency is the regimen subjects were on at least 50% of the time in the Maintenance Phase.

TABLE 90

Frequency of Dosing Frequency (Weekly or Every Other Week) Used the Majority of the Time; Maintenance Phase (Study ESKETINTRD3003: Full (Stable Responders) Analysis Set)

| Majority dosing frequency | Intranasal Esk + Oral AD (N = 62) | Oral AD + Intranasal Placebo (N = 59) |
|---|---|---|
| Weekly | 34 (54.8%) | 36 (61.0%) |
| Every other week | 21 (33.9%) | 19 (32.2%) |
| Weekly or every other week | 7 (11.3%) | 4 (6.8%) |

Majority dosing frequency is the regimen subjects were on at least 50% of the time in the Maintenance Phase.

Primary Endpoint Analysis

The interim efficacy analysis was performed at a significance level of 0.0097 (two-sided). As the study was not stopped for efficacy at the interim analysis, the final efficacy analysis was performed at a significance level of 0.046 (two-sided).

The primary efficacy analyses are based on the full (stable remitters) analysis set which is defined as randomized subjects who were in stable remission at the end of the optimization phase and who received at least 1 dose of intranasal study drug and 1 dose of oral antidepressant during the maintenance phase. One stable responder subject who was incorrectly randomized as a stable remitter was included in this analysis set. The primary efficacy endpoint is the time from randomization to the first documentation (earliest date) of a relapse during the maintenance phase in esketamine-treated subjects who achieved stable remission at the end of optimization phase.

Relapse is defined as any of the following:
MADRS total score for 2 consecutive assessments separated by 5 to 15 days. The date of the second MADRS assessment was used for the date of relapse.
Hospitalization for worsening depression or any other clinically relevant event determined per clinical judgment to be suggestive of a relapse of depressive illness such as suicide attempt, completed suicide, or hospitalization for suicide prevention. If hospitalized for any of these events, the start date of hospitalization was used for the date of relapse. Otherwise the date of the event was used if the subject is not hospitalized.
In case both relapse criteria are met, the earlier date was defined as the date of relapse for this subject.

One subject was randomized early (during the Week 12 of the OP phase) but did not start the MA phase until a week later. The time to relapse for this subject was calculated from the start date of the maintenance phase. The primary efficacy analysis was performed on the full (stable remitters) analysis set, which included 175 stable remitters and 1 stable responder (who was incorrectly randomized as a stable remitter) at the end of the optimization phase after treatment with intranasal esketamine plus an oral antidepressant. These subjects received at least 1 dose of intranasal study drug and 1 dose of oral antidepressant during the maintenance phase. As shown in Table 91 below, results favored intranasal esketamine+oral AD in delaying relapse compared to oral AD+ intranasal placebo. Overall, 24 (26.7%) subjects in the intranasal esketamine+oral AD group and 39 (45.3%) subjects in the oral AD+ intranasal placebo group experienced a relapse event during the maintenance phase. Based on the weighted combination test, the difference between treatment groups was statistically significant (two-sided p=0.003) and was less than 0.046 (the threshold of statistical significance). The estimated hazard ratio of intranasal esketamine+oral AD relative to oral AD+intranasal placebo based on weighted estimates was 0.49 (95% CI: 0.29, 0.84) using R. The calculation of the hazard ratio using ADDPLAN was very similar 0.49 (0.29; 0.83).

TABLE 91

Time to Relapse and Number (%) of Subjects That Remained Relapse Free; Maintenance Phase (Study ESKETINTRD3003: Full (Stable Remitters) Analysis Set)

| Time to Relapse (days) [a] | Intranasal Esk + Oral AD | Oral AD + Intranasal Placebo |
|---|---|---|
| Number assessed | 90 | 86 |
| Number censored (%) | 66 (73.3%) | 47 (54.7%) |
| Number of relapses (%) | 24 (26.7%) | 39 (45.3%) |
| 25% percentile (95% CI) | 153.0 (105.0; 225.0) | 33.0 (22.0; 48.0) |
| Median (95% CI) | NE | 273.0 (97.0; NE) |
| 75% percentile (95% CI) | NE | NE |
| Hazard Ratio (95% CI) [b] | 0.49 (0.29; 0.84) | |
| Two-sided P-value [c] | 0.003 | |

[a] Based on Kaplan-Meier product limit estimates.
[b] Hazard ratio and CI are weighted estimates based on Wassmer (2006) and calculated using R.
[c] Two-sided P-value is based on the final test statistic, which is a weighted combination of the log-rank test statistics calculated on the interim full analysis set and on the full analysis set in stable remitters.
NE stands for Not Estimable.

Kaplan-Meier curves of the time to relapse for the two treatment groups are presented in FIG. 51. The reasons for relapse events for subjects who experienced a relapse are summarized in Table 92. The most common reason for relapse was a MADRS total score ≥22 for 2 consecutive assessments separated by 5 to 15 days.

TABLE 92

Frequency Distribution of Reason for Relapse; Maintenance Phase
(Study ESKETINTRD3003: Full (Stable Remitters) Analysis Set)

|  | Intranasal Esk + Oral AD (N = 90) | Oral AD + Intranasal Placebo (N = 86) | Total (N = 176) |
|---|---|---|---|
| Total number of subjects with relapse | 24 | 39 | 63 |
| Reason for relapse |  |  |  |
| MADRS total score ≥22 for two consecutive assessments [a] | 18 (75.0%) | 38 (97.4%) | 56 (88.9%) |
| Completed suicide or hospitalization for depression worsening/suicide attempt/suicide prevention or other clinically relevant event | 6 (25.0%) | 1 (2.6%) | 7 (11.1%) |
| AE Preferred Term |  |  |  |
| Depression | 4 (16.7%) | 1 (2.6%) | 5 (7.9%) |
| Depressive symptom | 1 (4.2%) | 0 | 1 (1.6%) |
| Major depression | 1 (4.2%) | 0 | 1 (1.6%) |

[a] Based on two consecutive assessments separated by 5 to 15 days.

Subgroup Analyses

A forest plot showing the hazard ratio based on the Cox proportional hazards model for the preplanned subgroups are shown in FIG. 56. In general, the results favored esketamine+oral AD treatment groups for the subgroups.

Sensitivity Analysis

Two sensitivity analyses were performed on the full (stable remitters) analysis set using an unweighted log-rank test and Cox proportional hazards model with the accumulated 63 events and based on cutoff date of the 59$^{th}$ event. Note the sensitivity analysis at the 59$^{th}$ event was actually done with 61 relapses as 3 relapses occurred on the same day as the 59$^{th}$ event. Results are presented in Tables 93 and 94. The estimated hazard ratio of intranasal esketamine+oral AD relative to oral AD+intranasal placebo was 0.47 (95% CI: 0.28, 0.78) based on the 63 events and 0.46 (0.27, 0.77) based on the 61 events. The results are consistent with the primary efficacy analysis.

TABLE 93

Cox Regression of Time to Relapse (Days) With Treatment as a Factor; Maintenance Phase (Study ESKETINTRD3003: Full (Stable Remitters) Analysis Set)

| Time to Relapse (days)[a] | Intranasal Esk + Oral AD | Oral AD + Intranasal Placebo |
|---|---|---|
| Number of Assessed | 90 | 86 |
| Number of Censored (%) | 66 (73.3%) | 47 (54.7%) |
| Number of Events (%) | 24 (26.7%) | 39 (45.3%) |
| 25% percentile (95% CI) | 153.0 (105.0; 225.0) | 33.0 (22.0; 48.0) |
| Median (95% CI) | NE | 273.0 (97.0; NE) |
| 75% percentile (95% CI) | NE | NE |
| Hazard Ratio (95% CI)[b] | 0.47 (0.28; 0.78) |  |
| Two-sided P-value[c] | 0.003 |  |

[a] Based on Kaplan-Meier product limit estimates.
[b] Regression analysis of survival data based on Cox proportional hazards model with treatment as a factor.
[c] Log-rank test.
NE stands for Not Estimable.

TABLE 94

Cox Regression of Time to Relapse (Days) With Treatment as a Factor, Using Cut-off Day of 59th Event; Maintenance Phase (Study ESKETINTRD3003: Full (Stable Remitters) Analysis Set)

| Time to Relapse (days)[a] | Intranasal Esk + Oral AD | Oral AD + Intranasal Placebo |
|---|---|---|
| Number of Assessed | 90 | 86 |
| Number of Censored (%) | 67 (74.4%) | 48 (55.8%) |
| Number of Events (%) | 23 (25.6%) | 38 (44.2%) |
| 25% percentile (95% CI) | 153.0 (105.0; 225.0) | 33.0 (22.0; 48.0) |
| Median (95% CI) | NE | 273.0 (103.0; NE) |
| 75% percentile (95% CI) | NE | NE |
| Hazard Ratio (95% CI)[b] | 0.46 (0.27; 0.77) |  |
| Two-sided P-value[c] | 0.003 |  |

[a] Based on Kaplan-Meier product limit estimates.
[b] Regression analysis of survival data based on Cox proportional hazards model with treatment as a factor.
[c] Log-rank test.
NE stands for Not Estimable.

Other Secondary Efficacy Endpoint Analysis

Time to Relapse in Stable Responders (but not Remitters)

The time between subject randomization and the first documentation (earliest date) of a relapse in the maintenance phase was compared between treatment groups for subjects in the full (stable responders) analysis set. One subject was randomized early (during the Week 12 of the OP phase) but did not start the MA phase until a week later, and one subject skipped Week 1 of the MA phase. The time to relapse for these two subjects was calculated from the start date of the maintenance phase. As shown in Table 95 below, results favored intranasal esketamine+oral AD in delaying relapse compared to oral AD+intranasal placebo. Overall, 16 (25.8%) subjects on intranasal esketamine+oral AD and 34 (57.6%) subjects in the oral AD+intranasal placebo group experienced a relapse event during the maintenance phase. The difference between treatment groups was statistically significant (two-sided p<0.001) using a two-sided log-rank test. The estimated hazard ratio of intranasal esketamine+oral AD relative to oral AD+intranasal placebo based on the Cox proportional hazards model with treatment as a factor was 0.30 (95% CI: 0.16, 0.55). Kaplan-Meier curves of the time to relapse for the two treatment groups are presented in FIG. 52.

The median of time to relapse (95% CI) for the esketamine+oral AD group was 635.0 (264.0; 635.0) days; the median of time to relapse (95% CI) in the oral AD+nasal spray placebo group was 88.0 (46.0; 196.0) days, based on Kaplan-Meier estimates. As noted, the estimate of the median time to relapse for the esketamine plus oral AD group should be interpreted with caution as it is heavily influenced by one subject who had a long time to relapse.

TABLE 95

Time to Relapse and Number (%) of Subjects That Remained Relapse Free; Maintenance Phase (Study ESKETINTRD3003: Full (Stable Responders) Analysis Set)

| Time to Relapse (days) [a] | Intranasal Esk + Oral AD | Oral AD + Intranasal Placebo |
|---|---|---|
| Number assessed | 62 | 59 |
| Number censored (%) | 46 (74.2%) | 25 (42.4%) |
| Number of relapses (%) | 16 (25.8%) | 34 (57.6%) |
| 25% percentile (95% CI) | 217.0 (56.0; 635.0) | 24.0 (17.0; 46.0) |
| Median (95% CI) | 635.0 (264.0; 635.0) | 88.0 (46.0; 196.0) |
| 75% percentile (95% CI) | 635.0 (NE) | NE |
| Hazard Ratio (95% CI)[b] | 0.30 (0.16; 0.55) | |
| Two-sided P-value[c] | <0.001 | |

[a] Based on Kaplan-Meier product limit estimates.
[b] Regression analysis of survival data based on Cox proportional hazards model with treatment as a factor.
[c] Log-rank test.
NE stands for Not Estimable.

Safety
Summary of All Adverse Events

An overall summary of all treatment-emergent adverse events (TEAEs) during the IND, OP and MA phases for the safety (IND), safety (OP) and safety (MA) analysis sets (safety (OP) and safety (MA) analysis sets do not include the transferred-entry subjects who continued to receive oral AD+placebo (TEP) during the subsequent phases), are presented in Tables 96 to 98. Overall, 76.9% of subjects experienced at least one TEAE during the IND phase; 73.6% of subjects experienced at least one TEAE during the OP phase in the safety (OP) analysis set; 82.2% of subjects in the esketamine+oral AD group and 45.5% of subjects in the oral AD+placebo experienced at least one TEAE during the MA phase in the safety (MA) analysis set.

TABLE 96

Overall Summary of Treatment-emergent Adverse Events (TEAE); Open-label Induction Phase (Study ESKETINTRD3003: Safety (IND) Analysis Set)

|  | Intranasal Esk + Oral AD (N = 437) |
|---|---|
| TEAE | 336 (76.9%) |
| TEAE possibly related to intranasal drug [a] | 301 (68.9%) |
| TEAE possibly related to oral antidepressant [a] | 71 (16.2%) |
| TEAE leading to death | 0 |
| 1 or more serious TEAE | 13 (3.0%) |
| TEAE leading to intranasal drug withdrawn [b] | 22 (5.0%) |
| TEAE leading to oral antidepressant withdrawn [b] | 8 (1.8%) |

[a] Study drug relationships of possible, probable, and very likely are included in this category.
[b] An adverse event that started in the induction phase and resulted in discontinuation in a following phase is counted as treatment-emergent in the induction phase.
Incidence is based on the number of subjects experiencing at least one adverse event, not the number of events.
Adverse events are coded using MedDRA version 20.0.

TABLE 97

Overall Summary of Treatment-emergent Adverse Events (TEAE); Optimization Phase (Study ESKETINTRD3003: Safety (OP) Analysis Set)

|  | Intranasal Esk + Oral AD (N = 455) |
|---|---|
| TEAE | 335 (73.6%) |
| TEAE possibly related to intranasal drug [a] | 281 (61.8%) |
| TEAE possibly related to oral antidepressant [a] | 61 (13.4%) |
| TEAE leading to death | 0 |
| 1 or more serious TEAE | 11 (2.4%) |
| TEAE leading to intranasal drug withdrawn [b] | 5 (1.1%) |
| TEAE leading to oral antidepressant withdrawn [b] | 2 (0.4%) |

[a] Study drug relationships of possible, probable, and very likely are included in this category.
[b] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

TABLE 98

Overall Summary of Treatment-emergent Adverse Events (TEAE); Maintenance Phase (Study ESKETINTRD3003: Safety (MA) Analysis Set)

|  | Intranasal Esk + Oral AD (N = 152) | Oral AD + Intranasal Placebo (N = 145) |
|---|---|---|
| TEAE | 125 (82.2%) | 66 (45.5%) |
| TEAE possibly related to intranasal drug [a] | 106 (69.7%) | 37 (25.5%) |
| TEAE possibly related to oral antidepressant [a] | 13 (8.6%) | 9 (6.2%) |
| TEAE leading to death | 0 | 0 |
| Severe TEAE | 12 (7.9%) | 6 (4.1%) |
| Moderate TEAE | 72 (47.4%) | 38 (26.2%) |
| Mild TEAE | 41 (29%) | 22 (15.2%) |
| 1 or more serious TEAE | 4 (2.6%) | 1 (0.7%) |
| TEAE leading to intranasal drug withdrawn [b] | 4 (2.6%) | 3 (2.1%) |
| TEAE leading to oral antidepressant withdrawn [b] | 3 (2.0%) | 0 |

[a] Study drug relationships of possible, probable, and very likely are included in this category.
[b] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.

TEAEs for the transferred-entry subjects who continued to receive an oral AD+placebo during the OP and MA phase are summarized in the Tables 99 and 100. Overall, 61.6% of TEP subjects experienced at least one TEAE during the OP phase; 68.5% of TEP subjects experienced at least one TEAE during the MA phase.

TABLE 99

Overall Summary of Treatment-emergent Adverse Events (TEAE); Optimization Phase (Study ESKETINTRD3003: Safety (OP_TEP) Analysis Set)

| | Oral AD + Intranasal Placebo (N = 86) |
|---|---|
| TEAE | 53 (61.6%) |
| TEAE possibly related to intranasal drug [a] | 27 (31.4%) |
| TEAE possibly related to oral antidepressant [a] | 10 (11.6%) |
| TEAE leading to death | 0 |
| 1 or more serious TEAE | 0 |
| TEAE leading to intranasal drug withdrawn [b] | 0 |
| TEAE leading to oral antidepressant withdrawn [b] | 0 |

[a] Study drug relationships of possible, probable, and very likely are included in this category.
[b] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

TABLE 100

Overall Summary of Treatment-emergent Adverse Events (TEAE); Maintenance Phase (Study ESKETINTRD3003: Safety (MA_TEP) Analysis Set)

| | Oral AD + Intranasal Placebo (N = 54) |
|---|---|
| TEAE | 37 (68.5%) |
| TEAE possibly related to intranasal drug [a] | 19 (35.2%) |
| TEAE possibly related to oral antidepressant [a] | 8 (14.8%) |
| TEAE leading to death | 0 |
| 1 or more serious TEAE | 1 (1.9%) |
| TEAE leading to intranasal drug withdrawn [b] | 2 (3.7%) |
| TEAE leading to oral antidepressant withdrawn [b] | 1 (1.9%) |

[a] Study drug relationships of possible, probable, and very likely are included in this category.
[b] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.

Treatment-emergent adverse events occurring during the IND, OP and MA phase (≥5% of subjects in any treatment group) are summarized by treatment group for the safety (IND), safety (OP) and safety (MA) analysis sets in Tables 101-103. The most common TEAEs (≥10%) during the IND phase were vertigo (22.7%), dizziness (22.2%), nausea (21.5%), dysgeusia (20.6%), somnolence (14.9%), headache (13.7%), paresthesia (11.0%), dissociation (11.0%), feeling abnormal (10.8%), vision blurred (10.3%) and sedation (10.1%) in the safety (IND) analysis set. The most common TEAEs during the OP phase were vertigo (20.0%), dysgeusia (17.4%), somnolence (13.8%), dizziness (13.4%), headache (12.5%) and nausea (10.5%) in the safety (OP) analysis set. The most common TEAEs in the esketamine+oral AD group during the double-blind MA phase were dysgeusia (26.3%), vertigo (25.0%), somnolence (21.1%), dizziness (20.4%), headache (17.8%), nausea (16.4%), vision blurred (15.8%), dissociation (13.8%) and hypoesthesia oral (13.2%) in the safety (MA) analysis set. There were no TEAEs in ≥10% of subjects with oral AD+placebo group in the safety (MA) analysis set. Most AEs were observed post dose on dosing days and resolved on the same day.

TABLE 101

Treatment-emergent Adverse Events in at Least 5% of Subjects; Open-label Induction Phase (Study ESKETINTRD3003: Safety (IND) Analysis Set)

| | Intranasal Esk + Oral AD (N = 437) |
|---|---|
| Total no. subjects with TEAE | 336 (76.9%) |
| Nervous system disorders | 247 (56.5%) |
| Dizziness | 97 (22.2%) |
| Dysgeusia | 90 (20.6%) |
| Somnolence | 65 (14.9%) |
| Headache | 60 (13.7%) |
| Paresthesia | 48 (11.0%) |
| Sedation | 44 (10.1%) |
| Dizziness postural | 30 (6.9%) |
| Hypoesthesia | 30 (6.9%) |
| Psychiatric disorders | 153 (35.0%) |
| Dissociation | 48 (11.0%) |
| Anxiety | 31 (7.1%) |
| Gastrointestinal disorders | 150 (34.3%) |
| Nausea | 94 (21.5%) |
| Hypoesthesia oral | 32 (7.3%) |
| Vomiting | 29 (6.6%) |
| Ear and labyrinth disorders | 108 (24.7%) |
| Vertigo | 99 (22.7%) |
| General disorders and administration site conditions | 94 (21.5%) |
| Feeling abnormal | 47 (10.8%) |
| Respiratory, thoracic and mediastinal disorders | 87 (19.9%) |
| Nasal discomfort | 28 (6.4%) |
| Throat irritation | 26 (5.9%) |
| Eye disorders | 65 (14.9%) |
| Vision blurred | 45 (10.3%) |
| Investigations | 42 (9.6%) |
| Blood pressure increased | 34 (7.8%) |

Incidence is based on the number of subjects experiencing at least one adverse event, not the number of events.
Adverse events are coded using MedDRA version 20.0.

TABLE 102

Treatment-emergent Adverse Events in at Least 5% of Subjects; Optimization Phase (Study ESKETINTRD3003: Safety (OP) Analysis Set)

| | Intranasal Esk + Oral AD (N = 455) |
|---|---|
| Total no. subjects with TEAE | 335 (73.6%) |
| Nervous system disorders | 208 (45.7%) |
| Dysgeusia | 79 (17.4%) |
| Somnolence | 63 (13.8%) |
| Dizziness | 61 (13.4%) |
| Headache | 57 (12.5%) |
| Dizziness postural | 24 (5.3%) |
| Hypoesthesia | 24 (5.3%) |
| Paresthesia | 24 (5.3%) |
| Psychiatric disorders | 123 (27.0%) |
| Dissociation | 44 (9.7%) |
| Gastrointestinal disorders | 115 (25.3%) |
| Nausea | 48 (10.5%) |
| Hypoesthesia oral | 34 (7.5%) |
| Ear and labyrinth disorders | 101 (22.2%) |
| Vertigo | 91 (20.0%) |
| Respiratory, thoracic and mediastinal disorders | 74 (16.3%) |

TABLE 102-continued

Treatment-emergent Adverse Events in at Least
5% of Subjects; Optimization Phase (Study
ESKETINTRD3003: Safety (OP) Analysis Set)

| | Intranasal Esk + Oral AD (N = 455) |
|---|---|
| Nasal discomfort | 26 (5.7%) |
| General disorders and administration site conditions | 65 (14.3%) |
| Feeling abnormal | 33 (7.3%) |
| Investigations | 48 (10.5%) |
| Blood pressure increased | 26 (5.7%) |
| Eye disorders | 46 (10.1%) |
| Vision blurred | 29 (6.4%) |

Incidence is based on the number of subjects experiencing at least one adverse event, not the number of events.
Adverse events are coded using MedDRA version 20.0.

TABLE 104

Treatment-emergent Adverse Events in at Least
5% of Subjects; Optimization Phase (Study ESKETINTRD3003:
Safety (OP_TEP) Analysis Set)

| | Oral AD + Intranasal Placebo (N = 86) |
|---|---|
| Total no. subjects with TEAE | 53 (61.6%) |
| Nervous system disorders | 30 (34.9%) |
| Headache | 16 (18.6%) |
| Dysgeusia | 8 (9.3%) |
| Dizziness | 6 (7.0%) |
| Somnolence | 5 (5.8%) |
| Psychiatric disorders | 12 (14.0%) |
| Anxiety | 5 (5.8%) |

Incidence is based on the number of subjects experiencing at least one adverse event, not the number of events.
Adverse events are coded using MedDRA version 20.0.

TABLE 103

Treatment-emergent Adverse Events in at Least 5% of
Subjects in Either Treatment Group; Maintenance Phase
(Study ESKETINTRD3003: Safety (MA) Analysis Set)

| | Intranasal Esk + Oral AD (N = 152) | Oral AD + Intranasal Placebo (N = 145) |
|---|---|---|
| Total no. subjects with TEAE | 125 (82.2%) | 66 (45.5%) |
| Nervous system disorders | 83 (54.6%) | 30 (20.7%) |
| Dysgeusia | 40 (26.3%) | 10 (6.9%) |
| Somnolence | 32 (21.1%) | 3 (2.1%) |
| Dizziness | 31 (20.4%) | 7 (4.8%) |
| Headache | 27 (17.8%) | 14 (9.7%) |
| Paresthesia | 12 (7.9%) | 0 |
| Sedation | 10 (6.6%) | 1 (0.7%) |
| Hypoesthesia | 9 (5.9%) | 1 (0.7%) |
| Psychiatric disorders | 56 (36.8%) | 15 (10.3%) |
| Dissociation | 21 (13.8%) | 0 |
| Anxiety | 10 (6.6%) | 5 (3.4%) |
| Confusional state | 8 (5.3%) | 0 |
| Gastrointestinal disorders | 53 (34.9%) | 11 (7.6%) |
| Nausea | 25 (16.4%) | 1 (0.7%) |
| Hypoesthesia oral | 20 (13.2%) | 0 |
| Vomiting | 10 (6.6%) | 1 (0.7%) |
| Paresthesia oral | 8 (5.3%) | 1 (0.7%) |
| Ear and labyrinth disorders | 43 (28.3%) | 9 (6.2%) |
| Vertigo | 38 (25.0%) | 8 (5.5%) |
| Eye disorders | 32 (21.1%) | 1 (0.7%) |
| Vision blurred | 24 (15.8%) | 1 (0.7%) |
| Diplopia | 9 (5.9%) | 0 |
| Infections and infestations | 32 (21.1%) | 25 (17.2%) |
| Viral upper respiratory tract infection | 11 (7.2%) | 12 (8.3%) |
| Respiratory, thoracic and mediastinal disorders | 30 (19.7%) | 11 (7.6%) |
| Nasal discomfort | 11 (7.2%) | 4 (2.8%) |
| Throat irritation | 8 (5.3%) | 1 (0.7%) |
| General disorders and administration site conditions | 28 (18.4%) | 3 (2.1%) |
| Feeling abnormal | 14 (9.2%) | 1 (0.7%) |
| Investigations | 19 (12.5%) | 10 (6.9%) |
| Blood pressure increased | 10 (6.6%) | 5 (3.4%) |

Incidence is based on the number of subjects experiencing at least one adverse event, not the number of events.
Adverse events are coded using MedDRA version 20.0.

Treatment-emergent adverse events occurring during the OP and MA phase (≥5% of subjects) for the TEP subjects are summarized for the safety (OP_TEP) and safety (MA_TEP) analysis sets in the Tables 104 and 105. The most common TEAEs for the TEP subjects during the OP phase was headache (18.6%). The most common TEAEs for the TEP subjects during the MA phase were viral upper respiratory tract infection (24.1%), headache (22.2%) and dysgeusia (14.8%).

TABLE 105

Treatment-emergent Adverse Events in at Least 5% of Subjects; Maintenance Phase (Study ESKETINTRD3003: Safety (MA_TEP) Analysis Set)

| | Oral AD + Intranasal Placebo (N = 54) |
|---|---|
| Total no. subjects with TEAE | 37 (68.5%) |
| Infections and infestations | 24 (44.4%) |
| Viral upper respiratory tract infection | 13 (24.1%) |
| Urinary tract infection | 3 (5.6%) |
| Nervous system disorders | 18 (33.3%) |
| Headache | 12 (22.2%) |
| Dysgeusia | 8 (14.8%) |
| Somnolence | 4 (7.4%) |
| Gastrointestinal disorders | 11 (20.4%) |
| Diarrhea | 4 (7.4%) |
| Nausea | 3 (5.6%) |
| Musculoskeletal and connective tissue disorders | 8 (14.8%) |
| Musculoskeletal pain | 3 (5.6%) |
| Spinal pain | 3 (5.6%) |

Incidence is based on the number of subjects experiencing at least one adverse event, not the number of events.
Adverse events are coded using MedDRA version 20.0.

Adverse Events Leading to Study Drug Withdrawal

There were 22 subjects who discontinued the IND phase intranasal study medication due to treatment-emergent adverse events (Table 106) and 8 subjects who discontinued the oral AD medication due to TEAEs (Table 107) in the safety (IND) analysis set. There were 5 subjects who discontinued the OP phase intranasal study medication due to treatment-emergent adverse events (Table 108) and 2 subjects who discontinued the oral AD medication due to TEAEs (Table 109) in the safety (OP) analysis set. Subjects who discontinued intranasal study medication could continue the oral AD in the follow-up phase if appropriate.

TABLE 106

Treatment-emergent Adverse Events Leading to Discontinuation of Intranasal Study Medication; Open-label Induction Phase (Study ESKETINTRD3003: Safety (IND) Analysis Set)

| | Intranasal Esk + Oral AD (N = 437) |
|---|---|
| Total no. subjects with TEAE leading to discontinuation [a] | 22 (5.0%) |
| Psychiatric disorders | 11 (2.5%) |
| Anxiety | 7 (1.6%) |
| Depression | 2 (0.5%) |
| Dissociation | 2 (0.5%) |
| Nightmare | 1 (0.2%) |
| Suicidal ideation | 1 (0.2%) |
| Nervous system disorders | 8 (1.8%) |
| Akathisia | 1 (0.2%) |
| Autonomic nervous system imbalance | 1 (0.2%) |
| Dizziness postural | 1 (0.2%) |
| Headache | 1 (0.2%) |
| Hypertonia | 1 (0.2%) |
| Lacunar stroke | 1 (0.2%) |
| Paresthesia | 1 (0.2%) |
| Sedation | 1 (0.2%) |
| Simple partial seizures | 1 (0.2%) |
| Tremor | 1 (0.2%) |
| General disorders and administration site conditions | 3 (0.7%) |
| Asthenia | 1 (0.2%) |
| Chills | 1 (0.2%) |
| Feeling abnormal | 1 (0.2%) |
| Gastrointestinal disorders | 2 (0.5%) |
| Nausea | 2 (0.5%) |
| Vomiting | 1 (0.2%) |
| Investigations | 2 (0.5%) |
| Blood pressure increased | 2 (0.5%) |
| Musculoskeletal and connective tissue disorders | 2 (0.5%) |
| Muscular weakness | 1 (0.2%) |
| Musculoskeletal stiffness | 1 (0.2%) |
| Ear and labyrinth disorders | 1 (0.2%) |
| Vertigo | 1 (0.2%) |
| Renal and urinary disorders | 1 (0.2%) |
| Micturition urgency | 1 (0.2%) |
| Respiratory, thoracic and mediastinal disorders | 1 (0.2%) |
| Dyspnea | 1 (0.2%) |

[a] An adverse event that started in the induction phase and resulted in discontinuation in a following phase is counted as treatment-emergent in the induction phase.
Incidence is based on the number of subjects experiencing at least one adverse event, not the number of events.
Adverse events are coded using MedDRA version 20.0.

TABLE 107

Treatment-emergent Adverse Events Leading to Discontinuation of Oral Antidepressant; Open-label Induction Phase (Study ESKETINTRD3003: Safety (IND) Analysis Set)

| | Intranasal Esk + Oral AD (N = 437) |
|---|---|
| Total no. subjects with TEAE leading to discontinuation [a] | 8 (1.8%) |
| Psychiatric disorders | 5 (1.1%) |
| Depression | 3 (0.7%) |
| Anxiety | 1 (0.2%) |
| Suicidal ideation | 1 (0.2%) |
| Nervous system disorders | 3 (0.7%) |
| Headache | 1 (0.2%) |
| Lacunar stroke | 1 (0.2%) |
| Tremor | 1 (0.2%) |
| Renal and urinary disorders | 1 (0.2%) |
| Micturition urgency | 1 (0.2%) |

[a] An adverse event that started in the induction phase and resulted in discontinuation in a following phase is counted as treatment-emergent in the induction phase.
Incidence is based on the number of subjects experiencing at least one adverse event, not the numbe of events.
Adverse events are coded using MedDRA version 20.0.
1 subject who had completed the Day 25 intranasal medication and did not meet criteria for continuing to the next phase. The action taken for the adverse event (depression) was indicated as oral AD drug withdrawn. This subject is considered as a completer for the summary of study completion/withdrawal for the induction phase.

TABLE 108

Treatment-emergent Adverse Events Leading to Discontinuation of Intranasal Study Medication; Optimization Phase (Study ESKETINTRD3003: Safety (OP) Analysis Set)

| | Intranasal Esk + Oral AD (N = 455) |
|---|---|
| Total no. subjects with TEAE leading to discontinuation [a] | 5 (1.1%) |
| Investigations | 2 (0.4%) |
| Gamma-glutamyltransferase increased | 1 (0.2%) |
| Hepatic enzyme increased | 1 (0.2%) |
| Psychiatric disorders | 2 (0.4%) |
| Alcohol abuse | 1 (0.2%) |
| Depression | 1 (0.2%) |
| Ear and labyrinth disorders | 1 (0.2%) |
| Tinnitus | 1 (0.2%) |

[a] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

TABLE 109

Treatment-emergent Adverse Events Leading to Discontinuation of Oral Antidepressant; Optimization Phase (Study ESKETINTRD3003: Safety (OP) Analysis Set)

| | Intranasal Esk + Oral AD (N = 455) |
|---|---|
| Total no. subjects with TEAE leading to discontinuation [a] | 2 (0.4%) |
| Investigations | 1 (0.2%) |
| Hepatic enzyme increased | 1 (0.2%) |
| Psychiatric disorders | 1 (0.2%) |
| Deoression | 1 (0.2%) |

[a] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

There were 7 subjects (4 subjects in esketamine+oral AD, 3 subjects in oral AD+placebo) who discontinued the MA phase intranasal study medication due to treatment-emergent adverse events in the safety (MA) analysis set (Table 110). Four of these subjects (3 subjects in esketamine+oral AD, 1 subject in oral AD+placebo) had a relapse during the maintenance phase and indicated for the adverse event leading to relapse that the intranasal study medication was discontinued due to this event. These subjects could continue the oral AD in the follow-up phase if appropriate. Three subjects in esketamine+oral AD arm discontinued the MA phase oral antidepressant study medication due to treatment-emergent adverse events in the safety (MA) analysis set (Table 111). These three subjects had a relapse during the maintenance phase and indicated for the adverse event leading to relapse that the oral AD medication was discontinued due to this event. No subjects in oral AD+intranasal placebo arm discontinued the MA phase oral AD study medication due to treatment-emergent adverse events.

TABLE 110

Treatment-emergent Adverse Events Leading to Discontinuation of Intranasal Study Medication; Maintenance Phase (Study ESKETINTRD3003: Safety (MA) Analysis Set)

| | Intranasal Esk + Oral AD (N = 152) | Oral AD + Intranasal Placebo (N = 145) |
|---|---|---|
| Total no. subjects with TEAE leading to discontinuation [a] | 4 (2.6%) | 3 (2.1%) |
| Psychiatric disorders | 4 (2.6%) | 3 (2.1%) |
| Depression | 3 (2.0%) | 3 (2.1%) |
| Confusional state | 1 (0.7%) | 0 |

[a] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.
4 subjects (3 in esketamine + oral AD, 1 in oral AD + placebo) who had a relapse event (depression) are included in this summary. The action taken for the relapse adverse event was indicated as intranasal drug withdrawn. They are considered as completers for the summary of study completion/withdrawal for the maintenance phase.

TABLE 111

Treatment-emergent Adverse Events Leading to Discontinuation of Oral Antidepressant; Maintenance Phase (Study ESKETINTRD3003: Safety (MA) Analysis Set)

| | Intranasal Esk + Oral AD (N = 152) | Oral AD + Intranasal Placebo (N = 145) |
|---|---|---|
| Total no. subjects with TEAE leading to discontinuation [a] | 3 (2.0%) | 0 |
| Psychiatric disorders | 3 (2.0%) | 0 |
| Depression | 3 (2.0%) | 0 |

[a] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.
3 subjects who had a relapse event are included in this summary. The action taken for the relapse adverse event was indicated as oral AD drug withdrawn. They are considered as a completer for the summary of study completion/withdrawal for the maintenance phase.

There was no transferred-entry placebo subject who discontinued the OP phase intranasal study medication or oral AD due to treatment-emergent adverse events in the safety (OP_TEP) analysis set (Tables 112 and 113).

TABLE 112

Treatment-emergent Adverse Events Leading to Discontinuation of Intranasal Study Medication; Optimization Phase (Study ESKETINTRD3003: Safety (OP_TEP) Analysis Set)

| | Oral AD + Intranasal Placebo (N = 86) |
|---|---|
| Total no. subjects with TEAE leading to discontinuation [a] | 0 |
| No data to report | — |

[a] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

TABLE 113

Treatment-emergent Adverse Events Leading to Discontinuation of Oral Antidepressant; Optimization Phase (Study ESKETINTRD3003: Safety (OP_TEP) Analysis Set)

| | Oral AD + Intranasal Placebo (N = 86) |
|---|---|
| Total no. subjects with TEAE leading to discontinuation [a] | 0 |
| No data to report | — |

[a] An adverse event that started in the optimization phase and resulted in discontinuation in a following phase is counted as treatment-emergent in the optimization phase.
Incidence is based on the number of subjects experiencing at least one adverse event, not the number of events.
Adverse events are coded using MedDRA version 20.0.

There were 2 transferred-entry placebo subjects who discontinued the MA phase intranasal study medication in the safety (MA_TEP) analysis set. One of these subjects discontinued the MA phase due to both intranasal and oral AD medications and is included in both Tables 114 and 115.

TABLE 114

Treatment-emergent Adverse Events Leading to Discontinuation of Intranasal Study Medication; Maintenance Phase (Study ESKETINTRD3003: Safety (MA_TEP) Analysis Set)

|  | Oral AD + Intranasal Placebo (N = 54) |
|---|---|
| Total no. subjects with TEAE leading to discontinuation [a] | 2 (3.7%) |
| Infections and infestations | 1 (1.9%) |
| Nail infection | 1 (1.9%) |
| Investigations | 1 (1.9%) |
| Blood pressure increased | 1 (1.9%) |
| Skin and subcutaneous tissue disorders | 1 (1.9%) |
| Butterfly rash | 1 (1.9%) |
| Rash | 1 (1.9%) |

[a] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.

TABLE 115

Treatment-emergent Adverse Events Leading to Discontinuation of Oral Antidepressant; Maintenance Phase (Study ESKETINTRD3003: Safety (MA_TEP) Analysis Set)

|  | Oral AD + Intranasal Placebo (N = 54) |
|---|---|
| Total no. subjects with TEAE leading to discontinuation [a] | 1 (1.9%) |
| Infections and infestations | 1 (1.9%) |
| Nail infection | 1 (1.9%) |
| Skin and subcutaneous tissue disorders | 1 (1.9%) |
| Butterfly rash | 1 (1.9%) |
| Rash | 1 (1.9%) |

[a] An adverse event that started in the maintenance phase and resulted in discontinuation in the follow-up phase is counted as treatment-emergent in the maintenance phase.
Incidence is based on the number of subjects experiencing at least one adverse event, not the number of events.
Adverse events are coded using MedDRA version 20.0.

Serious Adverse Events

There were no deaths reported in this study.

There were 32 subjects with 39 serious adverse events (SAEs) reported in this study. A total of 13 subjects experienced serious treatment-emergent adverse events (TEAEs) during the IND phase in the safety (IND) analysis set (Table 116).

TABLE 116

Treatment-emergent Serious Adverse Events; Open-label Induction Phase (Study ESKETINTRD3003: Safety (IND) Analysis Set)

|  | Intranasal Esk + Oral AD (N = 437) |
|---|---|
| Total no. subjects with a serious TEAE | 13 (3.0%) |
| Psychiatric disorders | 7 (1.6%) |
| Depression | 3 (0.7%) |
| Anxiety | 2 (0.5%) |
| Disorientation | 1 (0.2%) |
| Suicidal ideation | 1 (0.2%) |
| Nervous system disorders | 3 (0.7%) |
| Autonomic nervous system imbalance | 1 (0.2%) |
| Lacunar stroke | 1 (0.2%) |
| Sedation | 1 (0.2%) |
| Simple partial seizures | 1 (0.2%) |
| General disorders and administration site conditions | 1 (0.2%) |
| Hypothermia | 1 (0.2%) |
| Injury, poisoning and procedural complications | 1 (0.2%) |
| Procedural pain | 1 (0.2%) |
| Renal and urinary disorders | 1 (0.2%) |
| Nephrolithiasis | 1 (0.2%) |
| Vascular disorders | 1 (0.2%) |
| Orthostatic hypotension | 1 (0.2%) |

Incidence is based on the number of subjects experiencing at least one adverse event, not the number of events.
Adverse events are coded using MedDRA version 20.0.

Three subjects had serious TEAEs considered as of very likely relationship to intranasal esketamine by the investigators: disorientation (Day 1), suicidal ideation (Day 8), sedation (Day 22), and one subject had two serious TEAEs considered as of very likely relationship to intranasal esketamine: autonomic nervous system imbalance (Day 5) and simple partial seizures (Day 5). One subject had a serious TEAE considered by the investigator as probably related to intranasal esketamine: lacunar stroke (Day 1). One subject had a serious TEAE considered possibly related to intranasal esketamine: hypothermia (Day 10). Eleven subjects experienced serious treatment-emergent adverse events during the OP phase in the safety (OP) analysis set (Table 117). No serious TEAEs were considered to be possibly, probably or very likely related to esketamine.

TABLE 117

Treatment-emergent Serious Adverse Events; Optimization Phase (Study ESKETINTRD3003: Safety (OP) Analysis Set)

|  | Intranasal Esk + Oral AD (N = 455) |
|---|---|
| Total no. subjects with a serious TEAE | 11 (2.4%) |
| Nervous system disorders | 3 (0.7%) |
| Headache | 1 (0.2%) |
| Migraine | 1 (0.2%) |
| Paresthesia | 1 (0.2%) |
| Infections and infestations | 2 (0.4%) |
| Pneumonia | 1 (0.2%) |
| Sepsis | 1 (0.2%) |
| Psychiatric disorders | 2 (0.4%) |
| Depression | 1 (0.2%) |
| Panic attack | 1 (0.2%) |
| Cardiac disorders | 1 (0.2%) |
| Sinus tachycardia | 1 (0.2%) |
| Gastrointestinal disorders | 1 (0.2%) |
| Anal fissure | 1 (0.2%) |
| General disorders and administration site conditions | 1 (0.2%) |
| Chest pain | 1 (0.2%) |
| Hepatobiliary disorders | 1 (0.2%) |
| Cholecystitis acute | 1 (0.2%) |
| Musculoskeletal and connective tissue disorders | 1 (0.2%) |
| Pain in extremity | 1 (0.2%) |
| Vascular disorders | 1 (0.2%) |
| Hypertensive crisis | 1 (0.2%) |

Incidence is based on the number of subjects experiencing at least one adverse event, not the number of events.
Adverse events are coded using MedDRA version 20.0.

Five subjects (4 subjects in esketamine+oral AD, 1 subject in oral AD+placebo) in the safety (MA) analysis set experienced serious treatment-emergent adverse events during the MA phase (Table 118). All the events were considered as not related to intranasal medication or oral AD.

TABLE 118

Treatment-emergent Serious Adverse Events; Maintenance Phase (Study ESKETINTRD3003: Safety (MA) Analysis Set)

| | Intranasal Esk + Oral AD (N = 152) | Oral AD + Intranasal Placebo (N = 145) |
|---|---|---|
| Total no. subjects with a serious TEAE | 4 (2.6%) | 1 (0.7%) |
| Psychiatric disorders | 3 (2.0%) | 1 (0.7%) |
| Depression | 2 (1.3%) | 1 (0.7%) |
| Major depression | 1 (0.7%) | 0 |
| Pregnancy, puerperium and perinatal conditions | 1 (0.7%) | 0 |
| Ectopic pregnancy | 1 (0.7%) | 0 |

Incidence is based on the number of subjects experiencing at least one adverse event, not the number of events.
Adverse events are coded using MedDRA version 20.0.

Two subjects had serious AEs considered not related to oral AD in the follow-up phase (Table 119). One subject experienced two serious AEs considered to be possibly related to oral AD.

TABLE 119

Serious Adverse Events; Follow-up Phase (Study ESKETINTRD3003: Follow-up Analysis Set)

| | Intranasal Esk + Oral AD for Any Phase (N = 481) | Oral AD + Intranasal Placebo for All Phases (N = 64) |
|---|---|---|
| Total no. subjects with a serious adverse event | 3 (0.6%) | 0 |
| General disorders and administration site conditions | 1 (0.2%) | 0 |
| Chest pain | 1 (0.2%) | 0 |
| Musculoskeletal and connective tissue disorders | 1 (0.2%) | 0 |
| Intervertebral disc protrusion | 1 (0.2%) | 0 |
| Psychiatric disorders | 1 (0.2%) | 0 |
| Depression | 1 (0.2%) | 0 |
| Mania | 1 (0.2%) | 0 |

Incidence is based on the number of subjects experiencing at least one adverse event, not the number of events.
Adverse events are coded using MedDRA version 20.0.

There was no transferred-entry placebo subject who experienced a serious treatment-emergent adverse event during the OP phase in the safety (OP_TEP) analysis set (Table 120).

TABLE 120

Treatment-emergent Serious Adverse Events; Optimization Phase (Study ESKETINTRD3003: Safety (OP_TEP) Analysis Set)

| | Oral AD + Intranasal Placebo (N = 86) |
|---|---|
| Total no. subjects with a serious TEAE | 0 |
| No data to report | — |

Incidence is based on the number of subjects experiencing at least one adverse event, not the number of events.
Adverse events are coded using MedDRA version 20.0.

One TEP subject experienced a serious TEAE during the MA phase which was considered not related to intranasal medication or oral AD Table 121).

TABLE 121

Treatment-emergent Serious Adverse Events; Maintenance Phase (Study ESKETINTRD3003: Safety (MA_TEP) Analysis Set)

| | Oral AD + Intranasal Placebo (N = 54) |
|---|---|
| Total no. subjects with a serious TEAE | 1 (1.9%) |
| Injury, poisoning and procedural complications | 1 (1.9%) |
| Clavicle fracture | 1 (1.9%) |

Incidence is based on the number of subjects experiencing at least one adverse event, not the number of events.
Adverse events are coded using MedDRA version 20.0.

Vital Signs

FIGS. 53 and 54 present means for blood pressure over time by treatment group in the maintenance phase.

Transient blood pressure increases peaked for the esketamine group at approximately 40 minutes post dose and returned closer to predose levels by 1.5 hours post dose.

Other Safety Observations

Clinician-Assessed Dissociative Symptom Scale (CADSS)

The Clinician Administered Dissociative States Scale (CADSS) was measured prior to the start of each dose, at 40 minutes, and 1.5 hours postdose. The CADSS is used to assess treatment emergent dissociative symptoms and perceptual changes and the total score ranges from 0 to 92 with a higher score representing a more severe condition.

The dissociative and perceptual change symptoms measured by the CADSS, suggest these symptoms had an onset shortly after the start of the dose and resolved by 1.5 hours postdose (FIG. 55).

Modified Observer's Assessment of Alertness/Sedation (MOAA/S)

The Modified Observer's Assessment of Alertness/Sedation (MOAA/S) was used to measure treatment-emergent sedation with correlation to levels of sedation defined by the American Society of Anesthesiologists (ASA) continuum. The MOAA/S scores range from 0 (No response to painful stimulus; corresponds to ASA continuum for general anesthesia) to 5 (Readily responds to name spoken in normal tone [awake]; corresponds to ASA continuum for minimal sedation).

The proportion of subjects with sedation (as measured by the MOAA/S scale ≤3) was ≤3.9% for esketamine+oral AD for each dosing day in all phases.

Conclusions

Continued treatment with esketamine plus an oral AD demonstrated statistically significant superiority to treatment with an oral AD plus intranasal placebo in delaying time to relapse in those who were in stable remission after 16 weeks of treatment with esketamine plus an oral AD.

In subjects who were in stable remission after 16 weeks of esketamine+oral AD treatment, continued treatment with esketamine plus an oral AD demonstrated clinically meaningful and statistically significant (two-sided p=0.003) superiority to treatment with an oral AD+placebo nasal spray as measured by delayed time to relapse.

Overall, 26.7% subjects on esketamine+oral AD and 45.3% subjects on an oral AD+placebo nasal spray experienced a relapse; the 6-month relapse rates based on Kaplan Meier estimates were 34.5% and 48.6%, respectively. The estimated hazard ratio (95% CI) of esketamine+oral AD relative to oral AD+placebo based on weighted estimates was 0.49 (0.29, 0.84), indicating, that at any time point during the study period, subjects who were stable remitters and continued treatment with esketamine+oral AD group were on average 51% less likely to relapse than subjects who switched to oral AD plus placebo. Based on Kaplan-Meier estimates, median time to relapse (time point at which the cumulative survival function equals 0.5 [or 50%]) for esketamine plus oral AD arm was not estimable (NE) as this group never reached 50%. The median time to relapse (95% CI) for oral AD plus placebo nasal spray was 273 (97.0; NE) days.

In subjects who are in stable response (but not In remission) after 16 weeks of esketamine+oral AD treatment, continued treatment with esketamine plus an oral AD demonstrated clinically meaningful and statistically significant superiority to an oral AD plus placebo nasal spray in delaying time to relapse (two-sided p<0.001).

The 6-month relapse rates based on Kaplan Meier estimates were 24.4% and 59.4%, respectively. The estimated hazard ratio of intranasal esketamine+oral AD relative to oral AD plus placebo nasal spray based on Cox proportional hazards model was 0.30 (95% CI: 0.16, 0.55), indicating that, at any time point during the study period, subjects who were stable responders and continued treatment with esketamine+oral AD group were on average 70% less likely to have a relapse than subjects who switched to the oral AD plus placebo nasal spray. Of note, the estimate of the median time to relapse for esketamine plus oral AD should be interpreted with caution as it is heavily influenced by one subject who had a long time to relapse (i.e. 635 days).

As shown, continued treatment with esketamine plus an oral AD demonstrated statistically significant superiority to treatment with an oral AD alone in delaying time to relapse in those who were in stable response (but not remission) after 16 weeks of treatment with esketamine plus an oral AD.

Example 5

Treatment Duration/Trial Duration

Each subject participated in up to 4 phases: up to 4-week screening phase (direct-entry subjects only), a 4-week open-label induction (IND) phase (direct-entry subjects and transferred-entry non responder subjects), a 48-week open-label optimization/maintenance (OP/MA) phase (all responder subjects from the open label IND phase of the current study, and transferred-entry responder subjects), and a 4-week follow-up phase. The maximum duration of the subject's participation in ESKETINTRD3004 study was 60 weeks for direct-entry subjects; 56 weeks for transferred-entry non-responder subjects, and 52 weeks for transferred-entry responder subjects. The sample size of 750 was estimated to have at least 300 subjects received treatment with intranasal esketamine for 6 months and at least 100 subjects for 12 months. In addition, transfer-entry subjects were enrolled from 3005 study to get 100 elderly subjects dosed with esketamine. See, FIG. 57 for the trial design.

Analysis Sets for Efficacy and Safety

The efficacy and safety analyses are based on the full (IND) analysis set and the full (OP/MA) analysis set. The full (IND) analysis set is defined as all subjects who receive at least 1 dose of intranasal study medication or 1 dose of oral antidepressant in the open-label IND phase (for direct-entry and transferred-entry non-responder subjects). The full (OP/MA) analysis is defined as all subjects who receive at least 1 dose of intranasal study medication or 1 dose of oral antidepressant in the OP/MA phase. Safety variables include cognition function over time, treatment-emergent adverse events (TEAEs), including TEAEs of special interest, vital signs over time, Clinician-Administered Dissociative Symptom Scale (CADDS) over time, and Modified Observer's Assessment of Alertness/Sedation (MOAA/S) score ≤3. Efficacy variables include the MADRS which consists of 10 items that cover all the core depressive symptoms: each item is scored from 0 (symptom is not present or is normal) to 6 (severe or continuous presence of the symptom). A total score (0 to 60) is calculated by summing the scores of all 10 items. A higher score represents a more severe condition.

Primary Objective

The primary objective of this study is to assess the long-term safety and tolerability of intranasal esketamine plus a newly initiated oral antidepressant in subjects with TRD, with special attention to the potential effects on cognitive function, potential treatment-emergent symptoms of cystitis and/or lower urinary tract symptoms, and potential withdrawal and/or rebound symptoms following cessation of intranasal esketamine treatment.

Secondary Objectives

To assess the effect of intranasal esketamine plus a newly initiated oral antidepressant in subjects with TRD on:

Safety and tolerability with special attention to the following:
  Treatment-emergent adverse events (TEAEs), including TEAEs of special interest
  Local nasal tolerability
  Effects on heart rate, blood pressure, respiratory rate and blood oxygen saturation
  Effects on alertness and sedation
  Potential psychorespiratory
  sis-like effects
  Dissociative symptoms
  Potential effects on suicidal ideation/behavior.

Long-term efficacy, including effects on:
  Depressive symptoms (clinician and self-reported), overall severity of depressive illness, functional impairment and associated disability, anxiety symptoms, and health-related quality of life and health status
  Response rate over time, defined as:
    percentage of subjects with 50% reduction from baseline (IND phase) in the Montgomery-Asberg Depression Rating Scale (MADRS) total score,
    percentage of subjects with 250% reduction from baseline (IND phase) in the Patient Health Questionnaire, 9-item (PHQ-9) total score
  Remission rate overtime, defined as:
    percentage of subjects with MADRS total score ≤12,
    percentage of subjects with PHQ-9 total score ≤5

Subject and Treatment Information

A total of 1161 subjects were screened or enrolled across 123 sites in 21 countries (Argentina, Australia, Austria, Belgium, Brazil, Bulgaria, Finland, France, Germany, Italy, Republic of Korea, Malaysia, Mexico, Poland, South Africa, Spain, Sweden, Taiwan, Turkey, United Kingdom, and United States). Excluding 338 screen failures and 21 subjects from site US10025 due to GCP issues, 802 subjects with a DSM-5 (Diagnostic and Statistical Manual of Mental Disorders, 5th Edition) diagnosis of MDD were enrolled.

Six hundred ninety-one subjects were directly enrolled into the 3004 study and 111 subjects were transferred from the TRD3005 study (88 non-responders and 23 responders).

This is an open-label, multicenter, long-term study to evaluate the safety and efficacy of intranasal esketamine plus a newly initiated oral antidepressant in subjects with TRD. The study included 802 enrolled male and female adult subjects with TRD. Of the 802 enrolled subjects, 691 (86.2%) were direct-entry subjects and 111 (13.8%) were transfer-entry subjects from study ESKETINTRD3005 (88 were non-responders entering the IND phase and 23 were responders entering the study in the OP/MA phase). In the all enrolled analysis set, 686 (85.5%) of the subjects were white and 502 (62.6%) of the subjects were female. The mean age was 52.2 years, ranging from 18 to 86 years. The gender distribution was similar to acute phase 3 studies (predominantly female), while the median age was somewhat higher, reflecting inclusion of elderly subjects. With 178 elderly subjects accounting for 22.2% of the enrolled analysis set, the study satisfied regulatory requirements with a minimum 100 elderly subjects enrolled.

Out of 779 direct entry or transfer-entry non-responder subjects from the TRD3005 study in the full (IND) analysis set, 580 (74.5%) completed the IND phase and 198 (25.4%) withdrew early. The majority of subjects were discontinued from the IND phase due to subject 'did not meet criteria for continuing into the next phase' (84 subjects) and 'adverse event' (52 subjects). Of the 603 subjects entered in the OP/MA phase (including 23 transfer entry responders from the TRD3005 study), 150 (24.9%) completed OP/MA phase. Of the 453 subjects discontinued prior to the end of the 48-week OP/MA phase, 331 were discontinued due to termination of the study by the sponsor (required number of subjects met sufficient treatment exposure). The other most frequent reasons for discontinuation were due 'withdrawal by subject'(30 subjects), and withdrew due to 'adverse event' and 'lack of efficacy' (25 subjects each). Subjects could enter the follow-up phase from either the IND phase or the OP/MA phase. A total of 357 subjected entered the follow-up phase and 326 (91.3%) completed the follow-up phase.

Of the 802 enrolled subjects, 1 subject did not receive intranasal study drug but did receive oral AD and subject received intranasal study drug but did not receive oral AD. These subjects are included in the all enrolled analysis set. See, Tables 122 and 123.

TABLE 122

Number of Subjects Entered from Study ESKETINTRD3005 (By Responder Status) and Direct Entry Subjects (Study ESKETINTRD3004: All Enrolled Analysis Set)

| | Intranasal Esk + Oral AD (N = 802) |
|---|---|
| Direct-entry subjects in study | |
| ESKETINTRD3004 | 691 (86.2%) |
| Transferred-entry subjects from study | |
| ESKETINTRD3005: | 111 (13.8%) |
| Non-responder subjects | 88 (11.0%) |
| Intranasal esk 28 mg + oral AD | 3 (0.4%) |
| Intranasal esk 56 mg + oral AD | 9 (1.1%) |
| Intranasal esk 84 mg + oral AD | 28 (3.5%) |
| Oral AD + Placebo | 48 (6.0%) |
| Responder subjects | 23 (2.9%) |
| Intranasal esk 28 mg + oral AD | 1 (0.1%) |
| Intranasal esk 56 mg + oral AD | 5 (0.6%) |
| Intranasal esk 84 mg + oral AD | 9 (1.1%) |
| Oral AD + Placebo | 8 (1.0%) |

The final dose in the TRD3005 study is presented for the Transferred-entry subjects.

TABLE 123

Number of Subjects in Each Analysis Set (Study ESKETINTRD3004: All Enrolled Analysis Set)

| | Intranasal Esk + Oral AD (N = 802) |
|---|---|
| Induction phase | |
| Full (IND) | 779 (97.1%) |
| Optimization/maintenance phase | |
| Full (OP/MA) | 603 (75.2%) |
| Follow-up phase | |
| Follow-up | 357 (44.5%) |

Subjects received flexible doses of intranasal ESK for the $1^{st}$ 2 weeks, followed by fixed doses (28 mg—in elderly subjects only, 56 mg or 84 mg in all age groups) plus a newly initiated oral antidepressant (one of the following: sertraline, escitalopram, venlafaxine XR or fluoxetine). Esketamine was dosed twice a week during the IND. In the OP/MA weekly administration occurred from weeks 5 to 8. From weeks 9 to 52 of the OP/MA phase, esketamine was dosed either weekly or every other week depending on the MADRS score with the aim of having the lowest frequency to sustain remission. Switching to every other week treatment (if total MADRS score was ≤12) or back to weekly treatment (if total MADRS score was >12) was possible at 4-week intervals, starting at week 8. From day 15 (patients <65 years) or day 18 (patients ≥65 years) the dose of esketamine nasal spray remained the same. After an initial period of dose up-titration, the dose of oral antidepressants remained the same. Dose reductions based on tolerability were allowed for both medications.

The subject's discharge readiness was assessed based on overall adverse events (including dizziness, sedation, perceptual changes, blood pressure): Approximately 60-65% of the subjects were ready for discharge by 1 hour after dosing and over 95% of subjects were ready for discharge 1.5 h post dose across the visits of the IND phase; the percentages of subjects ready to discharge were approximately 65-70% 1 hour post dose and 97-99% 1.5 h post dose in the OP/MA phase.

Study Completion Withdrawal Information

Of the 779 full (IND) analysis set subjects (direct entry and transfer entry non-responders), 580 (74.5%) subjects completed the 28-day IND phase and 198 (25.4%) withdrew early. Results are presented in Table 124. The majority of subjects were discontinued from the IND phase due to subject 'did not meet criteria for continuing into the next phase' (<50% improvement in MADRS total score) (84 subjects) and 'adverse event' (52 subjects).

TABLE 124

Completion/Withdrawal Information; Induction Phase (Study ESKETINTRD3004: Full (IND) Analysis Set)

| | Intranasal Esk + Oral AD (N = 779) |
|---|---|
| Continued to optimization/maintenance phase | 580 (74.5%) |
| Withdrawn during induction phase | 198 (25.4%) |
| Subject does not meet criteria for continuing into the next phase | 84 (10.8%) |
| Adverse event | 52 (6.7%) |
| Withdrawal by subject | 22 (2.8%) |
| Lack of efficacy | 21 (2.7%) |
| Lost to follow-up | 5 (0.6%) |

TABLE 124-continued

Completion/Withdrawal Information; Induction Phase
(Study ESKETINTRD3004: Full (IND) Analysis Set)

| | Intranasal Esk + Oral AD (N = 779) |
|---|---|
| Non-compliance with study drug | 1 (0.1%) |
| Protocol violation | 1 (0.1%) |
| Other | 12 (1.5%) |

One subject was dispensed study medication in OP/MA phase, but never took the drug in the OP/MA phase. This subject is not counted as continuing into the OP/MA phase since drug was not taken, but was discontinued in this phase.

Of the 603 subjects entering the OP/MA phase (including 23 transfer entry responders from the TRD3005 study), 150 (24.9%) subjects completed the 48-week OP/MA phase. Of the 453 subjects discontinued prior to the end of the 48-week OP/MA phase, 331 were discontinued due to termination of the study by the sponsor (required number of subjects met sufficient treatment exposure). Results are presented in Table 125. The most frequent reasons for discontinuation were due to 'study terminated by sponsor' (331 subjects), 'withdrawal by subject' (30 subjects), and withdrew due to 'adverse event' and 'lack of efficacy' (25 subjects each). (Note: the study was terminated after meeting esketamine exposure targets (at least 300 subjects treated for 6 months and 100 subjects treated for 12 months).

TABLE 125

Completion/Withdrawal Information; Optimization/Maintenance
Phase (Study ESKETINTRD3004: Full (OP/MA) Analysis Set)

| | Intranasal Esk + Oral AD (N = 603) |
|---|---|
| Completed optimization/maintenance phase | 150 (24.9%) |
| Withdrawn during optimization/maintenance phase | 453 (75.1%) |
| Study terminated by sponsor | 331 (54.9%) |
| Withdrawal by subject | 30 (5.0%) |
| Adverse event | 25 (4.1%) |
| Lack of efficacy | 25 (4.1%) |
| Lost to follow-up | 10 (1.7%) |
| Protocol violation | 3 (0.5%) |
| Subject missed assessments or treatment sessions | 3 (0.5%) |
| Death | 2 (0.3%) |
| Pregnancy | 2 (0.3%) |
| Non-compliance with study drug | 1 (0.2%) |
| Other | 21 (3.5%) |

Subjects could enter the follow-up phase from either the IND phase or the OP/MA phase. A total of 357 subjected entered the follow-up phase and 326 (91.3%) completed the follow-up phase.

2 subjects were discontinued from treatment during the OP/MA phase. Following the last menstruation, one subject was exposed twice to 56 mg ESK dose and the $2^{nd}$ subject was exposed once to ESK 84 mg dose. Both pregnancies spontaneously aborted during the first trimester, the investigator evaluation of causality to esketamine was not applicable. One case of paternal exposure to esketamine occurred during the study. The partner of subject had an uncomplicated pregnancy and delivered a normal mature female newborn via spontaneous delivery.

Demographic and Baseline Characteristics

Demographic and baseline characteristics are displayed in Table 126 for the all enrolled analysis set. The majority of subjects entering the study were female (62.6%) and white (85.5%). The mean (SD) age of all subjects was 52.2 (13.69) years, ranging from 18 to 86 years.

TABLE 126

Demographic and Baseline(IND) Characteristics (Study
ESKETINTRD3004: All Enrolled Analysis Set)

| | Intranasal Esk + Oral AD (N = 802) |
|---|---|
| Age (years) | |
| N | 802 |
| Mean (SD) | 52.2 (13.69) |
| Median | 53.5 |
| Range | (18; 86) |
| Age category (years), n (%) | |
| N | 802 |
| 18-44 | 225 (28.1%) |
| 45-64 | 399 (49.8%) |
| 65-74 | 159 (19.8%) |
| ≥75 | 19 (2.4%) |
| Sex, n (%) | |
| N | 802 |
| Male | 300 (37.4%) |
| Female | 502 (62.6%) |
| Race, n (%) | |
| N | 802 |
| Asian | 81 (10.1%) |
| Black or African American | 15 (1.9%) |
| White | 686 (85.5%) |
| Other | 8 (1.0%) |
| Multiple | 8 (1.0%) |
| Not Reported | 4 (0.5%) |
| Ethnicity, n (%) | |
| N | 802 |
| Hispanic or Latino | 149 (18.6%) |
| Not Hispanic or Latino | 640 (79.8%) |
| Not Reported | 10 (1.2%) |
| Unknown | 3 (0.4%) |
| Baseline weight (kg) | |
| N | 802 |
| Mean (SD) | 78.51 (18.426) |
| Median | 76.05 |
| Range | (39.0; 143.0) |
| Baseline height (cm) | |
| N | 802 |
| Mean (SD) | 167.46 (10.340) |
| Median | 166.50 |
| Range | (139.7; 196.0) |
| Baseline body mass index (kg/m$^2$) | |
| N | 802 |
| Mean (SD) | 27.9 (5.68) |
| Median | 26.9 |
| Range | (16; 52) |
| BMI category (kg/m$^2$), n (%) | |
| N | 802 |
| Underweight <18.5 | 9 (1.1%) |
| Normal 18.5-<25 | 262 (32.7%) |
| Overweight 25-<30 | 275 (34.3%) |
| Obese 30-<40 | 228 (28.4%) |
| Morbidly obese ≥40 | 28 (3.5%) |
| Employment status, n (%) [a] | |
| N | 802 |
| Any type of employment | 450 (56.1%) |
| Any type of unemployment | 175 (21.8%) |
| Other | 177 (22.1%) |
| Hypertension status, n (%) [b] | |
| N | 802 |
| Yes | 220 (27.4%) |
| No | 582 (72.6%) |

TABLE 126-continued

Demographic and Baseline(IND) Characteristics (Study ESKETINTRD3004: All Enrolled Analysis Set)

| | Intranasal Esk + Oral AD (N = 802) |
|---|---|
| Country, n (%) | |
| N | 802 |
| Argentina | 106 (13.2%) |
| Australia | 23 (2.9%) |
| Austria | 16 (2.0%) |
| Belgium | 5 (0.6%) |
| Brazil | 52 (6.5%) |
| Bulgaria | 94 (11.7%) |
| Finland | 2 (0.2%) |
| France | 4 (0.5%) |
| Germany | 13 (1.6%) |
| Italy | 7 (0.9%) |
| Korea, Republic of | 26 (3.2%) |
| Malaysia | 19 (2.4%) |
| Mexico | 10 (1.2%) |
| Poland | 6 (0.7%) |
| South Africa | 64 (8.0%) |
| Spain | 42 (5.2%) |
| Sweden | 90 (11.2%) |
| Taiwan, Province of China | 33 (4.1%) |
| Turkey | 31 (3.9%) |
| United Kingdom | 12 (1.5%) |
| United States | 147 (18.3%) |
| Region, n (%) | |
| N | 802 |
| Europe | 322 (40.1%) |
| North America | 147 (18.3%) |
| Other | 333 (41.5%) |
| Class of oral antidepressant, n (%) | |
| N | 801 |
| SNRI | 407 (50.8%) |
| SSRI | 394 (49.2%) |
| Oral antidepressant, n (%) | |
| N | 801 |
| Duloxetine | 251 (31.3%) |
| Escitalopram | 237 (29.6%) |
| Sertraline | 157 (19.6%) |
| Venlafaxine extended release (XR) | 156 (19.5%) |

[a] Any type of employment includes: any category containing "Employed", Sheltered Work, Housewife or Dependent Husband, and Student; any type of unemployment includes: any category containing "Unemployed"; Other includes: Retired and No Information Available.
[b] Hypertension status is classified as Yes if hypertension is recorded in medical history.

Baseline psychiatric history for the all enrolled analysis set is presented in Table 127. The mean (SD) baseline MADRS total score was 31.4 (5.39), ranging from 19 to 49.

TABLE 127

Baseline(IND) Psychiatric History (Study ESKETINTRD3004: All Enrolled Analysis Set)

| | Intranasal Esk + Oral AD (N = 802) |
|---|---|
| Age when diagnosed with MDD (years) | |
| N | 802 |
| Mean (SD) | 35.7 (13.75) |
| Median | 35.0 |
| Range | (8; 72) |
| Baseline MADRS total score | |
| N | 802 |
| Mean (SD) | 31.4 (5.39) |
| Median | 31.0 |
| Range | (19; 49) |
| Baseline CGI-S | |
| N | 802 |
| Mean (SD) | 4.8 (0.77) |
| Median | 5.0 |
| Range | (1; 7) |
| Baseline CGI-S category, n (%) | |
| N | 802 |
| Normal, not at all ill | 1 (0.1%) |
| Borderline mentally ill | 3 (0.4%) |
| Mildly ill | 18 (2.2%) |
| Moderately ill | 235 (29.3%) |
| Markedly ill | 409 (51.0%) |
| Severely ill | 130 (16.2%) |
| Among the most extremely ill patients | 6 (0.7%) |
| Baseline PHQ-9 total score | |
| N | 802 |
| Mean (SD) | 17.3 (5.01) |
| Median | 18.0 |
| Range | (0; 27) |
| Screening C-SSRS lifetime [a], n (%) | |
| N | 800 |
| No event | 474 (59.3%) |
| Suicidal ideation | 203 (25.4%) |
| Suicidal behavior | 123 (15.4%) |
| Screening C-SSRS past 6 or 12 months [a], n (%) | |
| N | 800 |
| No event | 583 (72.9%) |
| Suicidal ideation (past 6 months) | 215 (26.9%) |
| Suicidal behavior (past 12 months) | 2 (0.3%) |
| Duration of current episode (wks) | |
| N | 802 |
| Mean (SD) | 160.5 (261.80) |
| Median | 66.5 |
| Range | (6; 2184) |
| No. of previous antidepressant medications [b,c], n (%) | |
| N | 802 |
| 1 | 17 (2.1%) |
| 2 | 465 (58.0%) |
| 3 | 187 (23.3%) |
| 4 | 84 (10.5%) |
| 5 | 23 (2.9%) |
| 6 | 17 (2.1%) |
| 7 | 4 (0.5%) |
| 8 | 5 (0.6%) |
| Family history of depression, n (%) | |
| N | 802 |
| Yes | 346 (43.1%) |
| No | 456 (56.9%) |
| Family history of anxiety disorder, n (%) | |
| N | 802 |
| Yes | 61 (7.6%) |
| No | 741 (92.4%) |
| Family history of bipolar disorder, n (%) | |
| N | 802 |
| Yes | 35 (4.4%) |
| No | 767 (95.6%) |
| Family history of schizophrenia, n (%) | |
| N | 802 |
| Yes | 38 (4.7%) |
| No | 764 (95.3%) |

TABLE 127-continued

Baseline(IND) Psychiatric History (Study ESKETINTRD3004: All Enrolled Analysis Set)

| | Intranasal Esk + Oral AD (N = 802) |
|---|---|
| Family history of alcohol abuse, n (%) | |
| N | 802 |
| Yes | 61 (7.6%) |
| No | 741 (92.4%) |
| Family history of substance abuse, n (%) | |
| N | 802 |
| Yes | 24 (3.0%) |
| No | 778 (97.0%) |
| Number of prior ADs with nonresponse | 1 = 2.1% $^d$ 3 = 23.3% |
| | 2 = 58.0% ≥4 = 16.6% |

Baseline (IND) is the last observation prior to or on the start date of induction phase for direct-entry and transferred-entry non-responder subjects and is baseline (IND) from study 3005 for the transferred-entry responder subjects.
$^a$ C-SSRS category: No event = 0; Suicidal ideation = 1, 2, 3, 4, 5; Suicidal behavior = 6, 7, 8, 9, 10
$^b$ Number of antidepressant medications with non-response (defined as ≤25% improvement or 26%-<50% improvement for direct entry subjects and defined as ≤25% improvement for transfer entry subjects) taken for at least 6 weeks during the current episode as obtained from MGH-ATRQ at the time of the first screening visit.
$^c$ Direct entry subjects are to have to ≥2 oral antidepressant treatments in the current episode of depression and transfer entry subjects are to have ≥1 oral antidepressants in the current episode.
$^d$ Subjects from 3005 who had non-response to 1 AD and showed prospective non-response to 2$^{nd}$ AD during screening of the 3005 study.

Extent of Exposure

The number of doses of intranasal study medication during the IND phase is summarized in Table 128.

TABLE 128

Number of Days Dosed with Intranasal Study Medication; Induction Phase (Study ESKETINTRD3004: Full (IND) Analysis Set)

| Number of days dosed | Intranasal Esk + Oral AD (N = 779) |
|---|---|
| 1 | 29 (3.7%) |
| 2 | 24 (3.1%) |
| 3 | 12 (1.5%) |
| 4 | 11 (1.4%) |
| 5 | 6 (0.8%) |
| 6 | 22 (2.8%) |
| 7 | 52 (6.7%) |
| 8 | 622 (79.8%) |

A summary of mean, mode and final dose of intranasal study medication during the IND phase is summarized in Table 129. On Day 25 of the IND phase 28/675 (4.1%) were receiving the 28 mg dose of esketamine, 298/675 (44.1%) were receiving the 56 mg dose of esketamine and 349/675 (51.7%) were receiving the 84 mg dose of esketamine.

TABLE 129

Mean, Mode, and Final Daily Dose of Intranasal Study Medication; Induction Phase (Study ESKETINTRD3004: Full (IND) Analysis Set)

| | Intranasal Esk + Oral AD (N = 779) |
|---|---|
| Mean daily dose (mg) | |
| N | 778 |
| Mean (SD) | 64.4 (13.15) |
| Median | 63.0 |
| Range | (28; 81) |

TABLE 129-continued

Mean, Mode, and Final Daily Dose of Intranasal Study Medication; Induction Phase (Study ESKETINTRD3004: Full (IND) Analysis Set)

| | Intranasal Esk + Oral AD (N = 779) |
|---|---|
| Mode daily dose (mg) | |
| N | 741 |
| Mean (SD) | 68.5 (16.51) |
| Median | 56.0 |
| Range | (28; 84) |
| Final daily dose (mg) | |
| N | 778 |
| Mean (SD) | 68.2 (16.61) |
| Median | 56.0 |
| Range | (28; 84) |

The calculation of mean, mode, and final daily dose excludes days off intranasal study medication.
The final dose is the last non-zero dose received during the induction phase.

The extent of exposure to intranasal study medication during the combined IND and OP/MA phases is summarized in Table 130.

TABLE 130

Extent of Exposure to Intranasal Study Medication; Induction and Optimization/Maintenance Phases (Study ESKETINTRD3004: All Enrolled Analysis Set)

| | Intranasal Esk + Oral AD | |
|---|---|---|
| | Total Duration (N = 802) | Cumulative Distribution (N = 802) |
| Duration, weeks | | |
| N | 801 | 801 |
| Category, n (%) | | |
| ≤Week 4 (≤Day 28) | 202 (25.2%) | 202 (25.2%) |
| Weeks 4-8 (Days 29-56) | 35 (4.4%) | 237 (29.6%) |
| Weeks 8-12 (Days 57-84) | 23 (2.9%) | 260 (32.4%) |
| Weeks 12-16 (Days 85-112) | 48 (6.0%) | 308 (38.4%) |
| Weeks 16-20 (Days 113-140) | 52 (6.5%) | 360 (44.9%) |
| Weeks 20-24 (Days 141-168) | 50 (6.2%) | 410 (51.1%) |
| Weeks 24-28 (Days 169-196) | 52 (6.5%) | 462 (57.6%) |
| Weeks 28-32 (Days 197-224) | 34 (4.2%) | 496 (61.8%) |
| Weeks 32-36 (Days 225-252) | 30 (3.7%) | 526 (65.6%) |
| Weeks 36-40 (Days 253-280) | 32 (4.0%) | 558 (69.6%) |
| Weeks 40-44 (Days 281-308) | 45 (5.6%) | 603 (75.2%) |
| Weeks 44-48 (Days 309-336) | 35 (4.4%) | 638 (79.6%) |
| Weeks 48-52 (Days 337-364) | 155 (19.4%) | 793 (98.9%) |
| >Week 52 (>Day 364) | 8 (1.0%) | 801 (99.9%) |
| Mean (SD) | 24.9 (18.54) | |
| Median | 22.9 | |
| Range | (0; 56) | |

The duration of exposure is defined as the duration between the date of the first exposure and the date of the last exposure to intranasal study medication. It includes days on which subjects did not actually take intranasal study medication.

The frequency of subjects with 6 months and 12 months of exposure to esketamine is presented in Table 131.

TABLE 131

Frequency Distribution of Subjects with 6 Months and 12 Months of Exposure to Intranasal Study Medication (Study ESKETINTRD3004: All Enrolled Analysis Set)

| | Intranasal Esk + Oral AD (N = 802) |
|---|---|
| Subjects with 6 months of exposure | 364 (45.4%) |
| Subjects with 12 months of exposure | 136 (17.0%) |

6 months is defined as ≥180 days and 12 months is defined as ≥350 days.

A summary of mean, mode and final dose of intranasal study medication during the OP/MA phase is summarized in Table 132.

TABLE 132

Mean, Mode, and Final Daily Dose of Intranasal Study Medication; Optimization/Maintenance Phase (Study ESKETINTRD3004: Full (OP/MA) Analysis Set)

| | Intranasal Esk + Oral AD (N = 603) |
|---|---|
| Mean daily dose (mg) | |
| N | 603 |
| Mean (SD) | 68.8 (15.74) |
| Median | 68.3 |
| Range | (25; 84) |
| Mode daily dose (mg) | |
| N | 596 |
| Mean (SD) | 69.1 (15.75) |
| Median | 70.0 |
| Range | (28; 84) |
| Final daily dose (mg) | |
| N | 603 |
| Mean (SD) | 69.0 (16.05) |
| Median | 84.0 |
| Range | (28; 84) |

The calculation of mean, mode, and final daily dose excludes days off intranasal study medication.
The final dose is the last non-zero dose received during the optimization/maintenance phase.

On Week 48 of the OP/MA phase, 7/143 (4.9%), 69/143 (48.3%), 1/143 (0.7%) and 66/143 (46.2%) were receiving the 28 mg dose, 56 mg dose, 70 mg dose, and 84 mg dose of esketamine, respectively. Starting from Week 4 (OP/MA), the intranasal treatment session frequency could be adjusted (if applicable) at fixed, 4-week intervals. Of the 603 subjects treated with intranasal esketamine during the OP/MA phase, 275 (47.6%) subjects switched from weekly dosing to every other week at Week 4 (OP/MA). The majority of subjects did not switch dosing schedules during the remaining weeks of the OP/MA phase. See, Table 133.

TABLE 133

Frequency of Subjects who Changed the Dosing Frequency (Weekly to Every Other Week or Every Other Week to Weekly) Over Time Starting From Week 4 (OP/MA) of this Phase; Optimization/Maintenance Phase (Study ESKETINTRD3004: Full (OP/MA) Analysis Set)

| | Intranasal Esk + Oral AD (N = 603) |
|---|---|
| Week 4(OP/MA) | |
| N | 578 |
| Weekly to Every Other Week | 275 (47.6%) |
| Every Other Week to Weekly | 0 |
| Did not switch | 303 (52.4%) |
| Week 8(OP/MA) | |
| N | 548 |
| Weekly to Every Other Week | 80 (14.6%) |
| Every Other Week to Weekly | 65 (11.9%) |
| Did not switch | 403 (73.5%) |
| Week 12(OP/MA) | |
| N | 502 |
| Weekly to Every Other Week | 76 (15.1%) |
| Every Other Week to Weekly | 52 (10.4%) |
| Did not switch | 374 (74.5%) |
| Week 16(OP/MA) | |
| N | 463 |
| Weekly to Every Other Week | 58 (12.5%) |
| Every Other Week to Weekly | 43 (9.3%) |
| Did not switch | 362 (78.2%) |
| Week 20(OP/MA) | |
| N | 405 |
| Weekly to Every Other Week | 34 (8.4%) |
| Every Other Week to Weekly | 29 (7.2%) |
| Did not switch | 342 (84.4%) |
| Week 24(OP/MA) | |
| N | 357 |
| Weekly to Every Other Week | 23 (6.4%) |
| Every Other Week to Weekly | 42 (11.8%) |
| Did not switch | 292 (81.8%) |
| Week 28(OP/MA) | |
| N | 309 |
| Weekly to Every Other Week | 28 (9.1%) |
| Every Other Week to Weekly | 22 (7.1%) |
| Did not switch | 259 (83.8%) |
| Week 32(OP/MA) | |
| N | 287 |
| Weekly to Every Other Week | 30 (10.5%) |
| Every Other Week to Weekly | 21 (7.3%) |
| Did not switch | 236 (82.2%) |
| Week 36(OP/MA) | |
| N | 254 |
| Weekly to Every Other Week | 13 (5.1%) |
| Every Other Week to Weekly | 17 (6.7%) |
| Did not switch | 224 (88.2%) |
| Week 40(OP/MA) | |
| N | 211 |
| Weekly to Every Other Week | 13 (6.2%) |
| Every Other Week to Weekly | 14 (6.6%) |
| Did not switch | 184 (87.2%) |
| Week 44(OP/MA) | |
| N | 173 |
| Weekly to Every Other Week | 9 (5.2%) |
| Every Other Week to Weekly | 6 (3.5%) |
| Did not switch | 158 (91.3%) |

Table 134A displays the dosing regimen changes during the OP/MA phase.

TABLE 134A

Dosing Regimen Changes; Optimization/Maintenance Phase
(Study ESKETINTRD3004: Full (OP/MA) Analysis Set)

|  | Intranasal Esk + Oral AD (N = 603) |
|---|---|
| Total number of dosing regimen changes per subject | |
| N | 603 |
| 0 | 145 (24.0%) |
| 1 | 230 (38.1%) |
| 2 | 85 (14.1%) |
| 3 | 70 (11.6%) |
| 4 | 35 (5.8%) |
| 5 | 28 (4.6%) |
| 6 | 10 (1.7%) [a] |
| Dosing Regimen | |
| N | 603 |
| Weekly dose throughout entire OP/MA phase | 145 (24.0%) |
| One change only from weekly to every other week | 230 (38.1%) |
| Change back and forth from weekly to every other week | 228 (37.8%) |

The denominator is the number of subjects who have dosing ≥ Week 4(OP/MA)
Regimen: weekly esketamine dosing or every other week esketamine dosing.
Number of Changes: 0 = weekly dose throughout OP/MA phase; 1 = 1 change from weekly to every other week (EOW); 2 = change from EOW back to weekly; 3 = 2 changes from weekly to EOW remained on EOW; 4 = 2 changes from weekly to EOW and back to weekly; 5 = 3 changes from weekly to EOW, remaining on EOW; 6 = 3 changes from weekly to EOW and back to weekly.
[a] Approximately 22% returned to weekly in total 46% on weekly and 16% returned to every other week (in total 54% on every other week).

Safety

Cognition

A primary objective of the study was to assess potential effects of Esketamine on cognitive function. Potential impact of esketamine on cognition was assessed by the Cogstate Computerized Cognitive Battery.

Number of Subjects Analyzed
All Enrolled Analysis Set: A total of 796 subjects were analyzed.
Follow-up Analysis Set including only those subjects that were included in the follow-up phase): A total of 356 subjects were analyzed.
Timepoints Analyzed
All Enrolled Analysis Set:
Open-label induction phase
Baseline
Day 28
Optimization/Maintenance Phase
Week 20
Week 32
Week 44
Endpoint (the last timepoint in the optimization/maintenance phase subjects performed)
Follow-up Analysis Set:
Baseline
Endpoint (previous phase—the last timepoint in the last treatment phase subjects participated before entering the follow-up phase)
Week 4
Criteria for Evaluation
Cogstate Battery
Detection Test (DET; to measure attention)
Identification Test (IDN; to measure attention)
One Card Learning test (OCL; to measure visual learning)
One Back Test (ONB; to measure working memory)
Groton Maze Learning test (GML; to measure executive function)
Hopkins Verbal Learning Test—Revised (HVLT-R)
Total Recall (to measure verbal learning)
Delayed Recall (to measure verbal memory)
True Positives (to measure recognition memory
Recognition Discrimination Index (to measure recognition memory)

In general, group mean performance on the cognition tests assessing attention [detection (DET) and identification (IDN) tests evaluating simple and choice reaction times, respectively], visual memory, working memory, executive function and delayed verbal memory, and recognition memory for the all enrolled analysis set and separately for subjects <65, demonstrated either improvement from baseline or subjects remained at baseline levels, during both the IND Phase and the OP/MA Phase. This same pattern of cognitive performance was also evident for subjects ≥65 years of age, except for the tests assessing attention/processing speed (DET and IDN) for which there was a decline from baseline observed starting at Week 20 with the largest decline at Week 44 of the study. Although sample size decreased at Week 44 in elderly subjects, the decrease in attention performance in this age group was also apparent in completer's analysis.

The greatest mean decrease in the speed of performance for DET and IDN (−0.1032 and −0.0587, respectively) observed at week 44 of the study, was smaller as compared to the standard deviation (SD) of the measurement at baseline (0.15955 and 0.09465, for ATN and IDN, respectively). For reference, the difference observed was lower than decline in attention seen with 1 mg alprazolam tid. In a previous study in healthy subjects, the mean group performance decline in attention parameters of the magnitude of 1 SD following administration of 1 mg alprazolam tid was considered to be clinically significant (Maruff et al. 2006).

Initial evaluation of patient level data shows that 17 of 28 elderly subjects who completed the study, had persistent decline in attention measures (reliable change index [RCI] <−1.65 for at least 2 measurements]. The decline in performance on the detection and identification tests appears to be consistent in terms of magnitude and direction across subjects who are 65 to <75 and subjects ≥75 years old, although the sample size for the ≥75 year of age group is very small samples and does not allow to draw reliable conclusions about the change.

Cognitive performance, including performance on attention/reaction time measures remained stable during the Follow up period in both elderly and younger subjects. There was no evidence of the persistent cognitive decline that has been reported in substance abuse populations using large (often daily) doses of ketamine.

There were 2 subjects who experienced 'memory impairment' adverse events in the IND phase and 2 subjects in the OP/MA phase. Two subjects experienced treatment-emergent 'cognitive disorder' during the IND phase. No subjects experienced treatment-emergent 'cognitive disorder' during the OP/MA phase.

Overall, 723/802 (90.1%) subjects experienced at least one TEAE in the IND and OP/MA phases. The most common (210%) TEAEs during the IND and OP/MA phases were dizziness (33.0%), nausea (25.1%), headache (24.9%), dissociation (22.4%), somnolence (16.7%), dysgeusia and hypoesthesia (11.8% each), vomiting and vertigo (10.8% each), and viral upper respiratory tract infection (10.2%).

There were 76 (9.5%) subjects who discontinued the IND or OP/MA phase intranasal study medication due to treatment-emergent adverse events. The most common AEs leading to discontinuation of intranasal study medication were anxiety (1.1%), suicidal ideation (0.9%), depression, dizziness, and blood pressure increased (0.7% each), dissociation (0.6%), and muscular weakness (0.5%). These subjects could continue the oral AD in the follow-up phase if applicable. There were 33 (4.1%) subjects who discontinued IND or OP/MA phase oral antidepressant study medication due to treatment-emergent adverse events. The most common AEs leading to discontinuation of oral antidepressant study medication were anxiety (0.9%) and suicidal ideation (0.6%).

A total of 423 (52.7%) subjects experienced suggestive of potential drug abuse, dependence and withdrawal adverse events during the IND and OP/MA phases.

Transient blood pressure increases for the esketamine+ oral AD group peaked at 40 minutes post dose with the maximum mean increases (across all dosing days in the respective phase) in systolic/diastolic BP being 9.6/5.6 mm Hg and 8.6/5.2 mm Hg during the IND and OP/MA phases, respectively. The post dose increases in the systolic and diastolic blood pressure were observed in both study phases. Subjects with and without hypertension experienced similar magnitude of mean increases of SBP and DBP.

Transient changes in systolic and diastolic blood pressures were observed throughout the study, consistent with acute esketamine studies. Most subjects who withdrew due to blood pressure elevations, did so after the first 2 dosing sessions.

The frequency of subjects with treatment-emergent acute hypertension is shown in Table 134B. The incidence of acute hypertension was almost 3× greater in subjects with the history of hypertension vs. subjects without hypertension.

TABLE 134B

|  | Intranasal Esk + Oral AD (N = 802) |
|---|---|
| Hypertension status: Yes | 220 |
| Acute hypertension | 16 (7.3%) |
| Systolic BP ≥180 | 10 (4.5%) |
| Diastolic BP ≥110 | 9 (4.1%) |
| Hypertension status: No | 580 |
| Acute hypertension | 17 (2.9%) |

TABLE 134B-continued

|  | Intranasal Esk + Oral AD (N = 802) |
|---|---|
| Systolic BP ≥180 | 8 (1.4%) |
| Diastolic BP ≥110 | 10 (1.7%) |

Overall, the dissociative and perceptual change symptoms measured by the CADSS, suggest onset of these symptoms occurred shortly after the start of the dose and resolved at 1.5 hours post dose. These symptoms attenuated with repeated dosing over time. The magnitude of symptoms observed on the CADSS post dose decreased with repeated doses and continued to be low throughout OP/MA phase.

Efficacy: There was a clinically meaningful improvement in depressive symptoms: the mean change (SD) in MADRS total score from baseline (IND) to end point (IND) was −16.4 (8.76) for esketamine+oral AD with baseline (IND) (SD) of 31.2 (5.27). The mean change (SD) from baseline (OP/MA) to end point (OP/MA) was 0.3 (8.12) for esketamine +oral AD with baseline (OP/MA) (SD) of 11.0 (4.52), indicating that the antidepressant effect is sustained. Similarly, the median change (range) from baseline (IN) to end point (IND) was −18.0 and from baseline (OP/MA) to end point (OP/MA) was 0 for esketamine +oral AD.

The mean change (SD) from Baseline (IND) in PHQ-9 total score to End Point (IND) was −8.9 (6.67) for esketamine+oral AD. The mean change (SD) from Baseline (OP/MA) in PHQ-9 total score to End Point (OP/MA) was −0.2 (5.65) for esketamine+oral AD.

These results were consistent with MADRS in the direction of changes at the end of both study phases. Overall efficacy results in the IND phase were consistent with the results obtained in acute efficacy studies (3001 and 3002). This improvement was corroborated by shifts in the overall disease severity as assessed by CGI-S: the percentage of subjects who were normal/borderline/had mild disease increased from 2.7% at baseline to 63.8% at the end of IND phase. See, FIG. 58.

Tables 134-137 display summaries of mean and mean changes over time for Detection—Attention (simple reaction time) for subjects <65 years and ≥65 years of age, respectively.

TABLE 134

Cognitive Domains: Means and Mean Changes from Baseline (IND) Over Time by Age; Open-label Induction and Optimization/Maintenance Phases (Study ESKETINTRD3004: All Enrolled Analysis Set) Age Group: <65 years

|  |  |  |  |  |  |  | Base | |
|---|---|---|---|---|---|---|---|---|
|  | N | Mean | SD | Med | Min | Max | Mean | (SD) |
|  | Detection - Attention (simple reaction time)$^a$ |  |  |  |  |  |  |  |
|  | Esketamine |  |  |  |  |  |  |  |
| Baseline (IND) | 616 | 2.5943 | 0.15532 | 2.5803 | 2.266 | 3.120 |  |  |
| Day 28 (IND) | 509 | 2.5755 | 0.15174 | 2.5609 | 2.214 | 3.021 | 2.5930 | (0.15712) |
| Week 20 (OP/MA) | 357 | 2.5779 | 0.14060 | 2.5632 | 2.250 | 3.014 | 2.5903 | (0.15678) |
| Week 32 (OP/MA) | 252 | 2.5863 | 0.15081 | 2.5793 | 2.253 | 3.125 | 2.5971 | (0.16478) |
| Week 44 (OP/MA) | 171 | 2.5812 | 0.16642 | 2.5543 | 2.252 | 3.150 | 2.5780 | (0.17130) |
| End Point (OP/MA) | 449 | 2.5896 | 0.14519 | 2.5820 | 2.267 | 3.019 | 2.5950 | (0.15654) |

$^a$Speed of performance (log10 ms), lower score = better performance $^b$Number of errors, lower score = better performance $^c$Accuracy of performance, higher score = better performance $^d$Higher change from baseline is better performance

TABLE 135

Cognitive Domains: Means and Mean Changes from Baseline (IND) Over Time by Age; Open-label Induction and Optimization/Maintenance Phases (Study ESKETINTRD3004: All Enrolled Analysis Set) Age Group: <65 years

| | | | Change from Baseline[d] | | | |
|---|---|---|---|---|---|---|
| N | Mean | SE | SD | Med | Min | Max |
| Detection - Attention (simple reaction time)[a] | | | | | | |
| Esketamine | | | | | | |

| | N | Mean | SE | SD | Med | Min | Max |
|---|---|---|---|---|---|---|---|
| Baseline (IND) | | | | | | | |
| Day 28 (IND) | 503 | 0.0159 | 0.00525 | 0.11773 | 0.0130 | −0.499 | 0.449 |
| Week 20 (OP/MA) | 354 | 0.0127 | 0.00639 | 0.12023 | 0.0096 | −0.353 | 0.496 |
| Week 32 (OP/MA) | 250 | 0.0116 | 0.00849 | 0.13430 | 0.0028 | −0.383 | 0.508 |
| Week 44 (OP/MA) | 169 | −0.0037 | 0.00991 | 0.12880 | −0.0074 | −0.517 | 0.407 |
| End Point (OP/MA) | 442 | 0.0048 | 0.00600 | 0.12610 | 0.0025 | −0.509 | 0.462 |

[a] Speed of performance (log10 ms), lower score = better performance
[b] Number of errors, lower score = better performance
[c] Accuracy of performance, higher score = better performance
[d] Higher change from baseline is better performance

TABLE 136

Cognitive Domains: Means and Mean Changes from Baseline (IND) Over Time by Age; Open-label Induction and Optimization/Maintenance Phases (Study ESKETINTRD3004: All Enrolled Analysis Set) Age Group: ≥65 years

| | N | Mean | SD | Med | Min | Max | Base Mean | (SD) |
|---|---|---|---|---|---|---|---|---|
| Detection - Attention (simple reaction time)[a] | | | | | | | | |
| Esketamine | | | | | | | | |
| Baseline (IND) | 168 | 2.6133 | 0.15955 | 2.5713 | 2.321 | 3.048 | | |
| Day 28 (IND) | 121 | 2.6018 | 0.14091 | 2.5759 | 2.345 | 3.065 | 2.6085 | (0.14845) |
| Week 20 (OP/MA) | 74 | 2.6331 | 0.14690 | 2.6331 | 2.352 | 2.968 | 2.6051 | (0.14751) |
| Week 32 (OP/MA) | 46 | 2.6539 | 0.14168 | 2.6584 | 2.371 | 3.067 | 2.6088 | (0.14312) |
| Week 44 (OP/MA) | 29 | 2.7083 | 0.16773 | 2.7184 | 2.385 | 3.082 | 2.6012 | (0.16301) |
| End Point (OP/MA) | 122 | 2.6338 | 0.14625 | 2.6174 | 2.364 | 3.068 | 2.6009 | (0.15025) |

[a] Speed of performance ($\log_{10}$ ms), lower score = better performance
[b] Number of errors, lower score = better performance
[c] Accuracy of performance, higher score = better performance
[d] Higher change from baseline is better performance

TABLE 137

Cognitive Domains: Means and Mean Changes from Baseline (IND) Over Time by Age; Open-label Induction and Optimization/Maintenance Phases (Study ESKETINTRD3004: All Enrolled Analysis Set) Age Group: ≥65 years

| | | | Change from Baseline[d] | | | |
|---|---|---|---|---|---|---|
| N | Mean | SE | SD | Med | Min | Max |
| Detection - Attention (simple reaction time)[a] | | | | | | |
| Esketamine | | | | | | |

| | N | Mean | SE | SD | Med | Min | Max |
|---|---|---|---|---|---|---|---|
| Baseline (IND) | | | | | | | |
| Day 28 (IND) | 120 | 0.0076 | 0.01267 | 0.13876 | 0.0071 | −0.438 | 0.431 |
| Week 20 (OP/MA) | 72 | −0.0258 | 0.01684 | 0.14292 | −0.0152 | −0.374 | 0.496 |
| Week 32 (OP/MA) | 45 | −0.0427 | 0.02635 | 0.17679 | −0.0496 | −0.529 | 0.449 |
| Week 44 (OP/MA) | 28 | −0.1032 | 0.03067 | 0.16230 | −0.0914 | −0.544 | 0.129 |
| End Point (OP/MA) | 119 | −0.0313 | 0.01182 | 0.12889 | −0.0379 | −0.352 | 0.384 |

[a] Speed of performance ($\log_{10}$ ms), lower score = better performance
[b] Number of errors, lower score = better performance
[c] Accuracy of performance, higher score = better performance
[d] Higher change from baseline is better performance Tables 138-141 display summaries of mean and mean changes over time for Identification—Attention (choice reaction time) for subjects <65 years and ≥65 years of age, respectively. See, also, FIG. 59.

TABLE 138

Cognitive Domains: Means and Mean Changes from Baseline (IND) Over Time by Age; Open-label Induction and Optimization/Maintenance Phases (Study ESKETINTRD3004: All Enrolled Analysis Set) Age Group: <65 years

| | N | Mean | SD | Med | Min | Max | Base Mean | (SD) |
|---|---|---|---|---|---|---|---|---|
| | | Identification- Attention (choice reaction time)$^a$ Esketamine | | | | | | |
| Baseline (IND) | 616 | 2.7506 | 0.11272 | 2.7386 | 2.506 | 3.167 | | |
| Day 28 (IND) | 515 | 2.7381 | 0.09859 | 2.7332 | 2.479 | 3.101 | 2.7504 | (0.11222) |
| Week 20 (OP/MA) | 361 | 2.7438 | 0.09864 | 2.7437 | 2.510 | 3.068 | 2.7466 | (0.10801) |
| Week 32 (OP/MA) | 252 | 2.7476 | 0.10479 | 2.7320 | 2.509 | 3.149 | 2.7539 | (0.11351) |
| Week 44 (OP/MA) | 170 | 2.7471 | 0.11037 | 2.7289 | 2.532 | 3.156 | 2.7508 | (0.11555) |
| End Point (OP/MA) | 449 | 2.7557 | 0.09838 | 2.7510 | 2.482 | 3.100 | 2.7506 | (0.11105) |

$^a$Speed of performance (log$_{10}$ ms), lower score = better performance
$^b$Number of errors, lower score = better performance
$^c$Accuracy of performance, higher score = better performance
$^d$Higher change from baseline is better performance

TABLE 139

Cognitive Domains: Means and Mean Changes from Baseline (IND) Over Time by Age; Open-label Induction and Optimization/Maintenance Phases (Study ESKETINTRD3004: All Enrolled Analysis Set) Age Group: <65 years

| | Change from Baseline$^d$ | | | | | |
|---|---|---|---|---|---|---|
| | N | Mean | SE | SD | Med | Min | Max |
| | Identification- Attention (choice reaction time)$^a$ Esketamine | | | | | | |
| Baseline (IND) | | | | | | | |
| Day 28 (IND) | 509 | 0.0125 | 0.00389 | 0.08785 | 0.0102 | −0.297 | 0.463 |
| Week 20 (OP/MA) | 358 | 0.0026 | 0.00475 | 0.08983 | 0.0004 | −0.372 | 0.358 |
| Week 32 (OP/MA) | 251 | 0.0062 | 0.00684 | 0.10842 | 0.0084 | −0.496 | 0.379 |
| Week 44 (OP/MA) | 169 | 0.0034 | 0.00833 | 0.10828 | −0.0034 | −0.392 | 0.383 |
| End Point (OP/MA) | 442 | −0.0050 | 0.00485 | 0.10198 | −0.0084 | −0.370 | 0.441 |

$^a$Speed of performance (log$_{10}$ ms), lower score = better performance
$^b$Number of errors, lower score = better performance
$^c$Accuracy of performance, higher score = better performance
$^d$Higher change from baseline is better performance

TABLE 140

Cognitive Domains: Means and Mean Changes from Baseline (IND) Over Time by Age; Open-label Induction and Optimization/Maintenance Phases (Study ESKETINTRD3004: All Enrolled Analysis Set); Age Group: ≥65 years

| | N | Mean | SD | Med | Min | Max | Base Mean | (SD) |
|---|---|---|---|---|---|---|---|---|
| | | Identification- Attention (choice reaction time)$^a$ Esketamine | | | | | | |
| Baseline (IND) | 168 | 2.7498 | 0.09465 | 2.7302 | 2.564 | 3.085 | | |
| Day 28 (IND) | 122 | 2.7505 | 0.09061 | 2.7295 | 2.609 | 3.111 | 2.7491 | (0.08531) |
| Week 20 (OP/MA) | 74 | 2.7570 | 0.08077 | 2.7544 | 2.606 | 3.029 | 2.7416 | (0.08251) |
| Week 32 (OP/MA) | 47 | 2.7683 | 0.10237 | 2.7551 | 2.618 | 3.131 | 2.7453 | (0.08426) |
| Week 44 (OP/MA) | 29 | 2.7917 | 0.12868 | 2.7583 | 2.567 | 3.151 | 2.7294 | (0.08842) |
| End Point (OP/MA) | 122 | 2.7673 | 0.09180 | 2.7675 | 2.583 | 3.043 | 2.7455 | (0.09022) |

$^a$Speed of performance (log$_{10}$ ms), lower score = better performance
$^b$Number of errors, lower score = better performance
$^c$Accuracy of performance, higher score = better performance
$^d$Higher change from baseline is better performance

TABLE 141

Cognitive Domains: Means and Mean Changes from Baseline (IND) Over Time by Age; Open-label Induction and Optimization/Maintenance Phases (Study ESKETINTRD3004: All Enrolled Analysis Set); Age Group: ≥65 years

| | \multicolumn{7}{c}{Cange from Baseline$^d$} | | | | | | |
|---|---|---|---|---|---|---|---|
| | N | Mean | SE | SD | Med | Min | Max |
| | \multicolumn{7}{c}{Identification- Attention (choice reaction time)$^a$} | | | | | | |
| | \multicolumn{7}{c}{Esketamine} | | | | | | |
| Baseline (IND) | | | | | | | |
| Day 28 (IND) | 121 | −0.0001 | 0.00743 | 0.08175 | −0.0014 | −0.332 | 0.307 |
| Week 20 (OP/MA) | 72 | −0.0136 | 0.00918 | 0.07794 | −0.0058 | −0.294 | 0.252 |
| Week 32 (OP/MA) | 46 | −0.0210 | 0.01483 | 0.10060 | −0.0226 | −0.415 | 0.257 |
| Week 44 (OP/MA) | 28 | −0.0587 | 0.01955 | 0.10346 | −0.0391 | −0.435 | 0.122 |
| End Point (OP/MA) | 119 | −0.0203 | 0.00661 | 0.07206 | −0.0216 | −0.209 | 0.241 |

$^a$Speed of performance ($\log_{10}$ ms), lower score = better performance
$^b$ Number of errors, lower score = better performance
$^c$ Accuracy of performance, higher score = better performance
$^d$Higher change from baseline is better performance There were 2 subjects who experienced 'memory impairment' in the IND phase and 2 subjects in the OP/MA phase. Two subjects experienced treatment-emergent 'cognitive disorder' during the IND phase. No subjects experienced treatment-emergent 'cognitive disorder' during the OP/MIA phase.

Overall, predose cognitive assessments showed general preservation or improvement in cognition from baseline in subjects <65 years of age. Cognitive data in subjects a 65 years old also showed preservation or improvement in most of the domains tested, but relatively small performance decrements in two measures of attention were observed. The subject level data underlying these apparent changes are being further evaluated to assess the extent to which they may be clinically meaningful in some individuals.

Summary of All Adverse Events

An overall summary of all treatment-emergent adverse events (TEAEs) during the IND and OP/MA phases is presented in Table 142. Overall, 90.1% of subjects experienced at least one TEAE in the IND and OP/MA phases.

TABLE 142

Overall Summary of Treatment-emergent Adverse Events; Induction and Optimization/Maintenance Phases (Study ESKETINTRD3004: All Enrolled Analysis Set)

| | Intranasal Esk + Oral AD (N = 802) |
|---|---|
| TEAE | 723 (90.1%) |
| TEAE possibly related to intranasal drug $^a$ | 633 (78.9%) |
| TEAE possibly related to oral antidepressant $^a$ | 241 (30.0%) |
| TEAE leading to death | 2 (0.2%) |
| 1 or more serious TEAE | 55 (6.9%) |
| TEAE leading to intranasal drug withdrawn $^b$ | 76 (9.5%) |
| TEAE leading to oral antidepressant withdrawn $^b$ | 33 (4.1%) |

$^a$ Study drug relationships of possible, probable, and very likely are included in this category.
$^b$ An adverse event that started in the induction or optimization/maintenance phase and resulted in discontinuation in the follow-up phase is counted as treatment-emergent in this table.
Incidence is based on the number of subjects experiencing at least one adverse event, not the number of events.
Adverse events are coded using MedDRA version 20.0.

Treatment-emergent adverse events occurring during the IND and OP/MA phases (>5% of subjects) are summarized for the all enrolled analysis set in Tables 143A and 143B. The most common (≥10%) TEAEs during the IND and OP/MA phases were dizziness (33.0%), nausea (25.1%), headache (24.9%), dissociation (22.4%), somnolence (16.7%), dysgeusia and hypoesthesia (11.8% each), vomiting and vertigo (10.8% each), and viral upper respiratory tract infection (10.2%). The incidence of nausea was highest on Day 1 dosing (10.7%) and decreased on subsequent dosing days ranging from 0.0 to 4.4%. The incidence of vomiting was highest on Day 1 dosing (3.3%) and decreased on subsequent dosing days ranging from 0.0% to 1.9%.

TABLE 143A

Adverse Events in at Least 5% of Subjects; Induction and Optimization/Maintenance Phases (Study ESKETINTRD3004: All Enrolled Analysis Set)

| | Intranasal Esk + Oral AD (N = 802) |
|---|---|
| Total no. subjects with AE | 723 (90.1%) |
| Nervous system disorders | 528 (65.8%) |
| Dizziness | 265 (33.0%) |
| Headache | 200 (24.9%) |
| Somnolence | 134 (16.7%) |
| Dysgeusia | 95 (11.8%) |
| Hypoesthesia | 95 (11.8%) |
| Sedation | 71 (8.9%) |
| Dizziness postural | 67 (8.4%) |
| Paresthesia | 58 (7.2%) |
| Gastrointestinal disorders | 375 (46.8%) |
| Nausea | 201 (25.1%) |
| Vomiting | 87 (10.8%) |
| Hypoesthesia oral | 73 (9.1%) |
| Diarrhea | 60 (7.5%) |
| Psychiatric disorders | 368 (45.9%) |
| Dissociation | 180 (22.4%) |
| Anxiety | 72 (9.0%) |
| Insomnia | 64 (8.0%) |
| Infections and infestations | 279 (34.8%) |
| Viral upper respiratory tract infection | 82 (10.2%) |
| Urinary tract infection | 65 (8.1%) |
| Influenza | 43 (5.4%) |
| General disorders and administration site conditions | 201 (25.1%) |
| Feeling abnormal | 67 (8.4%) |
| Fatigue | 63 (7.9%) |
| Musculoskeletal and connective tissue disorders | 156 (19.5%) |
| Back pain | 41 (5.1%) |
| Investigations | 140 (17.5%) |
| Blood pressure increased | 73 (9.1%) |
| Ear and labyrinth disorders | 125 (15.6%) |
| Vertigo | 87 (10.8%) |
| Eye disorders | 106 (13.2%) |
| Vision blurred | 59 (7.4%) |

Incidence is based on the number of subjects experiencing at least one adverse event, not the number of events.
Adverse events are coded using MedDRA version 20.0.

TABLE 143B

Treatment-emergent adverse events(full analysis sets [IND and OP/MAINT] and all enrolled analysis set)

| | 4-week IND phase (N = 779) | 48-week OP/ MAINT phase (N = 603) | IND and OP/ MAINT phases (N = 802) |
|---|---|---|---|
| | n (%) | n (%) | n (%) |
| Patients with ≥1 TEAEs | 653 (83.8) | 516 (85.6) | 723 (90.1) |
| Patients with ≥1 SAEs | 17 (2.2) | 38 (6.3) | 55 (6.9) |
| TEAEs leading to discontinuation of intranasal spray medication | 53 (6.8) | 23 (3.8) | 76 (9.5) |
| TEAEs leading to discontinuation of oral AD | 20 (2.6) | 14 (2.3) | 33 (4.1) |
| TEAEs leading to death | 0 | 2 (0.3) | 2 (0.2) |
| Most common TEAEs (≥10% patients in the combined phases group) | | | |
| Dizziness | 228 (29.3) | 135 (22.4) | 264 (32.9) |
| Dissociation | 180 (23.1) | 112 (18.6) | 220 (27.4) |
| Nausea | 157 (20.2) | 84 (13.9) | 201 (25.1) |
| Headache | 137 (17.6) | 114 (18.9) | 200 (24.9) |
| Somnolence | 94 (12.1) | 85 (14.1) | 134 (16.7) |
| Dysgeusia | 77 (9.9) | 54 (9.0) | 95 (11.8) |
| Hypoesthesia | 79 (10.1) | 40 (6.6) | 95 (11.8) |
| Vertigo | 68 (8.7) | 43 (7.1) | 88 (11.0) |
| Vomiting | 56 (7.2) | 45 (7.5) | 87 (10.8) |
| Viral upper respiratory tract infection | 19 (2.4) | 70 (11.6) | 82 (10.2) |
| Increased blood pressure-related TEAEs | | | |
| Increased blood pressure | 53 (6.8) | 46 (7.6) | 75 (9.4) |
| Hypertension | 13 (1.7) | 13 (2.2) | 25 (3.1) |
| Increased heart rate-related TEAEs | | | |
| Tachycardia | 6 (0.8) | 8 (1.3) | 13 (1.6) |
| Cystitis-related TEAEs | | | |
| Cystitis | 4 (0.5) | 1 (0.2) | 5 (0.6) |

FIGS. 60-62 show the level of impairment for the EQ-5D-5L by measuring anxiety/depression, usual activities, and pain/discomfort, respectively. Scores ranged from levels 1-5: 1 (none), s (slight), 3 (moderate), 4 (Severe), and 5 (Extreme).

Serious Adverse Events

Two deaths were reported during the OP/MA phase of the study.

One 60-year old male with a medical history of hypertension and vein surgery, experienced death due to acute cardiac and respiratory failure on Day 113 of the treatment with esketamine which were considered doubtfully related to esketamine. This subject did not experience any prior cardiac adverse events during treatment with esketamine and oral AD and had normal blood pressures during the study. The subject had been receiving esketamine 56 mg, with the last dose administered 5 days prior to the death.

One 55-year old female died as a result of suicide on Day 188 of the study. This subject manifested remission of depressive symptoms as evidenced by MADRS score of 7 and 9 measured at the last 2 clinic visits, 13 days and 6 days prior to the event, respectively. The event was considered not related to esketamine. The subject had been receiving esketamine 84 mg, with the last dose administered 13 days prior to the death.

A total of 55 (6.9%) subjects experienced a total of 68 serious treatment-emergent adverse event during the IND and OP/MA phases for the all enrolled analysis set. Four subjects had serious TEAE assessed as related (possibly, probably or very likely) to intranasal esketamine by the investigators: delirium, anxiety and delusion, suicidal ideation and suicidal attempt. The following SAEs led to discontinuation of esketamine treatment: 5 cases of suicidal ideation; 2 cases each of suicidal attempts, depression, anxiety, and toxicity to various agents (listed as "zolpidem and oxazepam intoxication" in one participant, and; "drug intoxication" in the other); and 1 event of each of the following: alcohol abuse, depression suicidal (depression with suicidal thoughts), delusions, delirium and hepatitis B.

The SAE of delirium was reported on Day 127 in a subject who remained on alcohol abuse prevention treatment throughout the study (though had no current abuse), within minutes after dosing with 56 mg of esketamine. The SAE was assessed as very likely related to ESK, and not related to the oral AD. During the event the subject had a period of agitation with random limb movements followed by 10 min period of non-responsiveness to stimuli. This subject tolerated esketamine well prior to this event. No drug or alcohol test was done during that visit. Subject was hospitalized, withdrawn from the study and recovered from the event in 18 days. CT scan, MRI and EEG were all normal. The exact cause of delirium remains unknown, the use of other substances cannot be excluded.

The SAEs of anxiety and delusions were reported prior to dosing with ESK on Day together with SAE of alcohol abuse (which was assessed as not related to esketamine in the opinion of the Investigator). This subject had no history of psychosis or delusions and negative alcohol screening tests. Subsequently, the subject disclosed excessive alcohol consumption. Subject was hospitalized and withdrawn from the study.

The SAEs related to renal function included pyelonephritis, acute pyelonephritis and 1 case of tubulointerstitial nephritis. All these SAEs resolved after appropriate treatment without sequalae and subjects continued in the study.

Three subjects had a serious TEAEs that were considered related to oral antidepressant by the investigators: gastroenteritis, colitis microscopic, and suicidal ideation. See, Tables 144A and 144B.

TABLE 144A

Treatment-emergent Serious Adverse Events; Induction and Optimization/Maintenance Phases (Study ESKETINTRD3004: All Enrolled Analysis Set)

|  | Intranasal Esk + Oral AD (N = 802) |
|---|---|
| Total no. subjects with a serious TEAE | 55 (6.9%) |
| Psychiatric disorders | 26 (3.2%) |
| Depression | 8 (1.0%) |
| Suicidal ideation | 6 (0.7%) |
| Suicide attempt | 6 (0.7%) |
| Anxiety | 2 (0.2%) |
| Alcohol abuse | 1 (0.1%) |
| Completed suicide | 1 (0.1%) |
| Delirium | 1 (0.1%) |
| Delusion | 1 (0.1%) |
| Depression suicidal | 1 (0.1%) |
| Intentional self-injury | 1 (0.1%) |
| Major depression | 1 (0.1%) |
| Infections and infestations | 8 (1.0%) |
| Gastroenteritis | 2 (0.2%) |
| Bronchitis | 1 (0.1%) |
| Dengue fever | 1 (0.1%) |
| Hepatitis B | 1 (0.1%) |
| Pyelonephritis | 1 (0.1%) |
| Pyelonephritis acute | 1 (0.1%) |
| Urinary tract infection | 1 (0.1%) |
| Gastrointestinal disorders | 6 (0.7%) |
| Anal incontinence | 1 (0.1%) |
| Colitis microscopic | 1 (0.1%) |
| Hemorrhoids | 1 (0.1%) |
| Large intestinal obstruction | 1 (0.1%) |
| Oesophageal ulcer | 1 (0.1%) |
| Pancreatitis | 1 (0.1%) |
| Injury, poisoning and procedural complications | 6 (0.7%) |
| Toxicity to various agents | 2 (0.2%) |
| Costochondral separation | 1 (0.1%) |
| Fibula fracture | 1 (0.1%) |
| Foot fracture | 1 (0.1%) |
| Poisoning | 1 (0.1%) |
| Musculoskeletal and connective tissue disorders | 4 (0.5%) |
| Arthralgia | 1 (0.1%) |
| Back pain | 1 (0.1%) |
| Osteoarthritis | 1 (0.1%) |
| Synovial cyst | 1 (0.1%) |
| Nervous system disorders | 2 (0.2%) |
| Headache | 1 (0.1%) |
| Psychomotor hyperactivity | 1 (0.1%) |
| Renal and urinary disorders | 2 (0.2%) |
| Stress urinary incontinence | 1 (0.1%) |
| Tubulointerstitial nephritis | 1 (0.1%) |
| Vesical fistula | 1 (0.1%) |
| Cardiac disorders | 1 (0.1%) |
| Cardiac failure acute | 1 (0.1%) |
| General disorders and administration site conditions | 1 (0.1%) |
| Pyrexia | 1 (0.1%) |
| Investigations | 1 (0.1%) |
| Transaminases increased | 1 (0.1%) |
| Neoplasms benign, malignant and unspecified (incl cysts and polyps) | 1 (0.1%) |
| Ovarian cancer | 1 (0.1%) |
| Pregnancy, puerperium and perinatal conditions | 1 (0.1%) |
| Abortion spontaneous | 1 (0.1%) |
| Reproductive system and breast disorders | 1 (0.1%) |
| Menorrhagia | 1 (0.1%) |
| Respiratory, thoracic and mediastinal disorders | 1 (0.1%) |
| Acute respiratory failure | 1 (0.1%) |

Incidence is based on the number of subjects experiencing at least one adverse event, not the number of events.
Adverse events are coded using MedDRA version 20.0.

TABLE 144B

Most Common Serious Adverse Events in at least 2 patients in the combined phases (full analysis sets [IND and OP/MAINT] and all enrolled analysis set)

| Most common SAEs (≥2 patients) | IND phase (N = 779) n (%) | OP/MAINT phase (N = 604) n (%) | IND and OP/MAINT phases (N = 802) n (%) |
|---|---|---|---|
| Depression | 5 (0.6) | 3 (0.5) | 8 (1.0) |
| Suicidal ideation | 2 (0.3) | 4 (0.7) | 6 (0.7) |
| Suicide attempt | 4 (0.5) | 2 (0.3) | 6 (0.7) |
| Anxiety | 2 (0.3) | 0 | 2 (0.2) |
| Gastroenteritis | 0 | 2 (0.3) | |

The event of suicidal ideation (moderate intensity) started on Day 207 of the study and led to discontinuation. The same subject was also reported with akathisia on Day 206 (mild). Subject recovered from suicidal ideation within 30 days.

Adverse Events Leading to Study Drug Withdrawal

The number of treatment-emergent adverse events (TEAEs) leading to discontinuation of study treatment was low for of this study and TRD patient population. Most of the discontinuations due to AE'S during the IND phase were after the initial ESK treatment sessions.

There were 76 (9.5%) subjects who discontinued the IND or OP/MA phase intranasal study medication due to treatment-emergent adverse events (Tables 145A and 145B). A total of 53/779 (6.8%) subjects discontinued intranasal study medication in the IND phase and 23/603 (3.8%) subjects discontinued intranasal study medication in the OP/MA phase due to treatment-emergent adverse events. This is much lower than other drugs used for TRD, e.g. 23.7% rate in a quetiapine 52-week safety study in MDD/TRD subjects (Berman et al., 2011) and a 24.5% over 76 weeks treated with Symbyax in MDD/TRD subjects (Corya, Long-term antidepressant efficacy and safety of olanzapine/fluoxetine combination: a 76-week open-label study. Journal of Clinical Psychiatry: 64 (11) p. 1349-56. 2003).

The most common AEs leading to discontinuation of intranasal study medication were anxiety (1.1%), suicidal ideation (0.9%), depression, dizziness, and blood pressure increased (0.7% each), dissociation (0.6%), and muscular weakness (0.5%). These subjects could continue the oral AD in the follow-up phase if applicable. There were 33 (4.1%) subjects who discontinued the IND or OP/MA phase oral antidepressant study medication due to treatment-emergent adverse events (Table 146). A total of 20/779 (2.6%) subjects discontinued oral antidepressant in the IND phase and 14/603 (2.3%) discontinued oral antidepressant study medication in the OP/MA phase due to treatment-emergent adverse events. One subject discontinued one oral antidepressant during the IND phase and switched to another oral antidepressant. The most common AEs leading to discontinuation of oral antidepressant study medication were anxiety (0.9%) and suicidal ideation (0.6%). Twenty-six subjects discontinued the IND or OP/MA phase due to adverse events related to both intranasal and oral AD medications and are included in both tables.

One subject was diagnosed with the SAEs of severe hepatitis B and moderate ovarian cancer were considered not related to ESK by the investigator). This subject had clinically significant elevations in the liver function tests, suspected initially to be a manifestation of drug-induced liver injury. This subject however responded with laboratory and clinical improvement to initiated antiviral treatment which, together with positive hepatitis serology, confirmed the diagnosis of hepatitis B.

Among the 76 subjects with TEAEs leading to discontinuation of intranasal esketamine during the IND or OP/MA phases, 51 subjects had an AE that was considered related (possibly, probably, or very likely) to esketamine. Among the 33 subjects with TEAEs leading to discontinuation of oral AD during the IND or OP/MA phases, 14 subjects had an AE that was considered related to oral AD.

Nine subjects discontinued due to blood pressure increase or hypertension. Six of these subjects discontinued early in the IND phase (on Day 1, 2, 4, 4, 8 and 9 of the study). Four of these subjects met withdrawal criteria for elevated blood pressure (SBP≥200 mm Hg and/or DBP; 120 mm Hg for subjects <65 years old and SBP≥190 and DBP≥110).

A total of 7 subjects had suicidal ideation and 2 attempted suicide during the IND or OP/MA phases that led to study drug withdrawal of esketamine. In one suicide attempt, a 46-year old female subject on Day 44 overdosed on medication and was intoxicated with carbon monoxide. This SAE was assessed as life-threatening, probably related to esketamine and not related to oral antidepressant. The subject was a responder, however had chronic and acute life stressors. Subject recovered from the event within 11 days.

TABLE 145A

Treatment-emergent Adverse Events Leading to Discontinuation of Intranasal Study Medication; Induction and Optimization/Maintenance Phases (Study ESKETINTRD3004: All Enrolled Analysis Set)

| | Intranasal Esk + Oral AD (N = 802) |
|---|---|
| Total no. subjects with TEAE leading to discontinuation [a] | 76 (9.5%) |
| Psychiatric disorders | 32 (4.0%) |
| Anxiety | 9 (1.1%) |
| Suicidal ideation | 7 (0.9%) |
| Depression | 6 (0.7%) |
| Dissociation | 5 (0.6%) |
| Suicide attempt | 2 (0.2%) |
| Alcohol abuse | 1 (0.1%) |
| Delirium | 1 (0.1%) |
| Delusion | 1 (0.1%) |
| Depression suicidal | 1 (0.1%) |
| Hallucination, auditory | 1 (0.1%) |
| Major depression | 1 (0.1%) |
| Panic attack | 1 (0.1%) |
| Paranoia | 1 (0.1%) |
| Psychogenic tremor | 1 (0.1%) |
| Nervous system disorders | 13 (1.6%) |
| Dizziness | 6 (0.7%) |
| Headache | 2 (0.2%) |
| Sedation | 2 (0.2%) |
| Somnolence | 2 (0.2%) |
| Cognitive disorder | 1 (0.1%) |
| Depressed level of consciousness | 1 (0.1%) |
| Generalized tonic-clonic seizure | 1 (0.1%) |
| Psychomotor hyperactivity | 1 (0.1%) |
| Reduced facial expression | 1 (0.1%) |
| Investigations | 7 (0.9%) |
| Blood pressure increased | 6 (0.7%) |
| Electrocardiogram QT prolonged | 1 (0.1%) |
| Musculoskeletal and connective tissue disorders | 7 (0.9%) |
| Muscular weakness | 4 (0.5%) |
| Muscle rigidity | 1 (0.1%) |
| Myalgia | 1 (0.1%) |
| Pain in extremity | 1 (0.1%) |
| Gastrointestinal disorders | 6 (0.7%) |
| Vomiting | 3 (0.4%) |
| Nausea | 2 (0.2%) |
| Abdominal discomfort | 1 (0.1%) |
| Abdominal pain | 1 (0.1%) |
| General disorders and administration site conditions | 4 (0.5%) |
| Asthenia | 1 (0.1%) |
| Feeling drunk | 1 (0.1%) |
| Malaise | 1 (0.1%) |
| Therapeutic response changed | 1 (0.1%) |
| Cardiac disorders | 3 (0.4%) |
| Angina pectoris | 1 (0.1%) |
| Arrhythmia | 1 (0.1%) |
| Coronary artery disease | 1 (0.1%) |
| Ventricular arrhythmia | 1 (0.1%) |
| Eye disorders | 3 (0.4%) |
| Blepharitis | 1 (0.1%) |
| Vision blurred | 1 (0.1%) |
| Vitreous detachment | 1 (0.1%) |
| Injury, poisoning and procedural complications | 3 (0.4%) |
| Toxicity to various agents | 2 (0.2%) |
| Fall | 1 (0.1%) |
| Vascular disorders | 3 (0.4%) |
| Hypertension | 3 (0.4%) |
| Ear and labyrinth disorders | 2 (0.2%) |
| Vertigo | 2 (0.2%) |
| Deafness bilateral | 1 (0.1%) |
| Metabolism and nutrition disorders | 2 (0.2%) |
| Failure to thrive | 1 (0.1%) |
| Hyperglycemia | 1 (0.1%) |
| Infections and infestations | 1 (0.1%) |
| Hepatitis B | 1 (0.1%) |
| Renal and urinary disorders | 1 (0.1%) |
| Urinary incontinence | 1 (0.1%) |
| Respiratory, thoracic and mediastinal disorders | 1 (0.1%) |
| Asthma | 1 (0.1%) |
| Oropharyngeal pain | 1 (0.1%) |
| Skin and subcutaneous tissue disorders | 1 (0.1%) |
| Eczema | 1 (0.1%) |

[a] An adverse event that started in the induction or optimization/maintenance phases and resulted in discontinuation in the follow-up phase is counted as treatment-emergent in this table.
Incidence is based on the number of subjects experiencing at least one adverse event, not the number of events.
Adverse events are coded using MedDRA version 20.0.

TABLE 145B

Treatment-emergent Adverse Events Leading to Discontinuation of Intranasal Study Medication in at least 2 Patients in the Combined Phases (IND and OP/MAINT and All Enrolled Analysis Set)

| Most common TEAEs (≥2 patients) | IND phase (N = 779) n (%) | OP/MAINT phase (N = 603) n (%) | IND and OP/ MAINT phases (N = 802) n (%) |
|---|---|---|---|
| Anxiety | 9 (1.2) | 0 | 9 (1.1%) |
| Suicidal ideation | 3 (0.4) | 4 (0.7) | 7 (0.9%) |
| Depression | 3 (0.4) | 3 (0.5) | 6 (0.7%) |
| Dizziness | 6 (0.8) | 0 | 6 (0.7%) |
| Blood pressure increased | 4 (0.5) | 2 (0.3) | 6 (0.7%) |
| Dissociation | 5 (0.6) | 0 | 5 (0.6%) |
| Muscular weakness | 4 (0.5) | 0 | 4 (0.5%) |
| Vomiting | 3 (0.4) | 0 | 3 (0.4%) |
| Hypertension | 2 (0.3) | 1 (0.2) | 3 (0.4%) |
| Suicide attempt | 1 (0.1) | 1 (0.2) | 2 (0.2%) |
| Headache | 2 (0.3) | 0 | 2 (0.2%) |
| Sedation | 2 (0.3) | 0 | 2 (0.2%) |
| Somnolence | 2 (0.3) | 0 | 2 (0.2%) |
| Nausea | 2 (0.3) | 0 | 2 (0.2%) |
| Vertigo | 1 (0.1) | 1 (0.2) | 2 (0.2%) |

TABLE 146

Treatment-emergent Adverse Events Leading to Discontinuation of Oral Antidepressant; Induction or Optimization/Maintenance Phases (Study ESKETINTRD3004: All Enrolled Analysis Set)

| | Intranasal Esk + Oral AD (N = 802) |
|---|---|
| Total no. subjects with TEAE leading to discontinuation [a] | 33 (4.1%) |
| Psychiatric disorders | 20 (2.5%) |
| Anxiety | 7 (0.9%) |
| Suicidal ideation | 5 (0.6%) |
| Depression | 3 (0.4%) |
| Suicide attempt | 2 (0.2%) |
| Alcohol abuse | 1 (0.1%) |
| Anorgasmia | 1 (0.1%) |
| Delirium | 1 (0.1%) |
| Delusion | 1 (0.1%) |
| Dissociation | 1 (0.1%) |
| Insomnia | 1 (0.1%) |
| Gastrointestinal disorders | 5 (0.6%) |
| Abdominal discomfort | 1 (0.1%) |
| Abdominal pain | 1 (0.1%) |
| Colitis microscopic | 1 (0.1%) |
| Dry mouth | 1 (0.1%) |
| Nausea | 1 (0.1%) |
| Nervous system disorders | 3 (0.4%) |
| Dizziness | 1 (0.1%) |
| Headache | 1 (0.1%) |
| Reduced facial expression | 1 (0.1%) |
| Somnolence | 1 (0.1%) |
| Injury, poisoning and procedural complications | 2 (0.2%) |
| Fall | 1 (0.1%) |
| Toxicity to various agents | 1 (0.1%) |
| Musculoskeletal and connective tissue disorders | 2 (0.2%) |
| Muscle rigidity | 1 (0.1%) |
| Myalgia | 1 (0.1%) |
| Vascular disorders | 2 (0.2%) |
| Hot flush | 1 (0.1%) |
| Hypertension | 1 (0.1%) |
| Cardiac disorders | 1 (0.1%) |
| Ventricular arrhythmia | 1 (0.1%) |
| Ear and labyrinth disorders | 1 (0.1%) |
| Deafness bilateral | 1 (0.1%) |
| Vertigo | 1 (0.1%) |
| General disorders and administration site conditions | 1 (0.1%) |
| Therapeutic response changed | 1 (0.1%) |
| Infections and infestations | 1 (0.1%) |
| Hepatitis B | 1 (0.1%) |
| Investigations | 1 (0.1%) |
| Blood pressure increased | 1 (0.1%) |
| Metabolism and nutrition disorders | 1 (0.1%) |
| Failure to thrive | 1 (0.1%) |
| Renal and urinary disorders | 1 (0.1%) |
| Urinary incontinence | 1 (0.1%) |
| Reproductive system and breast disorders | 1 (0.1%) |
| Erectile dysfunction | 1 (0.1%) |
| Respiratory, thoracic and mediastinal disorders | 1 (0.1%) |
| Asthma | 1 (0.1%) |
| Oropharyngeal pain | 1 (0.1%) |

[a] An adverse event that started in the induction or optimization/maintenance phases and resulted in discontinuation in the follow-up phase is counted as treatment-emergent in this table.
Incidence is based on the number of subjects experiencing at least one adverse event, not the number of events.
Adverse events are coded using MedDRA version 20.0.

Cystitis, Urinary Tract Infections and Other Renal and Urinary Disorders

There were no cases of interstitial cystitis or ulcerative cystitis. Five (0.6%) subjects experienced a treatment-emergent cystitis during the IND and OP/MA phases. Three subjects experienced mild cystitis with durations of 2, 4, and 9 days and one subject experienced moderate cystitis for 7 days during the IND phase. One subject experienced mild cystitis for 7 days in the OP/MA phase. There were no dose changes or discontinuations to either intranasal esketamine or oral antidepressant for these events. See, Table 147.

TABLE 147

Treatment-emergent Cystitis Adverse Events; Induction and Optimization/Maintenances Phase (Study ESKETINTRD3004: All Enrolled Analysis Set)

| | Intranasal Esk + Oral AD (N = 802) |
|---|---|
| Total no. subjects with TEAE | 5 (0.6%) |
| Infections and infestations | 5 (0.6%) |
| Cystitis | 5 (0.6%) |

Incidence is based on the number of subjects experiencing at least one adverse event, not the number of events.
Adverse events are coded using MedDRA version 20.0.

A total of 65 subjects (8.1%) experienced urinary tract infections and 84 subjects (10.5%) experienced renal and urinary disorders during the IND and OP/MA phases.

The TEAEs of cystitis were mostly of mild severity, mostly reported in the IND phase (Days 13, 15, 20, 40 and 78), transient and self-limiting, pointing towards an infectious etiology of UTI cases. Four subjects reported urinary incontinence assessed as ESK-related (i.e. possibly, probably or very likely related)

Drug Abuse, Dependence and Withdrawal Adverse Events

Drug abuse, dependence and withdrawal adverse events during the IND and OP/MA phases are presented in Table 148. A total of 423 (52.7%) subjects experienced drug abuse, dependence and withdrawal during the IND and OP/MA phases.

TABLE 148

Treatment-emergent Drug Abuse, Dependence, and Withdrawal Adverse Events; Induction and Optimization/Maintenance Phases (Study ESKETINTRD3004: All Enrolled Analysis Set)

| | Intranasal Esk + Oral AD (N = 802) |
|---|---|
| Total no. subjects with TEAE | 423 (52.7%) |
| Nervous system disorders | 320 (39.9%) |
| Dizziness | 265 (33.0%) |
| Somnolence | 134 (16.7%) |
| Mental impairment | 4 (0.5%) |
| Psychomotor hyperactivity | 2 (0.2%) |
| Psychiatric disorders | 209 (26.1%) |
| Dissociation | 180 (22.4%) |
| Euphoric mood | 24 (3.0%) |
| Confusional state | 14 (1.7%) |
| Hallucination, visual | 10 (1.2%) |
| Disorientation | 6 (0.7%) |
| Thinking abnormal | 5 (0.6%) |
| Inappropriate affect | 4 (0.5%) |
| Hallucination, auditory | 3 (0.4%) |
| Hallucination | 2 (0.2%) |
| General disorders and administration site conditions | 77 (9.6%) |
| Feeling abnormal | 67 (8.4%) |
| Feeling drunk | 12 (1.5%) |
| Feeling of relaxation | 5 (0.6%) |

Incidence is based on the number of subjects experiencing at least one adverse event, not the number of events;
Adverse events are coded using MedDRA version 20.0.

Vital Signs and Body Weight

FIGS. 63 and 64 present means for blood pressure over time during the IND and OP/MA phases.

Transient blood pressure increases for the esketamine+ oral AD group peaked at 40 minutes past dose with the maximum mean increases (across all dosing days within the respective phase) in systolic BP being 9.6 and 8.6 during the IND and OP/MA phases, respectively. The maximum mean increases (across all dosing days within the respective phase) in diastolic BP were 5.6 and 5.2 in the IND and OP/MA phases, respectively.

A total of 18 subjects experienced systolic blood pressure ≥180 and 18 experienced diastolic blood pressure ≥110 at any time during the IND and OP/MA phases.

Six subjects discontinued intranasal esketamine due to increased blood pressure and 1 subject discontinued oral AD due to increased blood pressure. These subjects could have continued the oral AD during the follow-up phase if applicable.

The mean body weight at baseline of the IND phase was 78.53 kg and on Day 28 of the IND phase was 78.24 kg. The mean body weight at baseline of the OP/MA phase was 79.01 kg and at the endpoint was 79.16 kg.

Overall, nasal tolerability was favorable, as evidenced by the results of nasal examination performed by the investigator before dosing and nasal safety questionnaire completed by subjects predose and 1 hour post dose.

No apparent, clinically significant, drug-related changes from baseline in the mean laboratory hematology and/or biochemistry parameters were observed during the IND and OP/MA phase. Asymptomatic increases in ALT >3×ULN (upper limit of normal) were reported in 13 subjects (1.6%), most of which occurred in the first 1-3 months of treatment. These increases normalized while treatment was ongoing in most subjects. No persistent increases in ALT were observed. One case of suspected DILI was reported with ALT/AST >5× and bilirubin >2×uln elevation, where alternative etiology (hepatitis B) was found.

Other Safety Observations

Clinician-Assessed Dissociative Symptom Scale (CADSS)

The Clinician Administered Dissociative States Scale (CADSS) was measured prior to the start of each dose, at 40 minutes, and 1.5 hours postdose. The CADSS is used to assess treatment emergent dissociative symptoms and perceptual changes and the total score ranges from 0 to 92 with a higher score representing a more severe condition.

The dissociative and perceptual change symptoms measured by the CADSS, suggest these symptoms had an onset shortly after the start of the dose and resolved by 1.5 hours postdose (FIG. 65). The greatest increase in CADSS score at 40 minutes was observed after the first esketamine dose in the induction phase.

Modified Observer's Assessment of Alertness/Sedation (MOAA/S)

MOAA/S was used to measure treatment-emergent sedation with correlation to levels of sedation defined by the American Society of Anesthesiologists (ASA) continuum. The MOAA/S scores range from 0 (No response to painful stimulus; corresponds to ASA continuum for general anesthesia) to 5 (Readily responds to name spoken in normal tone [awake]; corresponds to ASA continuum for minimal sedation).

There were 65/777 (8.4%) subjects with MOAA/S score ≤3 at any time during the IND phase and 42/603 (7.0%) subjects with MOAA/S≤3 at any time during the OP/MA phase.

Two subjects experienced deep sedation equivalent to MOAA/S score of 0 at one of the study visits. In one of these subjects, a decrease in MOAA/S score on Day 8 (IND) was reported as an adverse event of sedation of moderate intensity, with a duration of 1 hour 30 minutes. The subject discontinued Esketamine due to nausea and GI discomfort occurring on the same day. Another subject was reported with an AE of 'unresponsive to stimuli' on Day 15 (IND) of severe intensity and the dose of esketamine was reduced from 84 mg to 56 mg.

In addition, 3 subjects experienced a transient decrease of MOAA/S to the score of 1 at one visit and single timepoint post dose (Day 4 (IND), Day 11 (IND) and Week 10 (OP/MA)).

No subject in the study required cardiovascular resuscitation. Subjects with MOAA/S of 0 had normal pulse oximetry and no decreases in the blood pressure or respiratory rate. Overall respiratory rate and pulse oximetry after ESK administration remained stable during both IND and OP/MA phase. Although individual subjects showed decreases in pulse oximetry <93% these decreases were asymptomatic, subjects remained alert and no case of respiratory depression was observed.

Brief Psychiatric Rating Positive Symptom Subscale (BPRS+)

FIG. 66 is a plot showing the mean (t) SE for the of the brief psychiatric rating positive symptom subscale total score over time during the induction and optimization/maintenance phases (all enrolled analysis set) for Example 5.

Efficacy Analyses

The efficacy analyses were performed on the full analysis sets for the IND and OP/MA phases including all enrolled subjects who received at least 1 dose of intranasal study medication or 1 dose of oral antidepressant study medication in the respective phases.

Montgomery-Asberg Depression Rating Scale (MADRS)

The MADRS consists of 10 items each scored from 0 (symptom is not present or is normal) to 6 (severe or continuous presence of the symptom). A total score (0 to 60) is calculated by summing the scores of all 10 items. A higher score represents a more severe condition.

The mean change (SD) from Baseline (IND) in MADRS total score to End Point (IND) was −16.4 (8.76) for esketamine+oral AD. The mean change (SD) from Baseline (OP/MA) in MADRS total score to End Point (OP/MA) was 0.3 (8.12) for esketamine+oral AD. See, FIG. 67.

Response (≥50% improvement from Baseline (IND) in the MADRS total score) and Remission (MADRS total score is ≤12) rates are presented for the IND and OP/MA phases in Tables 149 and 150, respectively.

At End Point in the IND phase, the response rate was 78.4% and remission rate was 47.2%; of the responders proceeding to the OP/MA phase, 76.5% were responders and 58.2% were remitters at endpoint. Functional recovery measured by SDS followed with some lag time after mood improvement. At endpoint of the IND, remission rate measured by SDS at endpoint of the IND phase (21.1%, observed case). The remission rate doubled throughout the OP/MA phase (25.2% at week 4 to 51.1% at week 48, observed case). See, FIG. 68.

TABLE 149

Response and Remission Rates Based on Montgomery-Asberg Depression Rating Scale (MADRS); Induction Phase (Study ESKETINTRD3004: Full (IND) Analysis Set)

| | Response<br>Intranasal Esk + Oral AD | Remission<br>Intranasal Esk + Oral AD |
|---|---|---|
| Day 8 | 86/739 (11.6%) | 54/739 (7.3%) |
| Day 15 | 185/702 (26.4%) | 115/702 (16.4%) |
| Day 22 | 312/683 (45.7%) | 199/683 (29.1%) |
| Day 28 | 581/688 (84.4%) | 349/688 (50.7%) |
| End Point (IND) | 593/756 (78.4%) | 357/756 (47.2%) |

A subject is defined as a responder at a given time point if the percent improvement from baseline (IND) in MADRS total score is at least 50%. A subject is in remission at a given time point if the MADRS total score is ≤12.

TABLE 150

Response and Remission Rates Based on Montgomery-Asberg Depression Rating Scale (MADRS); Optimization/Maintenance Phase (Study ESKETINTRD3004: Full (OP/MA) Analysis Set)

|  | Response<br>Intranasal Esk + Oral AD | Remission<br>Intranasal Esk + Oral AD |
|---|---|---|
| Week 1 | 513/583 (88.0%) | 325/583 (55.7%) |
| Week 8 | 408/530 (77.0%) | 277/530 (52.3%) |
| Week 16 | 355/446 (79.6%) | 273/446 (61.2%) |
| Week 24 | 278/346 (80.3%) | 203/346 (58.7%) |
| Week 32 | 226/284 (79.6%) | 178/284 (62.7%) |
| Week 40 | 171/210 (81.4%) | 127/210 (60.5%) |
| Week 48 | 124/139 (89.2%) | 95/139 (68.3%) |
| End Point (OP/MA) | 461/603 (76.5%) | 351/603 (58.2%) |

A subject is defined as a responder at a given time point if the percent improvement from baseline (IND) in MADRS total score is at least 50%. A subject is in remission at a given time point if the MADRS total score is ≤12.

Patient Health Questionnaire (PHQ-9) Total Score

The PHQ-9 is a 9-item, self-report scale assessing depressive symptoms. Each item is rated on a 4-point scale (0=Not at all, 1=Several Days, 2=More than half the days, and 3=Nearly every day), with a total score range of 0-27. A higher score indicates greater severity of depression.

The mean change (SD) from Baseline (IND) in PHQ-9 total score to End Point (IND) was −8.9 (6.67) for esketamine+oral AD. The mean change (SD) from Baseline (OP/MA) in PHQ-9 total score to End Point (OP/MA) was −0.2 (5.65) for esketamine+oral AD. See, FIG. 69.

Example 6

While ketamine is well known for its neurotoxic potential in rats, esketamine has not been investigated in this respect. A single and repeated dose neurotoxicity study were conducted in 12 to 14 weeks old female Sprague-Dawley rats in order to investigate whether intranasal instillation of esketamine HCl at a single dose up to 72 mg or during 14 consecutive days at doses up to 54 mg/day results in histopathological evidence of neurodegeneration (necrosis) in the brain. Prominent central nervous system-related clinical signs were noted in the esketamine HCl-treated rats including dose-related salivation, ataxia, decreased motor activity accompanied by decubitus and catalepsy, increased motor activity, bradypnea and audible respiration. Extensive brain histopathology examinations showed no morphological evidence of neuronal degeneration. In rats that received a single subcutaneous injection of the positive control (+)MK-801 maleate, neuronal necrosis was observed as expected in the posterior cingulate gyrus and the retrosplenial cortex. The esketamine $C_{max}$- and AUC-based safety margins compared with the maximum 84 mg dose in humans were approximately 60- and 86-fold in the single dose neurotoxicity study, and approximately 17- and 11-fold in the 14-day neurotoxicity study, respectively.

1. Introduction

This study includes a single dose and 14-day repeated dose neurotoxicity studies with intranasally administered esketamine in female rats 12 to 14 weeks of age. These studies were conducted to investigate whether single or repeated intranasal administrations of esketamine induced neurodegenerative changes in the rat brain. The study results were used to estimate an esketamine exposure-based safety margin compared with the maximum dose of esketamine administered intranasally to depressed adult patients in clinical trials.

2. Material and Methods 2.1. Test Facility

The single dose and 14-day repeated dose neurotoxicity studies were performed at Janssen Research & Development (JRD), a division of Janssen Pharmaceutica NV, in Beerse, Belgium. Janssen Pharmaceutica NV is a pharmaceutical company of Johnson & Johnson. The test facility was approved by the Association for Assessment and Accreditation of Laboratory Animal Care International (AAALAC). All animals were treated humanely and cared for in accordance with the European (European Convention (ETS No. 123) for the protection of Vertebrate Animals Used for Experimental and Other Scientific Purposes. Council Directive of Nov. 24, 1986 (86/609/EEG) on the approximation of laws, regulations and administrative provisions of the Member States regarding the protection of animals used for experimental and other scientific purposes, complemented with the COMMISSION RECOMMENDATION of 18 Jun. 2007 (2007/526/EC) on guidelines for the accommodation and care of animals used for experimental and other scientific purposes) and Belgian (Belgian Law (Oct. 18, 1991): Protection of Vertebrate Animals used for Experimental and other Scientific Purposes. Royal Decree of Nov. 14, 1993 for the protection of laboratory animals) guidelines, and with the principles of euthanasia as stated in the Report of the American Veterinary Medical Association Panel (American Veterinary Medical Association (AVMA), 2013. AVMA Guidelines for the Euthanasia of Animals, 2013 Edition. American Veterinary Medical Association (AVMA), Schaumburg). The studies were performed in accordance with JRD ethical protocols, which were approved by the local ethical committee.

2.2. Regulations

All activities were carried out in compliance with the current Good Laboratory Practice (GLP) principles of the OECD (Organization of Economic Co-operation and Development; OECD, 1998. OECD Series on principles of good laboratory practice and compliance monitoring. No. 1, Principles on Good Laboratory Practice. Accessed from: http://www.oecd.org/officialdocuments/publicdisplaydocumentpdf/?cote=env/mc/chem(98)17&doclanguage=en).

OECD Principles of GLP are accepted by Regulatory Authorities throughout the Member Countries of the OECD organization as described in the Mutual Acceptance of Data document (12 May 1981—C(81)30/Final, Amended on 26 Nov. 1997-C(97) 186/Final). Outsourcing and monitoring of the bioanalysis of esketamine was done according to the OECD principles of GLP to the organization and management of multi-site studies (OECD, 2002. OECD Series on principles of good laboratory practice and compliance monitoring. No. 13, The application of the OECD principles of GLP to the organisation and management of multi-site studies. Accessed from: http://www.oecd.org/officialdocuments/publicdisplaydocumentpdf/?docianguage=en&cote=env/jm/mono(2002)9). The bioanalysis part of the study was conducted in compliance with the US FDA's GLP Regulations for Nonclinical Laboratory Studies, 21 CFR Part 58 (FDA, 2014. FDA 21 CFR Part 58 Good Laboratory Practice for Nonclinical Laboratory Studies. United States Food and Drug Administration (FDA)), and in accordance with the appropriate JRD standard operating procedures. The design of this study was based on international guidelines (European Union (2001). Directive 2001/83/EC of the European Parliament and of the Council of 6 Nov. 2001 on the Community code relating to medicinal products for human use; FDA, 2007. Toxicological principles for the safety assessment of direct food additives and color additives in food. Redbook 2000. FDA (United States Food and Drug Administration); ICH Guideline S3A, 1994. Note for guidance of toxicokinetics: the assessment of systemic exposure in toxicity studies; ICH Guideline M3 (Rs), 2009. Guidance on Non-clinical safety studies for the conduct of human clinical trials and marketing authorization for pharmaceuticals; JMHW, 1995. Japanese Guidelines for Non-clinical Studies of Drugs Manual 1995. Yakuji Nippo, Tokyo. JMHW (Japanese Ministry of Health and Welfare); OECD, 2008. Test No. 407: Repeated Dose 28-day Oral Toxicity Study in Rodents, OECD Guidelines for the Testing of Chemicals, Section 4, OECD Publishing, Paris. DOI: http://dx.doi.org/10.1787/9789264070684-en).

2.3. Animals and Housing

For these studies, female specific pathogen free (SPF) Sprague-Dawley rats were used, which were approximately 12 to 14 weeks at start of dosing and weighed between 227 to 293 grams in the single dose study and between 235 to 296 grams in the 14-day repeated dose study. The rats were supplied by Charles River (Sulzfeld, Germany). They were group housed in polysulphone cages with floor area of 3000 cm$^2$ and Corn Cob (size 12, Eurocob, France) was provided as bedding material. Environmental enrichment existed of a rodent retreat (Bio-Serv, US) and aspen wood blocks (Datesand, UK). The animal room was air-conditioned (own supply of filtered fresh air) and had a 12 hour light cycle (300 Lux at 1 m height). The animals were fed ad libitum with irradiated R/M-H pelleted maintenance diet from Ssniff (Germany). Hydrogelt™ (supplied by Bio-services, Uden, the Netherlands) was provided to the MK-801 dosed rats in the single dose study.

2.4. Formulations 2.4.1. Esketamine HCl

The clinical investigational product is an aqueous solution of the drug substance, esketamine hydrochloride (HCl). This formulation is administered intranasally to patients using a dual nasal spray device, which delivers one spray into each nostril. At room temperature the maximum solubility of esketamine HCl at pH 4.5 is 207 mg/mL (i.e., 180 mg esketamine base/mL when applying a factor 1.15 to convert the esketamine HCl salt to esketamine base concentration). The formulation was stored at 37° C. for stability reasons until dosing.

2.4.2. (+)MK-801 maleate

An aqueous solution of (+)MK-801 maleate with pyrogenic-free water containing NaOH/HCl to pH 4.5 and mannitol till isotonic was used as the positive control. A factor of 1.52 was used to convert the maleate salt into base dose levels.

2.4.3. Vehicle

The clinical investigational formulation without esketamine HCl was used as the vehicle.

2.5. Experimental Design of the Single Dose Neurotoxicity Study

Esketamine HCl was instilled intranasally at doses of 0 (vehicle), 36, 54 or 72 mg (expressed as esketamine base) to female rats on a single day. The dose levels were obtained by 2, 3 or 4 subsequent intranasal instillations, respectively, into both nostrils at a volume of 50 μL per nostril. At each instillation, the second nostril was dosed immediately after the first nostril. The interval between subsequent instillations into both nostrils was 5 minutes.

The vehicle control group received 4 subsequent intranasal instillations of the vehicle into both nostrils (50 μL per nostril) with 5-minute intervals.

The positive control (+)MK-801 maleate was injected once subcutaneously at 1 mg/kg body weight (expressed as base). The injection volume was 5 mL/kg.

The vehicle- and the 36 and 54 mg-dosed groups consisted of 24 animals per group, while the 72 mg-dosed and positive control groups involved 30 animals per group. Four satellite animals were added to the esketamine HCl-dosed groups of main study animals for toxicokinetic (TK) purposes. In these animals the plasma exposure to esketamine was measured on the day of dosing at various time points up to and including 24 hours after the first instillation.

In order to prepare for brain histopathology examination, all main study animals were perfused at necropsy. Prior to the perfusion, rats were anesthetized with isoflurane. After injection of 0.1 ml heparin, the blood of the rat was flushed out with a physiological saline solution by intraarterial insertion of a needle in the abdominal aorta. Thereafter the rat was perfused with glutaraldehyde 3% in potassium phosphate 0.09M and 1.4% sucrose. Due to logistic constraints at maximum 30 animals could undergo the whole-body perfusion procedure on a given day. Therefore, a staggered start of treatment was applied to all 5 groups of main study animals. Consequently, subgroups of 4 main study animals of the vehicle- and 36 and 54 mg-dosed groups, and 5 main study animals of the 72 mg-dosed and positive control groups, were dosed on 6 consecutive days, respectively. Table 151 summarizes the study design of the single dose neurotoxicity study.

TABLE 151

Design of the single dose neurotoxicity study

Vehicle- and esketamine HCl-dosed groups of main study animals[1]

| Group number | Dose groups | Volume instilled intranasally into each nostril (μl) | Dose per rat (μl) | Dose per rat (mg) | Concentration (mg/ml) |
|---|---|---|---|---|---|
| 1 | Vehicle | 4*50 | 4*100 | 0 | 0 |
| 2 | Low | 2*50 | 2*100 | 36 | 180 |
| 3 | Medium | 3*50 | 3*100 | 54 | 180 |
| 4 | High | 4*50 | 4*100 | 72 | 180 |

Positive control group treated with (+)MK-801 maleate[2]

| Group number | Dose (mg/kg body weight) | Concentration (mg/ml) |
|---|---|---|
| 5 | 1 | 0.2 |

[1]Single treatment session consisting of multiple intranasal instillations on a given day;
[2]Single subcutaneous injection The vehicle control, positive control, and esketamine HCl-dosed animals were sacrificed at either 48 hours (i.e., the first 12 or 15 rats per group) or 96 hours after the dose administration time (i.e., the last 12 or 15 rats per group). The brain tissue of the vehicle control-, positive control- and esketamine HCl-treated rats were processed at the same time and handled in the same way in batches of 4 or 5 animals per group.

2.6. Experimental Design of the 14-Day Repeated Dose Neurotoxicity Study

Esketamine HCl was administered into each nostril of female rats at a volume of 50 μl per nostril either once, twice or thrice daily by intranasal instillation for 14 consecutive days at doses of 0 (vehicle), 18, 36 or 54 mg/day. At each instillation, the second nostril was dosed immediately after the first nostril. The interval between subsequent instillations into both nostrils was 5 minutes when dosed 2 or 3 times per day.

The vehicle control group received 3 subsequent intranasal instillations of the vehicle into both nostrils (50 μL per nostril) with 5-minute intervals for 14 consecutive days.

The positive control group received a single subcutaneous injection of (+)MK-801 at 48 hours prior to the necropsy of the vehicle control and esketamine HCl-treated animals. The dose level of (+)MK-801 maleate was 1 mg/kg body weight.

Each group of main study animals consisted of 12 female rats. Four satellite animals were added to the esketamine HCl-dosed groups of main study animals for TK purposes. The plasma exposure to esketamine was measured in these animals on the first and the last day of dosing at various time points up to and including 24 hours after the first instillation.

Due to logistic constraints associated with the whole body perfusion procedure of the animals at necropsy, a staggered start was applied to the study. Consequently, all 5 groups of main study animals were divided into three subgroups of 4 animals each. For each of these subgroups treatment started on a different day. The perfusion procedure is the is the same as described for the single dose study. Table 152 summarizes the study design of the 14-day repeated dose neurotoxicity study.

TABLE 152

Design of the 14-day repeated dose neurotoxicity study

Vehicle- and esketamine HCl-dosed groups of main study animals[1]

| Group number | Dose groups | Volume instilled intranasally into each nostril (μl/day) | Dose per rat (μl/day) | Dose per rat (mg/day) | Concentration (mg/ml) |
|---|---|---|---|---|---|
| 1 | Vehicle | 3*50 | 3*100 | 0 | 180 |
| 2 | Low | 1*50 | 1*100 | 18 | 180 |
| 3 | Medium | 2*50 | 2*100 | 36 | 180 |
| 4 | High | 3*50 | 3*100 | 54 | 180 |

Positive control group treated with (+)MK-801 maleate[2]

| Group number | Dose (mg/kg body weight) | Concentration (mg/ml) |
|---|---|---|
| 5 | 1 | 0.2 |

[1]Daily treatment sessions each consisting of a single (group 2) or multiple intranasal instillations (groups 1, 3 and 4).
[2]Single subcutaneous injection All vehicle- and esketamine HCl-treated animals were sacrificed at 48 hours after the last instillation. All (+)MK-801 maleate-treated animals were sacrificed at 48 hours post-dose. The brain tissue of the vehicle control-, positive control- and esketamine HCl-treated rats were processed at the same time and handled in the same way in batches of 4 animals per group.

2.7. Examined Parameters in the Single Dose and Repeated Dose Neurotoxicity Studies All animals were checked at least once daily for ill health, abnormal behavior or unusual appearance, clinical signs, toxic or pharmacological response, moribund state or mortality. Furthermore, clinical observations were recorded for the esketamine HCl-dosed rats on the day of dosing at 0 till 5 minutes, 15 and 30 minutes, and at 1, 2, 4, 6 hours post-dose, at the end of the working day and at 24 hours after the last instillation in the single dose study and on the first day of dosing, after one week and towards the end of the dosing period in the repeated dose study. Body weight and body weight gain were measured daily. Food consumption was measured weekly in the repeated dose study.

On the day of terminal kill, a complete physical examination was performed on the rats in fasted condition and body weight was recorded. The surviving animals were anaesthetized by inhalation of an isoflurane (IsoFlo® Zoetis, Belgium)/oxygen mixture and killed by exsanguination via the carotid artery. A full necropsy was performed on all animals and all macroscopic changes were recorded. All terminally killed rats or those killed pre-terminally were perfused with 4% paraformaldehyde in the single dose study and with glutaraldehyde 3% in potassium phosphate buffer 0.09 M with 1.4% sucrose in the repeated dose study.

Brain tissue was sampled and processed routinely. The trimmed and embedded tissue was sectioned and stained with hematoxylin-eosin (HE). Histoprocessing and staining were carried out in three batches of 4 animals per group (each batch thus containing 4 animals from vehicle control-, positive control- and the three esketamine HCl-treated groups). In the single dose study duplicate brain sections were stained with Fluoro-Jade (FJ).

All tissues showing gross abnormalities were examined macroscopically.

Histopathological examination was performed on 7 levels of brain tissue according to Bolon (2013. Toxicol. Pathol. 41(7), 1028-1048) from the vehicle control-, positive control-, and high dose esketamine HCl-treated groups in the single dose study, and in all groups in the repeated dose study.

The microscopic finding of neuronal necrosis in the PCG/RSC of the brain was graded unilaterally according to the number of necrotic neurons observed over the total length of the PCG/RSC structure visible in the tissue section (usually around 3-5 mm) utilizing the following criteria:

Grade 1: minimal histological change (<10 necrotic neurons),

Grade 2: slight histological change (10-20 necrotic neurons),

Grade 3: moderate histological change (20-30 necrotic neurons) or

Grade 4: marked histological change (>30 necrotic neurons)

2.8. Statistical Analyses

The significance of differences between each dose group and the vehicle group was assessed by a one-sided Fisher Exact Probability test for mortality and histopathology, a two-sided Fisher Exact Probability test for clinical observations and a two-sided Mann-Whitney U test for body weight and weight gain. No statistical analysis was conducted for food consumption and gross pathology. All tests were performed at a significance level of five percent ($\alpha=0.05$).

3. Results 3.1 Single Dose Study 3.1.1. Esketamine HCl

No test article related mortality or gross pathology changes were noted when female rats were dosed once with esketamine HCl up to 54 mg. No relevant effects were noted on body weight up to 72 mg.

At 72 mg two main study animals and two satellite TK animals died within 30 minutes after having received 4 instillations of esketamine HCl into both nostrils. Clinical signs noted just before death were ataxia, bradypnea, severely decreased general activity, decubitus, catalepsy (rigid posture), and salivation. One of these rats also showed narrowed palpebral fissures. The two main study animals were necropsied and gross changes were observed in the lungs (discoloration [in one rat], and swollen aspect) and the pleural cavity (hemorrhagic aspect). A cause of death could not be determined. However, the mortalities were considered related to the combination of the large dose volume and the high dose of esketamine HCl.

Prominent clinical observations were noted in all dose groups of esketamine HCl. Salivation, audible respiration, ataxia and in general a slight increase in general activity were noted directly after dosing. Subsequently, severely decreased activity accompanied by decubitus, bradypnea, ptosis and catalepsy were observed from <15 minutes post-dose onwards. The duration of these findings was dependent on the dose of esketamine HCl. At 36 mg, these findings were noted mainly up to 15-30 minutes, at 54 mg up to 30 minutes to one hour, and at 72 mg up to 1-2 hours after the last instillation. During this time period narrowed palpebral fissure occurred in a dose-dependent manner affecting approximately one third of the animals at 36 mg up to approximately two thirds of the animals at 72 mg. After the decrease in activity had gradually subsided, ataxia was again observed in most animals and lasted approximately 1.5 hours at 36 mg, 1.5 to 3 hours at 54 mg, and up to 3 hours or longer at 72 mg. The ataxia was accompanied by slightly (or incidentally moderately) increased general activity in approximately half of the rats. Audible respiration was noted after dosing in approximately half of the animals dosed at 36 mg, and in 2 or 3 rats at 54 and 72 mg, respectively. All findings except for audible respiration fully subsided within 24 hours. In one high dose rat audible respiration was still present on Day 2. More details can be found in Table 153. The time course of decreased and increased general activity is illustrated in FIG. 70.

Although mortality and prominent CNS-findings (e.g. catalepsy) were noted, histopathological lesions were absent in the brain of esketamine HCl-treated rats sacrificed at either 48 or 96 hours after a single dose of 72 mg. In particular no Olney lesions were found in the PCG/RSC of any esketamine HCl-treated animal. More details can be found in Table 155 (see Section 3.3).

The $C_{max}$- and AUC-based safety margins for esketamine compared with the maximum 84 mg clinical dose were approximately 60- and 86-fold, respectively.

3.2. Repeated Dose Study 3.2.1. Esketamine HCl

No test article related mortality occurred. Body weight, weight gain, and food consumption were unaffected when female rats were dosed with esketamine HCl up to 54 mg/day for 14 days.

At all dose levels of esketamine HCl, a dose-dependent increase in duration of ataxia and salivation was recorded. Slightly increased general activity was noted in all esketamine HCl-dosed animals starting at 5 minutes after dosing and lasting up to 1 or 2 hour after the last daily dose administration. This increased motor activity was seen daily at 18 mg/day, from Day 3 to 5 until the end of the study at 36 mg/day, and mainly during the last week of the study at 54 mg/day. Also a slight to severe decrease in general activity was seen in all animals with a dose-related increase in severity and duration (from 15 or 30 minutes up to 1 or 2 hours after dosing). Decubitus was occasionally noticed during the first days of the study at 36 and 54 mg/day. After the decrease in activity had gradually subsided, increased general activity accompanied by ataxia was again observed (FIG. 71A to FIG. 71C). At 36 or 54 mg/day, periods of respiratory abnormalities (bradypnoea, audible respiration) were noted in almost all animals and were observed on several days throughout the study, from 5 to 30 minutes or 1 to 4 hours after dosing. More details can be found in Table 154.

TABLE 153

Main clinical observations: incidences per group

| Observation | Vehicle control X/N | Esketamine HCl 36 mg X/N | Esketamine HCl 54 mg X/N | Esketamine HCl 72 mg | Positive control X/N |
|---|---|---|---|---|---|
| Ataxia | 0/24 | 24/24 *** | 24/24 *** | *** | 27/30 *** |
| Catalepsy | 0/24 | 20/24 *** | 23/24 *** | 30/30 *** | 15/30 *** |
| Chromodacryorrhea | 0/24 | 0/24 | 0/24 | 0/30 | 24/30 *** |
| Decubitus | 0/24 | 23/24 *** | 23/24 *** | 30/30 *** | 30/30 *** |
| Decreased general activity | 0/24 | 23/24 *** | 23/24 *** | 30/30 *** | 30/30 *** |
| Increased general activity | 0/24 | 24/24 *** | 24/24 *** | 29/30 *** | 4/30 |
| Piloerection | 0/24 | 0/24 | 0/24 | 0/30 | 8/30** |
| Narrowed palpebral fissure | 0/24 | 7/24** | 10/24 *** | 22/30 *** | 4/30 |
| Abnormal respiration | 0/24 | 22/24 *** | 22/24 *** | 30/30 *** | 12/30 *** |
| audible respiration | 0/24 | 10/24 *** | 3/24 | 2/30 | 0/30 |
| bradypnoea | 0/24 | 22/24 *** | 21/24 *** | 30/30 *** | 12/30 *** |
| Salivation (out of normal) | 0/24 | 23/24 *** | 24/24 *** | 29/30 *** | 17/30 *** |

Significance for 36, 54 and 72 mg esketamine HCl-treated and positive control group(s) computed versus vehicle by Fisher Exact probability test (one-tailed right probability):
*p < 0.05;
**p < 0.01;
*** p < 0.001;
X = number of affected animals; N = total number of animals.

TABLE 154

Main clinical observations in the repeated dose neurotoxicity study (incidences per group)

| Observation | Vehicle control X/N | Esketamine HCl 18 mg/day X/N | Esketamine HCl 36 mg/day X/N | Esketamine HCl 54 mg/day X/N | Positive control X/N |
|---|---|---|---|---|---|
| Ataxia | 0/12 | 12/12*** | 12/12*** | 12/12*** | 12/12*** |
| Chromodacryorrhea | 0/12 | 0/12 | 0/12 | 0/12 | 12/12*** |
| Decubitus | 0/12 | 0/12 | 2/12 | 8/12*** | 0/12 |
| Decreased general activity | 1/12 | 5/12 | 12/12*** | 12/12*** | 12/12*** |
| Increased general activity | 0/12 | 12/12*** | 12/12*** | 12/12*** | 12/12*** |
| Abnormal respiration | 0/12/12 | 2/12 | 11/12*** | 12/12*** | 12/12*** |
| audible respiration | 0/12 | 2/12 | 6/12** | 6/12** | 0/12 |
| bradypnoea | 0/12 | 0/12 | 11/12*** | 12/12*** | 12/12*** |
| Salivation (out of normal) | 0/12 | 12/12*** | 12/12*** | 12/12*** | 2/12 |

Significance for 18, 36 and 54 mg/day esketamine HCl-treated and positive control group(s) computed versus vehicle by Fisher Exact probability test (one-tailed right probability):
*p < 0.05;
**p < 0.01
***p < 0.001;
X = number of affected animals; N = total number of animals; Gross pathology did not reveal any tissue changes.

At 48 hours after the last intranasal Instillation no histopathological lesions were noted in the brain of esketamine HCl-dosed animals up to 54 mg/day. Notably no Olney lesions were found in the PCG/RSC of any esketamine HCl-treated animal. More details can be found in Table 6 and FIGS. 72A, 72B, and 73 (see Section 3.3).

In the 14-day study the $C_{max}$- and AUC-based safety margins for esketamine were approximately 17- and 11-fold, respectively.

3.3. Results for (+)MK-801 Maleate in the Single Dose and Repeated Dose Neurotoxicity Studies with Esketamine HCl No mortality was noted in either the single dose or repeated dose study when female rats received a single subcutaneous dose of (+)MK-801 maleate at 1 mg/kg body weight.

Ataxia, moderately to severely decreased general activity and decubitus were noted in most animals. Additionally, catalepsy, bradypnea, tremors and salivation were noted. A single animal showed clonic convulsions.

During the follow-up period prior to necropsy, decreased activity and ataxia remained present, but became gradually less severe, and catalepsy and bradypnea were only noted occasionally. Additionally almost all animals showed chromodacryorrhea. Other signs of general discomfort were occasionally noted in some animals such as piloerection, hunched back, ocular discharge and narrowed palpebral fissures. Occasionally slight increases in general activity were noted. The time course of decreased and increased activity is illustrated in FIG. 70.

(+)MK-801 maleate-dosed rats showed approximately 13-14% body weight loss within the first 48 hours after treatment. In the single dose study, where half of the animals was maintained until 96 hours post-dose, the animals regained weight between 48 and 96 hours post-dose.

At 48 and 96 hours post-dose in the single dose study, and at 48 hours after the last dose administration in the repeated dose study, (+)MK-801 maleate induced Olney lesions as evidenced by the occurrence of neuronal necrosis in the PCG/RSC of all animals treated with this positive control test article. In both studies, most lesions were graded as moderate or marked (grade 3 or 4). There was no remarkable difference in the severity of the neuronal necrosis between the animals necropsied at either 48 or 96 hours post-dose in the single dose study. In that study, necrotic neurons tended to be slightly more numerous upon FJ staining compared with the HE staining. In both studies the lesions were consistently more severe in the RSC compared with the PCG.

Tables 155 and 156 below provide an overview of the incidences and severity.

TABLE 155

Single dose neurotoxicity study. Incidence and severity of neuronal necrosis in the posterior cingulate gyrus (PCG) and the retrosplenial cortex (RSC) of esketamine HCl- and (+)MK-801 maleate-treated rats

| | Vehicle control | Esketamine HCl 36 | Esketamine HCl 54 | Esketamine HCl 72 | Positive control |
|---|---|---|---|---|---|
| BRAIN, POSTERIOR CINGULATE GYRUS (HE) | | | | | |
| No. Examined | 24 | — | — | 30 | 30 |
| Neuronal Necrosis | — | — | — | — | 30** |
| Grade 1 | — | — | — | — | 1 |
| Grade 2 | — | — | — | — | 5 |
| Grade 3 | — | — | — | — | 19 |
| Grade 4 | — | — | — | — | 5 |
| BRAIN, POSTERIOR CINGULATE GYRUS (Fluoro-Jade) | | | | | |
| No. Examined | 24 | — | — | 30 | 30 |
| Neuronal Necrosis | — | — | — | — | 30** |
| Grade 2 | — | — | — | — | 2 |
| Grade 3 | — | — | — | — | 9 |
| Grade 4 | — | — | — | — | 19 |
| BRAIN, RETROSPLENIAL CORTEX (HE) | | | | | |
| No. Examined | 24 | — | — | 30 | 30 |
| Neuronal Necrosis | — | — | — | — | 30** |
| Grade 1 | — | — | — | — | 1 |
| Grade 2 | — | — | — | — | 6 |
| Grade 3 | — | — | — | — | 10 |
| Grade 4 | — | — | — | — | 13 |
| BRAIN, RETROSPLENIAL CORTEX (Fluoro-Jade) | | | | | |
| No. Examined | 24 | — | — | 30 | 30 |
| Neuronal Necrosis | — | — | — | — | 30** |

TABLE 155-continued

Single dose neurotoxicity study. Incidence and severity
of neuronal necrosis in the posterior cingulate gyrus
(PCG) and the retrosplenial cortex (RSC) of esketamine
HCl- and (+)MK-801 maleate-treated rats

| | Dose of esketamine HCl (mg) | | | | |
|---|---|---|---|---|---|
| | Vehicle control | Esketamine HCl 36 | 54 | 72 | Positive control |
| Grade 3 | — | — | — | — | 5 |
| Grade 4 | — | — | — | — | 25 |

Significance for 36, 54 and 72 mg esketamine HCl-treated and positive control group(s) computed versus vehicle by one-sided Exact Fisher test:
*p ≤ 0.05;
**p ≤ 0.01.

TABLE 156

Repeated dose neurotoxicity study. Incidence and severity
of neuronal necrosis in the posterior cingulate gyrus
(PCG) and the retrosplenial cortex (RSC) of esketamine
and (+)MK-801 maleate-treated rats

| | Dose of esketamine HCl (mg/day) | | | | |
|---|---|---|---|---|---|
| | Vehicle control | Esketamine HCl 18 | 36 | 54 | Positive control |
| BRAIN, POSTERIOR CINGULATE GYRUS (HE) | | | | | |
| No. Examined | 12 | 12 | 12 | 12 | 12 |
| Necrosis | | | | | 12** |
| Grade 1 | — | — | — | — | 1 |
| Grade 2 | — | — | — | — | 4 |
| Grade 3 | — | — | — | — | 4 |
| Grade 4 | — | — | — | — | 3 |
| BRAIN, RETROSPLENIAL CORTEX (HE) | | | | | |
| No. Examined | 12 | 12 | 12 | 12 | 12 |
| Necrosis | | | | | 12** |
| Grade 1 | — | — | — | — | 1 |
| Grade 2 | — | — | — | — | 1 |
| Grade 3 | — | — | — | — | 3 |
| Grade 4 | — | — | — | — | 7 |

Significance for 18, 36 and 54 mg/day esketamine HCl and positive control group(s) computed versus vehicle by one-sided Exact Fisher Test:
*p ≤ 0.05;
**p ≤ 0.01

4. Discussion

Ketamine is a drug with contradictory properties ascribed to it. On one hand, it can be neuroprotective (Hudetz, 2010. J. Cardiothor. Vasc. Anesth. 24, 131-142), as for example was shown by the decreases in plasma catecholamines and the improved outcome from incomplete cerebral ischemia in rats (Hoffman, 1992. J. Anesthesiology 76(5), 755-762). A reduction in neuronal degeneration and anxiety levels was observed when ketamine was administered during early life-induced status epilepticus in rats (Loss, 2012. Brain Research 1474, 110-117). In a rat model of global forebrain ischemia induced by hypobaric hypotension, a single IP administration of esketamine at 60 or 90 mg/kg body weight 15 minutes after cerebral ischemia significantly reduced neuronal cell loss in the cerebral cortex, whereas other brain structures such as hippocampus were less protected (Proescholdt, 2001. Brain Res. 904, 245-251). On the other hand, ketamine has been reported to provoke Olney lesions in the rat brain after a single (Olney 1989; Jevtovic-Todorovic 2000; Jevtovic-Todorovic 2005) or repeated dose administration (Horváth, 1997. Brain Res. 753(2), 181-195). The precise thresholds for dose and duration of exposure causing neurotoxicity in animals remain to be established. The relevance to humans of ketamine's neurotoxic action in animals is unknown.

The potential induction of neuronal lesions after an acute intranasal administration of esketamine HCl was studied in the single dose neurotoxicity study in which adult female Sprague-Dawley rats (12 to 14 weeks of age) received doses of 36, 54 or 72 mg. These doses were achieved by a single treatment session consisting of 2, 3 or 4 subsequent intranasal instillations, respectively, into each nostril of 50 µL of an aqueous solution containing 180 mg/mL of esketamine HCl. The interval between the subsequent instillations of both nostrils was 5 minutes. The highest dose of 72 mg represented the maximum feasible dose for an acute study based on the maximum dose volume that could be administered multiple times at 5-minute intervals (50 µL per nostril) and the maximum solubility of esketamine HCl in water being 180 mg/mL. Consequently, the highest dose of 72 mg each nostril was instilled with in total 200 µL of esketamine HCl spread over 15 minutes. A higher dose volume was not feasible considering that the rat is an obligate nasal breather with a nasal cavity which has a volume of approximately 200 µL per nostril (Gizurarson, 1990. Acta Pharm. Nord. 2(2), 105-122). Brain histopathology was examined at 48 hours and 96 hours post-dose. The selection of these time points was guided by published experiments reporting that acute exposure to MK-801 or (+)MK-801 depending on the dose, induces neuronal necrosis in the PCG/RSC of rats at 1 to 14 days after single dose administration (Auer 1996; Bender, 2010a. Neuroscience 169, 720-732; Colbourne 1999; De Olmos, 2009. Neuroscience 164(3), 1347-1359; Fix 1993; Fix 1994; Fix 1995; Fix 1996; Fix 2000; Jevtovic-Todorovic 2001; Willis, 2007. NeuroToxicology 28, 161-167). No signs of neuronal necrosis were found at these two time points in any of the esketamine HCl-treated animals tested in the single dose study. The $C_{max}$- and AUC-based safety margins for esketamine compared with the maximum 84 mg clinical dose were approximately 60- and 86-fold, respectively.

To date, no previous literature data exist on the potential induction of neuronal necrosis in the PCG/RSC of adult female Sprague Dawley rats acutely treated with either esketamine or ketamine. There is however ample evidence that ketamine induces neuronal vacuolation in these brain areas of female rats shortly after single dose treatment. In this respect ketamine resembles MK-801 or (+)MK-801 (Auer and Coulter 1994; Farber 1995; Fix 1993; Fix 1994; Fix 1996; Fix 2000; Jevtovic-Todorovic, 1997. Journal of Cerebral Blood Flow and Metabolism 17, 168-174; Jevtovic-Todorovic 2001). Neuronal vacuolization was observed in the PCG/RSC of adult Sprague Dawley rats at 4 hours after a single subcutaneous injection with ketamine at 40 mg/kg body weight, but not at 10 or 20 mg/kg (Olney 1989). The RSC of female Sprague Dawley rats 2 months of age, which received a single dose of ketamine at 60 mg/kg body weight, showed neuronal vacuolation at 3 hours post-dose. The reaction was more prominent at 3 months of age (Jevtovic-Todorovic 2001). The $ED_{50}$-value for the induction of neuronal vacuolation in the PCG/RSC of adult female Sprague Dawley rats at 3 hours after a single intraperitoneal injection of ketamine has been reported to be 47.5 mg/kg body weight (Jevtovic-Todorovic 2000). Such early time points after dose administration were not examined in the single dose neurotoxicity study, because neuronal vacuolation is considered to be reversible. The latter neurodegenerative lesion is thought to be more severe than neuronal vacuolation and irreversible (Bender 2010a; Zhang 1996).

In the current single dose study with intranasally administered esketamine HCl in Sprague Dawley rats, the mean body weight was 255 g. Therefore, the highest dose of 72 mg corresponds with approximately 282 mg/kg body weight. This dose is considerably larger than the dose levels of ketamine previously described to provoke vacuolated neurons in the PCG/RSC (Olney 1989; Jevtovic-Todorovic 2000; Jevtovic-Todorovic 2005). It is not clear why no histopathological neuronal lesions were present after a single intranasal dose of 282 mg/kg body weight esketamine, while neuronal vacuolation was observed from a single intraperitoneal injection of 47.5 mg/kg body weight ketamine onwards. A possible reason could be that in the current study, neuronal necrosis was studied 48 and 96 hours after an acute dose of esketamine, while the literature with ketamine only describes neuronal vacuolation some hours after acute administration. Perhaps the neuronal vacuolation was not observed because it recovered by the 48 hour time point (as shown by Auer and Coulter 1994 for MK-801). Another reason could be that intranasally administered esketamine and parenterally administered ketamine differ in bioavailability and hence result in different plasma exposures and/or different brain kinetics.

Olney lesions or other neuropathological changes of the rat brain after repeated dosing of esketamine or ketamine have not been reported. Additionally, neuropathological examinations of the rat brain after repeated dosing of MK-801 are scarce in the open literature. The brains of rats SC treated with 0.3 mg/kg body weight/day of MK-801 on 4 consecutive days did not show neuronal vacuolation at 4 hours after the last dose administration (Olney 1989). When rats were treated daily with MK-801 for 4 days at higher or more steeply increasing dose schedules, and the brains were examined 4 hours after the last dose, neuronal vacuolation was observed. There was no evidence of a cumulative effect or of the reaction progressing to an irreversible state (Olney 1989). In rats treated 3 times/day with (+)MK-801 for two days, neurodegeneration was reported not only in the RSC, but in other brain areas as well although less prominent (Horváth 1997).

To investigate the potential formation of neurodegenerative lesions after repeated intranasal administration of esketamine HCl, a 14-day repeated dose neurotoxicity study was performed in Sprague Dawley rats of the same sex and age as used in the single dose study. The highest dose of 54 mg/day esketamine HCl was selected based on a 14-day dose-range finding study, where upon repeated intranasal administration this dose level was considered to be the maximum tolerated dose (MTD) on the basis of severely decreased general activity, decubitus and respiratory abnormalities (internal study). In the 14-day neurotoxicity study, the vehicle control and esketamine HCl-dosed animals were sacrificed at 48 hours after the $14^{th}$ dose administration of esketamine, and the (+)MK-801-treated animals at 48 hours after an acute dose of (+)MK-801-maleate, which was administered on the last dosing day of the study. Fix 1996 reported neuronal necrosis in the PCG/RSC of the rat brain upon a single dose of MK-801 from 24 hours to 14 days post-dose. At 24 hours the effect was only slight and occasionally present, while it was prominent at 72 hours post-dose. Fix 1993 reported neuronal necrosis in the rat RSC at 48 hours to 14 days after a single dose of (+)MK-801. The 48-hour time point of sacrifice was selected since the primary goal of the study was to explore the potential occurrence of neuronal necrosis in the brain. Fourteen days of repeated administration of esketamine HCl was considered a reasonable duration of treatment to allow detection of degenerating neurons at 48 hours after the last dose administration. Neuronal vacuolation was not expected to be detectable after 14 days of treatment since it has a short time course and has been reported to be reversible (Auer and Coulter 1994; Bender 2010a; Farber 1995; Fix 1993; Fix 1994; Fix 1996; Fix 2000; Jevtovic-Todorovic 1997; Jevtovic-Todorovic 2000; Jevtovic-Todorovic 2001; Olney 1989; Zhang 1996). Consequently, neuronal vacuolation was not considered an endpoint of interest. Neuronal necrosis in the PCG/RSC was observed at 48 hours after a single dose of (+)MK-801 at 1 mg/kg body weight, it was decided to dose the positive control group only once on the day that the esketamine HCl-treated rats received their last dose administration and evaluate all brain tissue samples at 48 hours after the last dose. While as expected the (+)MK-801 treated rats showed neuronal necrosis, the esketamine HCl-treated animals did not. At the highest dose tested of 54 mg/day esketamine HCl, the $C_{max}$- and AUC-based safety margins for esketamine compared with the maximum 84 mg clinical dose were approximately 17- and 11-fold.

When esketamine HCl was administered intranasally to adult female rats once up to 72 mg (corresponding to approximately 282 mg/kg body weight) or repeatedly up to 54 mg/day (corresponding to approximately 196 mg/kg body weight), similar clinical observations were noted. The duration of anesthesia was 15-30 minutes at 36 mg, 30 minutes to an hour at 54 mg, and one to 2 hours for the 72 mg-dosed rats. During the anesthetic period, bradypnea was occasionally observed. Although ketamine is seen as an agent causing minimal respiratory depression, some respiratory depression may occur at higher dose levels as demonstrated by the higher pCO2 values for ketamine at 80 mg/kg body weight (Hoffmann, 2003. Pharmacology, Biochemistry and Behavior 74, 933-941). Ketamine is a widely used anesthetic in rats, but is mostly used in combination with other agents (e.g. xylazine) to induce dissociative anesthesia with analgesia and immobility. The onset of anesthesia after intramuscular dosing a rat with 50 mg/kg ketamine is rapid (within 5 minutes), with loss of righting reflex after 7 minutes and a duration of full anesthesia for 35 minutes. 45 Minutes later the righting reflex starts to be present again. Intramuscular doses up to 150 mg/kg body weight caused a peak effect within 10 minutes, which could be sustained for 30-40 minutes. A total recovery of the anesthesia was seen after 1.5 hours (Green 1981. Lab. Anim. 1981, 15: 163).

The esketamine HCl-induced anesthesia was mostly preceded by ataxia and slightly increased activity of the rats during the first minutes after dosing, before decubitus and catalepsy was noted within 15 minutes. Hyperactivity and ataxia were also noted after recovery from anesthesia and lasted approximately up to 1.5 hours at 36 mg, up to 1-3 hours at 54 mg and up to 3 hours or longer at 72 mg. Subanesthetic doses of ketamine are known to cause hyperactivity and ataxia. An intraperitoneal dose of 10 mg/kg body weight ketamine results in increased open field activity, which is thought to be related to changes in dopamine activity (Wilson, 2005. Pharmacology, Biochemistry and Behavior 81 (2005) 530-534). Intravenous dosing of ketamine at 5 to 80 mg/kg body weight showed an increased duration of ataxia and hyperactivity with increasing doses. The duration of hyperactivity was slightly longer that the duration of ataxia (Wilson 2005; Cohen 1973. Anesthesiol. 39: 370-376). Similar findings were reported by Compton (Compton, 2013. International Journal of Life Science and Medical Research Vol. 3 Iss. 5, 179-192), as rats injected intraperitoneally with ketamine at 5 mg/kg showed increased general activity, while rats dosed at 40 mg/kg did not.

The positive control in both studies was (+)MK-801-maleate. This non-selective NMDA receptor antagonist is well known for causing neuronal vacuolation and degeneration (necrosis) in the PCG/RSG of the rat brain (Auer and Coulter 1994; De Olmos 2009; Fix 1993; Fix 1994; Fix 1995; Fix 1996; Fix 2000; Olney 1989; Olney 1991). The (+)-enantiomer is 7 times more potent than the (−)-enantiomer. In the present studies it was administered by a single subcutaneous injection at 1 mg/kg. In a dose-range finding study, this 1 mg/kg body weight dose was considered to be the MTD for a single subcutaneous injection of (+)MK-801-maleate in female Sprague-Dawley rats 13-14 weeks of age. A single SC or intraperitoneal (IP) administration of MK-801 at 5 mg/kg body weight has been reported to cause severe incoordination, increased motor activity, ataxia, head-waving movements prior to a recumbency period of 5.5 to 6 hours for male rats and 24 to 40 hours for females. This long period of recumbency resulted in severe body weight losses. Mortality of rats in a state of extreme immobility with shallow breathing was reported as well (Colbourne 1999; De Olmos 2008; Fix 1995; Auer 1996; Hur, 1999. Environmental Toxicology and Pharmacology 7, 143-146). Female rats injected IP with 5 mg/kg body weight of (+)MK-801 showed recumbency, severe hypothermia and loss of body weight lasting up to 3 to 7 days post-dose (Zajaczkowski, 2000. Neurotox. Res. 1(4), 299-310). Behavioural disturbance and recumbency have also been reported in rats treated once at 10 mg/kg IP (Bender, 2010b. Neurotoxicology and Teratology 32, 542-550). A single SC dose of 1 mg/kg MK-801 induced recumbency for at least 7 hours post-dose (Fix 1995). At lower dose levels (0.05 to 0.2 mg/kg SC or IP) MK-801 induced increased locomotion and ataxia in rats (Andine, 1999. J. Pharmacol. Exp. Ther. 290(3), 1393-408; Ahlander, 1999. Neuropsychopharmacol. 21, 414-426). In female rats, locomotion was maximal at 0.1 to 0.2 mg/kg, while stereotypic sniffing was reported at 0.1 to 0.5 mg/kg, and ataxia at 0.2 to 1 mg/kg of MK-801 (Andine 1999). The clinical findings reported in the literature were also observed in the studies after a single dose of (+)MK-801 at 1 mg/kg body weight. As a result of the long period of recumbency, the animals were not eating or drinking, causing a severe body weight loss of 13-14% during the first 48 hours after dosing. It has been claimed that any dose of MK-801 equal to or exceeding 0.2 mg/kg should probably be considered to be grossly intoxicating in rats (Wozniak, 1990. Psychopharmacology 101(1), 47-56). Remarkably, however, many other investigators did not mention any clinical observations at all even after a single dose as high as 10 mg/kg (Wozniak, 1998. Neurobiology of Disease. 5(5), 305-322; Farber 1995; Auer and Coulter 1994; Fix 1993; Fix 1996; Willis and Ray 2007; Bueno, 2003. Experimental and Toxicologic Pathology 54, 319-334; Horváth 1997; De Olmos 2009; Fix 2000).

The presence of the neuronal necrosis in the PCG/RSC was graded according to the number of necrotic neurons that were observed over the total length of the structure visible in the section (usually around 3-5 mm). Four grades were used and covered changes that ranged from minimal (<10 necrotic neurons) to marked (>30 necrotic neurons). With this grading system, it was shown that (+)MK-801 maleate upon a single SC injection at 1 mg/kg body weight caused the typical neuronal necrosis associated with neuronal necrosis in the PCG/RSC of all treated animals. The severity of the lesions was scored marked in the majority of the animals (i.e., 25 out of 30 females in the single dose study and 7 out of 12 animals in the repeated dose study). No relevant differences were seen between the single dose and repeated dose studies or between the 48- and 96-hour post-dose timepoints in the single dose study. Therefore it can be concluded that rats that were dosed once with (+)MK-801 maleate at 1 mg/kg served as a valid positive control group for both neurotoxicity studies and that the response was robust and consistent.

4.1. Conclusion

Although mortality and prominent CNS-related clinical observations (e.g. catalepsy) were noted with intranasally administered esketamine HCl in the single dose neurotoxicity study, no neuropathological lesions were observed in the adult female rat brain up to the highest tested dose of 72 mg when evaluated at 48 and 96 hours after dosing. The $C_{max}$- and AUC-based safety margins for esketamine compared with the maximum 84 mg clinical dose were approximately 60- and 86-fold, respectively. No histopathological lesions were found in the brains of the esketamine HCl-treated animals involved in 14-day repeat dose neurotoxicity study either. In the latter study, the highest tested dose was 54 mg/day. At that dose, the $C_{max}$- and AUC-based safety margins for esketamine compared with the maximum 84 mg clinical dose were approximately 17- and 11-fold. As expected, the positive control (+)MK801 maleate induced neurodegenerative lesions as evidenced by typical neuronal necrosis in the PCG/RSC of the brain in all rats treated with this positive control compound.

Example 7

The studies of this example assessed the efficacy, safety, and dose-response of intranasal esketamine in patients with treatment-resistant depression (TRD).

Materials and Methods

Ethical Practices

An Independent Review Board (United States)/Independent Ethics Committee (Belgium) approved the study protocol and amendments. The study was conducted in accordance with ethical principles that have their origin in the Declaration of Helsinki, consistent with Good Clinical Practices and applicable regulatory requirements. All individuals provided written informed consent before participating in the study. The study is registered at clinicaltrials.gov, NCT01998958.

Study Population

The study enrolled medically stable (based on physical examination, medical history, vital signs, and 12-lead ECG performed at screening) adults (20 to 64 years) with a diagnosis of MDD, according to the Diagnostic and Statistical Manual of Mental Disorders Fourth edition—Text revised (DSM-IV-TR). See, American Psychiatric Association. Diagnostic and statistical manual of mental disorders (DSM-IV-TR). 4th ed, text revised. Washington, D.C.: American Psychiatric Association, 2000.

All participants had TRD, defined as inadequate response to ≥2 antidepressants (assessed by Massachusetts General Hospital Antidepressant Treatment Response Questionnaire; Rush, "The Inventory of Depressive Symptomatology (IDS): Psychometric properties", Psychol. Med., 1996, 26(3):477-486), with at least 1 in the current depression episode. Otherwise, an antidepressant failure from a prior episode was acceptable. All participants continued the antidepressants they were taking at study entry during the study.

At screening and pre-dose on day 1, eligible participants had a score of ≥34 on the 30-item, clinician-rated Inventory of Depressive Symptomatology (IDS-$C_{30}$) (Rush 1996 and Trivedi, "The Inventory of Depressive Symptomatology, Clinician Rating (IDS-C) and Self-Report (IDS-SR), and the Quick Inventory of Depressive Symptomatology, Clinician Rating (QIDS-C) and Self-Report (QIDS-SR) in public sector patients with mood disorders: a psychometric evaluation", Psychol. Med., 2004, 34(1):73-82), corresponding to moderate-to-severe depression. Key exclusion criteria included recent or current suicidal ideation with intent to act, suicidal behavior, or homicidal ideation/intent, diagnosis of bipolar or related disorders, intellectual disability, psychotic disorder, MDD with psychosis, post-traumatic stress disorder, obsessive-compulsive disorder, substance/alcohol use disorders in the last year, and recent use of cannabis.

The study enrolled medically stable (based on physical examination, medical history, vital signs, and 12-lead ECG performed at screening) adults (20 to 64 years) with a diagnosis of MDD, according to the Diagnostic and Statistical Manual of Mental Disorders Fourth edition—Text revised (DSM-IV-TR). Participant's major depressive episode and treatment response were evaluated to confirm participant met criteria using the "State vs. Trait, Assessibility, Face Validity, Ecological Validity, Rule of Three P's" (SAFER) criteria interview [Targum, "Redefining affective disorders: relevance for drug Development", CNS Neurosci. Ther., 2008, 14(1):2-9], administered by remote, independent raters.

Key exclusion criteria included recent or current suicidal ideation with intent to act, suicidal behavior, or homicidal ideation/intent, diagnosis of bipolar or related disorders, intellectual disability, psychotic disorder, major depressive disorder (MDD) with psychosis, cluster B personality disorder (based on clinical assessment by the investigator), post-traumatic stress disorder, obsessive-compulsive disorder, history of non-response to electroconvulsive therapy. Individuals with substance or alcohol abuse or dependence during the past year were excluded, as well as those testing positive for cannabis at screening.

Study Design

This phase 2, 2-panel, double-blind, doubly-randomized, delayed-start, placebo-controlled study (a variant of sequential parallel comparison design) was conducted from 28 Jan. 2014 to 25 Sep. 2015. See, e.g., Chi, "On clinical trials with a high placebo rate. Contemporary Clinical Trials Communications", 2016, 2:34-53; Fava, "The problem of the placebo response in clinical trials for psychiatric disorders: culprits, possible remedies, and a novel study design approach", Psychother. Psychosom. 2003, 72(3):115-27; Chen, "Evaluation of performance of some enrichment designs dealing with high placebo response in psychiatric clinical trials", Contemp. Clin. Trials, 2011, 32(4):592-604; Fava, "A double-blind, placebo-controlled study of aripiprazole adjunctive to antidepressant therapy among depressed outpatients with inadequate response to prior antidepressant therapy (ADAPT-A Study)", Psychother. Psychosom., 2012, 81(2):87-97); Chen, "A sequential enriched design for target patient population in psychiatric clinical trials" Stat. Med., 2014, 33(17):2953-2967; Doros, "A repeated measures model for analysis of continuous outcomes in sequential parallel comparison design studies", Stat. Med., 2013, 32(16):2767-2789; Huang, "Comparison of test statistics for the sequential parallel design", Statistics in Biopharmaceutical Research, 2010, 2(1):42-50; Ivanova, "Optimality, sample size, and power calculations for the sequential parallel comparison design", Stat. Med., 2011, 30(23):2793-803; Papakostas, "L-methylfolate as adjunctive therapy for SSRI-resistant major depression: results of two randomized, double-blind, parallel-sequential trials", Am. J. Psychiatry, 2012, 169(12):1267-1274; Roy, "An examination of the efficiency of the sequential parallel design in psychiatric clinical trials", Clinical Trials. 2007, 4:309-317; Rybin, "Placebo non-response measure in sequential parallel comparison design studies", Stat. Med., 2015, 34(15):2281-2293; Tamura, "An examination of the efficiency of the sequential parallel design in psychiatric clinical trials", Clin. Trials. 2007, 4(4):309-317; and Tamura, "Estimation of treatment effect for the sequential parallel design", Stat. Med., 2011, 30(30):3496-506.

In Panel A, reported here, 14 study sites (13 in US, 1 in Belgium) enrolled participants into the study. The study consisted of four phases: 1) screening, 2) double-blind treatment (days 1 to 15), comprised of two 1-week periods (Period 1, Period 2), 3) optional open-label treatment (days 15 to 74) with tapering of intranasal dosing frequency, and 4) post-treatment follow-up (8 weeks). Based on prior studies of ketamine where efficacy was reported after 1-2 doses, the duration of each period in the double-blind phase was 1 week, during which time it was expected that efficacy could be achieved. This design allowed evaluation of the dose(s) needed to proceed to evaluation in phase 3. The purpose of the open-label flexible-dose phase was to evaluate the impact of less frequent dosing on sustaining efficacy.

At the beginning of double-blind Period 1, eligible participants were randomized (3:1:1:1) to intranasal placebo or esketamine 28, 56, or 84 mg, twice weekly (days 1 and 4) based on the first of two computer-generated randomization schedules (Period 1 and Period 2). Randomization was balanced by using randomly permuted blocks and stratified by study center. At the end of Period 1, those randomized to placebo who had moderate-to-severe symptoms (assessed by Quick Inventory of Depressive Symptomatology-Self Report (Trivedi 2016 and Rush, "The 16-item Quick Inventory of Depressive Symptomatology (QIDS) Clinician Rating (QIDS-C) and Self-Report (QIDS-SR): A psychometric evaluation in patients with chronic major depression", Biol. Psychiatry, 2003, 54(5):573-583) [QIDS-$SR_{16}$] total score: moderate, 11-16; severe, >16) were re-randomized (1:1:1:1) to intranasal esketamine 28, 56, or 84 mg or placebo, twice weekly (days 8 and 11), while those having mild or no symptoms continued on placebo. To maintain the blind, all participants completed an identical process prior to entry into Period 2, whether or not they were re-randomized. Regardless of response in the double-blind phase, all participants were eligible to enter the optional open-label phase. Esketamine (56 mg) was administered on the first day of the open-label phase (study day 15); subsequent doses could be adjusted (range: 28 to 84 mg) based on investigator's clinical judgment, with administration twice weekly for first 2 weeks, weekly for next 3 weeks, then every 2 weeks thereafter.

Study Drug and Administration

Study drug was provided in a disposable nasal spray device containing 200 µl of solution (i.e., 2 sprays). Each device delivered either 16.14 mg esketamine hydrochloride (14 mg esketamine base) per 100-µl spray or placebo. To maintain the blind, the placebo solution (intranasal solution of water for injection) had a bittering agent (denatonium benzoate) added to simulate the taste of esketamine intranasal solution. As described above, the antidepressant that participants had been receiving immediately prior to study entry was continued unchanged.

On each dosing day during the double-blind phase, participants self-administered 1 spray of study drug (esketamine or placebo) into each nostril at 3 time points, each 5 minutes apart. In the open-label phase, depending on the dose selected, participants self-administered 1 spray of esketamine into each nostril at 1, 2, or 3 time points (corresponding to 28, 56, or 84 mg, respectively), each separated by 5 minutes.

Efficacy Assessments

Efficacy was assessed with the Montgomery-Asberg Depression Rating Scale (MADRS; Montgomery, "A new depression scale designed to be sensitive to change", Br. J. Psychiatry, 1979, 134:382-389; Williams, "Development and reliability of a structured interview guide for the Montgomery Asberg Depression Rating Scale (SIGMA)", Br. J. Psychiatry, 2008, 192(1):52-58) on days 1 (pre-dose and 2 hour post-dose), 2, 8 (pre-dose), 9, and 15, using the structured interview guide (SIGMA). See, Williams 2008.

Overall illness severity was assessed on the Clinical Global Impression of Severity (CGI-S) scale (Guy, "ECDEU Assessment Manual for Psychopharmacology—Revised (DHEW Publ No ADM 76-338)", Rockville, Md.: U.S. Department of Health, Education, and Welfare, Public Health Service, Alcohol, Drug Abuse, and Mental Health Administration, NIMH Psychopharmacology Research Branch, Division of Extramural Research Programs; 1976, pp 218-222). Participants assessed their severity of anxiety on the Generalized Anxiety Disorder 7-item (GADS-7) Scale (See, Tables 157 and 158). See, Spitzer, "A brief measure for assessing generalized anxiety disorder—the GAD-7", Arch. Intern. Med., 2006, 166(10):1092-1097.

TABLE 157

GAD-7: ANCOVA Analysis of Change from Baseline to Study End Point[a]

|  | Placebo | Esketamine 28 mg | Esketamine 56 mg | Esketamine 84 mg |
|---|---|---|---|---|
| Period 1 | | | | |
| N | 33 | 11 | 11 | 12 |
| LS mean (SE) | −1.7 (0.88) | −1.5 (1.34) | −3.1 (1.34) | −5.1 (1.30) |
| LS mean difference from placebo (SE) | | −0.21 (1.461) | −1.40 (1.478) | −3.44 (1.414) |
| p-value[b] | | 0.558 | 0.174 | 0.009 |
| Period 2 | | | | |
| N | 6 | 8 | 9 | 5 |
| LS mean (SE) | 0.4 (1.02) | −1.6 (0.87) | 1.0 (0.98) | −0.9 (1.02) |
| LS mean difference from placebo (SE) | | −2.02 (1.089) | 0.60 (1.033) | −1.25 (1.205) |
| p-value[b] | | 0.039 | 0.718 | 0.156 |
| Periods 1 and 2 Combined | | | | |
| p-value | | 0.144 | 0.360 | 0.006 |

[a]Change from first day to day 8 in each period;
[b]Based on ANCOVA model with treatment, country, and Period 1 baseline value as a covariate;
[c]Based on ANCOVA model with treatment, country, and Period 2 baseline QIDS-SR$_{16}$ score (moderate or severe), and Period 2 baseline value as a covariate.

TABLE 158

CGI-S: ANCOVA Analysis of Change from Baseline to Study End Point[a]

|  | Placebo | Esketamine 28 mg | Esketamine 56 mg | Esketamine 84 mg |
|---|---|---|---|---|
| Period 1 | | | | |
| N | 33 | 11 | 11 | 12 |
| Median (Range) | 5.0 (1, 6) | 4.0 (3, 5) | 4.0 (1, 5) | 4.0 (1, 6) |
| Median Change (Range) | 0.0 (−3, 2) | −1.0 (−2, 1) | −1.0 (−3, 0) | −0.5 (−4, 0) |
| p-value[b] | | 0.028 | 0.004 | 0.049 |
| Period 2 | | | | |
| N | 6 | 8 | 9 | 5 |
| Median (Range) | 5.0 (4, 5) | 4.0 (3, 5) | 5.0 (4, 6) | 4.0 (3, 5) |
| Median Change (Range) | | −1.0 (−1, 0) | −1.0 (−2, 0) | −1.0 (−2, 0) |
| p-value[c] | 0.0 (0, 2) | 0.009 | 0.050 | 0.022 |
| Periods 1 and 2 Combined | | | | |
| p-value | | <0.001 | <0.001 | 0.004 |

[a]Change from first day to day 8 in each period;
[b]Based on ANCOVA model on ranks of change with treatment, country, and Period 1 baseline value (unranked) as a covariate;
[c]Based on ANCOVA model on ranks of change with treatment, country, Period 2 baseline QIDS-SR$_{16}$ score (moderate or severe), and Period 2 baseline value (unranked) as a covariate.

Safety Assessments

Adverse events were monitored throughout the study. Other safety assessments (i.e., laboratory tests, vital signs, physical examination) were performed at pre-specified time points. Vital signs, the Clinician Administered Dissociative States Scale (CADSS; Bremner, "Measurement of dissociative states with the clinician-administered dissociative states scale (CADSS)", J. Traumatic Stress, 1998, 11(1):125-136), and the 4-item positive symptom subscale from the Brief Psychiatric Rating Scale (BPRS; Overall, "The Brief Psychiatric Rating Scale. Psychological Reports", 1962, 10:799-812) were assessed pre-dose, at 40 minutes, and 2 hours post-dose.

Statistical Methods

Efficacy data were analyzed in intent-to-treat (ITT) analysis sets for each period and phase. The ITT analysis sets included all participants who received at least 1 dose of study medication during that period or phase and had baseline and at least one post-baseline MADRS total score within that period or phase.

Safety data were analyzed in Period 1, Period 2, double-blind, and open-label data sets, for all subjects receiving at least 1 dose of study medication.

Efficacy Endpoints and Analyses

The primary efficacy endpoint—change from baseline (pre-dose, day 1 in each period) to endpoint (day 8 in each period) in MADRS total score—was analyzed using the analysis of covariance (ANCOVA) model. For Period 1, the model included treatment and country as factors, and baseline MADRS total score as covariate. For Period 2, the model included treatment and country as factors, Period 2 baseline QIDS-SR$_{16}$ score (moderate or severe), and Period 2 baseline MADRS total score as a continuous covariate.

Given the consistency between Periods 1 and 2 results (Chi 2016), esketamine dose groups were compared to placebo using a combined test on the weighted test statistics for each period in the double-blind treatment phase. A dose-response analysis on primary efficacy endpoint was performed using data combined from both periods. The Multiple Comparison Procedure-Modelling (MCP-Mod) methodology was performed (Williams 2008; Bretz, "Combining multiple comparisons and modeling techniques in dose-response studies", Biometrics, 2005, 61:738-748).

Sample Size Determination

Sample size was determined based on the following differences between intranasal esketamine and placebo for mean change from baseline in MADRS total score: 9-point treatment difference was assumed for Period 1 (day 8), 7-point treatment difference for Period 2 (day 15) was assumed for individuals with a moderate QIDS-SR$_{16}$ score, and 9-point treatment difference for Period 2 (day 15) was assumed for individuals with severe QIDS-SR$_{16}$ score.

Based on results of an esketamine IV study (Singh 2016), it was estimated that 40% of placebo participants would have a moderate QIDS-SR$_{16}$ score and 55%, a severe QIDS-SR$_{16}$ score at the end of Period 1 (day 8 pre-dose). Additional assumptions for the sample size calculation included standard deviation of 10, 92.5% power for the combined data from day 8 and day 15 (Liu, "Doubly-randomized delayed-start design for enrichment studies with responders or nonresponders", J. Biopharm. Stat., 2012, 22(4):737-757), overall 1-sided significance level of 0.05, and 5% drop-out rate for Period 1. It was calculated that this panel of the doubly-randomized, outcome-based design required 60 individuals to be randomly assigned to treatment on day 1 in a 3:1:1:1 ratio (30 on placebo and 10 per intranasal esketamine dose group).

Study Results

Participants

A total of 126 individuals were screened, of which 67 met the eligibility criteria and were randomized. Of 33 participants randomized to placebo in Period 1, 28 had QIDS-SR$_{16}$ score ≥11 at the end of Period s and thus were randomly re-assigned to esketamine or placebo in Period 2 (FIG. 73). Most randomized participants (63/67, 94%) completed Period and the 2-week double-blind phase (i.e., Periods and 2 combined 60/67, 90%; hereafter termed "completers". Of these, 57 entered the open-label phase, with 51 subsequently entering the follow-up phase, of whom 41 completed the week 8 follow-up visit.

The treatment groups were similar with respect to demographic and baseline clinical characteristics (Table 159). Sixty-four percent of participants reported only 1 antidepressant treatment failure in the current episode (in addition to 1 in prior episodes), approximately 22% had 2, and the remainder reported ≥3 antidepressant failures. Of note, 39% of participants reported use of atypical antipsychotics as an adjunctive treatment of MDD prior to study entry.

TABLE 159

Demographics and Baseline Characteristics

| Parameter | Placebo N = 33 | Esketamine | | | Total N = 67 |
| --- | --- | --- | --- | --- | --- |
| | | 28 mg N = 11 | 56 mg N = 11 | 84 mg N = 12 | |
| Age, years | | | | | |
| Mean (SD) | 44.4 (9.60) | 42.1 (10.31) | 42.7 (11.23) | 49.8 (9.29) | 44.7 (10.04) |
| Range | 21-57 | 21-53 | 20-57 | 32-63 | 20-63 |
| Sex, n (%) | | | | | |
| Female | 18 (54.5) | 5 (45.5) | 9 (81.8) | 6 (50.0) | 38 (56.7) |
| Male | 15 (45.5) | 6 (54.5) | 2 (18.2) | 6 (50.0) | 29 (43.3) |
| Race, n (%) | | | | | |
| White | 24 (72.7) | 7 (63.6) | 6 (54.5) | 11 (91.7) | 48 (71.6) |
| Black or African American | 9 (27.3) | 4 (36.4) | 4 (36.4) | 1 (8.3) | 18 (26.9) |
| American Indian or Alaska native | 0 | 0 | 1 (9.1) | 0 | 1 (1.5) |
| BMI, kg/m$^2$ | | | | | |
| Mean (SD) | 29.7 (6.00) | 29.0 (6.18) | 30.1 (8.30) | 30.4 (8.47) | 29.8 (6.77) |
| Range | 17-49 | 23-44 | 19-45 | 21-49 | 17-49 |
| MADRS Total Score | | | | | |
| Mean (SD) | 35.0 (5.18) | 31.3 (3.80) | 33.2 (6.26) | 35.0 (4.22) | 34.1 (5.11) |
| Range | 25-45 | 26-37 | 23-46 | 27-41 | 23-46 |
| IDS-C$_{30}$ Total Score Category, n (%) | | | | | |
| Moderate (34-39) | 10 (30.3) | 4 (36.4) | 3 (27.3) | 3 (25.5) | 20 (29.9) |
| Severe (40-48) | 15 (45.5) | 7 (63.6) | 6 (54.5) | 9 (75.0) | 37 (55.2) |
| Very severe (≥49) | 8 (24.2) | 0 | 2 (18.2) | 0 | 10 (14.9) |
| Mean (SD) | 43.9 (6.81) | 41.1 (4.25) | 42.3 (6.72) | 42.5 (4.23) | 42.9 (6.02) |
| Range | 35-59 | 35-48 | 34-57 | 34-48 | 34-59 |

TABLE 159-continued

Demographics and Baseline Characteristics

| Parameter | Placebo N = 33 | Esketamine 28 mg N = 11 | Esketamine 56 mg N = 11 | Esketamine 84 mg N = 12 | Total N = 67 |
|---|---|---|---|---|---|
| Duration of Current Episode (wks) | | | | | |
| Mean (SD) | 65.2 (79.93) | 56.1 (39.28) | 39.9 (21.82) | 66.6 (51.54) | 59.8 (63.5) |
| Range | 12-302 | 14-122 | 10-75 | 18-162 | 10-302 |
| Number of Major Depressive Episodes | | | | | |
| <3 | 4 (12.1) | 3 (33.3) | 2 (20.0) | 2 (18.2) | 11 (17.5) |
| ≥3 | 29 (87.9) | 6 (66.7) | 8 (80.0) | 9 (81.8) | 52 (82.5) |
| Number of Antidepressants in Current Episode of Major Depression | | | | | |
| 1 | 21 (63.6) | 6 (54.5) | 8 (72.7) | 8 (66.7) | 43 (64.2) |
| 2 | 7 (21.2) | 4 (36.4) | 2 (18.2) | 2 (16.7) | 15 (22.4) |
| ≥3 | 5 (15.2) | 1 (9.1) | 1 (9.1) | 2 (16.7) | 9 (13.4) |

Efficacy Results

Mean MADRS total score decreased from baseline to day 8 in Period E and from day 8 to day 15 in Period 2 in all groups, with greater improvement in all esketamine dose groups compared to placebo (LS mean difference ranging from −5.0 to −10.5 in Period 1 and from −3.1 to −6.9 in Period 2; Table 160). Change from baseline in MADRS total score was greater in all 3 esketamine groups than in the placebo group after 1 week of treatment (p=0.02, p=0.001, and p<0.001 for esketamine 28 mg, 56 mg and 84 mg, respectively); the ascending dose-response relationship was significant (p<0.001). Response was rapid in onset (FIGS. 74A and 74B; FIGS. 76A and 76B) and appeared to increase over time during repeated dosing, as evidenced by a decrease in mean MADRS total score over the open-label phase (mean [SE] change from open-label baseline to day 74: −7.2 [1.84]) despite reduced dosing frequency in the open-label phase. In addition, improvement in mean MADRS ratings persisted over the 8-week follow-up phase (without additional esketamine doses) in those participants who remained in the study (FIG. 75).

TABLE 160

MADRS Total Score: Change from Baseline to 2 Hours, 24 Hours, and to Period Endpoint

| | Placebo | Esketamine 28 mg | Esketamine 56 mg | Esketamine 84 mg |
|---|---|---|---|---|
| Period 1 | | | | |
| N | 33 | 11 | 11 | 12 |
| Mean (SD) MADRS total score at baseline | 35.0 (5.18) | 31.3 (3.80) | 33.2 (6.26) | 35.0 (4.22) |
| Change at 2 hours | | | | |
| LS mean change (SE) | −9.7 (1.76) | −16.4 (2.76) | −14.3 (2.70) | −17.6 (2.60) |
| LS mean difference placebo (SE) | | −6.7 (3.03) | −4.6 (2.96) | −7.9 (2.84) |
| p-value | | 0.02 | 0.06 | 0.003 |
| Responders, n (%) | 6 (18.2) | 6 (54.5) | 4 (36.4) | 7 (58.3) |
| Remitters, n (%) | 1 (3.0) | 3 (27.3) | 2 (18.2) | 3 (25.0) |
| Change at 24 hours | | | | |
| LS mean change (SE) | −5.7 (1.79) | −14.8 (2.80) | −15.7 (2.74) | −16.4 (2.64) |
| LS mean difference placebo (SE) | | −9.1 (3.08) | −10.0 (3.00) | −10.7 (2.88) |
| p-value | | 0.002 | <0.001 | <0.001 |
| Responders, n (%) | 1 (3.0) | 4 (36.4) | 3 (27.3) | 5 (41.7) |
| Remitters, n (%) | 0 | 4 (36.4) | 2 (18.2) | 3 (25.0) |
| Change at study period endpoint | | | | |
| LS mean change (SE) | −4.9 (1.74) | −9.8 (2.72) | −12.4 (2.66) | −15.3 (2.56) |
| LS mean difference placebo (SE) | | −5.0 (2.99) | −7.6 (2.91) | −10.5 (2.79) |
| p-value | | 0.05 | 0.006 | <0.001 |
| Responders, n (%) | 2 (6.1) | 1 (9.1) | 2 (18.2) | 5 (41.7) |
| Remitters, n (%) | 1 (3.0) | 1 (9.1) | 1 (9.1) | 3 (25.0) |
| Period 2* | | | | |
| N | 6 | 8 | 9 | 5 |
| Mean (SD) MADRS total score at baseline | 29.3 (5.79) | 31.3 (7.09) | 34.9 (6.13) | 30.4 (4.67) |

TABLE 160-continued

MADRS Total Score: Change from Baseline to 2 Hours, 24 Hours, and to Period Endpoint

|  | Placebo | Esketamine 28 mg | Esketamine 56 mg | Esketamine 84 mg |
|---|---|---|---|---|
| Change at 2 hours |  |  |  |  |
| LS mean change (SE) | −6.8 (3.74) | −10.3 (3.18) | −11.7 (3.22) | −11.6 (3.44) |
| LS mean difference placebo (SE) |  | −3.5 (3.82) | −4.9 (3.92) | −4.9 (4.36) |
| p-value |  | 0.18 | 0.11 | 0.14 |
| Responders, n (%) | 1 (16.7) | 1 (12.5) | 2 (22.2) | 2 (40.0) |
| Remitters, n (%) | 1 (16.7) | 1 (12.5) | 0 | 2 (40.0) |
| Change at 24 hours |  |  |  |  |
| LS mean change (SE) | −4.1 (4.09) | −8.9 (3.48) | −10.2 (3.52) | −11.6 (3.76) |
| LS mean difference placebo (SE) |  | −4.8 (4.18) | −6.1 (4.29) | −7.5 (4.77) |
| p-value |  | 0.13 | 0.09 | 0.07 |
| Responders, n (%) | 0 | 0 | 1 (11.1) | 2 (40.0) |
| Remitters, n (%) | 0 | 0 | 0 | 1 (20.0) |
| Change at study period endpoint |  |  |  |  |
| LS mean change (SE) | −4.5 (2.92) | −7.6 (2.49) | −8.9 (2.51) | −11.4 (2.68) |
| LS mean difference placebo (SE) |  | −3.1 (2.99) | −4.4 (3.06) | −6.9 (3.41) |
| p-value |  | 0.15 | 0.08 | 0.03 |
| Responders, n (%) | 0 | 1 (12.5) | 0 | 1 (20.0) |
| Remitters, n (%) | 0 | 1 (12.5) | 0 | 1 (20.0) |
| Period 1 and Period 2 Combined |  |  |  |  |
| Mean difference placebo (SE) |  | −4.2 (2.09) | −6.3 (2.07) | −9.0 (2.13) |
| 90% CI for mean difference vs. placebo |  | −7.67, −0.79 | −9.71, −2.88 | −12.53, −5.52 |
| Test statistic |  | −2.02 | −3.04 | −4.24 |
| p-value |  | 0.02 | 0.001 | <0.001 |

*The study samples reported here for Period 2 include only the placebo nonresponsive participants re-randomized following Period 1.

For completers who received 2 weeks of the same treatment in the double-blind phase, mean decrease in MADRS total score was greater in each esketamine dose group as compared with placebo at day 15, with the magnitude of decrease directly related to dose (treatment differences relative to placebo of −12.5, −8.3, and −6.0 for esketamine 84 mg, 56 mg, and 28 mg, respectively). Efficacy appeared to be better sustained between drug administrations with the 2 higher doses (FIG. 73).

Among those who received the same treatment for bath periods and completed the double-blind phase, the proportion of responders (defined as ≥50% improvement from baseline in MADRS total score) in each esketamine dose group was numerically higher than in the placebo group at the Period 2 endpoint (28 mg: 37.5% [3/8], 56 mg: 36.4% [4/11], 84 mg: 50.0% [5/10], placebo 10% [1/10]). A similar trend for remission (defined as MADRS total score ≤10) was observed across groups. Among completers who received the same treatment in both periods, more participants treated with the 2 higher esketamine doses, as compared to placebo, remitted after 2 weeks of treatment (12.5%, 27.3%, and 40.0% in the 28 mg, 56 mg and 84 mg groups, respectively, and 10.0%, in the placebo group). Response and remission rates at the end of the open-label and follow-up phases are presented by type of treatment in the double-blind and open-label phases in Table 161.

TABLE 161

Response, Remission, and Relapse Rates for Participants who Completed the Open-Label and Follow-up Phases

|  | Placebo/ Placebo/OL Esketamine N = 10 | Placebo/ Esketamine/OL Esketamine N = 20 | Esketamine/ Esketamine/OL Esketamine N = 27 | Total N = 57 |
|---|---|---|---|---|
| Response Rate |  |  |  |  |
| OL endpoint - day 74, n | 6 | 10 | 18 | 34 |
| ≥50% improvement, n (%) | 6 (100) | 5 (50.0) | 11 (61.1) | 22 (64.7) |
| Week 8 (Follow-up), n | 7 | 12 | 22 | 41 |
| ≥50% improvement, n (%) | 5 (71.4) | 3 (25.0) | 15 (68.2) | 23 (56.1) |
| Remission Rate |  |  |  |  |
| OL endpoint - day 74, n | 6 | 10 | 18 | 34 |
| No, n (%) | 4 (66.7) | 6 (60.0) | 13 (72.2) | 23 (67.6) |
| Yes, n (%) | 2 (33.3) | 4 (40.0) | 5 (27.8) | 11 (32.4) |

TABLE 161-continued

Response, Remission, and Relapse Rates for Participants who Completed the Open-Label and Follow-up Phases

|  | Placebo/ Placebo/OL Esketamine N = 10 | Placebo/ Esketamine/OL Esketamine N = 20 | Esketamine/ Esketamine/OL Esketamine N = 27 | Total N = 57 |
|---|---|---|---|---|
| Week 8 (Follow-up), n | 7 | 12 | 22 | 41 |
| No, n (%) | 3 (42.9) | 9 (75.0) | 12 (54.5) | 24 (58.5) |
| Yes, n (%) | 4 (57.1) | 3 (25.0) | 10 (45.5) | 17 (41.5) |

Percentages calculated with the number of participants per a visit as denominator; percentage change is calculated based on Period 1 baseline; Response: MADRS total score ≥50%; Remission: MADRS total score ≤10. The follow-up phase includes data from 7 subjects enrolled under the original version of the protocol in which participants received 2 weeks of study drug during the open-label phase of the study and data from 50 subjects enrolled under a protocol amendment in which participants received up to 9 weeks of study drug during the open-label phase of the study.

Safety Results

Three of 56 (5%) esketamine-treated participants during the double-blind phase (compared to 0 on placebo) and 1 of 57 (2%) during the open-label phase had adverse events leading to discontinuation of study drug (1 event each of syncope, headache, dissociative syndrome, and ectopic pregnancy). During the double-blind phase, the 3 most common treatment-emergent adverse events observed among esketamine-treated participants were dizziness, headache, and perceptual changes/dissociative symptoms; the frequency of each was >2-fold higher for esketamine than for placebo (Table 162). A dose-response trend was noted for dizziness and nausea, but not for other adverse events. The type and frequency of adverse events reported in the open-label phase were similar to those in the double-blind phase; events reported for >10% of open-label participants included dizziness (38.6%), dysgeusia (22.8%), nausea (15.8%), headache (14.0%), and sedation (10.5%). Overall, 24.6% (14/57) of participants reported transient dissociative symptoms. The majority of adverse events occurring on dosing days were transient and either mild or moderate in severity. No death was reported.

TABLE 162

Summary of Most Frequently Reported[a] Treatment-Emergent Adverse Events (Double-Blind Safety Analysis Data Set)

| Preferred Term | Placebo N = 33 | 28 mg N = 19 | 56 mg N = 20 | 84 mg N = 17 | Total N = 56 |
|---|---|---|---|---|---|
| Total with events | 18 (55) | 11 (58) | 16 (80) | 15 (88) | 42 (75) |
| Dizziness | 1 (3) | 4 (21) | 8 (40) | 8 (47) | 20 (36) |
| Headache | 3 (9) | 6 (32) | 3 (15) | 3 (18) | 12 (21) |
| Dissociation[b,c] | 1 (3) | 0 | 7 (35) | 4 (24) | 11 (20) |
| Dysgeusia | 7 (21) | 2 (11) | 3 (15) | 5 (29) | 10 (18) |
| Nausea | 3 (9) | 2 (11) | 4 (20) | 4 (24) | 10 (18) |
| Dissociative disorder[b,c] | 0 | 2 (11) | 1 (5) | 4 (24) | 7 (13) |
| Hypoesthesia oral | 0 | 1 (5) | 4 (20) | 2 (12) | 7 (13) |
| Vertigo | 0 | 2 (11) | 1 (5) | 1 (6) | 4 (7) |
| Sedation | 0 | 1 (5) | 2 (10) | 1 (6) | 4 (7) |
| Feeling abnormal | 0 | 2 (11) | 1 (5) | 1 (6) | 4 (7) |
| Nasal discomfort | 3 (9) | 0 | 2 (10) | 1 (6) | 3 (5) |
| Hypertension | 2 (6) | 0 | 2 (10) | 1 (6) | 3 (5) |
| Oropharyngeal pain | 2 (6) | 0 | 1 (5) | 2 (12) | 3 (5) |
| Throat irritation | 0 | 1 (5) | 0 | 2 (12) | 3 (5) |
| Vision blurred | 0 | 0 | 0 | 2 (12) | 2 (4) |
| Insomnia | 1 (3) | 0 | 2 (10) | 0 | 2 (4) |
| Tunnel vision | 0 | 0 | 0 | 2 (12) | 2 (4) |
| Hypersomnia | 0 | 2 (11) | 0 | 0 | 2 (4) |
| Polyuria | 0 | 0 | 2 (10) | 0 | 2 (4) |

[a]Defined as ≥10% of participants in any esketamine dose group. Events presented in descending order in the total esketamine (combined doses) group.
[b]Participants reported either dissociative reaction or dissociative symptoms and, depending on the verbatim term used these events were coded as dissociative disorder or dissociative symptoms, respectively.
[c]All adverse events coded to dissociation or dissociative disorder resolved on the same day as dosing.

Most of the esketamine-treated participants manifested transient elevations in blood pressure (maximum mean change: systolic, 19.0 mmHg; diastolic, 10.3 mmHg) and heart rate (maximum mean change: 9.4 bpm) on dosing days. Maximum blood pressure values were observed in most cases at 10 or 40 minutes post-dose (systolic: 199 mmHg; diastolic: 115 mmHg); elevated values typically returned to the normal range by 2 hours post-dose (FIGS. 77 and 78). A dose effect was not observed for heart rate, although the greatest mean increases from baseline during both periods were observed in the 84 mg esketamine group.

Perceptual changes/dissociative symptoms, as measured by the CADSS, began shortly after the start of intranasal dosing, peaked around 30-40 minutes, and resolved by 2 hours (FIG. 79). Perceptual changes/dissociative symptoms attenuated in all dose groups with repeated dosing.

No participant manifested symptoms suggestive of psychosis based on the BPRS-positive assessment.

Discussion

A significant and clinically meaningful treatment effect (versus placebo) with 28 mg, 56 mg, and 84 mg doses of esketamine was observed, as evidenced by change in MADRS total score, with a significant relationship between esketamine dose and antidepressant response observed after 1 week of treatment. Duration of efficacy appeared shorter with the 28 mg dose administered twice weekly. Results from the open-label phase suggest that improvement in depressive symptoms can be sustained with lower frequency (weekly/every 2 weeks) of esketamine administration. Of note, the size of the medication-placebo difference was substantial from baseline to one week, and was larger than the mean difference from placebo seen at 6-8 weeks in antidepressant studies in the FDA database (Khan, "Has the rising placebo response impacted antidepressant clinical trial outcome? Data from the US Food and Drug Administration 1987-2013", World Psychiatry. 2017, 16(2):181-192). The majority of participants maintained improvement over the 2-month follow-up phase.

Of note, the 56 and 84 mg intranasal doses of esketamine produce plasma esketamine levels that are in the pharmacokinetic range achieved by IV esketamine at 0.2 mg/kg, which produced a similar clinical outcome as reported for ketamine 0.5 mg/kg IV (consistent with higher affinity for NMDA receptors relative to arketamine (White, "Comparative pharmacology of the ketamine isomers. Studies in volunteers", Br. J. Anaesth., 1985, 57(2):197-2030). See, Singh 2016.

In this first study of intranasal esketamine for TRD, efficacy and safety were compared to placebo using a double-blind, doubly-randomized, delayed-start design (Chi 2016), allowing for a smaller sample size to assess efficacy, dose-response, and safety than a standard parallel-group design, while preserving a low chance of type 2 error in order not to miss the efficacy signal. The key aim of the design was to only include placebo participants from Period 1 who required treatment in Period 2 and to re-randomize them to receive 1 of 3 intranasal esketamine doses or intranasal placebo. At the end of the trial, efficacy data from both randomizations (day 1 and day 8) were combined in an integrated analysis. As the re-randomized placebo non-responders were expected to have a lower placebo response, this approach was used to mitigate high placebo responses observed in psychiatric clinical trials (Chi 2016). The consistency in results obtained from the Period 1 and Period 2 samples support their combination using weights (Chi 2016), although caution is required in interpretation due to the small sample size.

In general, the esketamine doses evaluated in this study (28, 56, and 84 mg) appeared safe, with no new or unexpected safety concerns observed. Analysis of perceptual change symptoms (measured by CADSS assessment) suggests onset shortly after initiation of esketamine and resolution by 2 hours after administration. These symptoms were dose-dependent and attenuated with repeated administration. In contrast, antidepressant efficacy did not attenuate across administrations.

Overall, transient increases in blood pressure post-dose, particularly increases in systolic blood pressure, support an increase in cardiac output as the underlying mechanism, consistent with previous reports for ketamine (Murrough 2013).

Generalizability of study findings is limited by small sample size and enrollment criteria that excluded individuals with a history of psychotic symptoms, substance/alcohol use disorders, recent use of cannabis, or significant medical comorbidities. Also excluded were individuals having current suicidal ideation with intent, a group that was evaluated in a separate, study (Murrough 2013). Difficulty blinding esketamine, despite adding a bittering agent to placebo to mimic the taste of esketamine, is another limitation.

Conclusions

In summary, intranasal esketamine administered at doses of 28, 56, and 84 mg appeared efficacious in treating TRD. There was evidence of robust and durable efficacy in the double-blind treatment phase (56 and 84 mg). Improvement in depressive symptoms persisted over the open-label phase, despite reduced dosing frequency, and for up to 2 months after cessation of esketamine dosing.

Example 8: Validated Pharmacokinetic Method

This example provides an LC-MS/MS method for the determination of ketamine and norketamine in sodium heparin human plasma using ketamine-$d_4$ and norketamine-$d_4$ as the respective internal standards (IS).

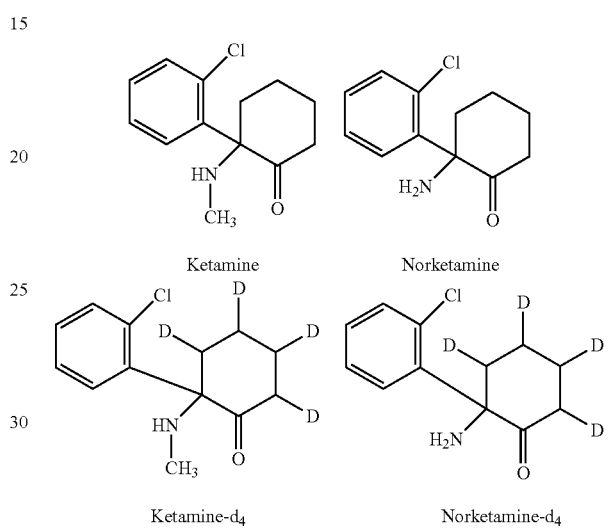

All the data presented herein met the method validation acceptance criteria defined in the validation protocol and fulfilled the requirements and recommendations in the FDA guidance for bioanalytical method validations for the parameters tested.

In summary, this method has been validated for the determination of ketamine and norketamine in sodium heparin human plasma. Based on a 25 µL sample volume, the lower limit of quantitation (LLOQ) is 0.500/0.500 ng/mL for ketamine/norketamine. The dynamic range of the method is 0.500/0.500-500/500 ng/mL for ketamine/norketamine. The re-injected samples were reproducible at room temperature for at least 161.5 hours after the initial injection. There was no significant injection carryover detected.

The validation study successfully evaluated intra-run and inter-run accuracy and precision, selectivity, sensitivity, linearity, recovery, matrix effect, maximum batch-size evaluation, reinjection reproducibility, and carry-aver evaluation. This method was determined to be suitable for the determination of ketamine and norketamine in human plasma using solid phase extraction (SPE) automation. See, Table 163.

TABLE 163

| Validation Summary for the Determination of Ketamine and Norketamine | |
|---|---|
| Method description | The method is an LC-MS/MS method for the determination of ketamine and norketamine in sodium heparin human plasma using ketamine-$d_4$ and norketamine-$d_4$ as the respective internal standards (IS). Ketamine, norketamine, and the internal standards were extracted from human plasma using automated solid phase extraction. Reversed-phase HPLC separation was achieved with a Phenomenex Synergi Polar-RP column, (50 × 2.0 mm, 4 micron). MS/MS detection was set at mass transitions of m/z 238.1→125.0 for ketamine, m/z 224.1→125.0 for norketamine, m/z 242.1→129.0 for ketamine-$d_4$ (IS), and m/z 228.1→129.0 for norketamine-$d_4$ (IS) in TIS positive mode. |

TABLE 163-continued

Validation Summary for the Determination of Ketamine and Norketamine

| | | | | | |
|---|---|---|---|---|---|
| Sample volume | 25 µL | | | | |
| Regression | Linear Regression | | | | |
| Weighting factor | $1/x^2$ | | | | |
| Dynamic range | 0.500-500 ng/mL for ketamine | | | | |
| | 0.500-500 ng/mL for norketamine | | | | |
| QC concentrations | 0.500 ng/mL (LLOQ), 1.50 ng/mL, 80.0 ng/mL, 375 ng/mL for ketamine | | | | |
| | 0.500 ng/mL (LLOQ), 1.50 ng/mL, 80.0 ng/mL, 375 ng/mL for norketamine | | | | |
| Analytes | Ketamine | | | Norketamine | |
| Internal standards | Ketamine-$d_4$ | | | Norketamine-$d_4$ | |
| Linearity | $R^2 \geq 0.9986$ | | | $R^2 \geq 0.9979$ | |
| Lower limit of quantitation (LLOQ) | 0.500 ng/mL | | | 0.500 ng/mL | |
| Average recovery of the Analyte (%) | 88.6 | | | 88.5 | |
| Average recovery of the IS (%) | Per BIO-201 guidelines, if a stable isotope labeled IS was used, the recovery established for the unlabeled analyte will suffice and the recovery for the stable isotope labeled IS will not be required. | | | | |

| QC Levels | | LLOQ | Low, Mid, High | LLOQ | Low, Mid, High |
|---|---|---|---|---|---|
| QC Intra-run | Intra-run 1 | 7.1 | 1.0 to 3.1 | 7.4 | 2.4 to 5.7 |
| precision range | Intra-run 2 | 4.7 | 1.6 to 3.1 | 5.3 | 2.7 to 3.6 |
| (% CV) | Intra-run 3 | 6.5 | 1.3 to 1.8 | 4.3 | 1.3 to 3.5 |
| QC Intra-run | Intra-run 1 | 1.0 | −2.0 to 0.8 | −2.0 | 0.0 to 1.1 |
| accuracy range | Intra-run 2 | 7.8 | −1.3 to 2.1 | 2.0 | −4.0 to 1.6 |
| (% Bias) | Intra-run 3 | −2.0 | 2.7 to 2.3 | 0.2 | 0.0 to 1.9 |
| QC Inter-run precision range (% CV) | | 7.1 | 1.8 to 2.7 | 5.7 | 2.2 to 4.6 |
| QC Inter-run accuracy range (% Bias) | | 2.2 | −2.0 to 1.0 | 0.0 | −1.3 to 1.3 |

| | |
|---|---|
| QC sample bench-top stability | 68.5 hours at room temp |
| Stock solution stability | 629 days at −20° C. and 6 hours at room temperature under white light for ketamine and norketamine stock solutions. |
| | 610 days at −20° C. for ketamine/norketamine spike solutions |
| Processed sample stability | 146.5 hours at room temperature |
| Reinjection reproducibility | 161.5 hours at room temperature |
| QC sample freeze/thaw stability | 3 freeze (−20° C.)/thaw (ice-water bath) cycles |
| | 3 freeze (−20° C.)/thaw (room temperature) cycles |
| Dilution integrity | 7500/7500 ng/mL diluted 20-fold for ketamine/norketamine |
| QC sample long-term storage stability | 1552 days at −20° C. |
| Matrix Effect | IS-normalized Matrix factor = 1.03 ± 0.03 at 1.50 ng/mL with % CV = 2.9% for ketamine |
| | IS-normalized Matrix factor = 1.02 ± 0.06 at 375 ng/mL with % CV = 5.9% for ketamine |
| | IS-normalized Matrix factor = 1.05 ± 0.03 at 1.50 ng/mL with % CV = 2.9% for norketamine |
| | IS-normalized Matrix factor = 1.04 ± 0.05 at 375 ng/mL with % CV = 4.8% for norketamine |
| Hemolysis | The hemolysis evaluation met the acceptance criteria. |
| LLOQ Selectivity | The LLOQ selectivity samples prepared in human plasma were within acceptance criteria (the accuracy was within ±20.0% for five out of six lots of plasma for ketamine and within 20.0% for all six lots for norketamine). |
| Blank Selectivity | The blank selectivity samples were within acceptance criteria. All 6 blank samples at the retention time of the analytes were within 20.0% of the mean analyte peak area of the acceptable LLOQ selectivity samples and all 6 blank samples at the retention time of the IS were within 5.0% of the mean IS peak area of the acceptable LLOQ selectivity samples. |
| Batch Size | 214 samples |
| Injection Carryover | No significant carryover was observed in any of the double blank samples that were evaluated for injection carryover. |
| Whole Blood Stability | 120 minutes at room temperature and in an ice-water bath (0-4° C.) |
| Inter-conversion | The inter-conversion from ketamine to norketamine or vice versa was ≤5%. |
| Interference | There was no interference detected from either of the analytes on the internal standards. Nor was there any interference detected from dehydronorketamine on ketamine and norketamine. |
| Stock Solution Evaluation between S-isomer and Racemic Compound for Ketamine | No significant difference was found between the chiral s-ketamine and racemic solutions. |
| Stock Solution Evaluation between S-isomer and Racemic Compound for Norketamine | No significant difference was found between the chiral s-norketamine and racemic solutions. |

TABLE 163-continued

Validation Summary for the Determination of Ketamine and Norketamine

| | |
|---|---|
| S-Ketamine QC sample bench-top stability | 18 hours at room temperature |
| S-Ketamine QC sample freeze/thaw stability | 3 freeze (−20° C.)/thaw (room temperature) cycles |
| S-Ketamine QC sample long-term storage stability | 707 days at −20° C. |

1. Experimental
1.1. Bioanalytical Method

This bioanalytical method for the determination of ketamine and norketamine in sodium heparin human plasma using SPE automation was validated.

1.2. Equipment

LC-MS/MS, Sciex API 4000 (System Nos. 220 and 222) with Shimadzu HPLC (System Nos. 219 and 223) pump and autosampler Analyst Data Acquisition Software (1.4.2)

Column: Phenomenex Synergi Polar-RP, 50×2.0 mm, 4 micron

Switch Valve, Valco Instruments

ELGA Water Purification System (System 56-2), Model PL5231

Analytical Balance, Sartorius CP22P, capable of weighing 0.00001 g

Micro Balance, Mettler Toledo MX5, capable of weighing 0.000001 g

Centrifuge, Beckman GS-6R, (System No. 694)

Pulse Vortex Mixer, Glas Col® Cat No. 099A PVM12

Titer Plate Shaker, Thermo Scientific, Barnstead/Lab-Line, Model 4625

1.40 mL Non-coded Pushcap tubes U-bottom, Part No. MP32022, NOVA

Microliter plate, Deep Polypropylene Square Well/Conical Bottom, 2.0 mL, Microliter Analytical Supplies, Inc., Part No. 07-7400

96 Position Square Well, Pierceable Cover, EVA, Microliter Analytical Supplies, Inc., Product No. 07-0017N SPE Dry™ 96 system, Biotage Tomtec Automation System, Tomtec Quadra 3 (System No. 114)

Oasis MCX 96-well SPE plate 30 µm, 10 mg 1.3. Standards and Reagents

Ketamine Hydrochloride (U.S. Pharmacopeia, Purity 99.9% (a salt conversion factor of 237.73/274.19 was applied to the purity (99.9%) during use)

Ketamine-$d_4$ Hydrochloride (Cerilliant, 100.0±0.5 µg/mL in methanol (as freebase))

Norketamine Hydrochloride (Tocris Bioscience, Purity 100% (a salt conversion factor of 223.70/260.16 was applied to the purity (100%) during use.)

(±)-Norketamine-$d_4$ Hydrochloride (Cerilliant, 100.0±0.5 µg/mL in methanol (as freebase)

Water, purified

Methanol (Fisher Scientific, HPLC grade)

Ammonium Formate (ACROS, GR grade)

Ammonium Acetate (Fisher Scientific, ACS reagent grade)

Ammonium Hydroxide, 28-30% (Fisher Scientific, ACS reagent grade)

Formic Acid (ACROS, ACS reagent grade 1.4. Biological Matrix

Blank sodium heparin human plasma was purchased from Bioreclamation IVT. The pooled plasma was used to prepare the calibration standards, QC samples, validation samples, blanks, and double blanks. The plasma (pooled and individual lots) was stored at −20° C.

1.5. Concentrations of Working Standards

The working standards were freshly prepared on each day of analysis in pooled blank plasma, at the concentration levels listed in Table 164.

TABLE 164

Working Standard Concentrations

| Calibration Standard | Ketamine/Norketamine Concentration, ng/mL |
|---|---|
| STD 1 | 0.500/0.500 |
| STD 2 | 1.00/1.00 |
| STD 3 | 2.50/2.50 |
| STD 4 | 50.0/50.0 |
| STD 5 | 100/100 |
| STD 6 | 250/250 |
| STD 7 | 400/400 |
| STD 7 | 500/500 |

1.6. Concentrations of QC Samples

The QC samples were prepared in pooled human plasma at the concentration levels listed in Table 165. The QC samples were stored at −20° C.

TABLE 165

QC Sample Concentrations

| Quality Control | Ketamine/Norketamine[b] Concentration, ng/mL |
|---|---|
| LLOQ | 0.500/0.500 |
| Low QC | 1.50/1.50 |
| Mid QC | 80.0/80.0 |
| High QC | 375/375 |

2. Data Evaluation

Retention time and peak area were determined by Analyst® Data Acquisition/Processing Software (Version 1.4.2). Analyte concentrations were obtained from a calibration curve constructed by plotting the peak area ratio versus the concentration using Watson LIMS (Version 7.3). Watson LIMS and Microsoft Office Excel were used for statistical calculations. When Office Excel was used the calculations were 100% audited. Concentrations were calculated using linear regression according to the following equation:

$$y = ax + b$$

Where:
y=peak area ratio of analyte/internal standard
a=slope of the corresponding standard curve
x=concentration of analyte (ng/mL)
b=intercept of the corresponding standard curve
Use $1/x^2$ as weighting factor For calculation of accuracy and precision, the following formulas were used:

Accuracy:

$$\% \text{ Bias} = \frac{\text{Mean measured } conc. - \text{Nominal } conc.}{\text{Nominal } conc.} \times 100$$

Precision:

$$\% CV = \frac{\text{Standard Deviation}(SD)}{\text{Mean measured } conc.} \times 100$$

Precision and accuracy were reported to one decimal place. All concentration data was reported to three significant figures.

3. Matrix Selectivity

Selectivity is defined as the ability of a chromatographic method to measure a response from the analyte without interference from the biological matrix. This was accomplished by evaluating six individual lots of human plasma prepared as blank and at the lower limit of quantitation (LLOQ, 0.500 ng/mL).

3.1. Evaluation Based on LLOQ Samples

The LLOQ selectivity samples were acceptable if the accuracy was within ±20.0% for at least 5 of the 6 samples and the precision has to be ≤20.0% for all the samples.

3.2. Evaluation Based on Blank Samples

The peak areas of the analyte in the six blanks were compared with the mean peak area of the analyte in the LLOQ selectivity samples. The evaluation was acceptable if the peak area in 5 of the 6 blanks at the retention time of the analyte were within ≤20.0% of the mean peak area of the analyte of the LLOQ selectivity samples. In addition, the peak area in 5 of the 6 blanks at the retention time of the IS must be within ≤5.0% of the mean peak area of the IS of the LLOQ selectivity samples. The results for ketamine and norketamine met the acceptance criteria.

The retention times of ketamine and ketamine-$d_4$ (IS) were approximately 2.3 minutes. The retention times of norketamine and norketamine-$d_4$ (IS) were approximately 2.0 minutes.

3.3. Injection Carry-Over

The purpose of the injection carryover test is to evaluate the extent of carryover of the analyte of interest from one sample to the next in each analytical run. A double blank sample was injected following the high standard from the set of calibrators during the validation runs. The injection carryover of the analyte was less than 20% of the peak area of the LLOQ (Standard 1) for all double blank samples, thus meeting the acceptance criteria. In addition, the peak area of the IS was 0.0% of the mean IS peak area from accepted batch calibration standards and QC samples, well within the 5.0% acceptance criteria.

3.4. Matrix Effect

The matrix effect is defined as the suppression or enhancement of ionization of analytes by the presence of matrix components in the biological samples. See, e.g., C. T. Viswanathan, "Quantitative Bioanalytical Methods Validation and Implementation: Best Practices for Chromatographic and Ligand Binding Assays," Pharmaceutical Research, Vol. 24, No. 10, October 2007, p. 1969. The matrix effect was evaluated by extracting single replicates of six lots of blank human plasma and spiking each lot at the Low and High QC concentration levels (1.50 ng/mL and 375 ng/mL) post extraction. The area ratios of the six lots of post-extraction spiked plasma samples were compared to the mean area ratio obtained from three replicates of the neat solution prepared at the same concentration level in purified water.

The IS-normalized matrix factor was calculated according to the following formula:

$$IS\text{-normalized Matrix Factor} = \frac{\text{Peak Area Ratio in Presence of Matrix}}{\text{Mean Peak Area Ration in Absence of Matrix}}$$

The variability in the IS-normalized matrix factors (% CV) of the 6 lots of plasma samples was ≤15%, which was acceptable.

The quantification range was 0.5 to 500 ng/mL for both esketamine and noresketamine. All the assay acceptance criteria were met.

3.5. Back-Calculated Concentrations of Calibration Standards

Back-calculated concentrations of the calibration standards for ketamine and norketamine were determined. The mean back-calculated concentrations did not differ by more than 15% from the nominal concentrations (20.0% at the LLOQ) and the % CV for each concentration level was no more than 15.0% (20.0% at the LLOQ).

3.6. Regression Model

The linearity of the method was evaluated at a linear range of 0.500/0.500-500/500 ng/mL for ketamine/norketamine in human plasma. Linear regression (with a weighting factor of 1/x2) was used to produce the best fit for the concentration-detector response relationship for ketamine and norketamine in human plasma. All calibration curves for ketamine and norketamine had a coefficient of determination ($R^2$)≥0.98, which met acceptance.

3.7. Sensitivity

The validation was conducted with a target LLOQ of 0.500 ng/mL for ketamine and norketamine in human plasma. To evaluate the sensitivity, six QC samples prepared at the LLOQ were analyzed during three individual batch runs as part of the intra-run and inter-run accuracy and precision for the method. The concentrations were calculated with the calibration curve. The results demonstrated that the method met the acceptance criteria for sensitivity (accuracy within ±20.0% and % CV no more than 20.0%).

Therefore, the method was sensitive enough to determine ketamine and norketamine plasma at a concentration of 0.500 ng/mL.

3.8. Intra-Run and Inter-Run Accuracy and Precision

The intra-run and inter-run accuracy and precision of the method were investigated at four different QC concentration levels (0.500 ng/mL (LLOQ), 1.50 ng/mL, 80.0 ng/mL, and 375 ng/mL). The results demonstrated that the intra-run and inter-run precision and accuracy of the method met the acceptance criteria (accuracy within ±15.0% (within ±20.0% for LLOQ) and % CV no more than 15.0% (20.0% for LLOQ)).

3.9. Recovery

The recovery of the sample preparation was evaluated by comparing the mean area ratio of the QC samples with the mean area ratio of directly spiked ketamine/norketamine samples (at the same concentrations) in extracted pooled plasma. Recoveries were calculated according to the following formula:

$$\% \text{ Recovery} = \frac{\text{mean area ratio of Extracted } QC}{\text{mean area ratio of } Un-\text{extracted sample}} \times 100$$

Recovery was determined for ketamine and norketamine at three QC concentration levels (Low, Mid, and High). For each concentration, six measurements were performed. The variability (% CV) of the peak area ratio for each QC level should be ≤15%. The results were acceptable. Per BIO-201 guidelines, if a stable isotope labeled IS was used, the recovery established for the unlabeled analyte will suffice and the recovery for the stable isotope labeled IS will not be required.

3.10. Reinjection Reproducibility

To assess the reinjection reproducibility, an analyte batch containing a standard curve and QC samples was reinjected after being kept at room temperature for 161.5 hours. The calibration standards and QC samples (Low, Mid, and High) met the general batch run acceptance criteria, demonstrating that samples may be reinjected up to 161.5 hours after the initial injection.

3.11. Batch Size Evaluation

During validation, analytical run No. 3 was used to mimic the batch size for a sample analysis run. A total of 214 samples were run in the batch, which included both a standard curve and intra-run QC samples. The calibration standards and the intra-run QC samples met the general batch acceptance criteria for a sample analysis run.

Example 9: Pharmacokinetic Studies

The primary objective of this study was to evaluate the pharmacokinetics (PK) of intranasally-administered esketamine in healthy subjects.

1. Methods
1.1. Overview of Study Design
1.1.1. Overall Design

This was an open-label, single-center study. The subjects were healthy Caucasian men and women, 20 to 55 years of age, inclusive. As described in Example 1, esketamine was supplied as a clear, colorless intranasal solution of esketamine hydrochloride (16.14% weight/volume [w/v]; equivalent to 14% w/v of esketamine base) in a nasal spray pump. The solution consisted of:
  161.4 mg/mL esketamine hydrochloride;
  0.12 mg/mL ethylenediaminetetraacetic acid (EDTA);
  1.5 mg/mL citric acid;
  at a pH of 4.5 in water for injection.

The solution is provided in a nasal spray pump, which delivered 16.14 mg esketamine hydrochloride (14 mg esketamine base) per 100-μL spray.

All subjects self-administered each of the 3 different single-dose regimens of intranasal esketamine (Treatments A, B, and C), over 3 treatment periods (i.e., 1 treatment per period) in an open-label manner, under the direct supervision of the investigator or designee.
  Treatment A: 1 spray of 14% esketamine solution in each nostril at Time 0 (total dose 28 mg);
  Treatment B: 1 spray of 14% esketamine solution in each nostril at Time 0 and repeated after 5 minutes (total dose 56 mg);
  Treatment C: 1 spray of 14% esketamine solution in each nostril at Time 0 and repeated every 5 minutes ×2 (total dose 84 mg).

The subjects were randomly assigned to receive Treatment A and Treatment B in the first 2 periods (i.e., Treatment A in Period 1 and Treatment B in Period 2, or the reverse order). All subjects received Treatment C in Period 3 (Table 166). The regimens differed in the number of sprays to achieve the total dose and the total esketamine dose administered. A washout period of 5 to 14 days separated each intranasal esketamine treatment regimen.

TABLE 166

Treatment Sequences for Subjects

| Sequence | Period 1 | Period 2 | Period 3 |
|---|---|---|---|
| 1 | A | B | C |
| 2 | B | A | C |

A: 1 spray of 14% esketamine solution in each nostril at Time 0 (total dose 28 mg)
B: 1 spray of 14% esketamine solution in each nostril at Time 0 and repeated in 5 minutes (total dose 56 mg)
C: 1 spray of 14% esketamine solution in each nostril at Time 0 and repeated every 5 minutes x2 (total dose 84 mg)

After providing written informed consent, subjects were evaluated from Days −21 to Day −2 during the screening phase to determine eligibility for participation, which included review of the inclusion and exclusion criteria. All subjects were to meet the inclusion/exclusion criteria before admission to the study center for each treatment period. Subjects were admitted into the study center on Day −1 of each period and were discharged from the study center after collection of the final 24-hour PK sample on Day 2 of each treatment period. On Day −1 of the first treatment period, eligible subjects practiced self-administering a clear, colorless intranasal placebo solution for administration (water for injection with 0.001 mg/mL [0.0001%] of denatonium benzoate) in a semi-reclined position using devices identical to those used for esketamine administration. On Day 1 of each treatment period, subjects self-administered each intranasal regimen of esketamine (see Section 1.5, Dosage and Administration).

Pharmacokinetic blood samples for measurement of esketamine and noresketamine concentrations in plasma were collected from predose until up to 24 hours after each intranasal esketamine regimen on Day 1 of each period.

The subjects returned to the study center 11 (±2) days after the last dose of study medication for end-of-study assessments. Alternatively, the end-of-study assessments were conducted at the time of early withdrawal. The end of the study was the date of the last visit for the last subject participating in the study. The total study length, from the screening phase through Follow-up, was up to 63 days.

Study Design
Rationale
  Study Agent: Esketamine has a higher affinity to the NMDA receptor, thus reducing the required drug load and potentially producing a more rapid recovery of cerebral functions and less unpleasant psychotomimetic effects than racemic R-ketamine and ketamine, respectively;
  Study Population: A sample size of 12 subjects was expected to be sufficient to adequately characterize the PK of each intranasal esketamine regimen based on the variability reported in previous studies with intranasal ketamine and was considered to be representative of the profile in respective subjects with TRD who will enroll in future clinical studies;
  Study Design: A screening phase up to 21 days provided adequate time to assess subject eligibility per inclusion/ exclusion criteria for the study and the post-treatment Follow-up Visit at 11 (±2) days facilitated assessment to assess safety and tolerability of the subjects. Randomization was used to avoid bias in the assignment of subjects to a treatment sequence group and to increase the likelihood that known and unknown subject attributes (e.g., demographic and baseline characteristics) were evenly balanced across treatment sequences. The crossover design reduced the total number of subjects to be enrolled in the study and permitted within-subject comparisons;

Dose and Administration: The present study used intranasal esketamine dose regimens lower than the IV esketamine regimens typically used for induction and maintenance of anesthesia. The doses were expected to be well-tolerated based on the published studies;

Pharmacokinetics: The 24-hour postdose blood sampling interval was sufficient to evaluate the single-dose PK of both esketamine and its metabolite noresketamine.

1.2. Study Population

Fourteen healthy adult Caucasian subjects were enrolled, with similar number of subjects of each sex to have a similar ratio of men to women. Healthy men and women between 20 to 55 years of age, inclusive, with a body mass index (BMI) between 18 to 28 kg/m², inclusive and a body weight not less than 50 kg were enrolled in this study. Subjects had a systolic blood pressure between 90 mmHg to 145 mmHg, inclusive, and a diastolic blood pressure no higher than 90 mmHg, normal sinus rhythm, a pulse rate between 45 to 90 beats per minute, a QTc interval ≤450 milliseconds (msec), a QRS interval of ≤120 msec, a PR interval <210 msec, and an ECG morphology consistent with healthy cardiac conduction and function. Per protocol, subjects did not have a history of suicidal or homicidal ideation, significant primary sleep disorder, or any contraindication to the use of ketamine or esketamine.

Removal of subjects from therapy or assessment reasons for subject withdrawal from the study could include the following:

lost to follow-up;

withdrawal of consent;

subject not in compliance with requirements of the study, including inclusion criteria, exclusion criteria, and prohibitions and restrictions;

discontinuation of study treatment (final assessments were obtained). A subject was to be discontinued from study treatment if:

the investigator believed that for safety reasons (e.g., AE) it was in the best interest of the subject to stop treatment the subject became pregnant.

If a subject was lost to follow-up, every possible effort was to be made by the study center personnel to contact the subject and determine the reason for discontinuation. The measures taken to follow up were to be documented.

If a subject withdrew prior to completing the study, the reason for withdrawal was to be captured on the case report form (CRF) and in the source document. Study agent assigned to the withdrawn subject was not to be assigned to another subject. At least 12 subjects (including 4 of each sex) had to complete the study procedures of all treatment periods, including the 24-hour PK blood sample collections, and the end-of-study evaluations. Subjects who withdrew were to be replaced preferably with a subject of the same sex to complete the requisite 12 subjects per treatment.

Treatment Compliance

Study agent was self-administered in the controlled environment of a clinical research center, and the direct observation of the administration of the study agent by study staff ensured compliance with study requirements. The date and time of each study agent administration was recorded in the CRF.

Prior and Concomitant Therapy

Throughout the study, prescription or nonprescription medication other than the study agent (including vitamins and herbal supplements; vasoconstrictors and decongestants that are administered by the ophthalmic or intranasal routes) were prohibited, except for acetaminophen, oral contraceptives, and hormone replacement therapy. The use of acetaminophen was allowed until 3 days before each study agent administration.

Throughout the study, a maximum of 3 doses per day of 500 mg acetaminophen, and no more than 3 g per week, was allowed for the treatment of headache or other pain. If acetaminophen was used, the dose and dosage regimen and the reason for use were to be captured in the CRF.

Women using hormonal contraceptives as a means of birth control continued to use the same hormonal contraceptives throughout the study. Women using hormone replacement therapy continued to use the same hormone replacement therapy throughout the study.

The sponsor was to be notified immediately if prohibited therapies were administered. All medications taken by a subject (prescription or nonprescription) that were not the study agent were documented in the concomitant therapy section of the CRF. These included medications taken 30 days before, during, and through the end-of-study visit (9 to 13 days after the last study agent administration).

1.3. Study Drug Information

Intranasal esketamine and placebo for practice administration were supplied by the sponsor in a dual nasal spray device. Each device contained 200 µL and delivered 16.14 mg esketamine hydrochloride (14 mg esketamine base) or 0.1 µg of denatonium benzoate per 100 µL spray, respectively. The study agent information is given in Table 167:

TABLE 167

| Study agent name | Description, dose and mode of administration |
|---|---|
| Esketamine | 161.4 mg/mL esketamine hydrochloride clear, colorless intranasal solution |
| Esketamine placebo | Clear, colorless intranasal solution of water for injection with a bittering agent (denatonium benzoate) at a final concentration of 0.001 mg/mL |

1.4. Randomization and Blinding

This was an open-label study; therefore, no blinding of treatment was performed. Each intranasal dose regimen was labeled with the randomization code by site personnel and administered in an open-label manner.

If subjects were replaced, replacement subjects were assigned to the same treatment sequence as the subjects they were replacing. Replacement for subjects started with Period 1.

1.5. Dosage and Administration

Subjects self-administered intranasal esketamine in an open-label, crossover manner. They received the esketamine regimens over 3 treatment periods (i.e., 1 treatment per period, Table 168), as specified by treatment sequences (Table 166). The regimens differed in the number of sprays to achieve the total dose and the total esketamine dose administered.

TABLE 168

Description of Treatments for Subjects
Day 1 of Each Period

| | | Treatment Regimen | | | | | |
|---|---|---|---|---|---|---|---|
| | | Administration | | | Total | Total | |
| | Description[a, b] | Time 0 | +5 min | +10 min | Administration Interval | Number of Sprays | Total Dose[b] |
| Periods 1 and 2 | | | | | | | |
| A | 1 spray of 14% esketamine solution in each nostril at Time 0 | X | — | — | — | 2 | 28 mg |
| B | 1 spray of 14% esketamine solution in each nostril at Time 0 and repeated in 5 minutes | X | X | — | 5 min | 4 | 56 mg |
| Period 3 | | | | | | | |
| C | 1 spray of 14% esketamine solution in each nostril at Time 0 and repeated every 5 minutes × 2 | X | X | X | 10 min | 6 | 84 mg |

[a]Time 0 is defined as the time of the first 100-μL spray. Sprays to each nostril should be delivered in rapid succession at the scheduled time points (i.e., there should be no waiting between sprays in each nostril at each time point). Subjects must be in a semi-reclined position when administering the sprays and remain reclined for at least 10 minutes after the last spray.
[b]Esketamine concentration (percent esketamine solution) and Total Dose are expressed as esketamine base.

The intranasal esketamine regimens were self-administered under the direct supervision of the Investigator or designee using the modified instructions provided to the site (i.e., in a semi-reclined position for at least 10 minutes after the last spray; sniffing encouraged after dosing).

Food was restricted for at least 8 hours starting from the evening before dosing until 2 hours after each esketamine administration. Drinking of water or any other permitted beverage was restricted from 30 minutes before the first nasal spray and until 30 minutes after the last nasal spray of a given regimen. At approximately 2 hours after the last nasal spray dosing, subjects in all 3 treatment periods were required to drink 180 to 240 mL of water.

1.6. Study Evaluations and Statistical Methods
1.6.1. Pharmacokinetic Evaluations
1.6.1.1. Sample Collection and Handling Blood samples (4 mL each) for determination of esketamine and noresketamine plasma concentrations were collected into the appropriate collection tube (e.g., Vacutainer®) at timepoints 0.00, 0.12, 0.20, 0.37, 0.53, 0.67, 0.83, 1.00, 1.25, 1.50, 2.00, 3.00, 4.00, 6.00, 9.00, 12.00, 18.00, and 24.00 h. The total amount of blood to be drawn for clinical laboratory tests and PK evaluations is approximately 327 mL.

The exact date and time of sampling was recorded in the CRF, as appropriate. Before processing, the tubes were gently inverted 8 to 10 times to afford mixing, and were placed in a cryoblock (in an upright position) or in an ice water mixture to the approximate height of the blood in the tube. The blood samples were centrifuged within 60 minutes of collection in a clinical centrifuge at 1,300 g (about 2,500-3,000 rpm) for 10 minutes at 5° C. to yield approximately 1.8 mL of plasma from each 4-mL whole blood sample. All separated plasma was immediately transferred (equally divided) into 2 prelabeled polypropylene storage tubes with a dean, disposable glass or polyethylene pipette, while using a new pipette for each sample. One tube was labeled "esketamine, main" and the second tube "esketamine, back-up". The plasma samples were stored in an upright position, at −20° C. or lower until transferred to the bioanalytical facility. The time between blood collection and freezing the plasma was not to exceed 2 hours.

1.6.1.2. Bioanalytical Procedures

Plasma samples were analyzed for esketamine and noresketamine concentrations using the validated, specific and sensitive liquid chromatography coupled to tandem mass spectrometry (LC-MS/MS) achiral method of Example 8.

1.6.1.3. Pharmacokinetic Parameters

Serial PK blood samples (4 mL each) were collected for a 24-hour period from each subject (Periods 1, 2, and 3). Noncompartmental PK parameters of esketamine and its metabolite noresketamine estimated from plasma data included:

$C_{max}$ maximum plasma concentration during a dosing interval $t_{max}$ $t_{max}$ time to reach the maximum plasma concentration $AUC_{last}$ area under the plasma concentration-time curve from time 0 to time of the last quantifiable concentration AUC$_\infty$ area under the plasma concentration-time curve from time 0 to infinite time calculated as the sum of AUC$_{last}$ and C$_{last}$/$\lambda_z$, in which C$_{last}$ is the last observed quantifiable concentration t$_{1/2,\lambda}$ elimination half-life associated with the terminal slope ($\lambda_z$) of the semilogarithmic drug concentration-time curve, calculated as 0.693/$\lambda_z$ $\lambda_z$ first-order rate constant associated with the terminal portion of the curve, determined as the negative slope of the terminal log-linear phase of the drug concentration-time curve 1.6.4. Statistical Methods
1.6.4.1. Sample Size At least 12 subjects (including 4 of each sex) had to complete the study procedures of all treatment periods, including the 24 hour PK blood sample collections, and the end-of-study evaluations. Subjects who withdrew were replaced, preferably, with a subject of same sex to complete the requisite 12 subjects per treatment. Based on a previously completed study, the intersubject coefficient of variation for C$_{max}$ and AUC of intranasal racemic ketamine was estimated to be at least 55%. Assuming an intersubject coefficient of variation of 55% for PK parameters of esketamine, a sample size of 12 subjects was sufficient to ensure that the estimate of the mean PK parameters of esketamine fell within 71% and 142% of the true value with 95% confidence.

1.6.4.2. Initial Subject Characteristics

For all subjects who received at least 1 dose of study agent, descriptive statistics (mean, standard deviation [SD], median, minimum, maximum) were performed for age, BMI, weight, and height Sex and race were listed and tabulated.

1.6.4.3. Pharmacokinetic Analysis

For esketamine and noresketamine, data were listed for all subjects with available plasma concentrations. All plasma concentrations below the lowest quantifiable concentration in a sample or missing data were labeled as such in the concentration data presentations.

Concentrations below the lower quantifiable concentration were treated as zero when calculating PK parameters and summary statistics. All subjects and samples excluded from the analysis were to be clearly documented.

Descriptive statistics were used to summarize plasma esketamine and noresketamine concentrations at each sampling timepoint. The analysis included data from all subjects with available data from a least 1 dose of study agent. Plasma concentration data at each timepoint were summarized with mean, median, minimum, maximum, SD, and percent coefficient of variation for all subjects who received at least 1 dose of study agent.

The following key parameters of esketamine and noresketamine in plasma were calculated using noncompartmental methods and actual sampling times: C$_{max}$, t$_{max}$, AUC$_{last}$, AUC$_\infty$, t$_{1/2,\lambda}$, and $\lambda_z$.

All estimated PK parameters of esketamine and noresketamine were summarized for each treatment with mean, median, minimum, maximum, SD, percent coefficient of variation for each treatment provided.

2. Subject and Treatment Information
2.1. Subject Disposition and Study Completion/Withdrawal Information Initially a total of 14 Caucasian subjects were enrolled and treated with esketamine with 7 subjects randomized to each treatment sequence. Of these 14 subjects, 13 subjects completed the study, with 7 subjects in each treatment sequence (ABC and BAC). One subject discontinued the study; the subject did not meet entry criteria for Period 2, due to a positive result for the urine drug screen at Period 2 check in.

2.2. Demographic and Baseline Characteristics

Demographic and baseline characteristics of subjects who received a dose of esketamine are presented in (Table 169).

TABLE 169

Demographic and Baseline Characteristics; Safety Analysis Set

| | ABC | BAC | Total |
|---|---|---|---|
| Subjects treated | 7 | 7 | 14 |
| Age (years) | | | |
| N | 7 | 7 | 14 |
| Mean (SD) | 32.3 (8.20) | 33.9 (11.75) | 33.1 (9.77) |
| Median Range | 31.0 (24; 48) | 28.0 (22; 50) | 30.0 (22; 50) |
| Sex | | | |
| N | 7 | 7 | 14 |
| Female | 1 (14.3%) | 4 (57.1%) | 5 (35.7%) |
| Male | 6 (85.7%) | 3 (42.9%) | 9 (64.3%) |
| Race | 7 | 7 | 14 |
| Asian | 0 | 0 | 0 |
| White | 7 (100.0%) | 7 (100.0%) | 14 (100.0%) |
| Ethnicity | | | |
| N | 7 | 7 | 14 |
| Not Hispanic or Latino | 7 (100.0%) | 7 (100.0%) | 14 (100.0%) |
| Baseline Weight (kg) | | | |
| N | 7 | 7 | 14 |
| Mean (SD) | 79.39 (7.866) | 67.47 (11.265) | 73.43 (11.196) |
| Median | 79.50 | 63.60 | 75.15 |
| Range | (68.1; 93.1) | (56.9; 87.2) | (56.9; 93.1) |
| Baseline Height (cm) | | | |
| N | 7 | 7 | 14 |
| Mean (SD) | 181.79 (7.793) | 170.93 (5.992) | 176.36 (8.737) |
| Median | 179.90 | 168.30 | 175.35 |
| Range | (175.0; 197.6) | (164.0; 181.4) | (164.0; 197.6) |

TABLE 169-continued

Demographic and Baseline Characteristics; Safety Analysis Set

|  | ABC | BAC | Total |
|---|---|---|---|
| Baseline BMI (kg/m$^2$) | | | |
| N | 7 | 7 | 14 |
| Mean (SD) | 24.00 (1.489) | 22.97 (2.308) | 23.49 (1.941) |
| Median | 24.10 | 22.40 | 23.30 |
| Range | (21.6; 26.0) | (20.6; 26.5) | (20.6; 26.5) |

ABC = Esketamine 28 mg/Esketamine 56 mg/Esketamine 84 mg
BAC = Esketamine 56 mg/Esketamine 28 mg/Esketamine 84 mg 2.6. Extent of Exposure The subjects received all 3 different single-dose regimens of intranasal esketamine (Treatments A, B, and C) during Periods 1, 2, and 3 as per the randomized sequence. Sprays were administered as follows:
  in Treatment A, 28 mg at Time 0;
  in Treatment B, 28 mg at Time 0 and 5 minutes each (totaling 56 mg); and
  in Treatment C, 28 mg at Time 0, 5, and 10 minutes each (totaling 84 mg).
The discontinued subject received the study agent as follows:
  The subject of Treatment Sequence 2 received esketamine 28 mg at Time 0 and 5 minutes (totaling 56 mg) at Period 1, Day 1.

3. Pharmacokinetic Results

Plasma samples were analyzed for the concentrations of esketamine and noresketamine using a validated, specific, and sensitive liquid chromatography-tandem mass spectrometry (LC-MS/MS) method as described in Example 8. A total of 14 Caucasian subjects (9 men, 5 women) were enrolled in this study and received at least 1 dose of 28 mg, 56 mg, or 84 mg of esketamine. One subject withdrew from the study after completing the first treatment period in which the subject self-administered Treatment B (esketamine 56 mg).

In addition, one Treatment A (esketamine, 28 mg, pre-dose) sample was excluded from the entire PK analysis of esketamine and noresketamine as they were taken at time of withdrawal.

The terminal phase of the esketamine concentration-time profile could not be reliably estimated with either an $R^2_{adj}$ value <0.900 and/or an $AUC_\infty$ extrapolation >20%. As a result, esketamine $AUC_\infty$, $AUC_\infty$/Dose, $t_{1/2}$, and $\lambda_z$ were excluded from the descriptive statistics for the 3 subjects, i.e., Treatment A (esketamine 28 mg), Treatment B (esketamine 56 mg), and Treatment C (esketamine 84 mg).

The terminal phase of the noresketamine concentration-time profile could not be reliably estimated with either an $R^2_{adj}$ value <0.900 and/or an $AUC_\infty$ extrapolation >20%. As a result, noresketamine $AUC_\infty$, $AUC_\infty$/Dose, $t_{1/2}$, and $\lambda_z$ were excluded from the descriptive statistics for 2 subjects, i.e., Treatment B (esketamine 56 mg) and Treatment C (esketamine 84 mg).

In addition, the metabolite to parent ratio for $AUC_\infty$ was excluded from descriptive statistics as $AUC_\infty$ was excluded from the descriptive statistics for either esketamine or noresketamine for 5 subjects, i.e., Treatment A (esketamine 28 mg), Treatment B (2 subjects; esketamine 56 mg), and Treatment C (2 subjects; esketamine 84 mg).

All PK parameters were calculated using the actual times of blood sampling.

Pharmacokinetic Results

Mean plasma concentration-time profiles of esketamine and noresketamine are presented in FIGS. 80 and 81, respectively.

Following intranasal administration, maximum concentrations ($C_{max}$) of esketamine were reached with median $t_{max}$ ranging from 0.67 to 0.83 hours in healthy subjects, respectively, across the 3 intranasal regimens of esketamine (28, 56, and 84 mg) (Table 170). Maximum concentrations of metabolite noresketamine were observed later with median $t_{max}$ ranging from 1.25 to 1.5 hours in healthy subjects, respectively (Table 171).

For esketamine $C_{max}$, variability (expressed as percent coefficient of variation) across the 3 treatment groups ranged from 35.7% to 36.7%. For esketamine AUC (both $AUC_{last}$ and $AUC_\infty$), variability ranged from 25.0% to 30.4%. Between-subject variability for noresketamine $C_{max}$ ranged from 25.8% to 33.7% in subjects. For noresketamine AUC (both $AUC_{last}$ and $AUC_\infty$), variability ranged from 17.0% to 21.3% in subjects.

Plots of esketamine $C_{max}$ or AUC versus total body weight were constructed for each dose level. Similar plots were prepared for the metabolite. The results suggest there is a trend towards a decrease in esketamine and noresketamine $C_{max}$ and AUC with an increase in body weight. The strength of the trends varied across the dose groups.

Based on visual inspection, the mean $C_{max}$, $AUC_{last}$, and $AUC_\infty$ for esketamine and mean $C_{max}$ for noresketamine increased with increasing doses in a less than dose-proportional manner (FIGS. 80 and 81 and Tables 170 and 171). The mean noresketamine $AUC_{last}$ and $AUC_\infty$ values appeared to increase in a manner that was proportional to the esketamine dose.

Mean $t_{1/2}$ of esketamine ranged from 7.11 to 7.25 hours in the subjects (Table 170).

TABLE 170

Mean (SD) Esketamine Pharmacokinetic Parameters

| Subgroup/Treatment | $C_{max}$ (ng/mL) | $t_{max}{}^a$ (h) | $AUC_{last}$ (h*ng/mL) | $AUC_\infty$ (h*ng/mL) | $t_{1/2}$ (h) |
|---|---|---|---|---|---|
| A: Esketamine 28 mg (n = 13) | 49.7 (18.1) | 0.67 (0.20-1.50) | 128 (31.8) | 136$^d$ (33.9)$^d$ | 7.25$^d$ (1.19)$^d$ |

TABLE 170-continued

Mean (SD) Esketamine Pharmacokinetic Parameters

| Subgroup/Treatment | $C_{max}$ (ng/mL) | $t_{max}{}^a$ (h) | $AUC_{last}$ (h*ng/mL) | $AUC_\infty$ (h*ng/mL) | $t_{1/2}$ (h) |
|---|---|---|---|---|---|
| B: Esketamine 56 mg (n = 14) | 74.1 (27.2) | 0.67 (0.20-1.25) | 216 (61.5) | $222^b$ $(59.9)^b$ | $7.25^b$ $(1.67)^b$ |
| C: Esketamine 84 mg (n = 13) | 103 (36.8) | 0.83 (0.20-1.50) | 310 (92.0) | $329^d$ $(100)^d$ | $7.11^d$ $(1.78)^d$ |

$^a$Median (Min-Max),
$^b$n = 13,
$^c$n = 11,
$^d$n = 12

Mean $t_{1/2}$ of noresketamine ranged from 7.48 to 7.74 hours in the subjects (Table 171).

TABLE 171

Mean (SD) Noresketamine Pharmacokinetic Parameters

| Subgroup/ Treatment | $C_{max}$ (ng/mL) | $t_{max}{}^a$ (h) | $AUC_{last}$ (h*ng/mL) | $AUC_\infty$ (h*ng/mL) | $t_{1/2}$ (h) | Metabolite/Parent Ratio | | |
|---|---|---|---|---|---|---|---|---|
| | | | | | | $C_{max}$ | $AUC_{last}$ | $AUC_\infty$ |
| A: Esketamine 28 mg (n = 13) | 92.8 (24.6) | 1.25 (0.67-2.00) | 454 (89.0) | 508 (108) | 7.74 (1.66) | 1.96 (0.445) | 3.62 (0.589) | $3.80^b$ $(0.739)^b$ |
| B: Esketamine 56 mg (n = 14) | 154 (39.8) | 1.50 (0.83-3.00) | 851 (177) | $924^c$ $(195)^c$ | $7.71^c$ $(1.59)^c$ | 2.28 (0.818) | 4.07 (0.876) | $4.22^b$ $(0.991)^b$ |
| C: Esketamine 84 mg (n = 13) | 241 (81.1) | 1.50 (1.25-3.00) | 1287 (219) | $1392^b$ $(252)^b$ | $7.48^b$ $(1.47)^b$ | 2.55 (0.976) | 4.32 (0.871) | $4.46^d$ $(1.06)^d$ |

$^a$Median (Min-Max);
$^b$n = 12;
$^c$n = 13;
$^d$n = 11;
$^e$n = 10

The plasma concentrations of noresketamine were generally higher, relative to the parent compound. For $C_{max}$, the mean ratios of noresketamine to esketamine ranged from 1.96 to 2.55. For $AUC_{last}$, the mean ratios ranged from 3.62 to 4.32. For $AUC_\infty$, the mean ratios ranged from 3.80 to 4.46 (Table 171).

Conclusion:

Mean plasma esketamine $C_{max}$ and AUC increased in a less than dose-proportional manner across the 28-mg, 56-mg, and 84-mg intranasal dose regimens of esketamine.

Example 10

The data herein was assembled from 14 Phase 1 studies; each Phase 1 study was performed similarly to the study outlined in Example 9 in which the PK of esketamine was assessed.

The PK parameters of esketamine including $T_{max}$, $C_{max}$, $AUC_{last}$, and terminal $t_{1/2}$ after administration of 28 mg, 56 mg, or 84 mg of nasal esketamine are provided in Table 172. The $t_{max}$ of esketamine was typically observed at 20 to 40 minutes, 30 to 45 minutes, or 30 to 50 minutes after the first nasal spray of a 28 mg, 56 mg, or 84 mg of esketamine, respectively (i.e., approximately 20 to 40 minutes after the last spray of a given dose). A dose-dependent, linear increase in mean esketamine $C_{max}$ and $AUC_{last}$ is evident (FIGS. 82A and 82B).

TABLE 172

Pharmacokinetic Parameters of Esketamine in Young Adult Subjects After a Single Dose of Esketamine Nasal Spray

| Esketamine | $T_{max}$ (h) | $C_{max}$ (ng/mL) | $AUC_{last}$ (ng*h/mL) | Terminal $t_{1/2}$ (h) |
|---|---|---|---|---|
| 28 mg | 0.33-0.67 (n = 64) | 49.7-70.5 (n = 64) | 128-183 (n = 64) | 7.25-16.5 (n = 61) |
| 56 mg | 0.50-0.77 (n = 86) | 71.8-117 (n = 86) | 216-317 (n = 86) | 6.8-9.83 (n = 83) |
| 84 mg | 0.53-0.83 (n = 167) | 95.0-164 (n = 167) | 310-489 (n = 167) | 6.6-12.0 (n = 150) |

Range of median values are provided for $T_{max}$; range of mean values provided for $C_{max}$ and $AUC_{last}$.

After esketamine $C_{max}$ was reached following nasal administration, the decline in concentrations in plasma is rapid for the initial 2 to 4 hours and then more gradual. The esketamine mean terminal $t_{1/2}$ ranged from 7 to 12 hours. The median terminal $t_{1/2}$ in this study was 10.7 hours.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating major depressive disorder in a human patient in need thereof based on a dosing regimen, said regimen having an induction phase and, a subsequent maintenance phase, wherein the induction phase has a duration of 4 weeks, the method comprising:
intranasally administering an aqueous formulation comprising esketamine and/or a pharmaceutically acceptable salt thereof in the induction phase to provide a therapeutically effective amount of about 56 mg or about 84 mg of esketamine per induction phase treatment session to the patient, wherein the induction phase treatment session occurs at a frequency of twice weekly during the induction phase; and
intranasally administering an aqueous formulation comprising esketamine and/or a pharmaceutically acceptable salt thereof in the maintenance phase to provide a therapeutically effective amount of about 56 mg or about 84 mg of esketamine per maintenance phase treatment session to the patient, wherein the maintenance phase treatment session occurs at a frequency of once weekly or once every other week during the maintenance phase; and
wherein the patient has a worsening of depression symptoms following a missed treatment session during the maintenance phase and is returned to a previously higher frequency of treatment session before the missed treatment session.

2. The method of claim 1, wherein the missed treatment session is a once weekly treatment session, and the patient is returned to twice weekly treatment session.

3. The method of claim 1, wherein the missed treatment session is a once every other week treatment session, and the patient is returned to once weekly treatment session.

4. The method of claim 1, further comprising adjunctive treatment with a therapeutically effective amount of one or more antidepressants during the induction phase or the maintenance phase.

5. The method of claim 1, further comprising adjunctive treatment with a therapeutically effective amount of one or more antidepressants during the induction phase and the maintenance phase.

6. The method of claim 5 wherein the one or more antidepressants is an oral antidepressant.

7. The method of claim 1, wherein the major depressive disorder is major depressive disorder with suicidal ideation or behavior.

8. The method of claim 1, wherein the major depressive disorder is treatment resistant depression.

9. The method of claim 1, wherein the aqueous formulation comprises esketamine hydrochloride during the induction phase and maintenance phase.

10. The method of claim 2, wherein the major depressive disorder is treatment resistant depression.

11. The method of claim 10, wherein the aqueous formulation comprises esketamine hydrochloride during the induction phase and maintenance phase.

12. The method of claim 10, further comprising adjunctive treatment with a therapeutically effective amount of one or more antidepressants during the induction phase or the maintenance phase.

13. The method of claim 10, further comprising adjunctive treatment with a therapeutically effective amount of one or more antidepressants during the induction phase and the maintenance phase.

14. The method of claim 13 wherein the one or more antidepressants is an oral antidepressant.

15. The method of claim 14, wherein the aqueous formulation comprises esketamine hydrochloride during the induction phase and maintenance phase.

16. The method of claim 2, wherein the major depressive disorder is major depressive disorder with suicidal ideation or behavior.

17. The method of claim 16, wherein the aqueous formulation comprises esketamine hydrochloride during the induction phase and maintenance phase.

18. The method of claim 16, further comprising adjunctive treatment with a therapeutically effective amount of one or more antidepressants during the induction phase or the maintenance phase.

19. The method of claim 16, further comprising adjunctive treatment with a therapeutically effective amount of one or more antidepressants during the induction phase and the maintenance phase.

20. The method of claim 19 wherein the one or more antidepressants is an oral antidepressant.

21. The method of claim 20, wherein the aqueous formulation comprises esketamine hydrochloride during the induction phase and maintenance phase.

22. The method of claim 3, wherein the major depressive disorder is treatment resistant depression.

23. The method of claim 22, wherein the aqueous formulation comprises esketamine hydrochloride during the induction phase and maintenance phase.

24. The method of claim 22, further comprising adjunctive treatment with a therapeutically effective amount of one or more antidepressants during the induction phase or the maintenance phase.

25. The method of claim 22, further comprising adjunctive treatment with a therapeutically effective amount of one or more antidepressants during the induction phase and the maintenance phase.

26. The method of claim 25 wherein the one or more antidepressants is an oral antidepressant.

27. The method of claim 26, wherein the aqueous formulation comprises esketamine hydrochloride during the induction phase and maintenance phase.

28. The method of claim 3, wherein the major depressive disorder is major depressive disorder with suicidal ideation or behavior.

29. The method of claim 28, wherein the aqueous formulation comprises esketamine hydrochloride during the induction phase and maintenance phase.

30. The method of claim 28, further comprising adjunctive treatment with a therapeutically effective amount of one or more antidepressants during the induction phase or the maintenance phase.

31. The method of claim 28, further comprising adjunctive treatment with a therapeutically effective amount of one or more antidepressants during the induction phase and the maintenance phase.

32. The method of claim 31 wherein the one or more antidepressants is an oral antidepressant.

33. The method of claim 32, wherein the aqueous formulation comprises esketamine hydrochloride during the induction phase and maintenance phase.

* * * * *